US010179935B2

(12) United States Patent
Guilford et al.

(10) Patent No.: US 10,179,935 B2
(45) Date of Patent: Jan. 15, 2019

(54) MARKERS FOR DETECTION OF GASTRIC CANCER

(75) Inventors: Parry John Guilford, Dunedin (NZ); Andrew John Holyoake, Dunedin (NZ)

(73) Assignee: PACIFIC EDGE LIMITED, Dunedin (NZ)

( * ) Notice: Subject to any disclaimer, the term of this patent is extended or adjusted under 35 U.S.C. 154(b) by 1567 days.

(21) Appl. No.: 10/565,068

(22) PCT Filed: Jul. 16, 2004

(86) PCT No.: PCT/US2004/022959
§ 371 (c)(1),
(2), (4) Date: Jul. 13, 2006

(87) PCT Pub. No.: WO2005/010213
PCT Pub. Date: Feb. 3, 2005

(65) Prior Publication Data
US 2007/0184439 A1 Aug. 9, 2007

Related U.S. Application Data

(60) Provisional application No. 60/487,906, filed on Jul. 17, 2003.

(51) Int. Cl.
C12Q 1/6886 (2018.01)
G01N 33/574 (2006.01)
C12Q 1/6837 (2018.01)

(52) U.S. Cl.
CPC ..... *C12Q 1/6886* (2013.01); *G01N 33/57446* (2013.01); *C12Q 1/6837* (2013.01); *C12Q 2600/112* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

2003/0232350 A1* 12/2003 Afar et al. ............ 435/6
2004/0076955 A1* 4/2004 Mack et al. ............ 435/6
2006/0019256 A1* 1/2006 Clarke et al. ............ 435/6

FOREIGN PATENT DOCUMENTS

WO WO 1998/41864 9/1998
WO WO 2001/94629 12/2001
WO WO 03/057916 A2 * 7/2003
WO WO 2004/071530 * 8/2004

OTHER PUBLICATIONS

Salmela et al. Gut 2001 vol. 48 p. 496.*
Utsunomiya et al. Cystatin-like metastasis-associated protein mRNA expression in human colorectal cancer is associated with both liver metastatis and patient survival. Clinical Cancer Research 8: 2597-2594, Aug. 2002.*
Pfaffl, Michael W. Nucleic Acids Research 29(9): 2002-2007, 2001.*
Livak et al. Analysis of relative gene expression data using real-time quantitative PCR and the 2-deltadelta T method. Methods 25: 402-408, 2001.*
European Examination Report dated Oct. 6, 2010 in Application No. 04778461.6-1222 / 1649064.
Dezwart, Loeckie, L., Biomarkers of free radical damage applications in experimental animals and in humans, Free Radical Biology & Medicine, vol. 26, Nos. 1/2, pp. 202-226,1999.
Salmela, MT, Parallel expression of macrophage metalloelastase (MMP-12) in duedenal and skin lesions and patients with dermatitis herpetiformis, GUT online, Gut2001;48;496-502 Apr. 13, 2008.
Finlay, Martin BJ, Prostate Cancer Prostatic Dis.Mar. 9, 2004, PubMed, Louisiana University Health Sciences Center, New Orleans, LA.
Japanese Office Action translation, dated Apr. 27, 2010.
Yoshikawa, Takaki, Prognostic value of tissue inhibitor of matrix metalloproteinase-1 in polasma of patients with gastric cancer, Elsevier, Cancer Letters 151 (2000) 81-86.
Rudland, Philip S., Prognostic Significance of the Metastasis-associated Protein Osteopontin in Human Breast Cancer, Cancer Research 62, 3417-3427, Jun. 15, 2002.
Taiwanese Office Action, translation dated Feb. 24, 2009.
Buckhaults, Phillip, Secreted and cell surface genes expressed in benign and malignant colorectal tumors, Cancer Research 61, 6996-7001, Oct. 1, 2001.
Hotte, Sebastian J., Plasma Osteopontin, 2002, American Cancer Society.
Kim, Jae-Hoon, Osteopontin as a potential diagnostic biomarker for ovarian cancer, JAMA, American Medical Association, Apr. 3, 2002, vol. 287, No. 13. 1671-1682.

* cited by examiner

*Primary Examiner* — Alana Harris Dent
(74) *Attorney, Agent, or Firm* — D. Benjamin Borson; Borson Law Group PC

(57) ABSTRACT

Early detection of tumors is a major determinant of survival of patients suffering from tumors, including gastric tumors. Members of the GTM gene family can be over-expressed in gastric tumor tissue and other tumor tissue, and thus can be used as markers for gastric and other types of cancer. GTM proteins can be released from cancer cells, and can reach sufficiently high concentrations in the serum and/or other fluids to permit their detection. Thus, methods and test kits for detection and quantification of GTM can provide a valuable tool for diagnosis of gastric cancer.

7 Claims, 104 Drawing Sheets

Specification includes a Sequence Listing.

| name | symbol | Applied Biosystems "assay on demand" assay # | forward primer | Seq ID No. | reverse primer | Seq ID No. | probe | Seq ID No. |
|---|---|---|---|---|---|---|---|---|
| asporin (lrr class 1) | ASPN | | AAATACAAAGGACACATTCAAAGGA | 1 | TGCTTCTGCAATTCTGATATGGA | 23 | TTGGAAATGAGTGCAAACCCTCTTGATAATAATG | 45 |
| chondroitin sulfate proteoglycan 2 (versican) | CSPG2 | | GCCAGTGGAATGATGTTCCC | 2 | TCTTGGCATTTTCTACAACAGGG | 24 | AGGAACAGTTGCTTGGCGCAGC | 46 |
| cystatins SN, SA & S | CST1, 2, 4 | | AGTCCCAGGCCAACTTGA | 3 | GGGAACTTCGTAGATCTGGAAAGA | 25 | AGCCAGAACTGCAGAAGAAACAGTTGTGC | 47 |
| gamma-glutamyl hydrolase | GGH | | GTGGCAATGCGCGCTGAA | 4 | TGACAGGCAACAACTCAGTAGGAAA | 26 | TTCACTGGAGGTCAATTGCACACAGAAT | 48 |
| insulin-like growth factor binding protein 7 | IGFBP7 | | CAGGTCAGCAAGGCACC | 5 | TCAAGCTCAAGTACACCTGGG | 27 | AGCAAGGTCGTTCCATAGTCAGGGC | 49 |
| kallikrein 10 | KLK10 | | ACAACATGATATGTCCTGGACTGG | 6 | GAGAGGATGTCCTTGGAGGT | 28 | CTTGCCAGAGTGACTCTCTGAAGGCC | 50 |
| leucine proline-enriched proteoglycan 1 (leprecan 1) | LEPRE1 | | CTTGAGTACAAGCGTGACCTCTC | 7 | CCGTTGACACAGTTCTGCTTACAG | 29 | CCATCACAGATCATTCATCCAGGTCCTCA | 51 |
| lumican | LUM | | GATTCTTGTCCATAGTGCATCTGC | 8 | CCAATCAATGCCAGGAATGCA | 30 | TAAGGATTCAAACCATTTGCCAAAATAGTCTAAG | 52 |
| lysyl oxidase-like 2 | LOXL2 | | AGGGACGCTTCTGCTTGA | 9 | CCCTGATGCGGAGTTG | 31 | CGTAATTCTTCTGATGTCTTCTTCACATTCTG | 53 |
| matrix metalloproteinase 12 | MMP12 | | GCCTCTCTGCTGATGACATACGT | 10 | AGTGCAAGCATCAAAACTCAAATTG | 32 | TTCAGTCCCTGTATGGAGCACCCAAAAGAGA | 54 |
| metalloproteinase inhibitor 1 | TIMP1 | | CCAGACCACCTTATACCAGCG | 11 | GGAGCTGTTGAAGTATCCGC | 33 | CAAGATGCACCAAGATGTATAAAGGGTTCCAAGC | 55 |
| n-acylsphingosine amidohydrolase | ASAH1 | | CGCAGAACGGCTGCAA | 12 | ACAGGACATCATACATCCGTTCAA | 34 | TGTCTCAACCGCACCACCAGGCAAGAGAATA | 56 |
| secreted frizzled-related protein 2 | SFRP2 | | CGCTAGCAGGACACCT | 13 | TTTTGCAGGCTGTCACATACCTT | 35 | CTTGCCAGCCACCGGAGGAAGCTC | 57 |
| secreted protein, acidic, cysteine rich | SPARC | | TCTTCCCTGTACACTGGCAGTC | 14 | GAAAAGCGGGGTTGGTCA | 36 | TGGAACCAGCAGGGCATTCAGG | 58 |
| serine protease 11 (IGF binding) | PRSS11 | | TCGGGAGGCCGGTTAGTAA | 15 | AAGGAGATTCCAGCTGTCACTTTC | 37 | AGTGTTAATTCCAATCACTTCACCGTCAGG | 59 |
| thrombospondin 2 | THBS2 | | TGGAAGGACTACACGGCCTATAG | 16 | TAGGTTTGGTCATAGATAAGTCCTGAGT | 38 | AGGGCCAAGAACGGCTACATCAGAGTC | 60 |
| thyroglobulin | TG | | GACGGTTCCTGCAGTTCAA | 17 | TGTAAACGCTCCACTCACAT | 39 | TCTGCCAGATTCGGATCGCCAAA | 61 |
| human cell growth regulator with EF hand domain 1 | CGR11 | Hs00241844_m1 | CTGCCCACCCTTCA | 18 | TTCTGTCCTTCCTAGTGCCTTTAGG | 40 | CCAGCCAGGAGCAGTCGG | 62 |
| human serine or cysteine proteinase inhibitor clade B | SERPINB5 | | TCCAGCATTTTCCAGGATAA | 19 | AAGCCGAATTTGCTAGTTGCA | 41 | TGACTCCAGCCGCCAATGGA | 63 |
| transforming growth factor β1 | TGFB1 | | GGTCATGTCATCACCAATGTT | 20 | TCTGCAAGTCATCCCCTCTT | 42 | CAGCCTCAGCCAACGACCTGAGG | 64 |
| human proprotein convertase subtilisin/kexin type 5 | PCSK5 | | AAAATCTTTGCGGGAAATGC | 21 | AGTTCCTGGCCGTTGAAATACC | 43 | ACAGAATGTTAGGGATGGGTTAAGCCTCA | 65 |
| matrix metalloproteinase 2 | MMP2 | | TTGATGGCATGGCTCAGATC | 22 | TGTCACGTGGCGTCACAGT | 44 | TTCAAGGACCGGTTCATTTGGCG | 66 |
| human serine or cysteine proteinase inhibitor clade H | SERPINH1 | Hs00241844_m1 | | | | | | |
| adican | | Hs00377849_m1 | | | | | | |
| egf-containing fibulin-like extracellular matrix protein 2 | EFEMP2 | Hs00213545_m1 | | | | | | |
| secreted frizzled-related protein 4 | SFRP4 | Hs00180066_m1 | | | | | | |
| inhibin beta A chain | INHBA | Hs00170103_m1 | | | | | | |
| osteopontin | SPP1 | Hs00167093_m1 | | | | | | |
| transforming growth factor β-induced | TGFBI | Hs00165908_m1 | | | | | | |

Figure 1

Microarray - Identification of Markers for Gastric Malignancy

| name | symbol | MWG oligo # | NCBI mRNA ref sequence | protein ref sequence | fold change | fold change rank | original t-test | Bonferroni-adjusted p value | 2 sample Wilcoxon test |
|---|---|---|---|---|---|---|---|---|---|
| adlican | - | C:0531 | NM_015419 | NP_056234 | 1.8 | -17818 | 1.0E-28 | 3.04E-24 | 0.0E+00 |
| asporin (lrr class 1) | ASPN | A:07749 | NM_017680 | NP_060150 | 2.6 | -22292 | 6.4E-23 | 1.9E-18 | 0.0E+00 |
| carboxypeptidase N | CPN2 | B:4922 | - | P22792 | 2.7 | -22367.5 | 2.3E-42 | 7.0E-38 | 0.0E+00 |
| cell growth regulatory factor with EF-hand domain | CGR11 | A:07876 | NM_006569 | NP_006560 | 3.0 | -21188.5 | 4.33E-42 | 1.3E-37 | 0.0E+00 |
| chondroitin sulfate proteoglycan 2 (versican) | CSPG2 | A:10008 | NM_004385 | NP_004376 | 2.3 | -21606.5 | 2.23E-33 | 6.65E-29 | 0.00E+00 |
| cystatin SN | CST1 | A:06089 | NM_001898 | NP_001889 | 2.1 | -17475 | 1.3E-18 | 3.8E-14 | 0.0E+00 |
| cystatin SA | CST2 | A:06089 | NM_001322 | NP_001313 | 2.1 | -17475 | 1.3E-18 | 3.8E-14 | 0.0E+00 |
| cystatin S | CST4 | A:06089 | NM_001899 | NP_001890 | 2.1 | -17475 | 1.3E-18 | 3.8E-14 | 0.0E+00 |
| egf-containing fibulin-like extracellular matrix protein 2 | EFEMP2 | A:09072 | NM_016938 | NP_058634 | 2.4 | -22761 | 2.0E-35 | 5.9E-31 | 0.0E+00 |
| gamma-glutamyl hydrolase | GGH | A:03601 | NM_003878 | NP_003869 | 1.6 | -18092 | 1.6E-07 | 4.8E-03 | 5.7E-11 |
| inhibin beta A chain | INHBA | A:02189 | NM_002192 | NP_002183 | 2.1 | -21247 | 1.4E-30 | 4.3E-26 | 0.0E+00 |
| insulin-like growth factor binding protein 7 | IGFBP7 | A:03385 | NM_001553 | NP_001544 | 3.0 | -25854 | 5.4E-31 | 1.6E-26 | 0.0E+00 |
| kallikrein 10 | KLK10 | A:07907 | NM_002776 | NP_002767 | 2.3 | -17986.5 | 5.0E-10 | 1.5E-05 | 4.9E-06 |
| leucine proline-enriched proteoglycan 1 (leprecan 1) | LEPRE1 | A:04646 | NM_022356 | NP_071751 | 1.7 | -18019 | 8.2E-14 | 2.4E-09 | 1.1E-12 |
| lumican | LUM | A:09199 | NM_002345 | NP_002336 | 2.9 | -24927 | 4.2E-24 | 1.3E-19 | 0.0E+00 |
| lysyl oxidase-like 2 | LOXL2 | A:06085 | NM_002318 | NP_002309 | 1.6 | -16994.5 | 5.9E-10 | 1.7E-05 | 7.9E-10 |
| matrix metalloproteinase 2 | MMP2 | A:06749 | NM_004530 | P08253 | 1.8 | -18710 | 1.2E-11 | 3.6E-07 | 1.5E-10 |
| matrix metalloproteinase 12 | MMP12 | A:01762 | NM_002426 | NP_002417 | 2.1 | -20209.5 | 2.2E-12 | 6.6E-08 | 4.9E-11 |
| metalloproteinase inhibitor 1 | TIMP1 | A:08048 | NM_003254 | NP_003245 | 3.2 | -24177 | 7.5E-38 | 2.3E-33 | 0.0E+00 |
| n-acylsphingosine amidohydrolase | ASAH1 | A:10030 | NM_004315 | NP_004306 | 1.7 | -19636.5 | 9.6E-16 | 2.9E-11 | 0.0E+00 |
| olfactomedin | OLFM1 | B:3555 | NM_014279 | NP_055094 | 3.9 | -25782.5 | 6.5E-46 | 1.9E-41 | 0.0E+00 |
| osteopontin | SPP1 | A:09441 | NM_000582 | NP_000573 | 7.0 | -26668 | 4.0E-32 | 1.2E-27 | 0.0E+00 |
| human proprotein convertase subtilisin/kexin type 5 | PCSK5 | A:00704 | NM_006200 | Q92824 | 1.7 | -18736 | 2.0E-11 | 6.0E-07 | 7.3E-11 |
| group xiii secreted phospholipase a2 | PLA2G12b | B:1811 | NM_032562 | NP_115951 | 3.0 | -23212 | 7.92E-39 | 2.36E-34 | 0.00E+00 |
| secreted frizzled-related protein 2 | SFRP2 | B:1634 | XM_050625 | XP_050625 | 2.1 | -19217 | 2.75E-10 | 8.1E-06 | 4.1E-08 |
| secreted frizzled-related protein 4 | SFRP4 | A:07398 | NM_003014 | NP_003005 | 3.0 | -22153 | 6.0E-24 | 1.8E-19 | 0.0E+00 |
| serine (or cysteine) proteinase inhibitor clade H | SERPINH1 | A:08615 | NM_001235 | NP_001226 | 1.9 | -20252 | 2.8E-34 | 8.2E-30 | 0.0E+00 |
| human serine or cysteine proteinase inhibitor clade B | SERPINB5 | A:10485 | NM_002639 | P36952 | 1.5 | -17026 | 4.6E-06 | 1.4E-01 | 5.6E-06 |
| serine protease 11 (IGF binding) | PRSS11 | B:1274 | NM_002775 | NP_002766 | 1.6 | -17184.5 | 9.3E-18 | 2.8E-13 | 0.0E+00 |
| secreted protein, acidic, cysteine rich | SPARC | A:08092 | NM_003118 | NP_003109 | 2.5 | -22947.5 | 1.5E-44 | 4.6E-40 | 0.0E+00 |
| spondin 2 | SPON2 | B:2543 | NM_012445 | NP_036577 | 2.4 | -20390.5 | 2.9E-31 | 8.5E-27 | 0.0E+00 |
| stannin | SNN | A:09316 | NM_003498 | NP_003489 | 2.1 | -20162.5 | 3.25E-24 | 9.71E-20 | 0.00E+00 |
| thrombospondin 2 | THBS2 | B:9017 | NM_003247 | NP_003238 | 2.6 | -22095 | 5.8E-29 | 1.7E-24 | 0.0E+00 |
| thrombospondin repeat containing 1 | TSRC1 | B:7686 | NM_019032 | NP_061905 | 2.6 | -22608 | 1.3E-45 | 4.1E-41 | 0.0E+00 |
| thyroglobulin | TG | B:5402 | NM_003235 | NP_003226 | 2.4 | -23644 | 4.3E-36 | 1.3E-31 | 0.0E+00 |
| transforming growth factor β-induced | TGFBI | A:08124 | NM_000358 | NP_000349 | 2.5 | -23339.5 | 1.96E-24 | 9.71E-20 | 0.0E+00 |
| transforming growth factor β1 | TGFB1 | A:07050 | NM_000660 | P01137 | 1.6 | -17214 | 2.30E-18 | 6.86E-14 | 0.0E+00 |
| hyaluronan and proteoglycan link protein 4 | HAPLN4 | C:6300 | NM_023002 | NP_075378 | 3.4 | -23516.5 | 7.32E-44 | 2.2E-39 | 0.0E+00 |

Figure 2

Quantitative RT-PCR - Quantification of Expression of Selected Gastric Cancer Candidate Genes

| name | symbol | median T:N fold change | Maximum T:N fold change | % T >95th percentile [1] |
|---|---|---|---|---|
| adican | ASPN | 5 | 37 | 74 |
| asporin (lrr class 1) | CSPG2 | 12 | 73 | 91 |
| chondroitin sulfate proteoglycan 2 (versican) | CST1, 2, 4 | 6 | 24 | 78 |
| cystatins SN, SA & S | EFEMP2 | 525 | 25532 | 100 |
| egf-containing fibulin-like extracellular matrix protein 2 | GGH | 3 | 15 | 56 |
| gamma-glutamyl hydrolase | INHBA | 5 | 36 | 67 |
| inhibin beta A chain | IGFBP7 | 34 | 357 | 98 |
| insulin-like growth factor binding protein 7 | KLK10 | 4 | 19 | 80 |
| kallikrein 10 | LEPRE1 | 5 | 633 | 70 |
| leucine proline-enriched proteoglycan 1(leprecan 1) | LUM | 4 | 17 | 72 |
| lumican | LOXL2 | 5 | 47 | 80 |
| lysyl oxidase-like 2 | MMP12 | 6 | 26 | 93 |
| matrix metalloproteinase 12 | TIMP1 | 9 | 586 | 67 |
| metalloproteinase inhibitor 1 | ASAH1 | 8 | 19 | 91 |
| n-acylsphingosine amidohydrolase | SPP1 | 3 | 7 | 63 |
| osteopontin | SFRP2 | 40 | 481 | 96 |
| secreted frizzled-related protein 2 | SFRP4 | 5 | 85 | 63 |
| secreted frizzled-related protein 4 | SPARC | 56 | 600 | 100 |
| secreted protein, acidic, cysteine rich | PRSS11 | 9 | 56 | 93 |
| serine protease 11 (IGF binding) | THBS2 | 4 | 25 | 54 |
| thrombospondin 2 | TG | 25 | 239 | 91 |
| thyroglobulin | TGFBI | 5 | 153 | 54 |
| transforming growth factor B-induced | | 7 | 204 | 82 |

[1] percentage of tumors with expression levels greater than the 95th percentile of non-malignant samples.

Figure 3

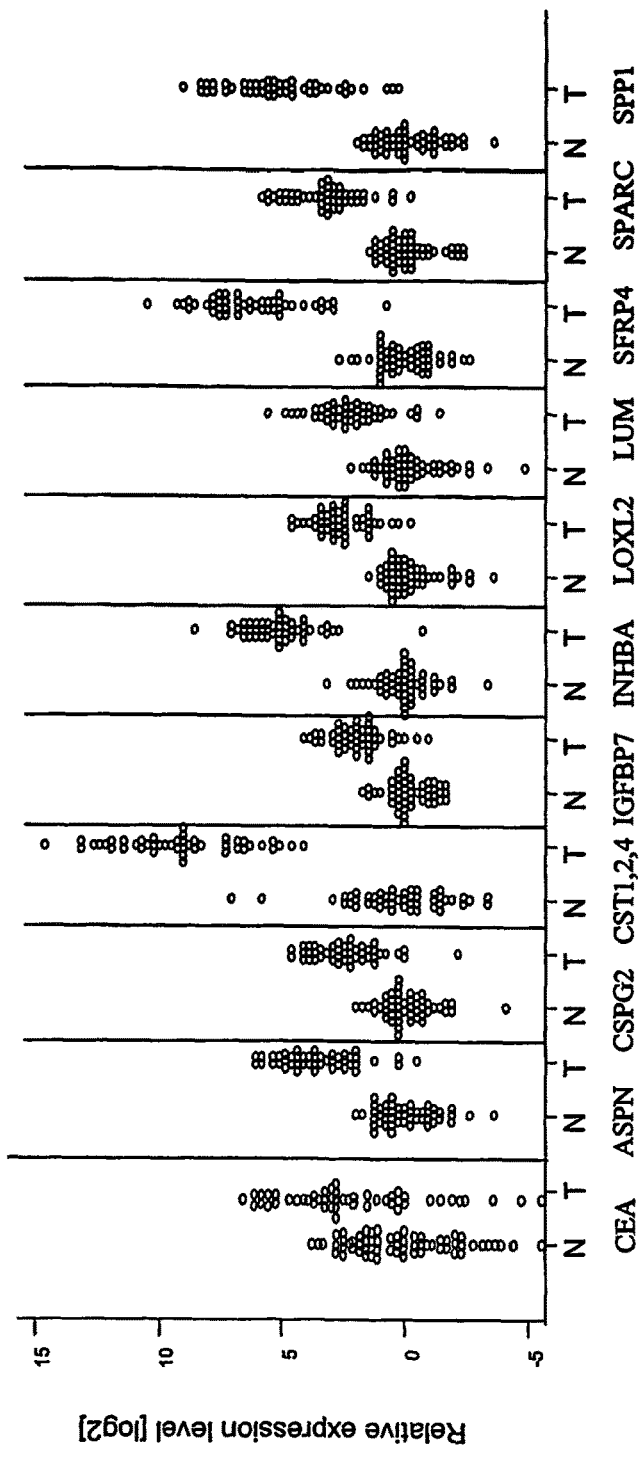
Fig.7a Relative expression of markers in tumor and normal samples compared to CEA

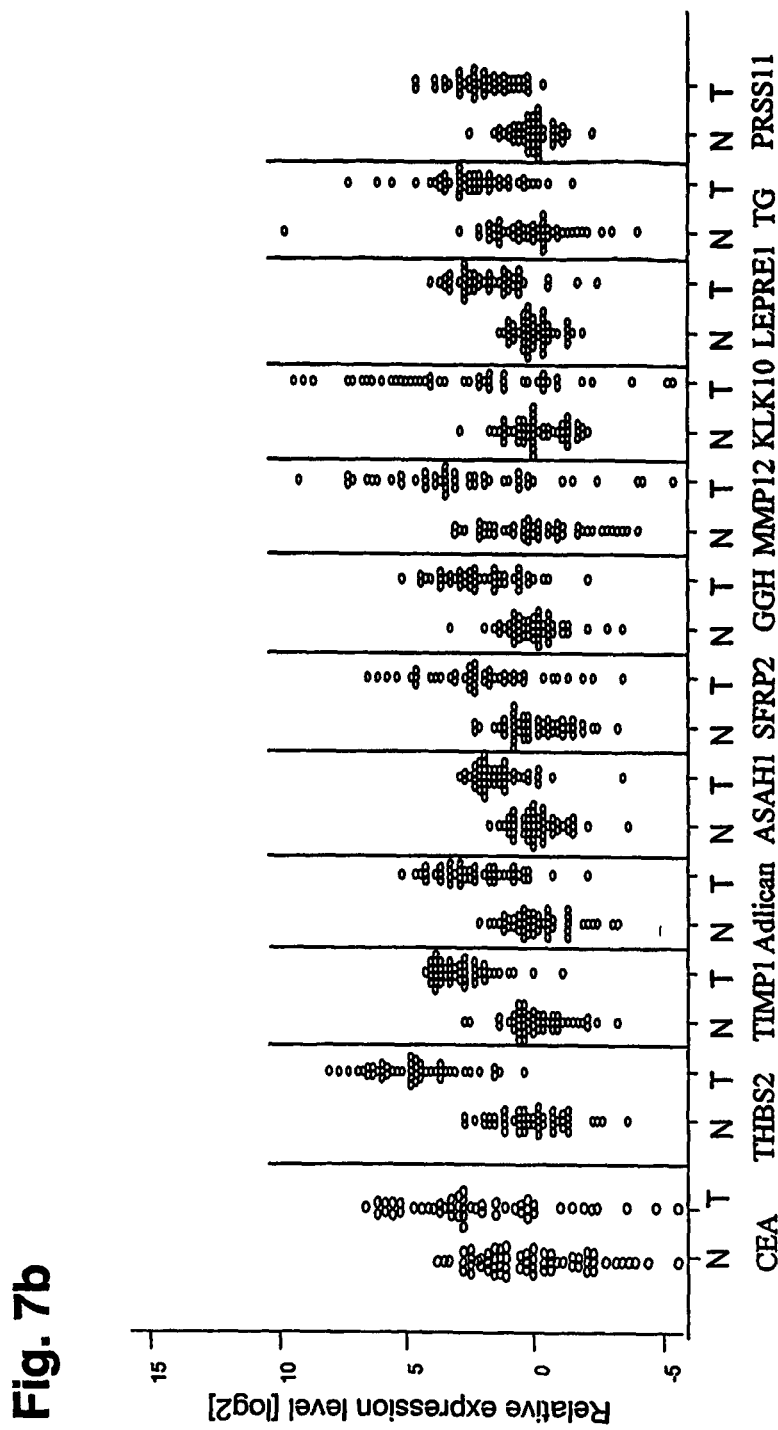

Fig. 8. Quantitative RT-PCR: expression in paired tumor and non-malignant samples of selected gastric cancer markers

| name | symbol | median T:N fold change | maximum T:N fold change | % tumor samples with expression >paired non-malignant sample |
|---|---|---|---|---|
| adican | ASPN | 5 | 146 | 88 |
| asporin (lrr class 1) | CSPG2 | 11 | 198 | 100 |
| chondroitin sulfate proteoglycan 2 (versican) | CST1, 2, 4 | 498 | 11911 | 100 |
| cystatins SN, SA & S | EFEMP2 | 3 | 17 | 93 |
| egf-containing fibulin-like extracellular matrix protein 2 | GGH | 4 | 34 | 83 |
| gamma-glutamyl hydrolase | INHBA | 27 | 630 | 95 |
| inhibin beta A chain | IGFBP7 | 5 | 38 | 93 |
| insulin-like growth factor binding protein 7 | KLK10 | 7 | 519 | 78 |
| kallikrein 10 | LEPRE1 | 4 | 23 | 85 |
| leucine proline-enriched proteoglycan 1 (leprecan 1) | LUM | 5 | 68 | 90 |
| lumican | LOXL2 | 7 | 53 | 95 |
| lysyl oxidase-like 2 | MMP12 | 9 | 468 | 85 |
| matrix metalloproteinase 12 | TIMP1 | 6 | 103 | 95 |
| metalloproteinase inhibitor 1 | ASAH1 | 3 | 15 | 88 |
| n-acylsphingosine amidohydrolase | SPP1 | 36 | 626 | 98 |
| osteopontin | SFRP2 | 5 | 48 | 83 |
| secreted frizzled-related protein 2 | SFRP4 | 54 | 375 | 100 |
| secreted frizzled-related protein 4 | SPARC | 10 | 66 | 95 |
| secreted protein, acidic, cysteine rich | PRSS11 | 4 | 63 | 90 |
| serine protease 11 (IGF binding) | THBS2 | 23 | 452 | 98 |
| thrombospondin 2 | TG | 4 | 174 | 93 |
| thyroglobulin | TGFBI | 5 | 78 | 95 |
| transforming growth factor B-induced | CGR11 | 3 | 33 | 75 |
| cell growth regulatory factor with EF-hand domain | SERPINH1 | 10 | 51 | 98 |
| serine (or cysteine) proteinase inhibitor H1 | MMP2 | 2 | 46 | 83 |
| matrix metalloproteinase 12 | PCSK5 | 2 | 63 | 80 |
| proprotein convertase subtilisin/kexin type 5 | SERPINB5 | 5 | 861 | 73 |
| serine (or cysteine) proteinase inhibitor B5 | TGFB1 | 3 | 16 | 88 |
| transforming growth factor β1 | | | | |
| carcinoembryonic antigen (CEA) | CEACAM5 | 3 | 177 | 68 |

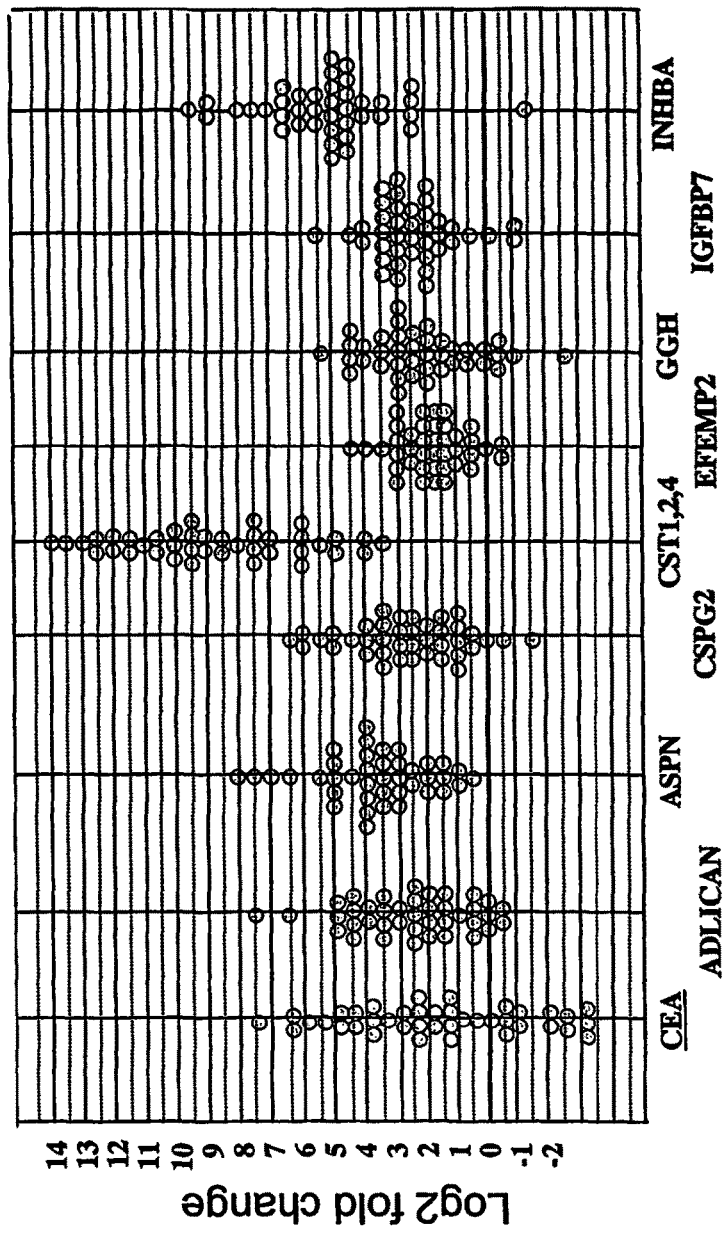
Fig. 9a Relative tumor:normal fold changes in paired tumor/normal gastric samples

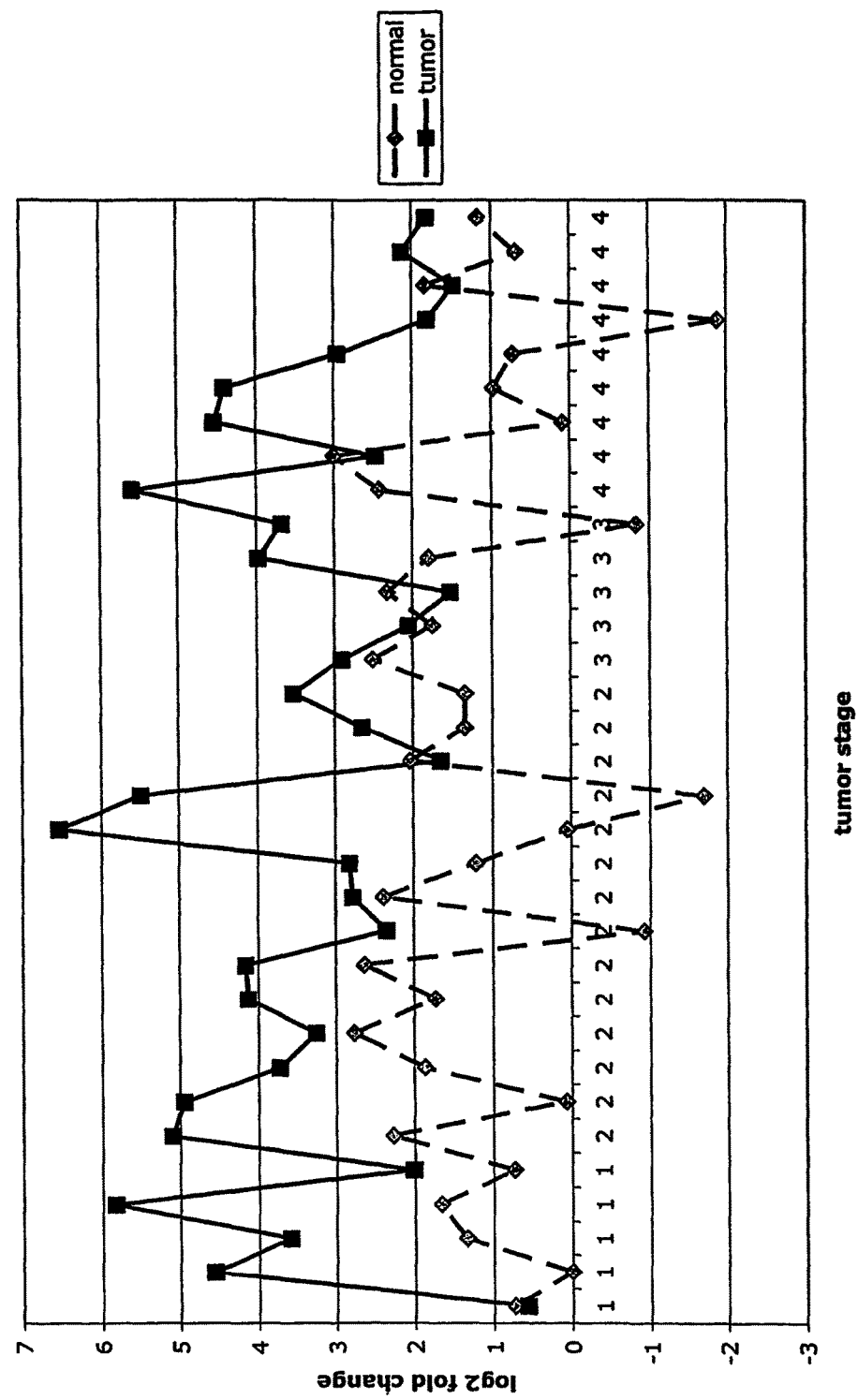

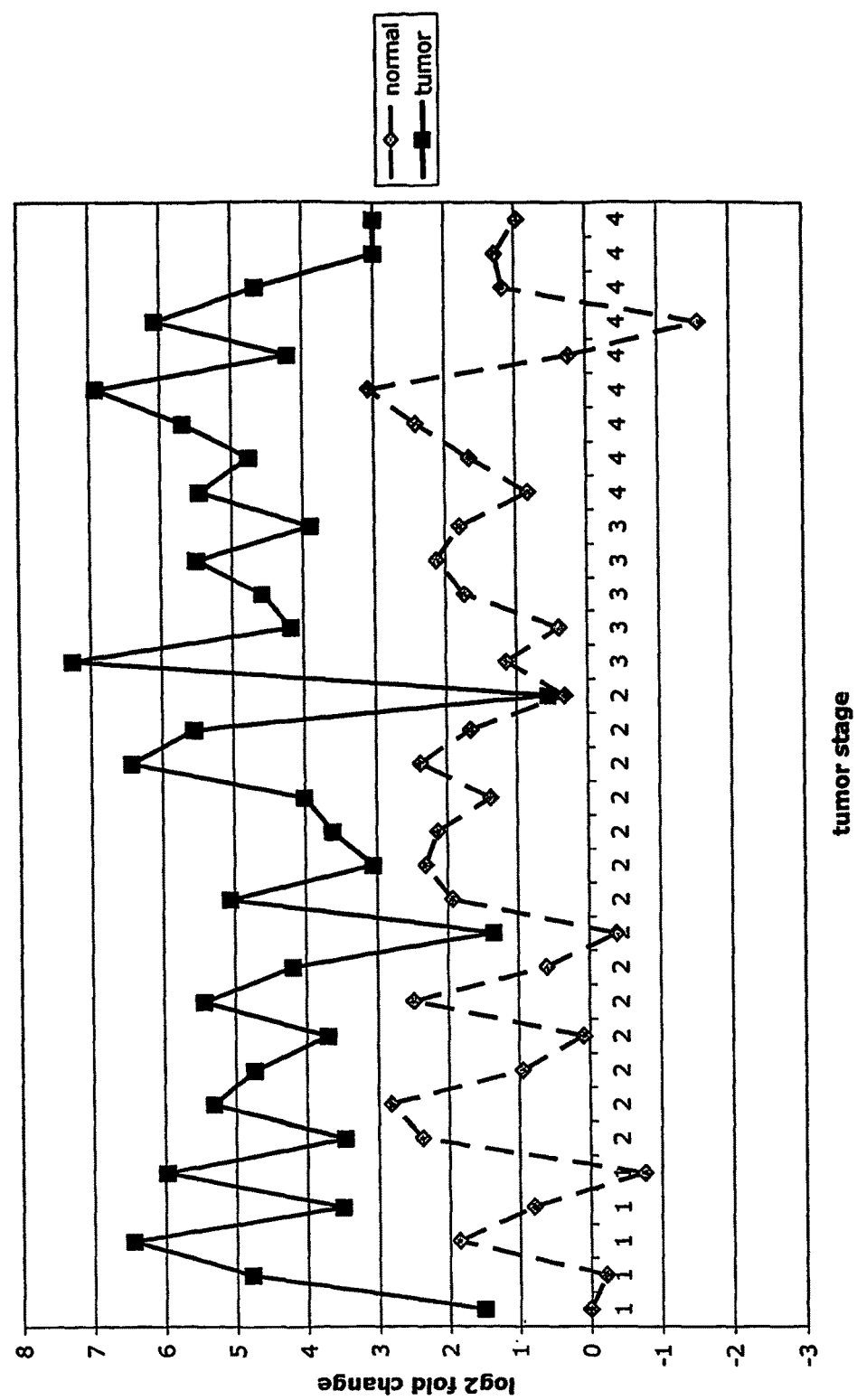

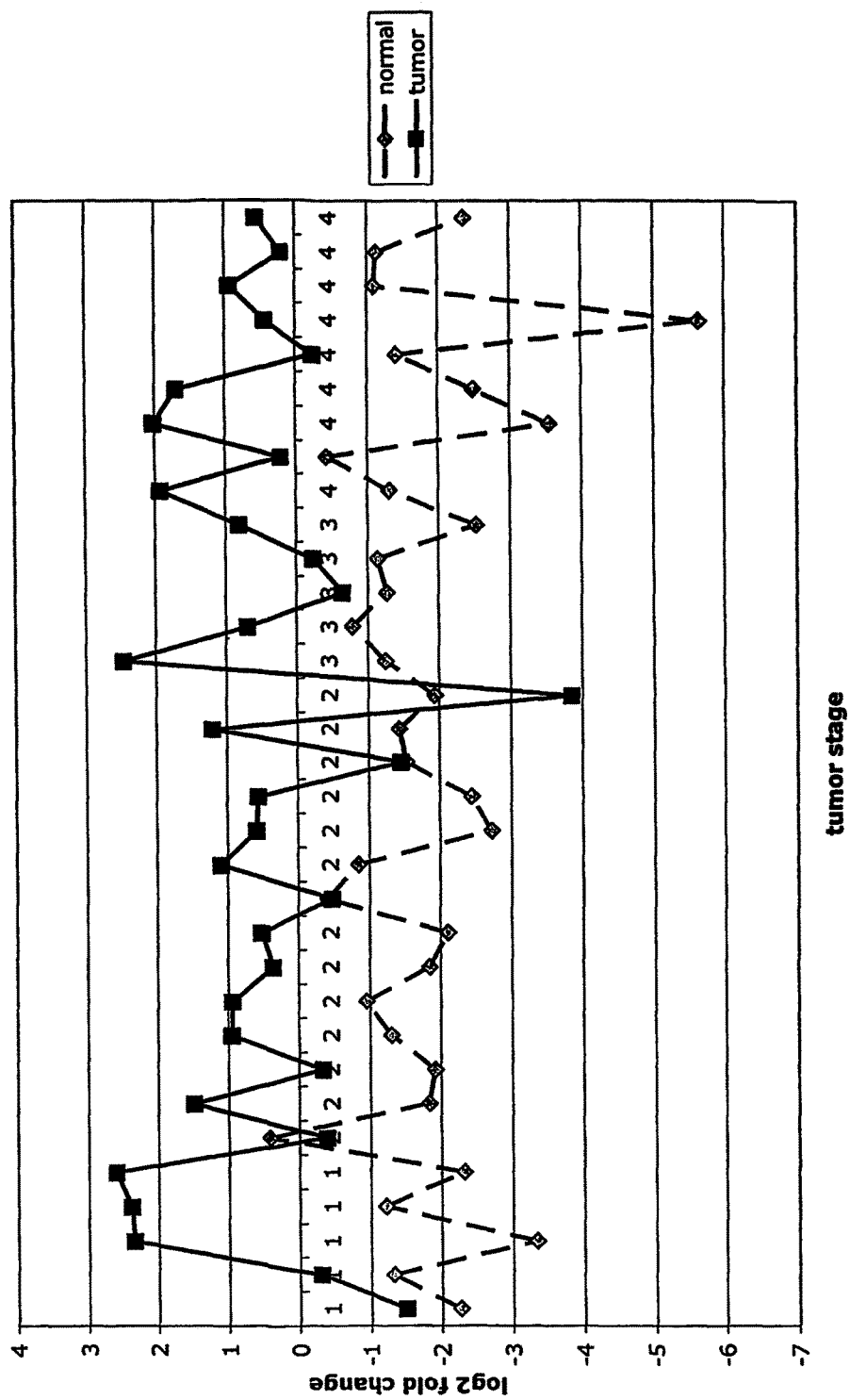

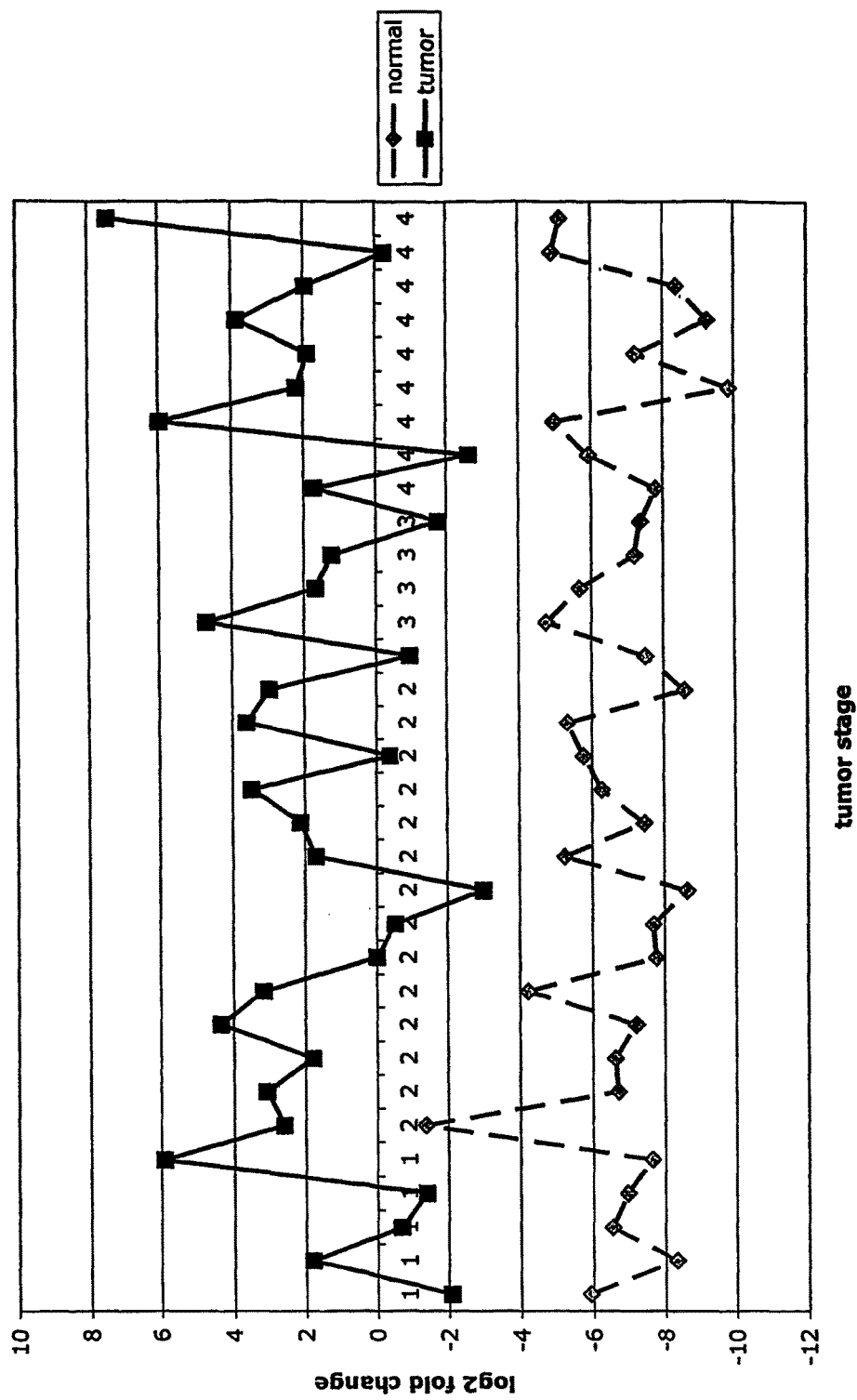

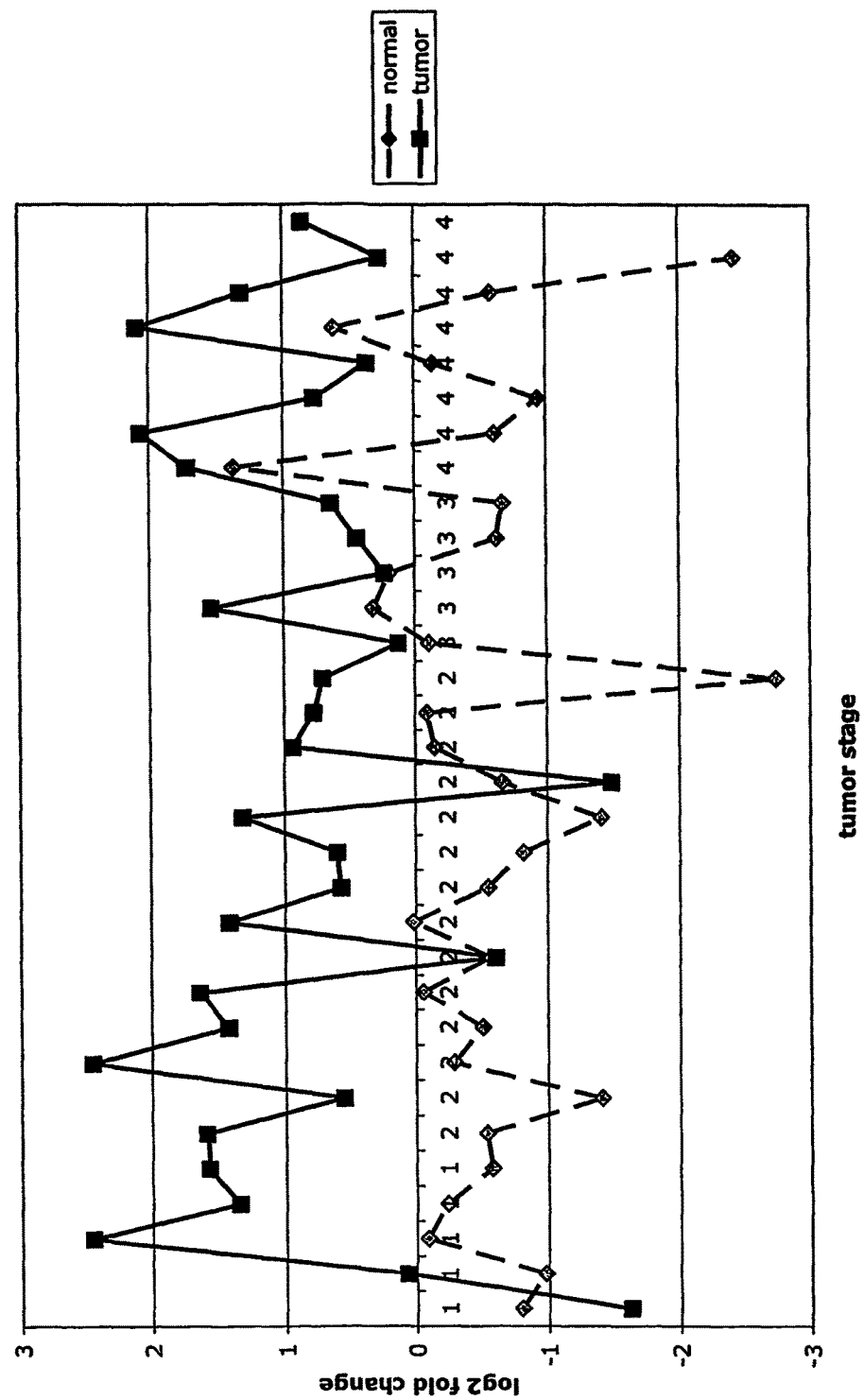
Fig. 10e EFEMP2

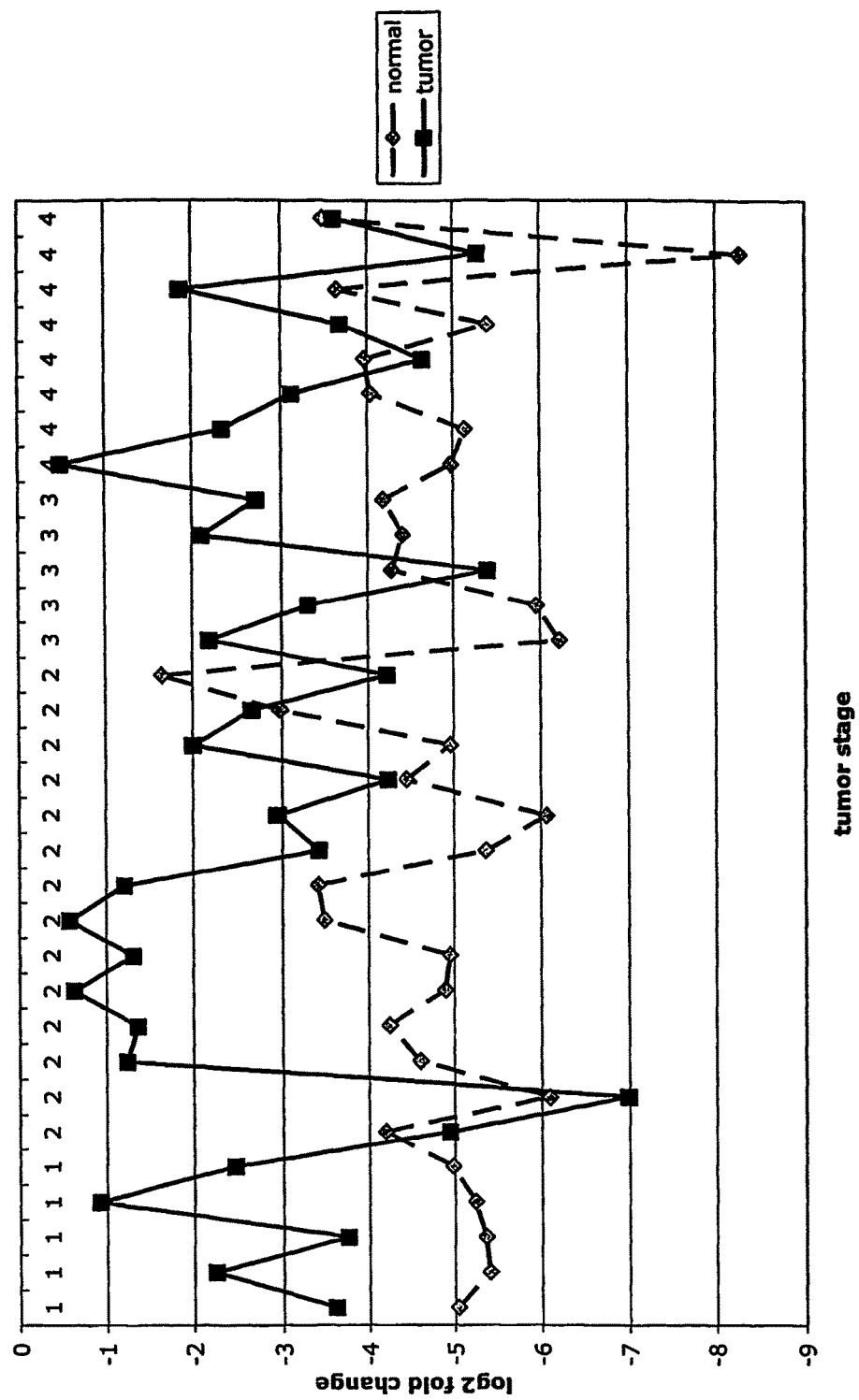
Fig. 10f GGH

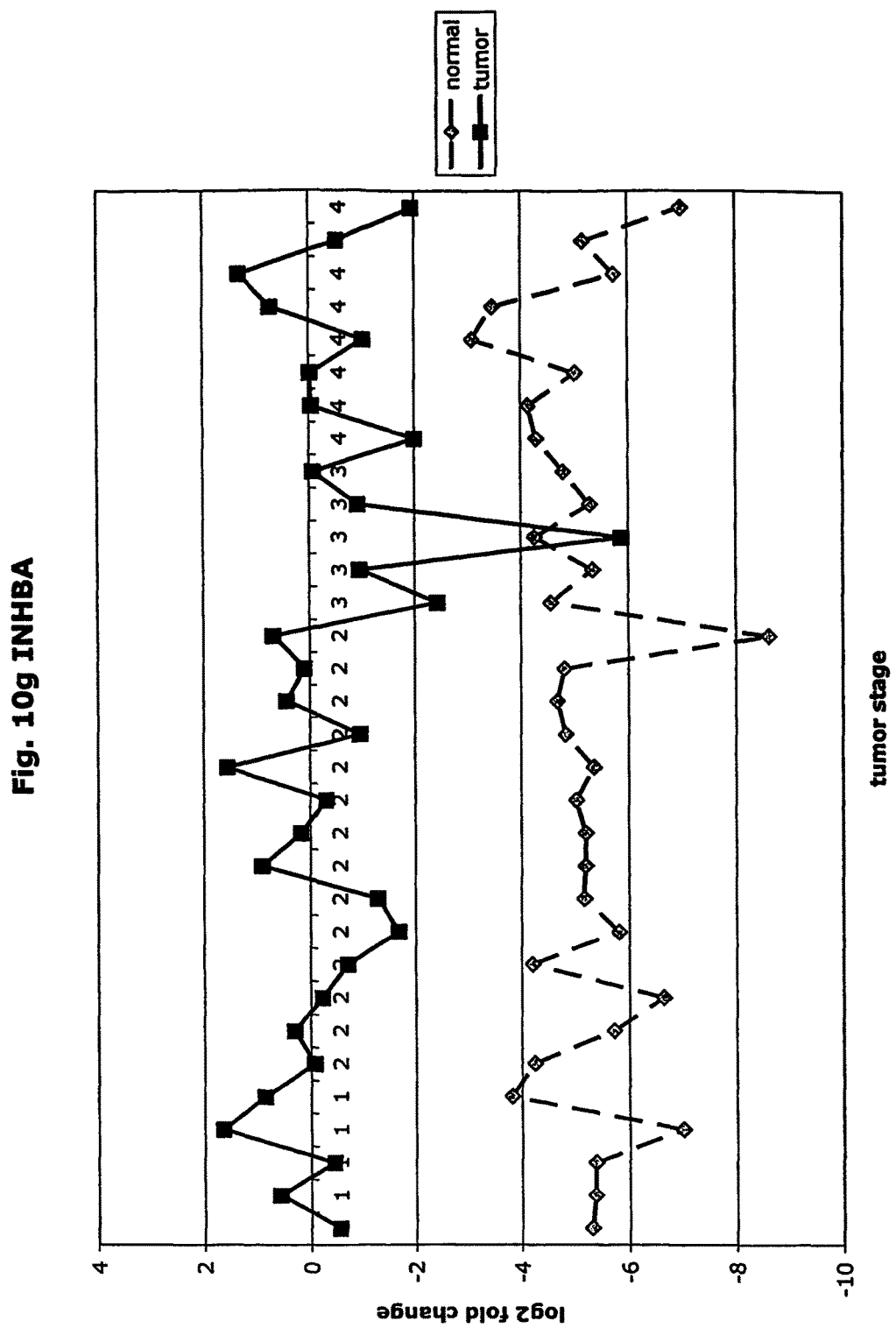

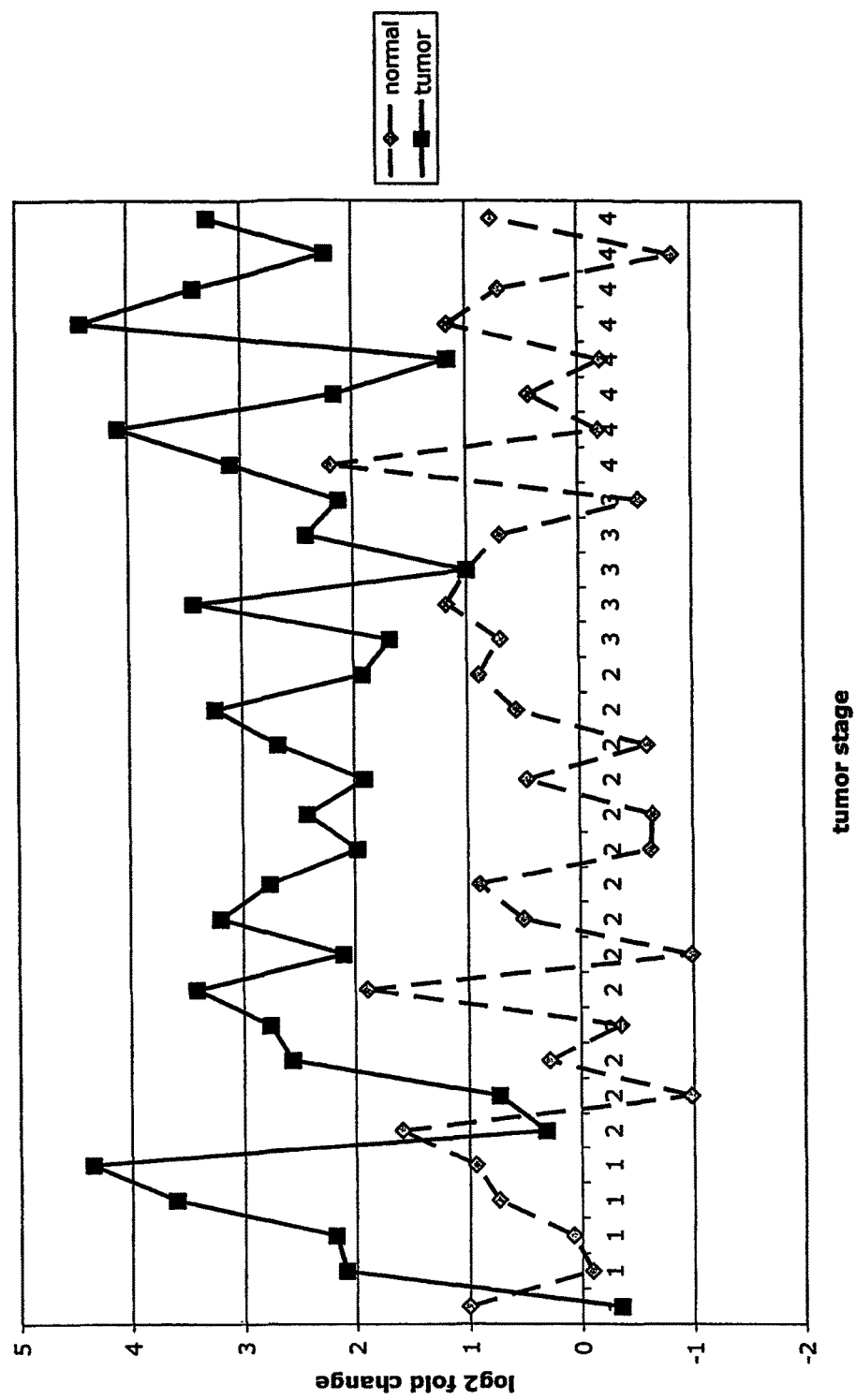

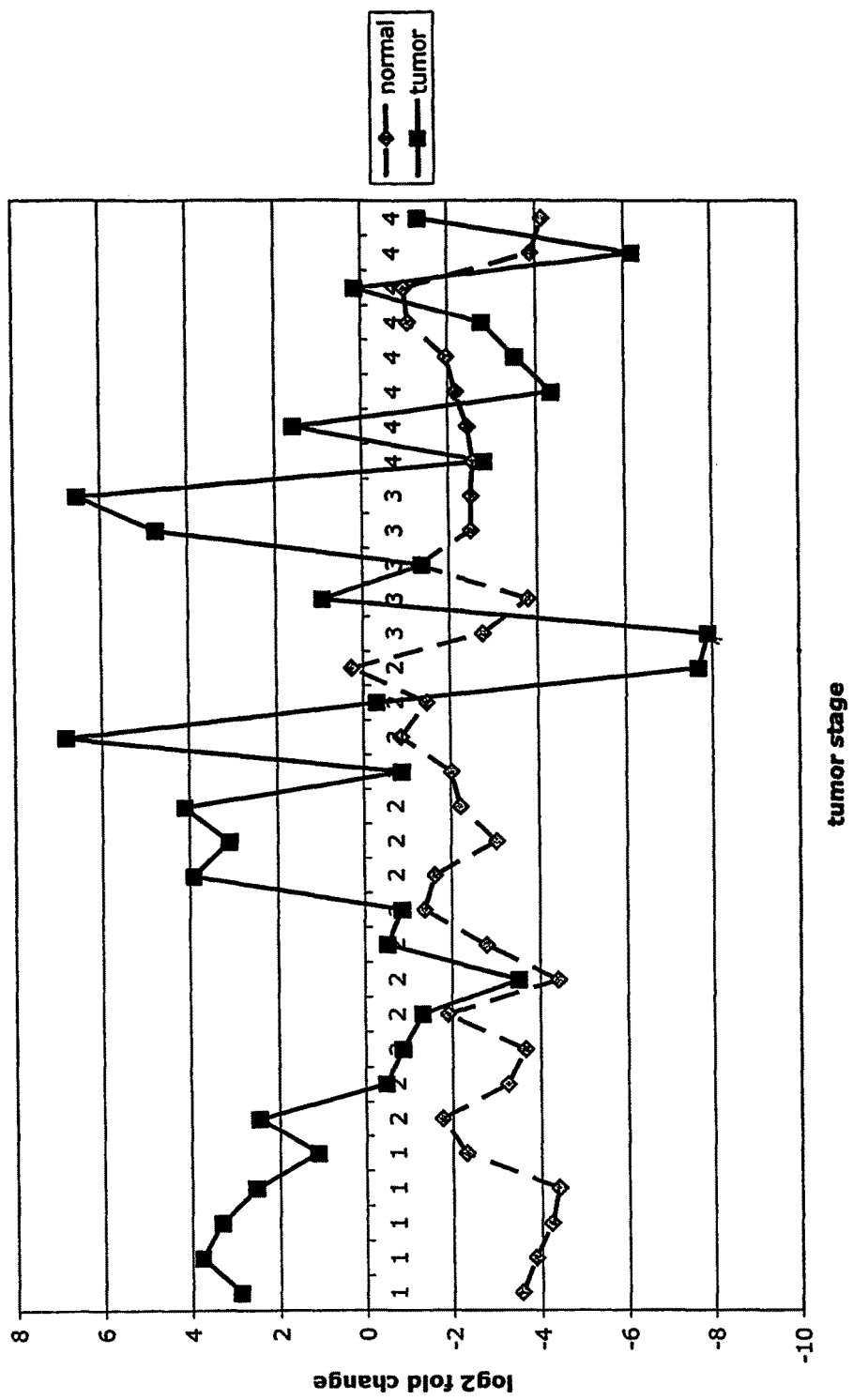

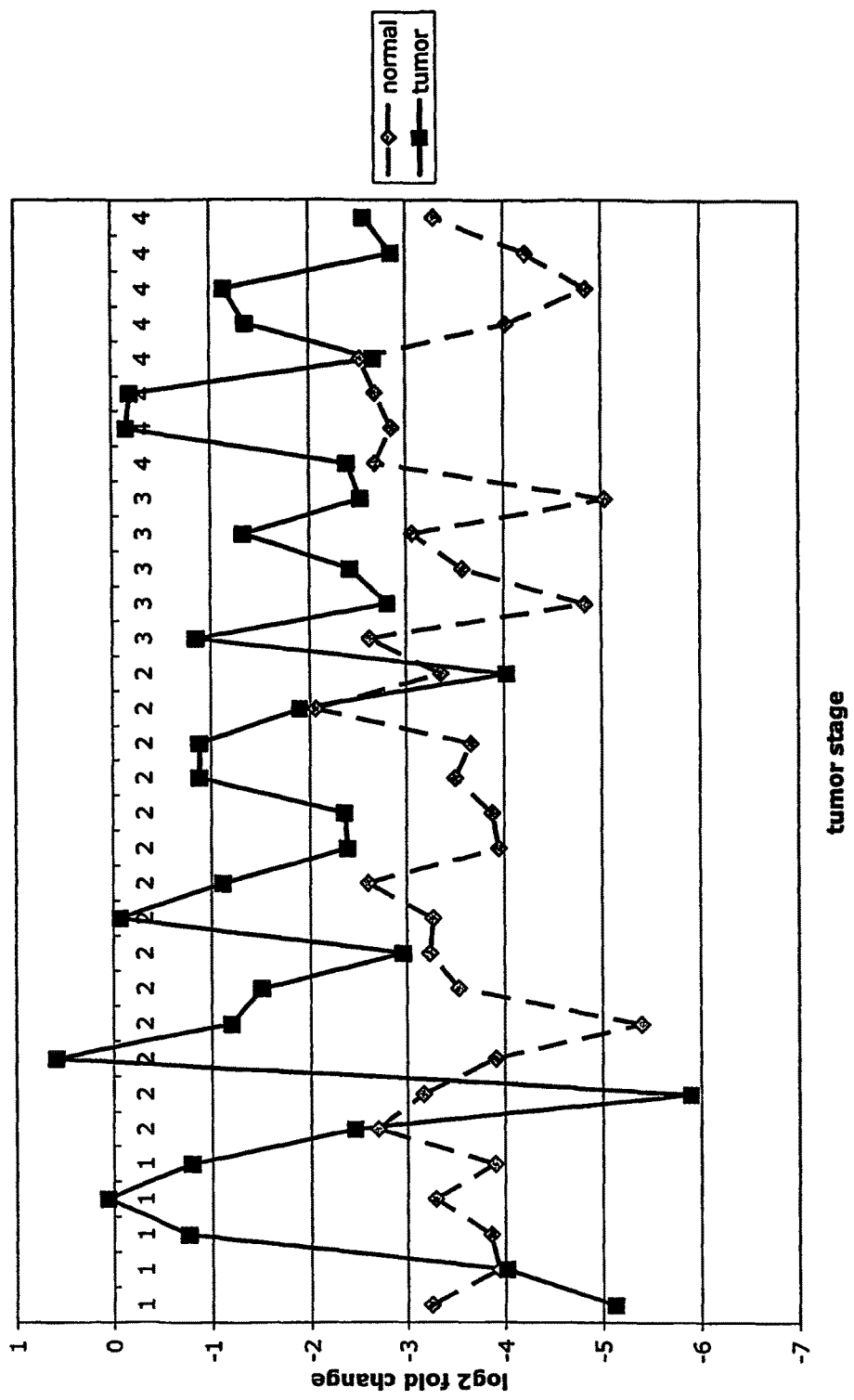

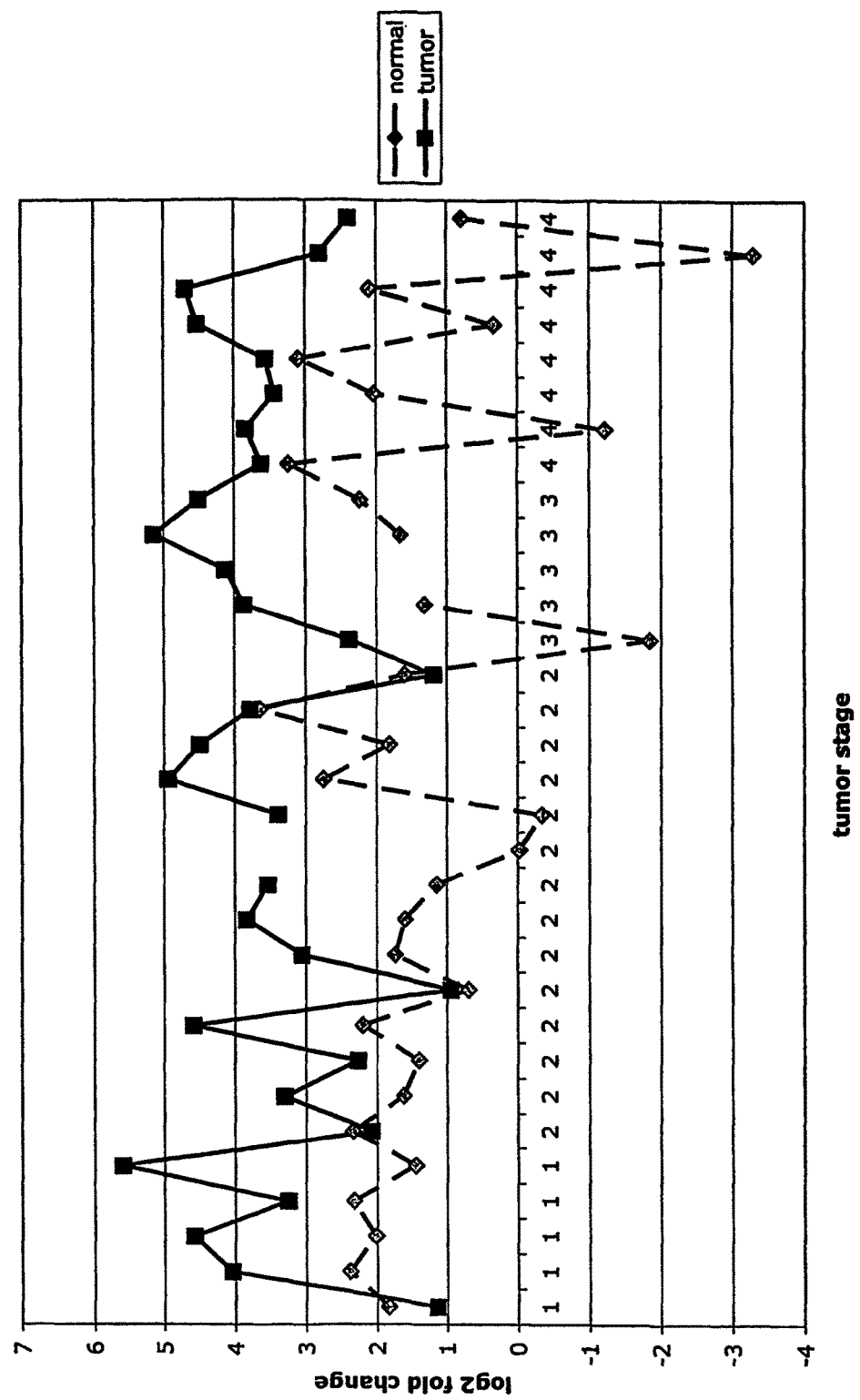

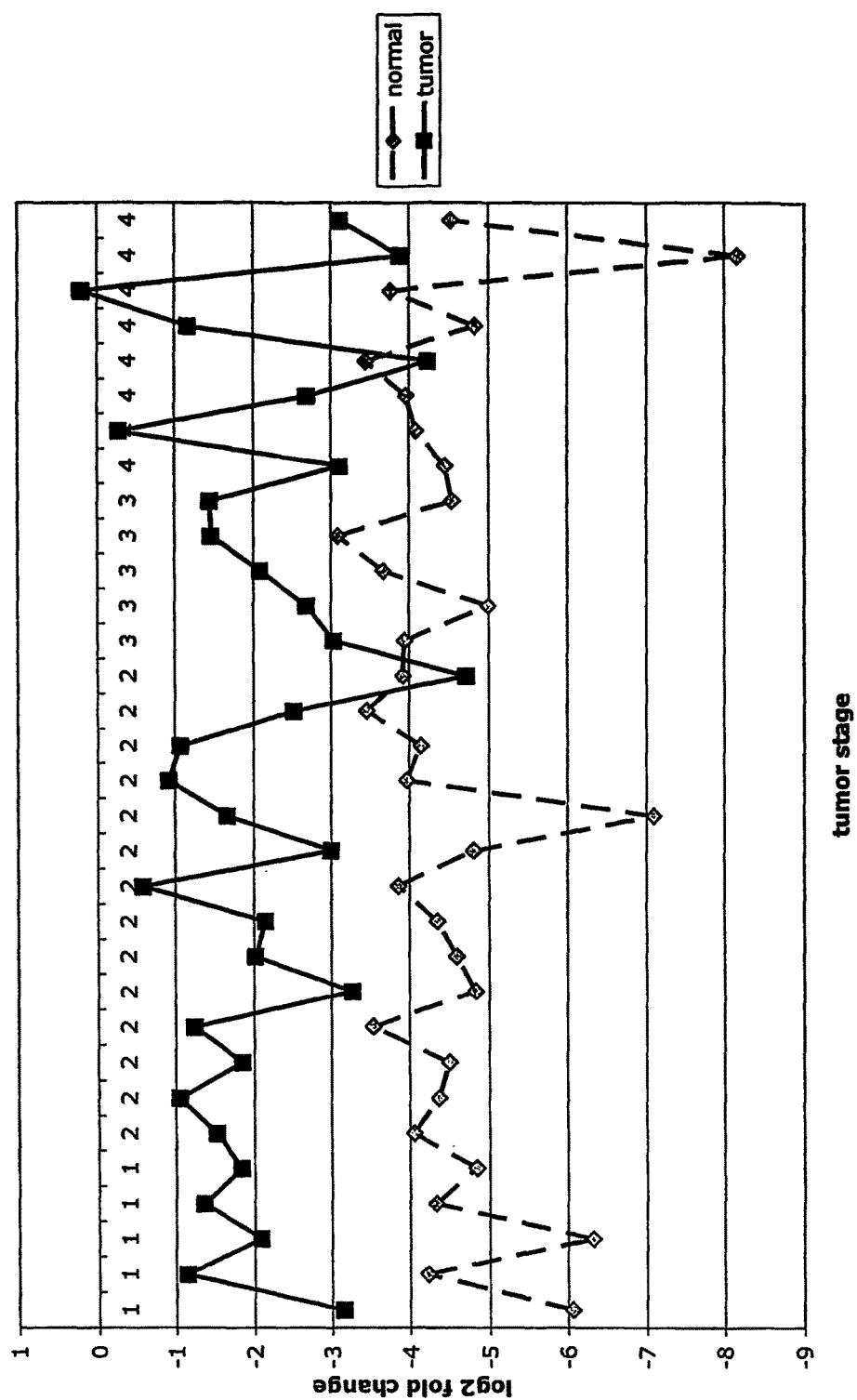

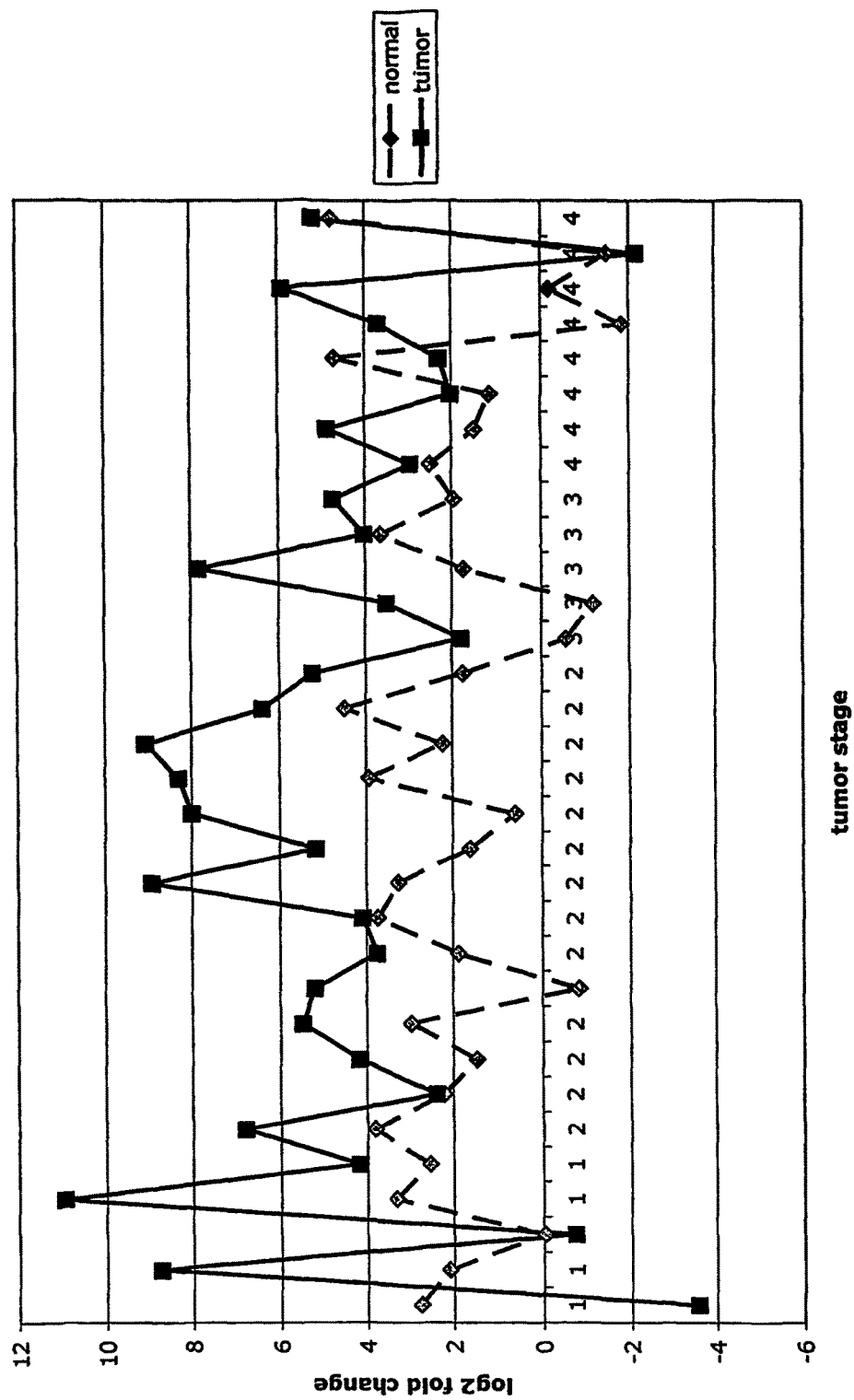

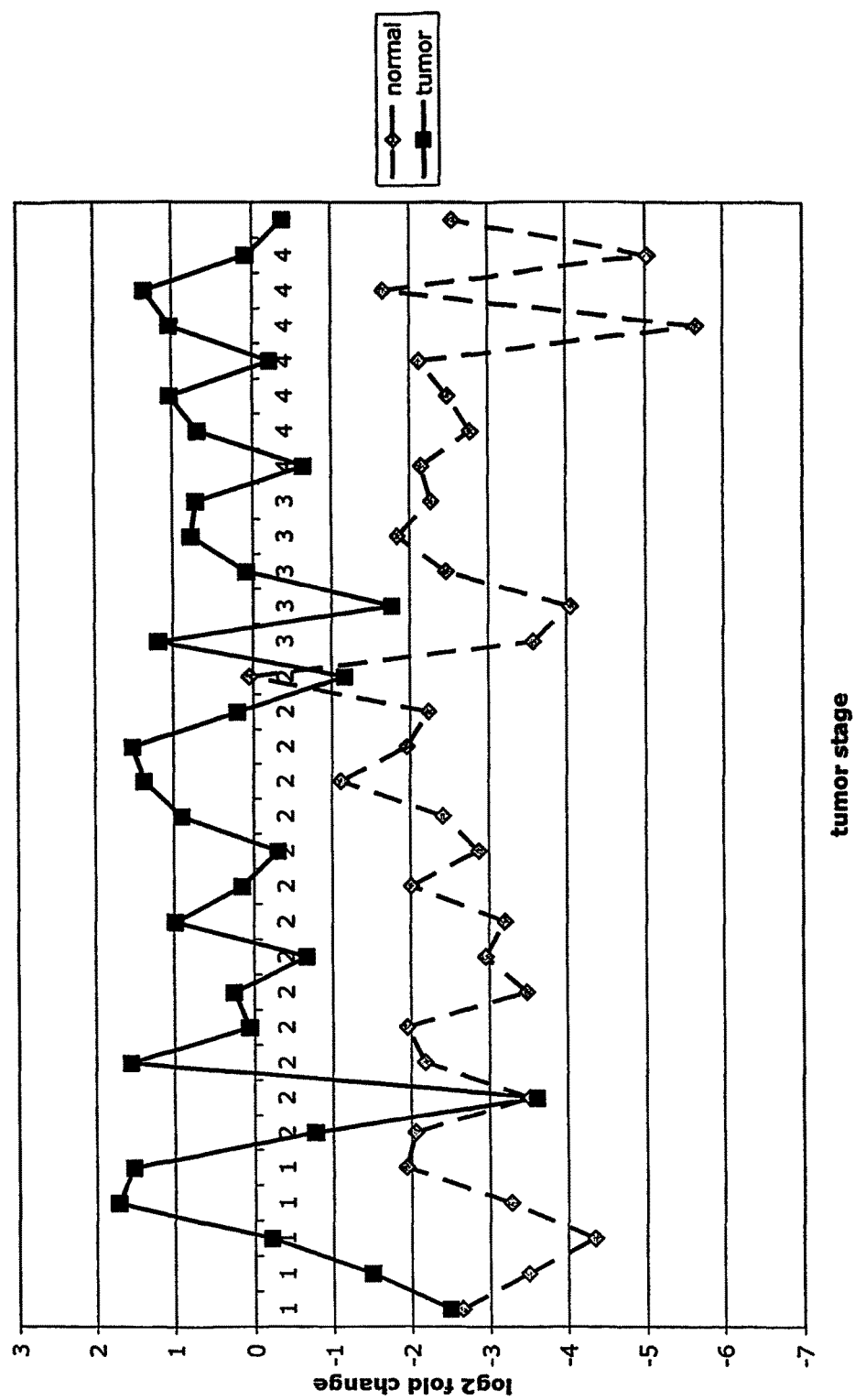

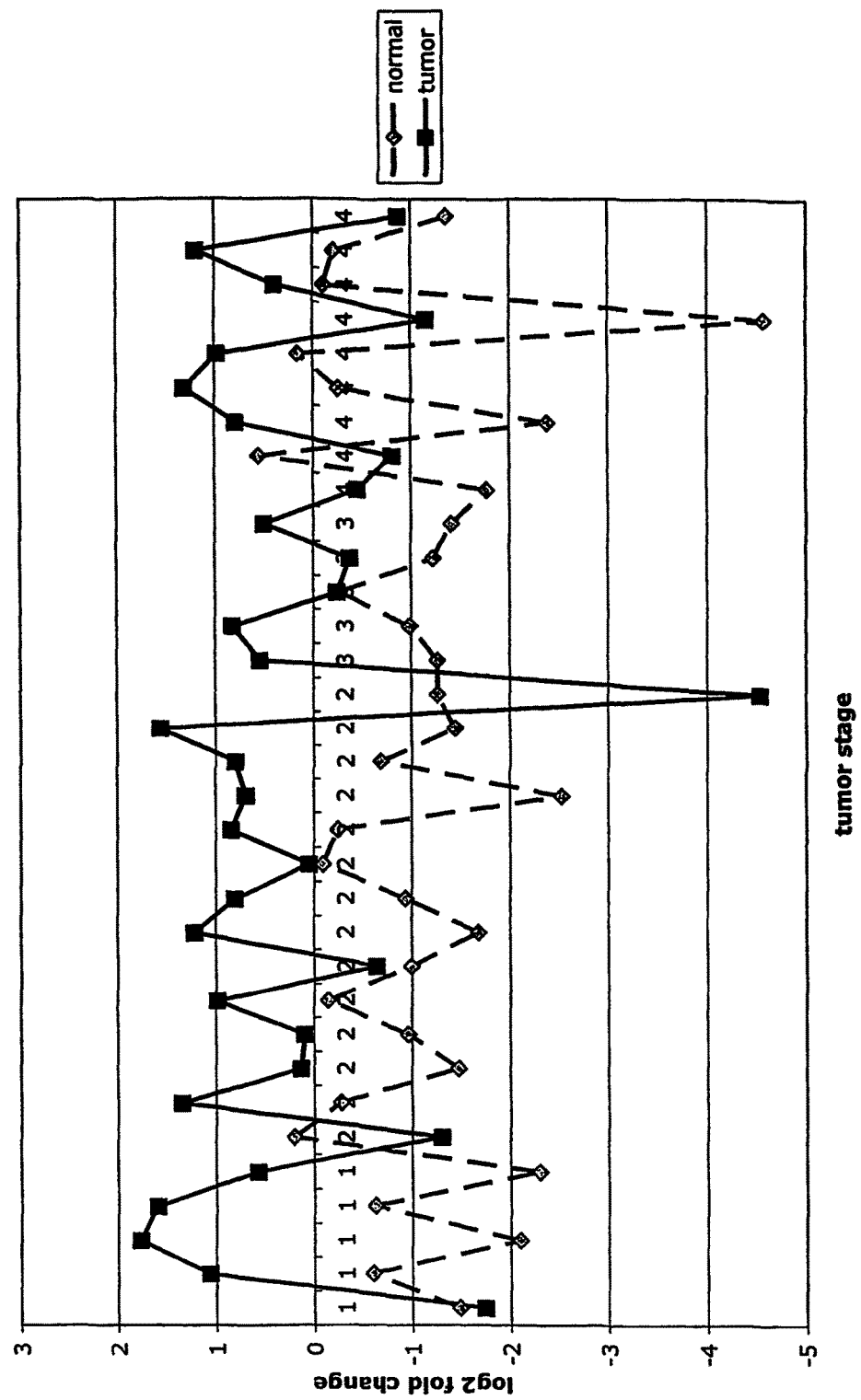

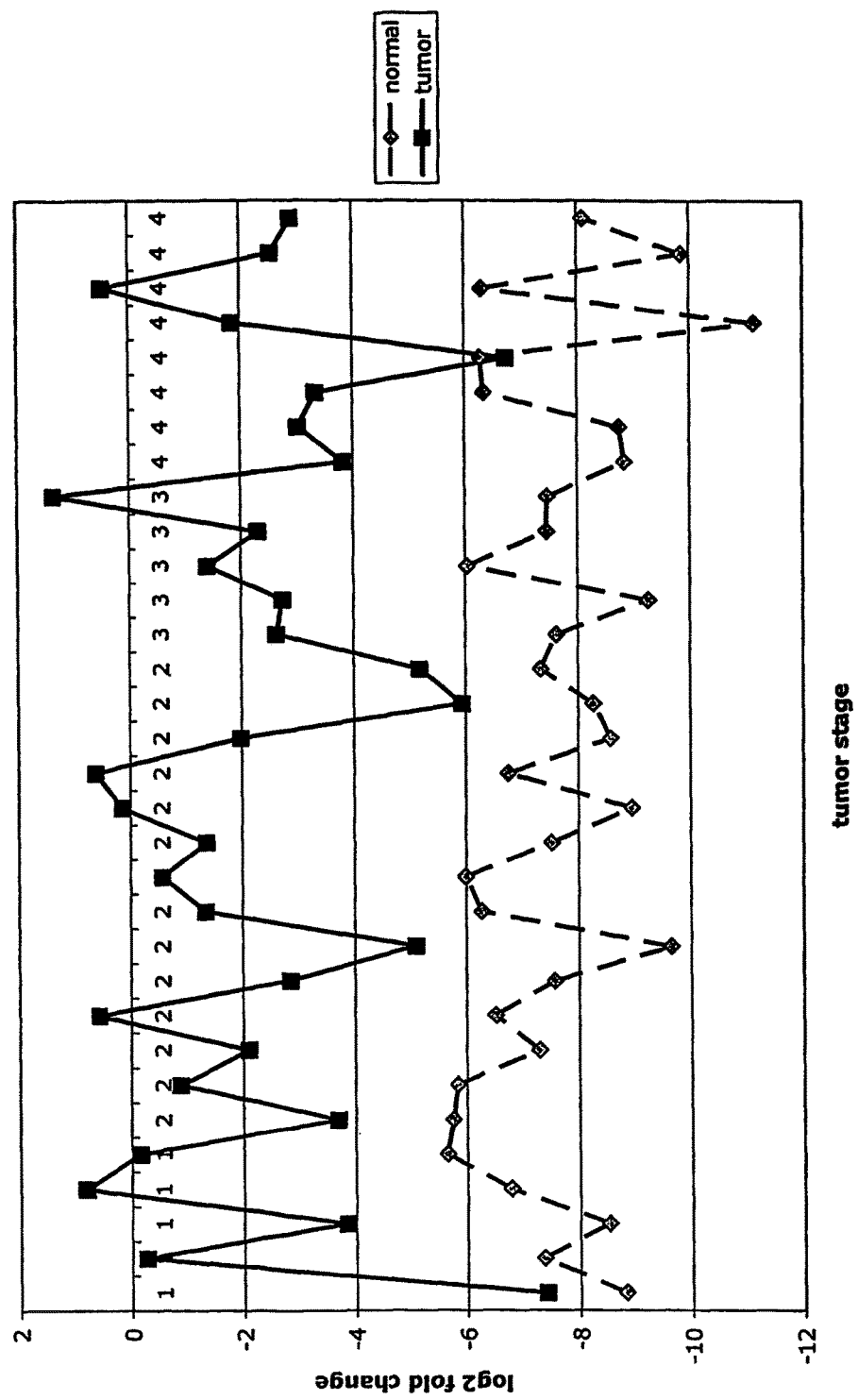

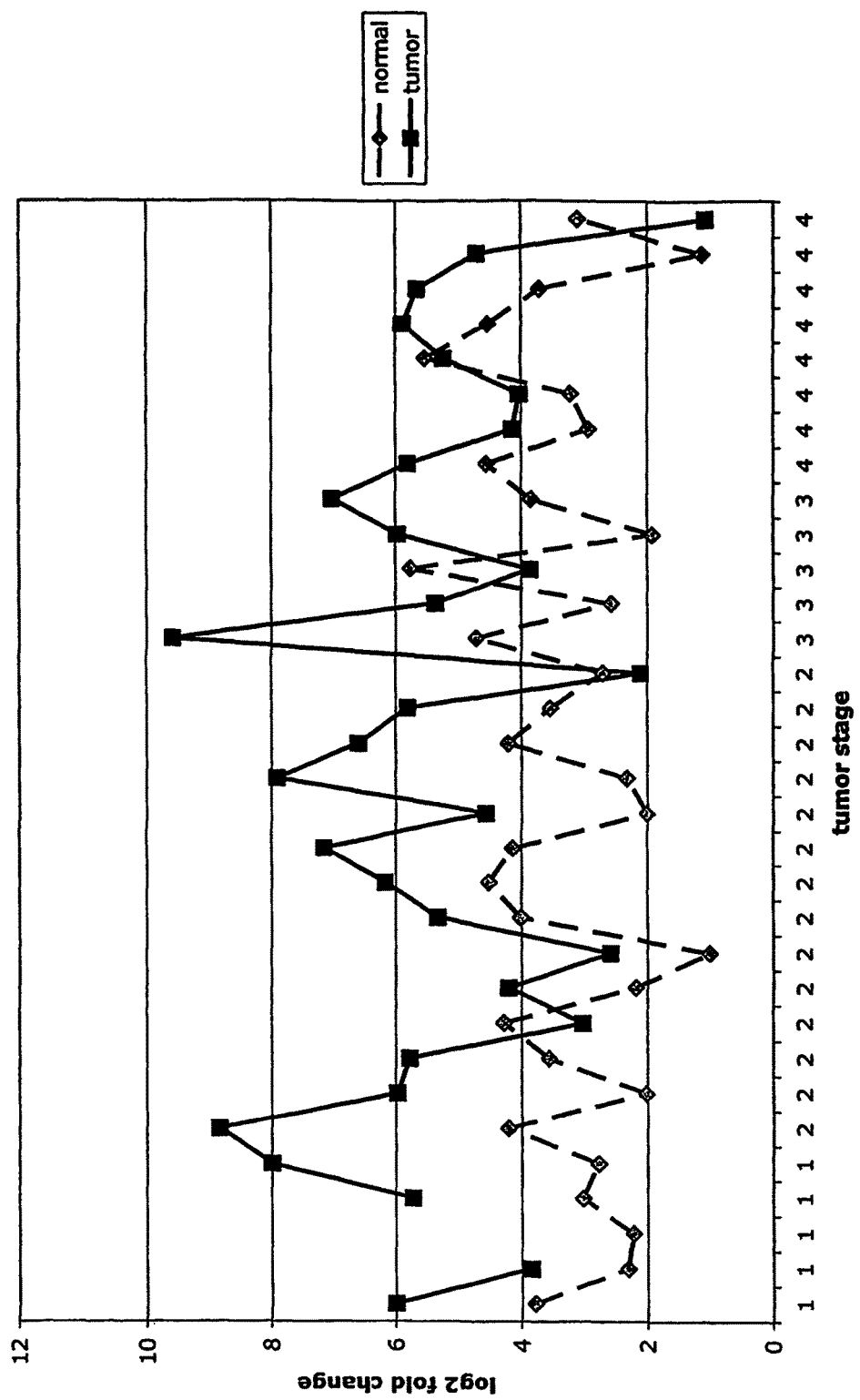
Fig. 10q SFRP2

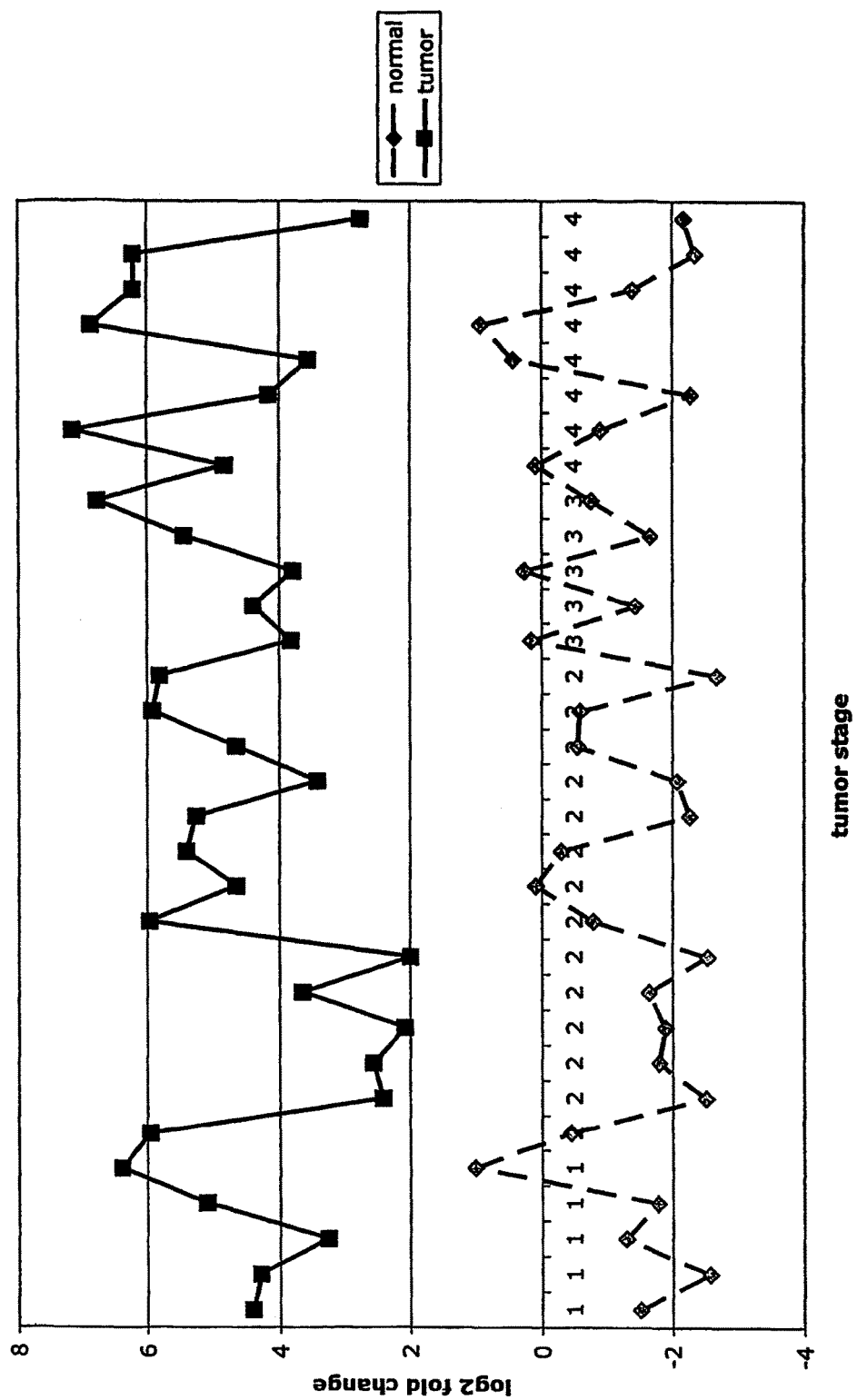
Fig. 10r SFRP4

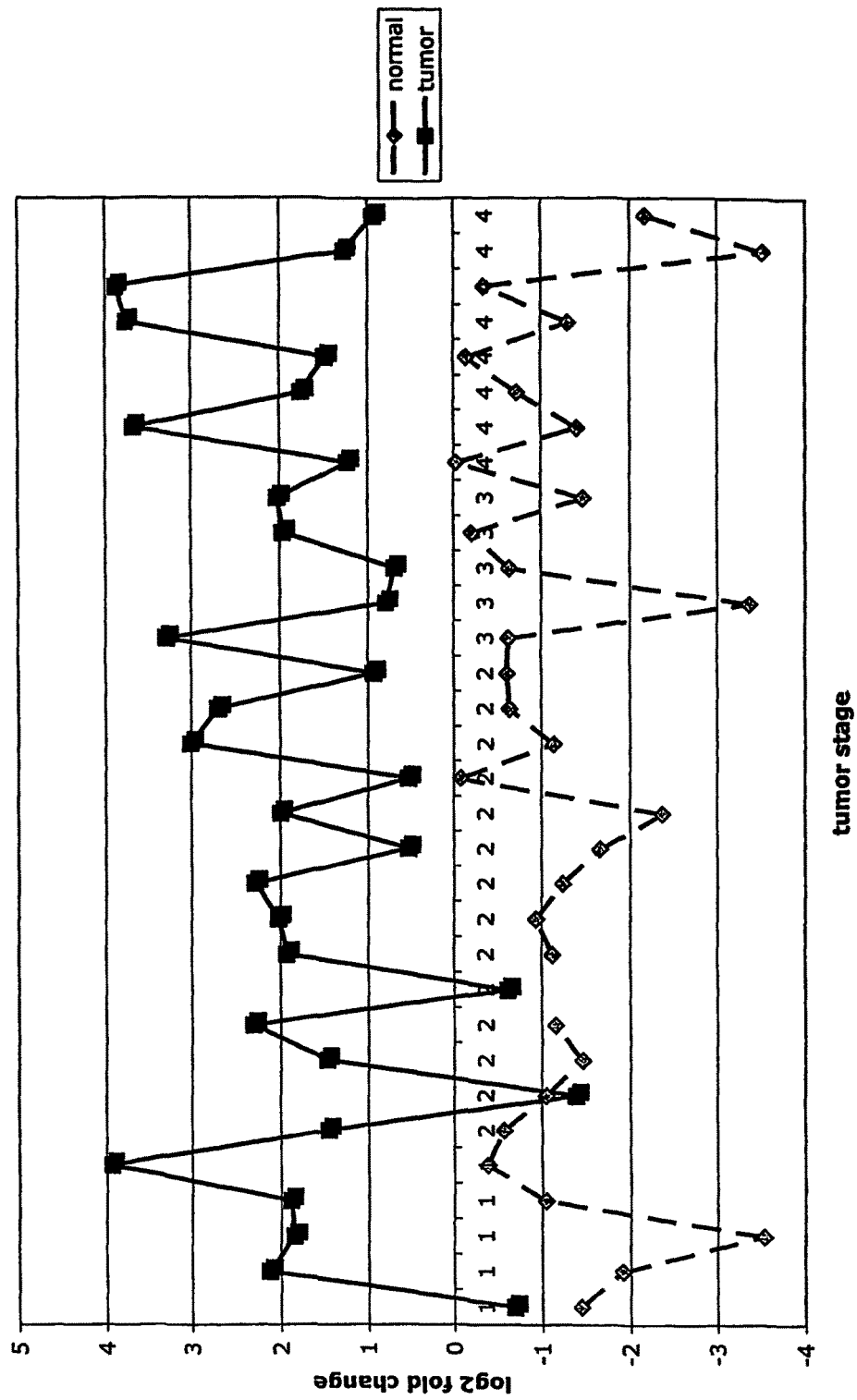
Fig. 10s SPARC

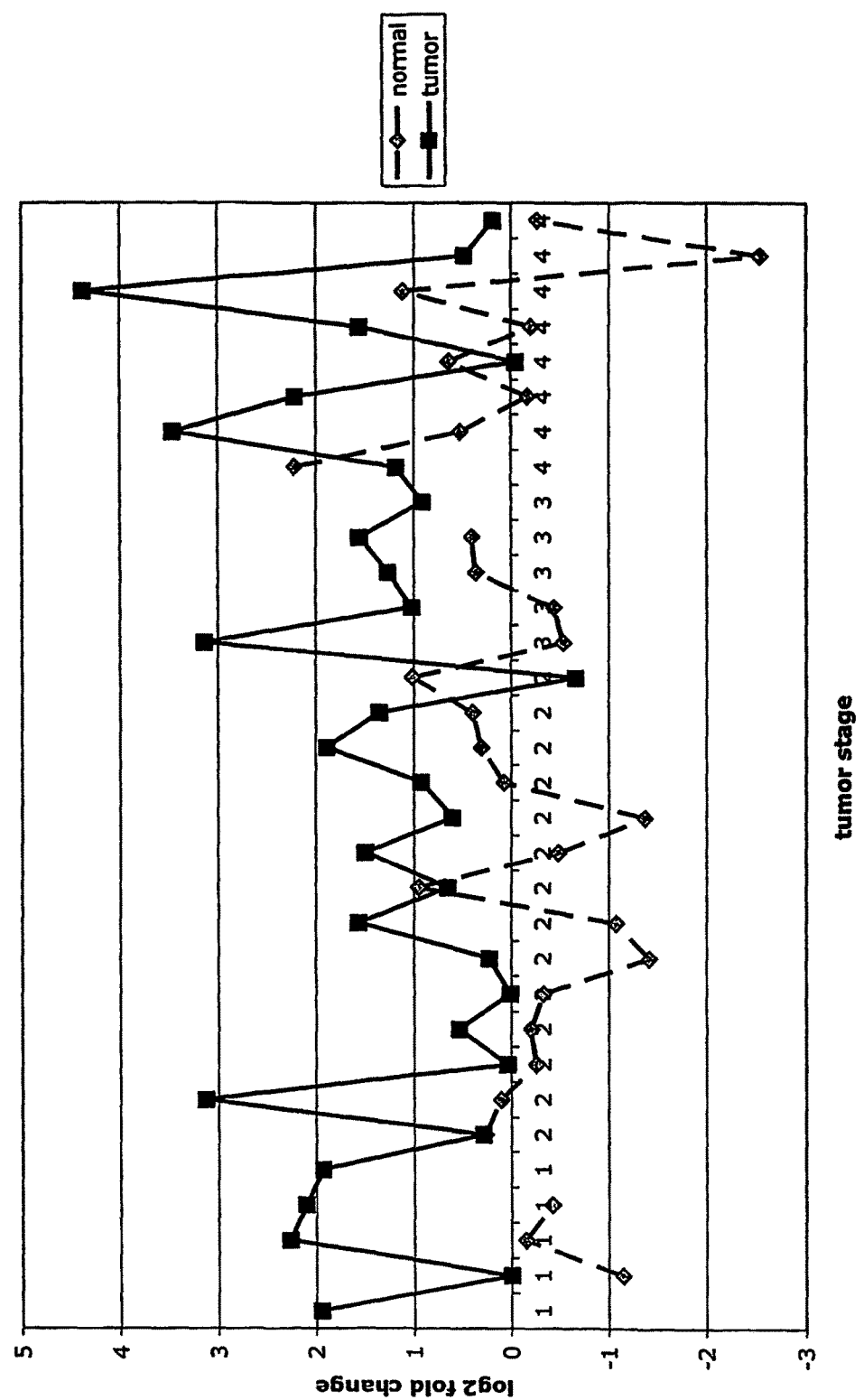

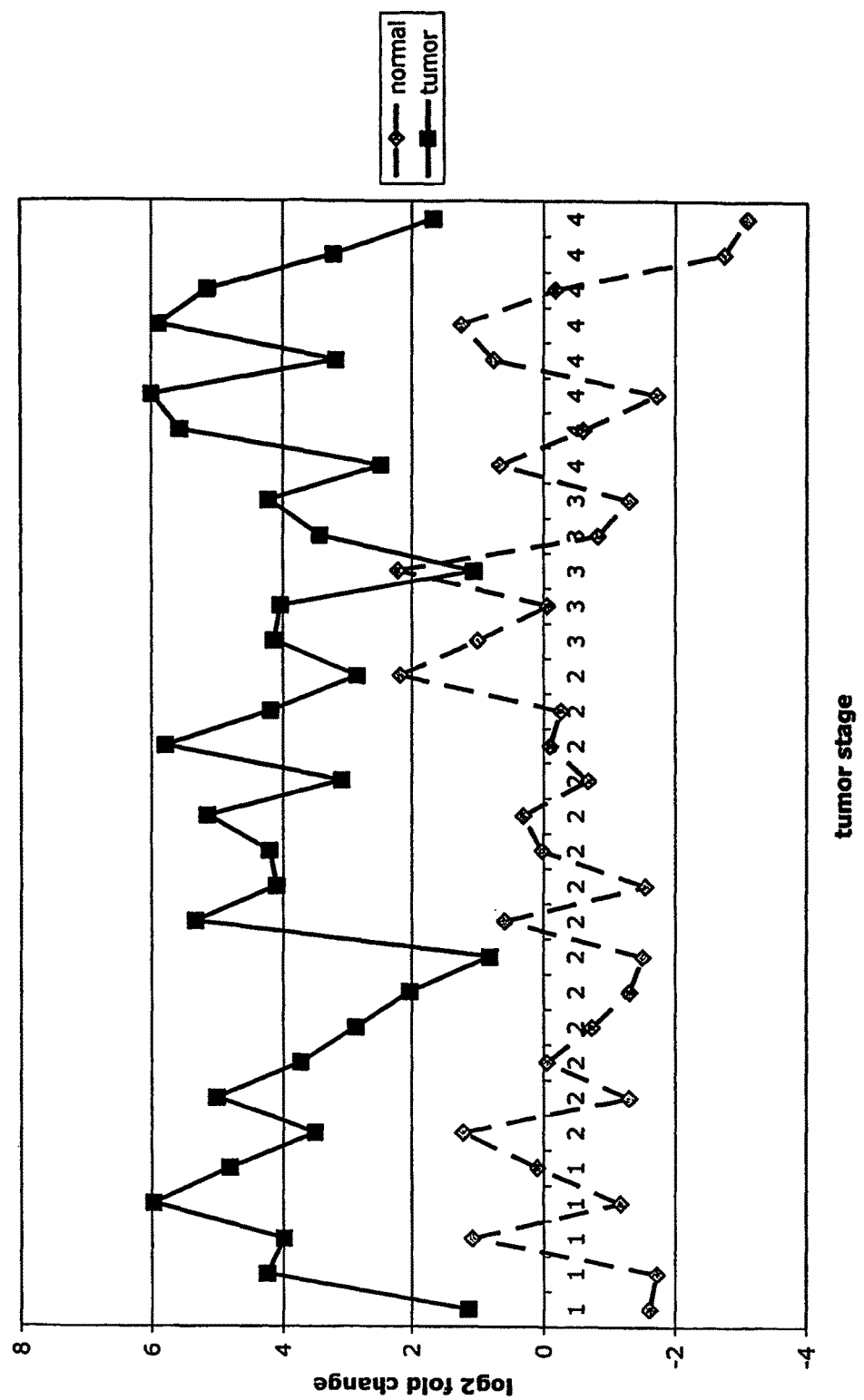
Fig. 10u THBS2

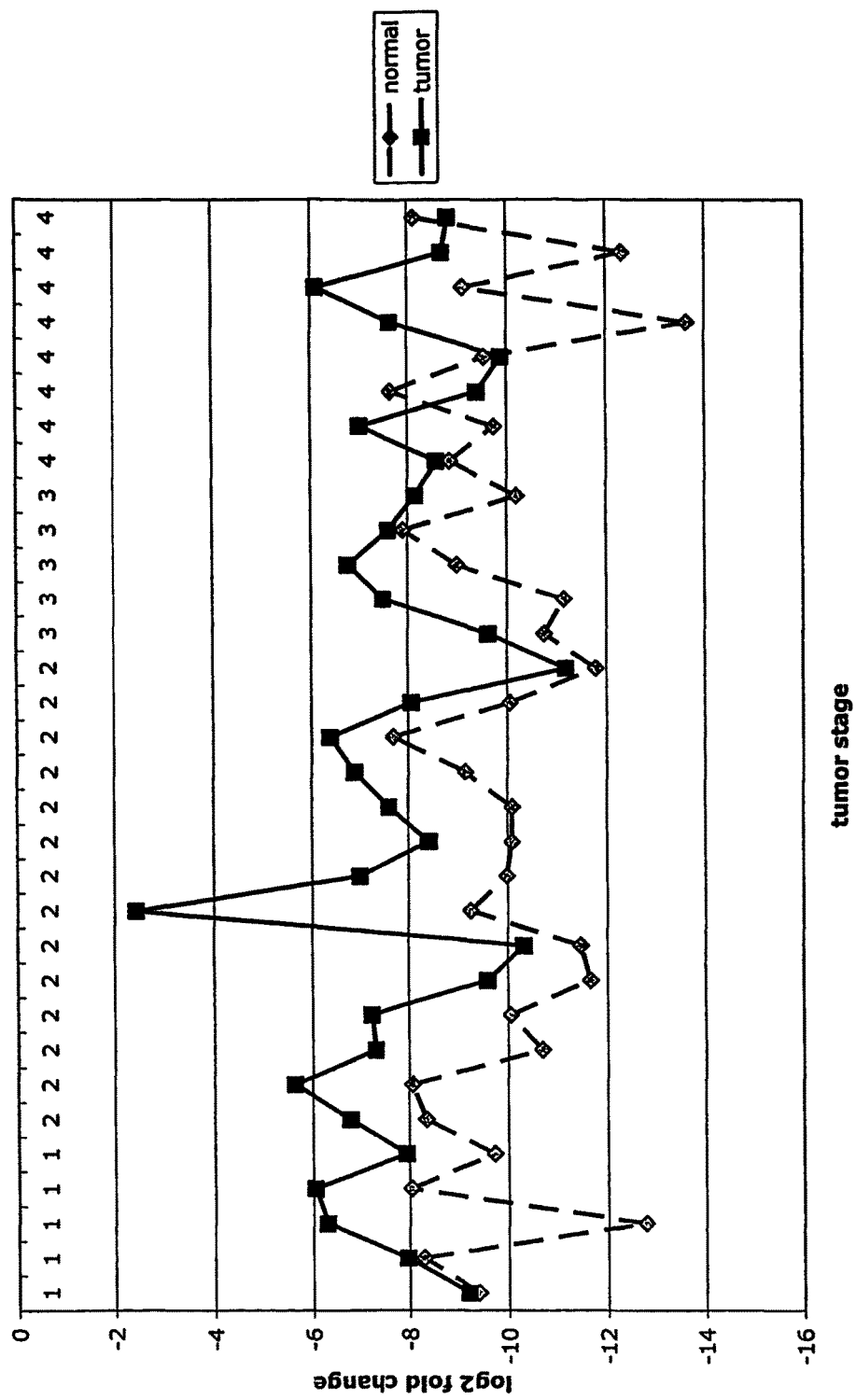

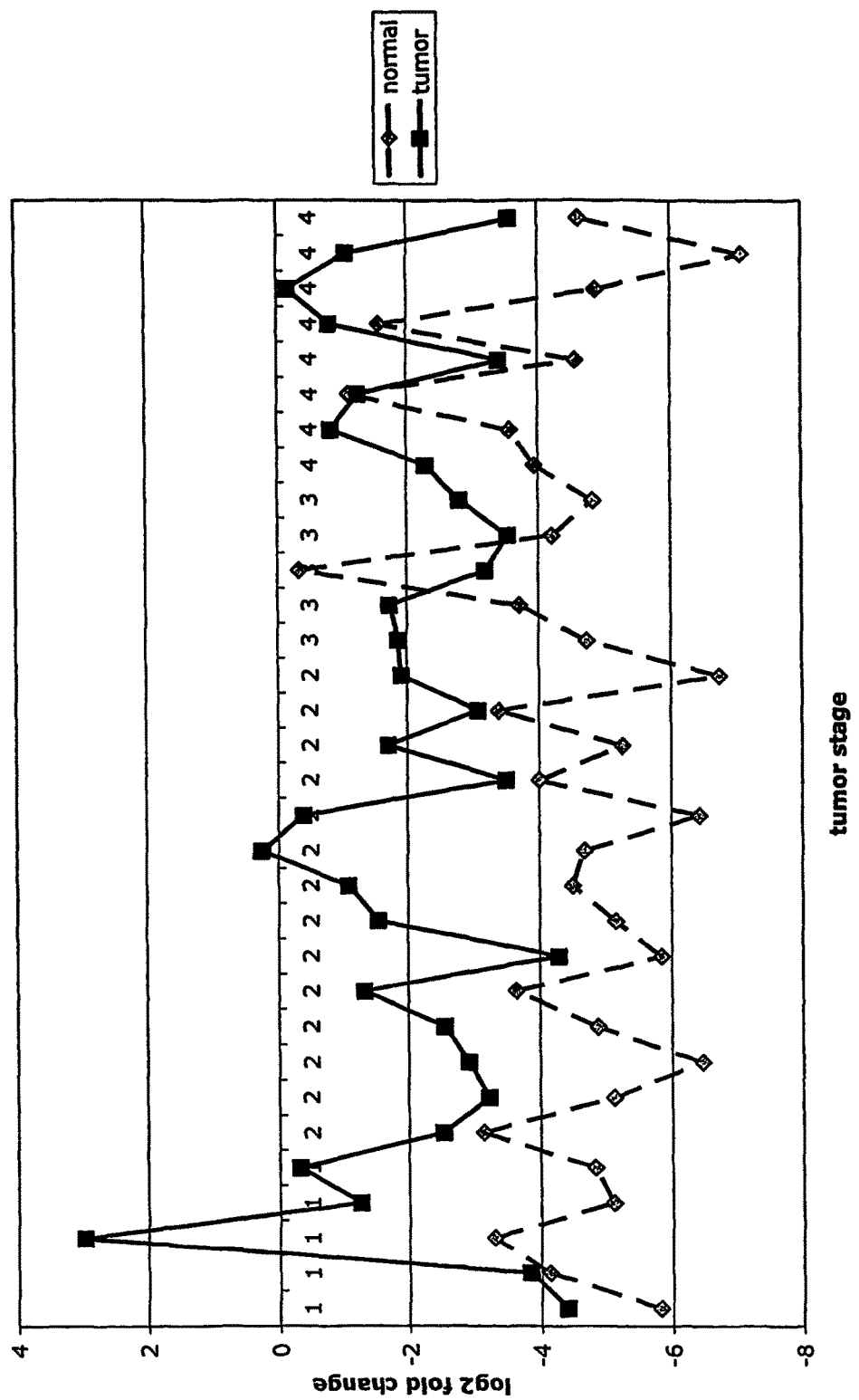

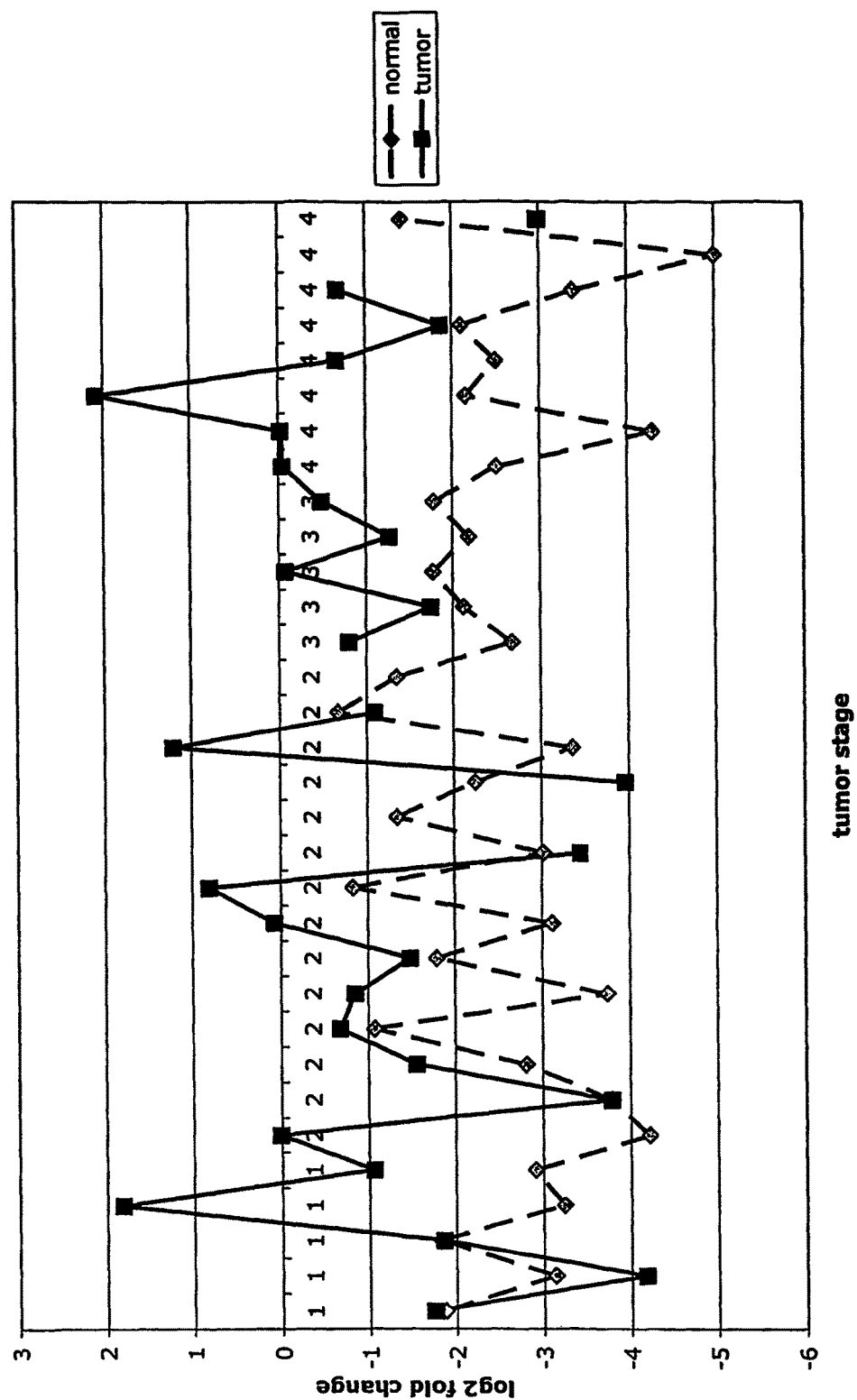
Fig. 10x CGR11

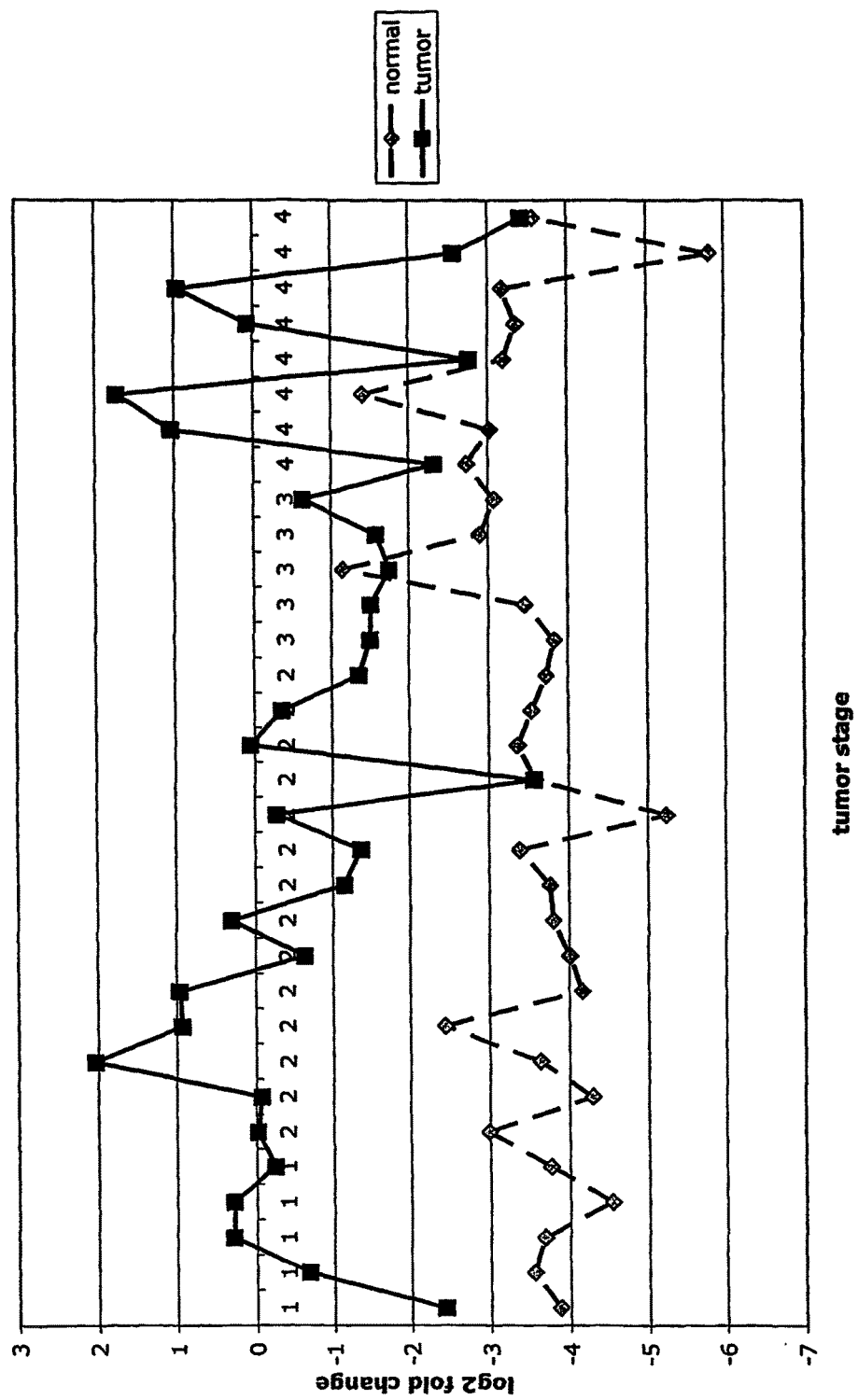
Fig. 10y SERPINH1

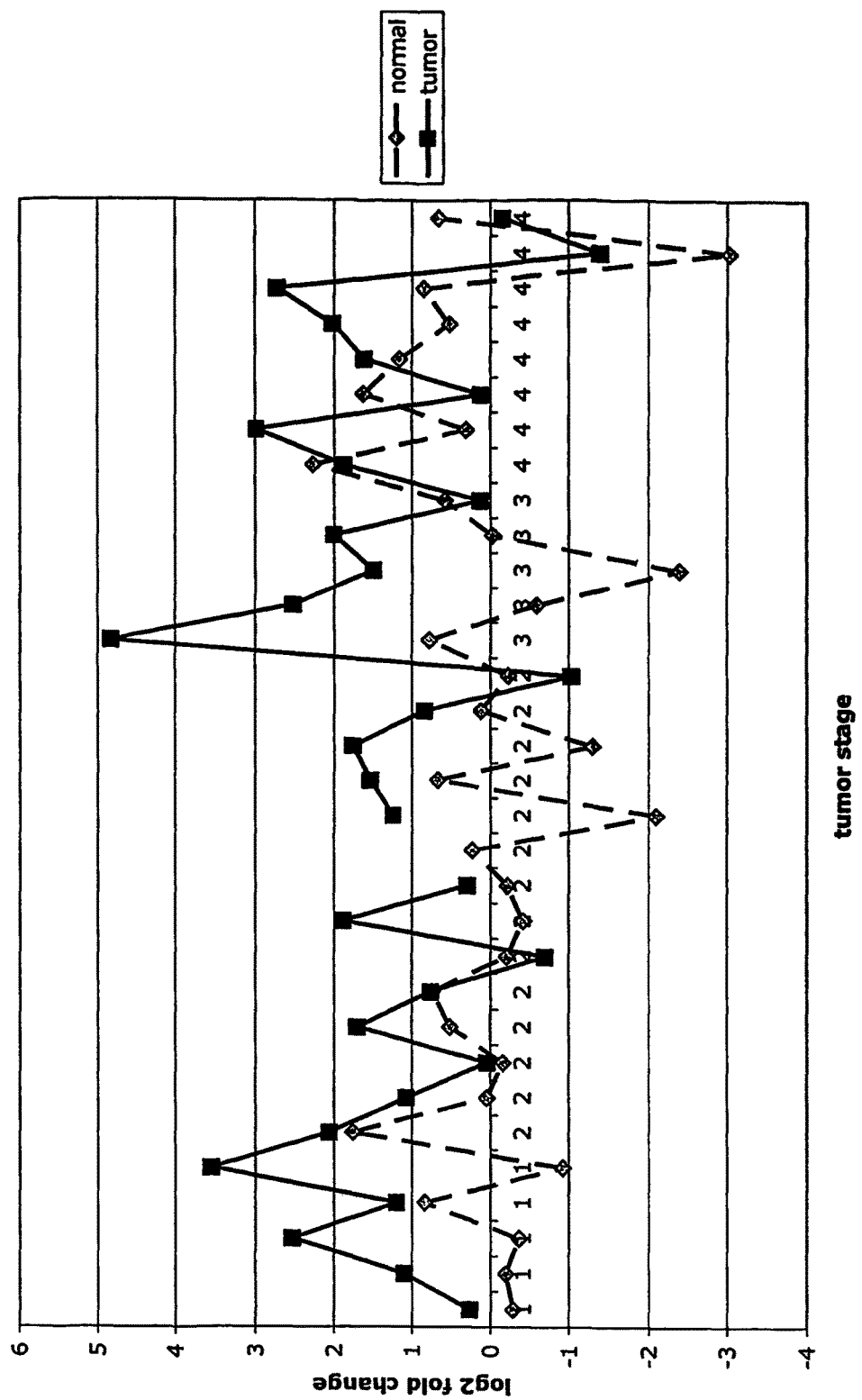
Fig. 10z MMP2

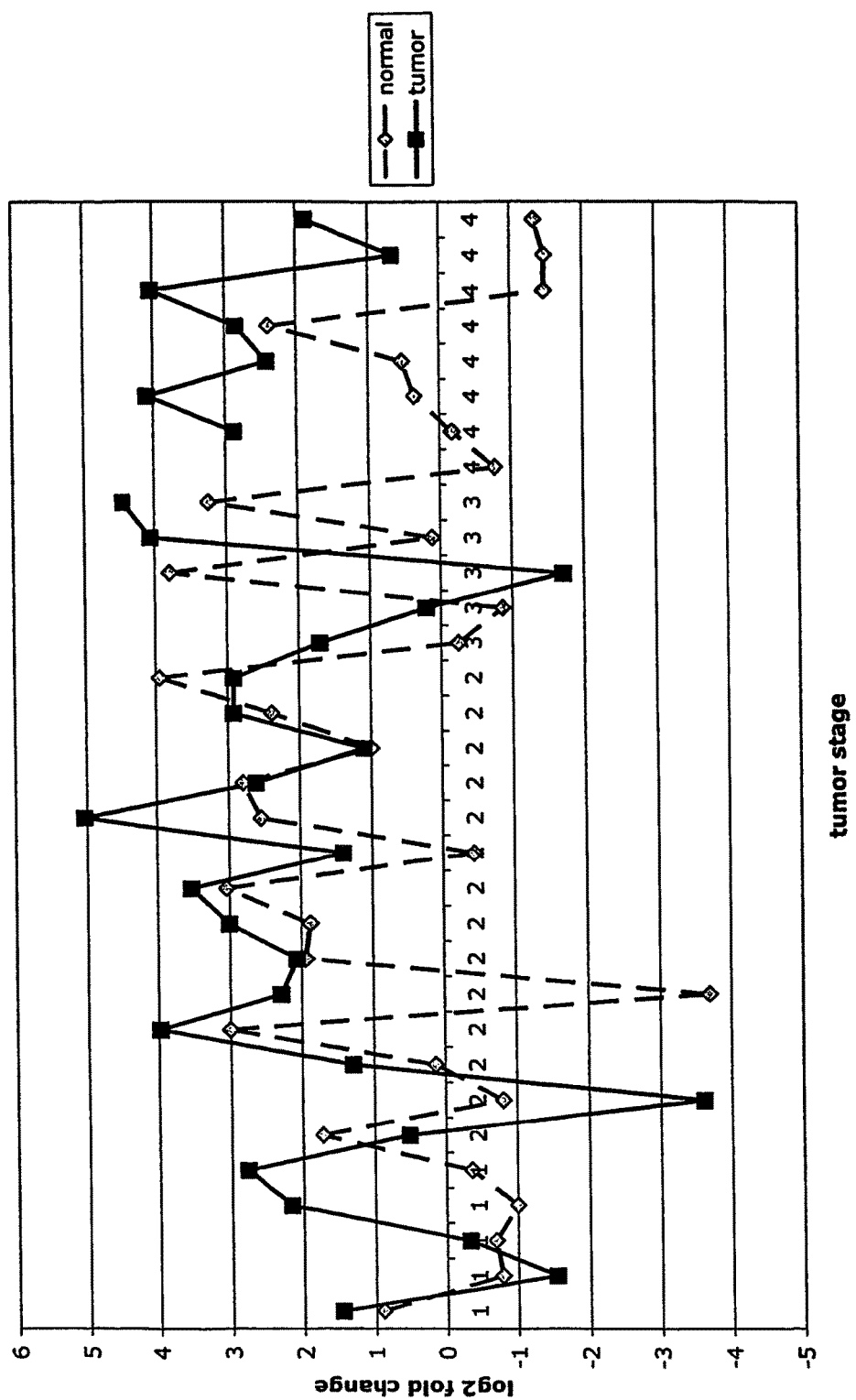

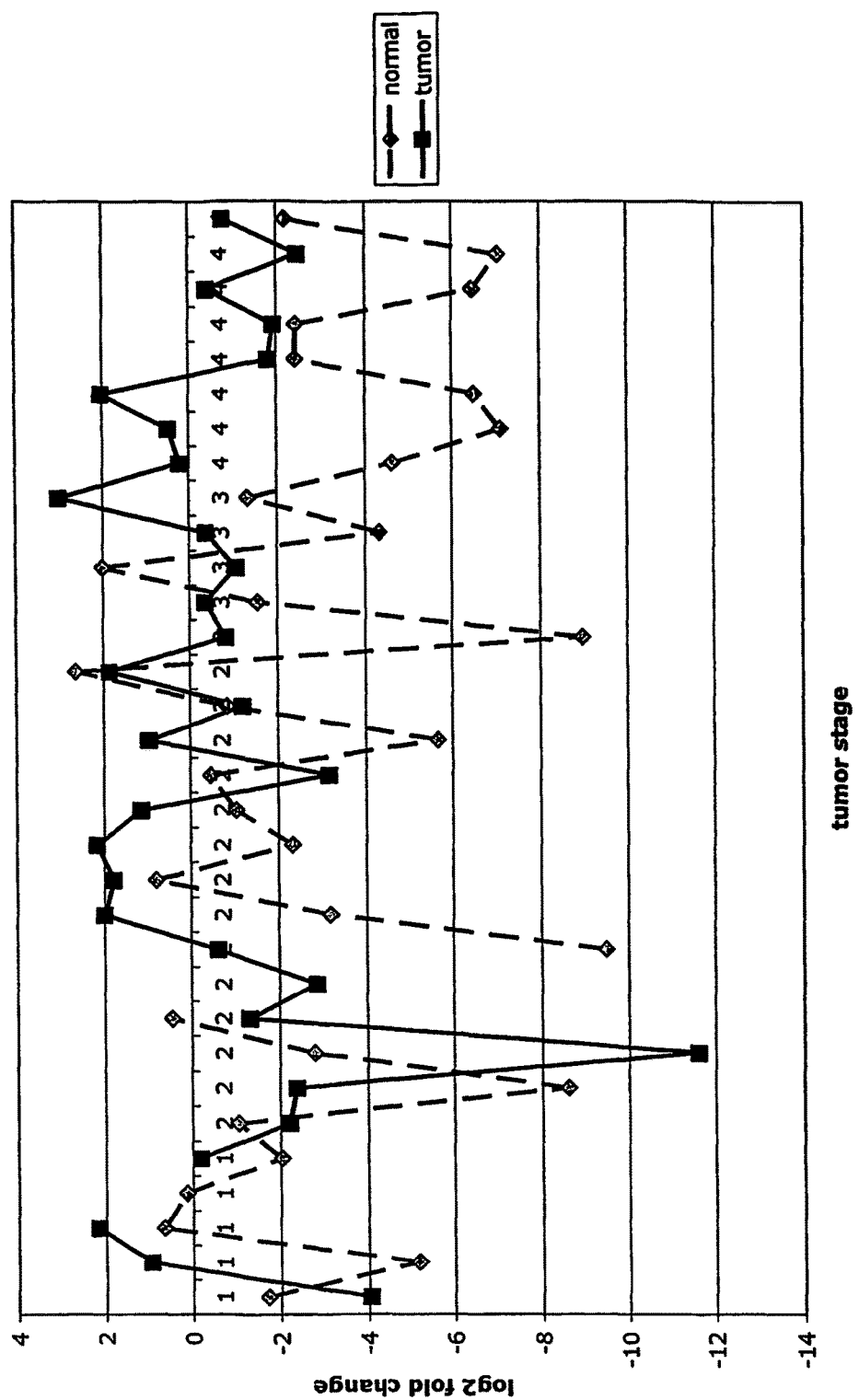
Fig. 10ab SERPINB5

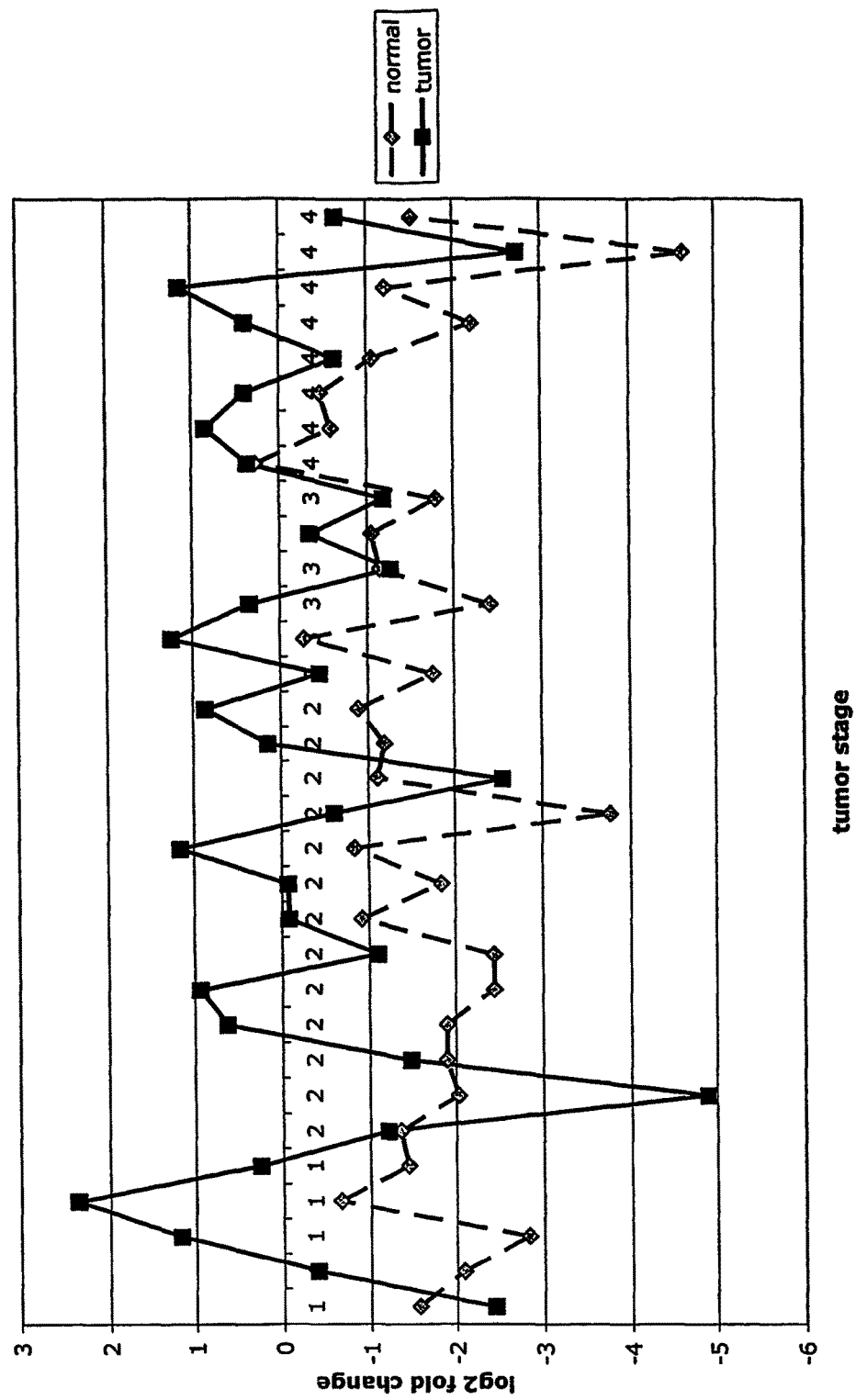

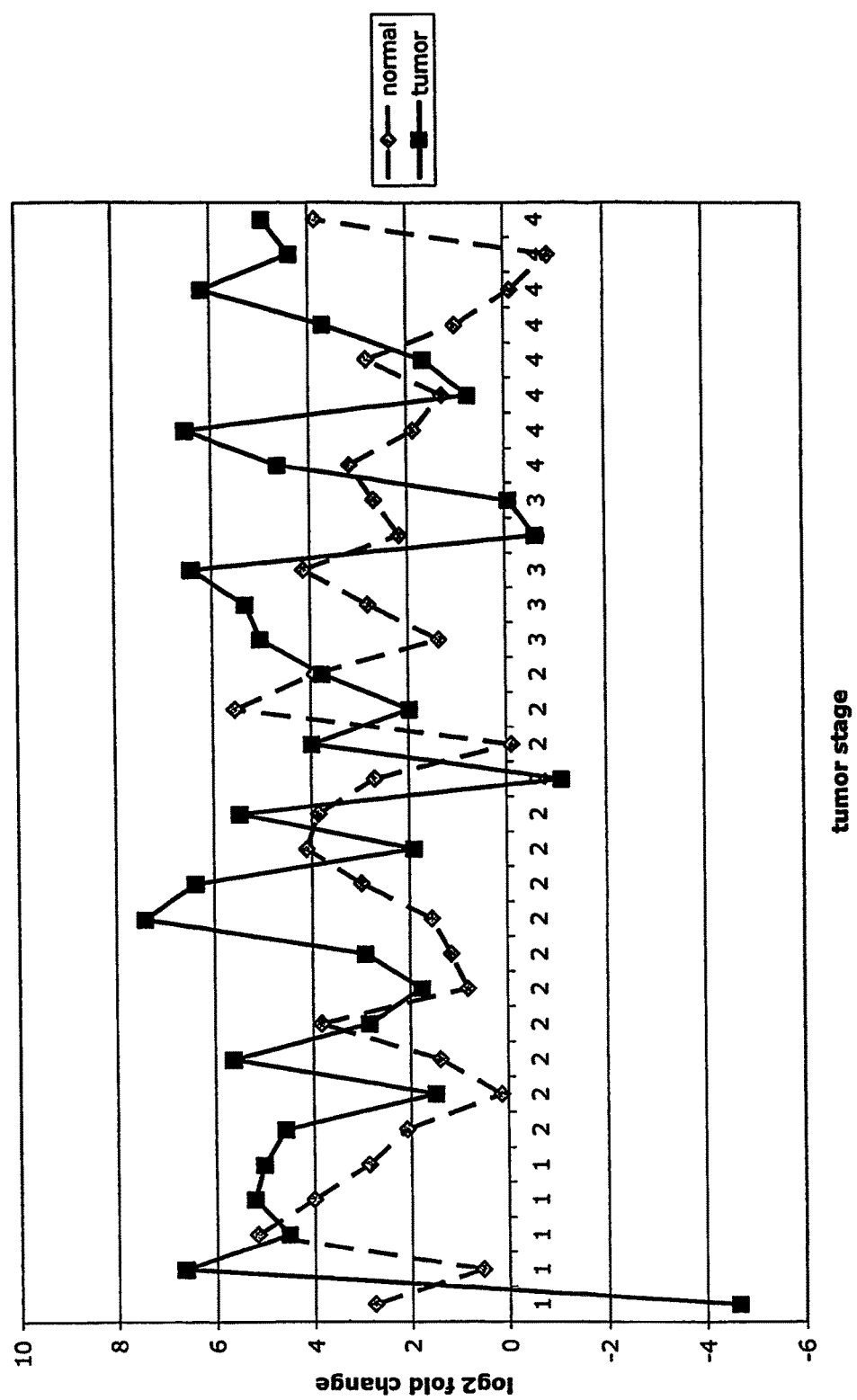

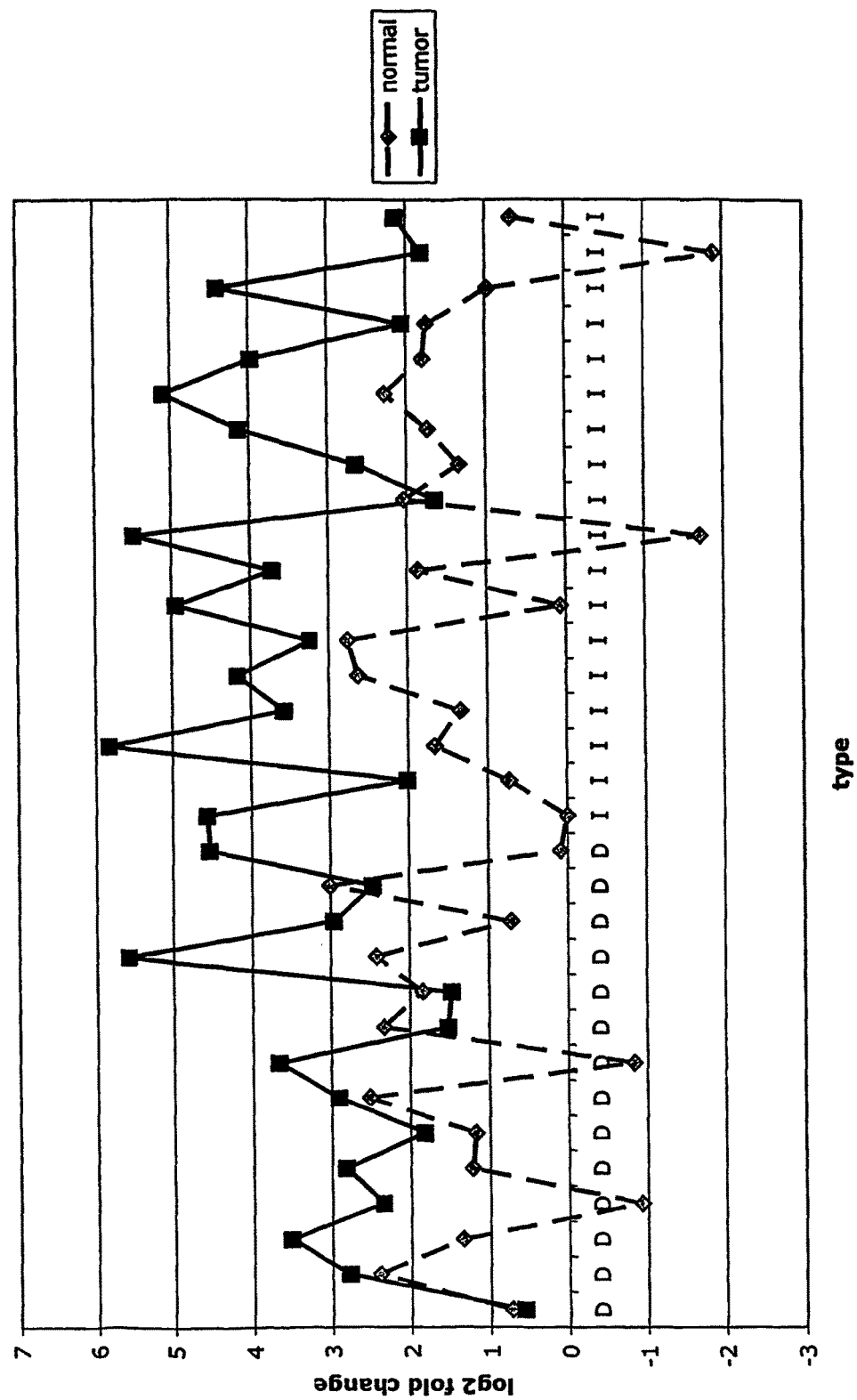

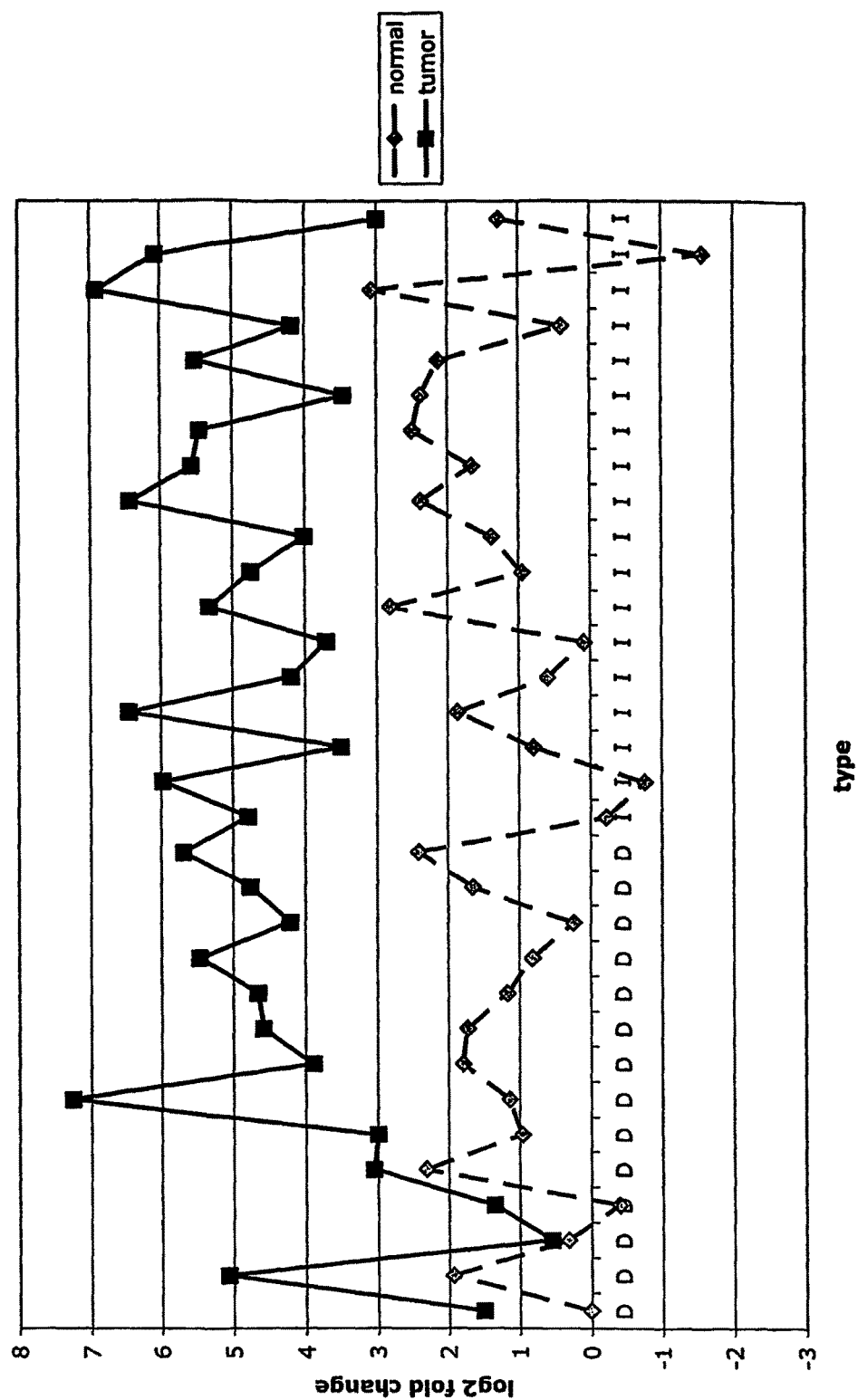
Fig. 11b ASPN

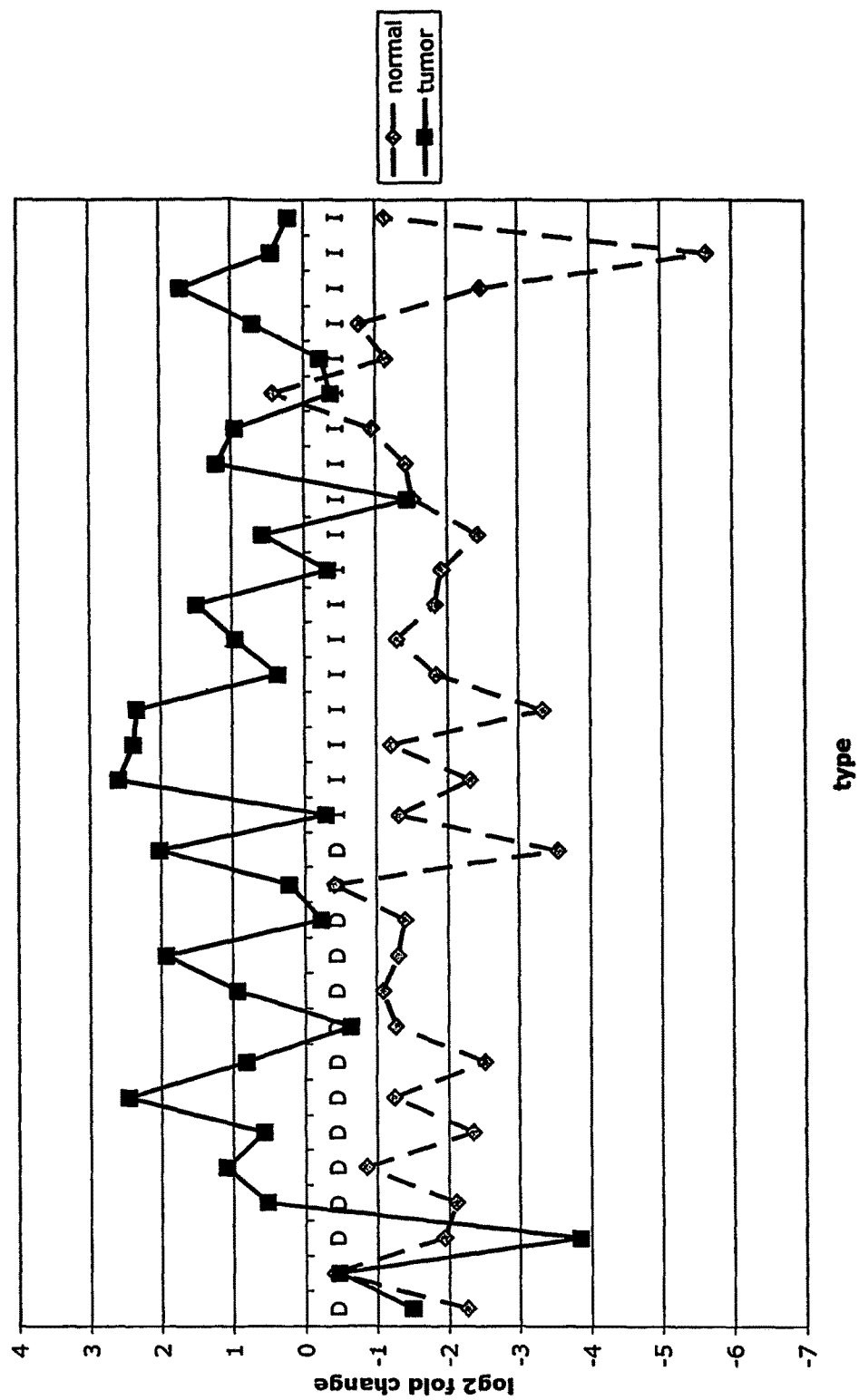

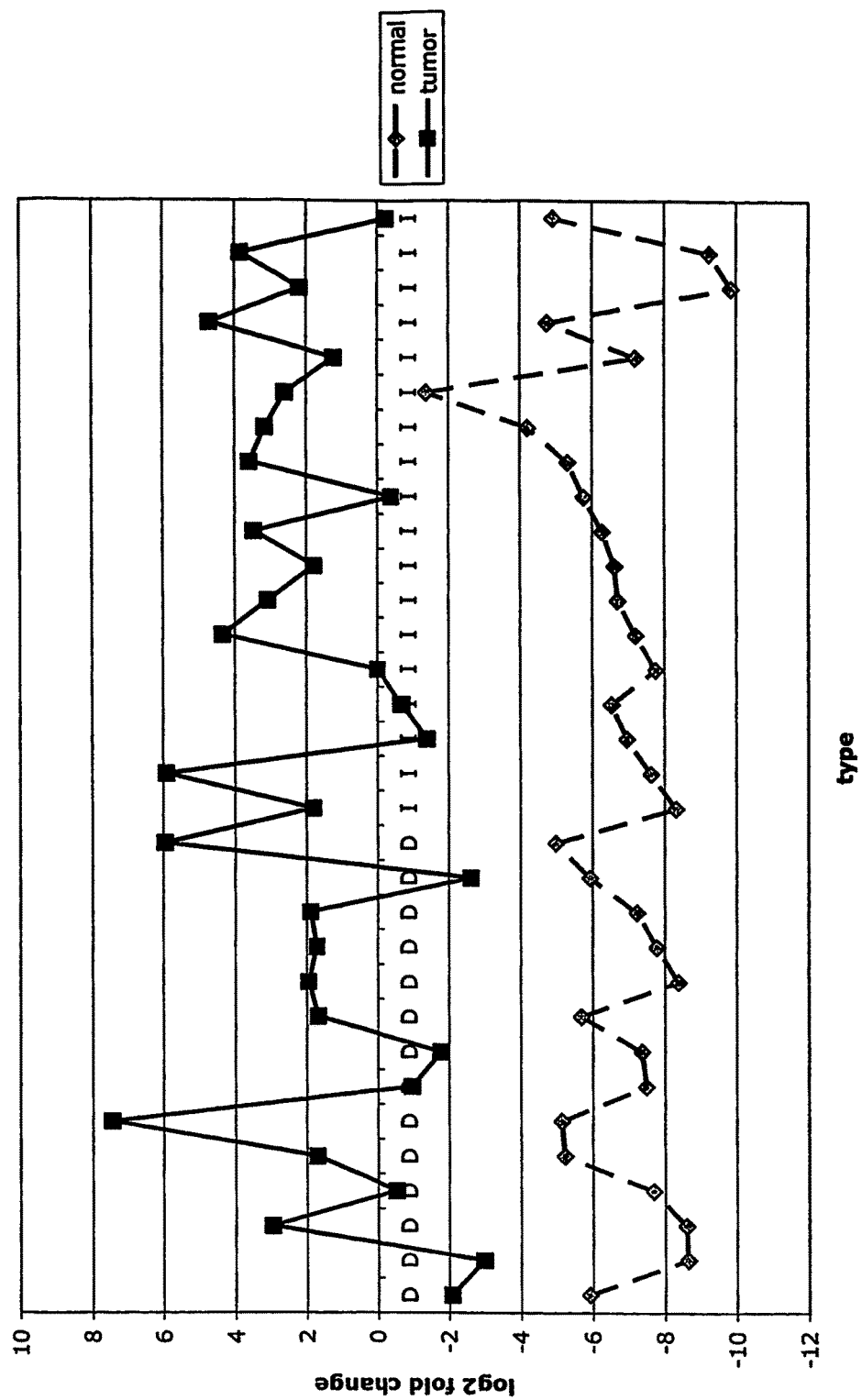
Fig. 11d CST1,2,4

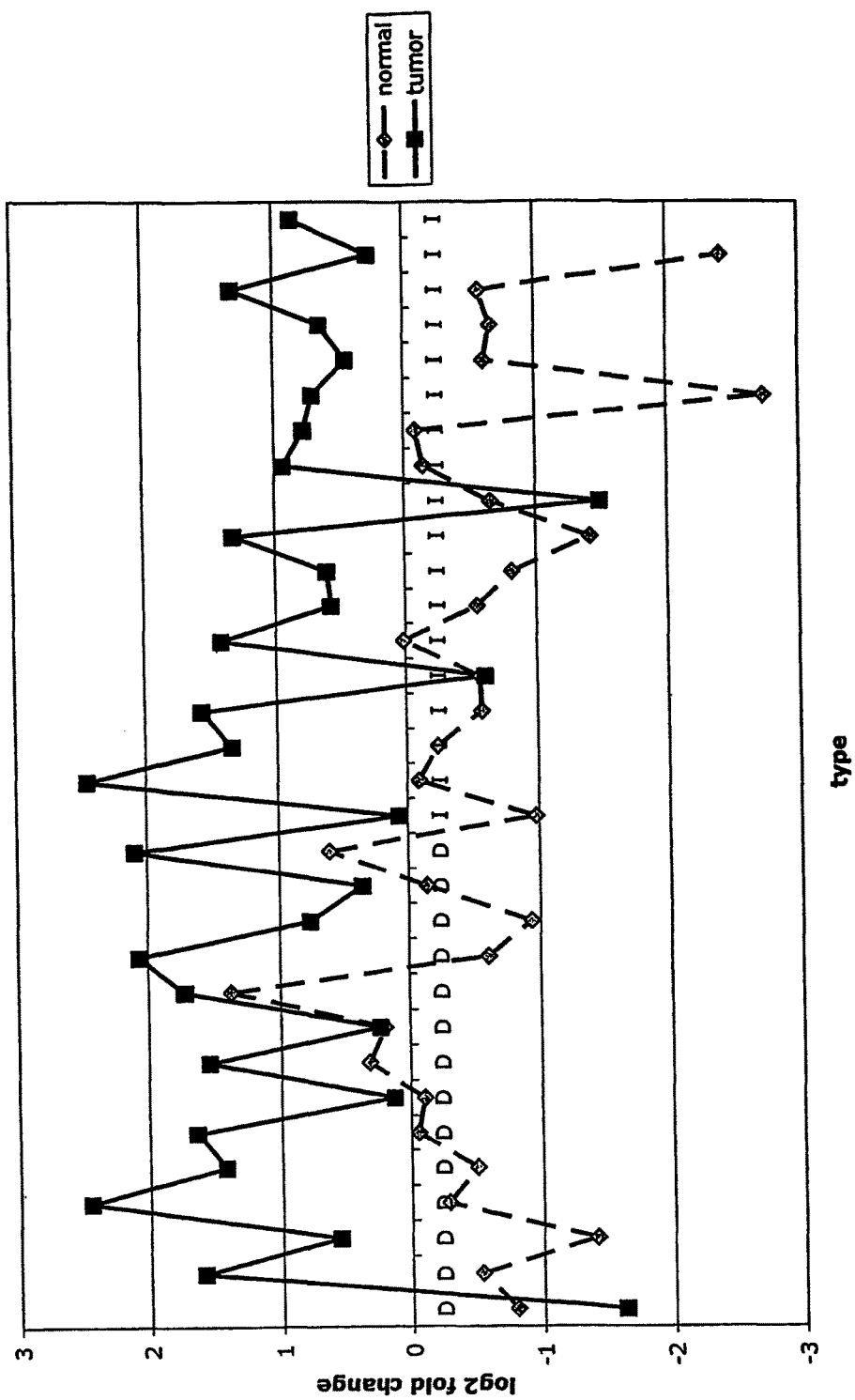
Fig. 11e EFEMP2

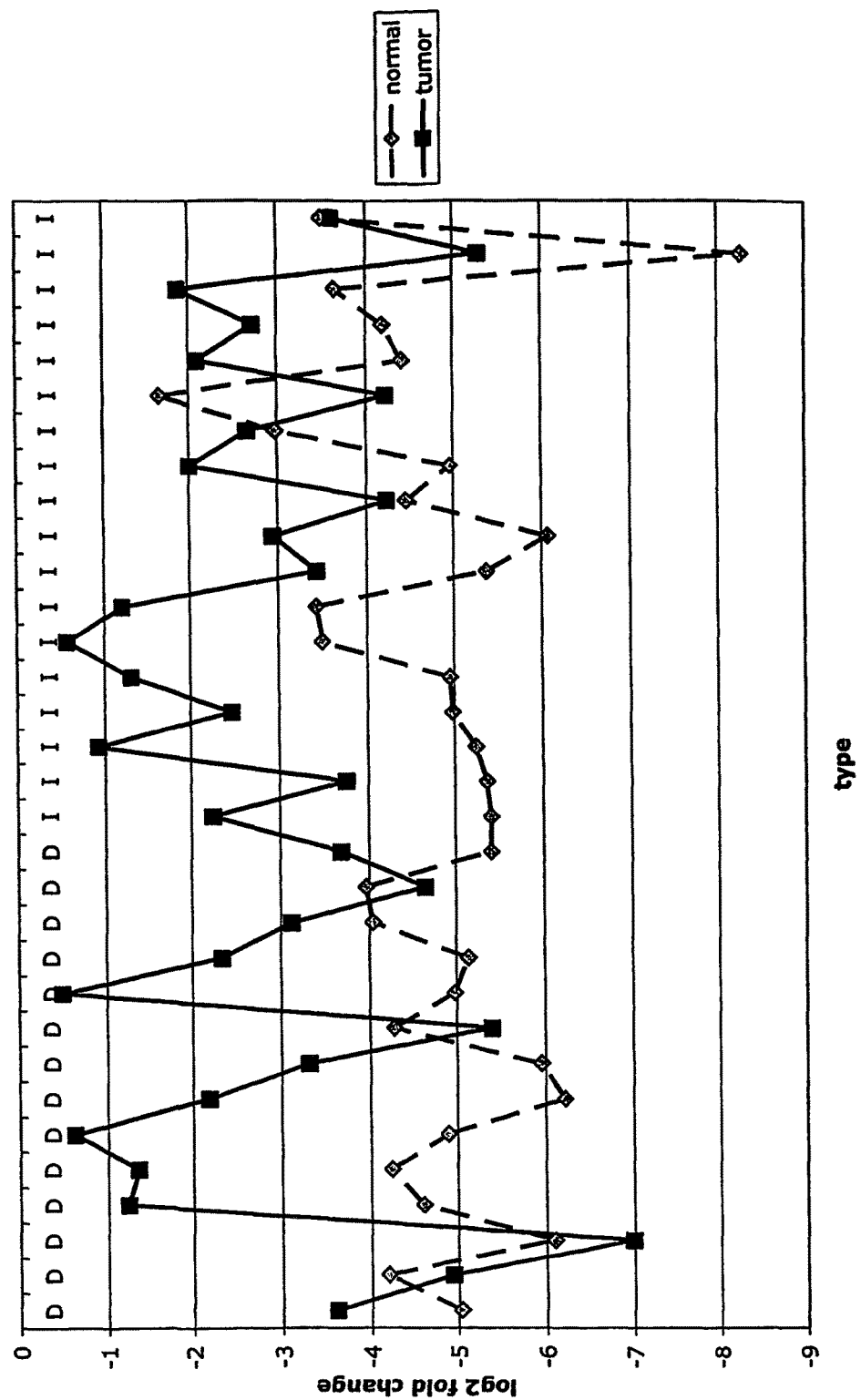
Fig. 11f GGH

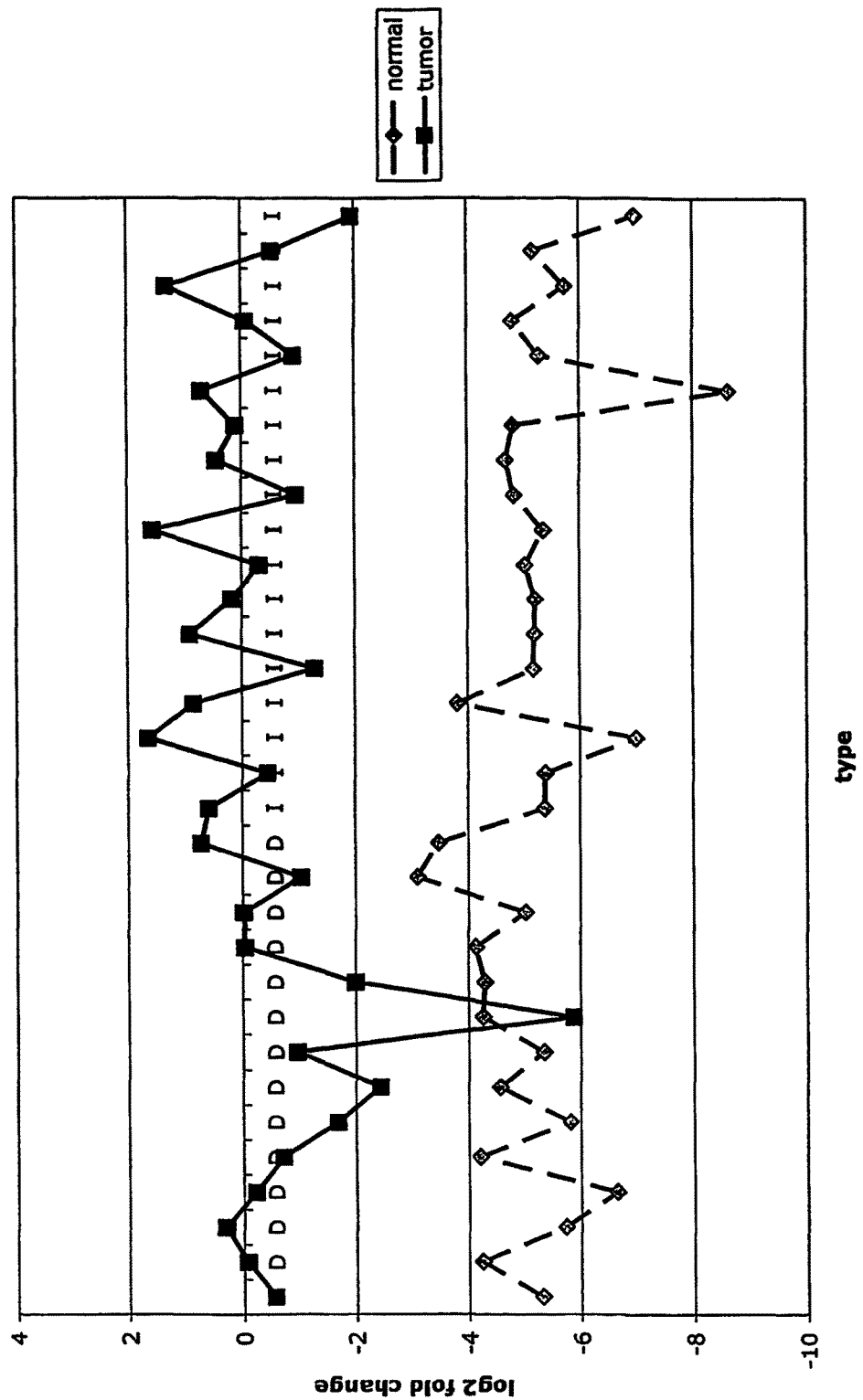

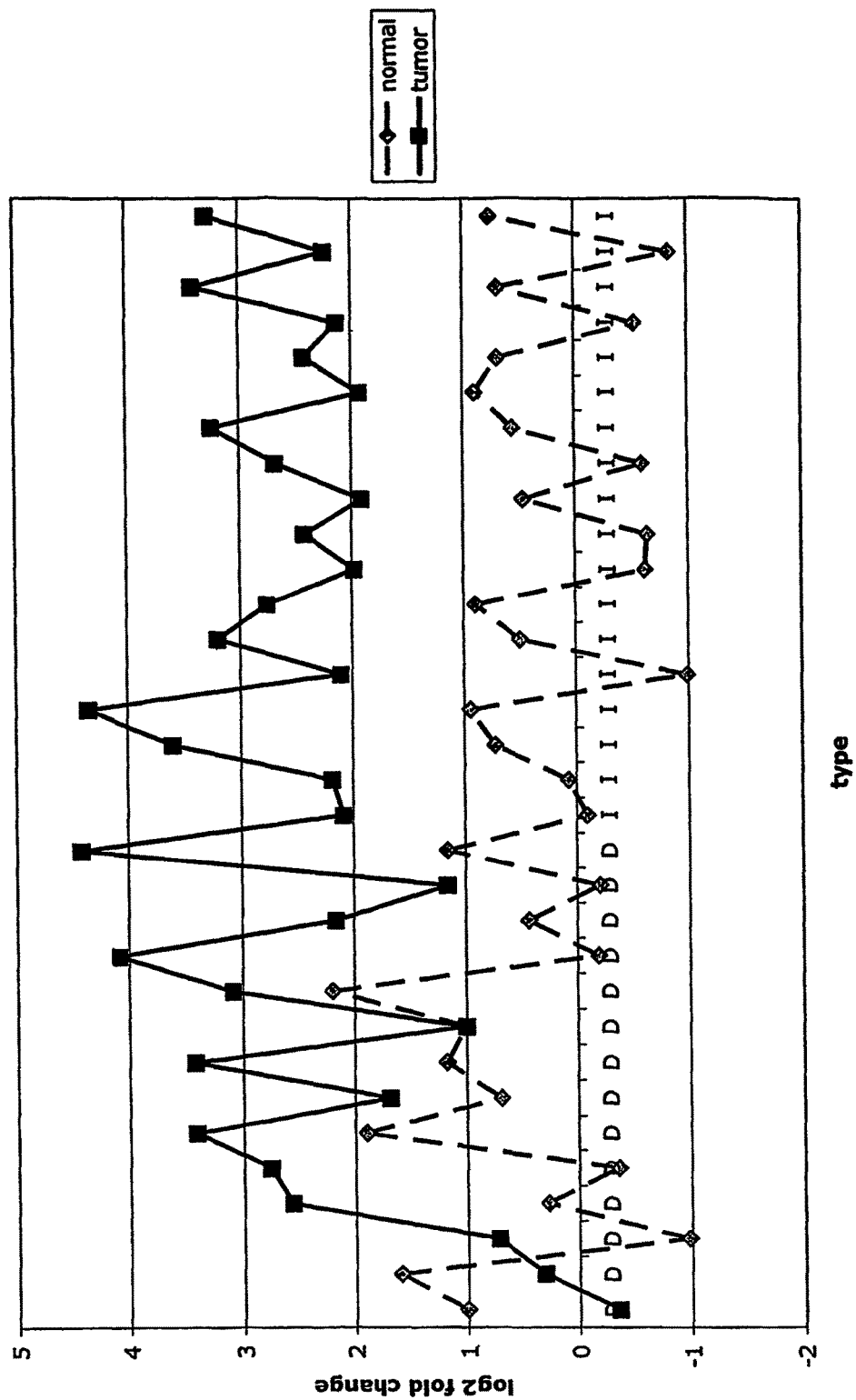

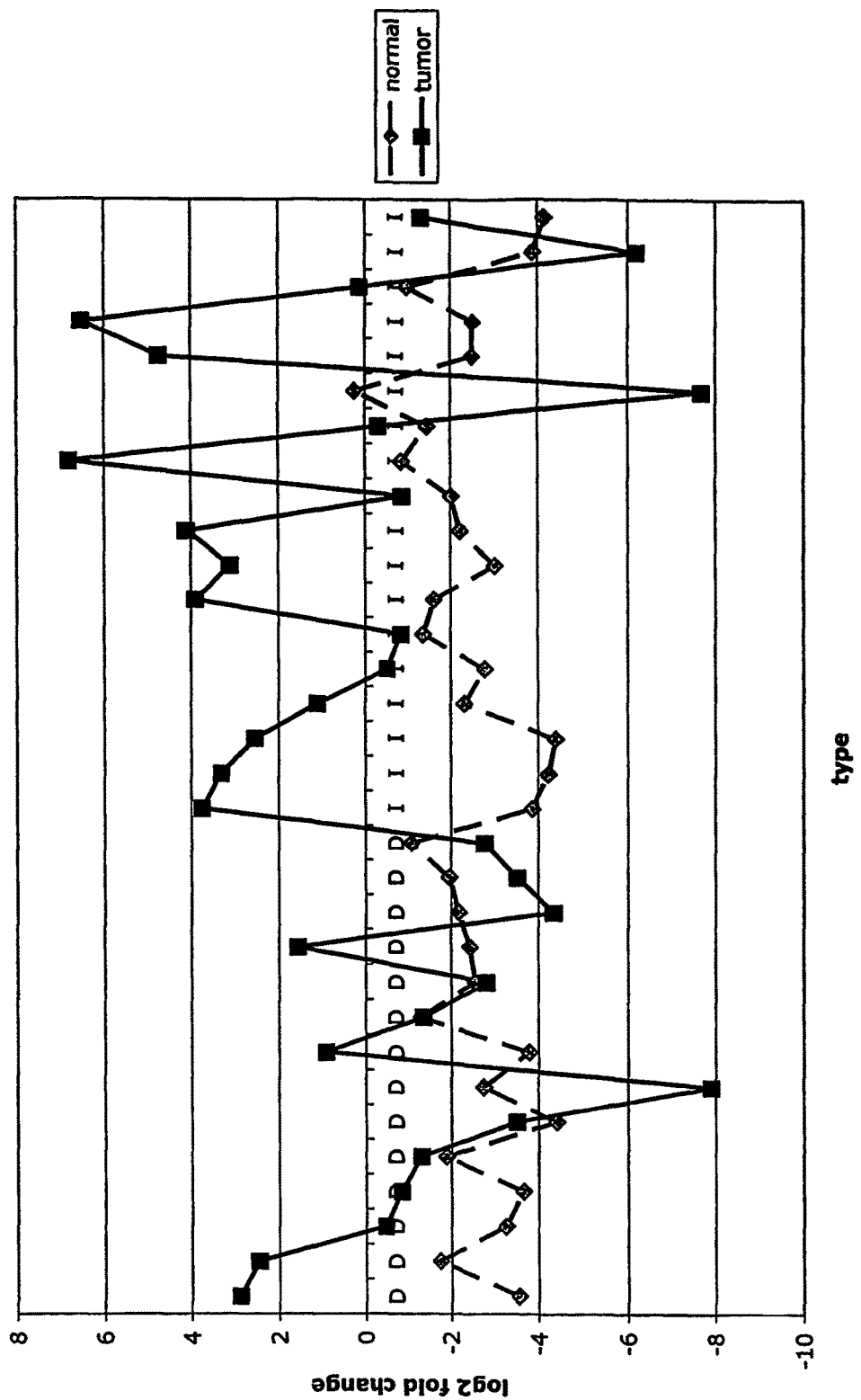

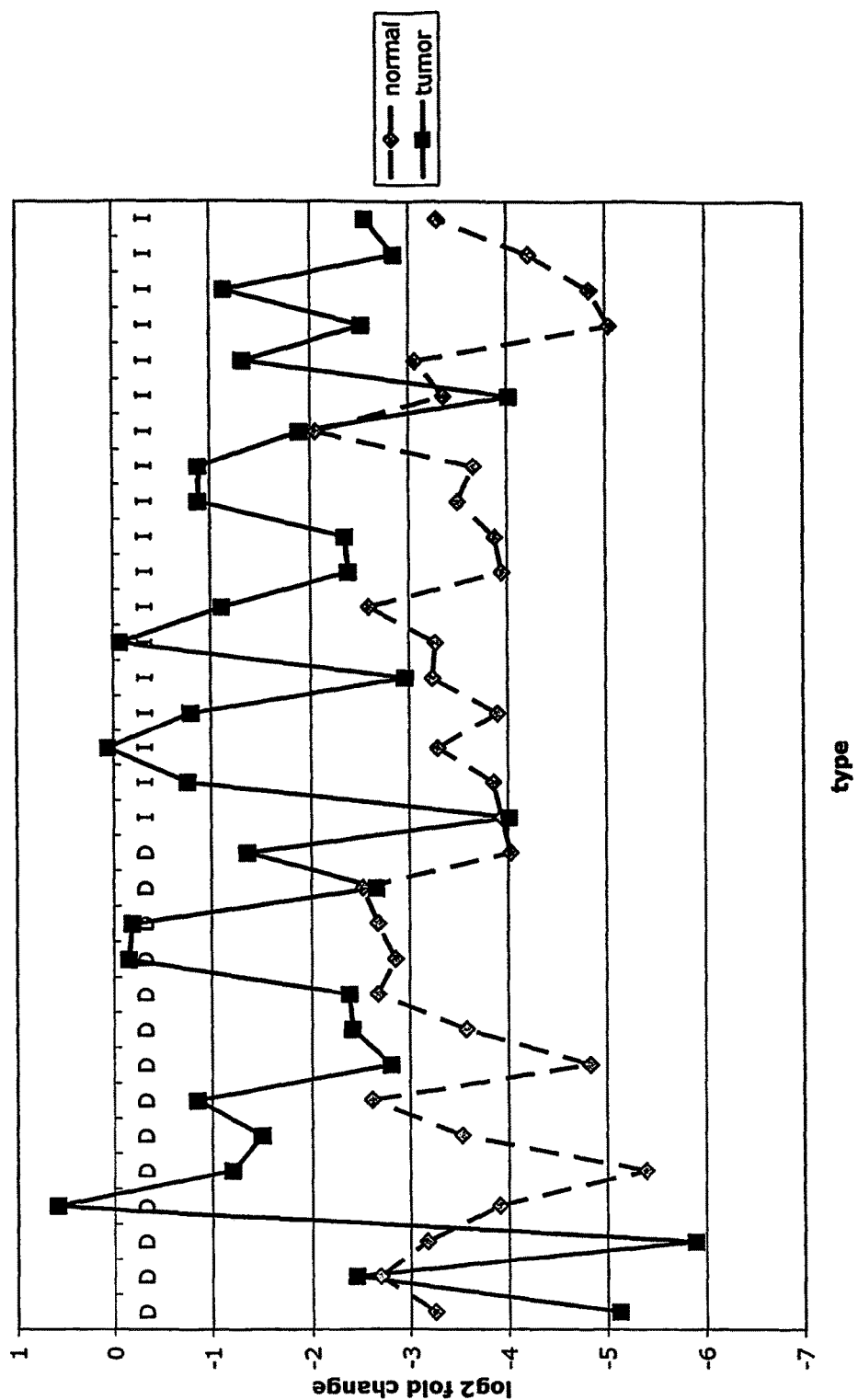

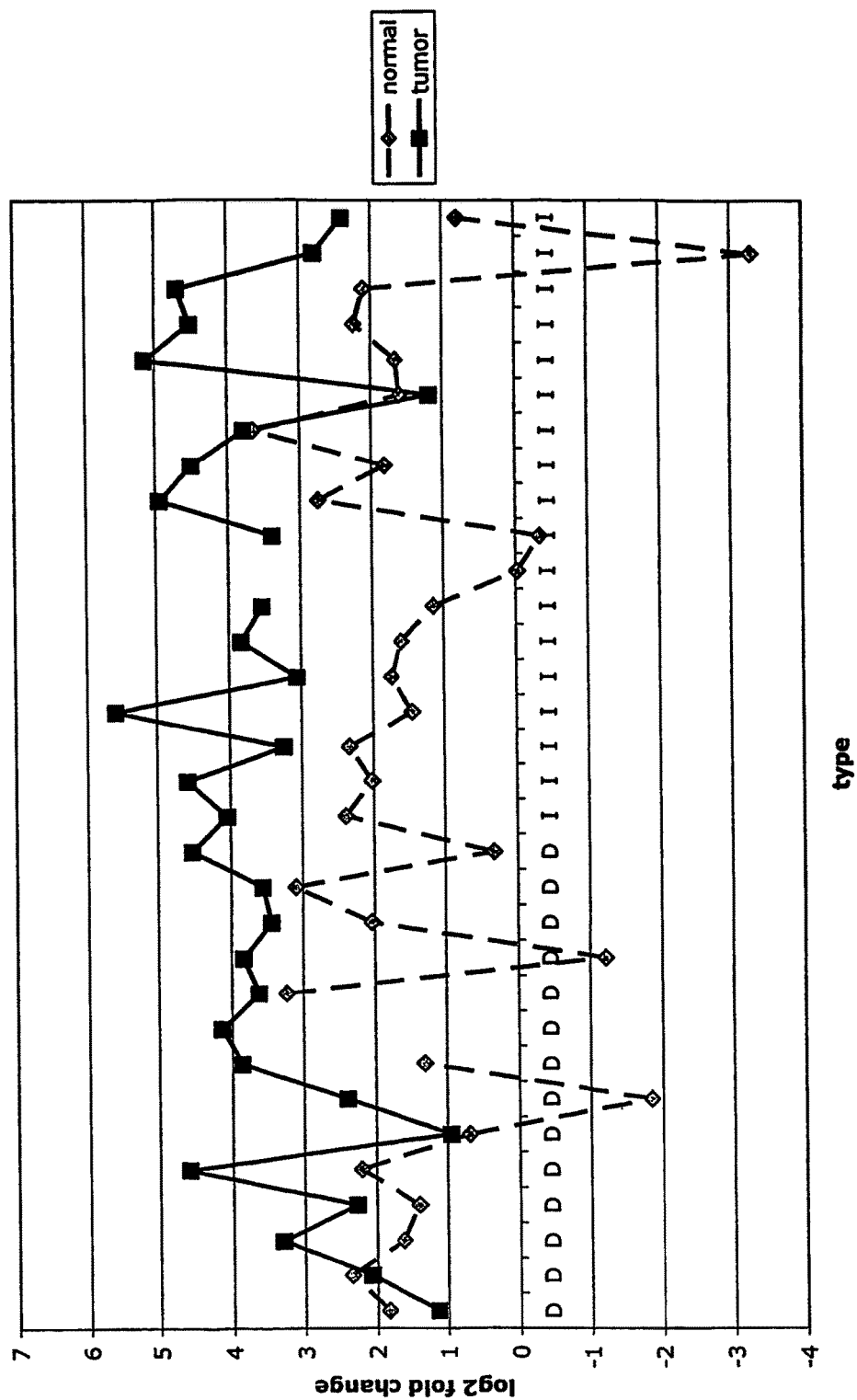

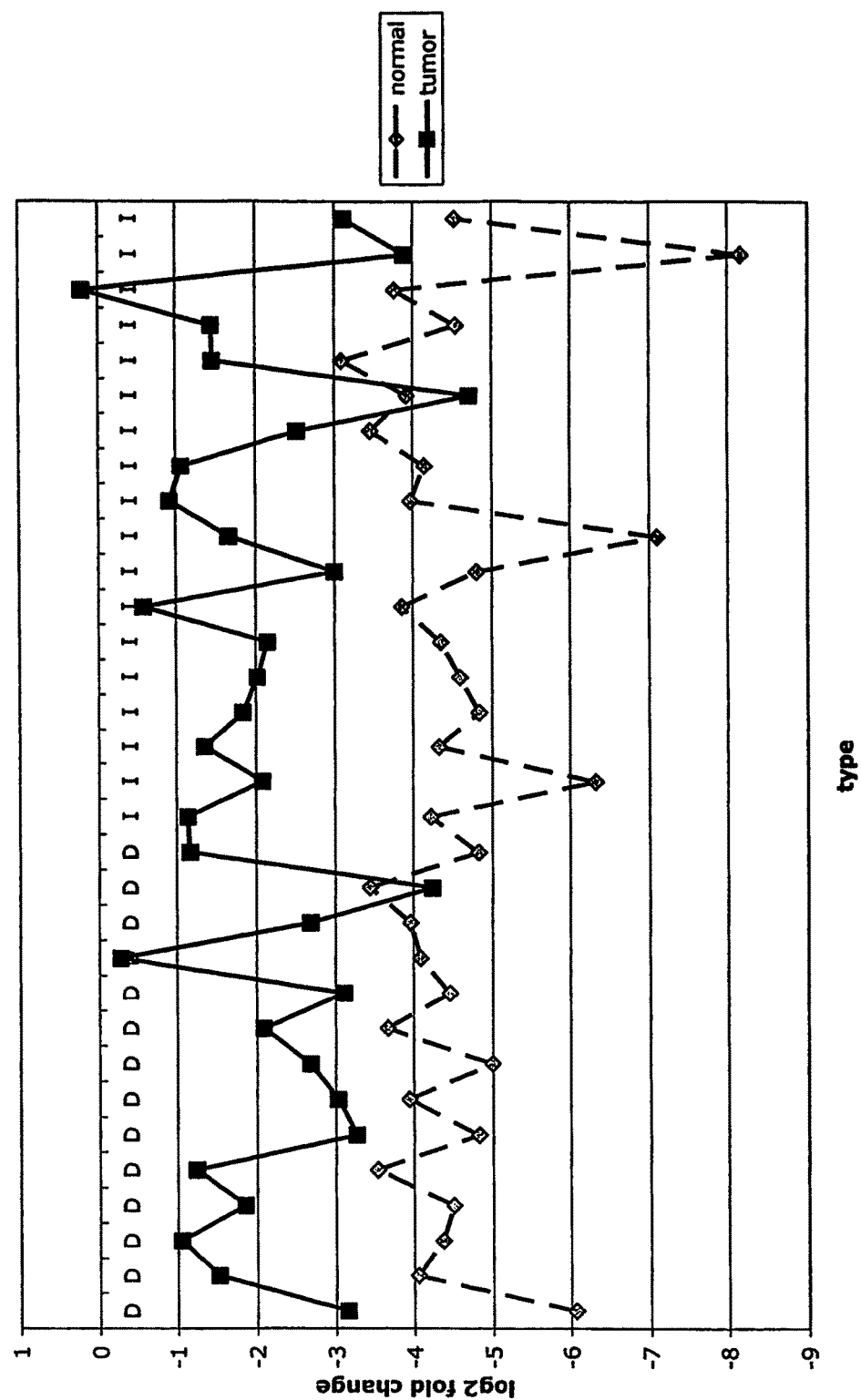
Fig. 11I LOXL2

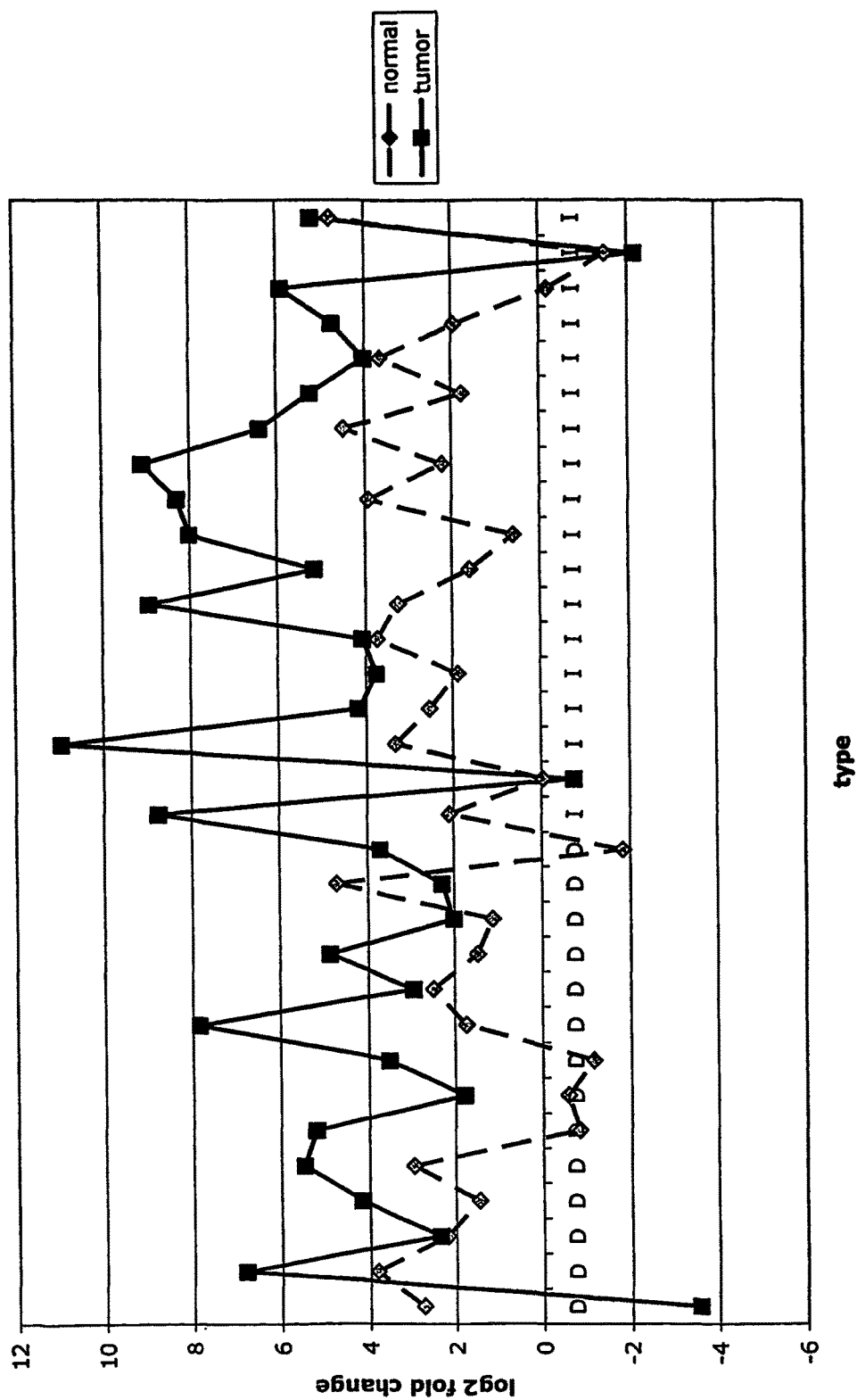
Fig. 11m MMP12

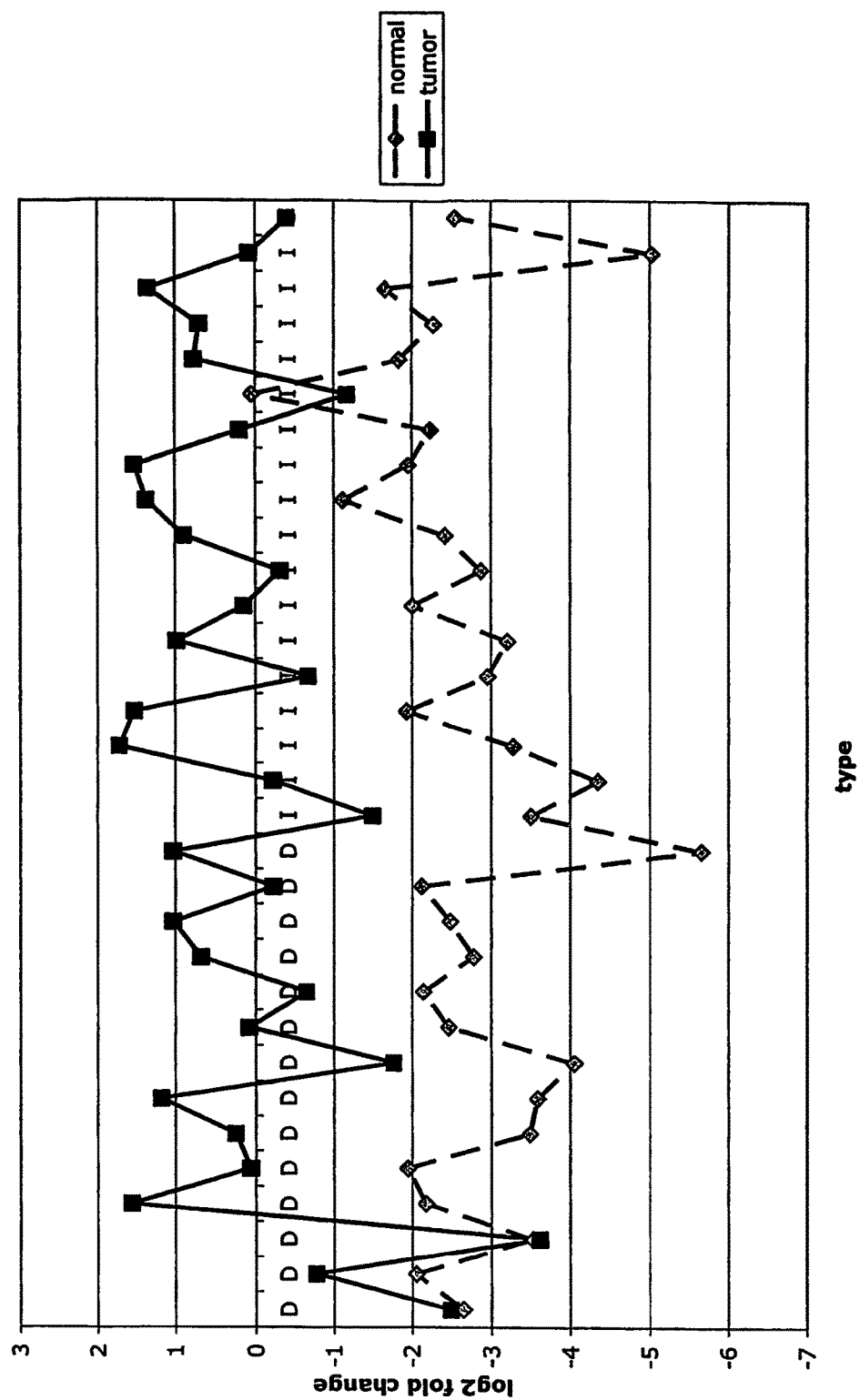
Fig. 11n TIMP1

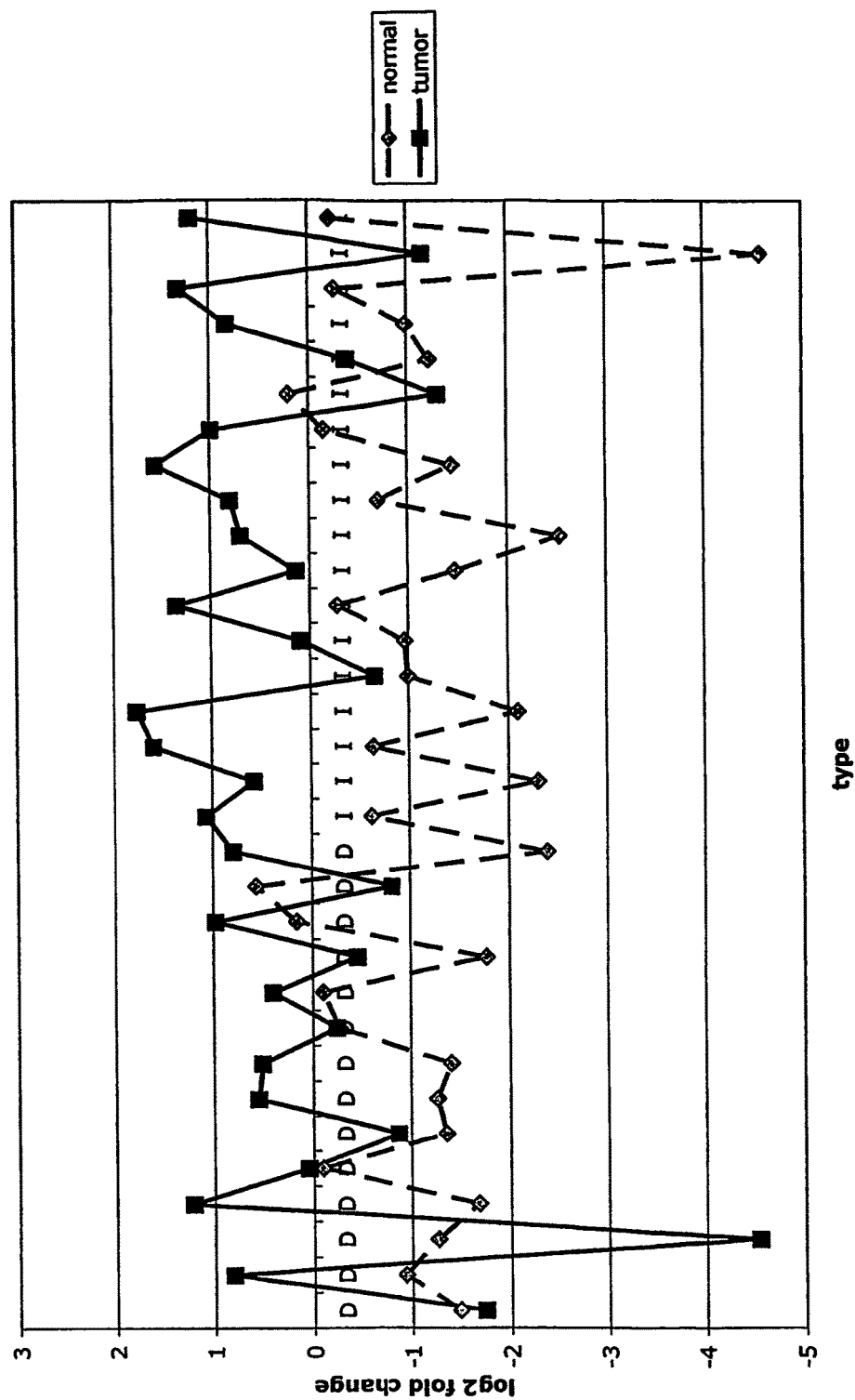
Fig. 11o ASAH1

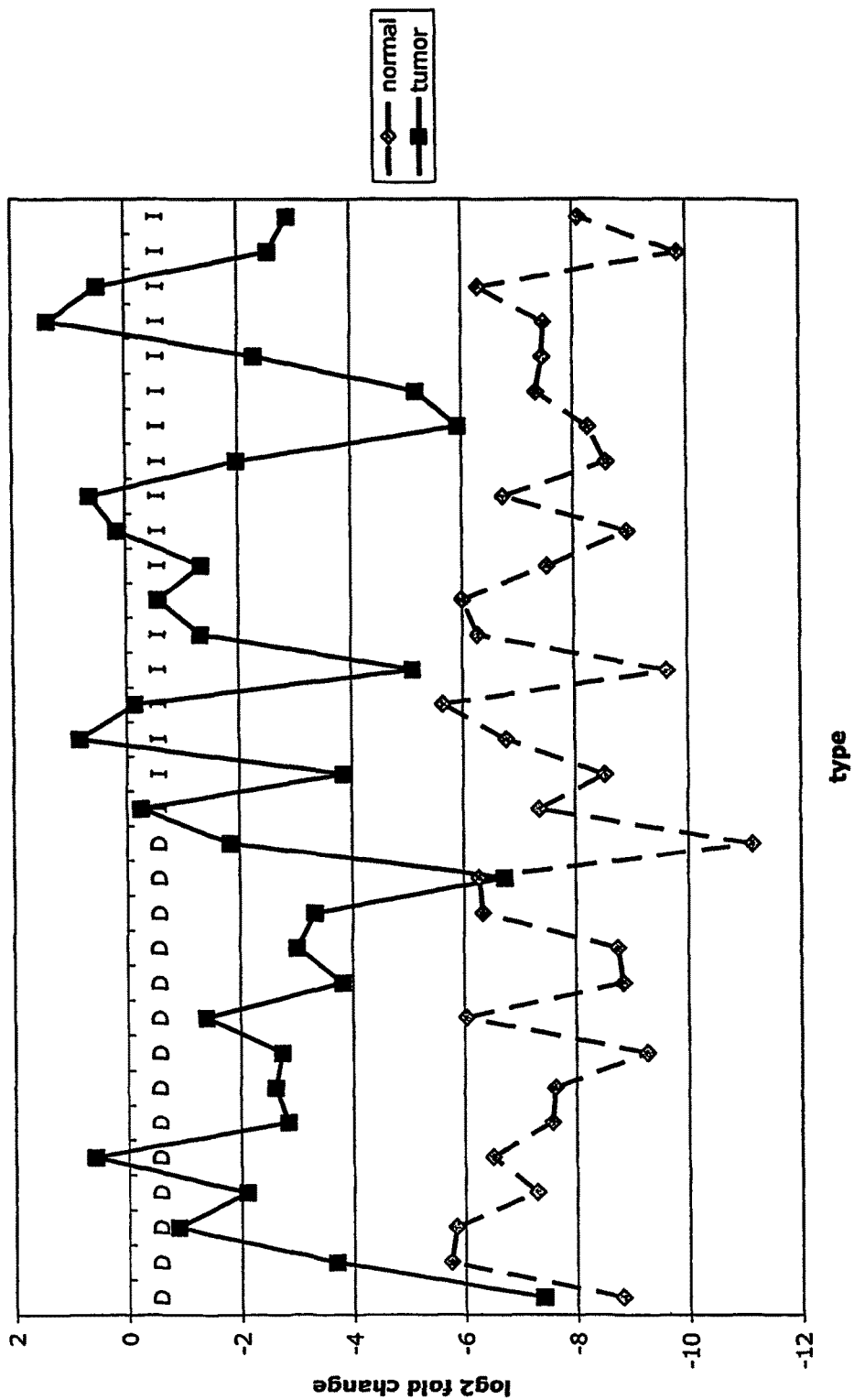

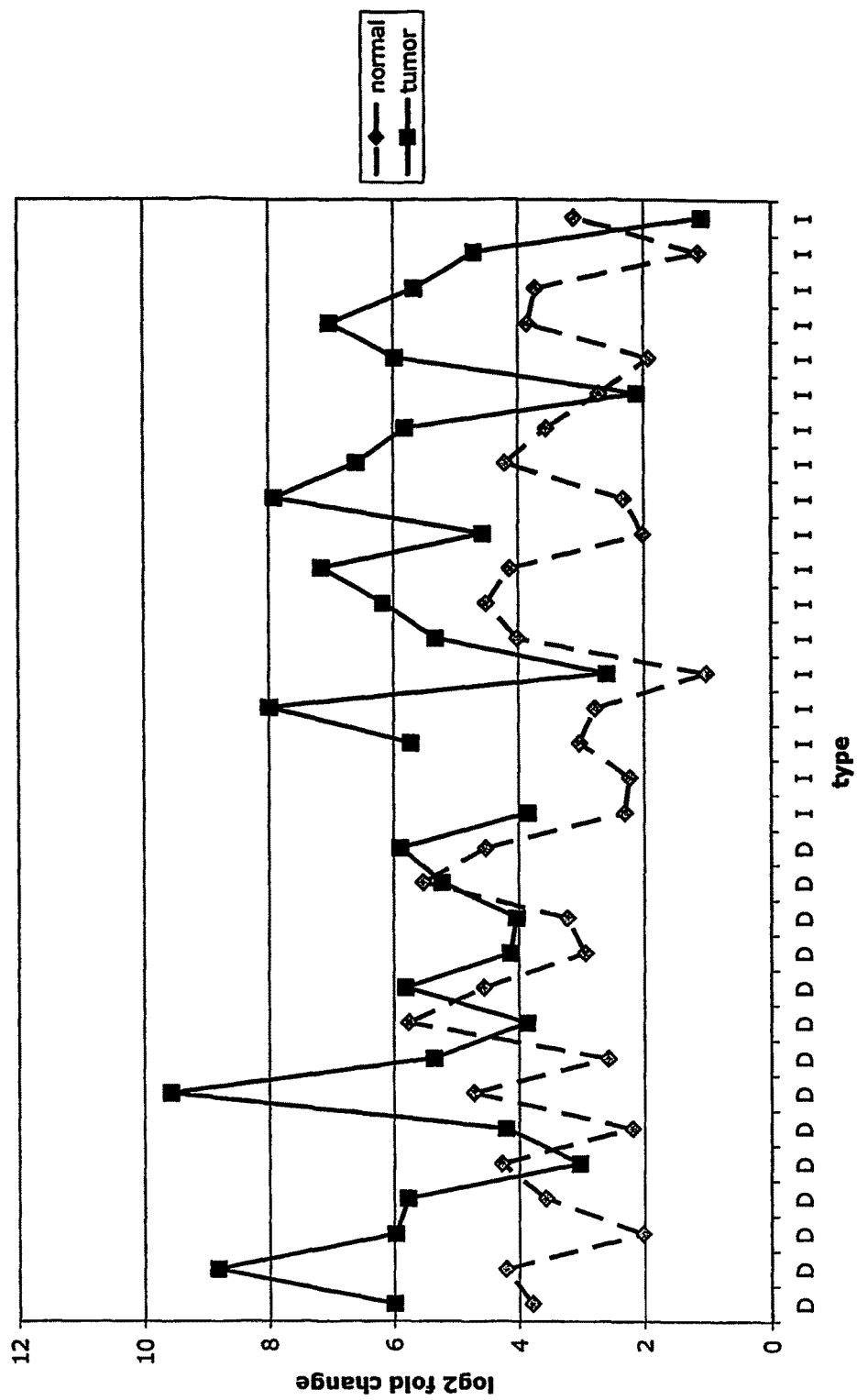
Fig. 11q SFRP2

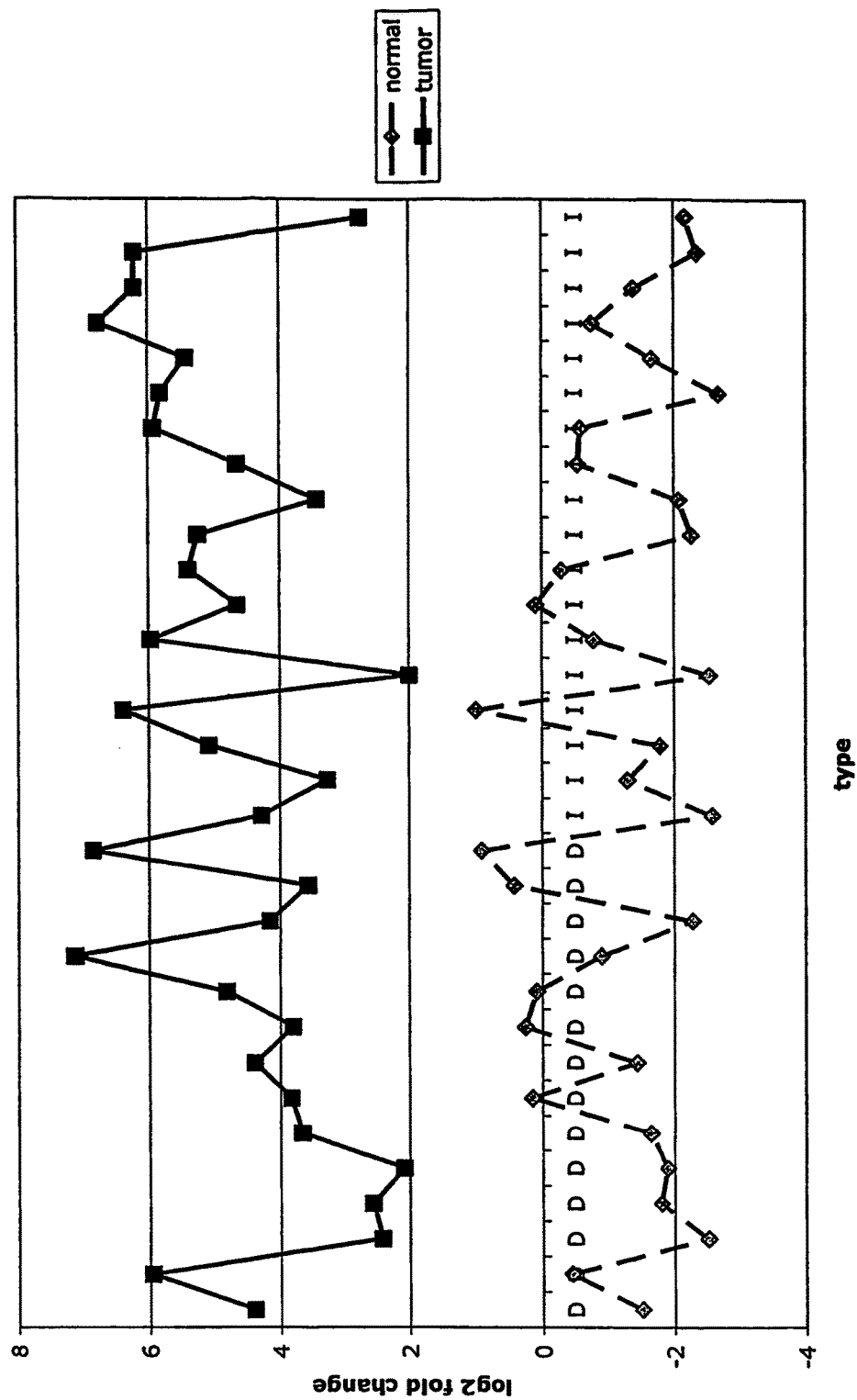

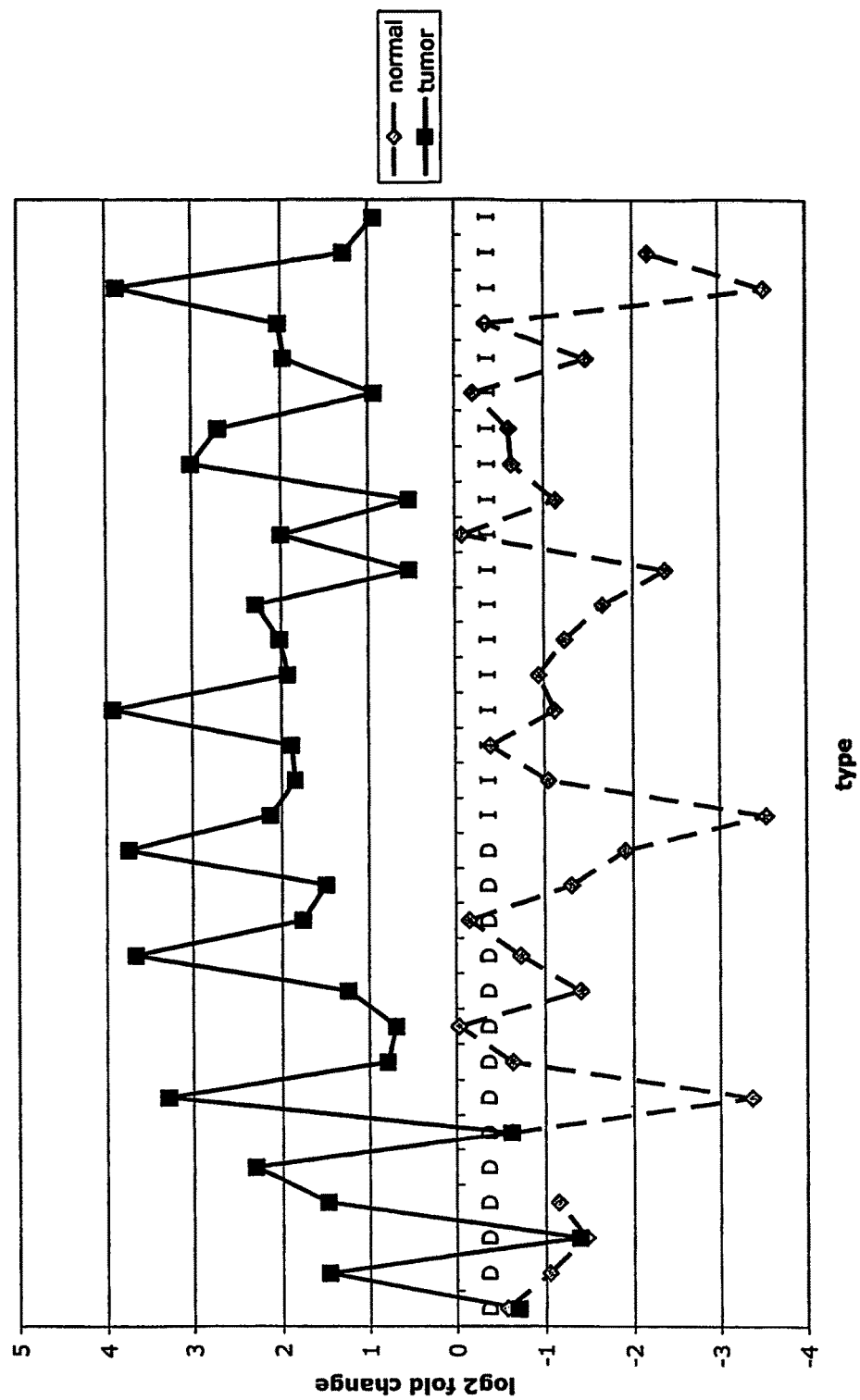
Fig. 11s SPARC

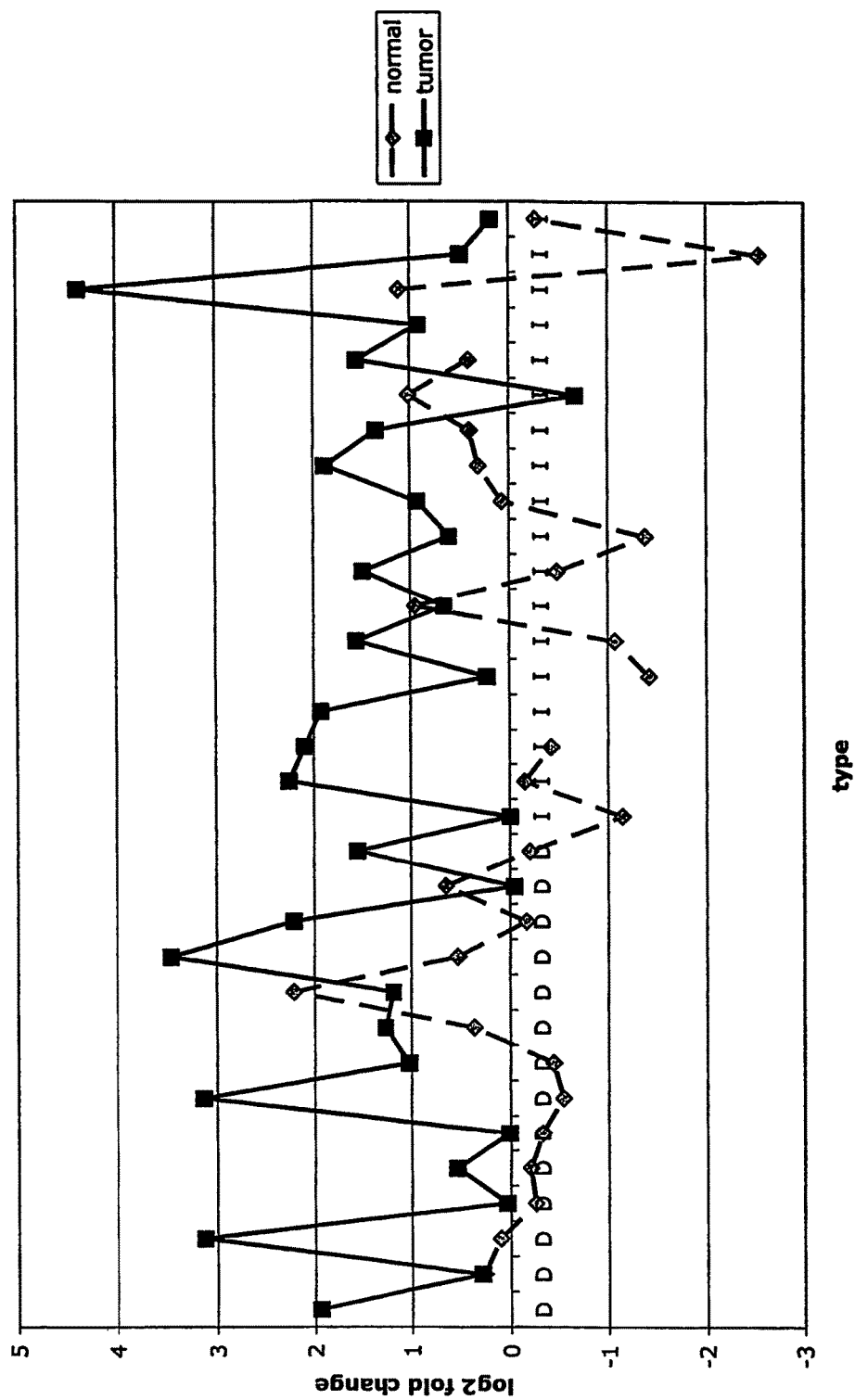

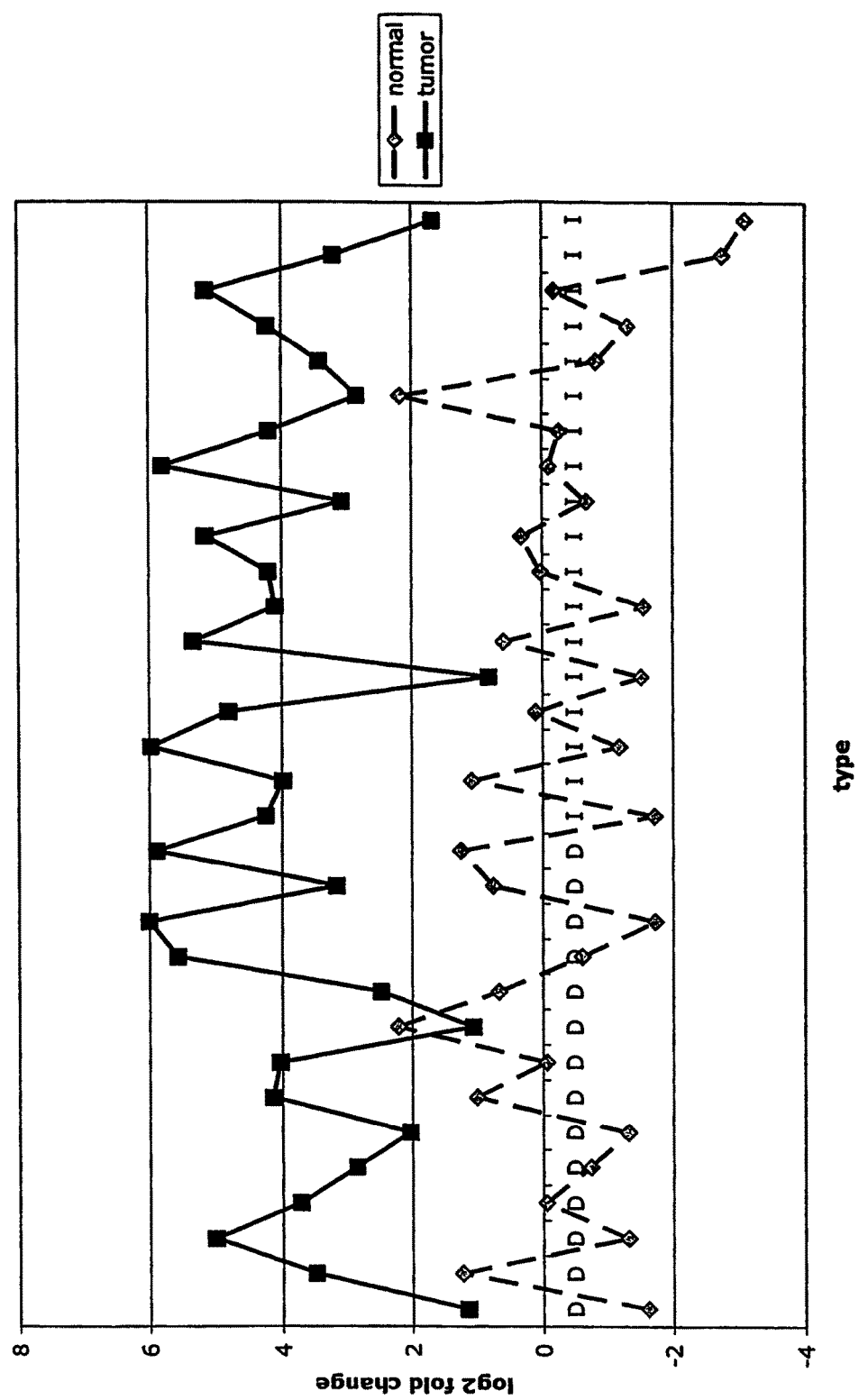

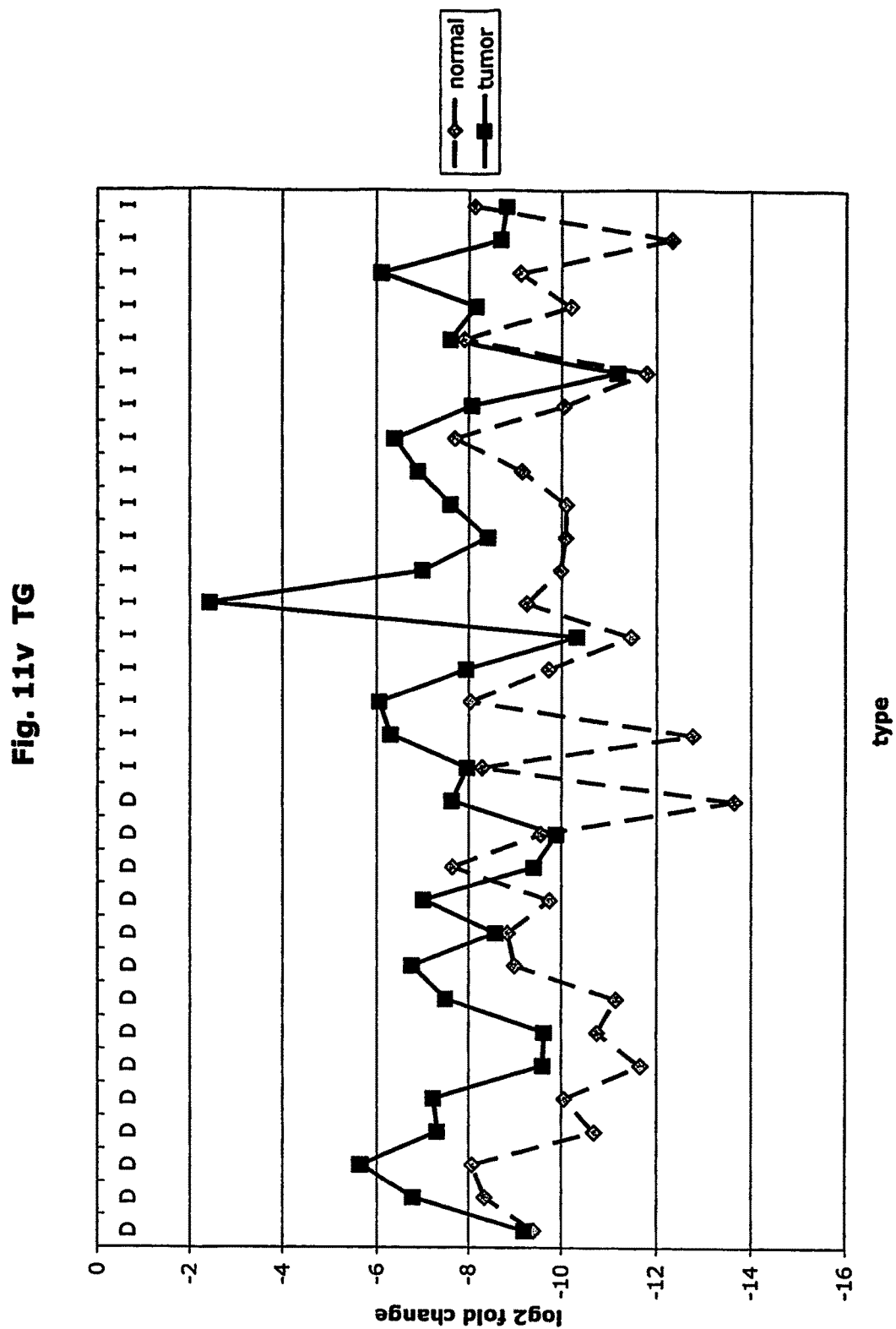
Fig. 11v TG

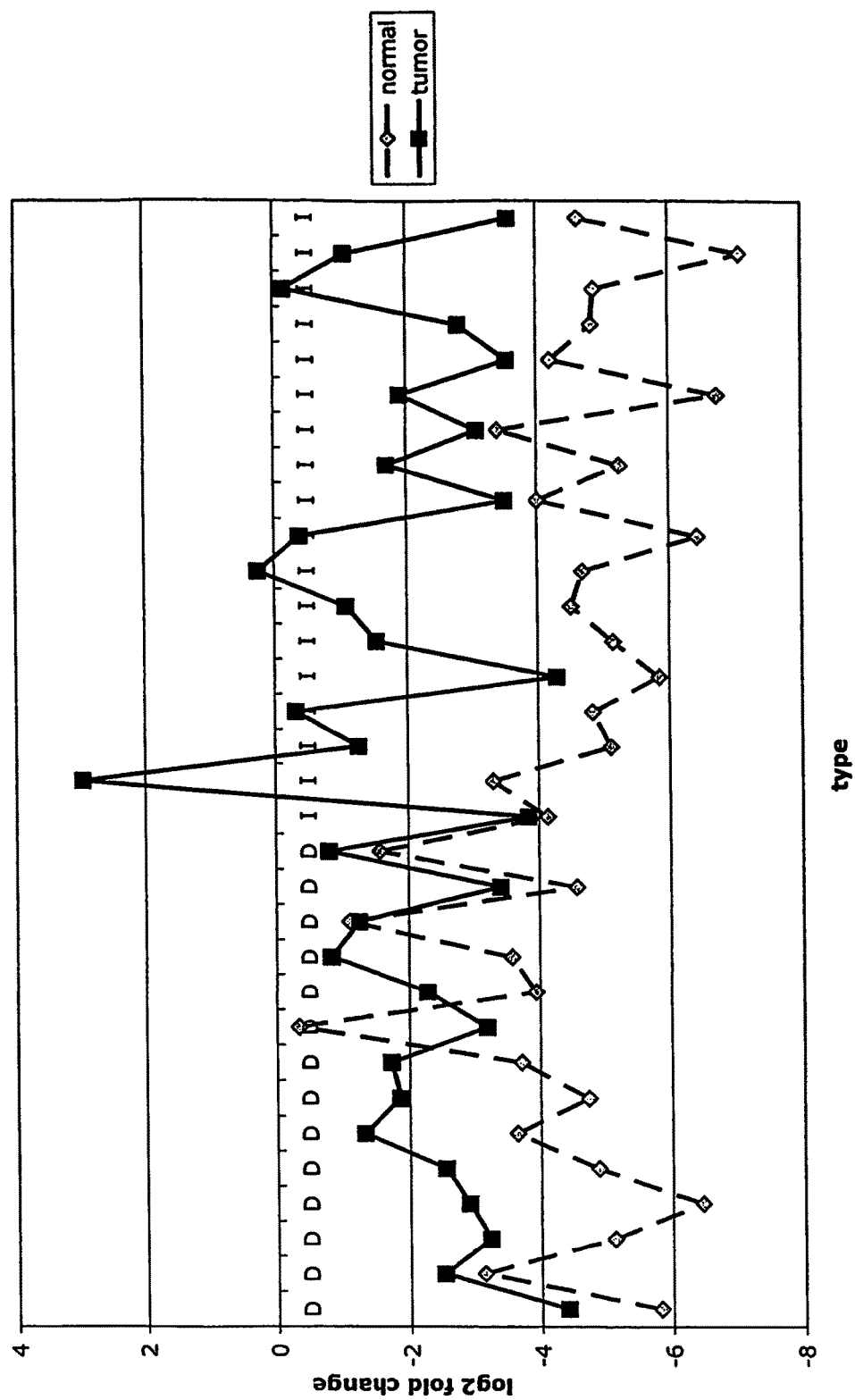
Fig. 11w TGFBI

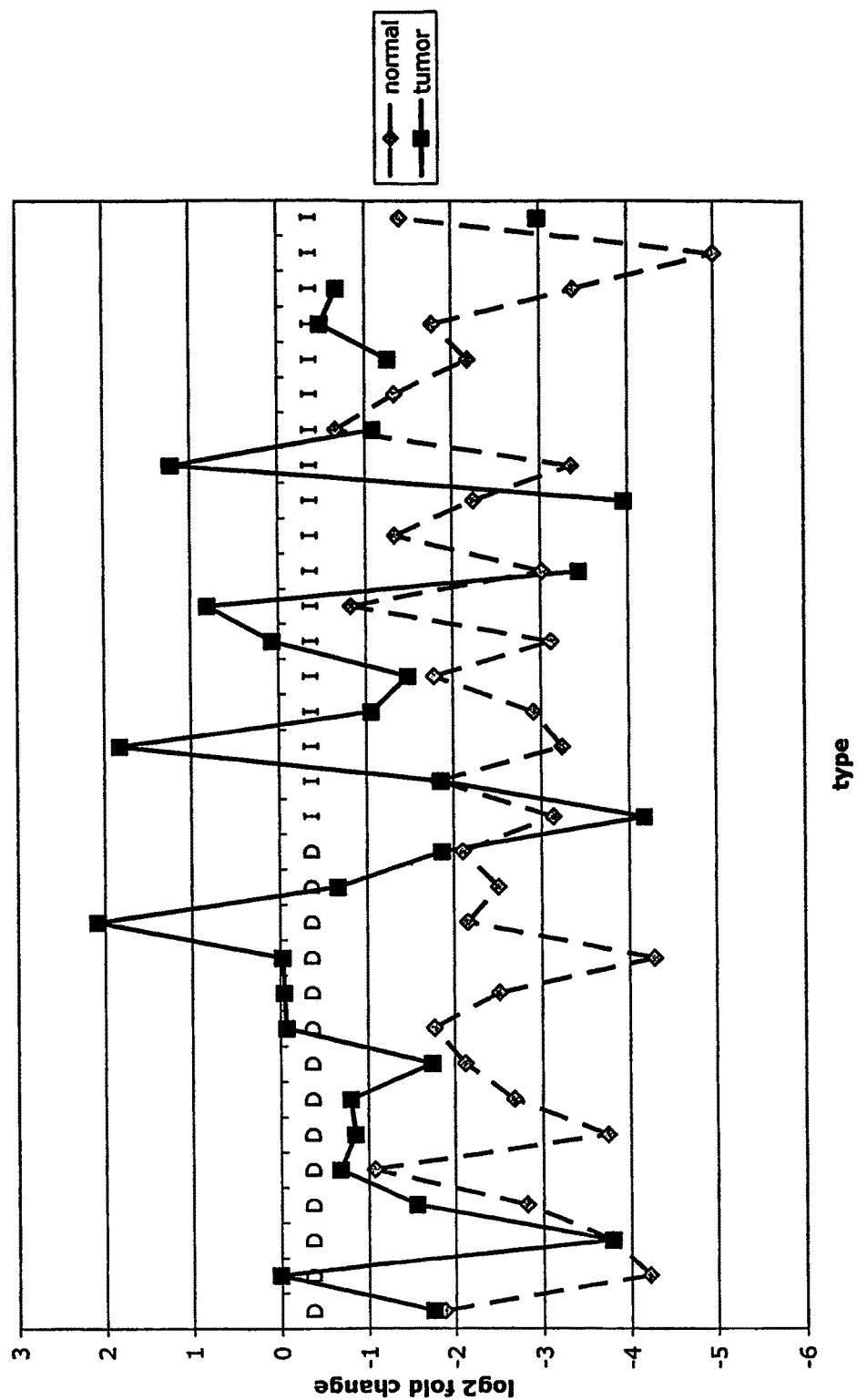

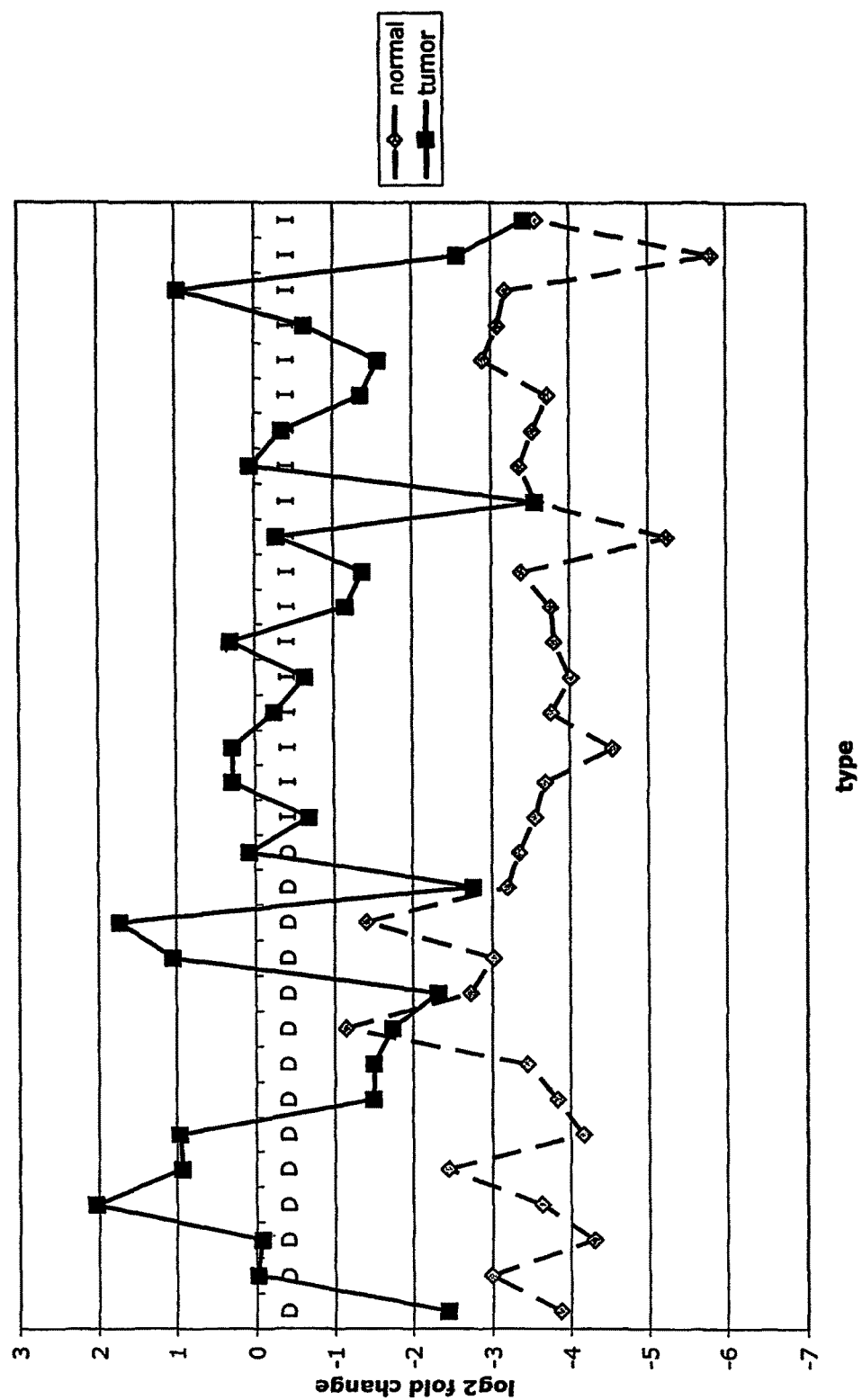
Fig. 11y SERPINH1

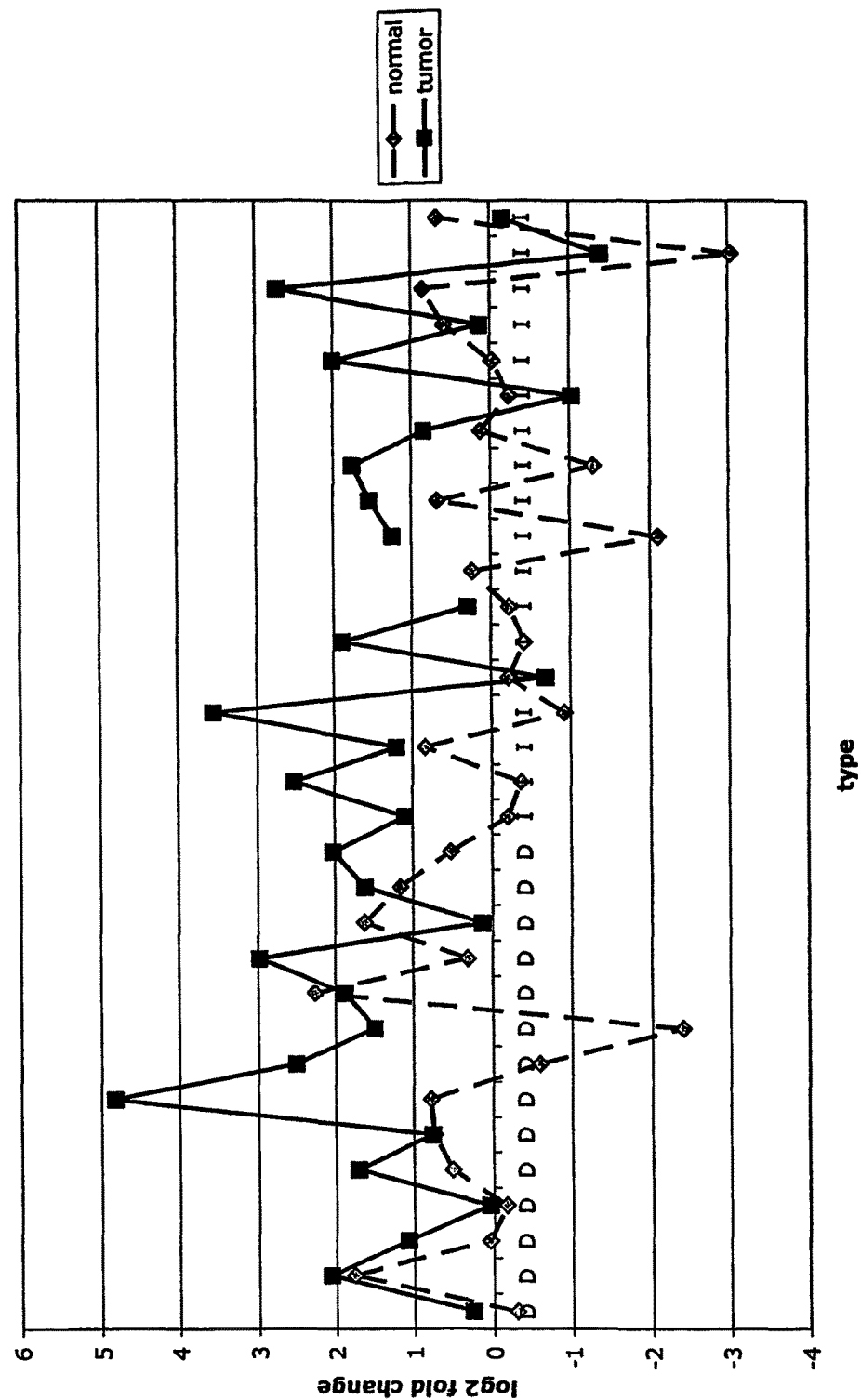

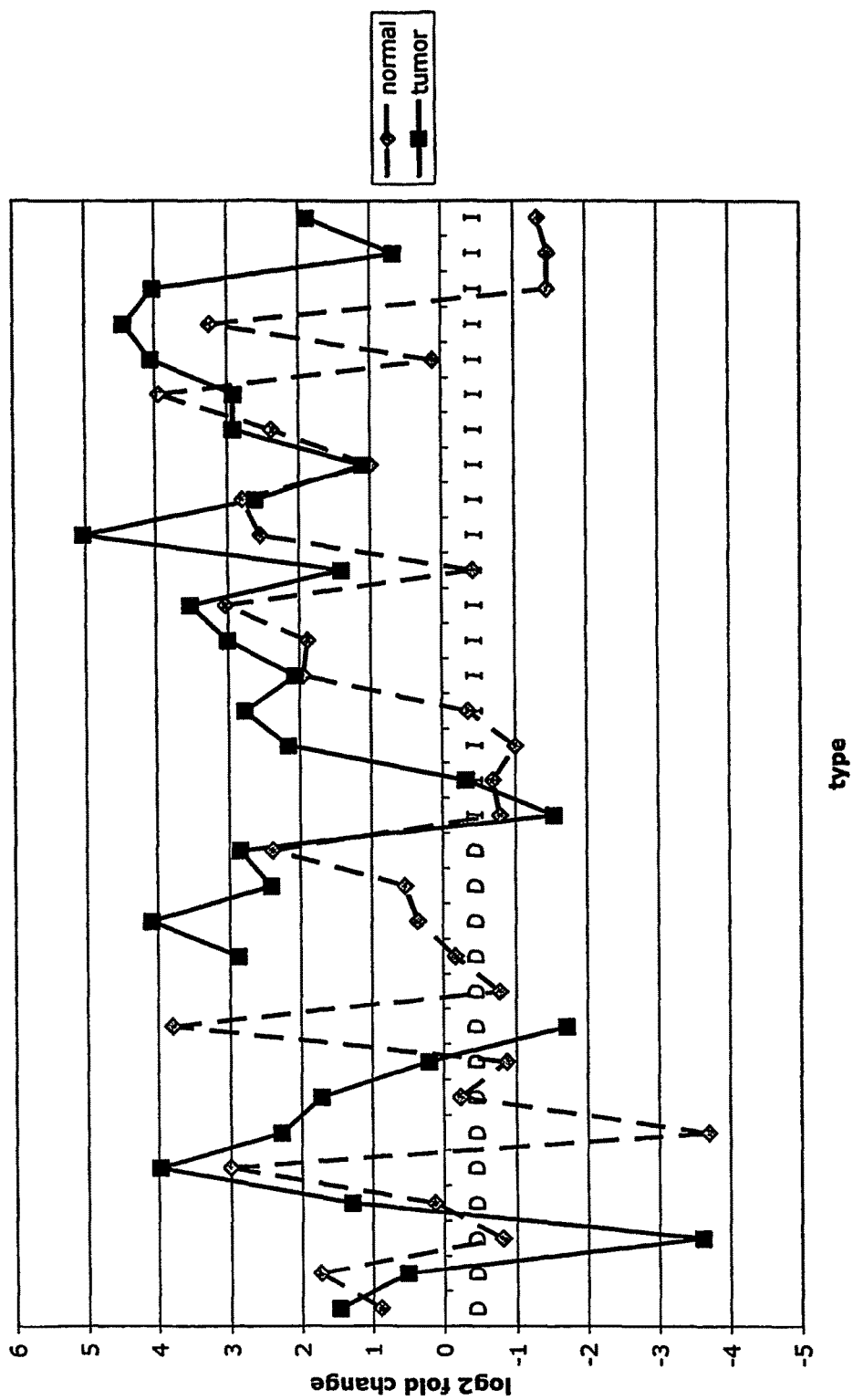
Fig. 11aa PCSK5

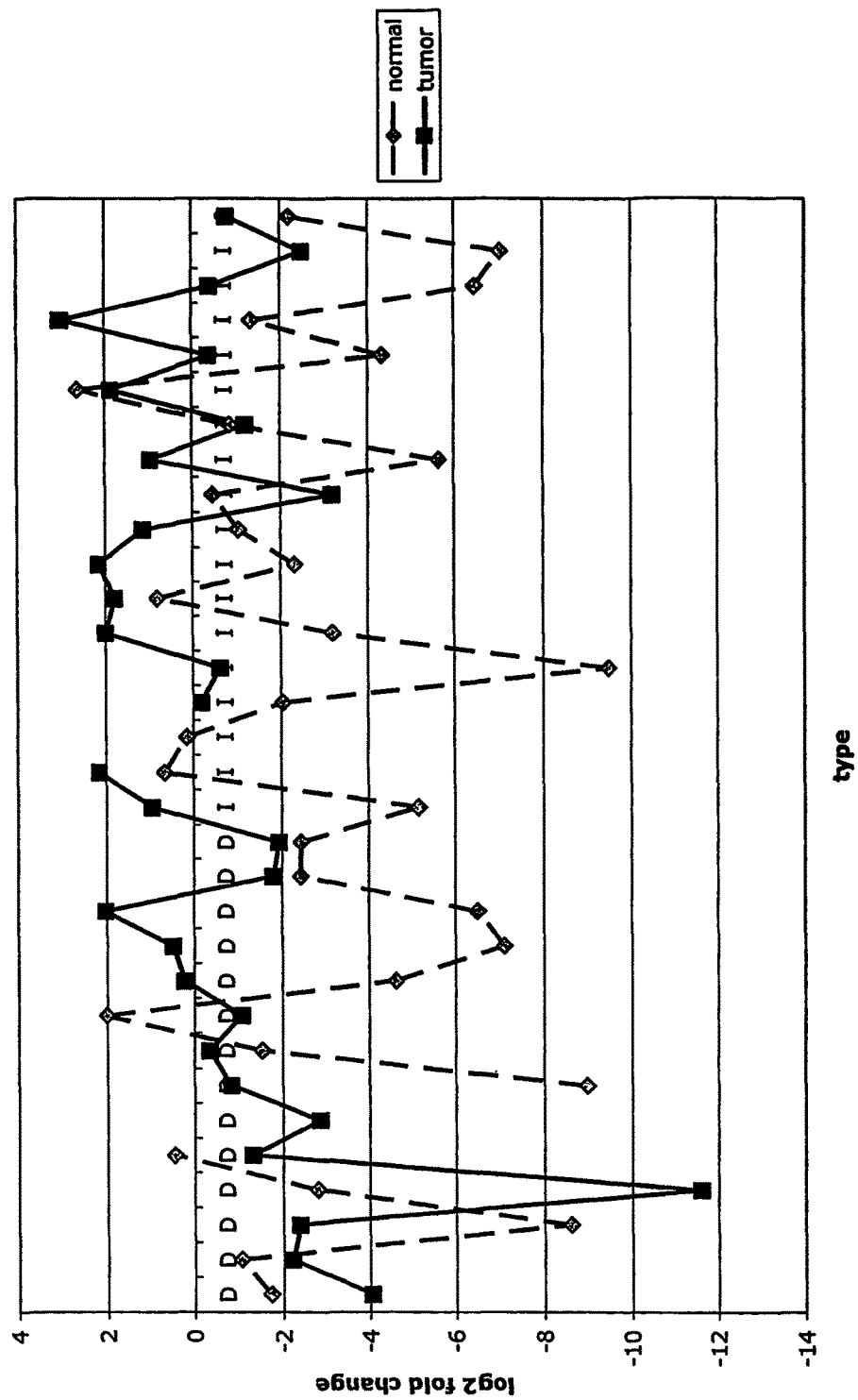

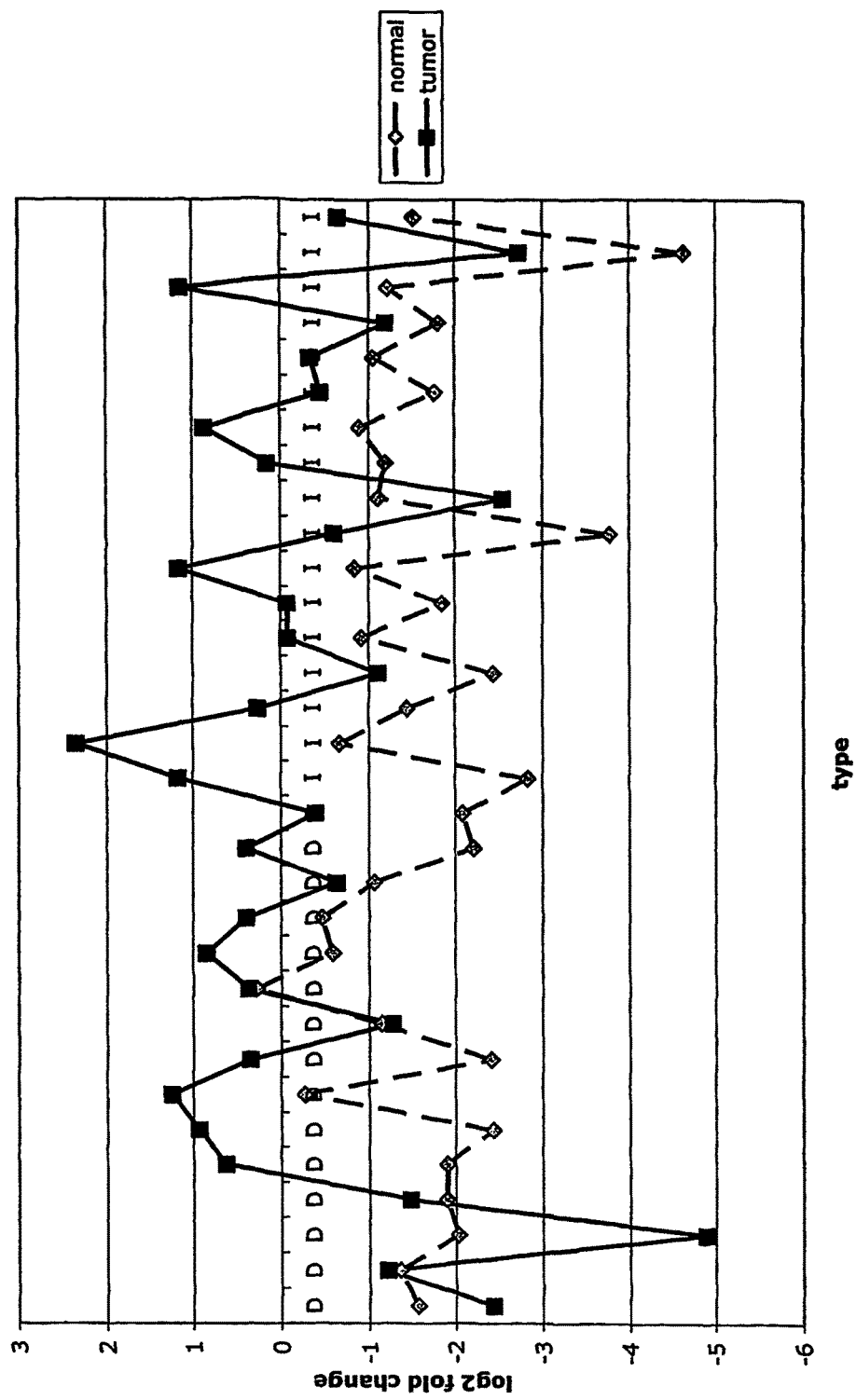

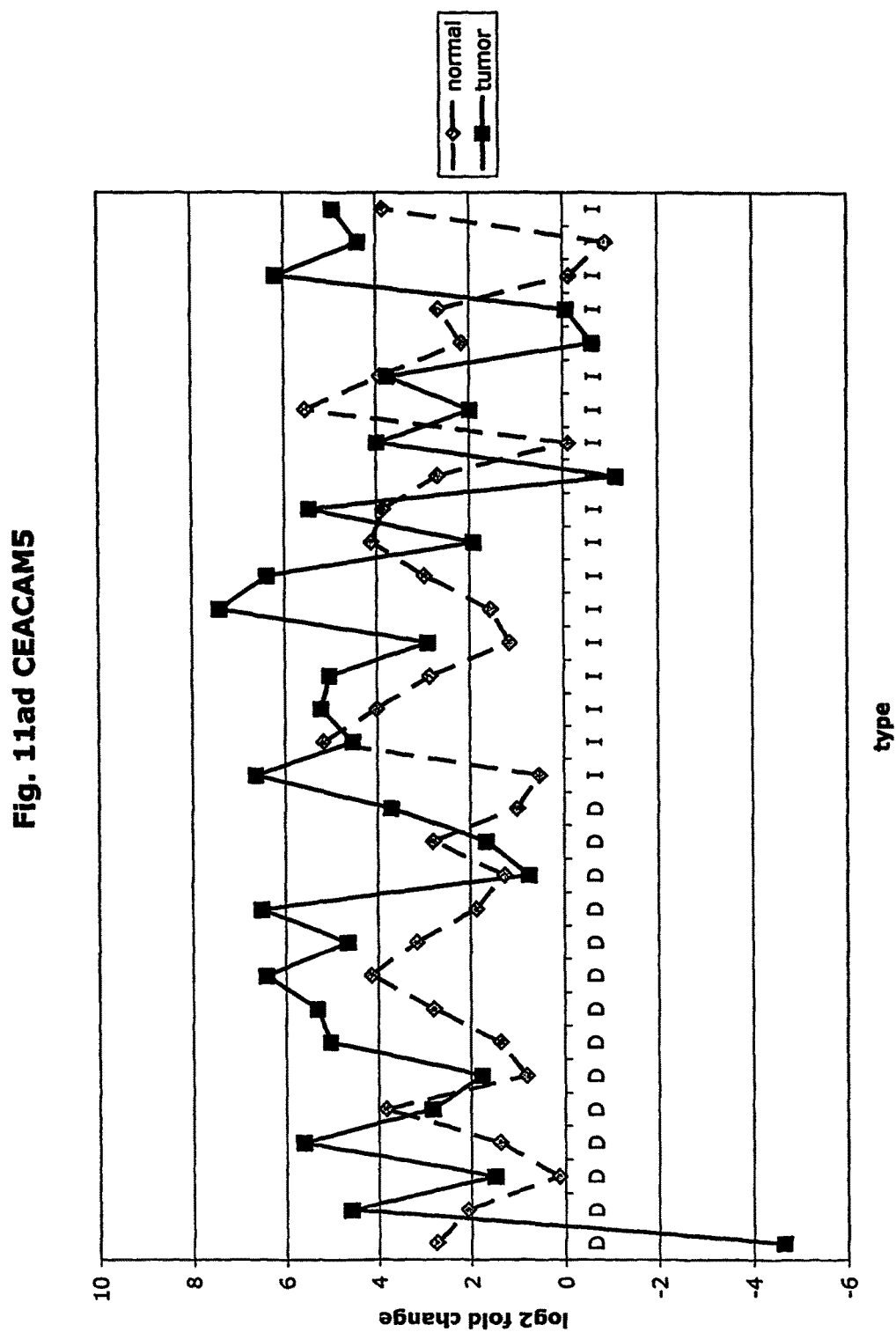
Fig. 11ad CEACAM5

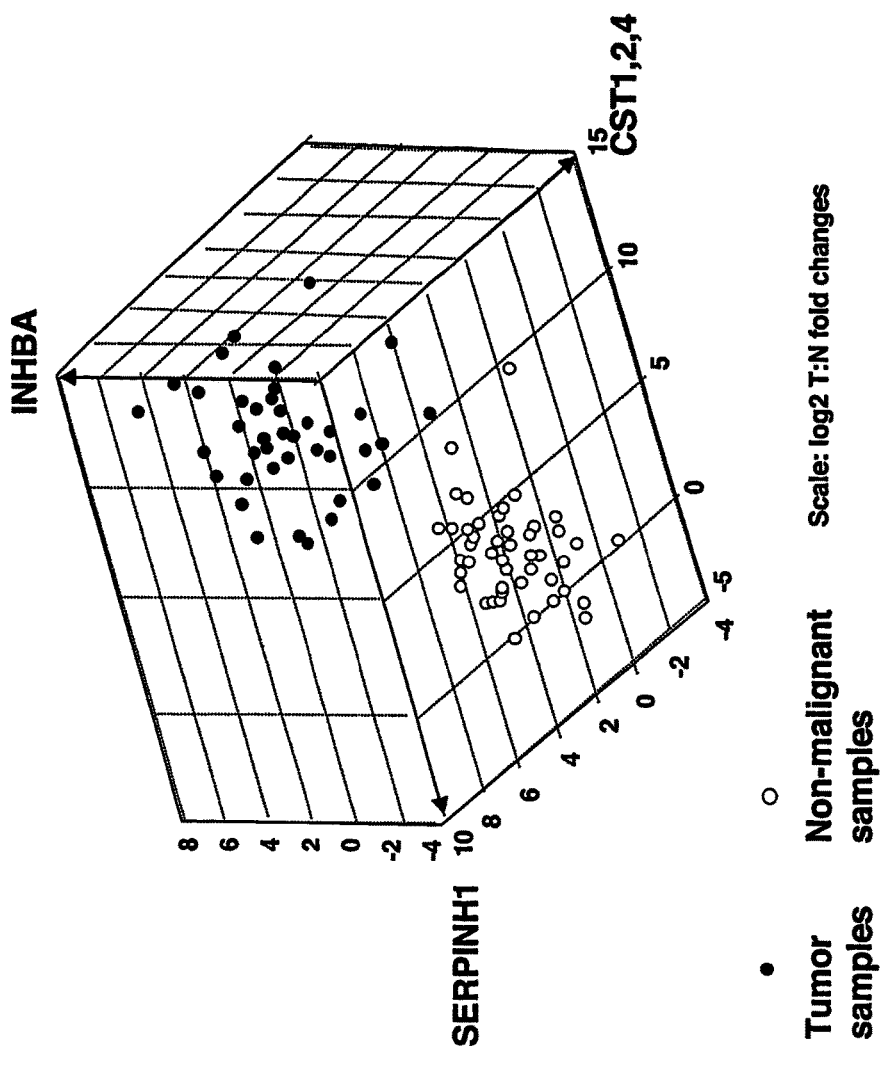
Fig. 12 The separation of gastric tumor samples from non-malignant samples using three markers

| Number of markers in test | Total possible tests | Number of tests with sensitivity | | | Proportion of tests with sensitivity | | |
|---|---|---|---|---|---|---|---|
| | | >=90% | >=95% | >=99% | >=90% | >=95% | >=99% |
| 1 | 29 | 2 | 1 | 0 | 6.9% | 3.4% | 0% |
| 2 | 406 | 33 | 27 | 1 | 8.1% | 6.7% | 0.2% |
| 3 | 3654 | 796 | 457 | 50 | 21.8% | 12.5% | 1.4% |

Fig. 13. The effect of multiple markers on the ability to accurately discriminate between tumor tissue and non-malignant tissue.

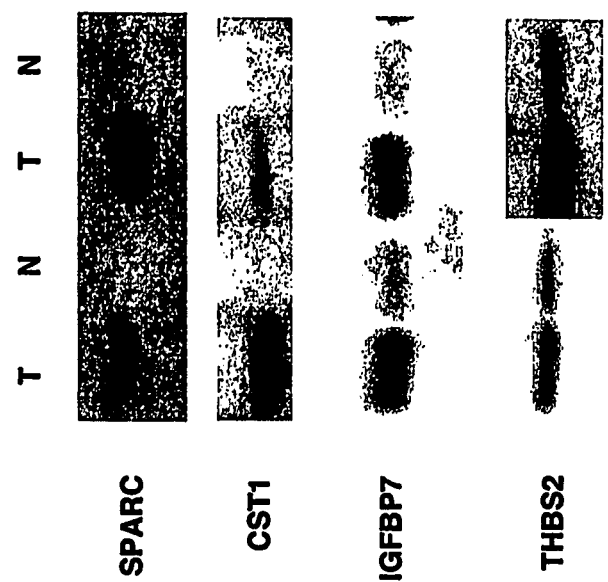
Fig. 14. Western analysis of markers in tumor and non-malignant tissue

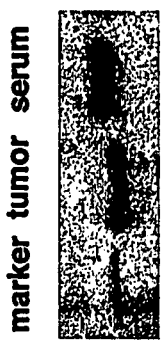
Fig. 15. Western analysis of SPARC in gastric tumor material and serum.

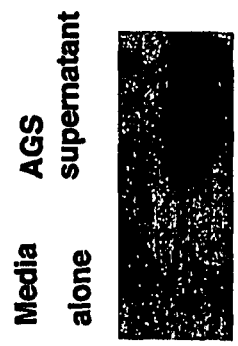
Fig. 16. Immunodetection of cystatin SN in the supernatant of the gastric cancer cell line, AGS.

MARKERS FOR DETECTION OF GASTRIC CANCER

RELATED APPLICATION

This application claims priority under 35 U.S.C. 119 to U.S. Provisional Patent Application Ser. No 60/487,906, filed Jul. 17, 2003, titled "Markers for Detection of Gastric Cancer," listing Parry John Guilford as inventor. The above application is herein incorporated fully by reference.

FIELD OF THE INVENTION

This invention relates to detection of cancer. Specifically, this invention relates to the use of genetic and/or protein markers for detection of cancer, and more particularly to the use of genetic and/or protein markers for detection of gastric cancer.

BACKGROUND

Survival of cancer patients is greatly enhanced when the cancer is detected and treated early. In the case of gastric cancer, patients diagnosed with early stage disease have 5-year survival rates of 90%, compared to approximately 10% for patients diagnosed with advanced disease. However, the vast majority of gastric cancer patients currently present with advanced disease. Therefore, developments that lead to early diagnosis of gastric cancer can lead to an improved prognosis for the patients.

Identification of specific cancer-associated markers in biological samples, including body fluids, for example, blood, urine, peritoneal washes and stool extracts can provide a valuable approach for the early diagnosis of cancer, leading to early treatment and improved prognosis. Specific cancer markers also can provide a means for monitoring disease progression, enabling the efficacy of surgical, radiotherapeutic and chemotherapeutic treatments to be tracked. However, for a number of major cancers, the available markers suffer from insufficient sensitivity and specificity. For example, the most frequently used markers for gastric cancer, ca19-9, ca72-4 and chorioembryonic antigen (CEA) detect only about 15-50% of gastric tumors of any stage, declining to approximately 2-11% for early stage disease. Thus, there is a very high frequency of false negative tests that can lead patients and health care practitioners to believe that no disease exists, whereas in fact, the patient may have severe cancer that needs immediate attention. Moreover, these markers can give false positive signals in up to ⅓ of individuals affected by benign gastric disease.

SUMMARY OF THE INVENTION

Thus, there is an acute need for better methods for detecting the presence of cancer. Aspects of this invention provide methods, compositions and devices that can provide for detection of early stage cancer, and decreasing the frequency of false positives and false negative test results.

In certain embodiments, molecular analysis can be used to identify genes that are over-expressed in gastric tumor tissue compared to non-malignant gastric tissue. Such analyses include microarray and quantitative polymerase chain reaction (qPCR) methods. Cancer genes and proteins encoded by those genes are herein termed gastric tumor markers (GTM). It is to be understood that the term GTM does not require that the marker be specific only for gastric tumors. Rather, expression of GTM can be increased in other types of tumors, including malignant or non-malignant tumors, including gastric, bladder, colorectal, pancreatic, ovarian, skin (e.g., melanomas), liver, esophageal, endometrial and brain cancers, among others. It should be understood, however that the term GTM does not include prior the art markers, ca19-9, ca72-4 and CEA. Some GTM are sufficiently over-expressed to be diagnostic of gastric cancer with a high degree of reliability, and in other cases, over-expression of two or more GTM can provide reliable diagnosis of gastric cancer.

In certain embodiments, microarray methods can be used to detect patterns of over-expression of one or more genes associated with cancer.

In other embodiments, quantitative polymerase chain reaction (qPCR) can be used to identify the presence of markers over expressed in tumor or other biological samples.

Some of the embodiments of GTM detection disclosed herein are over expressed in a highly selective fashion in tumor cells and little, if at all, in non-tumor cells, permitting sensitive and accurate detection of cancer with measurement of only one over expressed GTM. In other embodiments, over-expression of two, three or more GTM can be detected in a sample and can provide greater certainty of diagnosis.

Selected genes that encode proteins can be secreted by or cleaved from the cell. These proteins, either alone or in combination with each other, have utility as serum or body fluid markers for the diagnosis of gastric cancer or as markers for monitoring the progression of established disease. Detection of protein markers can be carried out using methods known in the ark and include the use of monoclonal antibodies, polyclonal antisera and the like.

BRIEF DESCRIPTION OF THE FIGURES

This invention is described with reference to specific embodiments thereof and with reference to the figures, in which:

FIG. 1 depicts a table of markers and oligonucleotide sequences of markers for gastric cancer of this invention.

FIG. 2 depicts a table of results obtained of studies carried out using microarray methods.

FIG. 3 depicts a table of results obtained of studies carried out using quantitative PCR.

FIG. 4a: ASPN. FIG. 4b: SPP1. FIG. 4c: SPARC. FIG. 4d: MMP12.

FIG. 5a: ASPN; FIG. 5w: TGFBI.

FIGS. 7a-7c depicts graphs that show relative log 2 expression of the markers in individual tumor samples and non-malignant samples compared to the expression of the gene for the tumor marker, CEA. CEA is the serum marker currently most used to monitor progression of gastric cancer.

FIG. 8 shows a table that complements FIG. 3. FIG. 8 summarizes expression levels determined by qPCR for the candidate tumor markers, but using the paired data (i.e., tumor ("T") and non-malignant ("N") samples from the same individual) to provide a T:N ratio. FIG. 8 also includes additional markers not included in FIG. 3, namely MMP2, CGR11, TGFB1, PCSK5, SERPINB5, SERPINH1. For comparison, the expression level of the established serum marker gene, CEACAM5 (CEA), is also shown. 27 of the 29 markers have a median T:N difference greater than or equal to CEA. Further, compared to CEA, 29/29 of the markers have a higher percentage of paired samples in which the expression in the tumor sample exceeds the expression in the normal sample. Three markers, CST1,2,44, ASPN and SFRP4 showed 100% discrimination between the paired tumor and normal samples. The gene sequences of these markers, and the location of the primers and probes used to detect them, are shown herein.

FIGS. 9a-9d depict individual and median T:N fold change data for 29 gastric cancer markers in 40 patients with paired samples.

FIGS. 10a-10ad depict graphs of tumor stage and log 2 fold change in expression of CEA and other GTM of this invention. FIG. 10a: adlican; FIG. 10b: ASPN; FIG. 10c: CSPG2; FIG. 10d: CST1,2,4; FIG. 10e: EFEMP2; FIG. 10f: GGF; FIG. 10g: INHBA; FIG. 10h: IGFBP7; FIG. 10i: KLK10; FIG. 10j: LEPRE1; FIG. 10k: LUM; FIG. 10l: LOXL2; FIG. 10m: MMP12; FIG. 10n: TIMP1; FIG. 10o: ASAH1; FIG. 10p: SPP1; FIG. 10q: SFRP2; FIG. 10r: SFRP4; FIG. 10s: SPARC; FIG. 10t: PRSS11; FIG. 10u: THBS2; FIG. 10v: TG; FIG. 10w: TGFBI; FIG. 10x: CGR11; FIG. 10y: SERPINH1; FIG. 10z: MMP2; FIG. 10aa: PCSK5; FIG. 10ab: SERPINB5; FIG. 10ac: TGFB1 and FIG. 10ad: CEA (CEACAM5).

FIGS. 11a-11ad depict graphs of tumor type (diffuse (D) or intestinal (I)) and log 2 fold change in expression 29 GTM of this invention and CEA. FIG. 11a: adlican; FIG. 11b: ASPN; FIG. 11c: CSPG2; FIG. 11d: CST1,2,4; FIG. 11e: EFEMP2; FIG. 11f: GGH; FIG. 11g: INHBA; FIG. 11h: IGFBP7; FIG. 11i: KLK10; FIG. 11j: LEPRE1; FIG. 11k: LUM; FIG. 11l: LOXL2; FIG. 11m: MMP12; FIG. 11n: TIMP1; FIG. 11o: ASAH1; FIG. 11p: SPP1; FIG. 11q: SFRP2; FIG. 11r: SFRP4: FIG. 11s; SPARC; FIG. 11t: PRSS11: FIG. 11u: THBS2; FIG. 11v: TG; FIG. 11w: TGFBI; FIG. 11x: CGR11: FIG. 11y: SERPINH1; FIG. 11z: MMP2; FIG. 11aa: PCSK5; FIG. 11ab:SERPINB5; FIG. 11ac: TGFB1 and FIG. 11ad: CEA (CEACAM5).

FIG. 12 depicts a three-dimensional graph showing 3 markers, SERPINH1, CST1,2,4 and INHBA, in a series of gastric tumor samples and non-malignant gastric samples.

FIG. 13 depicts a table that shows the effect of multiple markers on the ability to accurately discriminate between tumor tissue and non-malignant tissue. The table has been derived from normal distributions derived from qPCR data.

FIG. 14 is a Western blot of 4 tumor markers derived from tumor and non-tumor tissue.

FIG. 15 is a Western blot of the tumor marker SPARC in gastric tumor tissue and in serum.

FIG. 16 is an immunoblot depicting cystatin SN in the supernatant of a gastric cell line, AGS.

DETAILED DESCRIPTION

Definitions

Figure 4A:
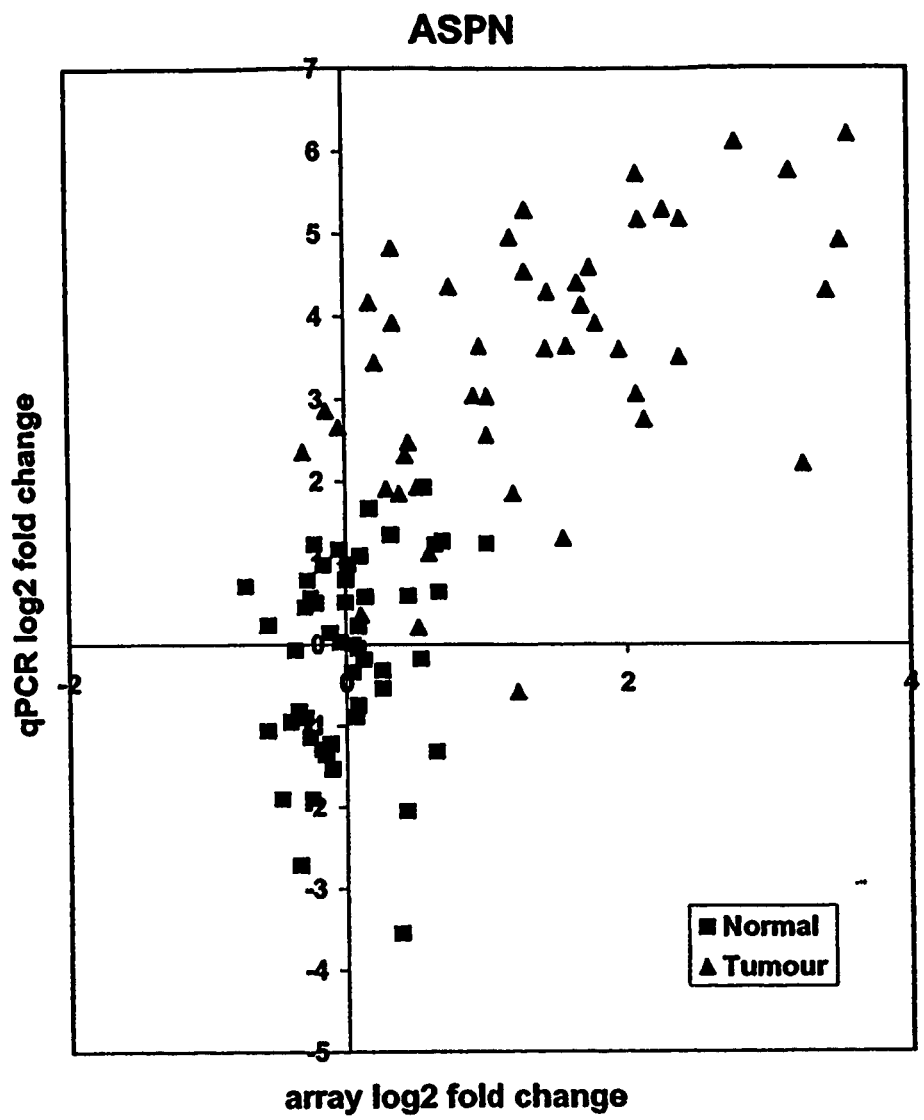
FIGS. 4a-4d depict relationships between log 2 fold results obtained using array and qPCR methods, in which the data is centered on the median normal for four gastric cancer markers. Grey squares correspond to nonmalignant ("normal") samples and black triangles to tumor samples.
Figure 4B:
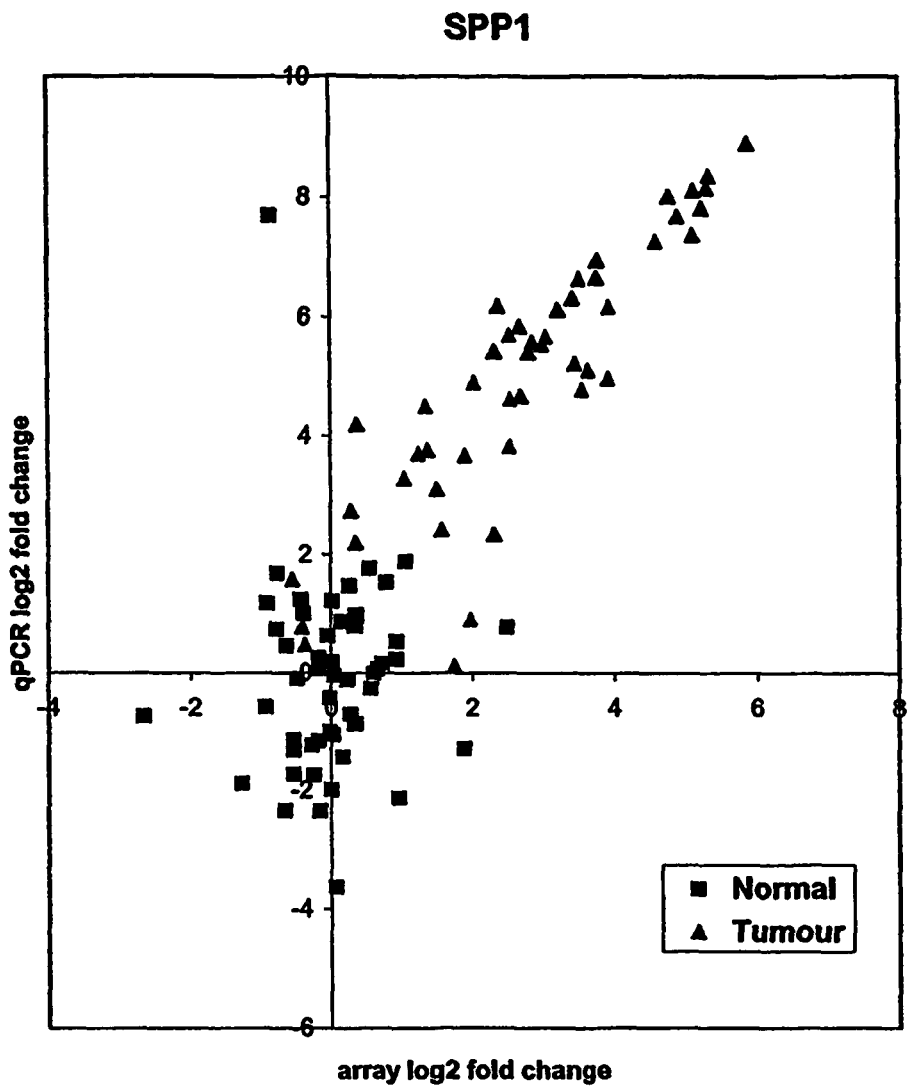
Figure 4C:
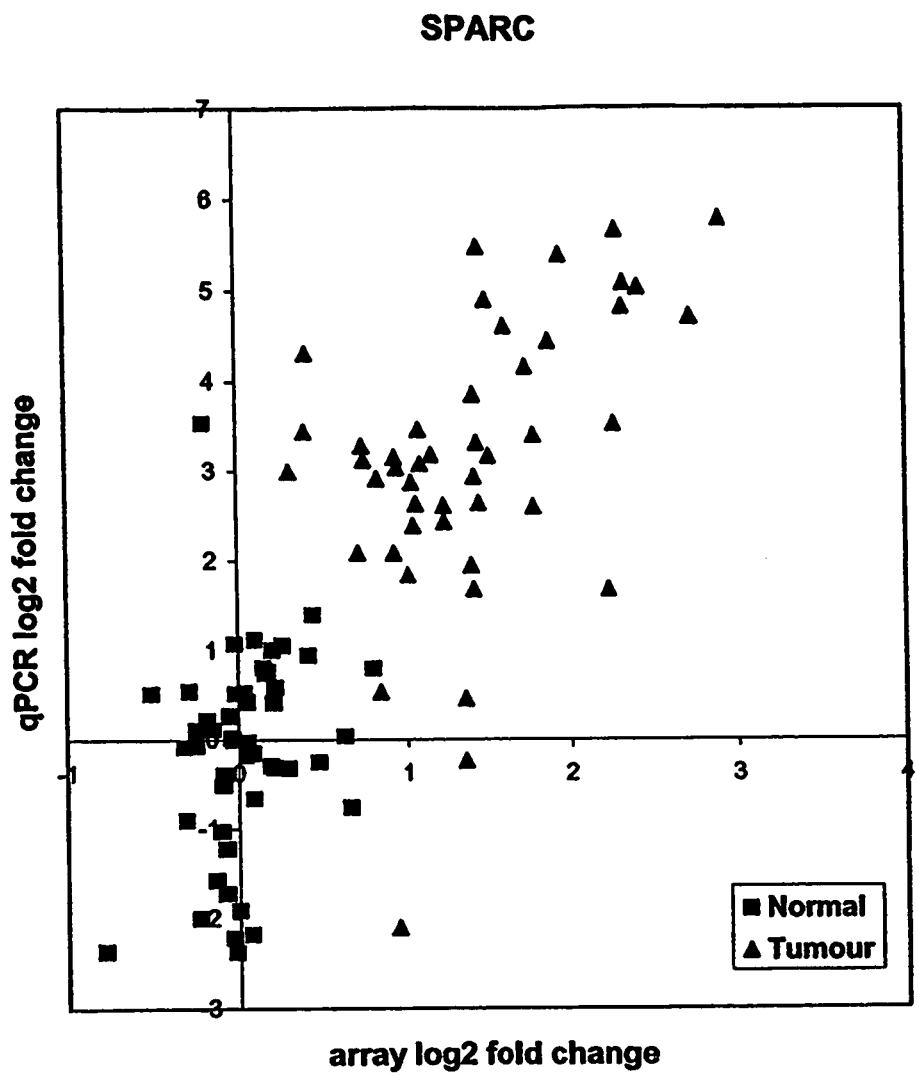
Figure 4D:
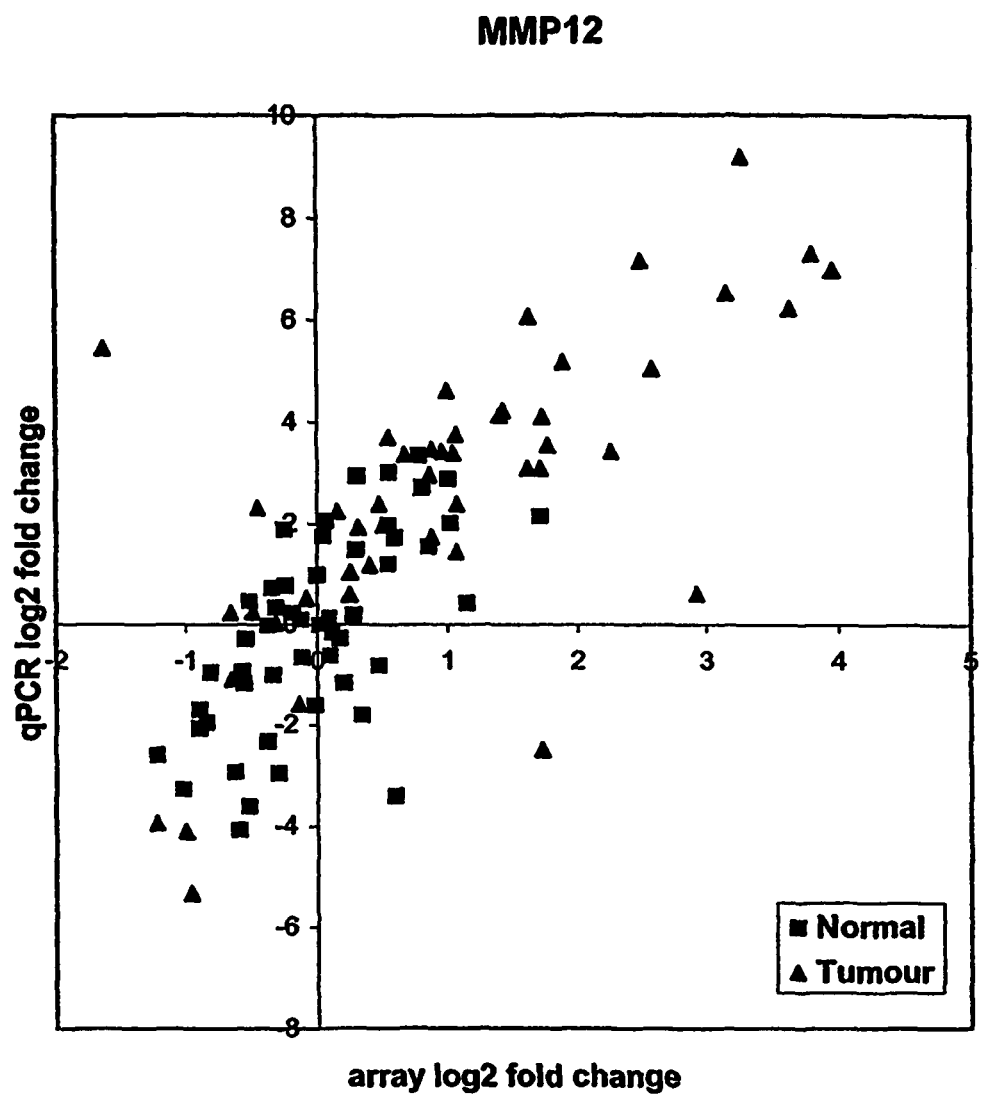

Before describing embodiments of the invention in detail, it will be useful to provide some definitions of terms as used herein.

The term "GTM" or "gastric tumor marker" or "GTM family member" means a gene, gene fragment, RNA, RNA fragment, protein or protein fragment related or other identifying molecule associated with gastric cancer that does not include molecules that are known in the prior art to be associated with gastric cancer, ca19-9, ca724 and CEA. Examples of GTMs are included herein below.

The term "marker" means a molecule that is associated quantitatively or qualitatively with the presence of a biological phenomenon. Examples of "markers" are GTMs, however, "markers" also includes metabolites, byproducts, whether related directly or indirectly to a mechanism underlying a condition.

The term "qPCR" means quantitative polymerase chain reaction.

The term "expression" includes production of mRNA from a gene or portion of a gene, and includes the production of a protein encoded by an RNA or gene or portion of a gene, and includes appearance of a detection material associated with expression. For example, the binding of a binding ligand, such as an antibody, to a gene or other oligonucleotide, a protein or a protein fragment and the visualization of the binding ligand is included within the scope of the term "expression." Thus, increased density of a spot on an immunoblot, such as a Western blot, is included within the term "expression" of the underlying biological molecule.

The term "CPN2" means human carboxypeptidase N, polypeptide 2, 83 kDa chain; and carboxypeptidase N.

The term "HAPLN4" means human hyaluronan glycoprotein link protein 4.

The term "MMP12" means human matrix metalloproteinase 12.

The term "INHBA" means human inhibin, beta A (also includes activin A, activin AB or alpha polypeptide).

The term "IGFBP7" means human insulin-like growth factor 7.

The term "GGH" means human gamma-glutamyl hydrolase (also known as conjugase, folylpolygammaglutamyl hydrolase).

The term "LEPRE1" means human leucine proline-enriched proteoglycan (also known as leprecan 1).

The term "CST4" means human cystatin S.

The term "SFRP4" means human secreted frizzled-related protein 4.

The term "ASPN" means human asporin (also known as LRR class 1).

The term "CGREF1" or "CGR11" means human cell growth regulator with EF hand domain 1.

The term "KLK" means either human kallikrein 10, variant 1 or human kallikrein 10, variant 2, or both, unless specified otherwise.

The term "TIMP1" means human tissue inhibitor of metalloproteinase 1 (also known as erythroid potentiating activity or collagenase inhibitor).

The term "SPARC" means human secreted protein, acidic, cysteine-rich (also known as osteonectin).

The term "TGFBI" means human transforming growth factor, beta-induced, 68 kDa.

The term "EFEMP2" means human EGF-containing fibulin-like extracellular matrix protein 2.

The term "LUM" means human lumican.

The term "SNN" means human stannin.

The term "SPP1" means human secreted phosphoprotein 1 (also known as osteopontin, or bone sialoprotein I, or early T-lymphocyte activation 1).

The term "CSPG2" means human chondroitin sulfate proteoglycan 2 (also known as versican).

The term "ASAH1" means human N-acylsphingosine amidohydrolase, variant 1, or N-acylsphingosine amidohydrolase, variant 2, or both N-acylsphingosine amidohydrolase variants 1 and 2 (also known as acid ceramidase 1, variants 1 and 2).

The term "PRSS11" means human protease, serine, 11 (also known as IGF binding serine protease).

The term "SFRP2" means human secreted frizzled-related protein 2.

The term "PLA2G12B" means human phospholipase A2, group XIIB.

The term "SPON2" means human spondin 2, extracellular matrix protein.

The term "OLFM1" means human olfactomedin 1.

The term "TSRC1" means human thrombospondin repeat containing 1.

The term "THBS2" means human thrombospondin 2.

The term "adlican" means DKFZp564I1922.

The term "CST2" means human cystatin SA.

The term "CST1" means human cystatin SN.

The term "LOXL2" means human lysyl oxidase-like enzyme 2.

The term "TG" means human thyroglobulin.

The term "TGFB1" means human transforming growth factor, beta1.

The term "SERPINH1" means human serine or cysteine proteinase inhibitor clade H (also known as heat shock protein 47, member 1, or collagen binding protein 1).

The term "SERPINB5" means human serine or cysteine proteinase inhibitor, clade B (also known as ovalbumin, member 5).

The term "CEACAM5" or "CEA" means human carcinoembryonic antigen-related cell adhesion molecule 5.

The term "MMP2" means human matrix metalloproteinase 2 (also known as gelatinase A, or 72 kDa gelatinase, or 72 kDa type IV collagenase).

The term "PCSK5" means human proprotein convertase subtilisin/kexin type 5.

It is to be understood that the above terms may refer to protein, DNA sequence and/or RNA sequence. It is also to be understood that the above terms also refer to non-human proteins, DNA and/or RNA having the same sequences as depicted herein.

DESCRIPTION OF EMBODIMENTS OF THE INVENTION

Markers for detection and evaluation of tumors including gastric cancer are provided that have a greater reliability in detecting gastric cancer than prior art markers. By the term "reliability" we include the absence of false positives and/or false negatives. Thus, with higher reliability of a marker, fewer false positives and/or false negatives are associated with diagnoses made using that marker Therefore, in certain embodiments, markers are provided that permit detection of gastric cancer with reliability greater than the reliability of prior art markers of about 50%. In other embodiments, markers are provided that have reliability greater than about 70%; in other embodiments, greater than about 73%, in still other embodiments, greater than about 80%, in yet further embodiments, greater than about 90%, in still others, greater than about 95%, in yet further embodiments greater than about 98%, and in certain embodiments, about 100% reliability.

Thus, we have surprisingly found numerous genes and proteins whose presence is associated with gastric tumors. Detection of gene products (e.g., oligonucleotides such as mRNA) and proteins and peptides translated from such oligonucleotides therefore can be used to diagnose tumors, such as gastric tumors. Array analysis of samples taken from patients with gastric tumors and from non-malignant tissues of the same subjects has led us to the surprising discovery that in many gastric tumors, specific patterns of overexpression of certain genes are associated with the disease.

Cancer markers can also be detected using antibodies raised against cancer markers.

By analyzing the presence and amounts of expression of a plurality of cancer markers can thus increase the sensitivity of diagnosis while decreasing the frequency of false positive and/or false negative results.

General Approaches to Cancer Detection

The following approaches are non-limiting methods that can be used to detect cancer including gastric cancer using GTM family members.

Microarray approaches using oligonucleotide probes selective for products of GTM genes.

Real-time quantitative PCR (qPCR) on tumor samples and normal samples using marker specific primers and probes.

Enzyme-linked immunological assays (ELISA).

Immunohistochemistry using anti-marker antibodies on gastric tumors and lymph node metastases.

Immunohistochemistry using anti-marker antibodies on other tumors including but not limited to colorectal, pancreatic, ovarian, melanoma, liver, esophageal, bladder, endometrial, and brain.

Immunodetection of marker family members in sera from gastric cancer patients taken before and after surgery to remove the tumor.

Immunodetection of marker family members in sera from healthy individuals and individuals with non-malignant diseases such as gastritis, ulceration, gastric metaplasia and dysplasia.

Immunodetection of marker family members in patients with other cancers including but not limited to colorectal, pancreatic, ovarian, melanoma, liver, esophageal, bladder, endometrial, and brain.

Detection of markers in body fluids, including serum, lymph, peritoneal fluid, cerebrospinal fluid, synovial fluid and the like.

Immunodetection of marker family members in gastric fluid, peritoneal washes, urine and stool from gastric cancer patients. Using array methods and/or qPCR.

Analysis of array or qPCR data using computers. Primary data is collected and fold change analysis is performed by comparison of levels of gastric tumor gene expression with expression of the same genes in non-tumor tissue. A threshold for concluding that expression is increased is provided (e.g., 1.5× increase, 2-fold increase, and in alternative embodiments, 3-fold increase, 4-fold increase or 5-fold increase). It can be appreciated that other thresholds for concluding that increased expression has occurred can be selected without departing from the scope of this invention. Further analysis of tumor gene expression includes matching those genes exhibiting increased expression with expression profiles of known gastric tumors to provide diagnosis of tumors.

In certain aspects, this invention provides methods for detecting cancer, comprising:
(a) providing a biological sample; and
(b) detecting the over expression of a GTM family member in said sample.

In other aspects, the invention includes a step of detecting over expression of GTM mRNA.

In other aspects, the invention includes a step of detecting over expression of a GTM protein.

In yet further aspects, the invention includes a step of detecting over-expression of a GTM peptide.

In still further aspects, the invention includes a device for detecting a GTM, comprising:

a substrate having a GTM capture reagent thereon; and a detector associated with said substrate, said detector capable of detecting a GTM associated with said capture reagent, wherein the capture reagent includes an oligonucleotide or an antibody.

Additional aspects include kits for detecting cancer, comprising:

a substrate;

a GTM capture reagent, including one or more of a GTM-specific oligonucleotide and a GTM-specific antibody; and instructions for use.

Yet further aspects of the invention include method for detecting a GTM using qPCR, comprising:

a forward primer specific for said GTM;

a reverse primer specific for said GTM;

PCR reagents;

a reaction vial; and instructions for use.

Additional aspects of this invention comprise a kit for detecting the presence of a GTM protein or peptide, comprising:

a substrate having a capture agent for said GTM protein or peptide;

an antibody specific for said GTM protein or peptide;

a reagent capable of labeling bound antibody for said GTM protein or peptide; and instructions for use.

Additional aspects of this invention include a method for manufacturing a monoclonal antibody, comprising the steps of:

In yet further aspects, this invention includes a method for detecting gastric cancer, comprising the steps of:

providing a sample from a patient suspected of having gastric cancer;

measuring the presence of a GTM protein using an ELISA method.

As described herein, detection of tumors can be accomplished by measuring expression of one or more tumor-specific markers. We have unexpectedly found that the association between increased expression of GTMs and the presence of diagnosed gastric cancer is extremely high. The least significant association detected had a p value of about $1.6 \times 10^{-6}$. Many of the associations were significant at p values of less than $10^{-20}$. With such a high significance, it may not be necessary to detect increased expression in more than one GTM. However, the redundancy in the GTMs of this invention can permit detection of gastric cancers with an increased reliability.

The methods provided herein also include assays of high sensitivity. qPCR is extremely sensitive, and can be used to detect gene products in very low copy number (e.g., 1-100) in a sample. With such sensitivity, very early detection of events that are associated with gastric cancer is made possible.

Methods

The following general methods were used to evaluate the suitability of various approaches to molecular identification of markers associated with gastric tumors.

Tumor Collection

Gastric tumor samples and non-malignant gastric tissues were collected from surgical specimens resected at Seoul National University Hospital, Korea and Dunedin Hospital, New Zealand. Diagnosis of gastric cancer was made on the basis of symptoms, physical findings and histological examination of tissues.

RNA Extraction

In some embodiments, expression of genes associated with gastric tumors was analyzed by determining the changes in RNA from samples taken from tumors. Frozen surgical specimens were embedded in OCT medium. 60 µm sections were sliced from the tissue blocks using a microtome, homogenized in a TriReagent:water (3:1) mix, then chloroform extracted. Total RNA was then purified from the aqueous phase using the RNeasy™ procedure (Qiagen). RNA was also extracted from 16 cancer cell lines and pooled to serve as a reference RNA.

Microarray Slide Preparation

Epoxy coated glass slides were obtained from MWG Biotech AG, Ebersberg, Germany) and were printed with ~30,000 50mer oligonucleotides using a Gene Machines microarraying robot, according to the manufacturer's protocol. Reference numbers (MWG oligo #) for relevant oligonucleotides, and the NCBI mRNA and protein reference sequences are shown in FIG. 2. Full DNA sequences of the GTM of this invention are shown herein below.

RNA Labeling and Hybridization cDNA was transcribed from long total RNA using Superscript II reverse transcriptase (Invitrogen) in reactions containing 5-(3-aminoallyl)-2' deoxyuridine-5'-triphosphate. The reaction was then de-ionized in a Microcon column before being incubated with Cy3 or Cy5 in bicarbonate buffer for 1 hour at room temperature. Unincorporated dyes were removed using a Qiaquick column (Qiagen) and the sample concentrated to 15 ul in a SpeedVac. Cy3 and Cy5 labeled cDNAs were then mixed with Ambion ULTRAhyb buffer, denatured at 100° C. for 2 minutes and hybridized to the microarray slides in hybridization chambers at 42° C. for 16 hours. The slides were then washed and scanned twice in an Axon 4000A scanner at two power settings to yield primary fluorescence data on gene expression.

Normalization Procedure

To compare expression of cancer genes from tumors and non-cancerous tissues, median fluorescence intensities detected by Genepix™ software were corrected by subtraction of the local background fluorescence intensities. Spots with a background corrected intensity of less than zero were excluded. To facilitate normalization, intensity ratios and overall spot intensities were log-transformed. Log-transformed intensity ratios were corrected for dye and spatial bias using local regression implemented in the LOCFIT™ package. Log-transformed intensity ratios were regressed simultaneously with respect to overall spot intensity and location. The residuals of the local regression provided the corrected log-fold changes. For quality control, ratios of each normalized microarray were plotted with respect to spot intensity and localization. The plots were subsequently visually inspected for possible remaining artifacts. Additionally, an analysis of variance (ANOVA) model was applied for the detection of pin-tip bias. All results and parameters of the normalization were inserted into a Postgres-database for statistical analysis.

Statistical Analysis

Statistically significant changes in gene expression in tumor samples vs. normal tissues were identified by measured fold changes between arrays. To accomplish this, log 2 (ratios) were scaled to have the same overall standard deviation per array. This standardization procedure reduced the average within-tissue class variability. The log 2 (ratios) were further shifted to have a median value of zero for each oligonucleotide to facilitate visual inspection of results. A rank-test based on fold changes was then used to improve the noise robustness. This test consisted of two steps: (i) calculation of the rank of fold change (Rfc) within arrays and ii) subtraction of the median (Rfc) for normal tissue from the median(Rfc) for tumor tissue. The difference of both median ranks defines the score of the fold change rank presented in FIG. 2. Two additional statistical tests were also performed on this standardized data: 1) Two sample student's t-test, with and without the Bonferroni adjustment and 2) the Wilcoxon test.

Statistical Analysis of Marker Combinations

To determine the value of using combinations of two or three of the markers to discriminate between tumor and non-malignant samples, the qPCR data from 40 paired samples (tumor and non-malignant samples from the same patient) were subjected to the following analysis. Normal distributions for the non-malignant and tumor samples were generated using the sample means and standard deviations. The probability that values taken from the tumor expression data would exceed a defined threshold (e.g., greater than 50%, 70%, 73%, 80%, 90%, 95%, 98%, 99% or 100%) in the non-malignant distribution was then determined (i.e., sensitivity). For combinations of markers, the probability that at least one marker exceeded the threshold was determined.

TABLE 1

FIG. 1

| name | symbol | Applied Biosystems "assay on demand" assay # | forward primer | Seq ID No. |
|---|---|---|---|---|
| asporin (lrr class 1) | ASPN | | AAATACAAAAGGACACATTCAAAGGA | 1 |
| chondroitin sulfate proteoglycan 2 (versican) | CSPG2 | | GCCAGTGGAATGATGTTCCC | 2 |
| cystatins SN, SA & S | CST1, 2, 4 | | AGTCCCAGCCCAACTTGGA | 3 |
| gamma-glutamyl hydrolase | GGH | | GTGGCAATGCCGCTGAA | 4 |
| insulin-like growth factor binding protein 7 | IGFBP7 | | CAGGTCAGCAAGGGCACC | 5 |
| kallikrein 10 | KLK10 | | ACAACATGATATGTGCTGGACTGG | 6 |
| leucine proline-enriched proteoglycan 1(leprecan 1) | LEPRE1 | | CTTGAGTACAACGCTGACCTCTTC | 7 |
| lumican | LUM | | GATTCTTGTCCATAGTGCATCTGC | 8 |
| lysyl oxidase-like 2 | LOXL2 | | AGGCCAGCTTCTGCTTGGA | 9 |
| matrix metalloproteinase 12 | MMP12 | | GCCTCTCTGCTGATGACATACGT | 10 |
| metalloproteinase inhibitor 1 | TIMP1 | | CCAGACCACCTTATACCAGCG | 11 |
| n-acylsphingosine amidohydrolase | ASAH1 | | CGCAGAACGCCTGCAAA | 12 |
| secreted frizzled-related protein 2 | SFRP2 | | CGCTAGCAGCGACCACCT | 13 |
| secreted protein, acidic, cysteine rich | SPARC | | TCTTCCCTGTACACTGGCAGTTC | 14 |
| serine protease 11 (IGF binding) | PRSS11 | | TCGGGAGGCCCGTTAGTAA | 15 |
| thrombospondin 2 | THBS2 | | TGGAAGGACTACACGGCCTATAG | 16 |
| thyroglobulin | TG | | GACGGTTCCTCGCAGTTCAA | 17 |
| human cell growth regulator with EF hand domain 1 | CGR11 | | CTGCCCACCCCTTCCA | 18 |
| human serine or cysteine proteinase inhibitor clade B | SERPINB5 | | TCCACGCATTTTCCAGGATAA | 19 |
| transforming growth factor β1 | TGFB1 | | GGTCCATGTCATCACCAATGTT | 20 |
| human proprotein convertase subtillsin/kexin type 5 | PCSK5 | | AAAAATCTTTGCCGGAAATGC | 21 |
| matrix metalloproteinase 2 | MMP2 | | TTGATGGCATCGCTCAGATC | 22 |
| human serine or cysteine proteinase inhibitor clade H | SERPINH1 | Hs00241844_m1 | | |
| adlican | — | Hs00377849_m1 | | |
| egf-containing fibulin-like extracellular matrix protein 2 | EFEMP2 | Hs00213545_m1 | | |
| secreted frizzled-related protein 4 | SFRP4 | Hs00180066_m1 | | |
| inhibin beta A chain | INHBA | Hs00170103_m1 | | |
| osteopontin | SPP1 | Hs00167093_m1 | | |
| transforming growth factor B-induced | TGFB1 | Hs00165908_ml | | |

| name | symbol | reverse primer | Seq ID No. |
|---|---|---|---|
| asporin (lrr class 1) | ASPN | TGCTTCTGCAATTCTGATATGGA | 23 |
| chondroitin sulfate proteoglycan 2 (versican) | CSPG2 | TCTTGGCATTTTCTACAACAGGG | 24 |
| cystatins SN, SA & S | CST1, 2, 4 | GGGAACTTCGTAGATCTGGAAAGA | 25 |
| gamma-glutamyl hydrolase | GGH | TGACAGCAACAACTCAGTAGGAAAA | 26 |
| insulin-like growth factor binding protein 7 | IGFBP7 | TCACAGCTCAAGTACACCTGGG | 27 |
| kallikrein 10 | KLK10 | GAGAGGATGCCTTGGAGGGT | 28 |
| leucine proline-enriched proteoglycan 1(leprecan 1) | LEPRE1 | CCGTGACACAGTTCTGCTTACAG | 29 |
| lumican | LUM | CCAATCAATGCCAGGAAGAGA | 30 |
| lysyl oxidase-like 2 | LOXL2 | CCCTGATCGCCGAGTTG | 31 |
| matrix metalloproteinase 12 | MMP12 | AGTGACAGCATCAAAACTCAAATTG | 32 |
| metalloproteinase inhibitor 1 | TIMP1 | GGACCTGTGGAAGTATCCGC | 33 |
| n-acylsphingosine amidohydrolase | ASAH1 | ACAGGACATCATACATGGTTTCAAA | 34 |
| secreted frizzled-related protein 2 | SFRP2 | TTTTGCAGGCTTCACATACCTTT | 35 |
| secreted protein, acidic, cysteine rich | SPARC | GAAAAAGCGGGTGGTGCA | 36 |
| serine protease 11 (IGF binding) | PRSS11 | AAGGAGATTCCAGCTGTCACTTTC | 37 |
| thrombospondin 2 | THBS2 | TAGGTTTGGTCATAGATAGGTCCTGAGT | 38 |
| thyroglobulin | TG | TGTAAACCGCTCCACTTCACAT | 39 |
| human cell growth regulator with EF hand domain 1 | CGR11 | TTCTGTCCTTCCTAGTCCCTTTAGG | 40 |
| human serine or cysteine proteinase inhibitor clade B | SERPINB5 | AAGCCGAATTTGCTAGTTGCA | 41 |
| transforming growth factor β1 | TGFB1 | TCTGCAAGTTCATCCCCTCTTT | 42 |
| human proprotein convertase subtillsin/kexin type 5 | PCSK5 | AGTCCTGGCCGTTGAAATACC | 43 |

TABLE 1-continued

FIG. 1

| name | symbol | probe | Seq ID No. |
|---|---|---|---|
| matrix metalloproteinase 2 | MMP2 | TGTCACGTGGCGTCACAGT | 44 |
| human serine or cysteine proteinase inhibitor clade H | SERPINH1 | | |
| adlican | — | | |
| egf-containing fibulin-like extracellular matrix protein 2 | EFEMP2 | | |
| secreted frizzled-related protein 4 | SFRP4 | | |
| inhibin beta A chain | INHBA | | |
| osteopontin | SPP1 | | |
| transforming growth factor B-induced | TGFB1 | | |

| name | symbol | probe | Seq ID No. |
|---|---|---|---|
| asporin (lrr class 1) | ASPN | TTGGAAATGAGTGCAAACCCTCTTGATAATAATG | 45 |
| chondroitin sulfate proteoglycan 2 (versican) | CSPG2 | AGGAACAGTTGCTTGCGGCCAGC | 46 |
| cystatins SN, SA & S | CST1, 2, 4 | AGCCAGAACTGCAGAAGAAACAGTTGTGC | 47 |
| gamma-glutamyl hydrolase | GGH | TTCACTGGAGGTCAATTGCACAGCAGAAT | 48 |
| insulin-like growth factor binding protein 7 | IGFBP7 | AGCAAGGTCCTTCCATAGTGACGCCC | 49 |
| kallikrein 10 | KLK10 | CTTGCCAGAGTGACTCTGGAGGCCC | 50 |
| leucine proline-enriched proteoglycan 1(leprecan 1) | LEPRE1 | CCATCACAGATCATTACATCCAGGTCCTCA | 51 |
| lumican | LUM | TAAGGATTCAAACCATTTGCCAAAAATGAGTCTAAG | 52 |
| lysyl oxidase-like 2 | LOXL2 | CGTAATTCTTCTGGATGTCTCCTTCACATTCTG | 53 |
| matrix metalloproteinase 12 | MMP12 | TCAGTCCCTGTATGGAGACCCAAAAGAGAA | 54 |
| metalloproteinase inhibitor 1 | TIMP1 | CAAGATGACCAAGATGTATAAAGGGTTCCAAGC | 55 |
| n-acylsphingosine amidohydrolase | ASAH1 | TGTCTGAACCGCACCAGCCAAGAGAATA | 56 |
| secreted frizzled-related protein 2 | SFRP2 | CTGCCAGCCACCGAGGAAGCTC | 57 |
| secreted protein, acidic, cysteine rich | SPARC | TGGACCAGCACCCCATTGACGG | 58 |
| serine protease 11 (IGF binding) | PRSS11 | AGTGTTAATTCCAATCACTTCACCGTCCAGG | 59 |
| thrombospondin 2 | THBS2 | AGGCCCAAGACCGGCTACATCAGAGTC | 60 |
| thyroglobulin | TG | TCTGGCAGATTCCGATGCCCCACAA | 61 |
| human cell growth regulator with EF hand domain 1 | CGR11 | CCAGGCCAGGAGCAGCTCGG | 62 |
| human serine or cysteine proteinase inhibitor clade B | SERPINB5 | TGACTCCAGGCCCGCAATGGA | 63 |
| transforming growth factor β1 | TGFB1 | CAGCCTCCAGCCAACAGACCTCAGG | 64 |
| human proprotein convertase subtillsin/kexin type 5 | PCSK5 | ACAGAATGTAGGGATGGGTTAAGCCTGCA | 65 |
| matrix metalloproteinase 2 | MMP2 | TTCAAGGACCGGTTCATTTGGCG | 66 |
| human serine or cysteine proteinase inhibitor clade H | SERPINH1 | | |
| adlican | — | | |
| egf-containing fibulin-like extracellular matrix protein 2 | EFEMP2 | | |
| secreted frizzled-related protein 4 | SFRP4 | | |
| inhibin beta A chain | INHBA | | |
| osteopontin | SPP1 | | |
| transforming growth factor B-induced | TGFB1 | | |

Quantitative Real-Time PCR

In other embodiments, real-time, or quantitative PCR (qPCR) can be used for absolute or relative quantitation of PCR template copy number. Taqman™ probe and primer sets were designed using Primer Express V 2.0™ (Applied Biosystems). Where possible, all potential splice variants were included in the resulting amplicon, with amplicon preference given to regions covered by the MWG-Biotech-derived microarray oligonucleotide. Alternatively, if the target gene was represented by an Assay-on-Demand™ expression assay (Applied Biosystems) covering the desired amplicons, these were used. The name of the gene, symbol, the Applied Biosystems "assay on demand" number, forward primer, reverse primer and probe sequence used for qPCR are shown in Table 1 and in FIG. 1. In the in-house designed assays, primer concentration was titrated using a SYBR green labeling protocol and cDNA made from the reference RNA. Amplification was carried out on an ABI Prism™ 7000 sequence detection system under standard cycling conditions. When single amplification products were observed in the dissociation curves, standard curves were generated over a 625-fold concentration range using optimal primer concentrations and 5'FAM-3'TAMRA phosphate Taqman™ probe (Proligo) at a final concentration of 250 nM. Assays giving standard curves with regression coefficients over 0.98 were used in subsequent assays. It can be appreciated that in other embodiments, regression coefficients need not be as high. Rather, any standard curve can be used so long as the regression coefficients are sufficiently high to permit statistically significant determination of differences in expression. Such regression coefficients may be above about 0.7, above about 0.8, above about 0.9 or above about 0.95 in alternative embodiments.

Assays were performed over two 96 well plates with each RNA sample represented by a single cDNA. Each plate contained a reference cDNA standard curve, over a 625-fold concentration range, in duplicate. Analysis consisted of calculating the ΔCT (target gene CT−mean reference cDNA CT). ΔCT is directly proportional to the negative log 2 fold change. Log 2 fold changes relative to the median non-malignant log 2 fold change were then calculated (log 2 fold change−median normal log 2 fold change). These fold changes were then clustered into frequency classes and graphed.

Microarray Analysis of Cancer Marker Genes

RNA from 58 gastric tumors and 58 non-malignant ("normal") gastric tissue samples were labeled with Cy5 and hybridized in duplicate or triplicate with Cy3 labeled reference RNA. After normalization, the change in expression in each of 29,718 genes was then estimated by three measures: (i) fold change: the ratio of the gene's median expression (un-standardized) in the tumor samples divided by the median level in the non-malignant samples. (ii) fold change rank and (iii) the statistical probability that the observed fold changes were significant.

Selection of Serum Markers for Gastric Malignancy

In certain embodiments, the cancer marker can be found in biological fluids, including serum. Serum markers were selected from the array data based on (i) the presence of a signal sequence characteristic of secreted proteins or cleaved from the outside of the membrane, (ii) the median level of over-expression (fold change) in tumors compared to non-malignant controls, (iii) the median change in expression rank between tumors and non-malignant controls, and (iv) the degree of overlap between the ranges of expression in the tumor and the non-malignant controls.

All 29 GTMs are known to have a signal peptide sequence at the 5'end of their coding sequences. The signal sequence targets the GTM proteins for transport to an extracellular compartment through the plasma membrane (Gunner von Heijne, Journal of Molecular Biology 173:243-251 (1984). In addition, none of the GTMs have transmembrane sequence motifs that would result in the full-length protein being retained within the plasma membrane. Consequently, all of the GTM markers of this invention are likely to be secreted into the extracellular compartment, and therefore can be in contact with the vasculature, either being taken up by capillaries, or by being transported into the lymphatic system and then into the vasculature. As a result, each of these tumor-derived markers will be present in the blood.

Next, genes were excluded if >50% of the tumor samples showed expression levels within the $95^{th}$ percentile of the non-malignant range. The variation in the degree of over-expression in the tumor samples reflects not only tumor heterogeneity but also variations in the extent of contamination of the tumor samples with "normal" tissue including muscle, stromal cells and non-malignant epithelial glands. This "normal" contamination ranged from 5 to 70% with a median of approximately 25%. Other genes were excluded because of high relative expression in hematopoietic cells, or elevated expression in metaplastic gastric tissue. It can be appreciated that depending on the degree of contamination by normal cells or cells that normally express the marker, different threshold ranges can be selected that can provide sufficient separation between a cancer source and a normal source.

GTM that we have found to be useful include genes (DNA), complementary DNA (cDNA), RNA, proteins, and protein fragments of the following markers: carboxypeptidase N, polypeptide 2, 83 kDa chain (also known as carboxypeptidase N (CPN2), matrix metalloproteinase 12 (MMP12), inhibin ("INHBA"), insulin-like growth factor 7 ("IGFBP7"), gamma-glutamyl hydrolase ("GGH"), leucine proline-enriched proteoglycan ("LEPRE1"), cystatin S ("CST4"), secreted frizzled-related protein 4 ("SFRP4"), asporin ("ASPN"), cell growth regulator with EF hand domain 1 ("CGREF1"), kallikrein (KLK10), tissue inhibitor of metalloproteinase 1 ("TIMP1"), secreted acidic cysteine-rich protein ("SPARC"), transforming growth factor, β-induced ("TGFBI"), EGF-containing fibulin-like extracellular matrix protein 2 ("EFEMP2"), lumican ("LUM"), stannin ("SNN"), secreted phosphoprotein 1 ("SPP1"), chondroitin sulfate proteoglycan 2 ("CSPG2"), N-acylsphingosine amidohydrolase ("ASAH1"), serine protease 11 ("PRSS11"), secreted frizzled-related protein 2 ("SFRP2"), phospholipase A2, group XIIB ("PLA2G12B"), spondin 2, extracellular matrix protein ("SPON2"), olfactomedin 1 ("OLFM1"), thrombospondin repeat containing 1 ("TSRC1"), thrombospondin 2 ("THBS2"), adlican, cystatin SA ("CST2"), cystatin SN ("CST1"), lysyl oxidase-like enzyme 2 ("LOXL2"), thyroglobulin ("TG"), transforming growth factor beta1 ("TGFB1"), serine or cysteine proteinase inhibitor clade H ("SERPINH1"), serine or cysteine proteinase inhibitor clade B ("SERPINB5"), matrix metalloproteinase 2 ("MMP2"), proprotein convertase subtilisin/kexin type 5 ("PCSK5"), and hyaluronan proteoglycan link protein 4 ("HAPLN4").

DNA sequences of GTM of this invention along with identifying information are shown herein below.

Matrix Metalloproteinase 12

>gi|4505206|ref|NM_002426.1| Homo sapiens matrix metalloproteinase 12 (macrophage elastase) (MMP12), mRNA|qPCR forward_primer match [758 . . . 780]|qPCR reverse_primer match [888 . . . 864]|qPCR probe match [786 . . . 815]

SEQ ID NO: 67

```
TAGAAGTTTACAATGAAGTTTCTTCTAATACTGCTCCTGCAGGCCACTG

CTTCTGGAGCTCTTCCCCTGAACAGCTCTACAAGCCTGGAAAAAAATAA

TGTGCTATTTGGTGAGAGATACTTAGAAAAATTTTATGGCCTTGAGATA

AACAAACTTCCAGTGACAAAAATGAAATATAGTGGAAACTTAATGAAGG

AAAAAATCCAAGAAATGCAGCACTTCTTGGGTCTGAAAGTGACCGGGCA

ACTGGACACATCTACCCTGGAGATGATGCACGCACCTCGATGTGGAGTC

CCCGATCTCCATCATTTCAGGGAATGCCAGGGGGGCCCGTATGGAGGA

AACATTATATCACCTACAGAATCAATAATTACACACCTGACATGAACCG

TGAGGATGTTGACTACGCAATCCGGAAAGCTTTCCAAGTATGGAGTAAT

GTTACCCCCTTGAAATTCAGCAAGATTAACACAGGCATGGCTGACATTT

TGGTGGTTTTTGCCCGTGGAGCTCATGGAGACTTCCATGCTTTTGATGG

CAAAGGTGGAATCCTAGCCCATGCTTTTGGACCTGGATCTGGCATTGGA

GGGGATGCACATTTCGATGAGGACGAATTCTGGACTACACATTCAGGAG

GCACAAACTTGTTCCTCACTGCTGTTCACAGAGATTGGCCATTCCTTAGG

TCTTGGCCATTCTACTGATCCAAAGGCTGTAATGTTCCCCACCTACAAA

TATGTCGACATCAACACATTTCGCCTCTCTGCTGATGACATACGTGGCA

TTCAGTCCCTGTATGGAGACCCAAAAGAGAACCAACGCTTGCCAAATCC

TGACAATTCAGAACCAGCTCTCTGTGACCCCAATTTGAGTTTTGATGCT

GTCACTACCGTGGGAAATAAGATCTTTTTCTTCAAAGACAGGTTCTTCT

GGCTGAAGGTTTCTGAGAGACCAAAGACCAGTGTTAATTTAATTTCTTC

CTTATGGCCAACCTTGCCATCTGGCATTGAAGCTGCTTATGAAATTGAA

GCCAGAAATCAAGTTTTTCTTTTTAAAGATGACAAATACTGGTTAATTA

GCAATTTAAGACCAGAGCCAAATTATCCCAAGAGCATACATTCTTTTGG

TTTTCCTAACTTTGTGAAAAAAATTGATGCAGCTGTTTTTAACCCACGT

TTTTATAGGACCTACTTCTTTGTAGATAACCAGTATTGGAGGTATGATG

AAAGGAGACAGATGATGGACCCTGGTTATCCCAAACTGATTACCAAGAA

CTTCCAAGGAATCGGGCCTAAAATTGATGCAGTCTTCTATTCTAAAAAC

AAATACTACTATTTCTTCCAAGGATCTAACCAATTTGAATATGACTTCC

TACTCCAACGTATCACCAAAACACTGAAAAGCAATAGCTGGTTTGGTTG

TTAGAAATGGTGTAATTAATGGTTTTTGTTAGTTCACTTCAGCTTAATA

AGTATTTATTGCATATTTGCTATGTCCTCAGTGTACCACTACTTAGAGA
```

-continued
```
TATGTATCATAAAAATAAAATCTGTAAACCATAGGTAATGATTATATAA

AATACATAATATTTTTCAATTTTGAAAACTCTAATTGTCCATTCTTGCT

TGACTCTACTATTAAGTTTGAAAATAGTTACCTTCAAAGCAAGATAATT

CTATTTGAAGCATGCTCTGTAAGTTGCTTCCTAACATCCTTGGACTGAG

AAATTATACTTACTTCTGGCATAACTAAAATTAAGTATATATATTTTGG

CTCAATAAAATTG
```

Inhibin Beta A

>gi|4504698|ref|NM_002192.1| Homo sapiens inhibin, beta A (activin A, activin AB alpha polypeptide) (INHBA), mRNA|qPCR assay_on_demand_context match [457 . . . 481]

SEQ ID NO: 68
```
TCCACACACACAAAAAACCTGCGCGTGAGGGGGAGGAAAAGCAGGGCCT

TTAAAAAGGCAATCACAACAACTTTTGCTGCCAGGATGCCCTTGCTTTGG

CTGAGAGGATTTCTGTTGGCAAGTTGCTGGATTATAGTGAGGAGTTCCCC

CACCCCAGGATCCGAGGGGCACAGCGCGGCCCCCGACTGTCCGTCCTGTG

CGCTGGCCGCCCTCCCAAAGGATGTACCCAACTCTCAGCCAGAGATGGTG

GAGGCCGTCAAGAAGCACATTTTAAACATGCTGCACTTGAAGAAGAGACC

CGATGTCACCCAGCCGGTACCCAAGGCGGCGCTTCTGAACGCGATCAGAA

AGCTTCATGTGGGCAAAGTCGGGGAGAACGGGTATGTGGAGATAGAGGAT

GACATTGGAAGGAGGGCAGAAATGAATGAACTTATGGAGCAGACCTCGGA

GATCATCACGTTTGCCGAGTCAGGAACAGCCAGGAAGACGCTGCACTTCG

AGATTTCCAAGGAAGGCAGTGACCTGTCAGTGGTGGAGCGTGCAGAAGTC

TGGCTCTTCCTAAAAGTCCCCAAGGCCAACAGGACCAGGACCAAAGTCAC

CATCCGCCTCTTCCAGCAGCAGAAGCACCCGCAGGGCAGCTTGGACACAG

GGGAAGAGGCCGAGGAAGTGGGCTTAAAGGGGGAGAGGAGTGAACTGTTG

CTCTCTGAAAAAGTAGTAGACGCTCGGAAGAGCACCTGGCATGTCTTCCC

TGTCTCCAGCAGCATCCAGCGGTTGCTGGACCAGGGCAAGAGCTCCCTGG

ACGTTCGGATTGCCTGTGAGCAGTGCCAGGAGAGTGGCGCCAGCTTGGTT

CTCCTGGGCAAGAAGAAGAAGAAAGAAGAGGAGGGGAAGGGAAAAAGAA

GGGCGGAGGTGAAGGTGGGCAGGAGCAGATGAGGAAAAGGAGCAGTCGC

ACAGACCTTTCCTCATGCTGCAGGCCCGGCAGTCTGAAGACCACCCTCAT

CGCCGGCGTCGGCGGGCTTGGAGTGTGATGGCAAGGTCAACATCTGCTG

TAAGAAACAGTTCTTTGTCAGTTTCAAGGACATCGGCTGGAATGACTGGA

TCATTGCTCCCTCTGGCTATCATGCCAACTACTGCGAGGGTGAGTGCCCG

AGCCATATAGCAGGCACGTCCGGGTCCTCACTGTCCTTCCACTCAACAGT

CATCAACCACTACCGCATGCGGGGCCATAGCCCCTTTGCCAACCTCAAAT

CGTGCTGTGTGCCCACCAAGCTGAGACCCATGTCCATGTTGTACTATGAT

GATGGTCAAAACATCATCAAAAAGGACATTCAGAACATGATCGTGGAGGA

GTGTGGGTGCTCATAGAGTTGCCCAGCCCAGGGGGAAAGGGAGCAAGAGT

TGTCCAGAGAAGACAGTGGCAAAATGAAGAAATTTTTAAGGTTTCTGAGT

TAACCAGAAAAATAGAAATTAAAAACAAAACAAAACAAAAAAAAAACAA

AAAAAAACAAAAGTAAATTAAAAACAAACCTGATGAAACAGATGAAACAG

ATGAAGGAAGATGTGGAAATCTTAGCCTGCCTTAGCCAGGGCTCAGAGAT

GAAGCAGTGAAGAGACAGATTGGGAGGGAAAGGGAGAATGGTGTACCCTT

TATTTCTTCTGAAATCACACTGATGACATCAGTTGTTTAAACGGGGTATT

GTCCTTTCCCCCCTTGAGGTTCCCTTGTGAGCTTGAATCAACCAATCTGA

TCTGCAGTAGTGTGGACTAGAACAACCCAAATAGCATCTAGAAAGCCATG

AGTTTGAAAGGGCCCATCACAGGCACTTTCCTAGCCTAAT
```

Insulin-Like Growth Factor Binding Protein 7

>gi|4504618|ref|NM_001553.1| Homo sapiens insulin-like growth factor binding protein 7 (IGFBP7), mRNA|qPCR forward_primer match [470 . . . 487]|qPCR reverse_primer match [567 . . . 546]|qPCR probe match [492 . . . 517]

SEQ ID NO: 69
```
GCCGCTGCCACCGCACCCCGCCATGGAGCGGCCGTCGTGCGCGCCCTGCT

CCTCGGCGCCGCTGGGCTGCTGCTCCTGCTCCTGCCCCTCTCCTCTTCCT

CCTCTTCGGACACCTGCGGCCCCTGCGAGCCGGCCTCCTGCCCGCCCCTG

CCCCCGCTGGGCTGCCTGCTGGGCGAGACCCGCGACGCGTGCGGCTGCTG

CCCTATGTGCGCCCGCGGCGAGGGCGAGCCGTGCGGGGGTGGCGGCGCCG

GCAGGGGGTACTGCGCGCCGGGCATGGAGTGCGTGAAGAGCCGCAAGAGG

CGGAAGGGTAAAGCCGGGGCAGCAGCCGGCGGTCCGGGTGTAAGCGGCGT

GTGCGTGTGCAAGAGCCGCTACCCGGTGTGCGGCAGCGACGGCACCACCT

ACCCCGAGCGGCTGCCAGCTGCGCGCCGCCAGCCAGAGGGCCGAGAGCCGC

GGGGAGAAGGCCATGACCCAGGTCAGCAAGGGCACCTGCGAGCAAGGTCC

TTCCATAGTGACGCCCCCCAAGGACATCTGGAATGTCACTGGTGCCCAGG

TGTACTTGAGCTGTGAGGTCATCGGAATCCCGACACCTGTCCTCATCTGG

AACAAGGTAAAAAGGGGTCACTATGGAGTTCAAAGGACAGAACTCCTGCC

TGGTGACCGGGACAACCTGGCCATTCAGACCCGGGGTGGCCCAGAAAAGC

ATGAAGTAACTGGCTGGGTGCTGGTATCTCCTCTAAGTAAGGAAGATGCT

GGAGAATATGAGTGCCATGCATCCAATTCCCAAGGACAGGCTTCAGCATC

AGCAAAAATTACAGTGGTTGATGCCTTACATGAAATACCAGTGAAAAAAG

GTGAAGGTGCCGAGCTATAAACCTCCAGAATATTATTAGTCTGCATGGTT

AAAAGTAGTCATGGATAACTACATTACCTGTTCTTGCCTAATAAGTTTCT

TTTAATCCAATCCACTAACACTTTAGTTATATTCACTGGTTTTACACAGA

GAAATACAAAATAAAGATCACACATCAAGACTATCTACAAAAATTTATTA

TATATTTACAGAAGAAAGCATGCATATCATTAAACAAATAAAATACTTT

TTATCACAAAAAAAAAAAAAAAA
```

Gamma-Glutamyl Hydrolase

>gi|4503986|ref|NM_003878.1| Homo sapiens gamma-glutamyl hydrolase (conjugase, folylpolygammaglutamyl hydrolase) (GGH), mRNA|qPCR forward_primer match [531 . . . 547]|qPCR reverse_primer match [611 . . . 587]|qPCR probe match [549 . . . 577]

SEQ ID NO: 70
TGCCGCAGCCCCCGCCCGCCCGCAGAGCTTTTGAAAGGCGGCGGGAGGCG
GCGAGCGCCATGGCCAGTCCGGGCTGCCTGCTGTGCGTGCTGGGCCTGCT
ACTCTGCGGGGCGGCGAGCCTCGAGCTGTCTAGACCCCACGGCGACACCG
CCAAGAAGCCCATCATCGGAATATTAATGCAAAAATGCCGTAATAAAGTC
ATGAAAAACTATGGAAGATACTATATTGCTGCGTCCTATGTAAAGTACTT
GGAGTCTGCAGGTGCGAGAGTTGTACCAGTAAGGCTGGATCTTACAGAGA
AAGACTATGAAATACTTTTCAAATCTATTAATGGAATCCTTTTCCCTGGA
GGAAGTGTTGACCTCAGACGCTCAGATTATGCTAAAGTGGCCAAAATATT
TTATAACTTGTCCATACAGAGTTTTGATGATGGAGACTATTTTCCTGTGT
GGGGCACATGCCTTGGATTTGAAGAGCTTTCACTGCTGATTAGTGGAGAG
TGCTTATTAACTGCCACAGATACTGTTGACGTGGCAATGCCGCTGAACTT
CACTGGAGGTCAATTGCACAGCAGAATGTTCCAGAATTTTCCTACTGAGT
TGTTGCTGTCATTAGCAGTAGAACCTCTGACTGCCAATTTCCATAAGTGG
AGCCTCTCCGTGAAGAATTTTACAATGAATGAAAAGTTAAAGAAGTTTTT
CAATGTCTTAACTACAAATACAGATGGCAAGATTGAGTTTATTTCAACAA
TGGAAGGATATAAGTATCCAGTATATGGTGTCCAGTGGCATCCAGAGAAA
GCACCTTATGAGTGGAAGAATTTGGATGGCATTTCCCATGCACCTAATGC
TGTGAAAACCGCATTTTATTTAGCAGAGTTTTTTGTTAATGAAGCTCGGA
AAAACAACCATCATTTTAAATCTGAATCTGAAGAGGAGAAAGCATTGATT
TATCAGTTCAGTCCAATTTATACTGGAAATATTTCTTCATTTCAGCAATG
TTACATATTTGATTGAAAGTCTTCAATTTGTTAACAGAGCAAATTTGAAT
AATTCCATGATTAAACTGTTAGAATAACTTGCTACTCATGGCAAGATTAG
GAAGTCACAGATTCTTTTCTATAATGTGCCTGGCTCTGATTCTTCATTAT
GTATGTGACTATTTATATAACATTAGATAATTAAATAGTGAGACATAAAT
AGAGTGCTTTTTCATGGAAAAGCCTTCTTATATCTGAAGATTGAAAAATA
AATTTACTGAAATACAAAAAAAAAAAAAAA

Leucine Proline-Enriched Proteoglycan 1
>gi|21361917|ref|NM_022356.2|Homo sapiens leucine proline-enriched proteoglycan (leprecan) 1 (LEPRE1), mRNA|qPCR forward_primer match [813 . . . 836]|qPCR reverse_primer match [894 . . . 872]|qPCR probe match [841 . . . 870]

SEQ ID NO: 71
GGTGGCGGGTGGCTGGCGGTTCCGTTAGGTCTGAGGGAGCGATGGCGGTA
CGCGCGTTGAAGCTGCTGACCACACTGCTGGCTGTCGTGGCCGCTGCCTC
CCAAGCCGAGGTCGAGTCCGAGGCAGGATGGGGCATGGTGACGCCTGATC
TGCTCTTCGCCGAGGGGACCGCAGCCTACGCGCGCGGGGACTGGCCCGGG
GTGGTCCTGAGCATGGAACGGGCGCTGCGCTCCCGGGCAGCCCTCCGCGC
CCTTCGCCTGCGCTGCCGCACCCAGTGTGCCGCCGACTTCCCGTGGGAGC
TGGACCCCGACTGGTCCCCCAGCCCGGCCCAGGCCTCGGGCGCCGCCGCC
CTGCGCGACCTGAGCTTCTTCGGGGGCCTTCTGCGTCGCGCTGCCTGCCT
GCGCCGCTGCCTCGGGCCGCCGGCCGCCCACTCGCTCAGCGAAGAGATGG
AGCTGGAGTTCCGCAAGCGGAGCCCCTACAACTACCTGCAGGTCGCCTAC
TTCAAGATCAACAAGTTGGAGAAAGCTGTTGCTGCAGCACACACCTTCTT
CGTGGGCAATCCTGAGCACATGGAAATGCAGCAGAACCTAGACTATTACC
AAACCATGTCTGGAGTGAAGGAGGCCGACTTCAAGGATCTTGAGACTCAA
CCCCATATGCAAGAATTTCGACTGGGAGTGCGACTCTACTCAGAGGAACA
GCCACAGGAAGCTGTGCCCCACCTAGAGGCGGCGCTGCAAGAATACTTTG
TGGCCTATGAGGAGTGCCGTGCCCTCTGCGAAGGGCCCTATGACTACGAT
GGCTACAACTACCTTGAGTACAACGCTGACCTCTTCCAGGCCATCACAGA
TCATTACATCCAGGTCCTCAACTGTAAGCAGAACTGTGTCACGGAGCTTG
CTTCCCACCCAAGTCGAGAGAAGCCCTTTGAAGACTTCCTCCCATCGCAT
TATAATTATCTGCAGTTTGCCTACTATAACATTGGGAATTATACACAGGC
TGTTGAATGTGCCAAGACCTATCTTCTCTTCTTCCCCAATGACGAGGTGA
TGAACCAAAATTTGGCCTATTATGCAGCTATGCTTGGAGAAGAACACACC
AGATCCATCGGCCCCCGTGAGAGTGCCAAGGAGTACCGACAGCGAAGCCT
ACTGGAAAAGAACTGCTTTTCTTCGCTTATGATGTTTTTGGAATTCCCT
TTGTGGATCCGGATTCATGGACTCCAGGAGAAGTGATTCCCAAGAGATTG
CAAGAGAAACAGAAGTCAGAACGGGAAACAGCCGTACGCATCTCCCAGGA
GATTGGGAACCTTATGAAGGAAATCGAGACCCTTGTGGAAGAGAAGACCA
AGGAGTCACTGGATGTGAGCAGACTGACCCGGGAAGGTGGCCCCCTGCTG
TATGAAGGCATCAGTCTCACCATGAACTCCAAACTCCTGAATGGTTCCCA
GCGGGTGGTGATGGACGGCGTAATCTCTGACCACGAGTGTCAGGAGCTGC
AGAGACTGACCAATGTGGCAGCAACCTCAGGAGATGGCTACCGGGGTCAG
ACCTCCCCACATACTCCCAATGAAAAGTTCTATGGTGTCACTGTCTTCAA
AGCCCTCAAGCTGGGGCAAGAAGGCAAAGTTCCTCTGCAGAGTGCCCACC
TGTACTACAACGTGACGGAGAAGGTGCGGCGCATCATGGAGTCCTACTTC
CGCCTGGATACGCCCCTCTACTTTTCCTACTCTCATCTGGTGTGCCGCAC
TGCCATCGAAGAGGTCCAGGCAGAGAGGAAGGATGATAGTCATCCAGTCC
ACGTGGACAACTGCATCCTGAATGCCGAGACCCTCGTGTGTGTCAAAGAG
CCCCCAGCCTACACCTTCCGCGACTACAGCGCCATCCTTTACCTAAATGG
GGACTTCGATGGCGGAAACTTTTATTTCACTGAACTGGATGCCAAGACCG
TGACGGCAGAGGTGCAGCCTCAGTGTGGAAGAGCCGTGGGATTCTCTTCA
GGCACTGAAAACCCACATGGAGTGAAGGCTGTCACCAGGGGGCAGCGCTG
TGCCATCGCCCTGTGGTTCACCCTGGACCCTCGACACAGCGAGCGGGTGA
GAGCAGCTCGAGCGGGTGAGAGCAGCTGGTGCTGTGGTGACCCGTTCCA
GAGCGCCCTTGGTTTGCCTTTCTCTTCCCCAAATCCCATTGCCAGTGGCT
GAGACACGAAAGGAGCACTTGGGACACCAGCTCCAACGCCCTGTCATTAT
GGTCACATTGCCTTGTCCTCCCTGGGCCTGCTGTGAACGGGATCCAGGTG
GGGAAAGAGGTCAAGACAGGGAGCGATGCTGAGTTCTTGGTTCCCTCCTT
GGGCCCCACTTCAGCTGTCCTTTTCCAGAGAGTAGGACCTGCTGGGAAGG
AGATGAGCCTGGGGCCATTAAGGAACCTTCCTTGTCCCCTGGGAAGTAGC

-continued
AGCTGAGAGATAGCGAGTGTCTGGAGCGGAGGCCTCTCTGAATGGGCAGG

GGTTTGTCCTTGCAGGACAGGGTGCAGGCAGATGACCTGGTGAAGATGCT

CTTCAGCCCAGAAGAGATGGTCCTCTCCCAGGAGCAGCCCCTGGATGCCC

AGCAGGGCCCCCCCGAACCTGCACAAGAGTGTCTCTCAGGCAGTGAATCG

AAGCCCAAGGATGAGCTATGACAGCGTCCAGGTCAGACGGATGGGTGACT

AGACCCATGGAGAGGAACTCTTCTGCACTCTGAGCTGGCCAGCCCCTCGG

GGCTGCAGAGCAGTGAGCCTACATCTGCCACTCAGCCGAGGGGACCCTGC

TCACAGCCTTCTACATGGTGCTACTGCTCTTGGAGTGGACATGACCAGAC

ACCGCACCCCTGGATCTGGCTGAGGGCTCAGGACACAGGCCCAGCCACC

CCCAGGGGCCTCCACAGGCCGCTGCATAACAGCGATACAGTACTTAAGTG

TCTGTGTAGACAACCAAAGAATAAATGATTCATGGTTTTTTTT

Cystatin S
>gi|19882254|ref|NM_001899.2|Homo sapiens cystatin S (CST4), mRNA qPCR forward_primer match [343 . . . 361]|qPCR reverse_primer match [434 . . . 411]|qPCR probe match [382 . . . 410]

SEQ ID NO: 72
GGCTCTCACCCTCCTCTCCTGCAGCTCCAGCTTTGTGCTCTGCCTCTGAG

GAGACCATGGCCCGGCCTCTGTGTACCCTGCTACTCCTGATGGCTACCCT

GGCTGGGGCTCTGGCCTCGAGCTCCAAGGAGGAGAATAGGATAATCCCAG

GTGGCATCTATGATGCAGACCTCAATGATGAGTGGGTACAGCGTGCCCTT

CACTTCGCCATCAGCGAGTACAACAAGGCCACCGAAGATGAGTACTACAG

ACGCCCGCTGCAGGTGCTGCGAGCCAGGGAGCAGACCTTTGGGGGGTGA

ATTACTTCTTCGACGTAGAGGTGGGCCGCACCCATATGTACCAAGTCCCAG

CCCAACTTGGACACCTGTGCCTTCCATGAACAGCCAGAACTGCAGAAGAA

ACAGTTGTGCTCTTTCGAGATCTACGAAGTTCCCTGGGAGGACAGAATGT

CCCTGGTGAATTCCAGGTGTCAAGAAGCCTAGGGGTCTGTGCCAGGCCAG

TCACACCGACCACCACCCACTCCCACCCACTGTAGTGCTCCCACCCCTGG

ACTGGTGGCCCCCACCCTGCGGGAGGCCTCCCCATGTGCCTGTGCCAAGA

GACAGACAGAGAAGGCTGCAGGAGTCCTTTGTTGCTCAGCAGGGCGCTCT

GCCCTCCCTCCTTCCTTCTTGCTTCTAATAGACCTGGTACATGGTACACA

CACCCCCACCTCCTGCAATTAAACAGTAGCATCGCC

Secreted Frizzle-Related Protein 4
>gi|8400733|ref|NM_003014.2|Homo sapiens secreted frizzled-related protein 4 (SFRP4), mRNA|qPCR assay_on_demand_context match [1079 . . . 1103]

SEQ ID NO: 73
GGCGGGTTCGCGCCCCGAAGGCTGAGAGCTGGCGCTGCTCGTGCCCTGTG

TGCCAGACGGCGGAGCTCCGCGGCCGGACCCCGCGGCCCCGCTTTGCTGC

CGACTGGAGTTTGGGGGAAGAAACTCTCCTGCGCCCCAGAAGATTTCTTC

CTCGGCGAAGGGACAGCGAAAGATGAGGGTGGCAGGAAGAGAAGGCGCTT

TCTGTCTGCCGGGGTCGCAGCGCGAGAGGGCAGTGCCATGTTCCTCTCCA

TCCTAGTGGCGCTGTGCCTGTGGCTGCACCTGGCGCTGGGCGTGCGCGGC

-continued
GCGCCCTGCGAGGCGGTGCGCATCCCTATGTGCCGGCACATGCCCTGGAA

CATCACGCGGATGCCCAACCACCTGCACCACAGCACGCAGGAGAACGCCA

TCCTGGCCATCGAGCAGTACGAGGAGCTGGTGGACGTGAACTGCAGCGCC

GTGCTGCGCTTCTTCTGTGCCATGTACGCGCGCCCATTTGCACCCTG

GAGTTCCTGCACGACCCTATCAAGCCGTGCAAGTCGGTGTGCCAACGCGC

GCGCGACGACTGCGAGCCCCTCATGAAGATGTACAACCACAGCTGGCCCG

AAAGCCTGGCCTGCGACGAGCTGCCTGTCTATGACCGTGGCGTGTGCATT

TCGCCTGAACCATCGTCACGGACCTCCCGGAGGATGTTAAGTGGATAGAC

ATCACACCAGACATGATGGTACAGGAAAGGCCTCTTGATGTTGACTGTAA

ACGCCTAAGCCCCGATCGGTGCAAGTGTAAAAAGGTGAAGCCAACTTTGG

CAACGTATCTCAGCAAAAACTACAGCTATGTTATTCATGCCAAAATAAAA

GCTGTGCAGAGGAGTGGCTGCAATGAGGTCACAACGGTGGTGGATGTAAA

AGAGATCTTCAAGTCCTCATCACCCATCCCTCGAACTCAAGTCCCGCTCA

TTACAAATTCTTCTTGCCAGTGTCCACACATCCTGCCCCATCAAGATGTT

CTCATCATGTGTTACGAGTGGCGTTCAAGGATGATGCTTCTTGAAAATTG

CTTAGTTGAAAAATGGAGAGATCAGCTTAGTAAAAGATCCATACAGTGGG

AAGAGAGGCTGCAGGAACAGCGGAGAACAGTTCAGGACAAGAAGAAAACA

GCCGGGCGCACCAGTCGTAGTAATCCCCCCAAACCAAAGGGAAAGCCTCC

TGCTCCCAAACCAGCCAGTCCCAAGAAGAACATTAAAACTAGGAGTGCCC

AGAAGAGAACAAACCCGAAAAGAGTGTGAGCTAACTAGTTTCCAAAGCGG

AGACTTCCGACTTCCTTACAGGATGAGGCTGGGCATTGCCTGGGACAGCC

TATGTAAGGCCATGTGCCCCTTGCCCTAACAACTCACTGCAGTGCTCTTC

ATAGACACATCTTGCAGCATTTTTCTTAAGGCTATGCTTCAGTTTTTCTT

TGTAAGCCATCACAAGCCATAGTGGTAGGTTTGCCCTTTGGTACAGAAGG

TGAGTTAAAGCTGGTGGAAAAGGCTTATTGCATTGCATTCAGAGTAACCT

GTGTGCATACTCTAGAAGAGTAGGGAAAATAATGCTTGTTACAATTCGAC

CTAATATGTGCATTGTAAAATAAATGCCATATTTCAAACAAAACACGTAA

TTTTTTTACAGTATGTTTTATTACCTTTTGATATCTGTTGTTGCAATGTT

AGTGATGTTTTAAAATGTGATGAAAATATAATGTTTTTAAGAAGGAACAG

TAGTGGAATGTTAAAAGATCTTTATGTGTTTATGGTCTGCAGAAGGATTT

TTGTGATGAAAGGGGATTTTTTGAAAAATTAGAGAAGTAGCATATGGAAA

ATTATAATGTGTTTTTTTACCAATGACTTCAGTTTCTGTTTTTAGCTAGA

AACTTAAAAACAAAAATAATAATAAAGAAAAATAAATAAAAGGAGAGGC

AGACAATGTCTGGATTCCTGTTTTTGGTTACCTGATTTCCATGATCATG

ATGCTTCTTGTCAACACCCTCTTAAGCAGCACCAGAAACAGTGAGTTTGT

CTGTACCATTAGGAGTTAGGTACTAATTAGTTGGCTAATGCTCAAGTATT

TTATACCCACAAGAGAGGTATGTCACTCATCTTACTTCCCAGGACATCCA

CCCTGAGAATAATTTGACAAGCTTAAAAATGGCCTTCATGTGAGTGCCAA

ATTTTGTTTTTCTTCATTTAAATATTTTCTTTGCCTAAATACATGTGAGA

GGAGTTAAATATAAATGTACAGAGAGGAAAGTTGAGTTCCACCTCTGAAA

-continued

```
TGAGAATTACTTGACAGTTGGGATACTTTAATCAGAAAAAAGAACTTAT

TTGCAGCATTTTATCAACAAATTTCATAATTGTGGACAATTGGAGGCATT

TATTTTAAAAAACAATTTTATTGGCCTTTTGCTAACACAGTAAGCATGTA

TTTTATAAGGCATTCAATAAATGCACAACGCCCAAAGGAAATAAAATCCT

ATCTAATCCTACTCTCCACTACACAGAGGTAATCACTATTAGTATTTTGG

CATATTATTCTCCAGGTGTTTGCTTATGCACTTATAAAATGATTTGAACA

AATAAAACTAGGAACCTGTATACATGTGTTTCATAACCTGCCTCCTTTGC

TTGGCCCTTTATTGAGATAAGTTTTCCTGTCAAGAAAGCAGAAACCATCT

CATTTCTAACAGCTGTGTTATATTCCATAGTATGCATTACTCAACAAACT

GTTGTGCTATTGGATACTTAGGTGGTTTCTTCACTGACAATACTGAATAA

ACATCTCACCGGAATTC
```

Asporin
>gi|41350213|ref|NM_017680.3| Homo sapiens asporin (LRR class 1) (ASPN), mRNA qPCR forward_primer match [798 . . . 823]|qPCR reverse_primer match [934 . . . 912]|qPCR probe match [842 . . . 875]

SEQ ID NO: 74
```
AGTACTAACATGGACTAATCTGTGGGAGCAGTTTATTCCAGTATCACCCA

GGGTGCAGCCACACCAGGACTGTGTTGAAGGGTGTTTTTTTTCTTTTAAA

ATGTAATACCTCCTCATCTTTTCTTCTTACACAGTGTCTGAGAACATTTA

CATTATAGATAAGTAGTACATGGTGGATAACTTCTACTTTTAGGAGGACT

ACTCTCTTCTGACAGTCCTAGACTGGTCTTCTACACTAAGACACCATGAA

GGAGTATGTGCTCCTATTATTCCTGGCTTTGTGCTCTGCCAAACCCTTCT

TTAGCCCTTCACACATCGCACTGAAGAATATGATGCTGAAGGATATGGAA

GACACAGATGATGATGATGATGATGATGATGATGATGATGATGATGATGA

GGACAACTCTCTTTTTCCAACAAGAGAGCCAAGAAGCCATTTTTTTCCAT

TTGATCTGTTTCCAATGTGTCCATTTGGATGTCAGTGCTATTCACGAGTT

GTACATTGCTCAGATTTAGGTTTGACCTCAGTCCCAACCAACATTCCATT

TGATACTCGAATGCTTGATCTTCAAAACAATAAAATTAAGGAAATCAAAG

AAAATGATTTTAAAGGACTCACTTCACTTTATGGTCTGATCCTGAACAAC

AACAAGCTAACGAAGATTCACCCAAAAGCCTTTCTAACCACAAAGAAGTT

GCGAAGGCTGTATCTGTCCCACAATCAACTAAGTGAAATACCACTTAATC

TTCCCAAATCATTAGCAGAACTCAGAATTCATGAAAATAAAGTTAAGAAA

ATACAAAAGGACACATTCAAAGGAATGAATGCTTTACACGTTTTGGAAAT

GAGTGCAAACCCTCTTGATAATAATGGGATAGAGCCAGGGGCATTTGAAG

GGGTGACGGTGTTCCATATCAGAATTGCAGAAGCAAAACTGACCTCAGTT

CCTAAAGGCTTACCACCAACTTTATTGGAGCTTCACTTAGATTATAATAA

AATTTCAACAGTGGAACTTGAGGATTTTAAACGATACAAAGAACTACAAA

GGCTGGGCCTAGGAAACAACAAAATCACAGATATCGAAAATGGGAGTCTT

GCTAACATACCACGTGTGAGAGAAATACATTTGGAAAACAATAAACTAAA

AAAAATCCCTTCAGGATTACCAGAGTTGAAATACCTCCAGATAATCTTCC

TTCATTCTAATTCAATTGCAAGAGTGGGAGTAAATGACTTCTGTCCAACA
```

```
GTGCCAAAGATGAAGAAATCTTTATACAGTGCAATAAGTTTATTCAACAA

CCCGGTGAAATACTGGGAAATGCAACCTGCAACATTTCGTTGTGTTTTGA

GCAGAATGAGTGTTCAGCTTGGGAACTTTGGAATGTAATAATTAGTAATT

GGTAATGTCCATTTAATATAAGATTCAAAAATCCCTACATTTGGAATACT

TGAACTCTATTAATAATGGTAGTATTATATATACAAGCAAATATCTATTC

TCAAGTGGTAAGTCCACTGACTTATTTTATGACAAGAAATTTCAACGGAA

TTTTGCCAAACTATTGATACATAAGGGTTGAGAGAAACAAGCATCTATTG

CAGTTTCTTTTTGCGTACAAATGATCTTACATAAATCTCATGCTTGACCA

TTCCTTTCTTCATAACAAAAAGTAAGATATTCGGTATTTAACACTTTGT

TATCAAGCATATTTTAAAAAGAACTGTACTGTAAATGGAATGCTTGACTT

AGCAAAATTTGTGCTCTTTCATTTGCTGTTAGAAAAACAGAATTAACAAA

GACAGTAATGTGAAGAGTGCATTACACTATTCTTATTCTTTAGTAACTTG

GGTAGTACTGTAATATTTTTAATCATCTTAAAGTATGATTTGATATAATC

TTATTGAAATTACCTTATCATGTCTTAGAGCCCGTCTTTATGTTTAAAAC

TAATTTCTTAAAATAAAGCCTTCAGTAAATGTTCATTACCAACTTGATAA

ATGCTACTCATAAGAGCTGGTTTGGGGCTATAGCATATGCTTTTTTTTTT

TTAATTATTACCTGATTTAAAAATCTCTGTAAAAACGTGTAGTGTTTCAT

AAAATCTGTAACTCGCATTTTAATGATCCGCTATTATAAGCTTTTAATAG

CATGAAAATTGTTAGGCTATATAACATTGCCACTTCAACTCTAAGGAATA

TTTTTGAGATATCCCTTTGGAAGACCTTGCTTGGAAGAGCCTGGACACTA

ACAATTCTACACCAAATTGTCTCTTCAAATACGTATGGACTGGATAACTC

TGAGAAACACATCTAGTATAACTGAATAAGCAGAGCATCAAATTAAACAG

ACAGAAACCGAAAGCTCTATATAAATGCTCAGAGTTCTTTATGTATTTCT

TATTGGCATTCAACATATGTAAAATCAGAAAACAGGGAAATTTTCATTAA

AAATATTGGTTTGAAATAAAAAAAAAAAAAAA
```

Cell Growth Regulator with EF Hand Domain 1
>gi|33589823|ref|NM_006569.2| Homo sapiens cell growth regulator with EF hand domain 1 (CGREF1), mRNA|qPCR forward_primer match [378 . . . 394]|qPCR reverse_primer match [455 . . . 431]|qPCR probe match [396 . . . 415]

SEQ ID NO: 75
```
CGCGCAGCCCCTCCGGCCGCGGGCGCAGCGGGGCGCTGGTGGAGCTGCG

AAGGGCCAGGTCCGGCGGGCGGGCGGCGGCTGGCACTGGCTCCGGACTC

TGCCCGGCCAGGGCGGCGGCTCCAGCCGGGAGGGCGACGTGGAGCGGCCA

CGTGGAGCGGCCCGGGGGAGGCTGGCGGCGGGAGGCGAGGCGCGGGCGGC

GCAGCAGCCAGGAGCGCCCACGGAGCTGGACCCCAGAGCCGCGCGGCGC

CGCAGCAGTTCCAGGAAGGATGTTACCTTTGACGATGACAGTGTTAATCC

TGCTGCTGCTCCCCACGGGTCAGGCTGCCCCAAAGGATGGAGTCACAAGG

CCAGACTCTGAAGTGCAGCATCAGCTCCTGCCCAACCCCTTCCAGCCAGG

CCAGGAGCAGCTCGGACTTCTGCAGAGCTACCTAAAGGGACTAGGAGGAC

AGAAGTGCAACTGGAGCATCTGAGCCGGGAGCAGGTTCTCCTCTACCTCT
```

Kallikrein 10, Transcript Variant 1
>gi|22208981|ref|NM_002776.3| Homo sapiens kallikrein 10 (KLK10), transcript variant 1, mRNA|qPCR forward_primer match [851 . . . 874]|qPCR reverse_primer match [950 . . . 931]|qPCR probe match [890 . . . 914]

SEQ ID NO: 76
```
CATCCTGCCACCCCTAGCCTTGCTGGGACGTGAACCCTCTCCCCGCGCC
TGGGAAGCCTTCTTGGCACCGGGACCCGGAGAATCCCCACGGAAGCCAGT
TCCAAAAGGGATGAAAAGGGGGCGTTTCGGGCACTGGGAGAAGCCTGTAT
TCCAGGGCCCCTCCCAGAGCAGGAATCTGGGACCCAGGAGTGCCAGCCTC
ACCCACGCAGATCCTGGCCATGAGAGCTCCGCACCTCCACCTCTCCGCCG
CCTCTGGCGCCCGGGCTCTGGCGAAGCTGCTGCCGCTGCTGATGGCGCAA
CTCTGGGCCGCAGAGGCGGCGCTGCTCCCCCAAAACGACACGCGCTTGGA
TTGCCCTCCATGACTATGACCAGAGTGGACAGCTGGATGGCCTGGAGCTG
CTGTCCATGTTGACAGCTGCTCTGGCCCCTGGAGCTGCCAACTCTCCTAC
CACCAACCCGGTGATATTGATAGTGGACAAAGTGCTCGAGACGCAGGACC
TGAATGGGGATGGGCTCATGACCCCTGCTGAGCTCATCAACTTCCCGGGA
GTAGCCCTCAGGCACGTGGAGCCCGGAGAGCCCCTTGCTCCATCTCCTCA
GGAGCCACAAGCTGTTGGAAGGCAGTCCCTATTAGCTAAAAGCCCATTAA
GACAAGAAACACAGGAAGCCCCTGGTCCCAGAGAAGAAGCAAAGGGCCAG
GTAGAGGCCAGAAGGGAGTCTTTGGATCCTGTCCAGGAGCCTGGGGCCA
GGCAGAGGCTGATGGAGATGTTCCAGGGCCCAGAGGGGAAGCTGAGGGCC
AGGCAGAGGCTAAAGGAGATGCCCCTGGGCCCAGAGGGGAAGCTGGGGGC
CAGGCAGAGGCTGAAGGAGATGCCCCCGGGCCCAGAGGGGAAGCTGGGGG
CCAGGCAGAGGCCAGGGAGAATGGAGAGGAGGCCAAGGAACTTCCAGGGG
AAACACTGGAGTCTAAGAACACCCAAAATGACTTTGAGGTGCAGATTGTT
CAAGTGGAGAATGATGAGATCTAGATCTTGAAGATACAGGTACCCCACGA
AGTCTCAGTGCCAGAACATAAGCCCTGAAGTGGGCAGGGGAAATGTACGC
TGGGACAAGGACCATCTCTGTGCCCCCTGTCTGGTCCCAGTAGGTATCAG
GTCTTTCTGTGCAGCTCAGGGAGACCCTAAGTTAAGGGGCAGATTACCAA
TAAAGAACTGAATGAATTCATCCCCCCGGGCCACCTCTCTACCCGTCCAG
CCTGCCCAGACCCTCTCAGAGGAACGGGGTTGGGGACCGAAAGGACAGGG
ATGCCGCCTGCCCAGTGTTTCTGGGCCTCACGGTGCTCCGGCAGCAGAGC
GCATGGTGCTAGCCATGGCCGGCTGCAGAGGACCCAGTGAGGAAAGCTCA
GTCTATCCCTGGGCCCCAAACCCTCACCGGTTCCCCCTCACCTGGTGTTC
AGACACCCCATGCTCTCCTGCAGCTCAGGGCAGGTGACCCCATCCCCAGT
AATATTAATCATCACTAGAACTTTTTGAGAGCCTTGTACACATCAGGCAT
CATGCTGGGCATTTTATATATGATTTTATCCTCACAATAATTCTGTAGCC
AAGCAGAATTGGTTCCATTTGACAGATGAAGAAATTGAGGCAGATTGCGT
TAAGTGCTGTACCCTAAGGTGATATGCAGCTAATTAAATGGCAGATTTGA
AAAAAAAAAAAAAAAAAAAAAAAAAAAAAAAAA
```

Kallikrein 10 Transcript Variant 2
>gi|22208983|ref|NM_145888.1| Homo sapiens kallikrein 10 (KLK10), transcript variant 2, mRNA|qPCR forward_primer match [714 . . . 737]|qPCR reverse_primer match [813 . . . 794]|qPCR probe match [753 . . . 777]

SEQ ID NO: 77
```
ACCAGCGGCAGACCACAGGCAGGGCAGAGGCACGTCTGGGTCCCC
TCCCTCCTTCCTATCGGCGACTCCCAGGATCCTGGCCATGAGAGCTCCGC
ACCTCCACCTCTCCGCCGCCTCTGGCGCCCGGGCTCTGGCGAAGCTGCTG
CCGCTGCTGATGGCGCAACTCTGGGCCGCAGAGGCGGCGCTGCTCCCCCA
AAACGACACGCGCTTGGACCCCGAAGCCTATGGCTCCCCGTGCGCGCGCG
GCTCGCAGCCCTGGCAGGTCTCGCTCTTCAACGCCTCTCGTTCCACTGC
GCGGGTGTCCTGGTGGACCAGAGTTGGGTGCTGACGGCCGCGCACTGCGG
AAACAAGCCACTGTGGGCTCGAGTAGGGGATGACCACCTGCTGCTTCTTC
AGGGAGAGCAGCTCCGCCGGACCACTCGCTCTGTTGTCCATCCCAAGTAC
CACCAGGGCTCAGGCCCCATCCTGCCAAGGCGAACGGATGAGCACGATCT
CATGTTGCTGAAGCTGGCCAGGCCCGTAGTGCTGGGGCCCCGCGTCCGGG
CCCTGCAGCTTCCCTACCGCTGTGCTCAGCCCGGAGACCAGTGCCAGGTT
GCTGGCTGGGGCACCACGGCCGCCCGGAGAGTGAAGTACAACAAGGGCCT
GACCTGCTCCAGCATCACTATCCTGAGCCCTAAAGAGTGTGAGGTCTTCT
ACCCTGGCGTGGTCACCAACAACATGATATGTGCTGGACTGGACCGGGGC
CAGGACCCTTGCCAGAGTGACTCTGGAGGCCCCTGGTCTGTGACGAGACC
CTCCAAGGCATCCTCTCGTGGGGTGTTTACCCCTGTGGCTCTGCCCAGCA
TCCAGCTGTCTACACCCAGATCTGCAAATACATGTCCTGGATCAATAAAG
TCATACGCTCCAACTGATCCAGATGCTACGCTCCAGCTGATCCAGATGTT
ATGCTCCTGCTGATCCAGATGCCCAGAGGCTCCATCGTCCATCCTCTTCC
TCCCCAGTCGGCTGAACTCTCCCCTTGTCTGCAGTGTTCAAACCTCTGCC
GCCCTCCACACCTCTAAACATCTCCCTCTCACCTCATTCCCCCACCTATC
CCCATTCTCTGCCTGTACTGAAGCTGAAATGCAGGAAGTGGTGGCAAAGG
TTTATTCCAGAGAAGCCAGGAAGCCGGTCATCACCCAGCCTCTGAGAGCA
GTTACTGGGGTCACCCAACCTGACTTCCTCTGCCACTCCCTGCTGTGTGA
CTTTGGGCAAGCCAAGTGCCCTCTCTGAACCTCAGTTTCCTCATCTGCAA
AATGGGAACAATGACGTGCCTACCTCTTAGACATGTTGTGAGGAGACTAT
GATATAACATGTGTATGTAAATCTTCATGGTGATTGTCATGTAAGGCTTA
ACACAGTGGGTGGTGAGTTCTGACTAAAGGTTACCTGTTGTCGTGA
```

-continued

```
CCCTGCAGCTTCCCTACCGCTGTGCTCAGCCCGGAGACCAGTGCCAGGTT

GCTGGCTGGGGCACCACGGCCGCCCGGAGAGTGAAGTACAACAAGGGCCT

GACCTGCTCCAGCATCACTATCCTGAGCCCTAAAGAGTGTGAGGTCTTCT

ACCCTGGCGTGGTCACCAACAACATGATATGTGCTGGACTGGACCGGGGC

CAGGACCCTTGCCAGAGTGACTCTGGAGGCCCCCTGGTCTGTGACGAGAC

CCTCCAAGGCATCCTGTCGTGGGGTGTTTACCCCTGTGGCTCTGCCCAGC

ATCCAGCTGTCTACACCCAGATCTGCAAATACATGTCCTGGATCAATAAA

GTCATACGCTCCAACTGATCCAGATGCTACGCTCCAGCTGATCCAGATGT

TATGCTCCTGCTGATCGAGATGCCCAGAGGCTCCATCGTCCATCCTCTTC

CTCCCCAGTCGGCTGAACTCTCCCCTTGTCTGCACTGTTCAAACCTCTGC

CGCCCTCCACACCTCTAAACATCTCCCCTCTCACCTCATTCCCCCACCTA

TCCCCATTCTCTGCCTGTACTGAAGCTGAAATGCAGGAAGTGGTGGCAAA

GGTTTATTCCAGAGAAGCCAGGAAGCCGGTCATCACCCAGCCTCTGAGAG

CAGTTACTGGGGTCACCCAACCTGACTTCCTCTGCCACTCCCTGCTGTGT

GACTTTGGGCAAGCCAAGTGCCCTCTCTGAACCTCAGTTTCCTCATCTGC

AAAATGGGAACAATGACGTGCCTACCTCTTAGACATGTTGTGAGGAGACT

ATGATATAACATGTGTATGTAAATCTTCATGGTGATTGTCATGTAAGGCT

TAACACAGTGGGTGGTGAGTTCTGACTAAAGGTTACCTGTTGTCGTGA
```

Tissue Inhibitor of Metalloproteinase 1

>gi|4507508|ref|NM_003254.1| Homo sapiens tissue inhibitor of metalloproteinase 1 (erythroid potentiating activity, collagenase inhibitor) (TIMP1), mRNA|qPCR forward_primer match [221 . . . 241]|qPCR reverse_primer match [359 . . . 340]|qPCR probe match [251 . . . 283]

SEQ ID NO: 78
```
AGGGGCCTTAGCGTGCCGCATCGCCGAGATCCAGCGCCCAGAGAG

ACACCAGAGAACCCACCATGGCCCCCTTTGAGCCCCTGGCTTCTGGCATC

CTGTTGTTGCTGTGGCTGATAGCCCCCAGCAGGGCCTGCACCTGTGTCCC

ACCCCACCCACAGACGGCCTTCTGCAATTCCGACCTCGTCATCAGGGCCA

AGTTCGTGGGGACACCAGAAGTCAACCAGACCACCTTATACCAGCGTTAT

GAGATCAAGATGACCAAGATGTATAAAGGGTTCCAAGCCTTAGGGGATGC

CGCTGACATCCGGTTCGTCTACACCCCCGCCATGGAGAGTGTCTGCGGAT

ACTTCCACAGGTCCCACAACCGCAGCGAGGAGTTTCTCATTGCTGGAAAA

CTGCAGGATGGACTCTTGCACATCACTACCTGCAGTTTCGTGGCTCCCTG

GAACAGCCTGAGCTTAGCTCAGCGCCGGGCTTCACCAAGACCTACACTG

TTGGCTGTGAGGAATGCACAGTGTTTCCTGTTTATCCATCCCTGCAAA

CTGCAGAGTGGCACTCATTGCTTGTGGACGGACCAGCCTCCAAGGCTC

TGAAAAGGGCTTCCAGTCCCGTCACCTTGCCTGCCTGCCTCGGGAGCCAG

GGCTGTGCACCTGGCAGTCCCTGCGGTCCCAGATAGCCTGAATCCTGCCC

GGAGTGGAACTGAAGCCTGCACAGTGTCCACCCTGTTCCCACTCCCATCT

TTCTTCCGGACAATGAAATAAAGAGTTACCACCCAGC
```

Secreted Protein, Acidic, Cysteine-Rich

>gi|48675809|ref|NM_003118.2| Homo sapiens secreted protein, acidic, cysteine-rich (osteonectin) (SPARC), mRNA|qPCR forward_primer match [788 . . . 810]|qPCR reverse_primer match [915 . . . 898]|qPCR probe match [818 . . . 839]

SEQ ID NO: 79
```
GTTGCCTGTCTCTAAACCCCTCCACATTCCCGCGGTCCTTCAGACTG

CCCGGAGAGCGCGCTCTGCCTGCCGCCTGCCTGCCTGCCACTGAGGGTTC

CCAGCACCATGAGGGCCTGGATCTTCTTTCTCCTTTGCCTGGCCGGGAGG

GCCTTGGCAGCCCCTCAGCAAGAAGCCCTGCCTGATGAGACAGAGGTGGT

GGAAGAAACTGTGGCAGAGGTGACTGAGGTATCTGTGGGAGCTAATCCTG

TCCAGGTGGAAGTAGGAGAATTTGATGATGGTGCAGAGGAAACCGAAGAG

GAGGTGGTGGCGGAAAATCCCTGCCAGAACCACCACTGCAAACACGGCAA

GGTGTGCGAGCTGGATGAGAACAACACCCCCATGTGCGTGTGCCAGGACC

CCACCAGCTGCCCAGCCCCCATTGGCGAGTTTGAGAAGGTGTGCAGCAAT

GACAACAAGACCTTCGACTCTTCCTGCCACTTCTTTGCCACAAAGTGCAC

CCTGGAGGGCACCAAGAAGGGCCACAAGCTCCACCTGGACTACATCGGGC

CTTGCAAATACATCCCCCCTTGCCTGGACTCTGAGCTGACCGAATTCCCC

CTGCGCATGCGGGACTGGCTCAAGAACGTCCTGGTCACCCTGTATGAGAG

GGATGAGGACAACAACCTTCTGACTGAGAAGCAGAAGCTGCGGGTGAAGA

AGATCCATGAGAATGAGAAGCGCCTGGAGGCAGGAGACCACCCCGTGGAG

CTGCTGGCCCGGGACTTCGAGAAGAACTATAACATGTACATCTTCCCTGT

ACACTGGCAGTTCGGCCAGCTGGACCAGCACCCCATTGACGGGTACCTCT

CCCACACCGAGCTGGCTCCACTGCGTGCTCCCCTCATCCCCATGGAGCAT

TGCACCACCCGCTTTTTCGAGACCTGTGACCTGGACAATGACAAGTACAT

CGCCCTGGATGAGTGGGCCGGCTGCTTCGGCATCAAGCAGAAGGATATCG

ACAAGGATCTTGTGATCTAAATCCACTCCTTCCACAGTACCGGATTCTCT

CTTTAACCCTCCCCTTCGTGTTTCCCCCAATGTTTAAAATGTTTGGATGG

TTTGTTGTTCTGCCTGGAGACAAGGTGCTAACATAGATTTAAGTGAATAC

ATTAACGGTGCTAAAAATGAAAATTCTAACCCAAGACATGACATTCTTAG

CTGTAACTTAACTATTAAGGCCTTTTCCACACGCATTAATAGTCCCATTT

TTCTCTTGCCATTTGTAGCTTTGCCCATTGTCTTATTGGCACATGGGTGG

ACACGGATCTGCTGGGCTCTGCCTTAAACACACATTGCAGCTTCAACTTT

TCTCTTTAGTGTTCTGTTTGAAACTAATACTTACCGAGTCAGACTTTGTG

TTCATTTCATTTCAGGGTCTTGGCTGCCTGTGGGCTTCCCCAGGTGGCCT

GGAGGTGGGCAAAGGGAAGTAACAGACACACGATGTTGTCAAGGATGGTT

TTGGGACTAGAGGCTCAGTGGTGGGAGAGATCCCTGCAGAACCCACCAAC

CAGAACGTGGTTTGCCTGAGGCTGTAACTGAGAGAAAGATTCTGGGGCTG

TGTTATGAAAATATAGACATTCTCACATAAGCCCAGTTCATCACCATTTC

CTCCTTTACCTTTCAGTGCAGTTTCTTTTCACATTAGGCTGTTGGTTCAA

ACTTTTGGGAGCACGGACTGTCAGTTCTCTGGGAAGTGGTCAGCGCATCC

TGCAGGGCTTCTCCTCCTCTGTCTTTTGGAGAACCAGGGCTCTTCTCAGG
```

-continued

```
GGCTCTAGGGACTGCCAGGCTGTTTCAGCCAGGAAGGCCAAAATCAAGAG
TGAGATGTAGAAAGTTGTAAAATAGAAAAAGTGGAGTTGGTGAATCGGTT
GTTCTTTCCTCACATTTGGATGATTGTCATAAGGTTTTTAGCATGTTCCT
CCTTTTCTTCACCCTCCCCTTTTTTCTTCTATTAATCAAGAGAAACTTCA
AAGTTAATGGGATGGTCGGATCTCACAGGCTGAGAACTCGTTCACCTCCA
AGCATTTCATGAAAAAGCTGCTTCTTATTAATCATACAAACTCTCACCAT
GATGTGAAGAGTTTCACAAATCCTTCAAAATAAAAAGTAATGACTTAGAA
ACTGCCTTCCTGGGTGATTTGCATGTGTCTTAGTCTTAGTCACCTTATTA
TCCTGACACAAAAACACATGAGCATACATGTCTACACATGACTACACAAA
TGCAAACCTTTGCAAACACATTATGCTTTTGCACACACACACCTGTACAC
ACACACCGGCATGTTTATACACAGGGAGTGTATGGTTCCTGTAAGCACTA
AGTTAGCTGTTTTCATTTAATGACCTGTGGTTTAACCCTTTTGATCACTA
CCACCATTATCAGCACCAGACTGAGCAGCTATATCCTTTTATTAATCATG
GTCATTCATTCATTCATTCATTCACAAAATATTTATGATGTATTTACTCT
GCACCAGGTCCCATGCCAAGCACTGGGGACACAGTTATGGCAAAGTAGAC
AAAGCATTTGTTCATTTGGAGCTTAGAGTCCAGGAGGAATACATTAGATA
ATGACACAATCAAATATAAATTGCAAGATGTCACAGGTGTGATGAAGGGA
GAGTAGGAGAGACCATGAGTATGTGTAACAGGAGGACACAGCATTATTCT
AGTGCTGTACTGTTCCGTACGGCAGCCACTACCCACATGTAACTTTTTAA
GATTTAAATTTAAATTAGTTAACATTCAAAACGCAGCTCCCCAATCACAC
TAGCAACATTTCAAGTGCTTGAGAGCCATGCATGATTAGTGGTTACCCTA
TTGAATAGGTCAGAAGTAGAATCTTTTCATCATCACAGAAAGTTCTATTG
GACAGTGCTCTTCTAGATCATCATAAGACTACAGAGCACTTTTCAAAGCT
CATGCATGTTCATCATGTTAGTGTCGTATTTTGAGCTGGGGTTTTGAGAC
TCCCCTTAGAGATAGAGAAACAGACCCAAGAAATGTGCTCAATTGCAATG
GGCCACATACCTAGATCTCCAGATGTCATTTCCCCTCTCTTATTTTAAGT
TATGTTAAGATTACTAAAACAATAAAAGCTCCTAAAAAATCAAAAAAAA
AAAAAAAAAAAAAAAAAAAAAAAAAAAAAA
```

Transforming Growth Factor, Beta-Induced
>gi|4507466|ref|NM_000358.1| Homo sapiens transforming growth factor, beta-induced, 68 kDa (TGFBI), mRNA|qPCR assay_on_demand_context match [170 ... 194]

SEQ ID NO: 80
```
GCTTGCCCGTCGGTCGCTAGCTCGCTCGGTGCGCGTCGTCCCGCTCC
ATGGCGCTCTTCGTGCGGCTGCTGGCTCTCGCCCTGGCTCTGGCCCTGGG
CCCCGCCGCGACCCTGGCGGGTCCCGCCAAGTCGCCCTACCAGCTGGTGC
TGCAGCACAGCAGGCTCCGGGGCCGCCAGCACGGCCCCAACGTGTGTGCT
GTGCAGAAGGTTATTGGCACTAATAGGAAGTACTTCACCAACTGCAAGCA
GTGGTACCAAAGGAAAATCTGTGGCAAATCAACAGTCATCAGCTACGAGT
GCTGTCCTGGATATGAAAAGGTCCCTGGGGAGAAGGGCTGTCCAGCAGCC
CTACCACTCTCAAACCTTTACGAGACCCTGGGAGTCGTTGGATCCACCAC
CACTCAGCTGTACACGGACCGCACGGAGAAGCTGAGGCCTGAGATGGAGG
GGCCCGGCAGCTTCACCATCTTCGCCCCTAGCAACGAGGCCTGGGCCTCC
TTGCCAGCTGAAGTGCTGGACTCCCTGGTCAGCAATGTCAACATTGAGCT
GCTCAATGCCCTCCGCTACCATATGGTGGGCAGGCGAGTCCTGACTGATG
AGCTGAAACACGGCATGACCCTCACCTCTATGTACCAGAATTCCAACATC
CAGATCCACCACTATCCTAATGGGATTGTAACTGTGAACTGTGCCCGGCT
CCTGAAAGCCGACCACCATGCAACCAACGGGGTGGTGCACCTCATCGATA
AGGTCATCTCCACCATCACCAACAACATCCAGCAGATCATTGAGATCGAG
GACACCTTTGAGACCCTTCGGGCTGCTGTGGCTGCATCAGGGCTCAACAC
GATGCTTGAAGGTAACGGCCAGTACACGCTTTTGGCCCCGACCAATGAGG
CCTTCGAGAAGATCCCTAGTGAGACTTTGAACCGTATCCTGGGCGACCCA
GAAGCCCTGAGAGACCTGCTGAACAACCACATCTTGAAGTCAGCTATGTG
TGCTGAAGCCATCGTTGCGGGGCTGTCTGTAGAGACCCTGGAGGGCACGA
CACTGGAGGTGGGCTGCAGCGGGGACATGCTCACTATCAACGGGAAGGCG
ATCATCTCCAATAAAGACATCCTAGCCACCAACGGGGTGATCCACTACAT
TGATGAGCTACTCATCCCAGACTCAGCCAAGACACTATTTGAATTGGCTG
CAGAGTCTGATGTGTCCACAGCCATTGACCTTTTCAGACAAGCCGGCCTC
GGCAATCATCTCTCTGGAAGTGAGCGGTTGACCCTCCTGGCTCCCCTGAA
TTCTGTATTCAAAGATGGAACCCCTCCAATTGATGCCCATACAAGGAATT
TGCTTCGGAACCACATAATTAAAGACCAGCTGGCCTCTAAGTATCTGTAC
CATGGACAGACCCTGGAAACTCTGGGCGGCAAAAAACTGAGAGTTTTTGT
TTATCGTAATAGCCTCTGCATTGAGAACAGCTGCATCGCGGCCCACGACA
AGAGGGGGAGGTACGGGACCCTGTTCACGATGGACCGGGTGCTGACCCCC
CCAATGGGACTGTCATGGATGTCCTGAAGGGAGACAATCGCTTTAGCAT
GCTGGTAGCTGCCATCCAGTCTGCAGGACTGACGGAGACCCTCAACCGGG
AAGGAGTCTACACAGTCTTTGCTCCCACAAATGAAGCCTTCCGAGCCCTG
CCACCAAGAGAACGGAGCAGACTCTTGGGAGATGCCAAGGAACTTGCCAA
CATCCTGAAATACCACATTGGTGATGAAATCCTGGTTAGCGGAGGCATCG
GGGCCCTGGTGCGGCTAAAGTCTCTCCAAGGTGACAAGCTGGAAGTCAGC
TTGAAAAACAATGTGGTGAGTGTCAACAAGGAGCCTGTTGCCGAGCCTGA
CATCATGGCCACAAATGGCGTGGTCCATGTCATCACCAATGTTCTGCAGC
CTCCAGCCAACAGACCTCAGGAAAGAGGGGATGAACTTGCAGACTCTGCG
CTTGAGATCTTCAAACAAGCATCAGCGTTTTCCAGGGCTTCCCAGAGGTC
TGTGCGACTAGCCCCTGTCTATCAAAAGTTATTAGAGAGGATGAAGCATT
AGCTTGAAGCACTACAGGAGGAATGCACCACGGCAGCTCTCCGCCAATTT
CTCTCAGATTTCCACAGAGACTGTTTGAATGTTTTCAAAACCAAGTATCA
CACTTTAATGTACATGGGCCGCACCATAATGAGATGTGAGCCTTGTGCAT
GTGGGGAGGAGGGAGAGAGATGTACTTTTTAAATCATGTTCCCCCTAAA
CATGGCTGTTAACCCACTGCATGCAGAAACTTGGATGTCACTGCCTGACA
TTCACTTCCAGAGAGGACCTATCCCAAATGTGGAATTGACTGCCTATGCC
```

-continued

AAGTCCCTGGAAAAGGAGCTTGAGTATTGTGGGGCTCATAAAACATGAAT

CAAGCAATCCAGCCTCATGGGAAGTCCTGGCACAGTTTTTGTAAAGCCCT

TGCACAGCTGGAGAAATGGCATCATTATAAGCTATGAGTTGAAATGTTCT

GTCAAATGTGTCTCACATCTACACGTGGCTTGGAGGCTTTTATGGGGCCC

TGTCCAGGTAGAAAAGAAATGGTATGTAGAGCTTAGATTTCCCTATTGTG

ACAGAGCCATGGTGTGTTTGTAATAATAAAACCAAAGAAACATA

EGF-Containing Fibulin-Like Extracellular Matrix Protein 2
>gi|8393298|ref|NM016938.1| Homo sapiens EGF-containing fibulin-like extracellular matrix protein 2 (EFEMP2), mRNA|qPCR assay_on_demand_context match [1248 . . . 1272]

SEQ ID NO: 81
CAAGCTTGGCACGAGGGCAGGCATTGCCCGAGCCAGCCGAGCCGC

CAGAGCCGCGGGCCGCGCGGGTGTCGCGGGCCCAACCCCAGGATGCTCCC

CTGCGCCTCCTGCCTACCCGGGTCTCTACTGCTCTGGGCGCTGCTACTGT

TGCTCTTGGGATCAGCTTCTCCTCAGGATTCTGAAGAGCCCGACAGCTAC

ACGGAATGCAGAGATGGCTATGAGTGGGACCCAGACAGCCAGCACTGCCG

GGATGTCAACGAGTGTCTGACCATCCCTGAGGCCTGCAAGGGGGAAATGA

AGTGCATCAACCACTACGGGGCTACTTGTGCCTGCCCCGCTCCGCTGCC

GTCATCAACGACCTACACGGCGAGGGACCCCCGCCACCAGTGCCTCCCGC

TCAACACCCCAACCCCTGCCCACCAGGCTATGAGCCCGACGATCAGGACA

GCTGTGTGGATGTGGACGAGTGTGCCCAGGCCCTGCACGACTGTCGCCCC

AGCCAGGACTGCCATAACTTGCCTGGCTCCTATCAGTGCACCTGCCCTGA

TGGTTACCGCAAGATCGGGCCCGAGTGTGTGGACATAGACGAGTGCCGCT

ACCGCTACTGCCAGCACCGCTGCGTGAACCTGCCTGGCTCCTTCCGCTGC

CAGTGCGAGCCGGGCTTCCAGCTGGGGCCTAACAACCGCTCCTGTGTTGA

TGTGAACGAGTGTGACATGGGGGCCCCATGCGAGCAGCGCTGCTTCAACT

CCTATGGGACCTTCCTGTGTCGCTGCCACCAGGGCTATGAGCTGCATCGG

GATGGCTTCTCCTGCAGTGATATTGATGAGTGTAGCTACTCCAGCTACCT

CTGTCAGTACCGCTGCGTCAACGAGCCAGGCCGTTTCTCCTGCCACTGCC

CACAGGGTTACCAGCTGCTGGCCACACGCCTCTGCCAAGACATTGATGAG

TGTGAGTCTGGTGCGCACCAGTGCTCCGAGGCCCAAACCTGTGTCAACTT

CCATGGGGGCTACCGCTGCGTGGACACCAACCGCTGCGTGGAGCCCTACA

TCCAGGTCTCTGAGAACCGCTGTCTCTGCCCGGCCTCCAACCCTCTATGT

CGAGAGCAGCCTTCATCCATTGTGCACCGCTACATGACCATCACCTCGGA

GCGGAGAGTACCCGCTGACGTGTTCCAGATCCAGGCGACCTCCGTCTACC

CCGGTGCCTACAATGCCTTTCAGATCCGTGCTGGAAACTCGCAGGGGGAC

TTTTACATTAGGCAAATCAACAACGTCAGCGCCATGCTGGTCCTCGCCCG

GCCGGTGACGGGCCCCCGGGAGTACGTGCTGGACCTGGAGATGGTCACCA

TGAATTCCCTCATGAGCTACCGGGCCAGCTCTGTACTGAGGCTCACCGTC

TTTGTAGGGGCCTACACCTTCTGAGGAGCAGGAGGGAGCCACCCTCCCTG

CAGCTACCCTAGCTGAGGAGCCTGTTGTGAGGGGCAGAATGAGAAAGGCC

CAGGGGCCCCCATTGACAGGAGCTGGGAGCTCTGCACCACGAGCTTCAGT

CACCCCGAGAGGAGAGGAGGTAACGAGGAGGGCGGACTCCAGGCCCCGGC

CCAGAGATTTGGACTTGGCTGGCTTGCAGGGGTCCTAAGAAACTCCACTC

TGGACAGCGCCAGGAGGCCCTGGGTTCCATTCCTAACTCTGCCTCAAACT

GTACATTTGGATAAGCCCTAGTAGTTCCCTGGGCCTGTTTTTCTATAAAA

CGAGGCAACTGG

Lumican
>gi|21359858|ref|NM_002345.2| Homo sapiens lumican (LUM), mRNA|qPCR forward_primer match [61 . . . 84]|qPCR reverse_primer match [182 . . . 162]|qPCR probe match [117 . . . 152]

SEQ ID NO: 82
GTATCACTCAGAATCTGGCAGCCAGTTCCGTCCTGACAGAGTTCAC

AGCATATATTGGTGGATTCTTGTCCATAGTGCATCTGCTTTAAGAATTAA

CGAAAGCAGTGTCAAGACAGTAAGGATTCAAACCATTTGCCAAAAATGAG

TCTAAGTGCATTTACTCTCTTCCTGGCATTGATTGGTGGTACCAGTGGCC

AGTACTATGATTATGATTTTCCCCTATCAATTTATGGGCAATCATCACCA

AACTGTGCACCAGAATGTAACTGCCCTGAAAGCTACCCAAGTGCCATGTA

CTGTGATGAGCTGAAATTGAAAAGTGTACCAATGGTGCCTCCTGGAATCA

AGTATCTTTACCTTAGGAATAACCAGATTGACCATATTGATGAAAAGGCC

TTTGAGAATGTAACTGATCTGCAGTGGCTCATTCTAGATCACAACCTTCT

AGAAAACTCCAAGATAAAAGGGAGAGTTTTCTCTAAATTGAAACAACTGA

AGAAGCTGCATATAAACCACAACAACCTGACAGAGTCTGTGGGCCCACTT

CCCAAATCTCTGGAGGATCTGCAGCTTACTCATAACAAGATCACAAAGCT

GGGCTCTTTTGAAGGATTGGTAAACCTGACCTTCATCCATCTCCAGCACA

ATCGGCTGAAAGAGGATGCTGTTTCAGCTGCTTTTAAAGGTCTTAAATCA

CTCGAATACCTTGACTTGAGCTTCAATCAGATAGCCAGACTGCCTTCTGG

TCTCCCTGTCTCTCTTCTAACTCTCTACTTAGACAACAATAAGATCAGCA

ACATCCCTGATGAGTATTTCAAGCGTTTTAATGCATTGCAGTATCTGCGT

TTATCTCACAACGAACTGGCTGATAGTGGAATACCTGGAAATTCTTTCAA

TGTGTCATCCCTGGTTGAGCTGGATCTGTCCTATAACAAGCTTAAAAACA

TACCAACTGTCAATGAAAACCTTGAAAACTATTACCTGGAGGTCAATCAA

CTTGAGAAGTTTGACATAAAGAGCTTCTGCAAGATCCTGGGGCCATTATC

CTACTCCAAGATCAAGCATTTGCGTTTGGATGGCAATCGCATCTCAGAAA

CCAGTCTTCCACCGGATATGTATGAATGTCTACGTGTTGCTAACGAAGTC

ACTCTTAATTAATATCTGTATCCTGGAACAATATTTTATGGTTATGTTTT

TCTGTGTGTCAGTTTTCATAGTATCCATATTTTATTACTGTTTATTACTT

CCATGAATTTTAAAATCTGAGGGAAATGTTTTGTAAACATTTATTTTTTT

TAAAGAAAAGATGAAAGGCAGGCCTATTTCATCACAAGAACACACACATA

TACACGAATAGACATCAAACTCAATGCTTTATTTGTAAATTTAGTGTTTT

-continued

```
TTTATTTCTACTGTCAAATGATGTGCAAAACCTTTTACTGGTTGCATGGA
AATCAGCCAAGTTTTATAATCCTTAAATCTTAATGTTCCTCAAAGCTTGG
ATTAAATACATATGGATGTTACTCTCTTGCACCAAATTATCTTGATACAT
TCAAATTTGTCTGGTTAAAAAATAGGTGGTAGATATTGAGGCCAAGAATA
TTGCAAAATACATGAAGCTTCATGCACTTAAAGAAGTATTTTTAGAATAA
GAATTTGCATACTTACCTAGTGAAACTTTTCTAGAATTATTTTTCACTCT
AAGTCATGTATGTTTCTCTTTGATTATTTGCATGTTATGTTTAATAAGCT
ACTAGCAAAATAAAACATAGCAAATGAAAAAAAAAAAAAAAAAAAAAAA
AAAAAAA
```

Stannin
>gi|29893560|ref|NM_003498.3| Homo sapiens stannin (SNN), mRNA

SEQ ID NO: 83
```
AGCGGGGCCGGACCGGGCGGGCGGAGCCGGGCCCGCGGGGCTGCT
GCGGGGCGATCGGGCCGGGCCGCTGCCGCGCCATGGACTCCCGTGTCCAG
CCTGAGTTCCAGCCTCACTGAGTGGCCACCCCCAAAGTGCTGCCAGCCGA
GGAAGCCCCAGCACTGACCATGTCTATTATGGACCACAGCCCCACCACG
GGCGTGGTCACAGTCATCGTCATCCTCATTGCCATCGCGGCCCTGGGGGC
CTTGATCCTGGGCTGCTGGTGCTACCTGCGGCTGCAGCGCATCAGCCAGT
CAGAGGACGAGGAGAGCATCGTGGGGATGGGGAGACCAAGGAAGCCCTT
CCTGCTGGTGCAGTATTCGGCCAAGGGACCGTGCGTGGAGAGAAAGGCCA
AGCTGATGACTCCCAACGGCCCGGAAGTCCACGGCTGAGCCAGGATGCAA
GGCTCCTGGTCCTGTTTGCAGCCGGCCAAGAGGCGCTGGGAGGGGCAAAA
CCATACGGATGCGCTGCTGTCTGAGAGGAAGGGCTGACACTTGCTGGCAT
GGCCTCTGCGGGCTTCGTCATCGCATGCACTGATGCCCGGGGACCTGGCT
GTCCTGGGCTTCCCCTCGGCCTCCAGGTGAGGCTGCCCATTGCAGGCACT
GGGCAGGCCTGACCTTGCTGGGGCTCATGGCCCTGTAGCGCTTTTGTTAC
TTGAATGTCTAGCTGAGCCTGTTTTTGATGGAGCTACTACTGTAATGCGT
GAACTAACAAACCTGTGAACTGTAAATAGGCCCCTGGAAGCACGTGCTTA
AGCCCTTTTGCTGATTTTTAAAAATATCATCTAGCGCACACGGGACTGGT
ATTCTGGCTGTACTAATGACAAGCTGAGTCAAGACCCTGGAGGGTCATAG
GCTTGTAAAGGCCCACGCCACACTCGGCAGGGGTCTCTCATGTGTGTCCA
TCTGCGTGTATGTCAAGGAAGTGAGATGCCAATTTGGGGTCTTGAGGCTG
ACCAGTTGGGGTGCTTGGGTGATCTCTGCTTCATTAGTCATGGGTGGAAG
AAAAACCACACCCCCGCACCCCTCCGTTCTTTCTGCATAGACTCACTTG
TTAAATAGCAGTTCTGTTGAGAGTGGAGTTACTGCAGGGAAGCTACCGGA
CCTGCCTGGGAGCCAGTGAAGGGCGAGTCAGGGCACGCGTCCTGGAGGCT
GCCAGCGTCCTTGTAGCAGAGCAGTTTCTTGCCGCTTGGGTCTTCAGCAC
GCCAAGCCCCCACCAACCCTCCACCCCGAGTGAAGGCTTCGCTGAAATT
GCTTTGGTCCTCATAGAGCCTGTGGTGGCTACTTTTGGTCTGAAACCCAC
TTGGCCCAGGAAAGAGAAAAGGTTGTATGTTTTGTGTTGGTGTTTCCTAT
TTTGCACTGGAGGGGAGGGGACTGTTGAGGTTCTGTCTTTTTTCTTCTTT
TCCTCTTCCCTCTTCACATCACTTGGCTTCCTTTCCTCTCTGATGACCGT
CCGCCTATGGGGTTCTGACTTCACTTTCCTCAGCGGGTCTCCAGTCCCCT
GACCCAGCTCTAAAGGCACTTAGGACCCAGGGAACATTTCTCACGTGCAC
ATTCCCCTAAGAGCCACCAGACTGCTTCCTGCCAGCCTGTGCTTGCGGCA
GGGAGCCGGGGCAGGGCAGAGGTGAACTTGAAGTTCAGGACTTGACTCTC
CCACAGGTGGTGAGCTGGTGGCTCTCTGGTGAGCTAGTGTCTCCACAGCC
TGTCTCCAAGGCCTCCCCTATGTACATTTCAGTGAGCTCACTTTGATTTT
TAATCCCACCACAAGCACATACTAATTTTATTTATGATTCAAATGTGACT
CGTGCCTGCCCATCCCTGTAATAGATGGAAGGTCAGCCCCGGCTTAACCA
CAGAGCACTGGCCCTTCATGGCTGAGCTCAGAGCTCTGGCCTCCTGCTCA
GACTAAAGGCACCTCCTCTGGCCTCACCCAAGCCTCTTCTAAAAACCATG
TTGAATGAATCCACGTTCTGGAACCCCGAGGCGGGAGAAGTAGGGAGCTG
TTCGTTTAAGCAGCATACACCTAAATTGGGGGTTTAAACATTAAGTAGGA
GCTTGGGGTGGAAGAGGGACAGCCGGCTGGGCCACCTGAGCAGAAGGTGG
TAATGAAACACCTCAGCTGGGCTCTTGGGAGACCTTAGGAAGCAGGAGAG
GCAACACCTCTGGCTACTGATGGTGTGGCAAGTTCAGAAGAGGTGGTGGT
GGGGTAGGCGTGATGTCAGCAGAAGCCCTGCAGGCTGGGTGGGCAGGACA
CGTGGTGGGGCCACTGAAACCAGGCCTAGGAGGGAGAACAAGTTCCAAA
GGTGCCGACTGGAAGAAGGGGGTAAAAGTTTGCTTTGGTGAGTGAGAAAA
GGCTGGGGCGTGTGATCCATCCCCTCACGTTTCAGAACTTCCAGGCTTTC
TACCTCGACTCTCACCACAGCCAGCACATACACCTAGGCTGTTTTTCCTT
CCTCCACACCTGAGGGACGCAGCAACAGCTAGGATCTGCATTTTCAGGTT
CCGAGCCTGACCCCTGGAACTGACCAGCGCTCGATTGTCAGCCTTGGCCT
GGGGTTTTGACCTTGCCAGTGAAGTTTCGGTTTTGAAGTGATTAAATGTC
ACTTCCTCATCAGTTTCACTTCTGGAGGTTTTCTTATCCTACTCCCTGGT
GCCAGGGACGTACCTGGGAGTTTGAATCAGGCCCATTTGAGCGTGGCAGC
CGTGTTGGGTGAAGGTCCGGGGCTCGGTGAGGCACTGGGGGGGTTTTCGG
GAGGAAAATGAAAATGCTTCTAGAATGAGTGAACCACATCATAGCTCTCA
CTGTTTTTTCAATAGCTACTTTTTTTAGCAGACACCAGAGCCACACTCAA
ATGGCTAAGTAGGTTATGACCTCTCTGGATTATTTTTGAATGCCCAACTG
TTGCATTCAAGTTTTCTGACTAATAAGAAATTAAGCATTCATCCTTCGTA
TCACTGCAGAAGCAACAGTGGGGGCACAGGGAGGGAACTCTTGACACTGA
GCCACTAAAATATGGACTAATTTTTTGGACAAATCTTCAAACGGACTGTG
CTACTGTATTTGTCTCAAAGCTACCAAGTTTGTGCAATAAGTGGAAGGGA
TGTCATCCTTCTTCAATAAATGCTGAATGACATTCAAGCTGATTTTCTAG
ACCACTGAGAAATCTTTATTTACAATAAATTTCAATAAAATTTGCATAA
ATATATTCCCAAAAAAAAAAAAAAAAAAAAAAGAAAAAAAAAAAA
```

Secreted Phosphoprotein 1
>gi|38146097|ref|NM_000582.2| Homo sapiens secreted phosphoprotein 1 (osteopontin, bone sialoprotein I, early T-lymphocyte activation 1) (SPP1), mRNA|qPCR assay_on_demand_context match [253 . . . 277]

SEQ ID NO: 84
CTCCCTGTGTTGGTGGAGGATGTCTGCAGCAGCATTTAAATTCTGG
GAGGGCTTGGTTGTCAGCAGCAGCAGGAGGAGGCAGAGCACAGCATCGT
CGGGACCAGACTCGTCTCAGGCCAGTTGCAGCCTTCTCAGCCAAACGCCG
ACCAAGGAAAACTCACTACCATGAGAATTGCAGTGATTTGCTTTTGCCTC
CTAGGCATCACCTGTGCCATACCAGTTAAACAGGCTGATTCTGGAAGTTC
TGAGGAAAGCAGCTTTACAACAAATACCCAGATGCTGTGGCCACATGGCT
AAACCCTGACCCATCTCAGAAGCAGAATCTCCTAGCCCCACAGACCCTTC
CAAGTAAGTCCAACGAAAGCCATGACCACATGGATGATATGGATGATGAA
GATGATGATGACCATGTGGACAGCCAGGACTCCATTGACTCGAACGACTC
TGATGATGTAGATGACACTGATGATTCTCACCAGTCTGATGAGTCTCACC
ATTCTGATGAATCTGATGAACTGGTCACTGATTTTCCCACGGACCTGCCA
GCAACCGAAGTTTTCACTCCAGTTGTCCCCACAGTAGACACATATGATGG
CCGAGGTGATAGTGTGGTTTATGGACTGAGGTCAAAATCTAAGAAGTTTC
GCAGACCTGACATCCAGTACCCTGATGCTACAGACGAGGACATCACCTCA
CACATGGAAAGCGAGGAGTTGAATGGTGCATACAAGGCCATCCCCGTTGC
CCAGGACCTGAACGCGCCTTCTGATTGGGACAGCCGTGGGAAGGACAGTT
ATGAAACGAGTCAGCTGGATGACCAGAGTGCTGAAACCCACAGCCACAAG
CAGTCCAGATTATATAAGCGGAAAGCCAATGATGAGAGCAATGAGCATTC
CGATGTGATTGATAGTCAGGAACTTTCCAAAGTCAGCCGTGAATTCCACA
GCCATGAATTTCAGAGCCATGAAGATATGCTGGTTGTAGACCCCAAAAGT
AAGGAAGAAGATAAACACCTGAAATTTCGTATTTCTCATGAATTAGATAG
TGCATCTTCTGAGGTCAATTAAAAGGAGAAAAAATACAATTTCTCACTTT
GCATTTAGTCAAAAGAAAAAATGCTTTATAGCAAATGAAAGAGAACATG
AAATGCTTCTTTCTCAGTTTATTGGTTGAATGTGTATCTATTTGAGTCTG
GAAATAACTAATGTGTTGATAATTAGTTTAGTTTGTGGCTTCATGGAAAC
TCCCTGTAAACTAAAAGCTTCAGGGTTATGTCTATGTTCATTCTATAGAA
GAAATGCAAACTATCACTGTATTTTAATATTTGTTATTCTCTCATGAATA
GAAATTTATGTAGAAGCAAACAAAATACTTTTACCCACTTAAAAAGAGAA
TATAACATTTTATGTCACTATAATCTTTTGTTTTTTAAGTTAGTGTATAT
TTTGTTGTGATTATCTTTTTGTGGTGTGAATAAATCTTTTATCTTGAATG
TAATAAGAATTTGGTGGTGTCAATTGCTTATTTGTTTTCCCACGGTTGTC
CAGCAATTAATAAAACATAACCTTTTTTACTGCCTAAAAAAAAAAAAAAAA
AAAAAAAAAAAAAAAAAAAAA

Chondroitin Sulfate Proteoglycan 2
>gi|21361115|ref|NM_004385.2| Homo sapiens chondroitin sulfate proteoglycan 2 (versican) (CSPG2), mRNA|qPCR forward_primer match [10087 . . . 10106] |qPCR reverse_primer match [10185 . . . 10163]|qPCR probe match [10139 . . . 10161]

SEQ ID NO: 85
GCTGCCCCGAGCCTTTCTGGGAAGAACTCCAGGCGTGCGGACGCA
ACAGCCGAGAACATTAGGTGTTGTGGACAGGAGCTGGGACCAAGATCTTC
GGCCAGCCCCGCATCCTCCCGCATCTTCCAGCACCGTCCCGCACCCTCCG
CATCCTTCCCCGGGCCACCACGCTTCCTATGTGACCCGCCTGGGCAACGC
CGAACCCAGTCGCGCAGCGCTGCAGTGAATTTTCCCCCCAAACTGCAATA
AGCCGCCTTCCAAGGCCAAGATGTTCATAAATATAAAGAGCATCTTATGG
ATGTGTTCAACCTTAATAGTAACCCATGCGCTACATAAAGTCAAAGTGGG
AAAAAGCCCACCGGTGAGGGGCTCCCTCTCTGGAAAAGTCAGCCTACCTT
GTCATTTTTCAACGATGCCTACTTTGCCACCCAGTTACAACACCAGTGAA
TTTCTCCGCATCAAATGGTCTAAGATTGAAGTGGACAAAAATGGAAAAGA
TTTGAAAGAGACTACTGTCCTTGTGGCCCAAAATGGAAATATCAAGATTG
GTCAGGACTACAAAGGGAGAGTGTCTGTGCCCACACATCCCGAGGCTGTG
GGCGATGCCTCCCTCACTGTGGTCAAGCTGCTGGCAAGTGATGCGGGTCT
TTACCGCTGTGACGTCATGTACGGGATTGAAGACACACAAGACACGGTGT
CACTGACTGTGGATGGGGTTGTGTTTCACTACAGGGCGGCAACCAGCAGG
TACACACTGAATTTTGAGGCTGCTCAGAAGGCTTGTTTGGACGTTGGGGC
AGTCATAGCAACTCCAGAGCAGCTCTTTGCTGCCTATGAAGATGGATTTG
AGCAGTGTGACGCAGGCTGGCTGGCTGATCAGACTGTCAGATATCCCATC
CGGGCTCCCAGAGTAGGCTGTTATGGAGATAAGATGGGAAAGGCAGGAGT
CAGGACTTATGGATTCCGTTCTCCCCAGGAAACTTACGATGTGTATTGTT
ATGTGGATCATCTGGATGGTGATGTGTTCCACCTCACTGTCCCCAGTAAA
TTCACCTTCGAGGAGGCTGCAAAAGAGTGTGAAAACCAGGATGCCAGGCT
GGCAACAGTGGGGAACTCCAGGCGGCATGGAGGAACGGCTTTGACCAGT
GCGATTACGGGTGGCTGTCGGATGCCAGCGTGCGCCACCCTGTGACTGTG
GCCAGGGCCCAGTGTGGAGGTGGTCTACTTGGGGTGAGAACCCTGTATCG
TTTTGAGAACCAGACAGGCTTCCCTCCCCCTGATAGCAGATTTGATGCCT
ACTGCTTTAAACCTAAAGAGGCTACAACCATCGATTTGAGTATCCTCGCA
GAAACTGCATCACCCAGTTTATCCAAAGAACCACAAATGGTTTCTGATAG
AACTACACCAATCATCCCTTTAGTTGATGAATTACCTGTCATTCCAACAG
AGTTCCCTCCCGTGGGAAATATTGTCAGTTTTGAACAGAAAGCCACAGTC
CAACCTCAGGCTATCACAGATAGTTTAGCCACCAAATTACCCACACCTAC
TGGCAGTACCAAGAAGCCCTGGGATATGGATGACTACTCACCTTCTGCTT
CAGGACCTCTTGGAAAGCTAGACATATCAGAAATTAAGGAAGAAGTGCTC
CAGAGTACAACTGGCGTCTCTCATTATGCTACGGATTCATGGGATGGTGT
CGTGGAAGATAAACAAACACAAGAATCGGTTACACAGATTGAACAAATAG
AAGTGGGTCCTTTGGTAACATCTATGGAAATCTTAAAGCACATTCCTTCC
AAGGAATTCCCTGTAACTGAAACACCATTGGTAACTGCAAGAATGATCCT
GGAATCCAAAACTGAAAAGAAAATGGTAAGCACTG2TTTCTGAATTGGTA
ACCACAGGTCACTATGGATTCACCTTGGGAGAAGAGGATGATGAAGACAG
AACACTTACAGTTGGATCTGATGAGAGCACCTTGATCTTTGACCAAATTC
CTGAAGTCATTACGGTGTCAAAGACTTCAGAAGACACCATCCACACTCAT
TTAGAAGACTTGGAGTCAGTCTCAGCATCCACAACTGTTTCCCCTTAATT

-continued

```
ATGCCTGATAATAATGGATCATCCATGGATGACTGGGAAGAGAGACAAAC
TAGTGGTAGGATAACGGAAGAGTTTCTTGGCAAATATCTGTCTACTACAC
CTTTTCCATCACAGCATCGTACAGAAATAGAATTGTTTCCTTATTCTGGT
GATAAAATATTAGTAGAGGGAATTTCCACAGTTATTTATCCTTCTCTACA
AACAGAAATGACACATAGAAGAGAAAGAACAGAAACACTAATACCAGAGA
TGAGAACAGATACTTATACAGATGAAATACAAGAAGAGATCACTAAAAGT
CCATTTATGGGAAAAACAGAAGAAGAAGTCTTCTCTGGGATGAAACTCTC
TACATCTCTCTCAGAGCCAATTCATGTTACAGAGTCTTCTGTGGAAATGA
CCAAGTCTTTTGATTTCCCAACATTGATAACAAAGTTAAGTGCAGAGCCA
ACAGAAGTAAGAGATATGGAGGAAGACTTTACAGCAACTCCAGGTACTAC
AAAATATGATGAAAATATTACAACAGTGCTTTTGGCCCATGGTACTTTAA
GTGTTGAAGCAGCCACTGTATCAAAATGGTCATGGGATGAAGATAATACA
ACATCCAAGCCTTTAGAGTCTACAGAACCTTCAGCCTCTTCAAAATTGCC
CCCTGCCTTACTCACAACTGTGGGGATGAATGGAAAGGATAAAGACATCC
CAAGTTTCACTGAAGATGGAGCAGATGAATTTACTCTTATTCCAGATAGT
ACTCAAAAGCAGTTAGAGGAGGTTACTGATGAAGACATAGCAGCCCATGG
AAAATTCACAATTAGATTTCAGCCAACTACATCAACTGGTATTGCAGAAA
AGTCAACTTTGAGAGATTCTACAACTGAAGAAAAAGTTCCACCTATCACA
AGCACTGAAGGCCAAGTTTATGCAACCATGGAAGGAAGTGCTTTGGGTGA
AGTAGAAGATGTGGACCTCTCTAAGCCAGTATCTACTGTTCCCCAATTTG
CACACACTTCAGAGGTGGAAGGATTAGCATTTGTTAGTTATAGTAGCACC
CAAGAGCCTACTACTTATGTAGACTCTTCCCATACCATTCCTCTTTCTGT
AATTCCCAAGACAGACTGGGGAGTGTTAGTACCTTCTGTTCCATCAGAAG
ATGAAGTTCTAGGTGAACCCTCTCAAGACATACTTGTCATTGATCAGACT
CGCCTTGAAGCGACTATTTCTCCAGAAACTATGAGAACAACAAAAATCAC
AGAGGGAACAACTCAGGAAGAATTCCCTTGGAAAGAACAGACTGCAGAGA
AACCAGTTCCTGCTCTCAGTTCTACACTTGGACTCCAAGGAGGCAGTAA
CACCACTGGATGAACAAGAGGGCGATGGATCAGCATATACAGTCTCTGAA
GATGAATTGTTGACAGGTTCTGAGAGGGTCCCAGTTTTAGAAACAACTCC
AGTTGGAAAAATTGATCACAGTGTGTCTTATCCACCAGGTGCTGTAACTG
AGCACAAAGTGAAAACAGATGAAGTGGTAACACTAACACCACGCATTGGG
CCAAAAGTATCTTTAAGTCCAGGGCCTGAACAAAAATATGAAACAGAAGG
TAGTAGTACAACAGGATTTACATCATCTTTGAGTCCTTTTAGTACCCACA
TTACCCAGCTTATGGAAGAAACCACTACTGAGAAAACATCCCTAGAGGAT
ATTGATTTAGGCTCAGGATTATTTGAAAAGCCCAAAGCCACAGAACTCAT
AGAATTTTCAACAATCAAAGTCACAGTTCCAAGTGATATTACCACTGCCT
TCAGTTCAGTAGACAGACTTCACACAACTTCAGCATTCAAGCCATCTTCC
GCGATCACTAAGAAACCACCTCTCATCGACAGGGAACCTGGTGAAGAAAC
AACCAGTGACATGGTAATCATTGGAGAATCAAGATCTCATGTTCCTCCCA
CTACCCTTGAAGATATTGTAGCCAAGGAAACAGAAACCGATATTGATAGA
GAGTATTTCACGACTTCAAGTCCTCCTGCTACACAGCCAACAAGACCACC
```

-continued

```
CACTGTGGAAGACAAAGAGGCCTTTGGACCTCAGGCGCTTTCTACGCCAC
AGCCCCCAGCAAGCACAAAATTTCACCCTGACATTAATGTTTATATTATT
GAGGTCAGAGAAATAAGACAGGTCGAATGAGTGATTTGAGTGTAATTGG
TCATCCAATAGATTCAGAATCTAAAGAAGATGAACCTTGTAGTGAAGAAA
CAGATCCAGTGCATGATCTAATGGCTGAAATTTTACCTGAATTCCCTGAC
ATAATTGAAATAGACCTATACCACAGTGAAGAAAATGAAGAAGAAGAAGA
AGAGTGTGCAAATGCTACTGATGTGACAACCACCCCATCTGTGCAGTACA
TAAATGGGAAGCATCTCGTTACCACTGTGCCCAAGGACCCAGAAGCTGCA
GAAGCTAGGCGTGGCCAGTTTGAAAGTGTTGCACCTTCTCAGAATTTCTC
GGACAGCTCTGAAAGTGATACTCATCCATTTGTAATAGCCAAAACGGAAT
TGTCTACTGCTGTGCAACCTAATGAATCTACAGAAACAACTGAGTCTCTT
GAAGTTACATGGAAGCCTGAGACTTACCCTGAAACATCAGAACATTTTTC
AGGTGGTGAGCCTGATGTTTTCCCCACAGTCCCATTCCATGAGGAATTTG
AAAGTGGAACAGCCAAAAAAGGGGCAGAATCAGTCACAGAGAGAGATACT
GAAGTTGGTCATCAGGCACATGAACATACTGAACCTGTATCTCTGTTTCC
TGAAGAGTCTTGAGGAGAGATTGCCATTGACCAAGAATCTCAGAAAATAG
CCTTTGCAAGGGCTACAGAAGTAACATTTGGTGAAGAGGTAGAAAAAAGT
ACTTCTGTCACATACACTCCCACTATAGTTCCAAGTTCTGCATCAGCATA
TGTTTCAGAGGAAGAAGCAGTTACCCTAATAGGAAATCCTTGGCCAGATG
ACCTGTTGTCTACCAAAGAAAGCTGGGTAGAAGCAACTCCTAGACAAGTT
GTAGAGCTCTCAGGGAGTTCTTCGATTCCAATTACAGAAGGCTCTGGAGA
AGCAGAAGAAGATGAAGATACAATGTTCACCATGGTAACTGATTTATCAC
AGAGAAATACTACTGATACACTCATTACTTTAGCACTAGCAGGATAATC
ACAGAAAGCTTTTTTGAGGTTCCTGCAACCACCATTTATCCAGTTCTGAA
CAACCTTCTGCAAAAGTGGTGCCTACCAAGTTTGTAAGTGAAACAGAGAC
TTCTGAGTGGATTTCCAGTACCACTGTTGAGGAAAAGAAAAGGAAGGAGG
AGGAGGGAACTACAGGTACGGCTTCTACATTTGAGGTATATTCATCTACA
CAGAGATCGGATCAATTAATTTTACCCTTTGAATTAGAAAGTCCAAATGT
AGCTACATCTAGTGATTCAGGTACCAGGAAAAGTTTTATGTCCTTGACAA
CACCAACACAGTCTGAAAGGGAAATGACAGATTCTACTCCTGTCTTTACA
GAAACAAATACATTAGAAAATTTGGGGGCACAGACCACTGAGCACAGCAG
TATCCATCAACCTGGGGTTCAGGAAGGGCTGACCACTCTCCCACGTAGTG
CTGCCTCTGTCTTTATGGAGCAGGGCTCTGGAGAAGCTGCTGCCGACCCA
GAAACCACCACTGTTTCTTCATTTTCATTAAACGTAGAGTATGCAATTCA
AGCCGAAAGGAAGTAGCTGGCACTTTGTCTCCGCATGTGGAAACTACAT
TCTCCACTGAGCCAACAGGACTGGTTTTGAGTACAGTAATGGACAGAGTA
GTTGCTGAAAATATAACCCAAACATCCAGGGAAATAGTGATTTCAGAGCG
ATTAGGAGAACCAAATTATGGGGCAGAAATAAGGGGCTTTTCCACAGGTT
TTCCTTTGGAGGAAGATTTCAGTGGTGACTTTAGAGAATACTCAACAGTG
TCTCATCCCATAGCAAAAGAAGAAACGGTAATGATGGAAGGCTCTGGAGA
```

-continued

```
TGCAGCATTTAGGGACACCCAGACTTCACCATCTACAGTACCTACTTCAG
TTCACATCAGTCACATATGTGACTCAGAAGGACCCAGTAGCACCATGGTC
AGCACTTCAGCCTTCCCCTGGGAAGAGTTTACATCCTCAGCTGAGGGCTC
AGGTGAGCAACTGGTCACAGTCAGCAGCTCTGTTGTTCCAGTGCTTCCCA
GTGCTGTGCAAAAGTTTTCTGGTACAGCTTCCTCCATTATCGACGAAGGA
TTGGGAGAAGTGGGTACTGTCAATGAAATTGATAGAAGATCCACCATTTT
ACCAACAGCAGAAGTGGAAGGTACGAAAGCTCCAGTAGAGAAGGAGGAAG
TAAAGGTCAGTGGCACAGTTTCAACAAACTTTCCCCAAACTATAGAGCCA
GCCAAATTATGGTCTAGGCAAGAAGTCAACCCTGTAAGACAAGAAATTGA
AAGTGAAACAACATCAGAGGAACAAATTCAAGAAGAAAAGTCATTTGAAT
CCCCTCAAAACTCTCCTGCAACAGAACAAACAATCTTTGATTCACAGACA
TTTACTGAAACTGAACTCAAAACCACAGATTATTCTGTACTAACAACAAA
GAAACTTACAGTGATGATAAAGAAATGAAGGAGGAAGACACTTCTTTAGT
TAACATGTCTACTCCAGATCCAGATGCAAATGGCTTGGAATCTTACACAA
CTCTCCCTGAAGCTACTGAAAAGTCACATTTTTTCTTAGCTACTGCATTA
GTAACTGAATCTATACCAGCTGAACATGTAGTCACAGATTCACCAATCAA
AAAGGAAGAAAGTACAAAACATTTTCCGAAAGGCATGAGACCAACAATTC
AAGAGTCAGATACTGAGCTCTTATTCTCTGGACTGGGATCAGGAGAAGAA
GTTTTACCTACTCTACCAACAGAGTCAGTGAATTTTACTGAAGTGGAACA
AATCAATAACACATTATATCCCCACACTTCTCAAGTGGAAAGTACCTCAA
GTGACAAAATTGAAGACTTTAACAGAATGGAAAATGTGGGAAAGAAGTT
GGACCACTCGTATCTCAAACAGACATCTTTGAAGGTAGTGGGTCAGTAAC
CAGCACAACATTAATAGAAATTTTAAGTGACACTGGAGCAGAAGGACCCA
CGGTGGCACCTCTCCCTTTCTCCACCGGACATCGGACATCCTCAAAATCA
GACTGTCAGGTGGGCAGAAGAAATCCAGACTAGTAGACCACAAACCATAA
CTGAACAAGACTCTAACAAGAATTCTTCAACAGCAGAAATTAACGAAACA
ACAACCTCATCTACTGATTTTCTGGCTAGAGCTTATGGTTTTGAAATGGC
CAAAGAATTTGTTACATCAGCACCAAAACCATCTGACTTGTATTATGAAC
CTTCTGGAGAAGGATCTGGAGAAGTGGATATTGTTGATTCATTTCACACT
TCTGCAACTACTCAGGCAACCAGACAAGAAAGCAGCACCACAATTTGTTT
CTGATGGGTCCCTGGAAAAACATCCTGAGGTGCCAAGCGCTAAAGCTGTT
ACTGCTGATGGATTCCCAACAGTTTCAGTGATGCTGCCTCTTCATTCAGA
GCAGAACAAAGCTCCCCTGATCCAACTAGCACACTGTCAAATACAGTGT
CATATGAGAGGTCCACAGACGGTAGTTTCCAAGACCGTTTCAGGGAATTG
GAGGATTCCACCTTAAAACCTAACAGAAAAAAACCCACTGAAAATATTAT
CATAGACCTGGACAAAGAGGACAAGGATTTAATATTGACAATTACAGAGA
GTACCATCCTTGAAATTCTACCTGAGCTGACATCGGATAAAAATACTATC
ATAGATATTGATCATACTAAACCTGTGTATGAAGACATTCTTGGAATGCA
AACAGATATAGATACGAGGTACCATCAGAACCACATGACAGTAATGATG
AAGTAATGATGACAGCACTCAAGTTCAAGAGATCTATGAGGCAGCTGTCA
ACCTTTCTTTAACTGAGGAAACATTTGAGGGCTCTGCTGATGTTCTGGCT

AGCTACACTCAGGCAACACATGATGAATCAATGACTTATGAAGATAGAAG
CCAACTAGATCACATGGGCTTTCACTTCACAACTGGGATCCCTGCTCCTA
GCACAGAACAGAATTAGACGTTTTACTTCCCACGGCAACATCCCTGCCAA
TTCCTCGTAAGTCTGCCACAGTTATTCCAGAGATTGAAGGAATAAAAGCT
GAAGCAAAAGCCCTGGATGACATGTTTGAATCAAGCACTTTGTCTGATGG
TCAAGCTATTGCAGACCAAAGTGAAATAATACCAACATTGGGCCAATTTG
AAAGGACTCAGGAGGAGTATGAAGACAAAAAACATGCTGGTCCTTCTTTT
CAGCCAGAATTCTCTTCAGGAGCTGAGGAGGCATTAGTAGACCATACTCC
CTATCTAAGTATTGCTACTACCCACCTTATGGATCAGAGTGTAACAGAGG
TGCCTGATGTGATGGAAGGATCCAATCCCCCATATTACACTGATACAACA
TTAGCAGTTTCAACATTTGCGAAGTTGTCTTCTCAGACACCATCATCTCC
CCTCACTATCTACTCAGGCAGTGAAGCCTCTGGACACACAGAGATCCCCC
AGCCCAGTGCTCTGCCAGGAATAGACGTCGGCTCATCTGTAATGTCCCCA
CAGGATTCTTTTAAGGAAATTCATGTAAATATTGAAGCAACTTTCAAACC
ATCAAGTGAGGAATACCTTCACATAACTGAGCCTCCCTCTTTATCTCCTG
ACACAAAATTAGAACCTTCAGAAGATGATGGTAAACCTGAGTTATTAGAA
GAAATGGAAGCTTCTCCCACAGAACTTATTGCTGTGGAAGGAACTGAGAT
TCTCCAAGATTTCCAAAACAAACCGATGGTCAAGTTTCTGGAGAAGCAA
TCAAGATGTTTCCCACCATTAAAACACCTGAGGCTGGAACTGTTATTACA
ACTGCCGATGAAATTGAATTAGAAGGTGCTACACAGTGGCCACACTCTAC
TTCTGCTTCTGCCACCTATGGGGTCGAGGCAGGTGTGGTGCCTTGGCTAA
GTCCACAGACTTCTGAGAGGCCCACGCTTTCTTCTTCTCCAGAAATAAAC
CCTGAAACTCAAGCAGCTTTAATCAGAGGGCAGGATTCCACGATAGCAGC
ATCAGAACAGCAAGTGGCAGCGAGAATTCTTGATTCCAATGATCAGGCAA
CAGTAAACCCTGTGGAATTTAATACTGAGGTTGCAACACCACCATTTTCC
CTTCTGGAGACTTCTAATGAAACAGATTTCCTGATTGGCATTAATGAAGA
GTCAGTGGAAGGCACGGCAATCTATTTACCAGGACCTGATCGCTGCAAAA
TGAACCCGTGCCTTAACGGAGGCACCTGTTATCCACTGAAACTTCCTACG
TATGCACCTGTGTGCCAGGATACAGCGGAGACCAGTGTGAACTTGATTTT
GATGAATGTCACTCTAATCCCTGTCGTAATGGAGCCACTTGTGTTGATGG
TTTTAACACATTCAGGTGCCTCTGCCTTCCAAGTTATGTTGGTGCACTTT
GTGAGCAAGATACCGAGACATGTGACTATGGCTGGCACAAATTCCAAGGG
CAGTGCTACAAATACTTTGCCCATCGACGCACATGGGATGCAGCTGAACG
GGAATGCCGTCTGCAGGGTGCCCATCTCACAAGCATCCTGTCTCACGAAG
AACAAATGTTTGTTAATCGTGTGGGCCATGATTATCAGTGGATAGGCCTC
AATGACAAGATGTTTGAGCATGACTTCCGTTGGACTGATGGCAGCACACT
GCAATACGAGAATGGAGACCCAACCAGCCAGACAGCTTCTTTTCTGCTGG
AGAAGACTGTGTTGTAATCATTTGGCATGAGAATGGCCAGTGGAATGATG
TTCCCTGCAATTACCATCTCACCTATACGTGCAAGAAAGGAACAGTTGCT
TGCGGCCAGCCCCCTGTTGTAGAAAATGCCAAGACCTTTGGAAAGATGAA
```

ACCTCGTTATGAAATCAACTCCCTGATTAGATACCACTGCAAAGATGGTT

TCATTCAACGTCACCTTCCAACTATCCGGTGCTTAGGAAATGGAAGATGG

GCTATACCTAAAATTACCTGCATGAACCCATCTGCATACCAAAGGACTTA

TTCTATGAAATACTTTAAAAATTCCTCATCAGCAAAGGACAATTCAATAA

ATACATCCAAACATGATCATCGTTGGAGCCGGAGGTGGCAGGAGTCGAGG

CGCTGATCCCTAAAATGGCGAACATGTGTTTTCATCATTTCAGCCAAAGT

CCTAACTTCCTGTGCCTTTCCTATCACCTCGAGAAGTAATTATCAGTTGG

TTTGGATTTTTGGACCACCGTTCAGTCATTTTGGGTTGCCGTGCTCCCAA

AACATTTTAAATGAAAGTATTGGCATTCAAAAAGACAGCAGACAAAATGA

AAGAAAATGAGAGCAGAAAGTAAGCATTTCCAGCCTATCTAATTTCTTTA

GTTTTCTATTTGCCTCCAGTGCAGTCCATTTCCTAATGTATACCAGCCTA

CTGTACTATTTAAAATGCTCAATTTCAGCACCGATGGCCATGTAAATAAG

ATGATTTAATGTTGATTTTAATCCTGTATATAAAATAAAAAGTCACAATG

AGTTTGGGCATATTTAATGATGATTATGGAGCCTTAGAGGTCTTTAATCA

TTGGTTCGGCTGCTTTTATGTAGTTTAGGCTGGAAATGGTTTCACTTGCT

CTTTGACTGTCAGCAAGACTGAAGATGGCTTTTCCTGGACAGCTAGAAAA

CACAAAATCTTGTAGGTCATTGCACCTATCTCAGCCATAGGTGCAGTTTG

CTTCTACATGATGCTAAAGGCTGCGAATGGGATCCTGATGGAACTAAGGA

CTCCAATGTCGAACTCTTCTTTGCTGCATTCCTTTTTCTTCACTTACAAG

AAAGGCCTGAATGGAGGACTTTTCTGTAACCAGG

N-Acylsphingosine Amidohydrosase 1
>gi|30089929|ref|NM_004315.2| Homo sapiens N-acylsphingosine amidohydrolase (acid ceramidase) 1 (ASAH1), transcript variant 2, mRNA|qPCR forward_primer match [1212 . . . 1228]|qPCR reverse_primer match [1290 . . . 1266]|qPCR probe match [1233 . . . 1260]

SEQ ID NO: 86
GGACTTTGAAATCCAACCCGGTCACCTACCCGCGCGACTGTGTCCA

CGGATGGCACGAAAGCCAAGCGAGTCCCCCTGCCGAGCTACTCGCGTCCG

CCTCCTCCCAAGCTGAGCTCTGCTCCGCCCACCTGAGTCCTTCGGCAGTT

AGGAGGAAACACAGCCGCTTAATGAACTGCTGCATCGGGCTGGGAGAGAA

AGCTCGCGGGTCCCACCGGGCCTCCTACCCAAGTCTCAGCGCGCTTTTCA

CCGAGGCCTCAATTCTGGGATTTGGCAGCTTTGCTGTGAAAGCCCAATGG

ACAGAGGACTGCAGAAAATCAACCTATCCTCCTTCAGGACCAACGTACAG

AGGTGCAGTTCCATGGTACACCATAAATCTTGACTTACCACCCTACAAAA

GATGGCATGAATTGATGCTTGACAAGGCACCAATGCTAAAGGTTATAGTG

AATTCTCTGAAGAATATGATAAATACATTCGTGCCAAGTGGAAAAGTTAT

GCAGGTGGTGGATGAAAAATTGCCTGGCCTACTTGGCAACTTTCCTGGCC

CTTTTGAAGAGGAAATGAAGGGTATTGCCGCTGTTACTGATATACCTTTA

GGAGAGATTATTTCATTCAATATTTTTATGAATTATTTACCATTTGTAC

TTCAATAGTAGCAGAAGACAAAAAAGGTCATCTAATACATGGGAGAAACA

TGGATTTTGGAGTATTTCTTGGGTGGAACATAAATAATGATACCTGGGTC

ATAACTGAGCAACTAAAACCTTAACAGTGAATTTGGATTTCCAAAGAAAC

AACAAAACTGTCTTCAAGGCTTCAAGCTTTGCTGGCTATGTGGGCATGTT

AACAGGATTCAAACCAGGACTGTTCAGTCTTACACTGAATGAACGTTTCA

GTATAAATGGTGGTTATCTGGGTATTCTAGAATGGATTCTGGGAAAGAAA

GATGCCATGTGGATAGGGTTCCTCACTAGAACAGTTCTGGAAAATAGCAC

AAGTTATGAAGAAGCCAAGAATTTATTGACCAAGACCAAGATATTGGCCC

CAGCCTACTTTATCCTGGGAGGCAACCAGTCTGGGGAAGGTTGTGTGATT

ACACGAGACAGAAAGGAATCATTGGATGTATATGAACTCGATGCTAAGCA

GGGTAGATGGTATGTGGTACAAACAAATTATGACCGTTGGAAACATCCCT

TCTTCCTTGATGATCGCAGAACGCCTGCAAAGATGTGTCTGAACCGCACC

AGCCAAGAGAATATCTCATTTGAAACCATGTATGATGTCCTGTCAACAAA

ACCTGTCCTCAACAAGCTGAGCCTATACACAACCTTGATAGATGTTACCA

AAGGTCAATTCGAAACTACCTGCGGGACTGCCCTGACCCTTGTATAGGTT

GGTGAGCACACGTCTGGCCTACAGAATGCGGCCTCTGAGACATGAAGACA

CCATCTCCATGTGACCGAACACTGCAGCTGTCTGACCTTCCAAAGACTAA

GACTCGCGGCAGGTTCTCTTTGAGTCAAAAGCTTGTCTTCGTCCATCTGT

TGACAAATGACAGACCTTTTTTTTTCCCCCATCAGTTGATTTTCTTATT

TACAGATAACTTCTTAGGGGAAGTAAAACAGTCATCTAGAATTCACTGAG

TTTTGTTTCACTTTGACATTTGGGGATCTGGTGGGCAGTCGAACCATGGT

GAACTCCACCTCCGTGGAATAAATGGAGATTCAGCGTGGGTGTTGAATCC

AGCACGTCTGTGTGAGTAACGGGACAGTAAACACTCCACATTCTTCAGTT

TTTCACTTCTACCTACATATTTGTATGTTTTTCTGTATAACAGCCTTTTC

CTTCTGGTTCTAACTGCTGTTAAAATTAATATATCATTATCTTTGCTGTT

ATTGACAGCGATATAATTTTATTACATATGATTAGAGGGATGAGACAGAC

ATTCACCTGTATATTTCTTTTAATGGGCACAAAATGGGCCCTTGCCTCTA

AATAGCACTTTTTGGGGTTCAAGAAGTAATCAGTATGCAAAGCAATCTTT

TATACAATAATTGAAGTGTTCCCTTTTTCATAATTACTGTACTTCCCAGT

AACCCTAAGGAAGTTGCTAACTTAAAAAACTGCATCCCACGTTCTGTTAA

TTTAGTAAATAAACAAGTCAAAGACTTGTGGAAAATAGGAAGTGAACCCA

TATTTTAAATTCTCATAAGTAGCATTCATGTAATAAACAGGTTTTTAGTT

TGTTCTTCAGATTGATAGGGAGTTTTAAAGAAATTTTAGTAGTTACTAAA

ATTATGTTACTGTATTTTTCAGAAATCAAACTGCTTATGAAAAGTACTAA

TAGAACTTGTTAACCTTTCTAACCTTCACGATTAACTGTGAAATGTACGT

CATTTGTGCAAGACCGTTTGTCCACTTCATTTTGTATAATCACAGTTGTG

TTCCTGACACTCAATAAACAGTCATTGGAAAGAGTGCCAGTCAGCAGTCA

TGCA

N-Acylsphingosine Amidohydrolase 1 Transcript Variant 1
>gi|30089927|ref|NM_177924.1| Homo sapiens N-acylsphingosine amidohydrolase (acid ceramidase) 1 (ASAH1), transcript variant 1, mRNA|qPCR forward_primer match [1050 . . . 1066]|qPCR reverse_primer match [1128 . . . 1104]|qPCR probe match [1071 . . . 1098]

SEQ ID NO: 87

GGCTCTTCTTTGCCTCTGCTGGAGTCCGGGGAGTGGCGTTGGCTGCT
AGAGCGATGCCGGGCCGGAGTTGCGTCGCCTTAGTCCTCCTGGCTGCCGC
CGTCAGCTGTGCCGTCGCGCAGCACGCGCCGCCGTGGACAGAGGACTGCA
GAAAATCAACCTATCCTCCTTCAGGACCAACGTACAGAGGTGCAGTTCCA
TGGTACACCATAAATCTTGACTTACCACCCTACAAAAGATGGCATGAATT
GATGCTTGACAAGGCACCAATGCTAAAGGTTATAGTGAATTCTCTGAAGA
ATATGATAAATACATTCGTGCCAAGTGGAAAAGTTATGCAGGTGGTGGAT
GAAAAATTGCCTGGCCTACTTGGCAACTTTCCTGGCCCTTTTGAAGAGGA
AATGAAGGGTATTGCCGCTGTTACTGATATACCTTTAGGAGAGATTATTT
CATTCAATATTTTTTATGAATTATTTACCATTTGTACTTCAATAGTAGCA
GAAGACAAAAAAGGTCATCTAATACATGGGAGAAACATGGATTTTGGAGT
ATTTCTTGGGTGGAACATAAATAATGATACCTGGGTCATAACTGAGCAAC
TAAAACCTTTAACAGTGAATTTGGATTTCCAAAGAAACAACAAAACTGTC
TTCAAGGCTTCAAGCTTTGCTGGCTATGTGGGCATGTTAACAGGATTCAA
ACCAGGACTGTTCAGTCTTACACTGAATGAACGTTTCAGTATAAATGGTG
GTTATCTGGGTATTCTAGAATGGATTCTGGGAAAGAAAGATGCCATGTGG
ATAGGGTTCCTCACTAGAACAGTTCTGGAAAATAGCACAAGTTATGAAGA
AGCCAAGAATTTATTGACCAAGACCAAGATATTGGCCCCAGCCTACTTTA
TCCTGGGAGGCAACCAGTCTGGGGAAGGTTGTGTGATTACACGAGACAGA
AAGGAATCATTGGATGTATATGAACTCGATGCTAAGCAGGGTAGATGGTA
TGTGGTACAAACAAATTATGACCGTTGGAAACATCCCTTCTTCCTTGATG
ATCGCAGAACGCCTGCAAAGATGTGTCTGAACCGCACCAGCCAAGAGAAT
ATCTCATTTGAAACCATGTATGATGTCCTGTCAACAAAACCTGTCCTCAA
CAAGCTGACCGTATACACAACCTTGATAGATGTTACCAAAGGTCAATTCG
AAACTTACCTGCGGGACTGCCCTGACCCTTGTATAGGTTGGTGAGCACAC
GTCTGGCCTACAGAATGCGGGCTCTGAGACATGAAGACACCATCTCCATG
TGACCGAACACTGCAGCTGTCTGACCTTCCAAAGACTAAGACTCGCGGCA
GGTTCTCTTTGAGTCAAAAGCTTGTCTTCGTCCATCTGTTGACAAATGAC
AGACCTTTTTTTTCCCCCATCAGTTGATTTTCTTATTTACAGATAACT
TCTTTAGGGGAAGTAAAACAGTCATCTAGAATTCACTGAGTTTTGTTTCA
CTTTGACATTTGGGGATCTGGTGGGCAGTCGAACCATGGTGAACTCCACC
TCCGTGGAATAAATGGAGATTCAGCGTGGGTGTTGAATCCAGCACGTCTG
TGTGAGTAACGGGACAGTAAACACTCCACATTCTTCAGTTTTTCACTTCT
ACCTACATATTTGTATGTTTTTCTGTATAACAGCCTTTTCCTTCTGGTTC
TAACTGCTGTTAAAATTAATATATCATTATCTTTGCTGTTATTGACAGCG
ATATAATTTTATTACATATGATTAGAGGGATGAGACAGACATTCACCTGT
ATATTTCTTTTAATGGGCACAAAATGGGCCCTTGCCTCTAAATAGCACTT
TTTGGGGTTCAAGAAGTAATCAGTATGCAAAGCAATCTTTTATACAATAA
TTGAAGTGTTCCCTTTTTCATAATTACTGTACTTCCCAGTAACCCTAAGG
AAGTTGCTAACTTAAAAAACTGCATCCCACGTTCTGTTAATTTAGTAAAT

-continued

AAACAAGTCAAAGACTTGTGGAAAATAGGAAGTGAACCCATATTTTAAAT
TCTCATAAGTAGCATTCATGTAATAAACAGGTTTTTAGTTTGTTCTTCAG
ATTGATAGGGAGTTTTAAAGAAATTTTAGTAGTTACTAAAATTATGTTAC
TGTATTTTTCAGAAATCAAACTGCTTATGAAAAGTACTAATAGAACTTGT
TAACCTTTCTAACCTTCACGATTAACTGTGAAATGTACGTCATTTGTGCA
AGACCGTTTGTCCACTTCATTTTGTATAATCACAGTTGTGTTCCTGACAC
TCAATAAACAGTCATTGGAAAGAGTGCCAGTCAGCAGTCATGCA

Protease, Serine 11
>gi|21327712|ref|NM_002775.2| Homo sapiens protease, serine, 11 (IGF binding) (PRSS11), mRNA|qPCR forward_primer match [1030 ... 1048]|qPCR reverse_primer match [1106 ... 1083]|qPCR probe match [1080 ... 1050]

SEQ ID NO: 88

CCGGCCCTCGCCCTGTCCGCCGCCACCGCCGCCGCCGCCAGAGTCG
CCATGCAGATCCCGCGCGCCGCTCTTCTCCCGCTGCTGCTGCTGCTGCTG
GCGGCGCCCGCCTCGGCGCAGCTGTCCCGGGCCGGCCGCTCGGCGCCTTT
GGCCGCCGGGTGCCCAGACCGCTGCGAGCCGGCGCGCTGCCCGCCGCAGC
CGGAGCACTGCGAGGGCGGCCGGGCCCGGGACGCGTGCGGCTGCTGCGAG
GTGTGCGGCGCGCCCGAGGGCGCCGCGTGCGGCCTGCAGGAGGGCCCGTG
CGGCGAGGGCTGCAGTGCGTGGTGCCCTTCGGGGTGCCAGCCTCGGCCA
CGGTGCGGCGGCGCGCGCAGGCCGGCCTCTGTGTGTGCGCCAGCAGCGAG
CCGGTGTGCGGCAGCGACGCCAACACCTACGCCAACCTGTGCCAGCTGCG
CGCCGCCAGCCGCCGCTCCGAGAGGCTGCACCGGCCGCCGGTCATCGTCC
TGCAGCGCGGAGCCTGCGGCCAAGGGCAGGAAGATCCCAACAGTTTGCGC
CATAAATATAACTTTATCGCGGACGTGGTGGAGAAGATCGCCCCTGCCGT
GGTTCATATCGAATTGTTTCGCAAGCTTCCGTTTTCTAAACGAGAGGTGC
CGGTGGCTAGTGGGTCTGGGTTTATTGTGTCGGAAGATGGACTGATCGTG
ACAAATGCCCACGTGGTGACCAACAAGCACCGGGTCAAAGTTGAGCTGAA
GAACGGTGCCACTTACGAAGCCAAAATCAAGGATGTGGATGAGAAAGCAG
ACATCGCACTCATCAAAATTGACCACCAGGGCAAGCTGCCTGTCCTGCTG
CTTGGCCGCTCCTCAGAGCTGCGGCCGGGAGAGTTCGTGGTCGCCATCGG
AAGCCCGTTTTCCCTTCAAAACACAGTCACCACCGGGATCGTGAGCACCA
CCCAGCGAGGCGGCAAAGAGCTGGGGCTCCGCAACTCAGACATGGACTA
CATCCAGACCGACGCCATCATCAACTATGGAAACTCGGGAGGCCCGTTAG
TAAACCTGGACGGTGAAGTGATTGGAATTAACACTTTGAAAGTGACAGCT
GGAATCTCCTTTGCAATCCCATCTGATAAGATTAAAAAGTTCCTCACGGA
GTCCCATGACCGACAGGCCAAAGGAAAAGCCATCACCAAGAAGAAGTATA
TTGGTATCCGAATGATGTCACTCACGTCCAGCAAAGCCAAAGAGCTGAAG
GACCGGCACCGGGACTTCCCAGACGTGATCTCAGGAGCGTATATAATTGA
AGTAATTCCTGATACCCCAGCAGAAGCTGGTGGTCTCAAGGAAAACGACG
TCATAATCAGCATCAATGGACAGTCCGTGGTCTCCGCCAATGATGTCAGC

```
GACGTCATTAAAAGGGAAAGCACCCTGAACATGGTGGTCCGCAGGGGTA

ATGAAGATATCATGATCACAGTGATTCCCGAAGAAATTGACCCATAGGCA

GAGGCATGAGCTGGACTTCATGTTTCCCTCAAAGACTCTCCCGTGGATGA

CGGATGAGGACTCTGGGCTGCTGGAATAGGACACTCAAGACTTTTGACTG

CCATTTTGTTTGTTCAGTGGAGACTCCCTGGCCAACAGAATCCTTCTTGA

TAGTTTGCAGGCAAAACAAATGTAATGTTGCAGATCCGCAGGCAGAAGCT

CTGCCCTTCTGTATCCTATGTATGCAGTGTGCTTTTTCTTGCCAGCTTGG

GCCATTCTTGCTTAGACAGTCAGCATTTGTCTCCTCCTTTAACTGAGTCA

TCATCTTAGTCCAACTAATGCAGTCGATACAATGCGTAGATAGAAGAAGC

CCCACGGGAGCCAGGATGGGACTGGTCGTGTTTGTGCTTTTCTCCAAGTC

AGCACCCAAAGGTCAATGCACAGAGACCCCGGGTGGGTGAGCGCTGGCTT

CTCAAACGGCCGAAGTTGCCTCTTTTAGGAATCTCTTTGGAATTGGGAGC

ACGATGACTCTGAGTTTGAGCTATTAAAGTACTTCTTACACATTG
```

Secreted Frizzled-Related Protein 2
>gi|42656988|ref|XM_050625.4| Homo sapiens secreted fizzled-related protein 2 (SFRP2), mRNA|qPCR forward_primer match [686 . . . 703]|qPCR reverse_primer match [750 . . . 728]|qPCR probe match [705 . . . 726]

```
                                          SEQ ID NO: 89
CCGGGTCGGAGCCCCCCGGAGCTGCGCGCGGGCTTGCAGCGCCTCG

CCCGCGCTGTCCTCCCGGTGTCCCGCTTCTCCGCGCCCCAGCCGCCGGCT

GCCAGCTTTTCGGGGCCCCGAGTCGCACCCAGCGAAGAGAGCGGGCCCGG

GACAAGCTCGAACTCCGGCCGCCTCGCCCTTCCCCGGCTCCGCTCCCTCT

GCCCCCTCGGGGTCGCGCGCCCACGATGCTGCAGGGCCCTGGCTCGCTGC

TGCTGCTCTTCCTCGCCTCGCACTGCTGCCTGGGCTCGGCGCGCGGGCTC

TTCCTCTTTGGCCAGCCCGACTTCTCCTACAAGCGCAGCAATTGCAAGCC

CATCCCTGCCAACCTGCAGCTGTGCCACGGCATCGAATACCAGAACATGC

GGCTGCCCAACCTGCTGGGCCACGAGACCATGAAGGAGGTGCTGGAGCAG

GCCGGCGCTTGGATCCCGCTGGTCATGAAGCAGTGCCACCCGGACACCAA

GAAGTTCCTGTGCTCGCTCTTCGCCCCCGTCTGCCTCGATGACCTAGACG

AGACCATCCAGCCATGCCACTCGCTCTGCGTGCAGGTGAAGGACCGCTGC

GCCCCGGTCATGTCCGCCTTCGGCTTCCCCTGGCCCGACATGCTTGAGTG

CGACCGTTTCCCCCAGGACAACGACCTTTGCATCCCCCTCGCTAGCAGCG

ACCACCTCCTGCCAGCCACCGAGGAAGCTCCAAAGGTATGTGAAGCCTGC

AAAAATAAAAATGATGATGACAACGACATAATGGAAACGCTTTGTAAAAA

TGATTTTGCACTGAAAATAAAAGTGAAGGAGATAACCTACATCAACCGAG

ATACCAAAATCATCCTGGAGACCAAGAGCAAGACCATTTACAAGCTGAAC

GGTGTGTCCGAAAGGGACCTGAAGAAATCGGTGCTGTGGCTCAAAGACAG

CTTGCAGTGCACCTGTGAGGAGATGAACGACATCAACGCGCCCTATCTGG

TCATGGGACAGAAACAGGGTGGGGAGCTGGTGATCACCTCGGTGAAGCGG

TGGCAGAAGGGGCAGAGAGAGTTCAAGCGCATCTCCCGCAGCATCCGCAA

GCTGCAGTGCTAGTCCCGGCATCCTGATGGCTCCGACAGGCCTGCTCCAG

AGCACGGCTGACCATTTCTGCTCCGGGATCTCAGCTCCCGTTCCCCAAGC

ACACTCCTAGCTGCTCCAGTCTCAGCCTGGGCAGCTTCCCCCTGCCTTTT

GCACGTTTGCATCCCCAGCATTTCCTGAGTTATAAGGCCACAGGAGTGGA

TAGCTGTTTTCACCTAAAGGAAAAGCCCACCCGAATCTTGTAGAAATATT

CAAACTAATAAAATCATGAATATTTTTATGAAGTTTAAAAA
```

Phospholipase A2, Group XIIB
>gi|45505134|ref|NM_032562.2| Homo sapiens phospholipase A2, group XIIB (PLA2G12B), mRNA

```
                                          SEQ ID NO: 90
TGTCCCTGGAATTCTGGGACACTGGCTGGGGTTTGAGGAGAGAAGC

CAGTACCTACCTGGCTGCAGGATGAAGCTGGCCAGTGGCTTCTTGGTTTT

GTGGCTCAGCCTTGGGGGTGGCCTGGCTCAGAGCGACACGAGCCCTGACA

CGGAGGAGTCCTATTCAGACTGGGGCCTTCGGCACCTCCGGGGAAGCTTT

GAATCCGTCAATAGCTACTTCGATTCTTTTCTGGAGCTGCTGGGAGGGAA

GAATGGAGTCTGTCAGTACAGGTGCCGATATGGAAAGGCACCAATGCCCA

GACCTGGCTACAAGCCCCAAGAGCCCAATGGCTGCGGCTCCTATTTCCTG

GGTCTCAAGGTACCAGAAAGTATGGACTTGGGCATTCCAGCAATGACAAA

GTGCTGCAACCAGCTGGATGTCTGTTATGACACTTGCGGTGCCAACAAAT

ATCGCTGTGATGCAAAATTCCGATGGTGTCTCCACTCGATCTGCTCTGAC

CTTAAGCGGAGTCTGGGCTTTGTCTCCAAAGTGGAAGCAGCCTGTGATTC

CCTGGTTGACACTGTGTTCAACACCGTGTGGACCTTGGGCTGCCGCCCCT

TTATGAATAGTCAGCGGGCAGCTTGCATCTGTGCAGAGGAGGAGAAGGAA

GAGTTATGAGGAAGAAGTGATTCCTTCCTGGTTTTGAGTGACACCACAGC

TGTCAGCCTTCAAGATGTCAAGTCTTCGAGTCAGCGTGACTCATTCATTC

TTCCAACAGTTTGGACACCACAAAGCAGGAGAAAGGGAACATTTTTCTAC

AGCTGGAAAGTGAGTCCTATCCTTTGAGGAAATTTGAAAAAGACATGGA

GTGGTTTGAAAGCTACTCTTCATTTAAGACTGCTCTCCCCAACCAAGACA

CATTTGCCTGGAAATTCAGTTCTTAGCTTAAAGACTAAAATGCAAGCAAA

CCCTGCAATTCCTGGACCTGATAGTTATATTCATGAGTGAAATTGTGGGG

AGTCCAGCCATTTGGGAGGCAATGACTTTCTGCTGGCCCATGTTTCAGTT

GCCAGTAAGCTTCTCACATTTAATAAAGTGTACTTTTTAGAACATT
```

Spondin 2, Extracellular Matrix Protein
>gi|6912681|ref|NM_012445.1| Homo sapiens spondin 2, extracellular matrix protein (SPON2), mRNA

```
                                          SEQ ID NO: 91
GCACGAGGGAAGAGGGTGATCCGACCCGGGGAAGGTCGCTGGGCA

GGGCGAGTTGGGAAAGCGGCAGCCCCGCCGCCCCCGCAGCCCCTTCTCC

TCCTTTCTCCCACGTCCTATCTGCCTCTCGCTGGAGGCCAGGCCGTGCAG

CATCGAAGACAGGAGGAACTGGAGCCTCATTGGCCGGCCGGGGCGCCGG

CCTCGGGCTTAAATAGGAGCTCCGGGCTCTGGCTGGACCCGACCGCTGC

CGGCCGCGCTCCCGCTGCTCCTGCCGGGTGATGGAAAACCCCAGCCCGGC
```

```
CGCCGCCCTGGGCAAGGCCCTCTGCGCTCTCCTCCTGGCCACTCTCGGCG

CCGCCGGCCAGCCTCTTGGGGGAGAGTCCATCTGTTCCGCCAGAGCCCCG

GCCAAATACAGCATCACCTTCACGGGCAAGTGGAGCCAGACGGCCTTCCC

CAAGCAGTACCCCCTGTTCCGCCCCCTGCGCAGTGGTCTTCGCTGCTGG

GGGCCGCGCATAGCTCCGACTACAGCATGTGGAGGAAGAACCAGTACGTC

AGTAACGGGCTGCGCGACTTTGCGGAGCGCGGCGAGGCCTGGGCGCTGAT

GAAGGAGATCGAGGCGGCGGGGGAGGCGCTGCAGAGCGTGCACGCGGTGT

TTTCGGCGCCCGCCGTCCCCAGCGGCACCGGGCAGACGTCGGCGGAGCTG

GAGGTGCAGCGCAGGCACTCGCTGGTCTCGTTTGTGGTGCGCATCGTGCC

CAGCCCCGACTGGTTCGTGGGCGTGGACAGCCTGGACCTGTGCGACGGGG

ACCGTTGGCGGGAACAGGCGGCGCTGGACCTGTACCCCTACGACGCCGGG

ACGGACAGCGGCTTCACCTTCTCCTCCCCCAACTTCGCCACCATCCCGCA

GGACACGGTGACCGAGATAACGTCCTCCTCTCCCAGCCACCCGGCCAACT

CCTTCTACTACCCGCGGCTGAAGGCCCTGCCTCCCATCGCCAGGGTGACA

CTGGTGCGGCTGCGACAGAGCCCCAGGGCCTTCATCCCTCCCGCCCCAGT

CCTGCCCAGCAGGGACAATGAGATTGTAGACAGCGCCTCAGTTCCAGAAA

CGCCGCTGGACTGCGAGGTCTCCCTGTGGTCGTCCTGGGGACTGTGCGGA

GGCCACTGTGGGAGGCTCGGGACCAAGAGCAGGACTCGCTACGTCCGGGT

CCAGCCCGCCAACAACGGGAGCCCCTGCCCCGAGCTCGAAGAAGAGGCTG

AGTGCGTCCCTGATAACTGCGTCTAAGACCAGAGCCCCGCAGCCCTGGG

GCCCCCGGAGCCATGGGGTGTCGGGGGCTCCTGTGCAGGCTCATGCTGCA

GGCGGCCGAGGCACAGGGGGTTTCGCGCTGCTCCTGACCGCGGTGAGGCC

GCGCCGACCATCTCTGCACTGAAGGGCCCTCTGGTGGCCGGCACGGGCAT

TGGGAAACAGCCTCCTCCTTTCCCAACCTTGCTTCTTAGGGGCCCCGTG

TCCCGTCTGCTCTCAGCCTCCTCCTCCTGCAGGATAAAGTCATCCCCAAG

GCTCCAGCTACTCTAAATTATGGTCTCCTTATAAGTTATTGCTGCTCCAG

GAGATTGTCCTTCATCGTCCAGGGGCCTGGCTCCCACGTGGTTGCAGATA

CCTCAGACCTGGTGCTCTAGGCTGTGCTGAGCCCACTCTCCCGAGGGCGC

ATCCAAGCGGGGCCACTTGAGAAGTGAATAAATGGGGCGGTTTCGGAAG

CGTCAGTGTTTCCATGTTATGGATCTCTCTGCGTTTGAATAAAGACTATC

TCTGTTGCTCAC
```

Olfactomedin 1, Transcript Variant 3
>gi|34335282|ref|NM_058199.2| Homo sapiens olfactomedin 1 (OLFM1), transcript variant 3, mRNA

SEQ ID NO: 92
```
CCCGCCCCCGCCCCTTCCGAGCAAACTTTTGGCACCCACCGCAGCC

CAGCGCGCGTTCGTGCTCCGCAGGGCGCGCCTCTCTCCGCCAATGCCAGG

CGCGCGGGGAGCCATTAGGAGGCGAGGAGAGAGGAGGGCGCAGCTCCC

GCCCAGCCCAGCCCTGCCCAGCCCTGCCCGGAGGCAGACGCGCCGGAACC

GGGACGCGATAAATATGCAGAGCGGAGGCTTCGCGCAGCAGAGCCCGCG

CGCCGCCCGCTCCGGGTGCTGAATCCAGGCGTGGGGACACGAGCCAGGCG

CCGCCGCCGGAGCCAGCGGAGCCGGGGCCAGAGCCGGAGCGCGTCCGCG

TCCACGCAGCCGCCGGCCGGCCAGCACCCAGGGCCCTGCATGCCAGGTCG

TTGGAGGTGGCAGCGAGACATGCACCCGGCCCGGAAGCTCCTCAGCCTCC

TCTTCCTCATCCTGATGGGCACTGAACTCACTCAAAATAAAAGAGAAAAC

AAAGCAGAGAAGATGGGAGGGCCAGAGAGCGAGAGGAAGACCACAGGA

GAGAAGACACTGAACGAGCTTCCCTTGTTTTGCCTGGAAGCCCACGCTGG

CTCCCTGGCTCTGCCCAGGATGTGCAGTCCAAATCCCAATCCAGCAGTGG

GGTTATGTCGTCCCGCTTACCCTCAGAGCCCTTCTCCTGGTGCTGCCCAG

ACGATCAGCCAGTCCCTCCTGGAGAGGTTCTGCATGGCCTCTAGGAGAGA

AGTTTTCTTGGCCCCAGGAAGGCCTGGTGGAGGGTGGTGGTTGTGCACTG

TTGCTGGACAGATGCATTCATTCATGTGCACACACACACACACATGCA

CACACAGGGGAGCAGATACCTGCAGAGAAGAGCCAACCAGGTCCTGATTA

GTGGCAAGCTGCCCCACAAAGGGCTATGCCTGTGTCTTATTGAGACACCT

TGGCAAAGAGATGGCTGATTCTGGGTGGTCCTGGACATGGCCGCACCCAA

GGGCCCTCCAAGCCTTAATGGCACCCTGAAGCCTCCATGCCCAGGCCAAA

AGATGCTTTTCCTCCCTAAAAAAAAAAAAAAAAAAAA
```

Thrombospondin Repeat Containing 1
>gi|38016903|ref|NM_019032.2| Homo sapiens thrombospondin repeat containing 1 (TSRC1), mRNA

SEQ ID NO: 93
```
GGGGCCCCAGTGGCCGCCGCGGAGCGAGGTTGCCTGGAGAGAGCG

CCTGGGCGCAGAAGGGTTAACGGGCCACCGGGGGCTCGCAGAGCAGGAG

GGTGCTCTCGGACGGTGTGTCCCCACTGCACTCCTGAACTTGGAGGACA

GGGTCGCCGCGAGGGACGCAGAGAGCACCCTCCACGCCCAGATGCCTGCG

TAGTTTTGTGACCAGTCCGCTCCTGCCTCCCCCTGGGGCAGTAGAGGGG

GAGCGATGGAGAACTGGACTGGCAGGCCCTGGCTGTATCTGCTGCTGCTT

CTGTCCCTCCCTCAGCTCTGCTTGGATCAGGAGGTGTTGTCCGGACACTC

TCTTCAGACACCTACAGAGGAGGGCCAGGGCCCCGAAGGTGTCTGGGGAC

CTTGGGTCCAGTGGGCCTCTTGCTCCCAGCCCTGCGGGGTGGGGGTGCAG

CGCAGGAGCCGGACATGTCAGCTCCCTACAGTGCAGCTCCACCCGAGTCT

GCCCCTCCCTCCCGGCCCCCAAGACATCCAGAAGCCCTCCTCCCCCGGG

GCCAGGGTCCCAGACCCCAGACTTCTCCAGAAACCCTCCCCTTGTACAGG

ACACAGTCTCGGGGAAGGGGTGGCCCACTTCGAGGTCCCGCTTCCCACCT

AGGGAGAGAGGAGACCCAGGAGATTCGAGCGGCCAGGAGGTCCCGGCTTC

GAGACCCGATCAAGCCAGGAATGTTCGGTTATGGGAGAGTGCCCTTTGCA

TTGCCACTGCACCGGAACCGCAGGCACCCTCGGAGCCCACCCAGATCTGA

GCTGTCCCTGATCTCTTCTAGAGGGGAAGAGGCTATTCCGTCCCCTACTC

CAAGAGCAGAGCCATTCTCCGCAAACGGCAGCCCCCAAACTGAGCTCCCT

CCCACAGAACTGTCTGTCCACACCCCATCCCCCCAAGCAGAACCTCTAAG

CCCTGAAACTGCTCAGACAGAGGTGGCCCCCAGAACCAGGCCTGCCCCCC

TACGGCATGACCCCAGAGCCCAGGCCTCTGGCACAGAGCCCCCCTCACCC
```

-continued
```
ACGCACTCCTTAGGAGAAGGTGGCTTCTTCCGTGCATCCCCTCAGCCACG
AAGGCCAAGTTCCCAGGGTTGGGCCAGTCCCCAGGTAGCAGGGAGACGCC
CTGATCCTTTTCCTTCGGTCCCTCGGGGCCGAGGCCAGCAGGGCCAAGGG
CCTTGGGGAACGGGGGGGACTCCTCACGGGCCCCGCCTGGAGCCTGACCC
TCAGCACCCGGGCGCCTGGCTGCCCCTGCTGAGCAACGGCCCCCATGCCA
GCTCCCTCTGGAGCCTCTTTGCTCCCAGTAGCCCTATTCCAAGATGTTCT
GGGGAGAGTGAACAGCTAAGAGCCTGCAGCCAAGCGCCCTGCCCCCCTGA
GCAGCCAGACCCCCGGGCCCTGCAGTGCGCAGCCTTTAACTCCCAGGAAT
TCATGGGCCAGCTGTATCAGTGGGAGCCCTTCACTGAAGTCCAGGGCTCC
CAGCGCTGTGAACTGAACTGCCGGCCCCGTGGCTTCCGCTTCTATGTCCG
TCACACTGAAAAGGTCCAGGATGGGACCCTGTGTCAGCCTGGAGCCCCTG
ACATCTGTGTGGCTGGACGCTGTCTGAGCCCCGGCTGTGATGGGATCCTT
GGCTCTGGCAGGCGTCCTGATGGCTGTGGAGTCTGTGGGGGTGATGATTC
TACCTGTCGCCTTGTTTCGGGGAACCTCACTGACCGAGGGGGCCCCCTGG
GCTATCAGAAGATCTTGTGGATTCCAGCGGGAGCCTTGCGGCTCCAGATT
GCCCAGCTCCGGCCTAGCTCCAACTACCTGGCACTTCGTGGCCCTGGGGG
CCGGTCCATCATCAATGGGAACTGGGCTGTGGATCCCCCTGGGTCCTACA
GGGCCGGCGGGACCGTCTTTCGATATAACCGTCCTCCCAGGGAGGAGGGC
AAAGGGGAGAGTCTGTCGGCTGAAGGCCCCACCACCCAGCCTGTGGATGT
CTATATGATCTTTCAGGAGGAAAACCCAGGCGTTTTTTATCAGTATGTCA
TCTCTTCACCTCCTCCAATCCTTGAGAACCCCACCCCAGAGCCCCCTGTC
CCCCAGCTTCAGCCGGAGATTCTGAGGGTGGAGCCCCCACTTGCTCCGGC
ACCCCGCCCAGCCCGGACCCCAGGCACCCTCCAGCGTCAGGTGCGGATCC
CCCAGATGCCCGCCCCGCCCCATCCCAGGACACCCCTGGGGTCTCCAGCT
GCGTACTGGAAACGAGTGGGACACTCTGCATGCTCAGCGTCCTGCGGAA
AGGTGTCTGGCGCCCCATTTTCCTCTGCATCTCCCGTGAGTCGGGAGAGG
AACTGGATGAACGCAGCTGTGCCGCGGGTGCCAGGCCCCAGCCTCCCCT
GAACCCTGCCACGGCACCCCATGCCCCCCATACTGGGAGGCTGGCGAGTG
GACATCCTGCAGCCGCTCCTGTGGCCCCGGCACCCAGCACCGCCAGCTGC
AGTGCCGGCAGGAATTTGGGGGGGTGGCTCCTCGGTGCCCCCGGAGCGC
TGTGGACATCTCCCCCGGCCCAACATCACCCAGTCTTGCCAGCTGCGCCT
CTGTGGCCATTGGGAAGTTGGCTCTCCTTGGAGCCAGTGCTCCGTGCGGT
GCGGCCGGGGCCAGAGAAGCCGGCAGGTTCGCTGTGTTGGGAACAACGGT
GATGAAGTGAGCGAGCAGGAGTGTGCGTCAGGCCCCCCGCAGCCCCCAG
CAGAGAGGCCTGTGACATGGGCCCTGTACTACTGCCTGGTTCCACAGCG
ACTGGAGCTCCAAGTGCTCAGCCGAGTGTGGGACGGGAATCCAGCGGCGC
TCTGTGGTCTGCCTTGGGAGTGGGGCAGCCCTCGGGCCAGGCCAGGGGA
AGCAGGAGCAGGAACTGGGCAGAGCTGTCCAACAGGAAGCCGGCCCCTG
ACATGCGCGCCTGCAGCCTGGGGCCCTGTGAGAGAACTTGGCGCTGGTAC
ACAGGGCCCTGGGGTGAGTGCTCCTCCGAATGTGGCTCTGGCACACAGCG
TAGAGACATCATCTGTGTATCCAAACTGGGGACGGAGTTCAACGTGACTT
```
-continued
```
CTCCGAGCAACTGTTCTCACCTCCCCAGGCCCCCTGCCCTGCAGCCCTGT
CAAGGGCAGGCCTGCCAGGACCGATGGTTTTCCACGCCCTGGAGCCCATG
TTCTCGCTCCTGCCAAGGGGGAACGCAGACACGGGAGGTCCAGTGCCTGA
GCACCAACCAGACCCTCAGCACCCGATGCCCTCCTCAACTGCGGCCCTCC
AGGAAGCGCCCCTGTAACAGCCAACCCTGCAGCCAGCGCCCTGATGATCA
ATGCAAGGACAGCTCTCCACATTGCCCCCTGGTGGTACAGGCCCGGCTCT
GCGTCTACCCCTACTACACAGCCACCTGTTGCCGCTCTTGCGCACATGTC
CTGGAGCGGTCTCCCCAGGATCCCTCCTGAAAGGGGTCCGGGGCACCTTC
ACGGTTTTCTGTGCCACCATCGGTCACCCATTGATCGGCCCACTCTGAAC
CCCCTGGCTCTCCAGCCTGTCCCAGTCTCAGCAGGGATGTCCTCCAGGTG
ACAGAGGGTGGCAAGGTGACTGACACAAAGTGACTTTCAGGGCTGTGGTC
AGGCCCATGTGGTGGTGTGATGGGTGTGTGCACATATGCCTCAGGTGTGC
TTTTGGGACTGCATGGATATGTGTGTGCTCAAACGTGTATCACTTTTCAA
AAAGAGGTTACACAGACTGAGAAGGACAAGACCTGTTTCCTTGAGACTTT
CCTAGGTGGAAAGGAAAGCAAGTCTGCAGTTCCTTGCTAATCTGAGCTAC
TTAGAGTGTGGTCTCCCCACCAACTCCAGTTTTGTGCCCTAAGCCTCATT
TCTCATGTTCAGACCTCACATCTTCTAAGCCGCCCTGTGTCTCTGACCCC
TTCTCATTTGCCTAGTATCTCTGCCCCTGCCTCCCTAATTAGCTAGGGCT
GGGGTCAGCCACTGCCAATCCTGCCTTACTCAGGAAGGCAGGAGGAAAGA
GACTGCCTCTCCAGAGCAAGGCCCAGCTGGGCAGAGGGTGAAAAAGAGAA
ATGTGAGCATCCGCTCCCCCACCACCCCGCCCAGCCCCTAGCCCCACTCC
CTGCCTCCTGAAATGGTTCCCACCCAGAACTAATTTATTTTTTATTAAAG
ATGGTCATGACAAATGAAAAAAAAAAAAAAAAA
```

Thrombospondin 2

>gi|140317627|ref|NM_003247.2| Homo sapiens thrombospondin 2 (THBS2), mRNA|qPCR forward_primer match [3558 . . . 3580]|qPCR reverse_primer match [3682 . . . 3655]|qPCR probe match [3597 . . . 3623]

SEQ ID NO: 94
```
GAGGAGGAGACGGCATCCAGTACAGAGGGGCTGGACTTGGACCCC
TGCAGCAGCCCTGCACAGGAGAAGCGGCATATAAAGCCGCGCTGCCCGG
GAGCCGCTCGGCCACGTCCACCGGAGCATCCTGCACTGCAGGGCCGGTCT
CTCGCTCCAGCAGAGCCTGCGCCTTTCTGACTCGGTCCGGAACACTGAAA
CCAGTCATCACTGCATCTTTTTGGCAAACCAGGAGCTCAGCTGCAGGAGG
CAGGATGGTCTGGAGGCTGGTCCTGCTGGCTCTGTGGGTGTGGCCCAGCA
CGCAAGCTGGTCACCAGGACAAAGACACGACCTTCGACCTTTTCAGTATC
AGCAACATCAACCGCAAGACCATTGGCGCCAAGCAGTTCCGCGGGCCCGA
CCCCGGCGTGCCGGCTTACCGCTTCGTGCGCTTTGACTACATCCCACCGG
TGAACGCAGATGACCTCAGCAAGATCACCAAGATCATGCGGCAGAAGGAG
GGCTTCTTCCTCACGGCCCAGCTCAAGCAGGACGGCAAGTCCAGGGCAC
GCTGTTGGCTCTGGAGGGCCCCGGTCTCTCCCAGAGGCAGTTCGAGATCG
```

```
TCTCCAACGGCCCCGCGGACACGCTGGATCTCACCTACTGGATTGACGGC
ACCCGGCATGTGGTCTCCCTGGAGGACGTCGGCCTGGCTGACTCGCAGTG
GAAGAACGTCACCGTGCAGGTGGCTGGCGAGACCTACAGCTTGCAGGTGG
GCTGCGACCTCATAGACAGCTTCGCTCTGGACGAGCCCTTCTACGAGCAC
CTGCAGGCGGAAAAGAGCCGGATGTACGTGGCCAAAGGCTCTGCCAGAG
AGAGTCACTTCAGGGGTTTGCTTCAGAACGTCCACCTAGTGTTTGAAAAC
TCTGTGGAAGATATTCTAAGCAAGAAGGGTTGCCAGCAAGGCCAGGGAGC
TGAGATCAACGCCATCAGTGAGAACACAGAGACGCTGCGCCTGGGTCCGC
ATGTCACCACCGAGTACGTGGGCCCCAGCTCGGAGAGGAGGCCCGAGGTG
TGCGAACGCTCGTGCGAGGAGCTGGGAAACATGGTCCAGGAGCTCTCGGG
GCTCCACGTCCTCGTGAACCAGCTCAGCGAGAACCTCAAGAGAGTGTCGA
ATGATAACCAGTTTCTCTGGGAGCTCATTGGTGGCCCTCCTAAGACAAGG
AACATGTCAGCTTGCTGGCAGGATGGCCGGTTCTTTGCGGAAAATGAAAC
GTGGGTGGTGGACAGCTGCACCACGTGTACCTGCAAGAAATTTAAAACCA
TTTGCCACCAAATCACCTGCCCGCCTGCAACCTGCGCCAGTCCATCCTTT
GTGGAAGGCGAATGCTGCCCTTCCTGCCTCCACTCGGTGGACGGTGAGGA
GGGCTGGTCTCCGTGGGCAGAGTGGACCCAGTGCTCCGTGACGTGTGGCT
CTGGGACCCAGCAGAGAGGCCGGTCCTGTGACGTCACCAGCAACACCTGC
TTGGGGCCCTCCATCCAGACACGGGCTTGCAGTCTGAGCAAGTGTGACAC
CCGCATCCGGCAGGACGGCGGCTGGAGCCACTGGTCACCTTGGTCTTCAT
GCTCTGTGACCTGTGGAGTTGGCAATATCACACGCATCCGTCTCTGCAAC
TCCCCAGTGCCCCAGATGGGGGGCAAGAATTGCAAAGGGAGTGGCCGGGA
GACCAAAGCCTGCCAGGGCGCCCCATGCCCAATGGATGGCCGGTGGAGCC
CCTGGTCCCCGTGGTCGGCCTGCACTGTCACCTGTGCCGGTGGGATCCGG
GAGCGCACCCGGGTCTGCAACAGCCCTGAGCCTCAGTACGGAGGGAAGGC
CTGCGTGGGGGATGTGCAGGAGCGTCAGATGTGCAACAAGAGGAGCTGCG
CCGTGGATGGCTGTTTATCCAACCCCTGCTTCCCGGGAGCCCAGTGCAGC
AGCTTCCGCGATGGGTCCTGGTCATGCGGCTCCTGCCCTGTGGGCTTCTT
GGGCAATGGCACCCACTGTGAGGACCTGGACGAGTGTGCCCTGGTCCCCG
ACATCTGCTTCTCCACCAGCAAGGTGCCTCGCTGTGTCAACACTCAGCCT
GGCTTCCACTGCCTGCCCTGCCCGCCCCGATACAGAGGGAACCAGCCCGT
CGGGGTCGGCCTGGAAGCAGCCAAGACGGAAAAGCAAGTGTGTGAGCCCG
AAAACCCATGCAAGGACAAGACACACAACTGCCACAAGCACGCGGAGTGC
ATCTACCTGGGCCACTTCAGCGACCCCATGTACAAGTGCGAGTGCCAGAC
AGGCTACGCGGGCGACGGGCTCATCTGCGGGGAGGACTCGGACCTGGACG
GCTGGCCCAACCTCAATCTGGTCTGCGCCACCAACGCCACCTACCACTGC
ATCAAGGATAACTGCCCCATCTGCCAAATTCTGGGCAGGAAGACTTTGA
CAAGGACGGGATTGGCGATGCCTGTGATGATGACGATGACAATGACGGTG
TGACCGATGAGAAGGACAACTGCCAGCTCCTCTTCAATCCCCGCCAGGCT
GACTATGACAAGGATGAGGTTGGGGACCGCTGTGACAACTGCCCTTACGT
GCACAACCCTGCCCAGATCGACACAGACAACAATGGAGAGGGTGACGCC
```

```
TGCTCCGTGGACATTGATGGGGACGATGTCTTCAATGAACGAGACAATG
TCCCTACGTCTACAACACTGACCAGAGGGACACGGATGGTGACGGTGTGG
GGGATCACTGTGACAACTGCCCCCTGGTGCACAACCCTGACCAGACCGAC
GTGGACAATGACCTTGTTGGGGACCAGTGTGACAACAACGAGGACATAGA
TGACGACGGCCACCAGAACAACCAGGACAACTGCCCCTACATCTCCAACG
CCAACCAGGCTGACCATGACAGAGACGGCCAGGGCGACGCCTGTGACCCT
GATGATGACAACGATGGCGTCCCCGATGACAGGGACAACTGCGGCTTGT
GTTCAACCCAGACCAGGAGGACTTGGACGGTGATGGACGGGGTGATATTT
GTAAAGATGATTTTGACAATGACAACATCCCAGATATTGATGATGTGTGT
CCTGAAAACAATGCCATCAGTGAGACAGACTTCAGGAACTTCCAGATGGT
CCCCTTGGATCCCAAAGGGACCACCCAAATTGATCCCAACTGGGTCATTC
GCCATCAAGGCAAGGAGCTGGTTCAGACAGCCAACTCGGACCCCGGCATC
GCTGTAGGTTTTGACGAGTTTGGGTCTGTGGACTTCAGTGGCACATTCTA
CGTAAACACTGACCGGGACGACGACTATGCCGGCTTCGTCTTTGGTTACC
AGTCAAGCAGCCGCTTCTATGTGGTGATGTGGAAGCAGGTGACGCAGACC
TACTGGGAGGACCAGCCCACGCGGGCCTATGGCTACTCCGGCGTGTCCCT
CAAGGTGGTGAACTCCACCACGGGGACGGGCGAGCACCTGAGGAACGCGC
TGTGGCACACGGGGAACACGCCGGGGCAGGTGCGAACCTTATGGCACGA
CCCCAGGAACATTGGCTGGAAGGACTACACGGCCTATAGGTGGCACCTGA
CTCACAGGCCCAAGACTGGCTACATCAGAGTCTTAGTGCATGAAGGAAAA
CAGGTCATGGCAGACTCAGGACCTATCTATGACCAAACCTACGCTGGCGG
GCGGCTGGGTCTATTTGTCTTCTCTCAAGAAATGGTCTATTTCTCAGACC
TCAAGTACGAATGCAGAGATATTTAAACAAGATTTGCTGCATTTCCGGCA
ATGCCCTGTGCATGCCATGGTCCCTAGACACCTCAGTTCATTGTGGTCCT
TGTGGCTTCTCTCTCTAGCAGCACCTCCTGTCCCTTGACCTTAACTCTGA
TGGTTCTTCACCTCCTGCCAGCAACCCCAAACCCAAGTGCCTTCAGAGGA
TAAATATCAATGGAACTCAGAGATGAACATCTAACCCACTAGAGGAAACC
AGTTTGGTGATATATGAGACTTTATGTGGAGTGAAAATTGGGCATGCCAT
TACATTGCTTTTTCTTGTTTGTTTAAAAGAATGACGTTTACATATAAAA
TGTAATTACTTATTGTATTTATGTGTATATGGAGTTGAAGGGAATACTGT
GCATAAGCCATTATGATAAATTAAGCATGAAAAATATTGCTGAACTACTT
TTGGTGCTTAAAGTTGTCACTATTCTTGAATTAGAGTTGCTCTACAATGA
CACACAAATCCCATTAAATAAATTATAAACAAGGGTCAATTCAAATTTGA
AGTAATGTTTTAGTAAGGAGAGATTAGAAGACAACAGGCATAGCAAATGA
CATAAGCTACCGATTAACTAATCGGAACATGTAAAACAGTTACAAAAATA
AACGAACTCTCCTCTTGTCCTACAATGAAAGCCCTCATGTGCAGTAGAGA
TGCAGTTTCATCAAAGAACAAACATCCTTGCAAATGGGTGTGACGCGGTT
CCAGATGTGGATTTGGCAAAACCTCATTTAAGTAAAAGGTTAGCAGAGCA
AAGTGCGGTGCTTTAGCTGCTGCTTGTGCCGCTGTGGCGTCGGGGAGGCT
CCTGCCTGAGCTTCCTTCCCCAGCTTTGCTGCCTGAGAGGAACCAGAGCA
```

-continued
```
GACGCACAGGCCGGAAAAGGCGCATCTAACGCGTATCTAGGCTTTGGTAA
CTGCGGACAAGTTGCTTTTACCTGATTTGATGATACATTTCATTAAGGTT
CCAGTTATAAATATTTTGTTAATATTTATTAAGTGACTATAGAATGCAAC
TCCATTTACCAGTAACTTATTTTAAATATGCCTAGTAACACATATGTAGT
ATAATTTCTAGAAACAAACATCTAATAAGTATATAATCCTGTGAAAATAT
GAGGCTTGATAATATTAGGTTGTCACGATGAAGCATGCTAGAAGCTGTAA
CAGAATACATAGAGAATAATGAGGAGTTTATGATGGAACCTTAAATATAT
AATGTTGCCAGCGATTTTAGTTCAATATTTGTTACTGTTATCTATCTGCT
GTATATGGAATTCTTTTAATTCAAACGCTGAAAAGAATCAGCATTTAGTC
TTGCCAGGCACACCCAATAATCAGTCATGTGTAATATGCACAAGTTTGTT
TTTGTTTTGTTTTTTGTTGGTTGGTTTGTTTTTTGCTTTAAGTTGCA
TGATCTTTCTGCAGGAAATAGTCACTCATCCCACTCCACATAAGGGGTTT
AGTAAGAGAAGTCTGTCTGTCTGATGATGGATAGGGGGCAAATCTTTTTC
CCCTTTCTGTTAATAGTCATCACATTTCTATGCCAAACAGGAACAATCCA
TAACTTTAGTCTAATGTACACATTGCATTTTGATAAAATTAATTTTGTTG
TTTCCTTTGAGGTTGATCGTTGTGTTGTTGTTTTGCTGCACTTTTTACTT
TTTGCGTGTGGAGCTGTATTCCCGAGACCAACGAAGCGTTGGGATACTTC
ATTAAATGTAGCGACTGTCAACAGCGTGCAGGTTTTCTGTTTCTGTGTTG
TGGGGTCAACCGTACAATGGTGTGGGAGTGACGATGATGTGAATATTTAG
AATGTACCATATTTTTTGTAAATTATTTATGTTTTTCTAAACAAATTTAT
CGTATAGGTTGATGAAACGTCATGTGTTTGCCAAAGACTGTAAATATTT
ATTTATGTGTTCACATGGTCAAAATTTCACCACTGAAACCCTGCACTTAG
CTAGAACCTCATTTTTAAAGATTAACAACAGGAAATAAATTGTAAAAAAG
GTTTTCTATACATGAAAAAAAAAAAAAAAAAA
```

Adlican
>gi|18390318|ref|NM_015419.1| Homo sapiens adlican DKFZp564I1922), mRNA|qPCR assay_on_demand_context match [694 . . . 718]

SEQ ID NO: 95
```
ATGCCCAAGCGCGCGCACTGGGGGCCCTCTCCGTGGTGCTGATCC
TGCTTTGGGGCCATCCGCGAGTGGCGCTGGCCTGCCCGCATCCTTGTGCC
TGCTACGTCCCCAGCGAGGTCCACTGCACGTTCCGATCCCTGGCTTCCGT
GCCCGCTGGCATTGCTAGACACGTGGAAAGAATCAATTTGGGGTTTAATA
GCATACAGGCCCTGTCAGAAACCTCATTTGCAGGACTGACCAAGTTGGAG
CTACTTATGATTCACGGCAATGAGATCCCAAGCATCCCCGATGGAGCTTT
AAGAGACCTCAGCTCTCTTCAGGTTTTCAAGTTCAGCTACAACAAGCTGA
GAGTGATCACAGGACAGACCCTCCAGGGTCTCTCTAACTTAATGAGGCTG
CACATTGACCACACAAGATCGAGTTTATCCACCCTCAAGCTTTCAACGGC
TTAACGTCTGTGAGGCTACTCCATTTGGAAGGAAATCTCCTCCACCAGCT
GCACCCCAGCACCTTCTCCACGTTCACATTTTTGGATTATTTCAGACTCT
CCACCATAAGGCACCTCTACTTAGCAGAGAACATGGTTAGAACTCTTCCT
GCCAGCATGCTTCGGAACATGCCGCTTCTGGAGAATCTTTACTTGCAGGG
AAATCCGTGGACCTGCGATTGTGAGATGAGATGGTTTTTGGAATGGGATG
CAAAATCCAGAGGAATTCTGAAGTGTAAAAAGGACAAAGCTTATGAAGGC
GGTCAGTTGTGTGCAATGTGCTTCAGTCCAAAGAAGTTGTACAAAACATG
AGATACACAAGCTGAAGGACATGACTTGTCTGAAGCCTTCAATAGAGTCC
CCTCTGAGACAGAACAGGAGCAGGAGTATTGAGGAGGAGCAAGAACAGGA
AGAGGATGGTGGCAGCCAGCTCATCCTGGAGAAATTCCAACTGCCCCAGT
GGAGCATCTCTTTGAATATGACCGACGAGCACGGGAACATGGTGAACTTG
GTCTGTGACATCAAGAAACCAATGGATGTGTACAAGATTCACTTGAACCA
AACGGATCCTCCAGATATGACATAAATGCAACAGTTGCCTTGGACTTTGA
GTGTCCAATGACCCGAGAAAACTATGAAAAGCTATGGAAATTGATAGCAT
ACTACAGTGAAGTTCCCGTGAAGCTACACAGAGAGCTCATGCTCAGCAAA
GACCCCAGAGTCAGCTACCAGTACAGGCAGGATGCTGATGAGGAAGCTCT
TTACTACACAGGTGTGAGAGCCCAGATTCTTGCAGAACCAGAATGGGTCA
TGCAGCCATCCATAGATATCCAGCTGAACCGACGTCAGAGTACGGCCAAG
AAGGTGCTACTTTCCTACTACACCCAGTATTCTCAAACAATATCCACCAA
AGATACAAGGCAGGCTCGGGGCAGAAGCTGGGTAATGATTGAGCCTAGTG
GAGCTGTGCAAAGAGATCAGACTGTCCTGGAAGGGGGTCCATGCCAGTTG
AGCTGCAACGTGAAAGCTTCTGAGAGTCCATCTATCTTCTGGGTGCTTCC
AGATGGCTCCATCCTGAAAGCGCCCATGGATGACCCAGACAGCAAGTTGT
CCATTCTCAGCAGTGGCTGGCTGAGGATCAAGTCCATGGAGCCATCTGAC
TCAGGCTTGTACCAGTGCATTGCTCAAGTGAGGGATGAAATGGACCGCAT
GGTATATAGGGTACTTGTGCAGTCTCCCTCCACTCAGCCAGCCGAGAAAG
ACACAGTGACAATTGGCAAGAACCCAGGGGAGTCGGTGACATTGCCTTGC
AATGCTTTAGCAATACCCGAAGCCCACCTTAGCTGGATTCTTCCAAACAG
AAGGATAATTAATGATTTGGCTAACACATCACATGTATACATGTTGCCAA
ATGGAACTCTTTCCATCCCAAAGGTCCAAGTCAGTGATAGTGGTTACTAC
AGATGTGTGGCTGTCAACCAGCAAGGGGCAGACCATTTTACGGTGGGAAT
CACAGTGACCAAGAAAGGGTCTGGCTTGCCATCCAAAAGAGGCAGACGCC
CAGGTGCAAAGGCTCTTTCCAGAGTCAGAGAAGACATCGTGGAGGATGAA
GGGGGCTCGGGCATGGGAGATGAAGAGAACACTTCAAGGAGACTTCTGCA
TCCAAAGGACCAAGAGGTGTTCCTCAAAACAAAGGATGATGCCATCAATG
GAGACAAGAAAGCCAAGAAGGGAGAAGAAAGCTGAAACTCTGGAAGCAT
TCGGAAAAAGAACCAGAGACCAATGTTGCAGAAGGTCGCAGAGTGTTTGA
ATCTAGACGAAGGATAAACATGGCAAACAAACAGATTAATCCGGAGCGCT
GGGCTGATATTTTAGCCAAAGTCCGTGGGAAAAATCTCCCTAAGGGCACA
GAAGTACCCCGTTGATTAAAACCACAAGTCCTCCATCCTTGAGCCTAGA
AGTCACACCACCTTTTCCTGCTGTTTCTCCCCCCTCAGCATCTCCTGTGC
AGACAGTAACCAGTGCTGAAGAATCCTCAGCAGATGTACCTCTACTTGGT
GAAGAAGAGCACGTTTTGGGTACCATTTCCTCAGCCAGCATGGGGCTAGA
ACACACAACCACAATGGAGTTATTCTTGTTGAACCTGAAGTAACAAGCAC
```

-continued

ACCTCTGGAGGAAGTTGTTGATGACCTTTCTGAGAAGACTGAGGAGATAA
CTTCCCACTGAAGGAGACCTGAAGGGGACAGCAGCCCCTACACTTATATC
TGAGCCTTATGAACCATCTCCTACTCTGCACACATTAGACACAGTCTATG
AAAGCCCACCCATGAAGAGACGGCAACAGAGGGTTGGTCTGCAGCAGATG
TTGGATCGTCACCAGAGCCCACATCCAGTGAGTATGAGCCTCCATTGGAT
GCTGTCTCCTTGGCTGAGTGTGAGCCCATGCAATACTTTGACCCAGATTT
GGAGACTAAGTCACAACCAGATGAGGATAAGATGAAAGAAGACACCTTTG
CACACCTTACTCCAACCCCACCATCTGGGTTAATGACTCCAGTACATCA
CAGTTATTTGAGGATTCTACTATAGGGGAACCAGGTGTCCCAGGCCAATC
ACATCTACAAGGACTGACAGACAACATCCACCTTGTGAAAAGTAGTCTAA
GCACTCAAGACACCTTACTGATTAAAAAGGGTATGAAAGAGATGTCTCAG
ACACTACAGGGAGGAAATATGCTAGAGGGAGACCCCACACACTCCAGAAG
TTCTGAGAGTGAGGGCCAAGAGAGCAAATCCATCACTTTGCCTGACTCCA
CACTGGGTATAATGAGCAGTATGTCTCCAGTTAAGAAGCCTGCGGAAACC
ACAGTTGGTACCCTCCTAGACAAAGACACCACAACAGTAACAACAACACC
AAGGCAAAAAGTTGCTCCGTCATCCACCATGAGCACTCACCCTTCTCGAA
GGAGACCCAACGGGAGAAGGAGATTACGCCCCAACAAATTCCGCCACCGG
CACAAGCAAACCCCACCCACAACTTTTGCCCCATCAGAGACTTTTTCTAC
TCAACCAACTCAAGCACCTGACATAAGATTTCAAGTCAAGTGGAGAGTTC
TCTGGTTCCTACAGCTTGGGTGGATAACACAGTTAATACCCCCAAACAGT
TGGAAATGGAGAAGAATGCAGAACCCACATCCAAGGGAACACCACGGAGA
AAACACGGGAAGAGGCCAAACAAACATCGATATACCCCTTCTACAGTGAG
CTCAAGAGCGTCCGGATCCAAGCCCAGCCCTTCTCCAGAAAATAAACATA
GAAACATTGTTACTCCCAGTTCAGAAACTATACTTTTGCCTAGAACTGTT
TCTCTGAAAACTGAGGGCCCTTATGATTCCTTAGATTACATGACAACGAC
CAGAAAAATATATTCATCTTACCCTAAAGTCCAAGAGACACTTCCAGTCA
CATATAAACCCACATCAGATGGAAAAGAAATTAAGGATGATGTTGCCACA
AATGTTGACAAACATAAAAGTGACATTTTAGTCACTGGTGAATCAATTAC
TAATGCCATACCAACTTCTCGCTCCTTGGTCTCCACTATGGGAGAATTTA
AGGAAGAATCCTCTCCTGTAGGCTTTCCAGGAACTCCAACCTGGAATCCC
TCAAGGACGGCCCAGCCTGGGAGGCTACAGACAGACATACCTGTTACCAC
TTCTGGGAAAATCTTACAGACCCTCCCCTTCTTAAAGAGCTTGAGGATG
TGGATTTCACTTCCGAGTTTTTGTCCTCTTTGACAGTCTCCACACCATTT
CACCAGGAAGAAGCTGGTTCTTCCACAACTCTCTCAAGCATAAAAGTGGA
GGTGGCTTCAAGTCAGGCAGAAACCACCACCCCTTGATCAAGATCATCTTG
AAACCACTGTGGCTATTCTCCTTTCTGAAACTAGACCACAGAATCACACC
CCTACTGCTGCCCGGATGAAGGAGCCAGCATCCTCGTCCCCATCCACAAT
TCTCATGTCTTTGGGACAAACCACCACCACTAAGCCAGCACTTCCCAGTC
CAAGAATATCTCAAGCATCTAGAGATTCCAAGGAAAATGTTTTCTTGAAT
TATGTGGGGAATCCAGAAACAGAAGCAACCCCAGTCAACAATGAAGGAAC
ACAGCATATGTCAGGGCCAAATGAATTATCAACACCCTCTTCCGACCGGG

-continued

ATGCATTTAACTTGTCTACAAAGCTGGAATTGGAAAAGCAAGTATTTGGT
AGTAGGAGTCTACCACGTGGCCCAGATAGCCAACCCGAGGATGGAAGAGT
TCATGCTTCTCATCAACTAACCAGAGTCCCTGCCAAACCCATCCTACCAA
CAGCAACAGTGAGGCTACCTGAAATGTCCACACAAAGCGCTTCCAGATAC
TTTGTAACTTCCCAGTCACCTCGTCACTGGACCAACAAACCGGAAATAAC
TACATATCCTTCTGGGGCTTTGCCAGAGAACAAACAGTTTACAACTCCAA
GATTATCAAGTACAACAATTCCTCTCCCATTGCACATGTCCAAACCCAGC
ATTCCTAGTAAGTTTACTGACCGAAGAACTGACCAATTCAATGGTTACTC
CAAAGTGTTTGGAAATAACAACATCCCTGAGGCAAGAAACCCAGTTGGAA
AGCCTCCCAGTCCAAGAATTCCTCATTATTCCAATGGAAGACTCCCTTTC
TTTACCAACAAGACTCTTTCTTTTCCACAGTTGGGAGTCACCCGGAGACC
CCAGATACCCACTTCTCCTGCCCCAGTAATGAGAGAGAGAAAAGTTATTC
CAGGTTCCTACAACAGGATACATTCCCATAGCACCTTCCATCTGGACTTT
GGCCCTCCGGCACCTCCGTTGTTGCACACTCCGCAGACCACGGGATCACC
CTCAACTAACTTACAGAATATCCCTATGGTCTCTTCCACCCAGAGTTCTA
TCTCCTTTATAACATCTTCTGTCCAGTCCTCAGGAAGCTTCCACCAGAGC
AGCTCAAAGTTCTTTGCAGGAGGACCTCCTGCATCCAAATTCTGGTCTCT
TGGGGAAAAGCCCCAAATCCTCACCAAGTCCCCACAGACTGTGTCCGTCA
CCGCTGAGACAGACACTGTGTTCCCCTGTGAGGCAACAGGAAAACCAAAG
CCTTTCGTTACTTGGACAAAGGTTTCCACAGGAGCTCTTATGACTCCGAA
TACCAGGATACAACGGTTTGAGGTTCTCAAGAACGGTACCTTAGTGATAC
GGAAGGTTCAAGTACAAGATCGAGGCCAGTATATGTGCACCGCCAGCAAC
CTGCACGGCCTGGACAGGATGGTGGTCTTGCTTTCGGTCACCGTGCAGCA
ACCTCAAATCCTAGCCTCCCACTACCAGGACGTCACTGTCTACCTGGGAG
ACACCATTGCAATGGAGTGTCTGGCCAAAGGGACCCCAGCCCCCCAAATT
TCCTGGATCTTCCCTGACAGGAGGGTGTGGCAAACTGTGTCCCCCGTGGA
GAGCCGCATCACCCTGCACGAAAACCGGACCCTTTCCATCAAGGAGGCGT
CCTTCTCAGACAGAGGCGTCTATAAGTGCGTGGCCAGCAATGCAGCCGGG
GCGGACAGCCTGGCCATCCGCCTGCACGTGGCGGCACTGCCCCCCGTTAT
CCACCAGGAGAAGCTGGAGAACATCTCGCTGCCCCCGGGGCTCAGCATTC
ACATTCACTGCACTGCCAAGGCTGCGCCCCTGCCCAGCGTGCGCTGGGTG
CTCGGGACGGTACCCAGATCCGCCCCTCGCAGTTCCTCCACGGGAACTT
GTTTGTTTCCCCAACGGGACGCTCTACATCCGCAACCTCGCGCCCAAGG
ACAGCGGGCGCTATGAGTGCGTGGCCGCCAACCTGGTAGGCTCCGCGCGC
AGGACGGTGCAGCTGAACGTGCAGCGTCCAGCAGCCAACGCGCGCATCAC
GGGCACCTCCCCGCGGAGGACGGACGTCAGGTACGGAGGAACCCTCAAGC
TGGACTGCAGCGCCTCGGGGGACCCCTGGCCGCGCATCCTCTGGAGGCTG
CCGTCCAAGAGGATGATCGACGCGCTCTTCAGTTTTGATAGCAGAATCAA
GGTGTTTGCCAATGGGACCCTGGTGGTGAAATCAGTGACGGACAAAGATG
CCGGAGATTACCTGTGCGTAGCTCGAAATAAGGTTGGTGATGACTACGTG

```
GTGCTCAAGTGGATGTGGTGATGAAACCGGCCAAGATTGAACACAAGGAG
GAGAACGACCACAAAGTCTTCTACGGGGGTGACCTGAAAGTGGACTGTGT
GGCCACCGGGCTTCCCAATCCCGAGATCTCCTGGAGCCTCCCAGACGGGA
GTCTGGTGAACTCCTTCATGCAGTCGGATGACAGCGGTGGACGCACCAAG
CGCTATGTCGTCTTCAACAATGGGACACTCTACTTTAACGAAGTGGGGAT
GAGGGAGGAAGGAGACTACACCTGCTTTGCTGAAAATCAGGTCGGGAAGG
ACGAGATGAGAGTCAGAGTCAAGGTGGTGACAGCGCCCGCCACCATCCGG
AACAAGACTTACTTGGCGGTTCAGGTGCCCTATGGAGACGTGGTCACTGT
AGCCTGTGAGGCCAAAGGAGAACCCATGCCCAAGGTGACTTGGTTGTCCC
CAACCAACAAGGTGATCCCCACCTCCTCTGAGAAGTATCAGATATACCAA
GATGGCACTCTCCTTATTCAGAAAGCCCAGCGTTCTGACAGCGGCAACTA
CACCTGCCTGGTCAGGAACAGCGCGGGAGAGGATAGGAAGACGGTGTGGA
TTCACGTCAACGTCCAGCCACCCAAGATCAACGGTAACCCCAACCCCATC
ACCACCGTGCGGGAGATAGCAGCCGGGGGCAGTCGGAAACTGATTGACTG
CAAAGCTGAAGGCATCCCCACCCCGAGGGTGTTATGGGCTTTTCCCGAGG
GTGTGGTTCTGCCAGCTCCATACTATGGAAACCGGATCACTGTCCATGGC
AACGGTTCCCTGGACATCAGGAGTTTGAGGAAGAGCGACTCCGTCCAGCT
GGTATGCATGGCACGCAACGAGGGAGGGGAGGCGAGGTTGATCGTGCAGC
TCACTGTCCTGGAGCCCATGGAGAAACCCATCTTCCACGACCCGATCAGC
GAGAAGATCACGGCCATGGCGGGCCACACCATCAGCCTCAACTGCTCTGC
CGCGGGGACCCCGACACCCAGCCTGGTGTGGGTCCTTCCCAATGGCACCG
ATCTGCAGAGTGGACAGCAGCTGCAGCGCTTCTACCACAAGGCTGACGGC
ATGCTACACATTAGCGGTCTCTCCTCGGTGGACGCTGGGGCCTACCGCTG
CGTGGCCCGCAATGCCGCTGGCCACACGGAGAGGCTGGTCTCCCTGAAGG
TGGGACTGAAGCCAGAAGCAAACAAGCAGTATCATAACCTGGTCAGCATC
ATCAATGGTGAGACCCTGAAGCTCCCCTGCACCCCTCCCGGGGCTGGGCA
GGGACGTTTCTCCTGGACGCTCCCCAATGGCATGCATCTGGAGGGGCCCC
AAACCCTGGGACGCGTTTCTCTTCTGGACAATGGCACCCTCACGGTTCGT
GAGGCCTCGGTGTTTGACAGGGGTACCTATGTATGCAGGATGGAGACGGA
GTACGGCCCTTCGGTCACCAGCATCCCCGTGATTGTGATCGCCTATCCTC
CCCGGATCACCAGCGAGCCCACCCCGGTCATCTACACCCGGCCCGGGAAC
ACCGTGAAACTGAACTGCATGGCTATGGGATTCCCAAAGCTGACATCAC
GTGGGAGTTACCGGATAAGTCGCATCTGAAGGCAGGGGTTCAGGCTCGTC
TGTATGGAAAGAGATTTCTTCACCCCCAGGGATCACTGACCATCCAGCAT
GCCACACAGAGAGATGCCGGCTTCTACAAGTGCATGGCAAAAAACATTCT
CGGCAGTGACTCCAAAACAACTTACATCCACGTCTTCTGAAATGTGGATT
CCAGAATGATTGCTTAGGAACTGACAACAAAGCGGGGTTTGTAAGGGAAG
CCAGGTTGGGGAATAGGAGCTCTTAAATAATGTGTCACAGTGCATGGTGG
CCTCTGGTGGGTTTCAAGTTGAGGTTGATCTTGATCTACAATTGTTGGGA
AAAGGAAGCAATGCAGACACGAGAAGGAGGGCTCAGCCTTGCTGAGACAC
TTTCTTTTGTGTTTACATCATGCCAGGGGCTTCATTCAGGGTGTCTGTGC
TCTGACTGCAATTTTTCTTCTTTTGCAAATGCCACTCGACTGCCTTCATA
AGCGTCCATAGGATATCTGAGGAACATTCATCAAAAATAAGCCATAGACA
TGAACAACACCTCACTACCCCATTGAAGACGCATCACCTAGTTAACCTGC
TGCAGTTTTTACATGATAGACTTTGTTCCAGATTGACAAGTCATCTTTCA
GTTATTTCCTCTGTCACTTCAAAACTCCAGCTTGCCCAATAAGGATTTAG
AACCAGAGTGACTGATATATATATATATTTTAATTCAGAGTTACATAC
ATACAGCTACCATTTTATATGAAAAAGAAAAACATTTCTTCCTGGAACT
CACTTTTTATATAATGTTTTATATATATATTTTTCCTTTCAAATCAGAC
GATGAGACTAGAAGGAGAAATACTTTCTGTCTTATTAAAATTAATAAATT
ATTGGTCTTTACAAGACTTGGATACATTACAGCAGACATGGAAATATAAT
TTTAAAAAATTTCTCTCCAACCTCCTTCAAATTCAGTCACCACTGTTATA
TTACCTTCTCCAGGAACCCTCCAGTGGGAAGGCTGCGATATTAGATTTC
CTTGTATGCAAAGTTTTTGTTGAAAGCTGTGCTCAGAGGAGGTGAGAGGA
GAGGAAGGAGAAAACTGCATCATAACTTTACAGAATTGAATCTAGAGTCT
TCCCCGAAAAGCCCAGAAACTTCTCTGCAGTATCTGGCTTGTCCATCTGG
TCTAAGGTGGCTGCTTCTTCCCCAGCCATGAGTCAGTTTGTGCCCATGAA
TAATACACGACCTGTTATTTCCATGACTGCTTTACTGTATTTTTAAGGTC
AATATACTGTACATTTGATAATAAAATAATATTCTCCCAAAAAAAAAA
```

Cystatin SA

>gi|19882252|ref|NM_001322.2| Homo sapiens cystatin SA (CST2), mRNA|qPCR forward_primer match [302 . . . 320]|qPCR reverse_primer match [393 . . . 370]|qPCR probe match [341 . . . 369]

SEQ ID NO: 96
```
GCCTCCGAGGAGACCATGGCCTGGCCCCTGTGCACCCTGCTGCTCC
TGCTGGCCACCCAGGCTGTGGCCCTGGCCTGGAGCCCCAGGAGGAGGAC
AGGATAATCGAGGGTGGCATCTATGATGCAGACCTCAATGATGAGCGGGT
ACAGCGTGCCCTTCACTTTGTCATCAGCGAGTATAACAAGGCCACTGAAG
ATGAGTACTACAGACGCCTGCTGCGGGTGCTACGAGCCAGGGAGCAGATC
GTGGGCGGGGTGAATTACTTCTTCGACATAGAGGTGGGCCGAACCATATG
TACCAAGTCCCAGCCCAACTTGGACACCTGTGCCTTCCATGAACAGCCAG
AACTGCAGAAGAAACAGTTGTGCTCTTTCCAGATCTACGAAGTTCCCTGG
GAGGACAGAATGTCCCTGGTGAATTCCAGGTGTCAAGAAGCCTAGGGATC
TGTGCCAGGGAGTCACACTGACCACCTCCTACTCCCACCCCTTGTAGTGC
TCCCACCCCTGGACTGGTGGCCCCACCCTGTGGGAGGTCTCCCCATGCA
CCTGCAGCAGGAGAAGACAGAGAAGGCTGCAGGAGGCCTTTGTTGCTCAG
CAGGGGACTCTGCCCTCCCTCCTTCCTTTTGCTTCTCATAGCCCTGGTAC
ATGGTACACACACCCCCACCTCCTGCAATTAAACAGTAGCATCACCTC
```

Cystatin SN

>gi|19882250|ref|NM_001898.2| Homo sapiens cystatin SN (CST1), mRNA|qPCR forward_primer match [358 . . . 376]|qPCR reverse_primer match [449 . . . 426]|qPCR probe match [397 . . . 425]

SEQ ID NO: 97

```
GGGCTCCGTGCCTCGGGCTCTCACCCTCCTCTCCTGCAGCTCCAGCTTTG
TGCTCTGCCTCTGAGGAGACCATGGCCCAGTATCTGAGTACCCTGCTGCT
CCTGCTGGCCACCCTAGCTGTGGCCCTGGCCTGGAGCCCCAAGGAGGAGG
ATAGGATAATCCCGGGTGGCATCTATAACGCAGACCTCAATGATGAGTGG
GTACAGCGTGCCCTTCACTTCGCCATCAGCGAGTATAACAAGGCCACCAA
AGATGACTACTACAGACGTCCGCTGCGGGTACTAAGAGCCAGGCAACAGA
CCGTTGGGGGGTGAATTACTTCTTCGACGTAGAGGTGGGCCGCACCATA
TGTACCAAGTCCCAGCCCAACTTGGACACCTGTGCCTTCCATGAACAGCC
AGAACTGCAGAAGAAACAGTTGTGCTCTTTCGAGATCTACGAAGTTCCCT
GGGAGAACAGAAGGTCCCTGGTGAAATCCAGGTGTCAAGAATCCTAGGGA
TCTGTGCCAGGCCATTCGCACCAGCCACCACCCACTCCCACCCCCTGTAG
TGCTCCCACCCCTGGACTGGTGGCCCCCACCCTGCGGGAGGCCTCCCCAT
GTGCCTGCGCCAAGAGACAGACAGAGAAGGCTGCAGGAGTCCTTTGTTGC
TCAGCAGGGCGCTCTGCCCTCCCTCCTTCCTTCTTGCTTCTAATAGCCCT
GGTACATGGTACACACCCCCCACCTCCTGCAATTAAACAGTAGCATCGC
CTCCCTCTGAAAAAAAAAAAAAAAAAAAAAAAA
```

Lysyl Oxidase-Like Enzyme 2
>gi|4505010|ref|NM_002318.1| Homo sapiens lysyl oxidase-like 2 (LOXL2), mRNA|qPCR forward_primer match [2205 . . . 2223]|qPCR reverse_primer match [2286 . . . 2269]|qPCR probe match [2261 . . . 22293]

SEQ ID NO: 98

```
ACTCCAGCGCGCGGCTACCTACGCTTGGTGCTTGCTTTCTCCAGCCATCG
GAGACCAGAGCCGCCCCTCTGCTCGAGAAAGGGGCTCAGCGGCGGCGGA
AGCGGAGGGGGACCACCGTGGAGAGCGCGGTCCCAGCCCGGCCACTGCGG
ATCCCTGAAACCAAAAAGCTCCTGCTGCTTCTGTACCCCGCCTGTCCCTC
CCAGCTGCGCAGGGCCCCTTCGTGGGATCATCAGCCCGAAGACAGGGATG
GAGAGGCCTCTGTGCTCCCACCTCTGCAGCTGCCTGGCTATGCTGGCCCT
CCTGTCCCCCTGAGCCTGGCACAGTATGACAGCTGGCCCCATTACCCCG
AGTACTTCCAGCAACCGGCTCCTGAGTATCACCAGCCCCAGGCCCCCGCC
AACGTGGCCAAGATTCAGCTGCGCCTGGCTGGGCAGAAGAGGAAGCACAG
CGAGGGCCGGGTGGAGGTGTACTATGATGGCCAGTGGGGCACCGTGTGCG
ATGACGACTTCTCCATCCACGCTGCCCACGTCGTCTGCCGGGAGCTGGGC
TATGTGGAGGCCAAGTCCTGGACTGCCAGCTCCTCCTACGGCAAGGGAGA
AGGGCCCATCTGGTTAGACAATCTCCACTGTACTGGCAACGAGGCGACCC
TTGCAGCATGCACCTCCAATGGCTGGGGCGTCACTGACTGCAAGCACACG
GAGGATGTCGGTGTGGTGTGCAGCGACAAAAGGATTCCTGGGTTCAAATT
TGACAATTCGTTGATCAACCAGATAGAGAACCTGAATATCCAGGTGGAGG
ACATTCGGATTCGAGCCATCCTCTCAACCTACCGCAAGCGCACCCCAGTG
ATGGAGGGCTACGTGGAGGTGAAGGAGGGCAAGACCTGGAAGCAGATCTG
TGACAAGCACTGGACGGCCAAGAATTCCCGCGTGGTCTGCGGCATGTTTG
GCTTCCCTGGGGAGAGGACATACAATACCAAAGTGTACAAAATGTTTGCC
TCACGGAGGAAGCAGCGCTACTGGCCATTCTCCATGGACTGCACCGGCAC
AGAGGCCCACATCTCCAGCTGCAAGCTGGGCCCCCAGGTGTCACTGGACC
CCATGAAGAATGTCACCTGCGAGAATGGGCTGCCGGCCGTGGTGAGTTGT
GTGCCTGGGCAGGTCTTCAGCCCTGACGGACCCTCGAGATTCCGGAAAGC
ATACAAGCCAGAGCAACCCCTGGTGCGACTGAGAGGCGGTGCCTACATCG
GGGAGGGCCGCGTGGAGGTGCTCAAAAATGGAGAATGGGGACCGTCTGC
GACGACAAGTGGGACCTGGTGTCGGCCAGTGTGGTCTGCAGAGAGCTGGG
CTTTGGGAGTGCCAAAGAGGCAGTCACTGGCTCCCGACTGGGGCAAGGGA
TCGGACCCATCCACCTCAACGAGATCCAGTGCACAGGCAATGAGAAGTCC
ATTATAGACTGCAAGTTCAATGCCGAGTCTCAGGGCTGCAACCACGAGGA
GGATGCTGGTGTGAGATGCAACACCCCTGCCATGGGCTTGCAGAAGAAGC
TGCGCCTGAACGGCGGCCGCAATCCCTACGAGGGCCGAGTGGAGGTGCTG
GTGGAGAGAAACGGGTCCCTTGTGTGGGGATGGTGTGTGGCCAAAACTG
GGGCATCGTGGAGGCCATGGTGGTCTGCCGCCAGCTGGGCCTGGGATTCG
CCAGCAACGCCTTCCAGGAGACCTGGTATTGGCACGGAGATGTCAACAGC
AACAAAGTGGTCATGAGTGGAGTGAAGTGCTCGGGAACGGAGCTGTCCCT
GGCGCACTGCCGCCACGACGGGGAGGACGTGGCCTGCCCCCAGGGCGGAG
TGCAGTACGGGGCCGGAGTTGCCTGCTCAGAAACCGCCCCTGACCTGGTC
CTCAATGCGGAGATGGTCAGCAGACCACCTACCTGGAGGACCGGCCCAT
GTTCATGCTGCAGTGTGCCATGGAGGAGAACTGCCTCTCGGCCTCAGCCG
CGCAGACCGACCCCACCACGGGCTACCGCCGGCTCCTGCGCTTCTCCTCC
CAGATCCACAACAATGGCCAGTCCGACTTCCGGCCCAAGAACGGCCGCCA
CGCGTGGATCTGGCACGACTGTCACAGGCACTACCACAGCATGGAGGTGT
TCACCCACTATGACCTGCTGAACCTCAATGGCACCAAGGTGGCAGAGGGC
CACAAGGCCAGCTTCTGCTTGGAGGACACAGAATGTGAAGGAGACATCCA
GAAGAATTACGAGTGTGCCAACTTCGGCGATCAGGGCATCACCATGGGCT
GCTGGGACATGTACCGCCATGACATCGACTGCCAGTGGGTTGACATCACT
GACGTGCCCCCTGGAGACTACCTGTTCCAGGTTGTTATTAACCCCAACTT
CGAGGTTGCAGAATCCGATTACTCCAACAACATCATGAAATGCAGGAGCC
GCTATGACGGCCACCGCATCTGGATGTACAACTGCCACATAGGTGGTTCC
TTCAGCGAAGAGACGGAAAAAAAGTTTGAGCACTTCAGCGGGCTCTTAAA
CAACCAGCTGTCCCCGCAGTAAAGAAGCCTGCGTGGTCAACTCCTGTCTT
CAGGCCACACCACATCTTCCATGGGACTTCCCCCCAACAACTGAGTCTGA
ACGAATGCCACGTGCCCTCACCCAGCCCGGCCCCCACCCTGTCCAGACCC
CTACAGCTGTGTCTAAGCTCAGGAGGAAAGGGACCCTCCCATCATTCATG
GGGGGCTGCTACCTGACCCTTGGGGCCTGAGAAGGCCTTGGGGGGGTGGG
GTTTGTCCACAGAGCTGCTGGAGCAGCACCAAGAGCCAGTCTTGACCGGG
ATGAGGCCCACAGACAGGTTGTCATCAGCTTGTCCCATTCAAGCCACCGA
GCTCACCACAGACACAGTGGAGCCGCGCTCTTTCCAGTGACACGTGGAC
AAATGCGGGCTCATCAGCCCCCCCAGAGAGGGTCAGGCCGAACCCCATTT
```

-continued

CTCCTCCTCTTAGGTCATTTTCAGCAAACTTGAATATCTAGACCTCTCTT

CCAATGAAACCCTCCAGTCTATTATAGTCACATAGATAATGGTGCCACGT

GTTTTCTGATTTGGTGAGCTCAGACTTGGTGCTTCCCTCTCCACAACCCC

CACCCCTTGTTTTTCAAGATACTATTATTATATTTTCACAGACTTTTGAA

GCACAAATTTATTGGCATTTAATATTGGACATCTGGGCCCTTGGAAGTAC

AAATCTAAGGAAAAACCAACCCACTGTGTAAGTGACTCATCTTCCTGTTG

TTCCAATTCTGTGGGTTTTTGATTCAACGGTGCTATAACCAGGGTCCTGG

GTGACAGGGCGCTCACTGAGCACCATGTGTCATCACAGACACTTACACAT

ACTTGAAACTTGGAATAAAAAGAAAGATTTATG

Thyroglobulin
>gi|33589851|ref|NM_003235.3| Homo sapiens thyroglobulin (TG), mRNA qPCR forward_primer match [886 . . . 905]|qPCR reverse_primer match [962 . . . 941]|qPCR probe match [915 . . . 939]

SEQ ID NO: 99
GCAGTGGTTTCTCCTCCTTCCTCCCAGGAAGGGCCAGGAAAATGGCCCTG

GTCCTGGAGATCTTCACCCTGCTGGCCTCCATCTGCTGGGTGTCGGCCAA

TATCTTCGAGTACCAGGTTGATGCCCAGCCCCTTCGTCCCTGTGAGCTGC

AGAGGGAAACGGCCTTTCTGAAGCAAGCAGACTACGTGCCCCAGTGTGCA

GAGGATGGCAGCTTCCAGACTGTCCAGTGCCAGAACGACGGCCGCTCCTG

CTGGTGTGTGGGTGCCAACGGCAGTGAAGTGCTGGGCAGCAGGCAGCCAG

GACGGCCTGTGGCTTGTCTGTCATTTTGTCAGCTACAGAAACAGCAGATC

TTACTGAGTGGCTACATTAACAGCACAGACACCTCCTACCTCCCTCAGTG

TCAGGATTCAGGGGACTACGCGCCTGTTCAGTGTGATGTGCAGCATGTCC

AGTGCTGGTGTGTGGACGCAGAGGGGATGGAGGTGTATGGGACCCGCCAG

CTGGGGAGGCCAAAGCGATGTCCAAGGAGCTGTGAAATAAGAAATCGTCG

TCTTCTCCACGGGGTGGGAGATAAGTCACCACCCCAGTGTTCTGCGGAGG

GAGAGTTTATGCCTGTCCAGTGCAAATTTGTCAACACCACAGACATGATG

ATTTTTGATCTGGTCCACAGCTACAACAGGTTTCCAGATGCATTTGTGAC

CTTCAGTTCCTTCCAGAGGAGGTTCCCTGAGGTATCTGGGTATTGCCACT

GTGCTGACAGCCAAGGGCGGGAACTGGCTGAGACAGGTTTGGAGTTGTTA

CTGGATGAAATTTATGACACCATTTTTGCTGGCCTGGACCTTCCTTCCAC

CTTCACTGAAACCACCCTGTACCGGATACTGCAGAGACGGTTCCTCGCAG

TTCAATCAGTCATCTCTGGCAGATTCCGATGCCCCACAAAATGTGAAGTG

GAGCGGTTTACAGCAACCAGCTTTGGTCACCCCTATGTTCCAAGCTGCCG

CCGAAATGGCGACTATCAGGCGGTGCAGTGCCAGACGGAAGGGCCCTGCT

GGTGTGTGGACGCCCAGGGGAAGGAAATGCATGGAACCCGGCAGCAAGGG

GAGCCGCCATCTTGTGCTGAAGGCCAATCTTGTGCCTCCGAAAGGCAGCA

GGCCTTGTCCAGACTCTACTTTGGGACCTCAGGCTACTTCAGCCAGCACG

ACCTGTTCTCTTCCCCAGAGAAAGATGGGCCTCTCCAAGAGTAGCCAGA

TTTGCCACATCCTGCCCACCCACGATCAAGGAGCTCTTTGTGGACTCTGG

GCTTCTCCGCCCAATGGTGGAGGGACAGAGCCAACAGTTTTCTGTCTCAG

AAAATCTTCTCAAAGAAGCCATCCGAGCAATTTTTCCCTCCCGAGGGCTG

GCTCGTCTTGCCCTTCAGTTTACCACCAACCCAAAGAGACTCCAGCAAAA

CCTTTTTGGAGGGAAATTTTTGGTGAATGTTGGCCAGTTTAACTTGTCTG

GAGCCCTTGGCACAAGAGGCACATTTAACTTCAGTCAATTTTTCCAGCAA

CTTGGTCTTGCAAGCTTCTTGAATGGAGGGAGACAAGAAGATTTGGCCAA

GCCACTCTCTGTGGGATTAGATTCAAATTCTTCCACAGGAACCCCTGAAG

CTGCTAAGAAGGATGGTACTATGAATAAGCCAACTGTGGGCAGCTTTGGC

TTTGAAATTAACCTACAAGAGAACCAAAATGCCCTCAAATTCCTTGCTTC

TCTCCTGGAGCTTCCAGAATTCCTTCTCTTCTTGCAACATGCTATCTCTG

TGCCAGAAGATGTGGCAAGAGATTTAGGTGATGTGATGGAAACGGTACTC

GACTCCCAGACCTGTGAGCAGACACCTGAAAGGCTATTTGTCCCATCATG

CACGACAGAAGGAAGCTATGAGGATGTCCAATGCTTTTCCGGAGAGTGCT

GGTGTGTGAATTCCTGGGGCAAAGAGCTTCCAGGCTCAAGAGTCAGAGAT

GGACAGCCAAGGTGCCCCACAGACTGTGAAAAGCAAAGGGCTCGCATGCA

AAGCCTCATGGGCAGCCAGCCTGCTGGCTCCACCTTGTTTGTCCCTGCTT

GTACTAGTGAGGGACATTTCCTGCCTGTCCAGTGCTTCAACTCAGAGTGC

TACTGTGTTGATGCTGAGGGTCAGGCCATTCCTGGAACTCGAAGTGCAAT

AGGGAAGCCCAAGAAATGCCCCACGCCCTGTCAATTACAGTCTGAGCAAG

CTTTTCCTCAGGACGGTGCAGGCCCTGCTCTCTAACTCCAGCATGCTACCC

ACCCTTTCCGACACCTACATCCCACAGTGCAGCACCGATGGGCAGTGGAG

ACAAGTGCAATGCAATGGGCCTCCTGAGCAGGTCTTCGAGTTGTACCAAC

GATGGGAGGCTCAGAACAAGGGCCAGGATCTGACGCCTGCCAAGCTGCTA

GTGAAGATCATGAGCTACAGAGAAGCAGCTTCCGGAAACTTCAGTCTCTT

TATTCAAAGTCTGTATGAGGCTGGCCAGCAAGATGTCTTCCCGGTGCTGT

CACAATACCCTTCTCTGCAAGATGTCCCACTAGCAGCACTGGAAGGGAAA

CGGCCCCAGCCCAGGGAGAATATCCTCCTGGAGCCCTACCTCTTCTGGCA

GATCTTAAATGGCCAACTCAGCCAATACCCGGGGTCCTACTCAGACTTCA

GCACTCCTTTGGCACATTTTGATCTTCGGAACTGCTGGTGTGTGGATGAG

GCTGGCCAAGAACTGGAAGGAATGCGGTCTGAGCCAAGCAAGCTCCCAAC

GTGTCCTGGCTCCTGTGAGGAAGCAAAGCTCCGTGTACTGCAGTTCATTA

GGGAAACGGAAGAGATTGTTTCAGCTTCCAACAGTTCTCGGTTCCCTCTG

GGGGAGAGTTTCCTGGTGGCCAAGGGAATCCGGCTGAGGAATGAGGACCT

CGGCCTTCCTCCGCTCTTCCCGCCCCGGGAGGCTTTCGCGGAGTTTCTGC

GTGGGAGTGATTACGCCATTCGCCTGGCGGCTCAGTCTACCTTAAGCTTC

TATCAGAGACGCCGCTTTTCCCCGGACGACTCGGCTGGAGCATCCGCCCT

TCTGCGGTCGGGCCCCTACATGCCACAGTGTGATGCGTTTGGAAGTTGGG

AGCCTGTGCAGTGCCACGCTGGGACTGGGCACTGCTGGTGTGTAGATGAG

AAAGGAGGGTTCATCCCTGGCTCACTGACTGCCCGCTCTCTGCAGATTCC

ACAGTGCCCGACAACCTGCGAGAAATCTCGAACCAGTGGGCTGCTTTCCA

GTTGGAAACAGGCTAGATCCCAAGAAAACCCATCTCCAAAAGACCTGTTC

```
GTCCCAGCCTGCCTAGAAACAGGAGAATATGCCAGGCTGCAGGCATCGGG
GGCTGGCACCTGGTGTGTGGACCCTGCATCAGGAGAAGAGTTGCGGCCTG
GCTCGAGCAGCAGTGCCCAGTGCCCAAGCCTCTGCAATGTGCTCAAGAGT
GGAGTCCTCTCTAGGAGAGTCAGCCCAGGCTATGTCCCAGCCTGCAGGGC
AGAGGATGGGGCTTTTCCCCAGTGCAATGTGACCAGGCCCAGGGCAGCT
GCTGGTGTGTCATGGACAGCGGAGAAGAGGTGCCTGGGACGCGCGTGACC
GGGGGCCAGCCCGCCTGTGAGAGCCCGCGGTGTCCGCTGCCATTCAACGC
GTCGGAGGTGGTTGGTGGAACAATCCTGTGTGAGACAATCTCGGGCCCCA
CAGGCTCTGCCATGCAGCAGTGCCAATTGCTGTGCCGCCAAGGCTCCTGG
AGCGTGTTTCCACCAGGGCCATTGATATGTAGCCTGGAGAGCGGACGCTG
GGAGTCACAGCTGCCTCAGCCCCGGGCCTGCCAACGGCCCCAGCTGTGGC
AGACCATCCAGACCCAAGGGCACTTTCAGCTCCAGCTCCCGCCGGGCAAG
ATGTGCAGTGCTGACTACGCGGGTTTGCTGCAGACTTTCCAGGTTTTCAT
ATTGGATGAGCTGACAGCCCGCGGCTTCTGCCAGATCCAGGTGAAGACTT
TTGGCACCCTGGTTTCCATTCCTGTCTGCAACAACTCCTCTGTGCAGGTG
GGTTGTCTGACCAGGGAGCGTTTAGGAGTGAATGTTACATGGAAATCACG
GCTTGAGGACATCCCAGTGGCTTCTCTTCCTGACTTACATGACATTGAGA
GAGCCTTGGTGGGCAAGGATCTCCTTGGGCGCTTCACAGATCTGATCCAG
AGTGGCTCATTCCAGCTTCATCTGGACTCCAAGACGTTCCCAGCGGAAAC
CATCCGCTTCCTCCAAGGGGACCACTTTGGCACCTCTCCTAGGACACGGT
TTGGGTGCTCGGAAGGATTCTACCAAGTCTTGACAAGTGAGGCCAGTCAG
GACGGACTGGGATGCGTTAAGTGCCATGAAGGAAGCTATTCCCAAGATGA
GGAATGCATTCCTTGTCCTGTTGGATTCTACCAAGAACAGGCAGGGAGCT
TGGCCTGTGTCCCATGTCCTGTGGGCAGAACGACCATTTCTGCCGGAGCT
TTCAGCCAGACTCACTGTGTCACTGACTGTCAGAGGAACGAAGCAGGCCT
GCAATGTGACCAGAATGGCCAGTATCGAGCCAGCCAGAAGGACAGGGGCA
GTGGGAAGGCCTTCTGTGTGGACGGCGAGGGCGGAGGCTGCCATGGTGG
GAAACAGAGGCCCCTCTTGAGGACTCACAGTGTTTGATGATGCAGAAGTT
TGAGAAGGTTCCAGAATCAAAGGTGATCTTCGACGCCAATGCTCCTGTGG
CTGTCAGATCCAAAGTTCCTGATTCTGAGTTCCCCGTGATGCAGTGCTTG
ACAGATTGCACAGAGGACGAGGCCTGCAGCTTCTTCACCGTGTCCACGAC
GGAGCCAGAGATTTCCTGTGATTTCTATGCTTGGACAAGTGACAATGTTG
CCTGCATGACTTCTGACCAGAAACGAGATGCACTGGGGAACTCAAAGGCC
ACCAGCTTTGGAAGTCTTCGCTGCCAGGTGAAAGTGAGGAGCCATGGTCA
AGATTCTCCAGCTGTGTATTTGAAAAAGGGCCAAGGATCCACCACAACAC
TTCAGAAACGCTTTGAACCCACTGGTTTCCAAAACATGCTTTCTGGATTG
TACAACCCCATTGTGTTCTCAGCCTCAGGAGCCAATCTAACCGATGCTCA
CCTCTTCTGTCTTCTTGCATGCGACCGTGATCTGTGTTGCGATGGCTTCG
TCCTCACACAGGTTCAAGGAGGTGCCATCATCTGTGGGTTGCTGAGCTCA
CCCAGTGTCCTGCTTTGTAATGTCAAAGACTGGATGGATCCCTCTGAAGC
```

```
CTGGGCTAATGCTACATGTCCTGGTGTGACATATGACCAGGAGAGCCACC
AGGTGATATTGCGTCTTGGAGACCAGGAGTTCATCAAGAGTCTGACACCC
TTAGAAGGAACTCAAGACACCTTTACCAATTTTCAGCAGGTTTATCTCTG
GAAAGATTCTGACATGGGGTCTCGGCCTGAGTCTATGGGATGTAGAAAAA
ACACAGTGCCAAGGCCAGCATCTCCAACAGAAGCAGGTTTGACAACAGAA
CTTTTCTCCCCTGTGGACCTCAACCAGGTCATTGTCAATGGAAATCAATC
ACTATCCAGCCAGAAGCACTGGCTTTTCAAGCACCTGTTTTCAGCCCAGC
AGGCAAACCTATGGTGCCTTTCTCGTTGTGTGCAGGAGCACTCTTTCTGT
CAGCTCGCAGAGATAACAGAGAGTGCATCCTTGTACTTCACCTGCACCCT
CTACCCAGAGGCACAGGTGTGTGATGACATCATGGAGTCCAATACCCAGG
GCTGCAGACTGATCCTGCCTCAGATGCCAAAGGCCCTGTTCCGGAAGAAA
GTTATACTGGAAGATAAAGTGAAGAACTTTTACACTCGCCTGCCGTTCCA
AAAACTGATGGGGATATCCATTAGAAATAAAGTGCCCATGTCTGAAAAAT
CTATTTCTAATGGGTTCTTTGAATGTGAACGACGGTGCGATGCGGACCCA
TGCTGCACTGGCTTTGGATTTCTAAATGTTTCCCAGTTAAAAGGAGGAGA
GGTGACATGTCTCACTCTGAACAGCTTGGGAATTCAGATGTGCAGTGAGG
AGAATGGAGGAGCCTGGCGCATTTTGGACTGTGGCTCTCCTGACATTGAA
GTCCACACCTATCCCTTCGGATGGTACCAGAAGCCCATTGCTCAAAATAA
TGCTCCCAGTTTTTGCCCTTTGGTTGTTCTGCCTTCCCTCACAGAGAAAG
TGTCTCTGGAATCGTGGCAGTCCCTGGCCCTCTCTTCAGTGGTTGTTGAT
CCATCCATTAGGCACTTTGATGTTGCCCATGTCAGCACTGCTGCCACCAG
CAATTTCTCTGCTGTCCGAGACCTCTGTTTGTCGGAATGTTCCCAACATG
AGGCCTGTCTCATCACCACTCTGCAAACCCAACTCGGGGCTGTGAGATGT
ATGTTCTATGCTGATACTCAAAGCTGCACACATAGTCTGCAGGGTCGGAA
CTGCCGACTTCTGCTTCGTGAAGAGGCCACCCACATCTACCGGAAGCCAG
GAATCTCTCTGCTCAGCTATGAGGCATCTGTACCTTCTGTGCCCATTTCC
ACCCATGGCCGGCTGCTGGGCAGGTCCCAGGCCATCCAGGTGGGTACCTC
ATGGAAGCAAGTGGACCAGTTCCTTGGAGTTCCATATGCTGCCCCGCCCC
TGGCAGAGAGGCACTTCCAGGCACCAGAGCCCTTGAACTGGACAGGCTCC
TGGGATGCCAGCAAGCCAAGGGCCAGCTGCTGGCAGCCAGGCACCAGAAC
ATCCACGTCTCCTGGAGTCAGTGAAGATTGTTTGTATCTCAATGTGTTCA
TCCCTCAGAATGTGGCCCCTAACGCGTCTGTGCTGGTGTTCTTCCACAAC
ACCATGGACAGGGAGGAGTGAAGGATGGCCGGCTATCGACGGCTCCTT
CTTGGCTGCTGTTGGCAACCTCATCGTGGTCACTGCCAGCTACCGAGTGG
GTGTCTTCGGCTTCCTGAGTTCTGGATCCGGAGAGGTGAGTGGCAACTGG
GGGCTGCTGGACCAGGTGGCGGCTCTGACCTGGGTGCAGACCCACATCCG
AGGATTTGGCGGGGACCCTCGGCGCGTGTCCCTGGCAGCAGACCGTGGCG
GGGCTGATGTGGCCAGCATCCACCTTCTCACGGCCAGGGCCACCAACTCC
CAACTTTTCCGGAGAGCTGTGCTGATGGGAGGCTCCGCACTCTCCCCGGC
CGCCGTCATCAGCCATGAGAGGGCTCAGCAGCAGGCAATTGCTTTGGCAA
AGGAGGTCAGTTGCCCCATGTCATCCAGCCAAGAAGTGGTGTCCTGCCTC
```

-continued

CGCCAGAAGCCTGCCAATGTCCTCAATGATGCCCAGACCAAGCTCCTGGC
CGTGAGTGGCCCTTTCCACTACTGGGGTCCTGTGATCGATGCCCACTTCC
TCCGTGAGCCTCCAGCCAGAGCACTGAAGAGGTCTTTATGGGTAGAGGTC
GATCTGCTCATTGGGAGTTCTCAGGACGACGGGCTCATCAACAGAGCAAA
GGCTGTGAAGCAATTTGAGGAAAGTCGAGGCCGGACCAGTAGCAAAACAG
CCTTTTACCAGGCACTGCAGAATTCTCTGGGTGGCGAGGACTCAGATGCC
CGCGTCGAGGCTGCTGCTACATGGTATTACTCTCTGGAGCACTCCACGGA
TGACTATGCCTCCTTCTCCCGGGCTCTGGAGAATGCCACCCGGGACTACT
TTATCATCTGCCCTATAATCGACATGGCCAGTGCCTGGGCAAAGAGGGCC
CGAGGAAACGTCTTCATGTACCATGCTCCTGAAAACTACGGCCATGGCAG
CCTGGAGCTGCTGGCGGATGTTCAGTTTGCCTTGGGGCTTCCCTTCTACC
CAGCCTACGAGGGGCAGTTTTCTCTGGAGGAGAAGAGCCTGTCGCTGAAA
ATCATGCAGTACTTTTCCCACTTCATCAGATCAGGAAATCCCAACTACCC
TTATGAGTTCTCACGGAAAGTACCCACATTTGCAACCCCCTGGCCTGACT
TTGTACCCCGTGCTGGTGGAGAGAACTACAAGGAGTTCAGTGAGCTGCTC
CCCAATCGACAGGGCCTGAAGAAAGCCGACTGCTCCTTCTGGTCCAAGTA
CATCTCGTCTCTGAAGACATCTGCAGATGGAGCCAAGGGCGGGCAGTCAG
CAGAGAGTGAAGAGGAGGAGTTGACGGCTGGATCTGGGCTAAGAGAAGAT
CTCCTAAGCCTCCAGGAACCAGGCTCTAAGACCTACAGCAAGTGACCAGC
CCTTGAGCTCCCCAAAAACCTCACCCGAGGCTGCCCACTATGGTCATCTT
TTTCTCTAAAATAGTTACTTACCTTCAATAAAGTATCTACATGCGGTG

Transforming Growth Factor, Beta 1
>gi|10863872|ref|NM_000660.1| Homo sapiens transforming growth factor, beta 1 (Camurati-Engelmann disease) (TGFB1), mRNA|qPCR forward_primer match [1651 . . . 1668]|qPCR reverse_primer match [1539 . . . 1557]|qPCR probe match [1687 . . . 1713]

SEQ ID NO: 100
ACCTCCCTCCGCGGAGCAGCCAGACAGCGAGGGCCCCGGCCGGGGGCAGG
GGGGACGCCCCGTCCGGGGCACCCCCCCCGGCTCTGAGCGCCCCGCGGGG
CCGGCCTCGGCCCGGAGCGGAGGAAGGAGTCGCCGAGGAGCAGCCTGAGG
CCCCAGAGTCTGAGACGAGCCGCCGCCGCCCCCGCCACTGCGGGGAGGAG
GGGGAGGAGGAGCGGGAGGAGGGACGAGCTGGTCGGGAGAAGAGGAAAAA
AACTTTTGAGACTTTTCCGTTGCCGCTGGGAGCCGGAGGCGCGGGGACCT
CTTGGCGCGACGCTGCCCCGCGAGGAGGCAGGACTTGGGGACCCCAGACC
GCCTCCCTTTGCCGCCGGGGACGCTTGCTCCCTCCCTGCCCCCTACACGG
CGTCCCTCAGGCGCCCCCATTCCGGACCAGCCCTCGGGAGTCGCCGACCC
GGCCTCCCGCAAAGACTTTTCCCCAGACCTCGGGCGCACCCCCTGCACGC
CGCCTTCATCCCCGGCCTGTCTCCTGAGCCCCGCGCATCCTAGACCCTT
TCTCCTCCAGGAGACGGATCTCTCTCCGACCTGCCACAGATCCCCTATTC
AAGACCACCCACCTTCTGGTACCAGATCGCGCCCATCTAGGTTATTTCCG
TGGGATACTGAGACACCCCCGGTCCAAGCCTCCCCTCCACCACTGCGCCC

TTCTCCCTGAGGAGCCTCAGCTTTCCCTCGAGGCCCTCCTACCTTTTGCC
GGGAGACCCCCAGCCCCTGCAGGGGCGGGGCCTCCCCACCACACCAGCCC
TGTTCGCGCTCTCGGCAGTGCCGGGGGGCGCCGCCTCCCCCATGCCGCCC
TCCGGGCTGCGGCTGCTGCCGCTGCTGCTACCGCTGCTGTGGCTACTGGT
GCTGACGCCTGGCCCGCCGGCCGCGGGACTATCCACCTGCAAGACTATCG
ACATGGAGCTGGTGAAGCGGAAGCGCATCGAGGCCATCCGCGGCCAGATC
CTGTCCAAGCTGCGGCTCGCCAGCCCCCCGAGCCAGGGGGAGGTGCCGCC
CGGCCCGCTGCCCGAGGCCGTGCTCGCCCTGTACAACAGCACCCGCGACC
GGGTGGCCGGGGAGAGTGCAGAACCGGAGCCCGAGCCTGAGGCCGACTAC
TACGCCAAGGAGGTCACCCGCGTGCTAATGGTGGAAACCCACAACGAAAT
CTATGACAAGTTCAAGCAGAGTACACACAGCATATATATGTTCTTCAACA
CATCAGAGCTCCGAGAAGCGGTACCTGAACCCGTGTTGCTCTCCCGGGCA
GAGCTGCGTCTGCTGAGGAGGCTCAAGTTAAAAGTGGAGCAGCACGTGGA
GCTGTACCAGAAATACAGCAACAATTCCTGGCGATACCTCAGCAACCGGC
TGCTGGCACCCAGCGACTCGCCAGAGTGGTTATCTTTTGATGTCACCGGA
GTTGTGCGGCAGTGGTTGAGCCGTGGAGGGGAAATTGAGGGCTTTCGCCT
TAGCGCCCACTGCTCCTGTGACAGCAGGGATAACACACTGCAAGTGGACA
TCAACGGGTTCACTACCGGCCGCCGAGGTGACCTGGCCACCATTCATGGC
ATGAACCGGCCTTTCCTGCTTCTCATGGCCACCCGCTGGAGAGGGCCCA
GCATCTGCAAAGCTCCCGGCACCGCCGAGCCCTGGACACCAACTATTGCT
TCAGCTCCACGGAGAAGAACTGCTGCGTGCGGCAGCTGTACATTGACTTC
CGCAAGGACCTCGGCTGGAAGTGGATCCACGAGCCCAAGGGCTACCATGC
CAACTTCTGCCTCGGGCCCTGCCCCTACATTTGGAGCCTGGACACGCAGT
ACAGCAAGGTCCTGGCCCTGTACAACCAGCATAACCCGGGCGCCTCGGCG
GCGCCGTGCTGCGTGCCGCAGGCGCTGGAGCCGCTGCCCATCGTGTACTA
CGTGGGCCGCAAGCCCAAGGTGGAGCAGCTGTCCAACATGATCGTGCGCT
CCTGCAAGTGCAGCTGAGGTCCCGCCCCGCCCCGCCCCGCCCCGGCAGGC
CCGGCCCCACCCCGCCCCGCCCCGCTGCCTTGCCCATGGGGCTGTATT
TAAGGACACCGTGCCCAAGCCCACCTGGGGCCCCATTAAAGATGGAGAG
AGGACTGCGGATCTCTGTGTCATTGGGCGCCTGCCTGGGGTCTCCATCCC
TGACGTTCCCCCACTCCCACTCCCTCTCTCCCTCTCTGCCTCCTCCTG
CCTGTCTGCACTATTCCTTTGCCCGGCATCAAGGCACAGGGGACCAGTGG
GGAACACTACTGTAGTTAGATCTATTTATTGAGCACCTTGGGCACTGTTG
AAGTGCCTTACATTAATGAACTCATTCAGTCACCATAGCAACACTCTGAG
ATGGCAGGGACTCTGATAACACCCATTTTAAAGGTTGAGGAAACAAGCCC
AGAGAGGTTAAGGGAGGAGTTCCTGCCCACCAGGAACCTGCTTTAGTGGG
GGATAGTGAAGAAGACAATAAAAGATAGTAGTTCAGGCCAGGCGGGGTGC
TCACGCCTGTAATCCTAGCACTTTTGGGAGGCAGAGATGGGAGGATACTT

Serine Proteinase Inhibitor, Clade H, Member 1
>gi|32454740|ref|NM_001235.2| Homo sapiens serine (or cysteine) proteinase inhibitor, clade H (heat shock protein 47), member 1, (collagen binding protein 1) (SERPINH1), mRNA|qPCR assay_on_demand_context match [184 . . . 208]

SEQ ID NO: 101
TCTTTGGCTTTTTTTGGCGGAGCTGGGGCGCCCTCCGGAAGCGTTTCCAA
CTTTCCAGAAGTTTCTCGGGACGGGCAGGAGGGGGTGGGGACTGCCATAT
ATAGATCCCGGGAGCAGGGGAGCGGGCTAAGAGTAGAATCGTGTCGCGGC
TCGAGAGCGAGAGTCACGTCCCGGCGCTAGCCCAGCCCGACCCAGGCCCA
CCGTGGTGCACGCAAACCACTTCCTGGCCATGCGCTCCCTCCTGCTTCTC
AGCGCCTTCTGCCTCCTGGAGGCGGCCCTGGCCGCCGAGGTGAAGAAACC
TGCAGCCGCAGCAGCTCCTGGCACTGCGGAGAAGTTGAGCCCCAAGGCGG
CCACGCTTGCCGAGCGCAGCGCCGGCCTGGCCTTCAGCTTGTACCAGGCC
ATGGCCAAGGACCAGGCAGTGGAGAACATCCTGGTGTCACCCGTGGTGGT
GGCCTCGTCGCTAGGGCTCGTGTCGCTGGGCGGCAAGGCGACCACGGCGT
CGCAGGCCAAGGCAGTGCTGAGCGCCGAGCAGCTGCGCGACGAGGAGGTG
CACGCCGGCCTGGGCGAGCTGCTGCGCTCACTCAGCAACTCCACGGCGCG
CAACGTGACCTGGAAGCTGGGCAGCCGACTGTACGGACCCAGCTCAGTGA
GCTTCGCTGATGACTTCGTGCGCAGCAGCAAGCAGCACTACAACTGCGAG
CACTCCAAGATCAACTTCCGCGACAAGCGCAGCGCGCTGCAGTCCATCAA
CGAGTGGGCCGCGCAGACCACCGACGGCAAGCTGCCCGAGGTCACCAAGG
ACGTGGAGCGCACGGACGGCGCCCTGCTAGTCAACGCCATGTTCTTCAAG
CCACACTGGGATGAGAAATTCCACCACAAGATGGTGGACAACCGTGGCTT
CATGGTGACTCGGTCCTATACCGTGGGTGTCATGATGATGCACCGGACAG
GCCTCTACAACTACTACGACGACGAGAAGGAAAAGCTGCAAATCGTGGAG
ATGCCCCTGGCCCACAAGCTCTCCAGCCTCATCATCCTCATGCCCCATCA
CGTGGAGCCTCTCGAGCGCCTTGAAAAGCTGCTAACCAAAGAGCAGCTGA
AGATCTGGATGGGGAAGATGCAGAAGAAGGCTGTTGCCATCTCCTTGCCC
AAGGGTGTGGTGGAGGTGACCCATGACCTGCAGAAACACCTGGCTGGGCT
GGGCCTGACTGAGGCCATTGACAAGAACAAGGCCGACTTGTCACGCATGT
CAGGCAAGAAGGACCTGTACCTGGCCAGCGTGTTCCACGCCACCGCCTTT
GAGTTGGACACAGATGGCAACCCCTTTGACCAGGACATCTACGGGCGCGA
GGAGCTGCGCAGCCCCAAGCTGTTCTACGCCGACCACCCCTTCATCTTCC
TAGTGCGGGACACCCAAAGCGGCTCCCTGCTATTCATTGGGCGCCTGGTC
CGGCCTAAGGGTGACAAGATGCGAGACGAGTTATAGGGCCTCAGGGTGCA
CACAGGATGGCAGGAGGCATCCAAAGGCTCCTGAGACACATGGGTGCTAT
TGGGGTTGGGGGGGAGGTGAGGTACCAGCCTTGGATACTCCATGGGGTGG
GGGTGGAAAAACAGACCGGGGTTCCCGTGTGCCTGAGCGGACCTTCCCAG
CTAGAATTCACTCCACTTGGACATGGGCCCCAGATACCATGATGCTGAGC
CCGGAAACTCCACATCCTGTGGGACCTGGGCCATAGTCATTCTGCCTGCC
CTGAAAGTCCCAGATCAAGCCTGCCTCAATCAGTATTCATATTTATAGCC
AGGTACCTTCTCACCTGTGAGACCAAATTGAGCTAGGGGGGTCAGCCAGC
CCTCTTCTGACACTAAAACACCTCAGCTGCCTCCCCAGCTCTATCCCAAC
CTCTCCCAACTATAAAACTAGGTGCTGCAGCCCCTGGGACCAGGCACCCC
CAGAATGACCTGGCCGCAGTGAGGCGGATTGAGAAGGAGCTCCCAGGAGG
GGCTTCTGGGCAGACTCTGGTCAAGAAGCATCGTGTCTGGCGTTGTGGGG
ATGAACTTTTTGTTTTGTTTCTTCCTTTTTTAGTTCTTCAAAGATAGGGA
GGGAAGGGGGAACATGAGCCTTTGTTGCTATCAATCCAAGAACTTATTTG
TACATTTTTTTTTCAATAAAACTTTTCCAATGACATTTTGTTGGAGCGT
GGAAAAAA

Serine Proteinase Inhibitor, Clade B, Member 5
>gi|4505788|ref|NM_002639.1| Homo sapiens serine (or cysteine) proteinase inhibitor, clade B (ovalbumin), member 5 (SERPINB5), mRNA|qPCR forward_primer match [36 . . . 56]|qPCR reverse_primer match [106 . . . 86]|qPCR probe match [60 . . . 80]

SEQ ID NO: 102
GGCACGAGTTGTGCTCCTCGCTTGCCTGTTCCTTTTCCACGCATTTTCCA
GGATAACTGTGACTCCAGGCCCGCAATGGATGCCCTGCAACTAGCAAATT
CGGCTTTTGCCGTTGATCTGTTCAAACAACTATGTGAAAAGGAGCCACTG
GGCAATGTCCTCTTCTCTCCAATCTGTCTCTCCACCTCTCTGTCACTTGC
TCAAGTGGGTGCTAAAGGTGACACTGCAAATGAAATTGGACAGGTTCTTC
ATTTTGAAAATGTCAAAGATATACCCTTTGGATTTCAAACAGTAACATCG
GATGTAAACAAACTTAGTTCCTTTTACTCACTGAAACTAATCAAGCGGCT
CTACGTAGACAAATCTCTGAATCTTTCTACAGAGTTCATCAGCTCTACGA
AGAGACCCTATGCAAAGGAATTGGAAACTGTTGACTTCAAAGATAAATTG
GAAGAAACGAAAGGTCAGATCAACAACTCAATTAAGGATCTCACAGATGG
CCACTTTGAGAACATTTTAGCTGACAACAGTGTGAACGACCAGACCAAAA
TCCTTGTGGTTAATGCTGCCTACTTTGTTGGCAAGTGGATGAAGAAATTT
CCTGAATCAGAAACAAAAGAATGTCCTTTCAGACTCAACAAGACAGACAC
CAAACCAGTGCAGATGATGAACATGGAGGCCACGTTCTGTATGGGAAACA
TTGACAGTATCAATTGTAAGATCATAGAGCTTCCTTTTCAAAATAAGCAT
CTCAGCATGTTCATCCTACTACCCAAGGATGTGGAGGATGAGTCCACAGG
CTTGGAGAAGATTGAAAAACAACTCAACTCAGAGTCACTGTCACAGTGGA
CTAATCCCAGCACCATGGCCAATGCCAAGGTCAAACTCTCCATTCCAAAA
TTTAAGGTGGAAAAGATGATTGATCCCAAGGCTTGTCTGGAAAATCTAGG
GCTGAAACATATCTTCAGTGAAGACACATCTGATTTCTCTGGAATGTCAG
AGACCAAGGGAGTGGCCCTATCAAATGTTATCCACAAAGTGTGCTTAGAA
ATAACTGAAGATGGTGGGGATTCCATAGAGGTGCCAGGAGCACGGATCCT

```
GCAGCACAAGGATGAATTGAATGCTGACCATCCCTTTATTTACATCATCA
GGCACAACAAAACTCGAAACATCATTTTCTTTGGCAAATTCTGTTCTCCT
TAAGTGGCATAGCCCATGTTAAGTCCTCCCTGACTTTTCTGTGGATGCCG
ATTTCTGTAAACTCTGCATCCAGAGATTCATTTTCTAGATACAATAAATT
GCTAATGTTGCTGGATCAGGAAGCCGCCAGTACTTGTCATATGTAGCCTT
CACACAGATAGACCTTTTTTTTTTCCAATTCTATCTTTTGTTTCCTTTT
TTCCCATAAGACAATGACATACGCTTTTAATGAAAAGGAATCACGTTAGA
GGAAAAATATTTATTCATTATTTGTCAAATTGTCCGGGGTAGTTGGCAGA
AATACAGTCTTCCACAAAGAAAATTCCTATAAGGAAGATTTGGAAGCTCT
TCTTCCCAGCACTATGCTTTCCTTCTTTGGGATAGAGAATGTTCCAGACA
TTCTCGCTTCCCTGAAAGACTGAAGAAAGTGTAGTGCATGGGACCCACGA
AACTGCCCTGGCTCCAGTGAAACTTGGGCACATGCTCAGGCTACTATAGG
TCCAGAAGTCCTTATGTTAAGCCCTGGCAGGCAGGTGTTTATTAAAATTC
TGAATTTTGGGGATTTTCAAAAGATAATATTTTACATACACTGTATGTTA
TAGAACTTCATGGATCAGATCTGGGGCAGCAACCTATAAATCAACACCTT
AATATGCTGCAACAAAATGTAGAATATTCAGACAAAATGGATACATAAAG
ACTAAGTAGCCCATAAGGGGTCAAAATTTGCTGCCAAATGCGTATGCCAC
CAACTTACAAAAACACTTCGTTCGCAGAGCTTTTCAGATTGTGGAATGTT
GGATAAGGAATTATAGACCTCTAGTAGCTGAAATGCAAGACCCCAAGAGG
AAGTTCAGATCTTAATATAAATTCACTTTCATTTTTGATAGCTGTCCCAT
CTGGTCATGTGGTTGGCACTAGACTGGTGGCAGGGGCTTCTAGCTGACTC
GCACAGGGATTCTCACAATAGCCGATATCAGAATTTGTGTTGAAGGAACT
TGTCTCTTCATCTAATATGATAGCGGGAAAAGGAGAGGAAACTACTGCCT
TTAGAAAATATAAGTAAAGTGATTAAAGTGCTCACGTTACCTTGACACAT
AGTTTTTCAGTCTATGGGTTTAGTTACTTTAGATGGCAAGCATGTAACTT
ATATTAATAGTAATTTGTAAAGTTGGGTGGATAAGCTATCCCTGTTGCCG
GTTCATGGATTACTTCTCTATAAAAAATATATATTTACCAAAAAATTTTG
TGACATTCCTTCTCCCATCTCTTCCTTGACATGCATTGTAAATAGGTTCT
TCTTGTTCTGAGATTCAATATTGAATTTCTCCTATGCTATTGACAATAAA
ATATTATTGAACTACC
```

Carcinoembryonic Antigen-Related Cell Adhesion Molecule 5
>gi|11386170|Ref|NM_004363.1| Homo sapiens carcinoembryonic antigen-related cell adhesion molecule 5 (CEACAM5), mRNA|qPCR assay_on_demand_context match [2128 . . . 2152]

```
                                              SEQ ID NO: 103
CTCAGGGCAGAGGGAGGAAGGACAGCAGACCAGACAGTCACAGCAGCCTT
GACAAAACGTTCCTGGAACTCAAGCTCTTCTCCACAGAGGAGGACAGAGC
AGACAGCAGAGACCATGGAGTCTCCCTCGGCCCCTCCCCACAGATGGTGC
ATCCCCTGGCAGAGGCTCCTGCTCACAGCCTCACTTCTAACCTTCTGGAA
CCCGCCCACCACTGCCAAGCTCACTATTGAATCCACGCCGTTCAATGTCG
CAGAGGGGAAGGAGGTGCTTCTACTTGTCCACAATCTGCCCCAGCATCTT
TTTGGCTACAGCTGGTACAAAGGTGAAAGAGTGGATGGCAACCGTCAAAT
TATAGGATATGTAATAGGAACTCAACAAGCTACCCCAGGGCCCGCATACA
GTGGTCGAGAGATAATATACCCCAATGCATCCCTGCTGATCCAGAACATC
ATCCAGAATGACACAGGATTCTACACCCTACACGTCATAAAGTCAGATCT
TGTGAATGAAGAAGCAACTGGCCAGTTCCGGGTATACCCGGAGCTGCCCA
AGCCCTCCATCTCCAGCAACAACTCCAAACCCGTGGAGGACAAGGATGCT
GTGGCCTTCACCTGTGAACCTGAGACTCAGGACGCAACCTACCTGTGGTG
GGTAAACAATCAGAGCCTCCCGGTCAGTCCCAGGCTGCAGCTGTCCAATG
GCAACAGGACCCTCACTCTATTCAATGTCACAAGAAATGACACAGCAAGC
TACAAATGTGAAACCCAGAACCCAGTGAGTGCCAGGCGCAGTGATTCAGT
CATCCTGAATGTCCTCTATGGCCCGGATGCCCCCACCATTTCCCCTCTAA
ACACATCTTACAGATCAGGGGAAAATCTGAACCTCTCCTGCCACGCAGCC
TCTAACCCACCTGCACAGTACTCTTGGTTTGTCAATGGGACTTTCCAGCA
ATCCACCCAAGAGCTCTTTATCCCCAACATCACTGTGAATAATAGTGGAT
CCTATACGTGCCAAGCCCATAACTCAGACACTGGCCTCAATAGGACCACA
GTCACGACGATCACAGTCTATGCAGAGCCACCCAAACCCTTCATCACCAG
CAACAACTCCAACCCCGTGGAGGATGAGGATGCTGTAGCCTTAACCTGTG
AACCTGAGATTCAGAACACAACCTACCTGTGGTGGGTAAATAATCAGAGC
CTCCCGGTCAGTCCCAGGCTGCAGCTGTCCAATGACAACAGGACCCTCAC
TCTACTCAGTGTCACAAGGAATGATGTAGGACCCTATGAGTGTGGAATCC
AGAACGAATTAAGTGTTGACCACAGCGACCCAGTCATCCTGAATGTCCTC
TATGGCCCAGACGACCCCACCATTTCCCCCTCATACACCTATTACCGTCC
AGGGGTGAACCTCAGCCTCTCCTGCCATGCAGCCTCTAACCCACCTGCAC
AGTATTCTTGGCTGATTGATGGGAACATCCAGCAACACACACAAGAGCTC
TTATCTCCAACATCACTGAGAAGAACAGCGGACTCTATACCTGCCAGGCC
AATAACTCAGCCAGTGGCCACAGCAGGACTACAGTCAAGACAATCACAGT
CTCTGCGGAGCTGCCCAAGCCCTCCATCTCCAGCAACAACTCCAAACCCG
TGGAGGACAAGGATGCTGTGGCCTTCACCTGTGAACCTGAGGCTCAGAAC
ACAACCTACCTGTGGTGGGTAAATGGTCAGAGCCTCCCAGTCAGTCCCAG
GCTGCAGCTGTCCAATGGCAACAGGACCCTCACTCTATTCAATGTCACAA
GAAATGACGCAAGAGCCTATGTATGTGGAATCCAGAACTCAGTGAGTGCA
AACCGCAGTGACCCAGTCACCCTGGATGTCCTCTATGGGCCGGACACCCC
CATCATTTCCCCCCCAGACTCGTCTTACCTTTCGGGAGCGAACCTCAACC
TCTCCTGCCACTCGGCCTCTAACCCATCCCCGCAGTATTCTTGGCGTATC
AATGGGATACCGCAGCAACACACACAAGTTCTCTTTATCGCAAAATCAC
GCCAAATAATAACGGGACCTATGCCTGTTTTGTCTCTAACTTGGCTACTG
GCCGCAATAATTCCATAGTCAAGAGCATCACAGTCTCTGCATCTGGAACT
TCTCCTGGTCTCTCAGCTGGGGCCACTGTCGGCATCATGATTGGAGTGCT
GGTTGGGGTTGCTCTGATATAGCAGCCCTGGTGTAGTTTCTTCATTTCAG
GAAGACTGACAGTTGTTTTGCTTCTTCCTTAAAGCATTTGCAACAGCTAC
```

-continued

```
AGTCTAAAATTGCTTCTTTACCAAGGATATTTACAGAAAAGACTCTGACC
AGAGATCGAGACCATCCTAGCCAACATCGTGAAACCCCATCTCTACTAAA
AATACAAAAATGAGCTGGGCTTGGTGGCGCGCACCTGTAGTCCCAGTTAC
TCGGGAGGCTGAGGCAGGAGAATCGCTTGAACCCGGGAGGTGGAGATTGC
AGTGAGCCCAGATCGCACCACTGCACTCCAGTCTGGCAACAGAGCAAGAC
TCCATCTCAAAAAGAAAAGAAAAGAAGACTCTGACCTGTACTCTTGAATA
CAAGTTTCTGATACCAGTGCACTGTCTGAGAATTTCCAAAACTTTAATGA
ACTAACTGACAGCTTCATGAAACTGTGCACCAAGATCAAGCAGAGAAAAT
AATTAATTTCATGGGACTAAATGAACTAATGAGGATTGCTGATTCTTTAA
ATGTCTTGTTTCCCAGATTTCAGGAAACTTTTTTTCTTTTAAGCTATCCA
CTCTTACAGCAATTTGATAAATATACTTTTGTGAACAAAAATTGAGACAT
TTACATTTTCTCCCTATGTGGTCGCTCCAGACTTGGGAAACTATTCATGA
ATATTTATATTGTATGGTAATATAGTTATTGCACAAGTTCAATAAAAATC
TGCTCTTTGTATAACAGAAAAA
```

Matrix Metalloproteinase 2
>gi|11342665|ref|NM_004530.1| Homo sapiens matrix metalloproteinase 2 (gelatinase A, 72 kDa gelatinase, 72 kDa type IV collagenase) (MMP2), mRNA|qPCR forward_primer match [1713 . . . 1732]|qPCR reverse_primer match [1793 . . . 1775]|qPCR probe match [1751 . . . 1773]

SEQ ID NO: 104
```
TGTTTCCGCTGCATCCAGACTTCCTCAGGCGGTGGCTGGAGGCTGCGCAT
CTGGGGCTTTAAACATACAAAGGGATTGCCAGGACCTGCGGCGGCGGCGG
CGGCGGCGGGGGCTGGGCGCGGGGGCCGGACCATGAGCCGCTGAGCCGG
GCAAACCCCAGGCCACCGAGCCAGCGGACCCTCGGAGCGCAGCCCTGCGC
CGCGGACCAGGCTCCAACCAGGCGGCGAGGCGGCCACACGCACCGAGCCA
GCGACCCCCGGGCGACGCGCGGGGCCAGGGAGCGCTACGATGGAGGCGCT
AATGGCCCGGGGCGCGCTCACGGGTCCCCTGAGGGCGCTCTGTCTCCTGG
GCTGCCTGCTGAGCGACGCCGCCGCCGCGCCGTCGCCCATCATCAAGTTC
CCCGGCGATGTCGCCCCCAAAACGGACAAAGAGTTGGCAGTGCAATACCT
GAACACCTTCTATGGCTGCCCCAAGGAGAGCTGCAACCTGTTTGTGCTGA
AGGACACACTAAAGAAGATGCAGAAGTTCTTTGGACTGCCCCAGACAGGT
GATCTTGACCAGAATACCATCGAGACCATGCGGAAGCCACGCTGCGGCAA
CCCAGATGTGGCCAACTACAACTTCTTCCCTCGCAAGCCCAAGTGGGACA
AGAACCAGATCACATACAGGATCATTGGCTACACACCTGATCTGGACCCA
GAGACAGTGGATGATGCCTTTGCTCGTGCCTTCCAAGTCTGGAGCGATGT
GACCCCACTGCGGTTTTCTCGAATCCATGATGGAGAGGCAGACATCATGA
TCAACTTTGGCCGCTGGGAGCATGGCGATGGATACCCCTTTGACGGTAAG
GACGGACTCCTGGCTCATGCCTTCGCCCCAGGCACTGGTGTTGGGGAGA
CTCCCATTTTGATGACGATGAGCTATGGACCTTGGGAGAAGGCCAAGTGG
TCCGTGTGAAGTATGGCAACGCCGATGGGGAGTACTGCAAGTTCCCCTTC
TTGTTCAATGGCAAGGAGTACAACAGCTGCACTGATACTGGCCGCAGCGA
TGGCTTCCTCTGGTGCTCCACCACCTACAACTTTGAGAAGGATGGCAAGT
ACGGCTTCTGTCCCCATGAAGCCCTGTTCACCATGGGCGGCAACGCTGAA
GGACAGCCCTGCAAGTTTCCATTCCGCTTCCAGGGCACATCCTATGACAG
CTGCACCACTGAGGGCCGCACGGATGGCTACCGCTGGTGCGGCACCACTG
AGGACTACGACCGCGACAAGAAGTATGGCTTCTGCCCTGAGACCGCCATG
TCCACTGTTGGTGGGAACTCAGAAGGTGCCCCCTGTGTCTTCCCCTTCAC
TTTCCTGGGCAACAAATATGAGAGCTGCACCAGCGCCGGCCGCAGTGACG
GAAAGATGTGGTGTGCGACCACAGCCAACTACGATGACGACCGCAAGTGG
GGCTTCTGCCCTGACCAGGGTACAGCCTGTTCCTCGTGGCAGCCCACGAG
TTTGGCCACGCCATGGGGCTGGAGCACTCCCAAGACCCTGGGGCCCTGAT
GGCACCCATTTACACCTACACCAAGAACTTCCGTCTGTCCCAGGATGACA
TCAAGGGCATTCAGGAGCTCTATGGGCCTCTCCTGACATTGACCTTGGC
ACCGGCCCCACCCCCACACTGGGCCCTGTCACTCCTGAGATCTGCAAACA
GGACATTGTATTTGATGGCATCGCTCAGATCCGTGGTGAGATCTTCTTCT
TCAAGGACCGGTTCATTTGGCGGACTGTGACGCCACGTGACAAGCCCATG
GGGCCCCTGCTGGTGGCCACATTCTGGCCTGAGCTCCCGGAAAAGATTGA
TGCGGTATACGAGGCCCCACAGGAGGAGAAGGCTGTGTTCTTTGCAGGGA
ATGAATACTGGATCTACTCAGCCAGCACCCTGGAGCGAGGGTACCCCAAG
CCACTGACCAGCCTGGGACTGCCCCCTGATGTCCAGCGAGTGGATGCCGC
CTTTAACTGGAGCAAAAACAAGAAGACATACATCTTTGCTGGAGACAAAT
TCTGGAGATACAATGAGGTGAAGAAGAAAATGGATCCTGGCTTTCCCAAG
CTCATCGCAGATGCCTGGAATGCCATCCCCGATAACCTGGATGCCGTCGT
GGACCTGCAGGGCGGCGGTCACAGCTACTTCTTCAAGGGTGCCTATTACC
TGAAGCTGGAGAACCAAAGTCTGAAGAGCGTGAAGTTTGGAAGCATCAAA
TCCGACTGGCTAGGCTGCTGAGCTGGCCCTGGCTCCCACAGGCCCTTCCT
CTCCACTGCCTTCGATACACCGGGCCTGGAGAACTAGAGAAGGACCCGGA
GGGGCCTGGCAGCCGTGCCTTCAGCTCTACAGCTAATCAGCATTCTCACT
CCTACCTGGTAATTTAAGATTCCAGAGAGTGGCTCCTCCCGGTGCCCAAG
AATAGATGCTGACTGTACTCCTCCCAGGCGCCCCTTCCCCCTCCAATCCC
ACCAACCCTCAGAGCCACCCCTAAAGAGATCCTTTGATATTTTCAACGCA
GCCCTGCTTTGGGCTGCCCTGGTGCTGCCACACTTCAGGCTCTTCTCCTT
TCACAACCTCTGTGGCTCACAGAACCCTTGGAGCCAATGGAGACTGTCTC
AAGAGGGCACTGGTGGCCCGACAGCCTGGCACAGGGCAGTGGGACAGGGC
ATGGCCAGGTGGCCACTCCAGACCCCTGGCTTTTCACTGCTGGCTGCCTT
AGAACCTTCTTACATTAGCAGTTTGCTTTGTATGCACTTTGTTTTTTTCT
TTGGGTCTTGTTTTTTTTTTCCACTTAGAAATTGCATTTCCTGACAGAAG
GACTCAGGTTGTCTGAAGTCACTGCACAGTGCATCTCAGCCCACATAGTG
ATGGTTCCCCTGTTCACTCTACTTAGCATGTCCCTACCGAGTCTCTTCTC
```

Proprotein Convertase Subtilisin/Kexin Type 5
>gi|20336245|ref|NM_006200.2| Homo sapiens proprotein convertase subtilisin/kexin type 5 (PCSK5), mRNA|qPCR forward_primer match [2677 . . . 2697]|qPCR reverse_primer match [2821 . . . 2801]|qPCR probe match [2737 . . . 2765]

SEQ ID NO: 105

CGGAGGGAGCGCTGGGAGCGAGCAAGCGAGCGTTTGGAGCCCGGGCCAGC
AGAGGGGGCGCCCGGTCGCTGCCTGTACCGCTCCCGCTGGTCATCTCCGC
CGCGCTCGGGGGCCCCGGGAGGAGCGAGACCGAGTCGGAGAGTCCGGGAG
CCAAGCCGGGCGAAACCCAACTGCGGAGGACGCCCGCCCCACTCAGCCTC
CTCCTGCGTCCGAGCCGGGGAGCATCGCCGAGCGCCCACGGGCCGGAGA
GCTGGGAGCACAGGTCCCGGCAGCCCCAGGGATGGTCTAGGAGCCGGCGT
AAGGCTCGCTGCTCTGCTCCCTGCCGGGGCTAGCCGCCTCCTGCCGATCG
CCCGGGGCTGCGAGCTGCGGCGGCCCGGGGCTGCTCGCCGGGCGGCGCAG
GCCGGAGAAGTTAGTTGTGCGCGCCCTTAGTGCGCGGAACCAGCCAGCGA
GCGAGGGAGCAGCGAGGCGCCGGGACCATGGGCTGGGGAGCCGCTGCTG
CTGCCCGGGACGTTTGGACCTGCTGTGCGTGCTGGCGCTGCTCGGGGGCT
GCCTGCTCCCCGTGTGTCGGACGCGCGTCTACACCAACCACTGGGCAGTC
AAAATCGCCGGGGGCTTCCCGGAGGCCAACCGTATCGCCAGCAAGTACGG
ATTCATCAACATAGGACAGATAGGGGCCCTGAAGGACTACTACCACTTCT
ACCATAGCAGGACGATTAAAAGGTCAGTTATCTCGAGCAGAGGGACCCAC
AGTTTCATTTCAATGGAACCAAAGGTGGAATGGATCCAACAGCAAGTGGT
AAAAAAGCGGACAAAGAGGGATTATGACTTCAGTCGTGCCCAGTCTACCT
ATTTCAATGATCCCAAGTGGCCCAGCATGTGGTATATGCACTGCAGTGAC
AATACACATCCCTGCCAGTCTGACATGAATATCGAAGGAGCCTGGAAGAG
AGGCTACACGGGAAAGAACATTGTGGTCACTATCCTGGATGACGGAATTG
AGAGAACCCATCCAGATCTGATGCAAAACTACGATGCTCTGGCAAGTTGC
GACGTGAATGGGAATGACTTGGACCCAATGCCTCGTTATGATGCAAGCAA
CGAGAACAAGCATGGGACTCGCTGTGCTGGAGAAGTGGCAGCCGCTGCAA
ACAATTCGCACTGCACAGTCGGAATTGCTTTCAACGCCAAGATCGGAGGA
GTGCGAATGCTGGACGGAGATGTCACGGACATGGTTGAAGCAAAATCAGT
TAGCTTCAACCCCCAGCACGTGCACATTTACAGCGCCAGCTGGGGCCCGG
ATGATGATGGCAAGACTGTGGACGGACCAGCCCCCCTCACCCGGCAAGCC
TTTGAAAACGGCGTTAGAATGGGGCGGAGAGGCCTCGGCTCTGTGTTTGT
TTGGGCATCTGGAAATGGTGGAAGGAGCAAAGACCACTGCTCCTGTGATG
GCTACACCAACAGCATCTACACCATCTCCATCAGCAGCACTGCAGAAAGC
GGAAAGAAACCTTGGTACCTGGAAGAGTGTTCATCCACGCTGGCCACAAC
CTACAGCAGCGGGGAGTCCTACGATAAGAAAATCATCACTACAGATCTGA
GGCAGCGTTGCACGGACAACCACACTGGGACGTCAGCCTCAGCCCCCATG
GCTGCAGGCATCATTGCGCTGGCCCTGGAAGCCAATCCGTTTCTGACCTG
GAGAGACGTACAGCATGTTATTGTCAGGACTTCCCGTGCGGACATTTGA
ACGCTAATGACTGGAAAACCAATGCTGCTGGTTTTAAGGTGAGCCATCTT
TATGGATTTGGACTGATGGACGCAGAAGCCATGGTGATGGAGGCAGAGAA
GTGGACCACCGTTCCCCGGCAGCACGTGTGTGTGGAGAGCACAGACCGAC
AAATCAAGACAATCCGCCCTAACAGTGCAGTGCGCTCCATCTACAAAGCT
TCAGGCTGCTCGGATAACCCCAACCGCCATGTCAACTACCTGGAGCACGT
CGTTGTGCGCATCACCATCACCCACCCCAGGAGAGGAGACCTGGCCATCT
ACCTGACCTCGCCCTCTGGAACTAGGTCTCAGCTTTTGGCCAACAGGCTA
TTTGATCACTCCATGGAAGGATTCAAAAACTGGGAGTTCATGACCATTCA
TTGCTGGGGAGAAAGAGCTGCTGGTGACTGGGTCCTTGAAGTTTATGATA
CTCCCTCTCAGCTAAGGAACTTTAAGACTCCAGGTAAATTGAAAGAATGG
TCTTTGGTCCTCTACGGCACCTCCGTGCAGCCATATTCACCAACCAATGA
ATTTCCGAAAGTGGAACGGTTCCGCTATAGCCGAGTTGAAGACCCCACAG
ACGACTATGGCACAGAGGATTATGCAGGTCCCTGCGACCCTGAGTGCAGT
GAGGTTGGCTGTGACGGGCCAGGACCAGACCACTGCAATGACTGTTTGCA
CTACTACTACAAGCTGAAAAACAATACCAGGATCTGTGTCTCCAGCTGCC
CCCCTGGCCACTACCACGCCGACAAGAAGCGCTGCAGGAAGTGTGCCCCC
AACTGTGAGTCCTGCTTTGGGAGCCATGGTGACCAATGCATGTCCTGCAA
ATATGGATACTTTCTGAATGAAGAAACCAACAGCTGTGTTACTCACTGCC
CTGATGGGTCATATCAGGATACCAAGAAAAATCTTTGCCGGAAATGCAGT
GAAAACTGCAAGACATGTACTGAATTCCATAACTGTACAGAATGTAGGGA
TGGGTTAAGCCTGCAGGGATCCCGGTGCTCTGTCTCCTGTGAAGATGGAC
GGTATTTCAACGGCCAGGACTGCCAGCCCTGCCACCGCTTCTGCGCCACT
TGTGCTGGGCAGGAGCTGATGGGTGCATTAACTGCACAGAGGGCTACTT
CATGGAGGATGGGAGATGCGTGCAGAGCTGTAGTATCAGCTATTACTTTG
ACCACTCTTCAGAGAATGGATACAAATCCTGCAAAAAATGTGATATCAGT
TGTTTGACGTGCAATGGCCCAGGATTCAAGAACTGTACAAGCTGCCCTAG
TGGGTATCTCTTAGACTTAGGAATGTGTCAAATGGGAGCCATTTGCAAGG
ATGCAACGAAGAGTCCTGGGCGGAAGGAGGCTTCTGTATGCTTGTGAAA
AAGAACAATCTGTGCCAACGGAAGGTTCTTCAACAACTTTGCTGCAAAAC
ATGTACATTTCAAGGCTGAGCAGCCATCTTAGATTTCTTTGTTCCTGTAG
ACTTATAGATTATTCCATATTATTAAAAAGAAAAAAAAAAGCCAAAAAG

Carboxypeptidase N, Polypeptide 2, 83 kD
>gi|18554966|ref|XM_087358.1| Homo sapiens carboxypeptidase N, polypeptide 2, 83 kD (CPN2), mRNA

SEQ ID NO: 106

ATGGGTTGTGACTGCTTCGTCCAGGAGGTGTTCTGCTCAGATGAGGAGCT
TGCCACCGTCCCGCTGGACATCCCGCCATATACGAAAAACATCATCTTTG
TGGAGACCTCGTTCACCACATTGGAAACCAGAGCTTTTGGCAGTAACCCC

AACTTGACCAAGGTGGTCTTCCTCAACACTCAGCTCTGCCAGTTTAGGCC
GGATGCCTTTGGGGGGCTGCCCAGGCTGGAGGACCTGGAGGTCACAGGCA
GTAGCTTCTTGAACCTCAGCACCAACATCTTCTCCAACCTGACCTCGCTG
GGCAAGCTCACCCTCAACTTCAACATGCTGGAGGCTCTGCCCGAGGGTCT
TTTCCAGCACCTGGCTGCCCTGGAGTCCCTCCACCTGCAGGGGAACCAGC
TCCAGGCCCTGCCCAGGAGGCTCTTCCAGCCTCTGACCCATCTGAAGACA
CTCAACCTGGCCCAGAACCTCCTGGCCCAGCTCCCGGAGGAGCTGTTCCA
CCCACTCACCAGCCTGCAGACCCTGAAGCTGAGCAACAACGCGCTCTCTG
GTCTCCCCCAGGGTGTGTTTGGCAAACTGGGCAGCCTGCAGGAGCTCTTC
CTGGACAGCAACAACATCTCGGAGCTGCCCCCTCAGGTGTTCTCCCAGCT
CTTCTGCCTAGAGAGGCTGTGGCTGCAACGCAACGCCATCACGCACCTGC
CGCTCTCCATCTTTGCCTCCCTGGGTAATCTGACCTTTCTGAGCTTGCAG
TGGAACATGCTTCGGGTCCTGCCTGCCGGCCTCTTTGCCCACACCCCATG
CCTGGTTGGCCTGTCTCTGACCCATAACCAGCTGGAGACTGTCGCTGAGG
GCACCTTTGCCCACCTGTCCAACCTGCGTTCCCTCATGCTCTCATACAAT
GCCATTACCCACCTCCCAGCTGGCATCTTCAGAGACCTGGAGGAGTTGGT
CAAACTCTACCTGGGCAGCAACAACCTTACGGCGCTGCACCCAGCCCTCT
TCCAGAACCTGTCCAAGCTGGAGCTGCTCAGCCTCTCCAAGAACCAGCTG
ACCACACTTCCGGAGGGCATCTTCGACACCAACTACAACCTGTTCAACCT
GGCCCTGCACGGTAACCCCTGGCAGTGCGACTGCCACCTGGCCTACCTCT
TCAACTGGCTGCAGCAGTACACCGATCGGCTCCTGAACATCCAGACCTAC
TGCGCTGGCCCTGCCTACCTCAAAGGCCAGGTGGTGCCCGCCTTGAATGA
GAAGCAGCTGGTGTGTCCCGTCACCCGGGACCACTTGGGCTTCCAGGTCA
CGTGGCCGGACGAAAGCAAGGCAGGGGGCAGCTGGGATCTGGCTGTGCAG
GAAAGGGCAGCCCGGAGCCAGTGCACCTACAGCAACCCCGAGGGCACCGT
GGTGCTCGCCTGTGACCAGGCCCAGTGTCGCTGGCTGAACGTCCAGCTCT
CTCCTTGGCAGGGCTCCCTGGGACTGCAGTACAATGCTAGTCAGGAGTGG
GACCTGAGGTCGAGCTGCGGTTCTCTGCGGCTCACCGTGTCTATCGAGGC
TCGGGCAGCAGGGCCCTAGTAGCAGCGCATACAGGAGCTGGGGAAGGGGG
CTTTGGGGCCTGCCCACGCGACAGGTAGGGGCGGAGGGGAGCTGAGTCTC
CGAAGCTTGGCTTT

Hyaluronan and Proteoglycan Link Protein 4
>gi|30794471|ref|NM_023002.1| Homo sapiens hyaluronan and proteoglycan link protein 4 (HAPLN4), mRNA SEQ ID NO: 107
CGGGGGCCGCGCGGGCAAGATGGTGTGCGCTCGGCGGCCCTCGGTCCCG
GCGCGCTCTGGGCCGCGGCCTGGGGCGTCCTGCTGCTCACAGCCCCTGCG
GGGGCGCAGCGTGGCCGGAAGAAGGTCGTGCACGTGCTGGAGGGTGAGTC
GGGCTCGGTAGTGGTACAGACAGCGCCTGGGCAGGTGGTAAGCCACCGTG
GTGGCACCATCGTCTTGCCCTGCCGCTACCACTATGAGGCAGCCGCCCAC
GGTCACGACGGCGTCCGGCTCAAGTGGACAAAGGTGGTGGACCCGCTGGC
CTTCACCGACGTCTTCGTGGCACTAGGCCCCCAGCACCGGGCATTCGGCA
GCTACCGTGGGCGGGCTGAGCTGCAGGGCGACGGGCCTGGGGATGCCTCC
CTGGTCCTCCGCAACGTCACGCTGCAAGACTACGGGCGCTATGAGTGCGA
AGTCACCAATGAGCTGGAAGATGACGCTGGCATGGTCAAGCTGGACCTGG
AAGGCGTGGTCTTTCCCTACCACCCCGTGGAGGCCGATACAAGCTGACC
TTCGCGGAGGCGCAGCGCGCGTGCGCCGAGCAGGACGGCATCCTGGCATC
TGCAGAACAGCTGCACGCGGCCTGGCGCGACGGCCTGGACTGGTGCAACG
CGGGCTGGTTGCGCGACGGCTCAGTGCAATACCCCGTGAACCGGCCCCGG
GAGCCCTGCGGCGGCCTGGGGGGGACCGGGAGTGCAGGGGGCGGCGGTGA
TGCCAACGGGGCCTGCGCAACTACGGGTATCGCCATAACGCCGAGGAAC
GCTACGACGCCTTCTGCTTCACGTCCAACCTGCCGGGGCGCGTGTTCTTC
CTGAAGCCGCTGCGACCTGTACCCTTCTCCGGAGCTGCGCGCGCGTGTGC
TGCGCGTGGCGCGACCCGTGGCCAAGGTGGGGCAGCTGTTCGCCGCGTGGA
AGCTGCAGCTGCTAGACCGCTGCACCGCGGGTTGGCTGGCCGATGGCAGT
GCGCGCTACCCCATCGTGAACCCGGGAGCGCGCTGCGGAGGCCGCAGGCC
TGGTGTGCGCAGCCTCGGCTTCCCGGACGCCACCCGACGGCTCTTCGGCG
TCTACTGCTACCGCGCTCCAGGAGCACCGGACCCGGCACCTGGCGGCTGG
GGCTGGGCTGGGCGGGCGGCGGCGGCTGGGCAGGGGGCGCGCGCGATCC
TGCTGCCTGGACCCCTCTGCACGTCTAGGCTGGGAGTAGGCGGACAGCCA
GGGCGCTTGACCACTGGTCTAGAGCCCTGTGGTCCCTGGAGCCTGGCCA
CGCCCTTGAAGCCCTGGACACTGGCCACATTCCCTGTGGTCCCTTACAAA
CTAACTGTGCCCTGGGGTCCCTGAAGACTGGCTAGTCCTGGCAGAACAG
TACTTTGGAGTTCCCTGGAGCCTGGCCAGCCCTCACCTCTTCTGGATAGA
GGATTCCCCCAACTCCCCAACTTTCTCCATGAGGGTCACGCCCCCTGAGG
ACCTCAGGAGGCCAGCAGAACCCGCAGGCTCCTGAAGACTGGCCACGCCT
CCTGAGACCACTTGGAAACAGACCAACTGCCCCCGTGGTCGCCTGGTGGC
TGGACCCCCGGGATTGACTAGAGACCGGCCGTACACCTTCTGCATCTCAC
TGGAGACTGAACACTAGTCCCTTGCGGTCACGTGGGACACTGGGCGCCTC
CTCCTCCCCCTCCTCCTCACCTGGAGAGACTACAGGAACTTCAGGGTCAC
TCCCCGTGGTCACATGGAGGTTGTGGGCCGAGGCGCTTATTTTCCCTTAT
GGTGACCTGAGTCCTGGAGACTCCCATTCTCCCCCTCTCCCTGAGAGTCC
CCTGCAGTTTCTGGGTAACAGGGCACACCCCTCTAGTTTCATGGGCGAGC
ACCCCCATCTGCCACCTCAGACTGACACACAGCCAGCTGGCTCACTTACT
GGGGGCCACGTCCCACCCCTCAGATATTTCTTTGAAGGGAGAGCAAACCC
ACCCTGTCCTCTGACGTCCCTTTCCCAACTGTCACCAAACAGACCATCTT
CCCAGGCCTGGGGACCGGTAAGATCCATGTCACTAGTTATGCAGAGCAGT
TGCCTTGGGTCCCACTGTCACCAAGGCAACCAGTCCTGCTGCTACCTGTC
ACCTAGAGTCACACACCCCTTCCCTCATCAGGCACACCCATGAAGACAGT
GCCTCCCTCCTCCAGCTGTAACCATGGATACCACACATTTCTCATCTCAT
TGGCCCCCACCCCAGAGACCTCCACCTCAACTTCTGGCTGTCCCTACCCT
GACTCACCGCCATGGAGATCACCCTCCCCGAAGCTGTCGCCAGGGTGACC -continued

```
CAACATCCAGTTCTCCGGCTCTCACCATGGAAACAAACTGTCCCTGTCCC

CAGGCCCACTCCAGTTCCAGACCACCCTCCATGCTCCACCCCCAGGCGGT

TTGGACCCCACCACTGTTGCCATGGTGACCAAACTCTGGAGTCCGAGGTA

ACAGAACACCTGTCCCCCTAGGCTTTTCCTTGTGGACAACGGGGCCCTGT

TCACCAAGCTGTTGCCATAGAGACTGTCAACGTTGTCCTCATGACAACCA

GACTTCCAGTTCTCAGGAACTTCTCATTGTGGGCCAGAAGTCCTGGGTGC

CTCCTACTAGGGCTACCCTACTGCACCCCATCAGGGGCCTGATGGCTGCC

CCTTCCCCAGACAGGGCTGGACTTCTGGAGCTGCTAAGCCACCCTCCGTT

TGCACGTTAACTCTATGCCGGATAGCAGCTGTGCACGAGACAATCTTGCA

ACACCCGGGCATGTTTGTCGTCGTCCTACAAATGAGGAAACCGAGCCTAT

GGCGTGCCCTGGTCTGTTGAGATATGCAAGCACTGAGCTCCTCTTTTGTC

CTCTGAGACCCCATCTCCATTCTCACCCAGTTCCTCTCTCCTTCCCTGAC

CCCCACCCACATTTCCCTCCTTAGAGATCCAGGAGGGATGGAATGTTCTT

TAAAATTCAACACCCACCAGGCTCTAAGCGGCGATCTGTGCTAAGAGGTC

AGGACCCAGCGGAAGTCCTCGGCGTTGACAGGCAGCTGGGGGGACATGAT

CCATGGACAAGGCCATCCCGGCCGTGGGAGACCCCAGTCCCGAAGTCTTG

CCTGCAGGAGTACTGGGGTCCCCCTGGGGCCCTCTTTACTGTCACGTCAT

CTCTAGGAAACCTATCTCTGAGTTTTGGGACCAGGTCGGTTTGGGTTTGA

ATTCTGCCTCTTCTTGCTCACTGTGTGACCAAGTGACAAACTCCTTCTGA

ACCTGTGTTCTCCCACTGTACCAGGGCTGTTCTGTGGTCCCCGTGAGTGC

CAAGCATACAGTAGGGGCTCAATAAATCCTTGT
```

Immunohistochemistry 8 uM frozen sections were cut from tissue blocks and mounted onto APES slides. The tissue was then fixed in acetone for 10 minutes before being air-dried. The slides were then soaked in 0.3% hydrogen peroxide in methanol for 10 minutes and washed in phosphate-buffered saline (PBS). Non-specific binding sites were blocked by incubating the slides in 20% serum from the appropriate animal and washing again in PBS. Primary antibody diluted in PBS containing 1% serum was then added to the slides. After incubation for 1 hour, the slides were again washed in PBS before incubating with the secondary antibody for a further 1 hour. After final washing in PBS, the secondary antibody was detected with diaminobenzidine tetrahydrochloride dissolved in Tris buffered saline (TBS), before being washed in TBS and water. The slides were then counter stained in haemotoxylin and viewed under a light microscope.

In certain embodiments, gastric tumors can be localized in situ using stains based on cancer markers of this invention. At least one marker may be forming amyloid structures that can be visualized using Congo red or equivalent, non-specific amyloid stains.

Tests for Gastric Cancer Markers in Body Fluids

In several embodiments, assays for GTM can be desirably carried out on samples obtained from blood, plasma, serum, peritoneal fluid obtained for example using peritoneal washes, or other body fluids, such as urine, lymph, cerebrospinal fluid, gastric fluid or stool samples.

In general, methods for assaying for oligonucleotides, proteins and peptides in these fluids are known in the art. Detection of oligonucleotides can be carried out using hybridization methods such as Northern blots, Southern blots or microarray methods, or qPCR. Methods for detecting proteins include such as enzyme linked immunosorbent assays (ELISA), protein chips having antibodies, suspension beads radioimmunoassay (RIA), Western blotting and lectin binding. However, for purposes of illustration, fluid levels of a GTM can be quantified using a sandwich-type enzyme-linked immunosorbent assay (ELISA). For plasma assays, a 5 uL aliquot of a properly diluted sample or serially diluted standard GTM and 75 uL of peroxidase-conjugated anti-human GTM antibody are added to wells of a microtiter plate. After a 30 minute incubation period at 30° C., the wells are washed with 0.05% Tween 20 in phosphate-buffered saline (PBS) to remove unbound antibody. Bound complexes of GTM and anti-GTM antibody are then incubated with o-phenylendiamine containing $H_2O_2$ for 15 minutes at 30° C. The reaction is stopped by adding 1 M $H_2SO_4$, and the absorbance at 492 nm is measured with a microtiter plate reader.

It can be appreciated that anti-GTM antibodies can be monoclonal antibodies or polyclonal antisera. It can also be appreciated that any other body fluid can be suitably studied.

Certain markers are known to be present in plasma or serum. These include osteopontin (Hotte et al., Cancer 95(3): 507-510 (2002)), prostate-specific antigen (Martin et al., Prostate Cancer Prostatic Dis. (Mar. 9, 2004) (Pub Med No: PMID: 15007379), thyroglobulin (Hall et al., Laryngoscope 113(1):77-81 (2003); Mazzaferri et al., J. Clin. Endocrinol. Metab. 88(4): 1433-14421 (2003), matrix metalloproteinase-2 and -9 (Kuo et al., Clin. Chem. Acta. 294(1-2): 157-168 (2000), CEA and TIMP1 (Pellegrini et al., Cancer Immunol. Immunother. 49(7): 388-394 (2000). Thus, because some of the above markers are also useful markers for GTM, plasma, serum or other fluid assays are already available for their detection and quantification. Because many proteins are either (1) secreted by cells, (2) sloughed from cell membranes, or (3) are lost from cells upon cell death, other GTM are also present in body fluids, such as plasma, serum and the like. Therefore, in embodiments of this invention, detection of GTM in conveniently obtained samples will be useful and desirable and can be a basis for diagnosis of gastric cancer.

Western Analysis

Proteins were extracted from gastric tissue using a TriReagent and guanidine HCl extraction method. The non-aqueous phase from the TriReagent extraction of RNA was mixed with 1.5 vols of ethanol and centrifuged to remove DNA and OCT medium. 0.5 mls of supernatant was mixed with 0.75 ml isopropanol, incubated at room temperature for 10 minutes, and then centrifuged. The pellet was washed three times in 1 ml 0.3M guanidine HCl in 95% ethanol and once in ethanol alone, then resuspended in 50 ul 1% SDS.

Proteins were quantified and electrophoresed on SDS polyacrylamide gels using standard methods. Briefly, the separated proteins were transferred to PVDF membrane using the BioRad trans-blot electrophoretic transfer cell using standard methodology. The membranes were then blocked with a solution containing non-fat milk powder for 30 minutes before being incubated with primary antibody for 2 hours at room temperature. After washing, the membrane was incubated with secondary antibody for 1 hour at room temperature. After final washes, bound antibody was visualized using the ECL detection system (Amersham Biosciences).

Detection of markers in the serum can be accomplished by providing a sample of serum using known methods and then subjecting the serum sample to analysis, either using oligonucleotide probes or antibodies directed against the protein of interest. Immunoblotting, including Western blotting analysis can be especially useful to determine whether alternatively expressed proteins are present in the serum. Additionally, other body fluids may contain markers, and include peritoneal fluid, cerebrospinal fluid and the like. It is not necessary for a marker to be secreted, in a physiological sense, to be useful. Rather, any mechanism by which a marker protein or gene enters the serum can be effective in producing a detectable, quantifiable level of the marker. Thus, normal secretion of soluble proteins from cells, sloughing of membrane proteins from plasma membranes, secretion of alternatively spliced forms of mRNA or proteins expressed therefrom, cell death (either apoptotic) can produce sufficient levels of the marker to be useful. There is increasing support for the use of serum markers as tools to diagnose and/or evaluate efficacy of therapy for a variety of cancer types.

Yoshikawa et al., (Cancer Letters, 151: 81-86 (2000) describes tissue inhibitor of matrix metalloproteinase-1 in plasma of patients with gastric cancer.

Rudland et al., (Cancer Research 62: 3417-3427 (2002) describes osteopontin as a metastasis associated protein in human breast cancer.

Buckhaults et al., (Cancer Research 61:6996-7001 (2002) describes certain secreted and cell surface genes expressed in colorectal tumors.

Kim et al., (JAMA 287(13):1671-1679 (2002) describes osteopontin as a potential diagnostic biomarker for ovarian cancer.

Hotte et al., (A. J. American Cancer Society 95(3):507-512 (2002) describes plasma osteopontin as a protein detectable in human body fluids and is associated with certain malignancies.

Martin et al., (Prostate Cancer Prostatic Dis. Mar. 9, 2004 (PMID: 15007379) (Abstract) described use of human kallikrein 2, prostate-specific antigen (PSA) and free PSA as markers for detection of prostate cancer.

Hall et al (Laryngoscope 113(1):77-81 (2003) (PMID: 12679418) (Abstract) described predictive value of serum thyroglobulin in thyroid cancer.

Mazzaferri et al., (J. Clin. Endocrinol. Metab. 88(4):1433-1441 (2003) (Abstract) describes thyroglobulin as a potential monitoring method for patients with thyroid carcinoma.

Whitley et al, (Clin. Lab. Med. 24(1):2947 (2004) (Abstract) describes thyroglobulin as a serum marker for thyroid carcinoma.

Kuo et al (Clin. Chim. Acta. 294(1-2):157-168 (2000) (Abstract) describes serum matrix metalloproteinase-2 and -9 in HCF- and HBV-infected patients.

Koopman et al., (Cancer Epidemiol. Biomarkers Prev 13(3):487-491 (2004) (Abstract) describes osteopontin as a biomarker for pancreatic adenocarcinoma.

Pellegrini et al., (Cancer Immunol. Immunother. 49(7): 388-394 (2000) (Abstract) describes measurement of soluble carcinoembryonic antigen and TIMP1 as markers for pre-invasive colorectal cancer.

Thus, we have identified numerous genes and/or proteins that are useful for developing reagents, devices and kits for detecting and evaluating gastric cancer. One or more markers of gastric can be used, either singly or in combination to provide a reliable molecular test for gastric cancer.

EXAMPLES

The examples described herein are for purposes of illustrating embodiments of the invention. Other embodiments, methods and types of analyses are within the scope of persons of ordinary skill in the molecular diagnostic arts and need not be described in detail hereon. Other embodiments within the scope of the art are considered to be part of this invention.

Example 1: Identification of Markers for Gastric Malignancy

FIG. 2 depicts a table that shows results of studies using 38 markers for gastric malignancy selected using the above criteria. The FIG. 2 includes the symbol for the gene ("symbol"), the MWG oligo number, the NCBI mRNA reference sequence number, the protein reference sequence number, the fold change between tumor and non-tumor gene expression, the fold change rank relative to other genes in the microarray analysis, the results of an original, unadjusted Student's t-test, the results of the Bonferroni-adjusted p value and the results of the 2-sample Wilcoxon test.

The median fold change (tumor: non malignant tissue) for these 34 genes ranged from 1.6 to 7 and the median change in fold change rank ranged from −16,995 to −25,783. The maximum possible change in fold change rank was −29,718. For each of the markers shown, the statistical significance of their specificity as cancer markers was found to be extremely high. The Bonferroni-adjusted p values were, in general, all below $10^{-6}$ or less, indicating that diagnosis using these markers is very highly associated with gastric cancer.

The three cystatins (CST1, CST2, and CST4) are highly homologous and represented by the same oligonucleotide on the microarray and unless otherwise stated, are referred to collectively as "CST1,2,4."

All proteins depicted in FIG. 2 were predicted to have signal peptides using the SMART package (European Molecular Biology Laboratory). The signal peptides are known to target synthesized proteins to the extracellular compartment and can therefore be secreted into the interstitial fluid, from which they can have access to the blood. In fact, some proteins of this invention have been detected in serum.

Each of the genes depicted in FIG. 2 exhibited a change in intensity rank greater than the two oligonucleotides on the array corresponding to CEA, the marker most frequently used in clinical practice to monitor gastric cancer progression.

Example 2: qPCR Analysis

More sensitive and accurate quantitation of gene expression was obtained for a subset of the genes shown in FIG. 3 using qPCR. RNA from 46 tumor and 49 non-malignant samples was analyzed for 23 genes identified by the microarray analysis (FIG. 2) and results are shown in FIG. 3. FIG. 3 includes the gene symbol, median fold change between cancer and normal tissue, and the % of tumor samples with expression levels greater than the $95^{th}$ percentile of expression levels in non-malignant samples. 12 tumor samples and 9 normal samples were excluded from the analysis because of high (>75%) normal cell contamination, a high degree of necrosis (>40%), or poor hybridization signal on the microarrays. The median fold change (tumor tissues compared to the median non-malignant tissue expression) for these 23 genes ranged from 3 to 525 fold FIG. 3).

The level of expression of genes ASPN, CST1,2,4, LOXL2, TIMP1, SPP1, SFRP4, INHBA, THBS2 and SPARC was greater in tumors than the $95^{th}$ percentile of the non-malignant range for ≥90% of cases (FIG. 3). For the remainder of genes, the expression in tumors was greater than the 95$^{th}$ percentile in >50% of samples. Each tumor over-expressed at least seven genes greater than the 95$^{th}$ percentile indicating that combinations of markers will lead to comprehensive coverage of all gastric tumors.

Example 3: Validation of Array Data Using qPCR

Array data was validated using quantitative, real-time PCR (qPCR) on the tumor and non-malignant samples with probes for 24 genes. Of all 24 genes studied, 20 showed a strong correlation between the two techniques. Four of these analyses are show in FIGS. 4a-4d, which depict graphs of the relative expression for the 4 selected cancer markers detected using array and qPCR methods. For each graph in FIG. 4, the horizontal axis represents the array log 2 fold change in gene expression, and the vertical axis represents the qPCR log 2 fold change in gene expression. We found that there was a strong correlation between the two methods, as indicated by the co-variant relationship between the methods. The strong correlation indicates that both microarray fold change analysis and qPCR are suitable methods for detecting changes in the expression of gastric cancer marker genes and therefore can be used as an accurate, sensitive screening method. It can also be appreciated from FIGS. 4a-4d that qPCR can be more sensitive at detecting changes in expression than are array methods. Thus, in situations in which early detection is especially desirable, qPCR may be especially useful.

Figure 5A:
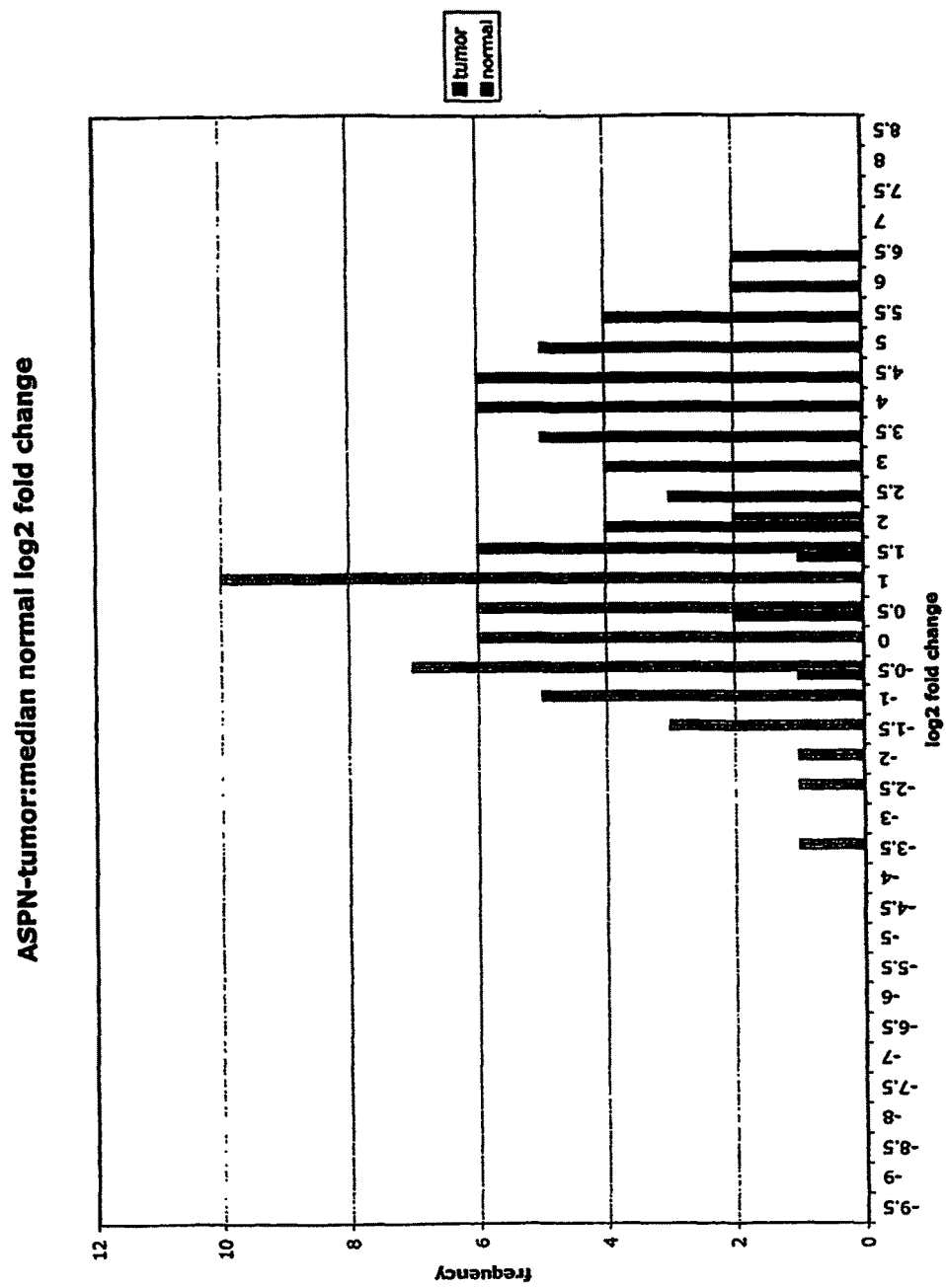
FIGS. 5a-5w depict histograms showing the relative frequency vs. log 2 fold change data obtained from quantitative PCR studies of various tumor markers.
Figure 5B:
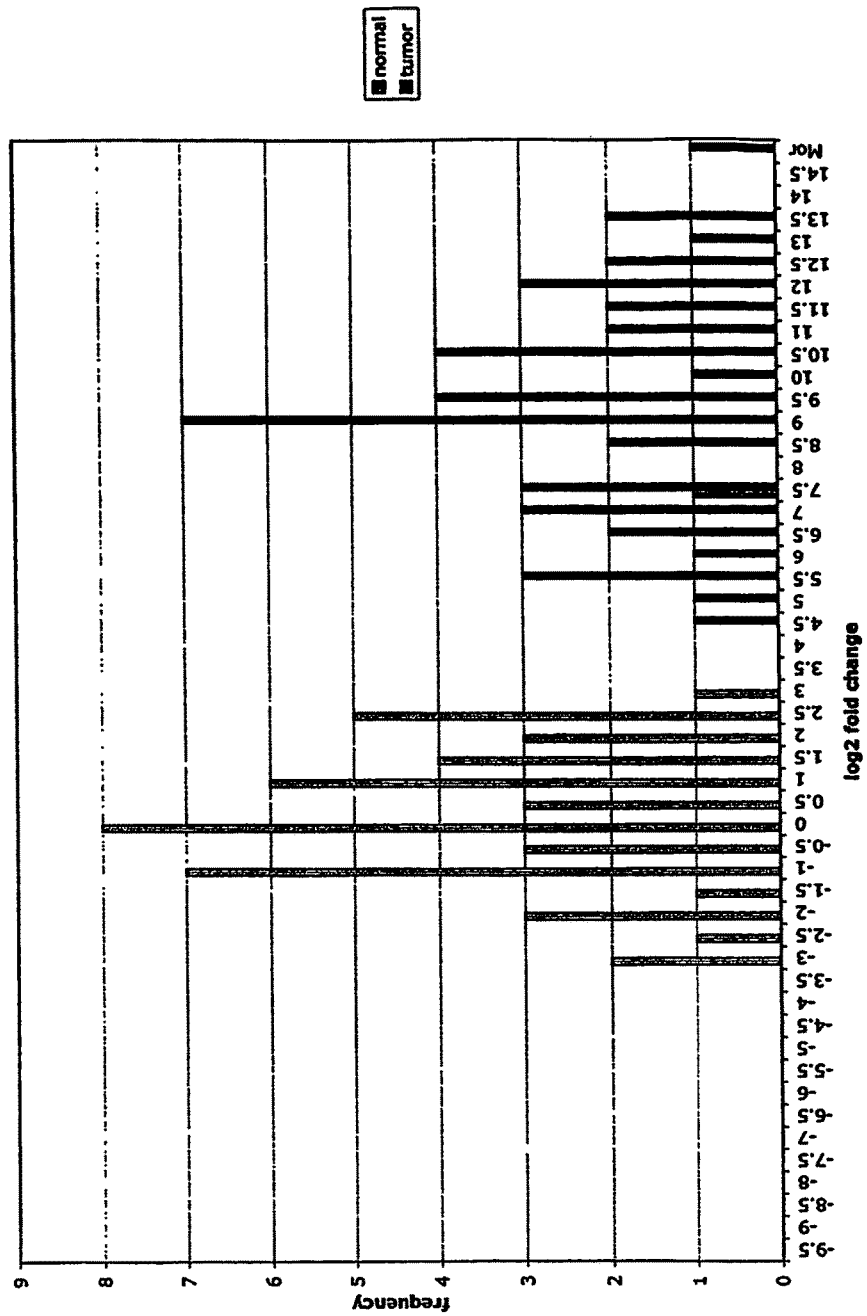
FIG. 5b: CST1, 2 & 4.
Figure 5C:
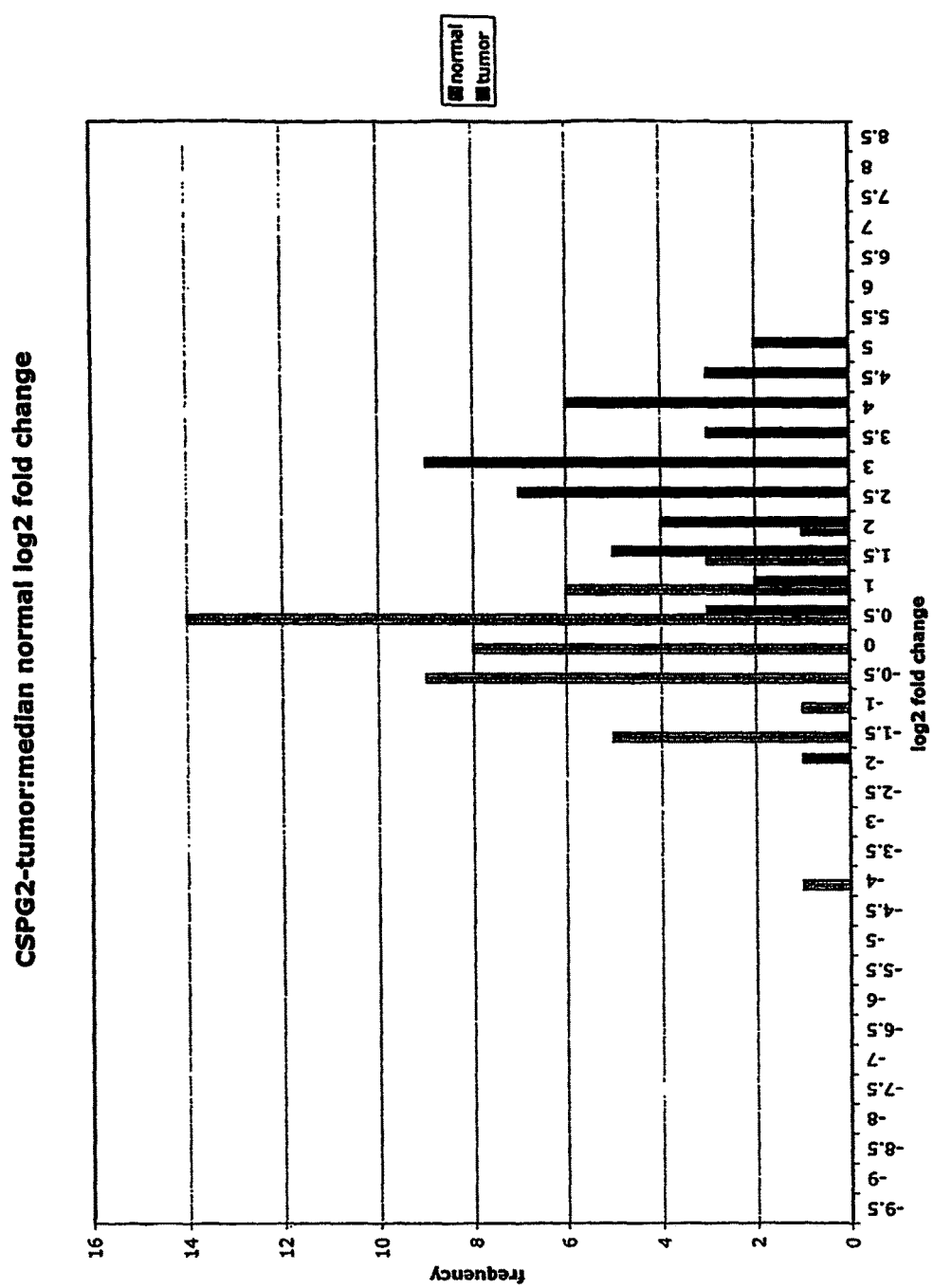
FIG. 5c: CSPG2.
Figure 5D:
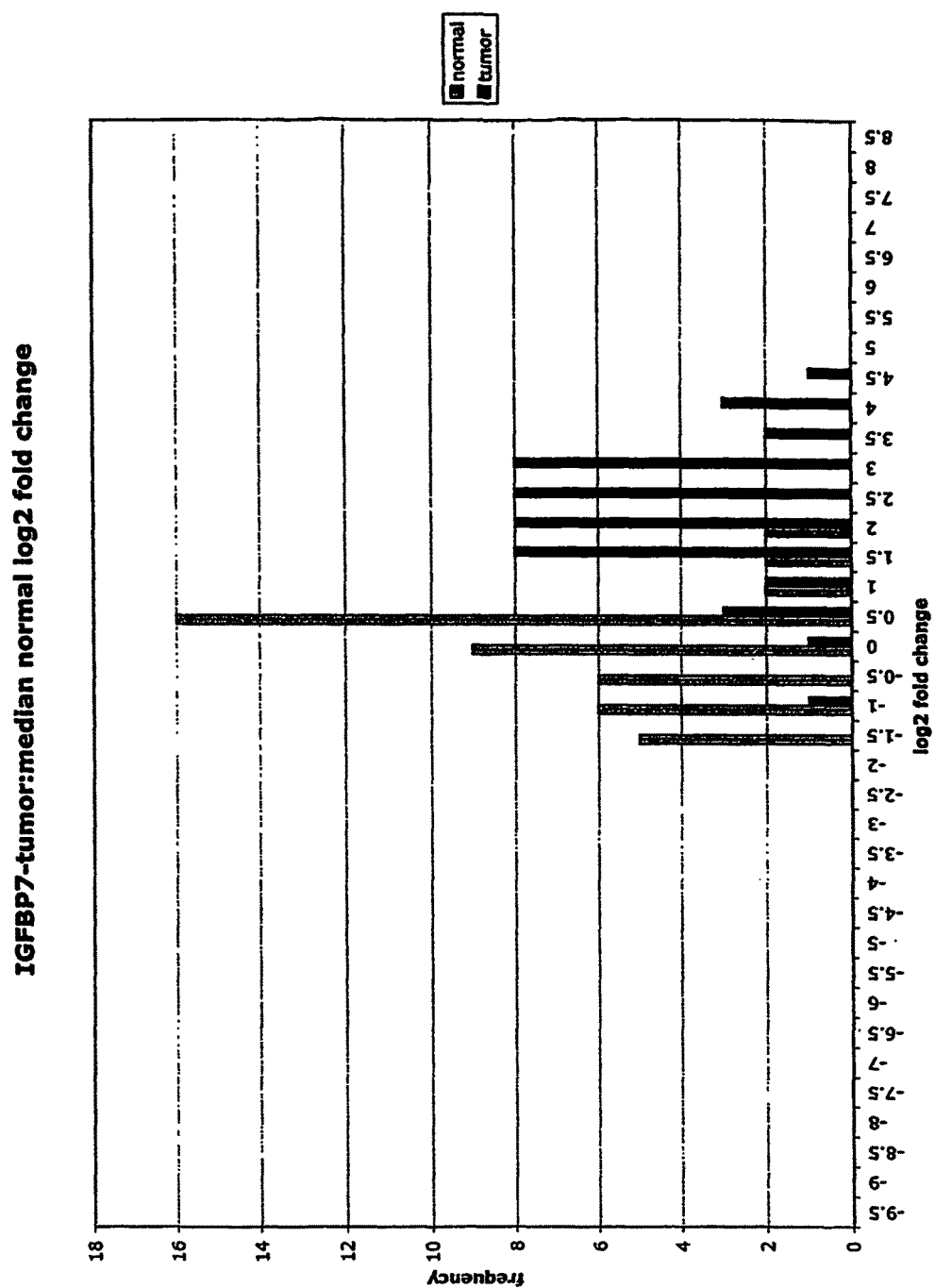
FIG. 5d: IGFBP7.
Figure 5E:
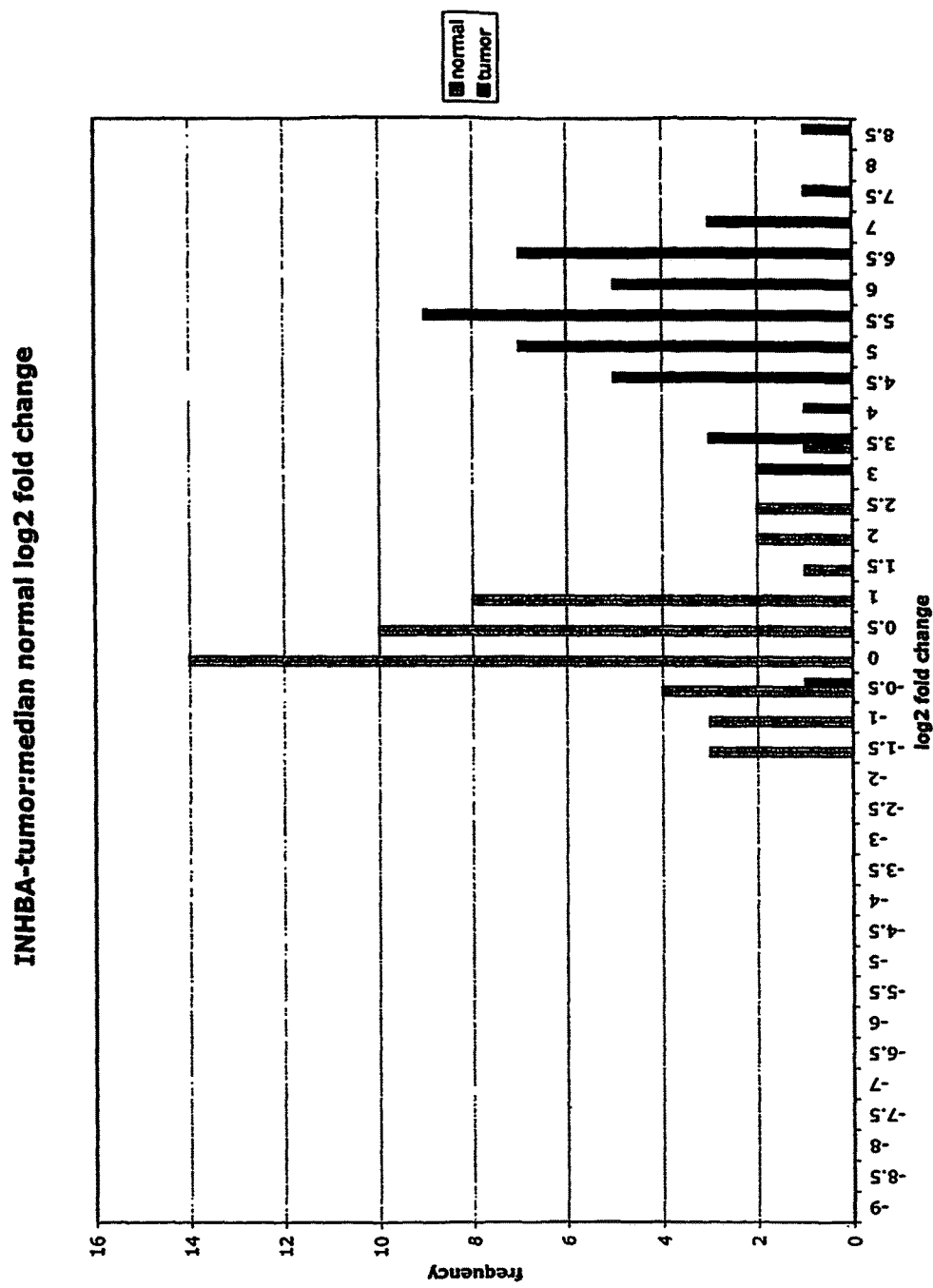
FIG. 5e: INHBA.
Figure 5F:
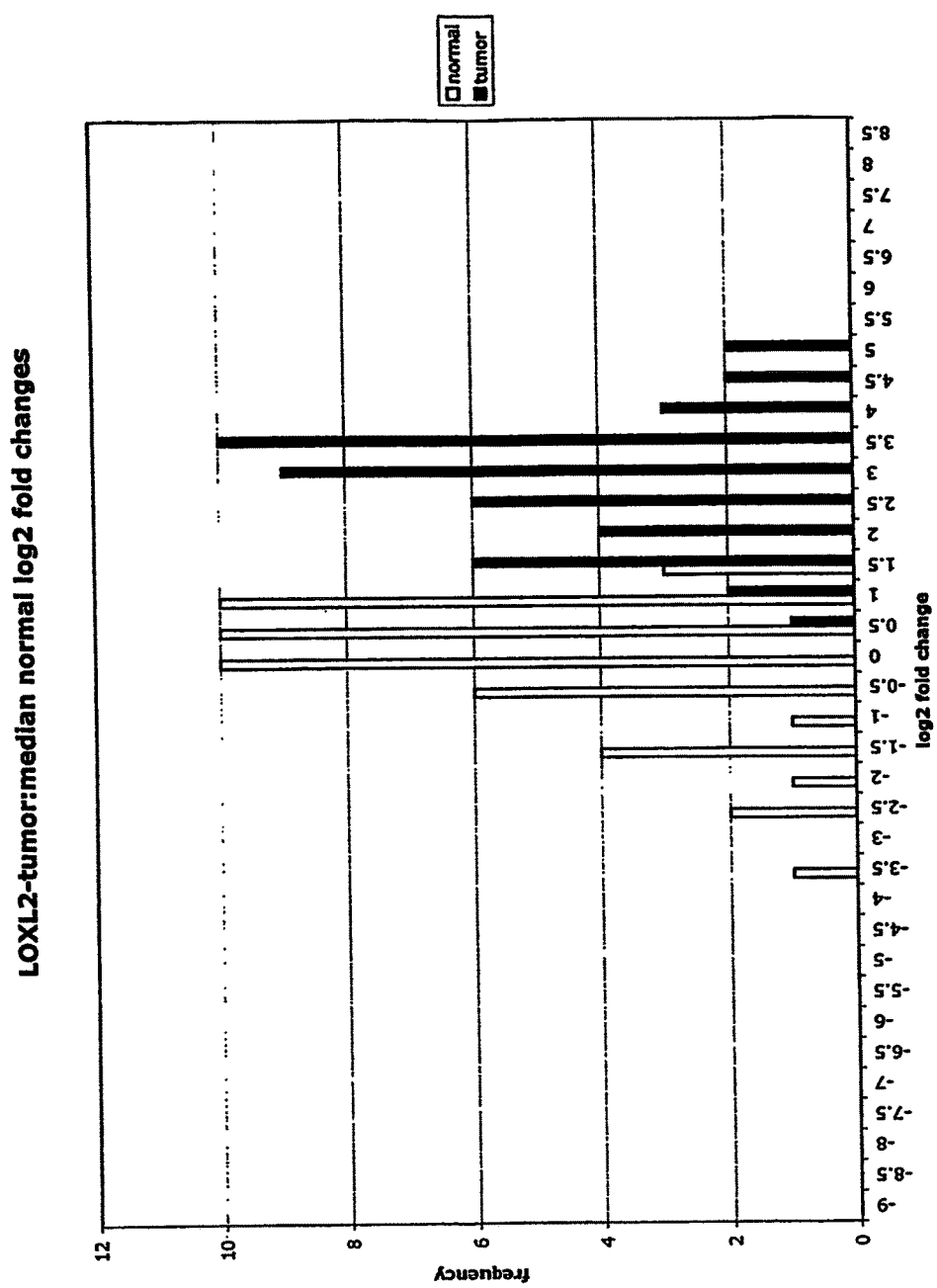
FIG. 5f: LOXL2.
Figure 5G:
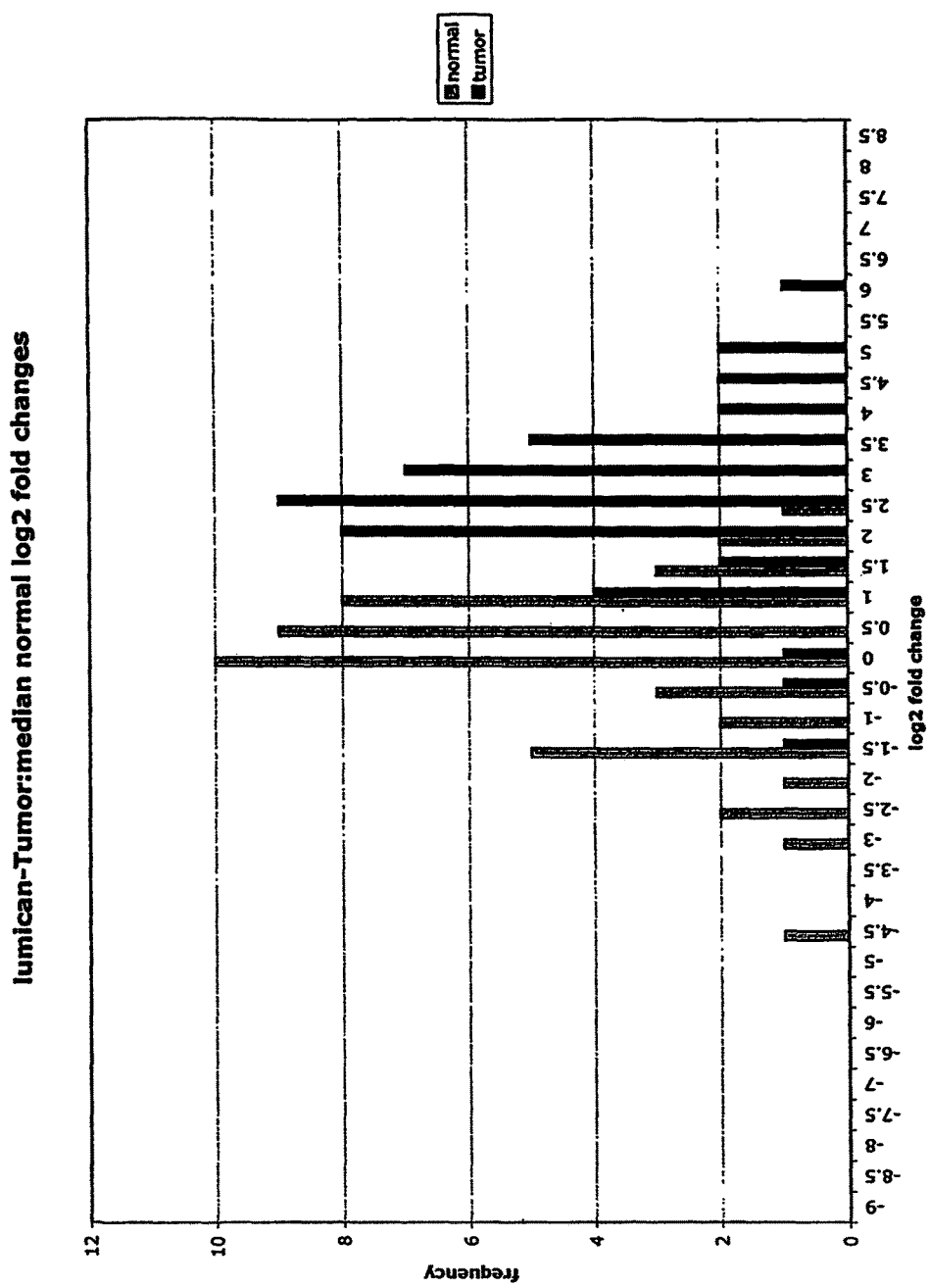
FIG. 5g: LUM.
Figure 5H:
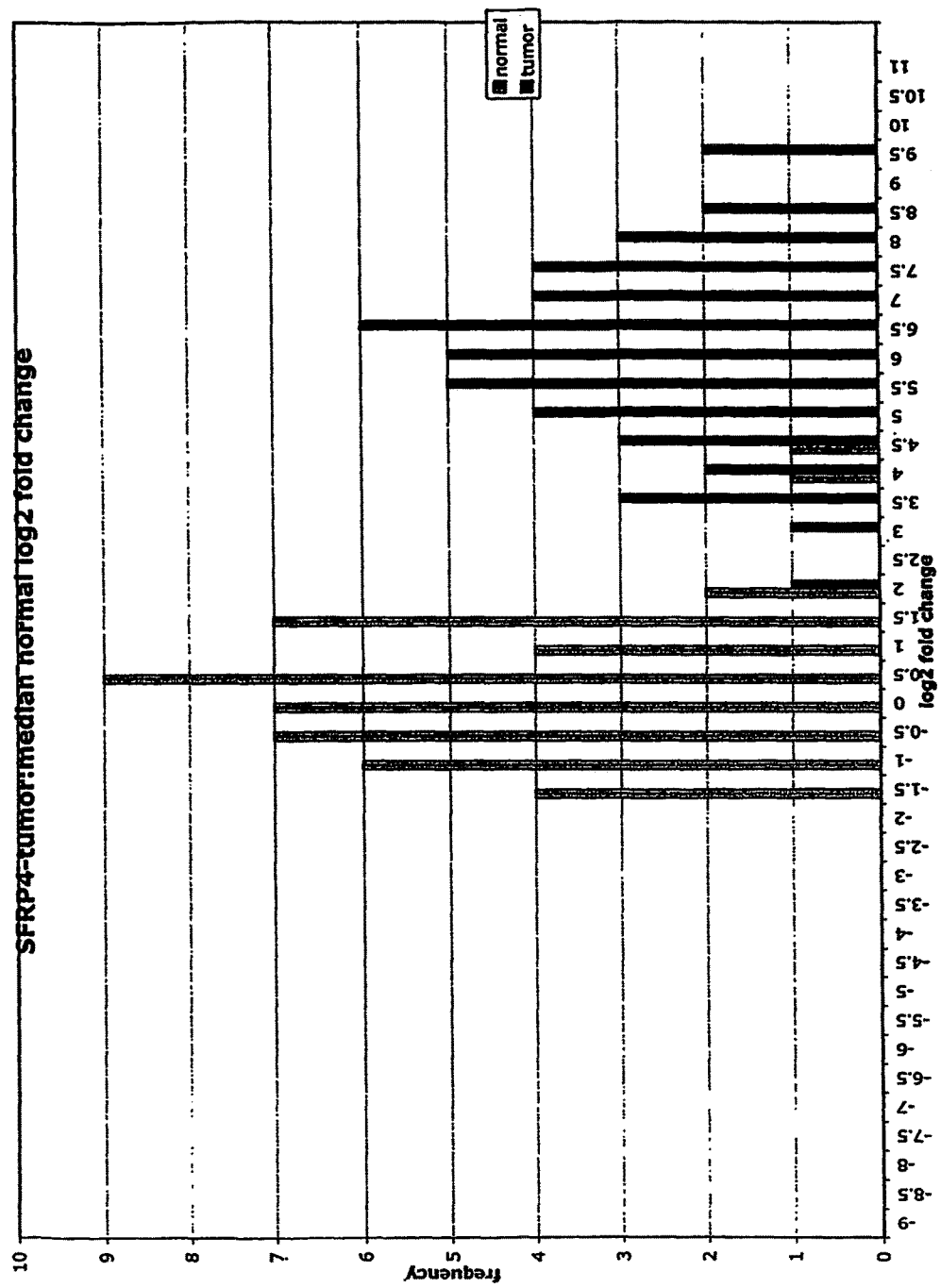
FIG. 5h: SFRP4.
Figure 5I:
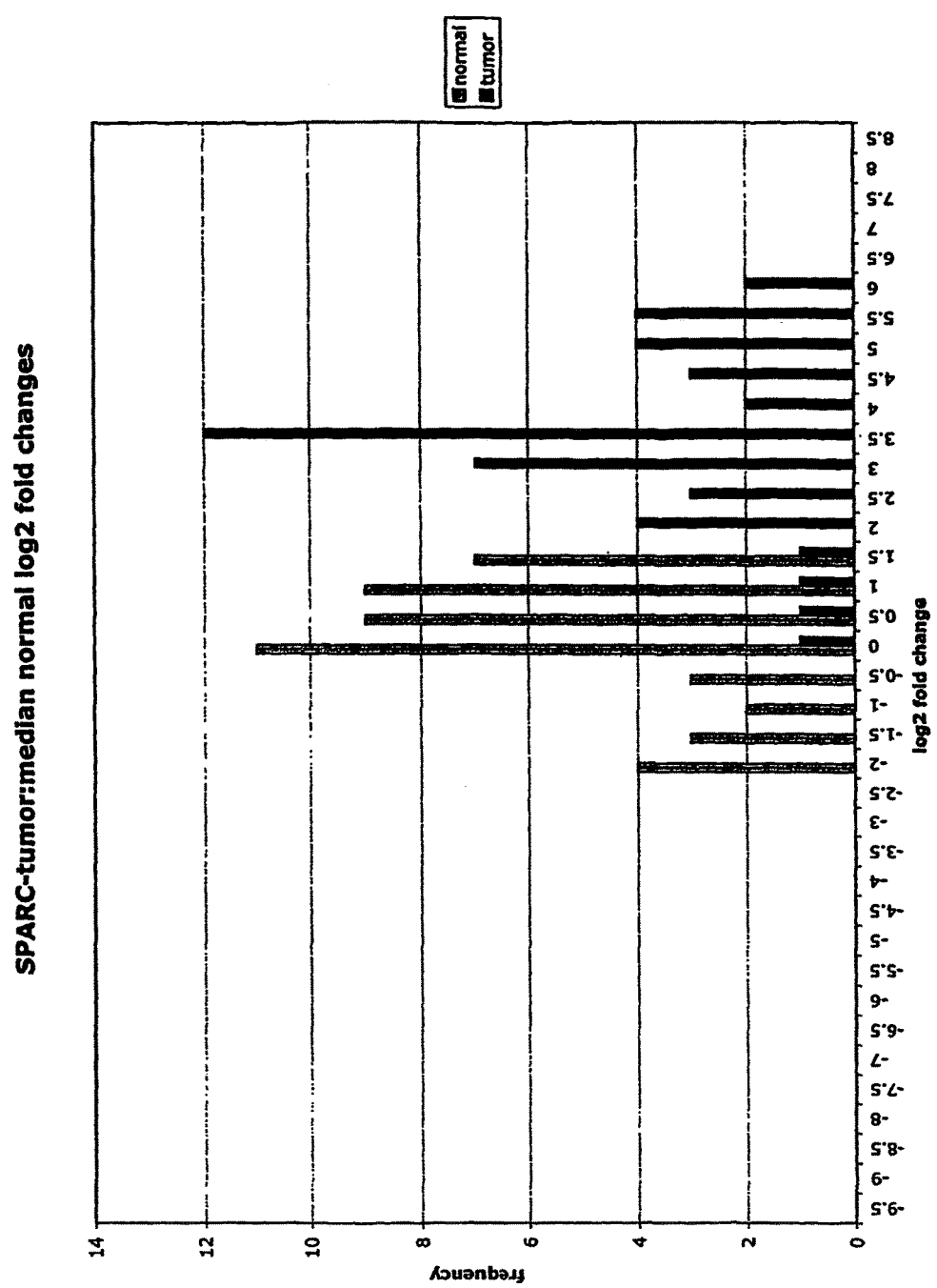
FIG. 5i: SPARC.
Figure 5J:
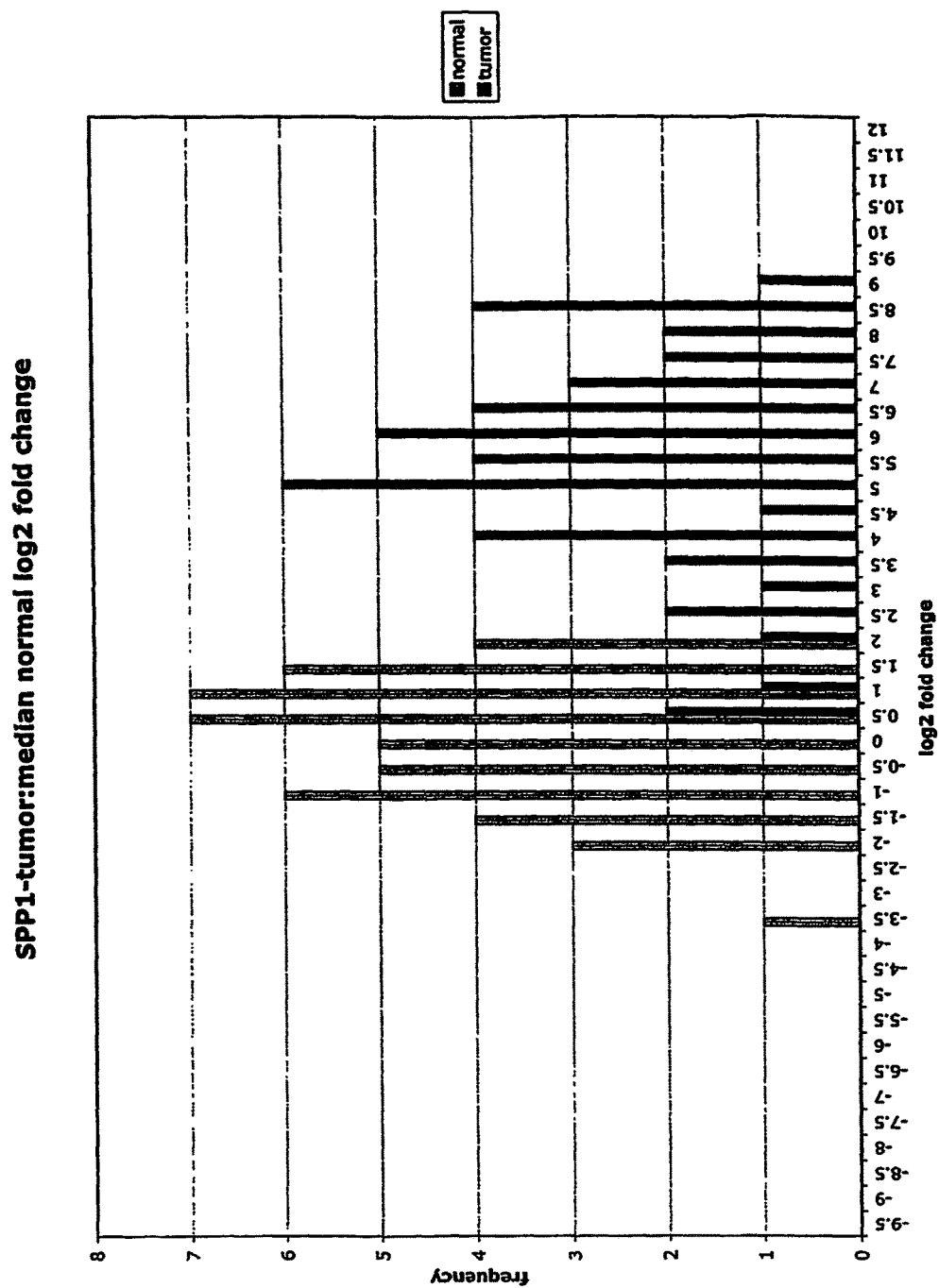
FIG. 5j: SPP1.
Figure 5K:
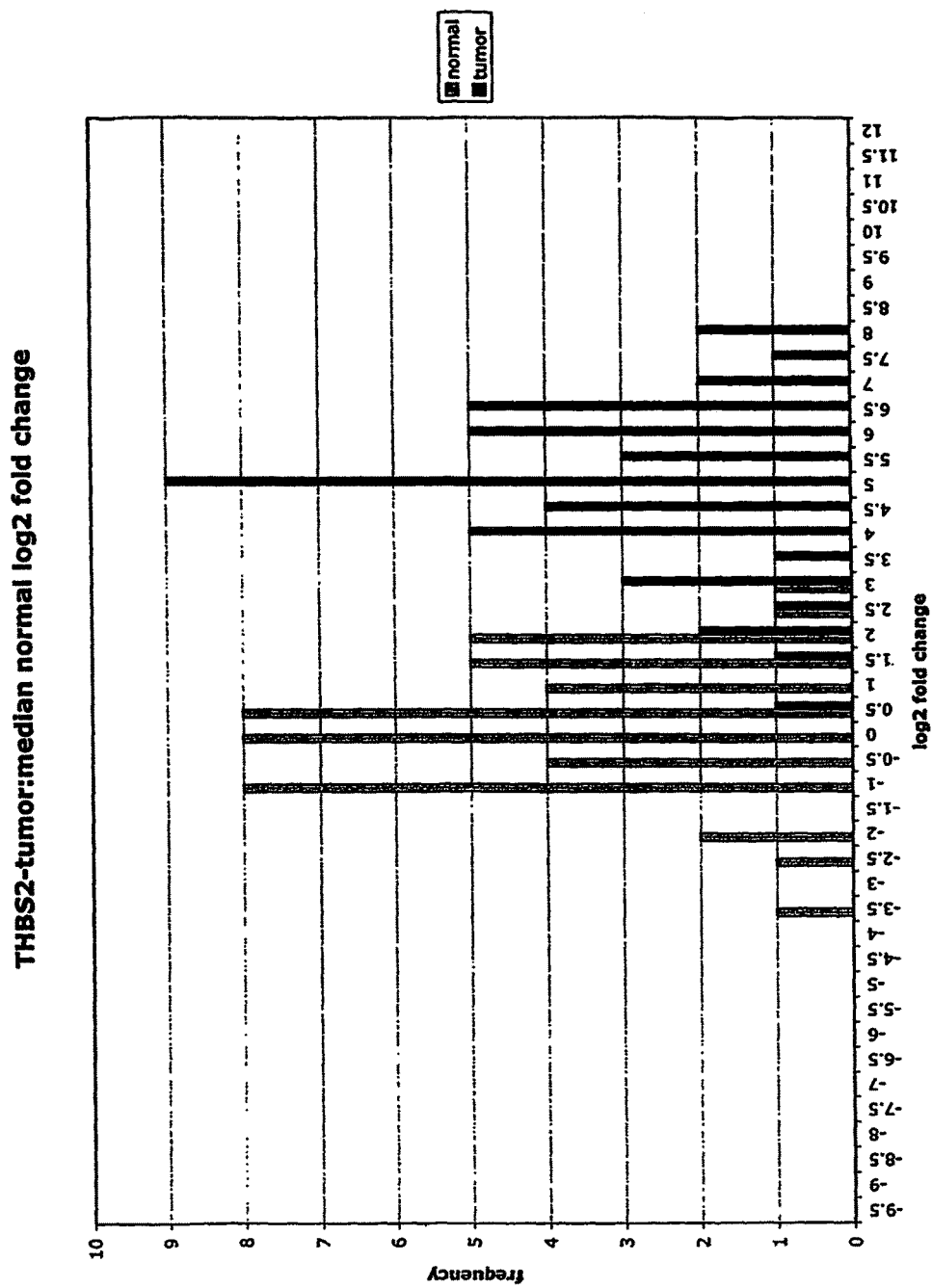
FIG. 5k: THBS2.
Figure 5L:
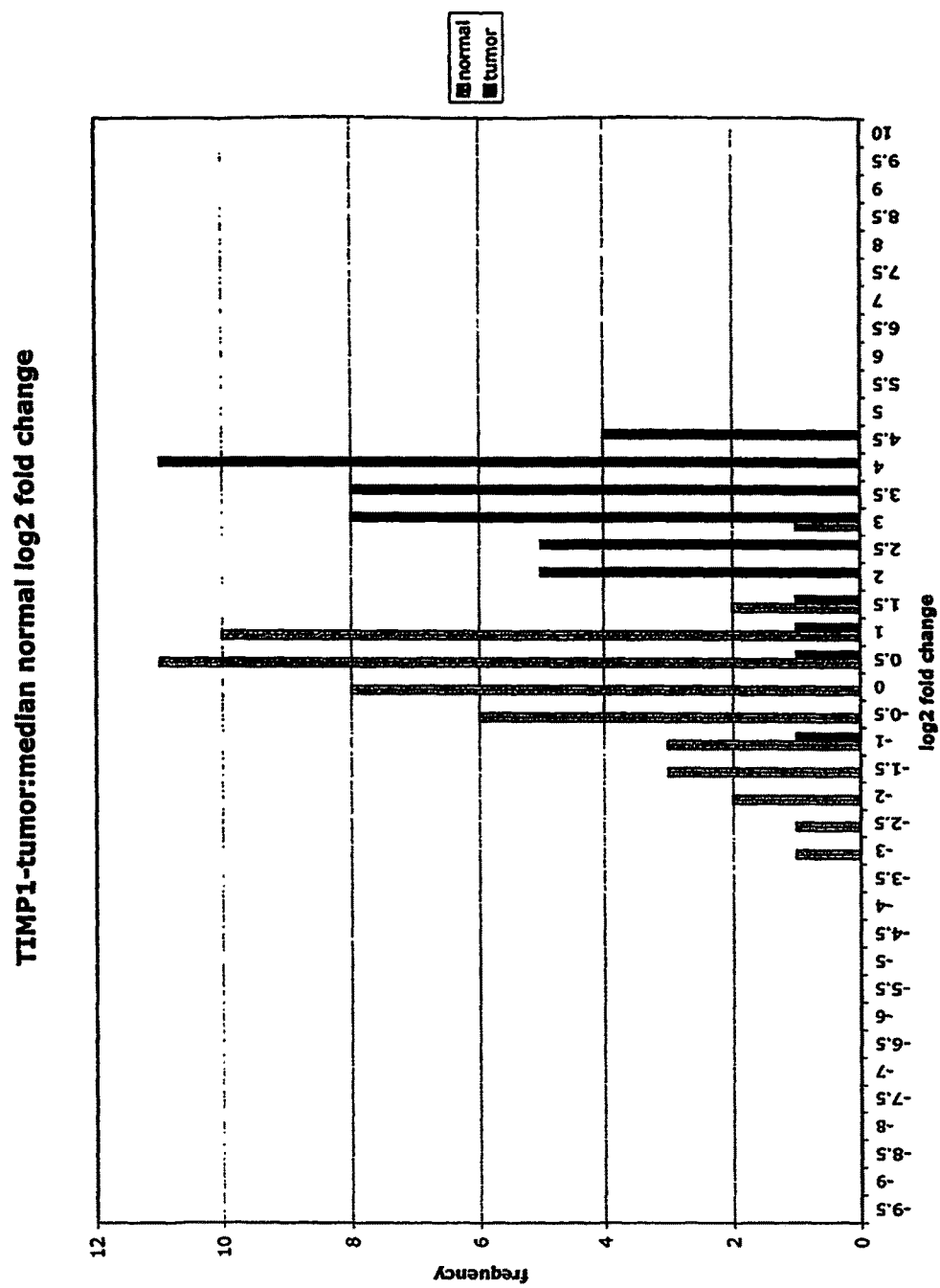
FIG. 5l: TIMP1.
Figure 5M:
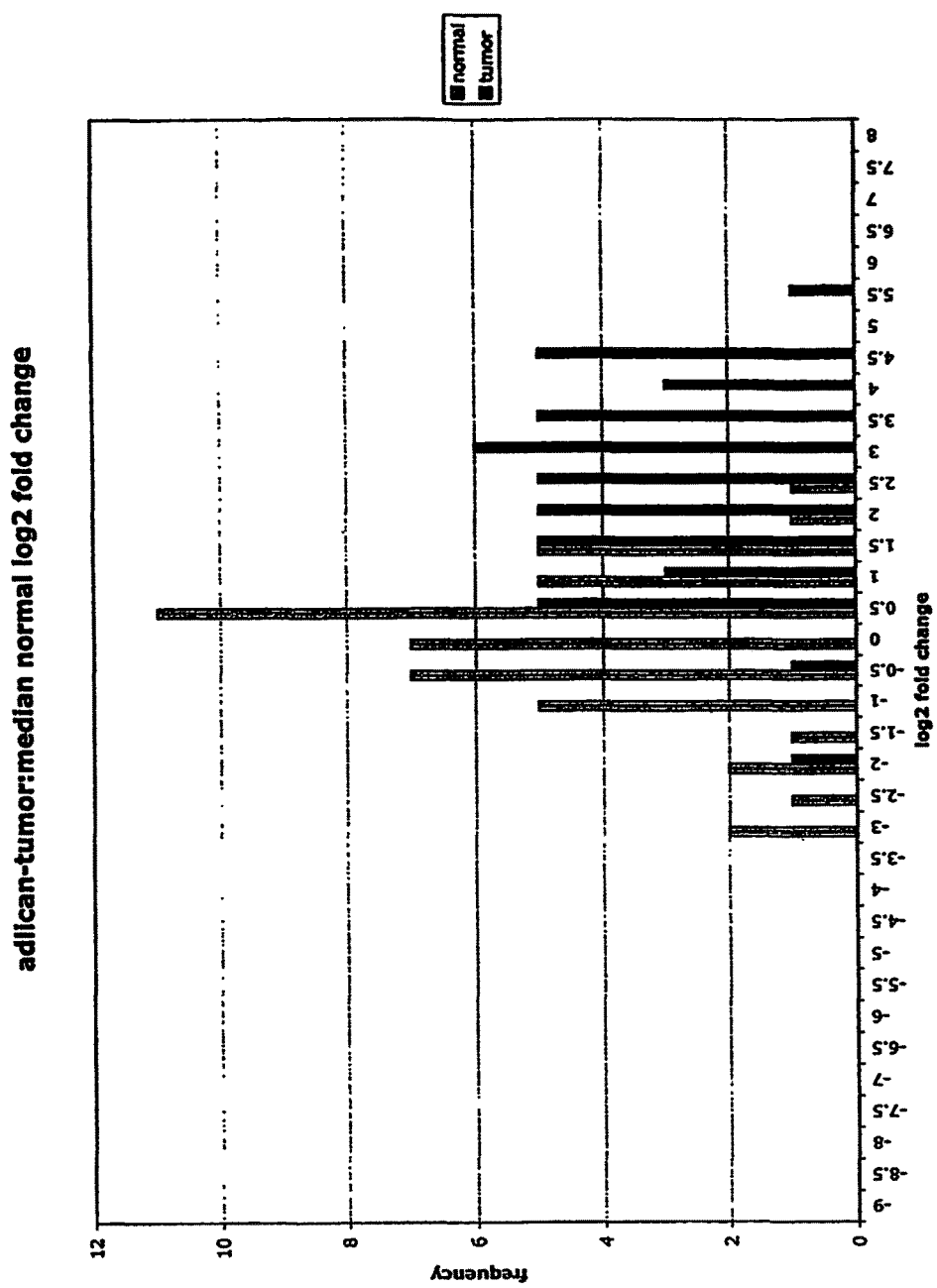
FIG. 5m: adlican.
Figure 5N:
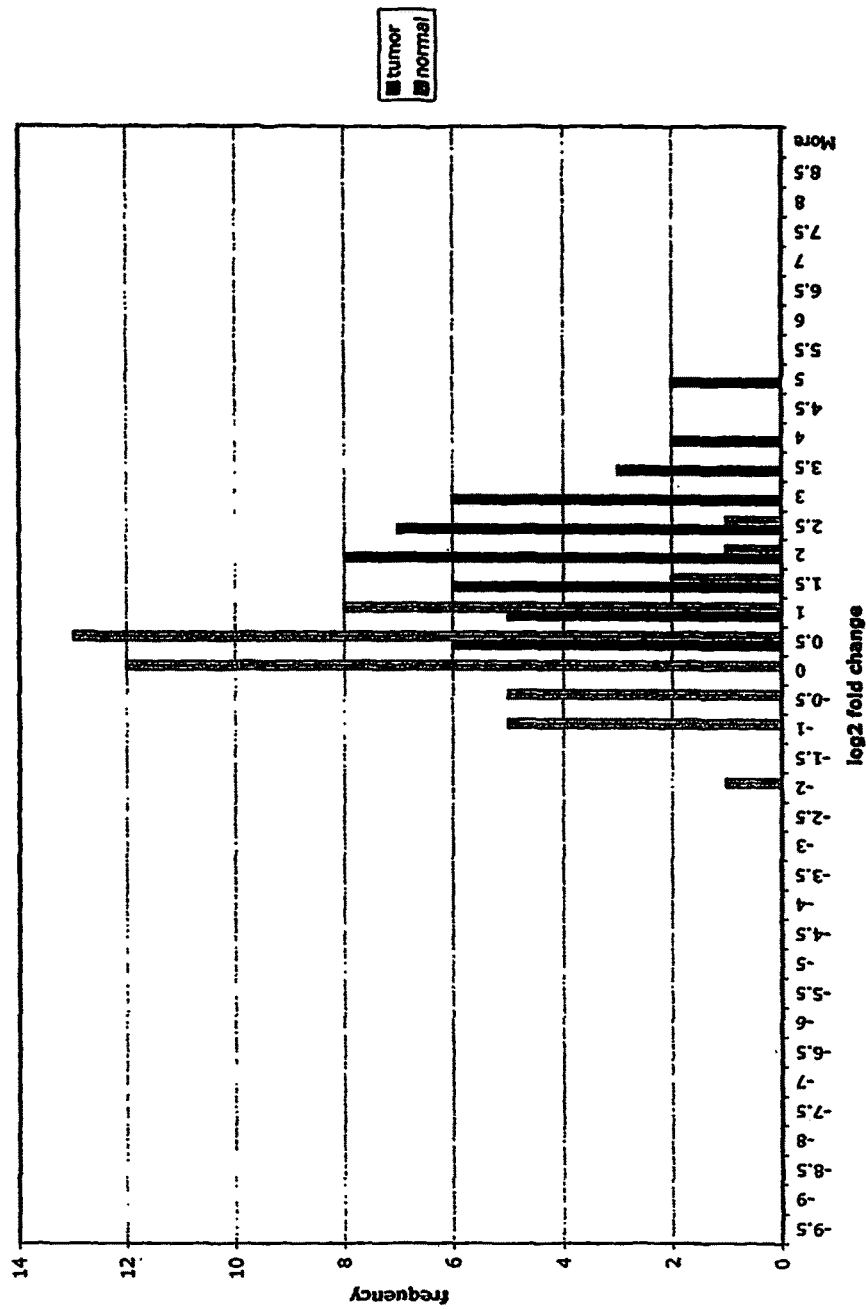
FIG. 5n: PRS11.
Figure 5O:
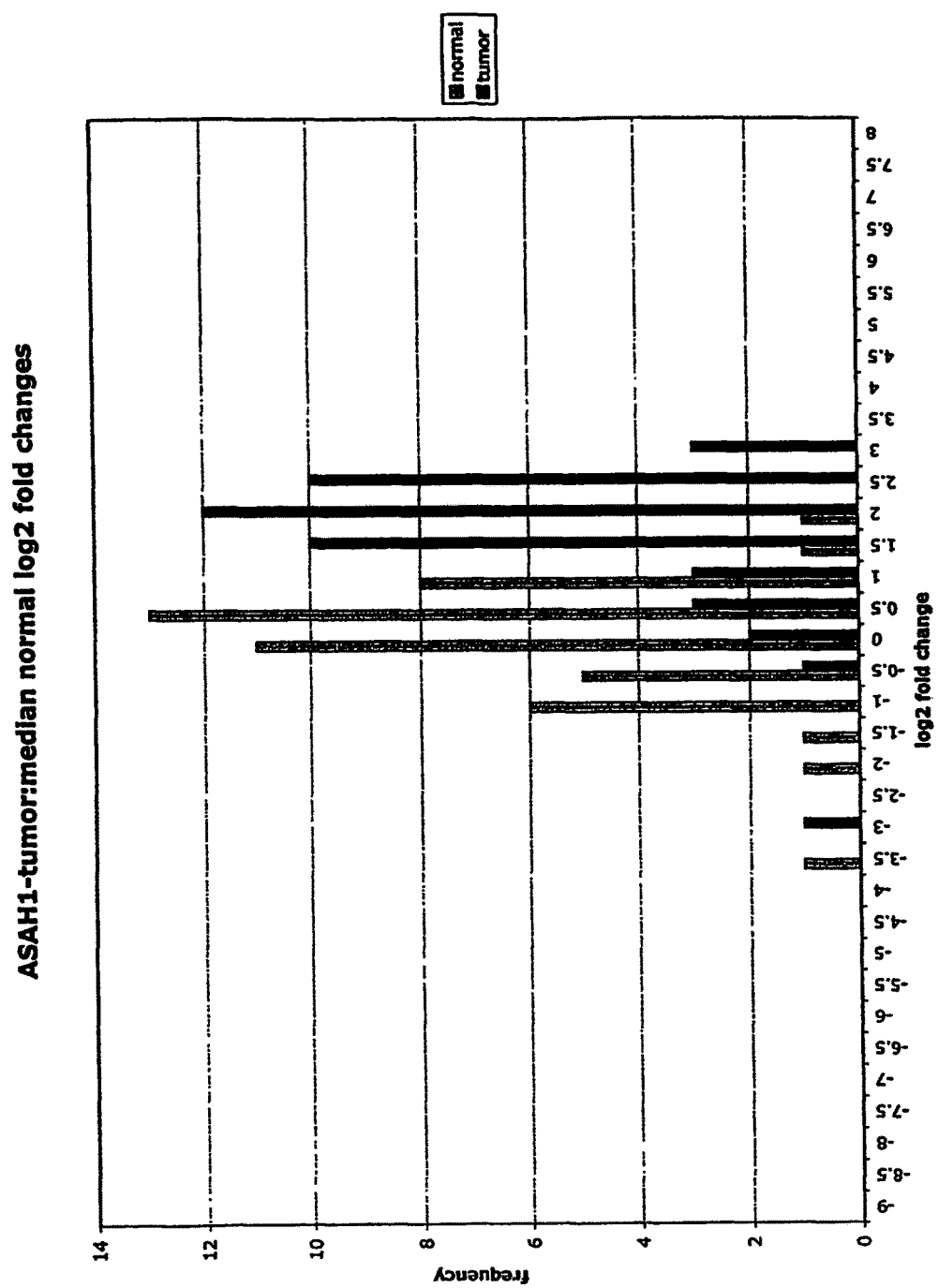
FIG. 5o: ASAH1.
Figure 5P:
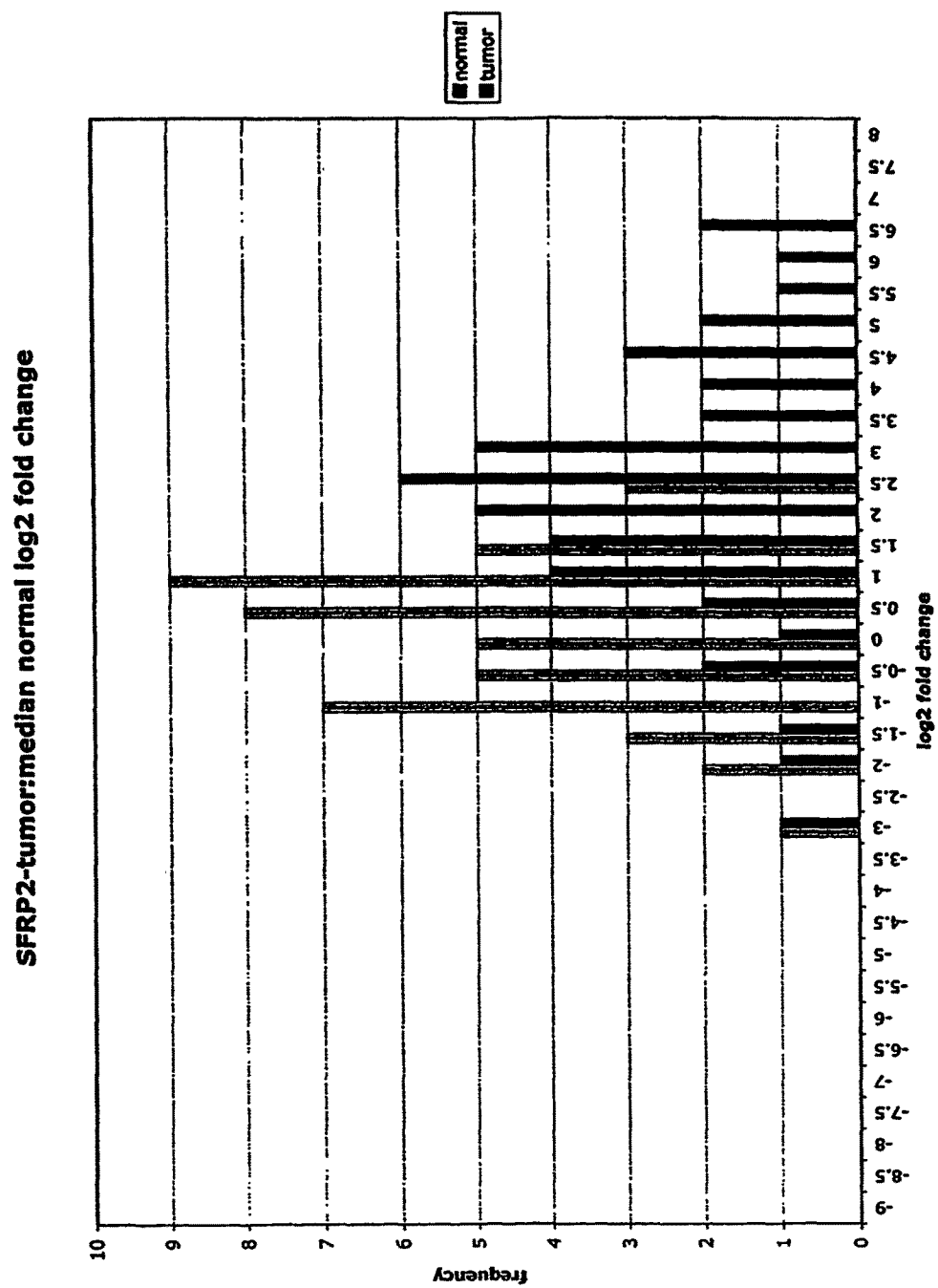
FIG. 5p: SFRP2.
Figure 5Q:
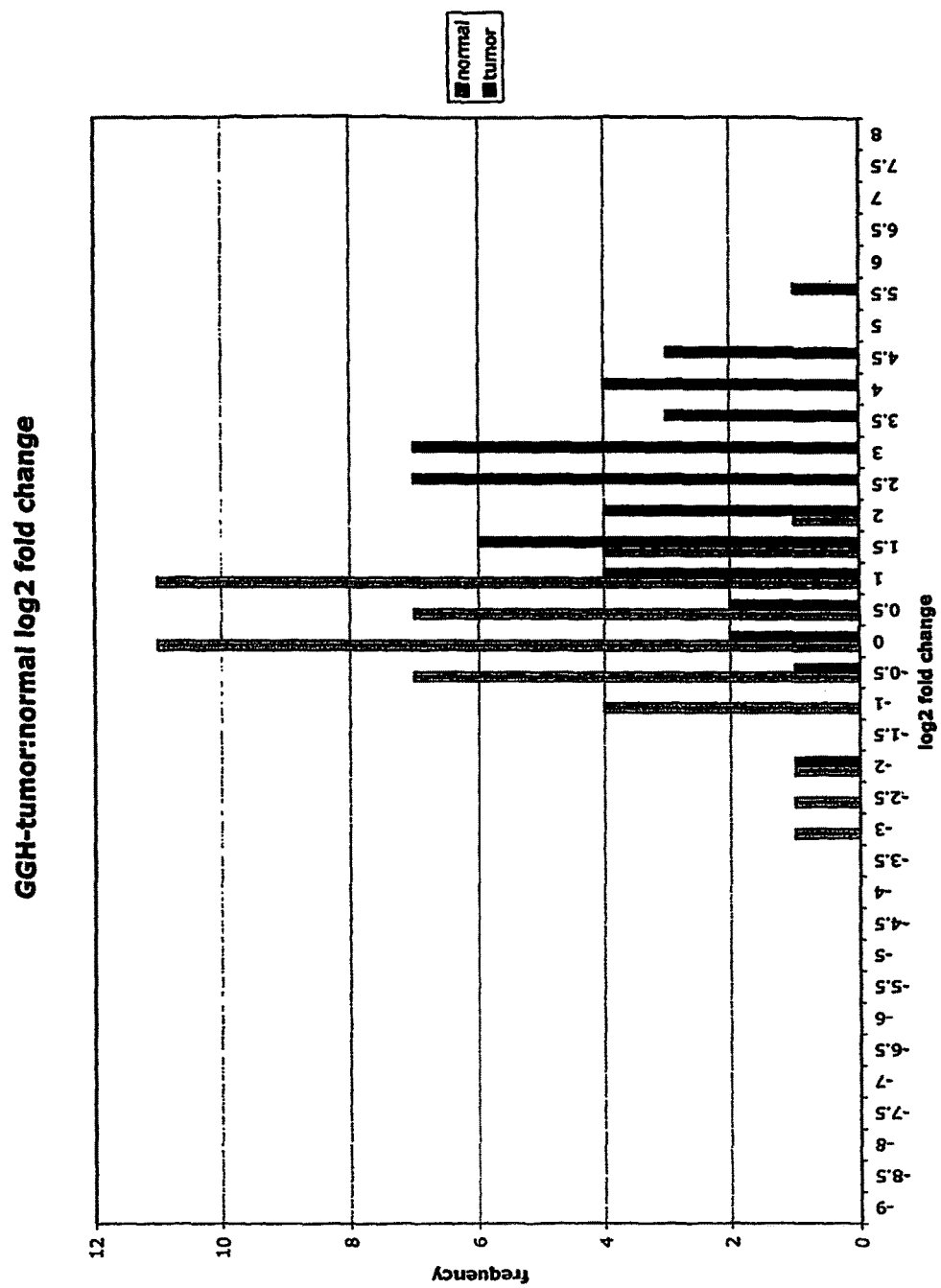
FIG. 5q: GGH.
Figure 5R:
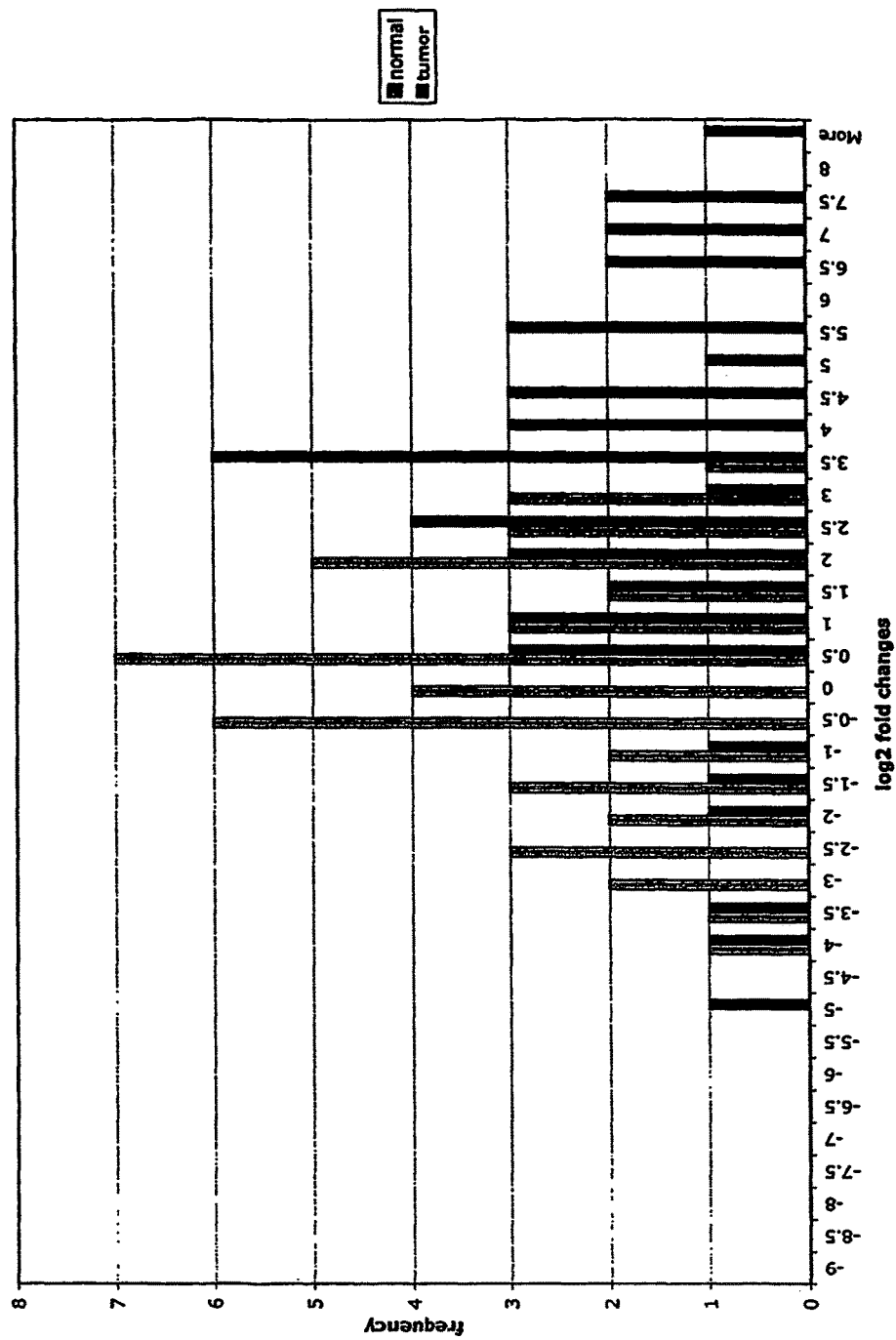
FIG. 5r: MMP12.
Figure 5S:
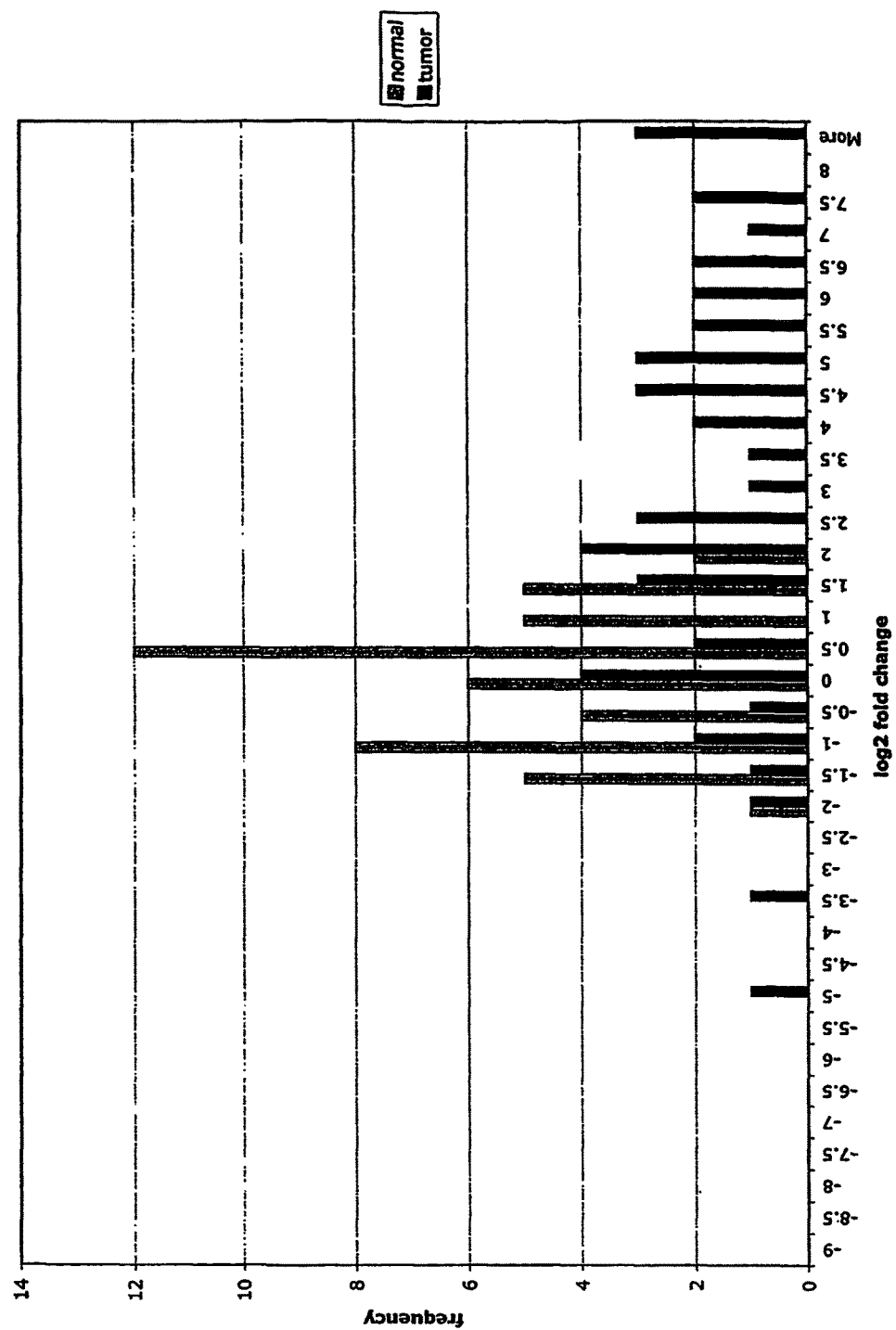
FIG. 5s: KLK10.
Figure 5T:
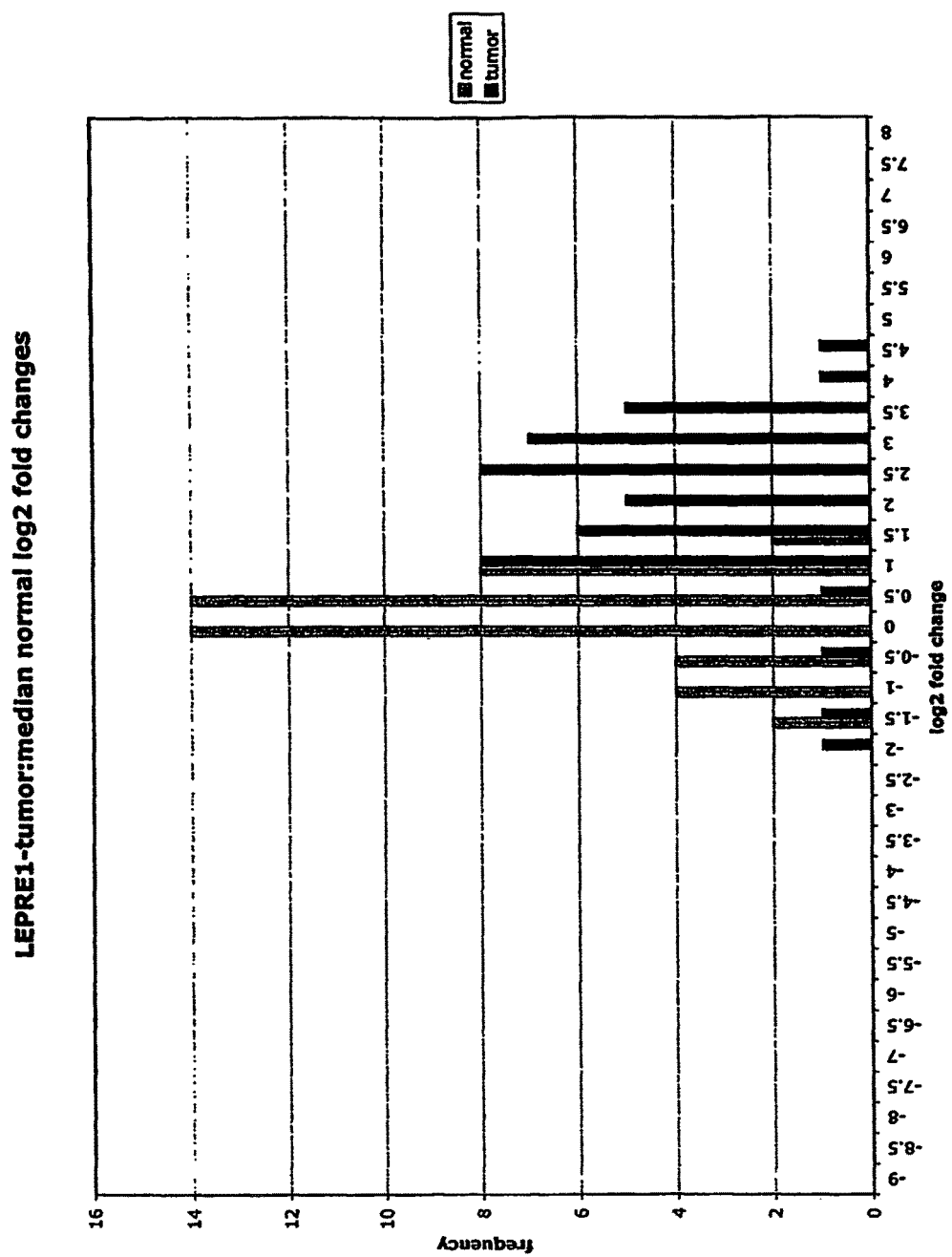
FIG. 5t: LEPRE1.
Figure 5U:
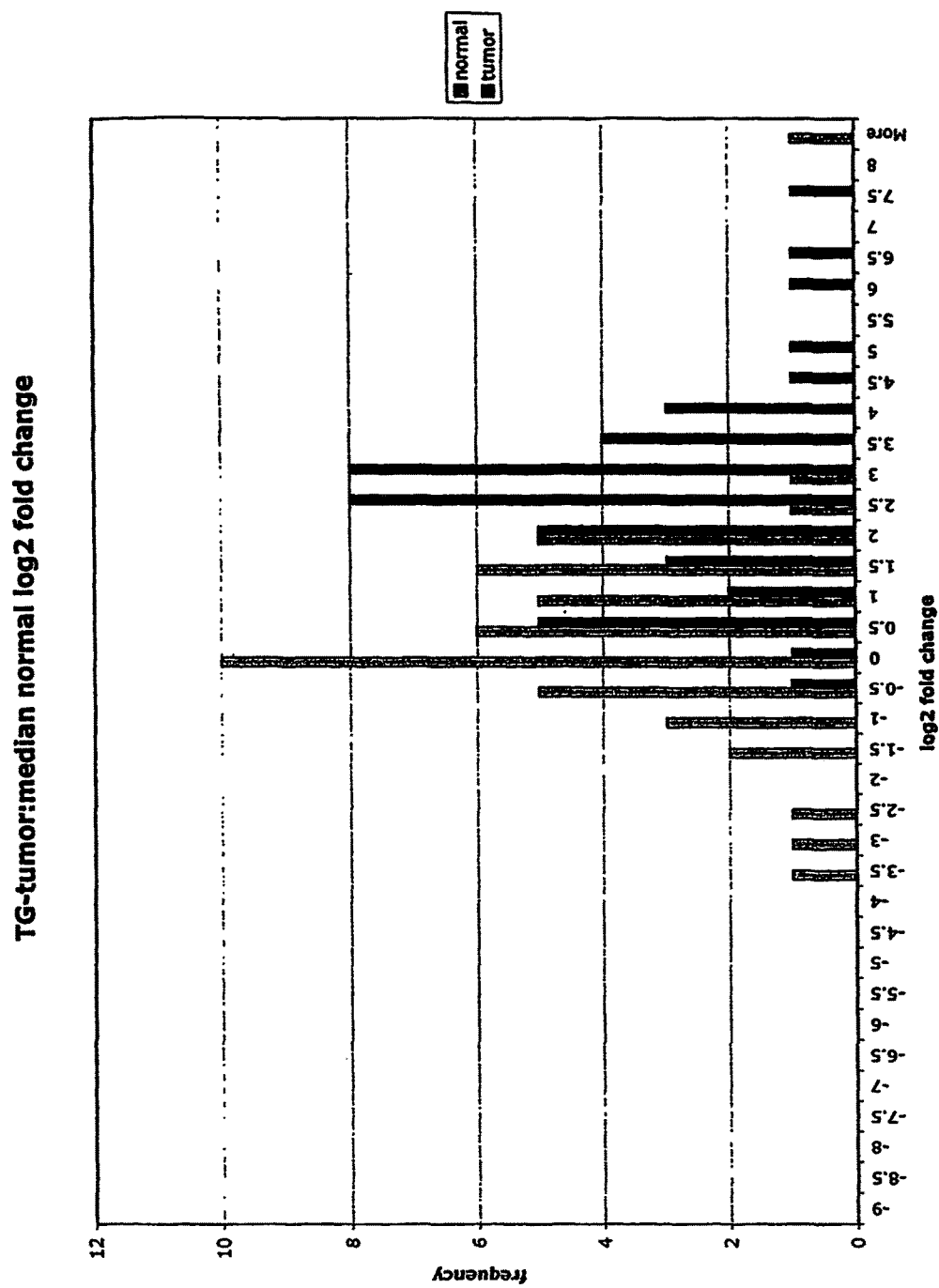
FIG. 5u: TG.
Figure 5V:
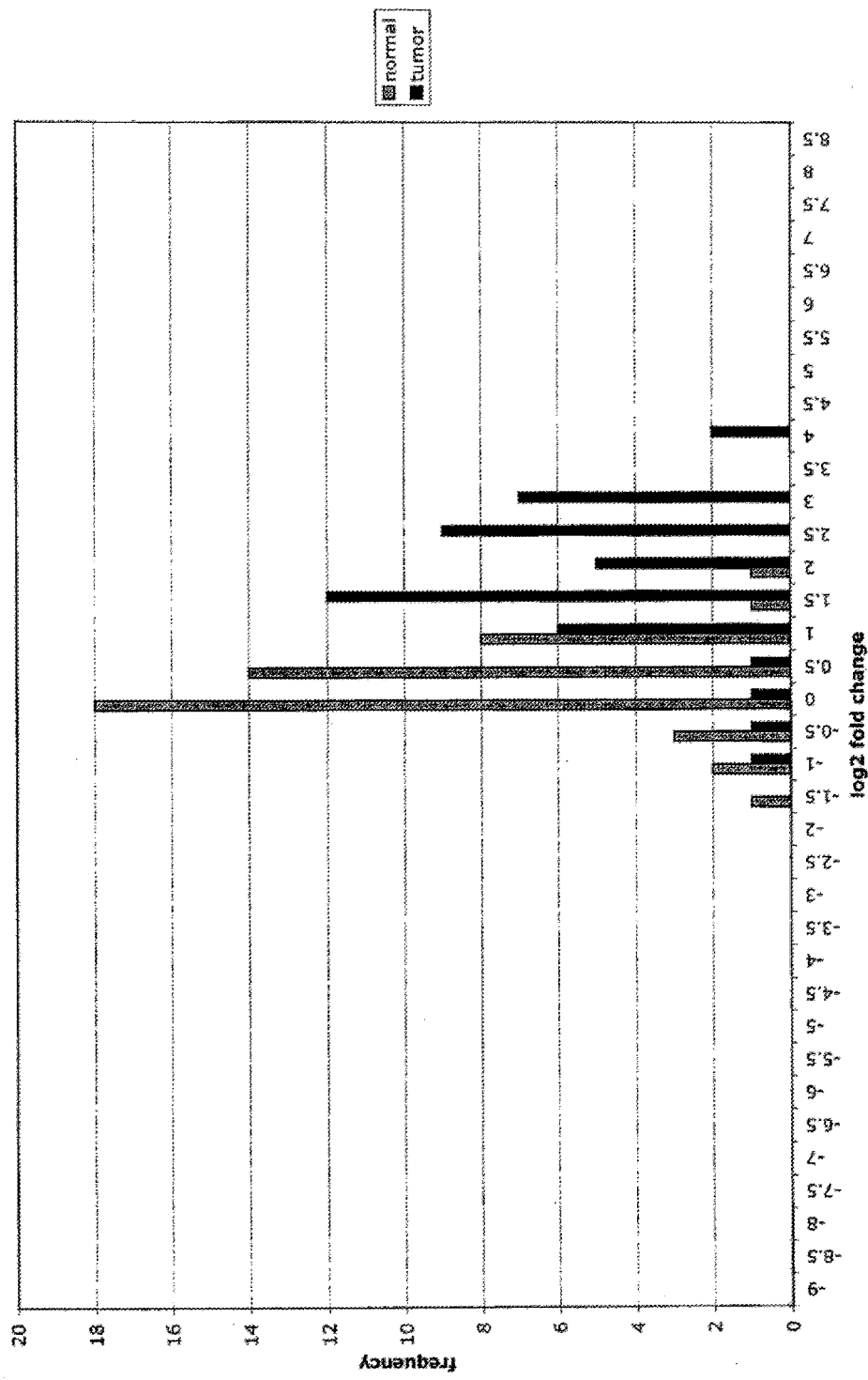
FIG. 5v: EFEMP2
Figure 5W:
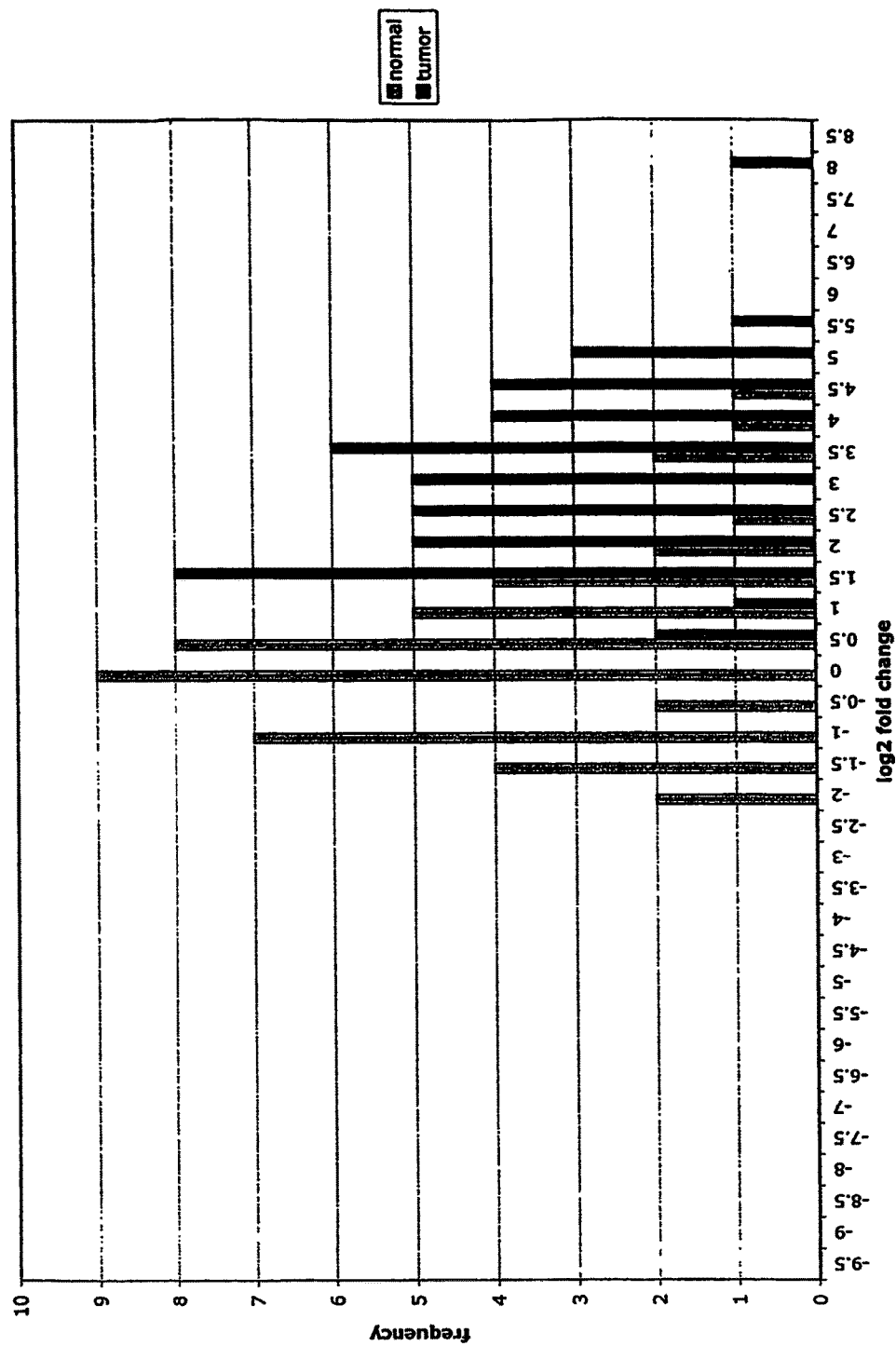

FIGS. 5a-5w depict histograms comparing frequency of observation of expression of each of a series of 23 genes (vertical axis) and the log 2 fold change in expression for that gene (horizontal axis), for both normal tissue (open bars) and tumor tissues (black bars). We found surprisingly that for each of these 23 genes, there was substantial separation in the frequency distributions between normal and tumor tissue, as reflected by the low degree of overlap between the frequency distribution curves. For example, FIG. 5b depicts the results for CST 1, 2, 4, for which there was only one normal sample observed to have an expression level in the tumor range. In other cases (e.g., FIG. 5n; for PRS11) each frequency distribution curve was relatively narrow and there was a degree of overlap. However, even for this marker, the median log 2 fold change showed a substantial separation of the amount of gene expression. In other cases, (e.g., FIG. 5a; ASPN), although there was some overlap, there was a clear separation of the median log 2 fold expression between normal and tumor samples.

Figure 6:
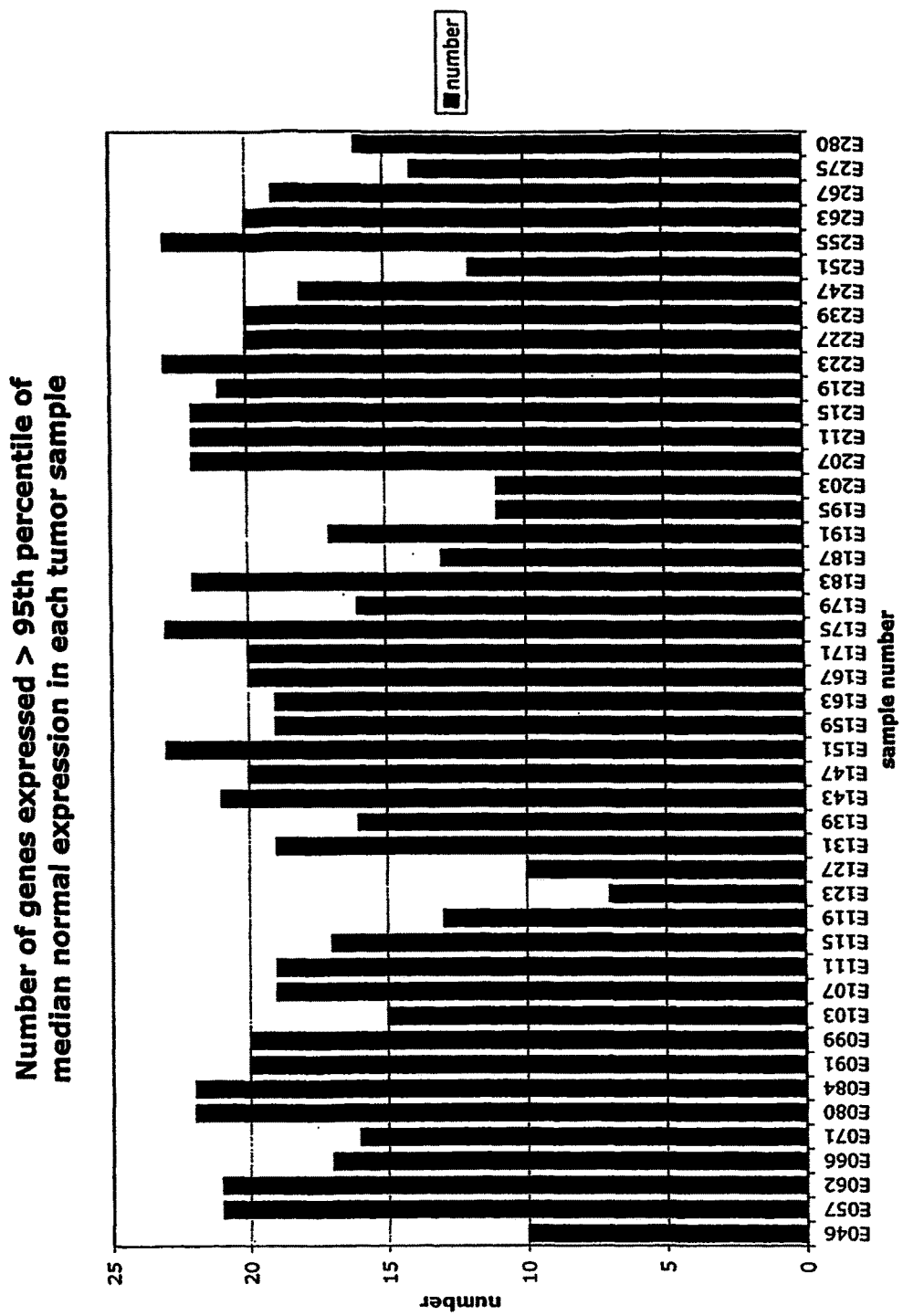
FIG. 6 is a histogram showing the number of markers with a higher expression than the 95th percentile of the median normal expression. Results are based on qPCR data and are shown separately for each tumor sample.

FIG. 6 depicts a histogram of the number of genes exhibiting a significantly increased expression ("over-expression") in tumor samples compared to normal samples (vertical axis) and the individual samples tested. In each case, the tumor sample exhibited multiple genes with elevated expression levels. The lowest number of genes having increased expression was 7, found in sample E123. This finding indicates that, in situations in which multiple genes are over-expressed relative to normal tissue, the reliability of cancer detection can be very high, making diagnosis of cancer more certain. However, in some cases, elevation of expression of a single marker gene is sufficient to lead to the diagnosis of cancer.

Our previous comparison with the serum marker most frequently used currently for detection of gastric cancer, CEA, was based on difference in intensity rank of array data between tumors and normal samples. This comparison was verified using qPCR data for the markers and CEA.

Figure 7C:
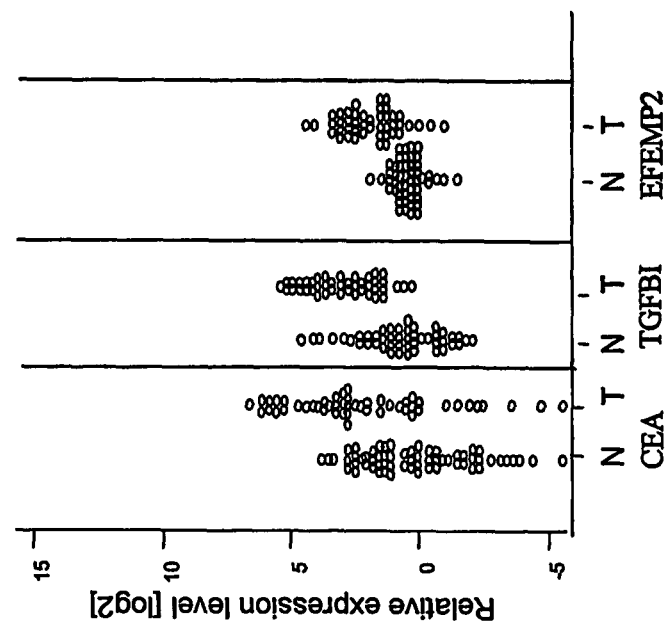
Figure 9B:
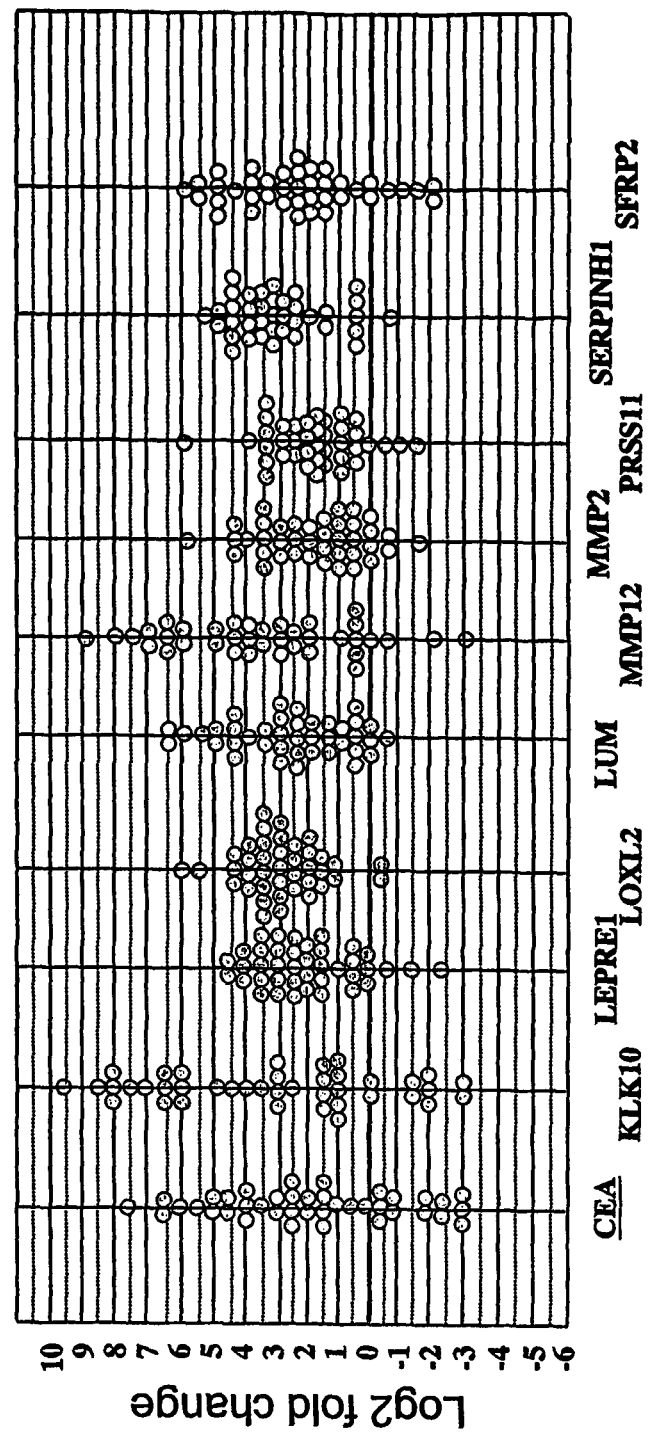
Figure 9C:
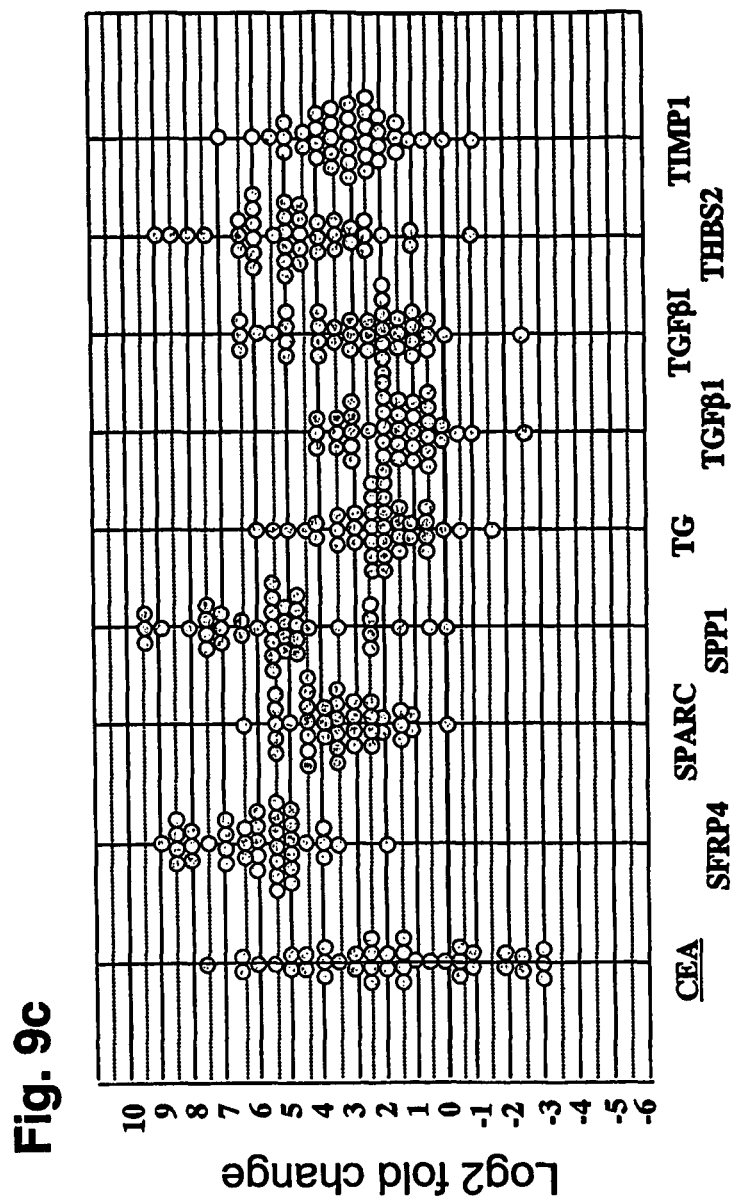
Figure 9D:
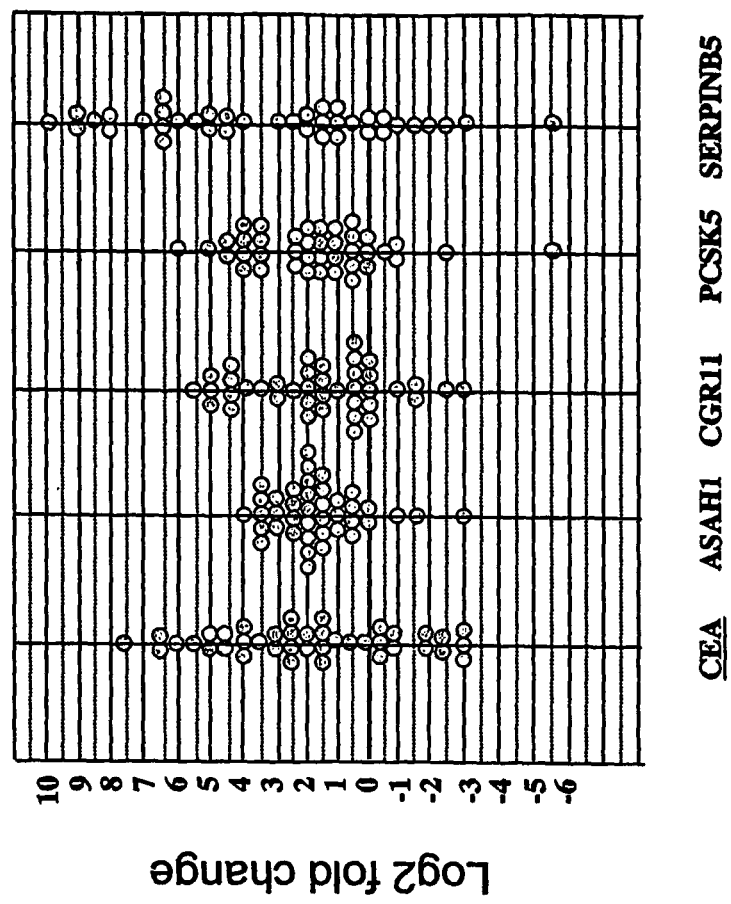

FIGS. 7a-7c depict graphs of the relative log 2 expression (compared to a reference RNA preparation) of markers in individual tumor samples and non-malignant samples compared to the expression of the gene for the tumor marker, CEA. CEA is the serum marker currently most used to monitor progression of gastric cancer. The zero point is defined to be the median normal expression for each marker. It can be seen that there is extensive overlap between the expression of the CEA gene (CEACAM5) in tumor samples and normal samples. This overlap is markedly less in the gastric cancer markers ASPN, CSPG2, CST1,2,4, IGFBP7, INHBA, LOXL2, LUM, SFRP4, SPARC, SPP1, THBS2, TIMP1, adlican, LEPRE1, and EFEMP2. For the other markers in FIGS. 7b-7c, ASAH1, SFRP2, GGH, MMP12, KLK10, TG, PRSS11 and TGFBI, the overlap between the tumor expression range and the non-malignant tissue expression range is greater than the overlap for the above markers, but still less than that of CEA, indicating that all of the herein described new markers are quantitatively better than CEA, and therefore can provide more reliable diagnosis.

To minimize effects of variable tissue handling, tumor: normal (non-malignant) fold changes were calculated using qPCR data from tumor and non-malignant tissue samples derived from the same patient. Such paired analysis corrects for differences in background levels of gene expression in different individuals and minimizes the effects of tissue handling on RNA quality. For example, if the resected stomach was at room temperature for an hour, the transcripts from the normal and tumor samples will be degraded to the same extent.

FIG. 8 summarizes the T:N expression levels determined by qPCR for the markers, but used paired data (i.e., tumor and non-malignant samples) from the same individual. FIG. 8 also includes expression data for six genes that were not included in FIG. 3. The additionally studied genes are MMP2, CGR11, TGFB1, PCSK5, SERPIB5, and SERPINH1. Identifying information and probes are shown in FIGS. 1 and 2. FIG. 8 shows the median T:N fold change and the maximum T:N fold change for 29 gastric cancer markers in these 40 patients with "paired" samples. 27 of the 29 markers have a median T:N difference greater than or equal to the prior art marker, CEA. 29/29 of the markers have a higher percentage of paired samples in which the expression in the tumor sample exceeds the expression in the normal sample.

FIGS. 9a-9d depict scatter dot plots of data from tumor and normal tissue from the same individuals. Each point represents the fold-change, within patient, in expression of the markers in tumor tissue relative to the expression in non-malignant tissue. All of the markers studied have better discrimination of tumor from non-tumor tissue than CEA. Three markers, CST1,2,4, ASPN and SFRP4 showed 100% discrimination between the paired tumor and normal samples. That is, for those markers, every tumor tissue had greater expression than did the corresponding non-tumor tissue from the same individual. In many other markers, for example, Adlican, CSPG2, EFEMP2, IGFBP7, INHBA, LOXL2, LUM, SERPINH1, SPARC, SPP1, TGFbI, THBS2 and TIMP1, each had only 2 or 3 individual points for which tumor tissue expression was less than that of the non-tumor tissue. Thus, for those markers, the likelihood that any one pair of tumor and non-tumor tissue would produce a false negative is relatively low (e.g., 3 of 40 or 7.5%; 2 of 40 or 5%, 1 of 40 or 2.5%). Thus, even if the other markers listed immediately above were used, use of multiple samples from an individual patient would produce reliable diagnostic information.

The gene sequences of these markers, and the location of the primers and probes used to detect them, are shown herein above.

To determine if over-expression of the marker genes is independent of the stage of the gastric tumors, the paired T:N log 2 fold changes were plotted against the tumor stage (FIGS. 10a-10ad). No stage dependency of expression on tumor stage was observed for 26 of the markers listed in FIG. 8. These markers were similarly over-expressed in early stage as well as late stage tumors. However, KLK10 showed more consistent over-expression in stage 1 and stage 2 tumors, and PCSK5 and SERPINB5 showed more consistent over-expression in stage 4 tumors. KLK10, PCSK5 and SERPINB5 therefore can be used in determining the stage of gastric tumors.

In a similar analysis, paired T:N log 2 fold changes were plotted against the Lauren classification of the tumor (either diffuse type or intestinal type). FIGS. 11a-11ad show that each of the 29 GTMs discriminated between tumor and non-tumor tissue, regardless of whether the type of tumor was intestinal (I) or diffuse (D)).

Example 4: Use of Multiple Markers

As described above, certain markers exhibit an ability to discriminate tumor from non-tumor tissue in 100% of the samples. Other markers, also described above, can be used in combination to achieve very high degrees of discrimination of tumor tissue from non-tumor tissue. FIG. 12 depicts a 3-dimensional plot of the expression of 3 markers, SERPINH1, CST1,2,4 and INHBA, expressed as log 2 T:N fold changes for a series of gastric tumor samples and non-malignant gastric samples. There is complete separation between the two groups of samples.

The reliability of successful discrimination of tumor and non-tumor samples using marker combinations is further illustrated by a statistical analysis summarized in FIG. 13. This analysis compared the normal distributions of data generated using the qPCR gene expression from paired tumor and non-malignant samples, shows the effect of increasing the numbers of markers used to discriminate between tumor and non-malignant samples on test sensitivity (with a fixed specificity of 95%). Although few of the 29 markers (as shown in FIG. 8) have a sensitivity of greater than 90, 95, or 99% when used alone in this analysis, the combination of two or three markers enabled high sensitivity to be reached with large numbers of combinations. For example, 50 combinations of three markers would discriminate between tumor and non-malignant samples with a sensitivity of ≥99% and specificity of ≥95%.

Example 5: Detection of Gastric Tumor Marker Proteins

In yet further embodiments, GTM proteins can be detected as a basis for diagnosis. In certain situations, the concentration of mRNA in a particular sample, such as a sample containing no cells, it may be difficult to use either microarray or qPCR methods to detect elevations in gene expression. Thus, in certain embodiments, detection of GTM proteins can be accomplished using antibodies directed against either the entire protein, a fragment of the protein (peptide) or the protein core. Methods for detecting and quantifying expression of proteins and peptides are known in the art and can include methods relying on specific antibodies raised against the protein or peptide. Monoclonal antibodies and polyclonal antisera can be made using methods that are well known in the art and need not be described herein further.

To demonstrate that GTM proteins can be used to discriminate tumor from non-tumor tissue, commercial antibodies were obtained against SPARC (R&D Systems; cat #AF941), THBS2 (Santa Cruz Biotechnology Inc; cat #sc-7655), CSPG2 (Calbiochem; cat #428060) and IGFBP7 (R&D Systems; cat #AF1334). An additional polyclonal antibody was raised in rabbits (Alpha Diagnostic International Inc; San Antonio) against the cystatin SN peptide sequence 50-66 (C) FAISEYNKATKDDYYRR. SEQ ID NO: 108.

These antibodies were used in either immunohistochemistry or Western analysis of tumor and non-malignant gastric tissue. Each of these markers showed strong tumor:normal differences at the protein level. This confirmed that the over-expression observed at the RNA level for these genes also occurred at the protein level.

FIG. 14 shows a Western blot analyses of total protein extracted from two pairs of tumor and non-malignant tissues using antibodies against the proteins encoded by SPARC, CST1 (cystatin SN), IGFBP7 and THBS2. For each marker, the signal is significantly higher in the tumor samples than the non-malignant samples.

The antibody raised against cystatin SN detected three major bands, corresponding to molecular weights of approximately 34, 45 and 65 kDa respectively. The lowest molecular weight band is shown in FIG. 14. The protein species were larger than the control cystatin SN protein, suggesting that the protein produced by tumors has undergone post-translational modifications or multimerization. Regardless of the mechanism responsible for the differences in molecular weights of CST proteins, FIG. 14 demonstrated that CST expression was low in the non-tumor tissue, but was easily observed in blots of tumor-derived proteins.

FIG. 14 also showed that SPARC protein is expressed substantially to a greater degree in tumor tissue than in non-tumor tissue. The SPARC protein had gel mobility slower than the form of this protein that was detected in serum (FIG. 15), also indicating the occurrence of different post-translational modifications in proteins produced by malignant gastric cells. Regardless of the mechanism(s) responsible for any such modification, the finding that SPARC is over-expressed in tumor tissue relative to non-malignant tissue indicates that SPARC is a useful protein marker. Similarly, IGFBP7 and THBS2 show over-expression in tumor tissue relative to non-malignant tissue.

Immunohistochemical analysis of tumor and non-malignant tissue was carried out using antibodies against the proteins encoded by CSPG2 (versican) and CST1 (cystatin SN). Immunohistochemical analysis of tissue with antibodies against versican identified strong staining in the extracellular matrix of tumor tissue, but not non-malignant tissue. With the anti-cystatin SN antibodies, strong staining was observed in the area around the outside of the tumor cells. In non-malignant cells, the staining with this antibody was weaker, and observed only on the mucosal surface of the tissue and the lining of the gastric pits. This demonstrated that in non-malignant cells, cystatin SN protein is directed out of the cell onto the mucosal surface and not into the extracellular spaces. Therefore, not only is the cystatin SN protein being produced in higher amounts in tumor tissue than non-malignant tissue, but, unlike the protein produced by the non-malignant tissue, the tumor cystatin SN is in direct contact with the tissue vasculature. To extend these observations, cystatin SN was immunoprecipitated from the supernatant of the gastric cancer cell line, AGS with a monoclonal antibody (R&D Systems; cat #MAB1285) (FIG. 16). Large amounts of cystatin SN were detected in the supernatant, confirming that this protein is produced by, and secreted from, gastric epithelial cells.

Example 6: Analysis of Tumor Markers in Serum

For a marker to be useful for rapid screening, it is desirable for the marker to be present in the serum in sufficient levels for detection. Certain proteins described in FIG. 8 can be secreted into the blood at detectable levels from gastric cancers. One marker known to be secreted from gastric tumors into blood in detectable levels is TIMP1. However, if a protein is secreted or shed from any surface of a cell other than a mucosal surface, it will have contact with the interstitial fluid. From there, it can pass either directly into the blood supply through a capillary or via the lymph system. Thus, any shed GTM will be present in blood. Osteopontin, thyroglobulin, and members of the MMP and kallikrein families have previously been described to be elevated in the serum of patients with a range of epithelial cancers, but not gastric cancer. TIMP1 has, however, previously been observed to be elevated in the serum of gastric cancer patients. These findings suggest that the selection criteria for markers in this study, namely over-expression of secreted proteins in tumor tissue but not non-malignant tissue, can be effectively used to detect markers in the serum, and thus can be of substantial use clinically, without the need for tissue or organ biopsies.

From FIG. 15, it is apparent that the serum SPARC has a different molecular weight (depicted here in the Western blot) with the tumor SPARC having a lower molecular weight than the SPARC produced by blood cells. Thus, even though SPARC is produced by tumor and non-tumor blood cells, the presence of tumor SPARC can be determined using molecular size, such as determined using Western analysis, or with an antibody specific for the glycosylated protein produced by the tumor cells.

In another study, we detected cystatin SN in the supernatant of a gastric cancer cell line, AGS. FIG. 16 depicts a Western analysis of media alone or a supernatant from AGS cells in culture. The right hand lane of FIG. 16 shows a dense band corresponding to cystatin SN protein.

Thus, we conclude from FIG. 10 that GTM of this invention are suitable for diagnosing gastric cancers at early, middle or late stages of progression of the disease.

Although certain marker proteins can be glycosylated, variations in the pattern of glycosylation can, in certain circumstances, lead to mis-detection of forms of GTMs that lack usual glycosylation patterns. Thus, in certain embodiments of this invention, GTM immunogens can include deglycosylated GTM or deglycosylated GTM fragments. Deglycosylation can be accomplished using one or more glycosidases known in the art. Alternatively, GTM cDNA can be expressed in glycosylation-deficient cell lines, such as prokaryotic cell lines, including *E. coli*, thereby producing non-glycosylated proteins or peptides. It can also be appreciated that the level and quality of glycosylation can be sensitive to the presence of essential precursors for sugar side-chains. Thus, in the absence of an essential sugar, "normal" glycosylation may not occur, but rather, shorter or missing side chain sugars may be found. Such "glycosylation variants" can be used as immunogens to produce antibodies specific for different types of marker genes.

Additionally, certain GTMs may form homo- or heterodimers or other types of multimeric forms. For example, inhibin beta A is a 47 kDa protein that can form homodimers of 97 kDa molecular weight (activin A) and 92 kDa heterodimers with the 45 kDa protein inhibin beta B (the heterodimers are known as activin AB). Thus, it can be appreciated that Western analysis or other type of assay that provides molecular weight need not be limited to only detection of a monomeric form of a GTM. Rather, one can readily appreciate that any form of a GTM can be detected, regardless of the molecular weight. Thus, detection of a multimeric form of a GTM can be readily used to diagnose the presence of gastric cancer. Further, for those GTM that are selective for stage (1-4) or type of gastric tumor (diffuse or intestinal), detection of a multimeric form can provide suitable target for evaluating stage or type of gastric cancer.

Once an antibody or antiserum against a GTM is produced, such antibody preparations can be used for in a variety of ways. First, enzyme-linked immunosorbent assay (ELISA) or radioimmunoassay (RIA) methods can be used to quantify GTM proteins or peptides. Immunodetection can be accomplished in tissue samples using immunohistochemistry. These methods are all known in the art and need not be described further herein.

Example 7: Vectors Containing GTM Oligonucleotides

Other embodiments of this invention include vectors useful for in vitro expression of marker genes or portions thereof ("marker peptides") or fragments of marker gene products. For example, vectors can be made having oligonucleotides for encoding GTMs therein. Many such vectors can be based on standard vectors known in the art. This invention also includes vectors that can be used to transfect a variety of cell lines to prepare GTM-producing cell lines, which can be used to produce desired quantities of GTMs for development of specific antibodies or other reagents for detection of GTMs or for standardizing developed assays for GTMs.

It is to be understood that to manufacture such vectors, an oligonucleotide containing the entire open reading frame or a portion of such an open reading frame encoding a portion of the protein to be expressed can be inserted into a vector containing a promoter region, one or more enhancer regions operably linked to the oligonucleotide sequence, with an initiation codon, an open reading frame, and a stop codon. Methods for producing expression vectors are known in the art and need not be repeated herein.

It can also be appreciated that one or more selectable markers can be inserted into an expression vector to permit the expansion of cell lines selected to contain the expression vector of interest. Moreover, one can also insert leader sequences known in the art, in frame, to direct secretion, internal storage or membrane insertion of the protein or protein fragment in the expressing cell.

Example 8: Cells Transfected with GTM-Containing Vectors

In still further embodiments, cells are provided that can express GTMs, GTM fragments or peptide markers. Both prokaryotic and eukaryotic cells can be so used. For example, *E. coli* (a prokaryotic cell) can be use to produce large quantities of GTMs lacking in mature glycosylation (if the particular GTM normally is glycosylated). COS cells, 293 cells and a variety of other eukaryotic cells can be used to produce GTMs that are glycosylated, or have proper folding and therefore, three-dimensional structure of the native form of the GTM protein. Methods for transfecting such cells are known in the art and need not be described further herein.

Example 9: Kits

Based on the discoveries of this invention, several types of test kits can be produced. First, kits can be made that have a detection device pre-loaded with a detection molecule (or "capture reagent"). In embodiments for detection of GTM mRNA, such devices can comprise a substrate (e.g., glass, silicon, quartz, metal, etc) on which oligonucleotides as capture reagents that hybridize with the mRNA to be detected. In some embodiments, direct detection of mRNA can be accomplished by hybridizing mRNA (labeled with cy3, cy5, radiolabel or other label) to the oligonucleotides on the substrate. In, other embodiments, detection of mRNA can be accomplished by first making complementary DNA (cDNA) to the desired mRNA. Then, labeled cDNA can be hybridized to the oligonucleotides on the substrate and detected.

Regardless of the detection method employed, comparison of test GTM expression with a standard measure of expression is desirable. For example, RNA expression can be standardized to total cellular DNA, to expression of constitutively expressed RNAs (for example, ribosomal RNA) or to other relatively constant markers.

Antibodies can also be used in kits as capture reagents. In some embodiments, a substrate (e.g., a multiwell plate) can have a specific GTM capture reagent attached thereto. In some embodiments, a kit can have a blocking reagent included. Blocking reagents can be used to reduce non-specific binding. For example, non-specific oligonucleotide binding can be reduced using excess DNA from any convenient source that does not contain GTM oligonucleotides, such as salmon sperm DNA. Non-specific antibody binding can be reduced using an excess of a blocking protein such as serum albumin. It can be appreciated that numerous methods for detecting oligonucleotides and proteins are known in the art, and any strategy that can specifically detect GTM associated molecules can be used and be considered within the scope of this invention.

In embodiments relying upon antibody detection, GTM proteins or peptides can be expressed on a per cell basis, or on the basis of total cellular, tissue, or fluid protein, fluid volume, tissue mass (weight). Additionally, GTM in serum can be expressed on the basis of a relatively high-abundance serum protein such as albumin.

In addition to a substrate, a test kit can comprise capture reagents (such as probes), washing solutions (e.g., SSC, other salts, buffers, detergents and the like), as well as detection moieties (e.g., cy3, cy5, radiolabels, and the like). Kits can also include instructions for use and a package.

Although this invention is described with reference to specific embodiments thereof, it can be appreciated that other embodiments involving the use of the disclosed markers can be used without departing from the scope of this invention.

INDUSTRIAL APPLICABILITY

Methods for detecting GTM family members include detection of nucleic acids using microarray and/or real time PCR methods and detection of proteins and peptides. The compositions and methods of this invention are useful in the manufacture of diagnostic devices and kits, diagnosis of disease, evaluating efficacy of therapy, and for producing reagents suitable for measuring expression of GTM family members in biological samples.

We claim:

1. A method for detecting specific cancer markers to determine the efficacy of surgical, radiotherapeutic, and/or chemotherapeutic treatments in a patient having gastric cancer and treating said patient, comprising:
   (a) providing a tissue sample from said patient;
   (b) detecting, using quantitative polymerase chain reaction (qPCR) over-expression of the gastric tumor markers (GTMs), cystatin SN (CST1) protein having the sequence of SEQ ID NO:108 using a forward primer consisting of SEQ ID NO:3, a reverse primer consisting of SEQ ID NO:25 and a probe consisting of SEQ ID NO:47, and measuring expression of one or more of the GTMs, inhibin beta A (INHBA), osteopontin (SPP1), and secreted frizzled-related protein 4 (SFRP4) in said sample;
   (c) calculating the ratios of expression of said CST1, INHBA, SPP1 and SFRP4 in said tissue sample compared to expression of said CST1, INHBA, SPP1 and SFRP4 from non-tumor tissue, by calculating the ΔCT (target gene CT−mean reference cDNA CT), where ΔCT is directly proportional to the negative log 2 fold change, relative to the median non-malignant log 2 fold change, where the ratios of expression in said tissue sample to the level of expression in said non-tumor tissue are greater than 525, 34, 40 and 56, respectively, thereby indicating the presence of gastric cancer; and
   (d) treating the patient by surgery, radiotherapy or chemotherapy.

2. The method of claim 1, further comprising detecting over-expression of at least one additional GTM family member protein selected from the group consisting of serum proteinase inhibitor, Clade H (heat shock protein 47) member 1 (collagen binding protein 1), (SERPINH1), matrix metalloproteinase 12 (MMP12), insulin-like growth factor 7 (IGFBP7), gamma-glutamyl hydrolase (GGH), leucine proline-enriched proteoglycan (LEPRE1), cystatin S (CST4), asporin (ASPN), cell growth regulator with EF hand domain 1 (CGREF1), kallikrein, tissue inhibitor of metalloproteinase 1 (TIMP1), secreted acidic cysteine-rich protein (SPARC), transforming growth factor (TGFB1), EGF-containing fibulin-like extracellular matrix protein 2 (EFEMP2), lumican (LUM), stannin (SNN), chondroitin sulfate proteoglycan 2 (CSPG2), carboxypeptidase N (CPN2), N-acyl-sphingosine amidohydrolase (ASAH1), serine protease 11 (PRSS11), secreted frizzled-related protein 2 (SFRP2), phospholipase A2, group XIIB (PLA2G12B), extracellular matrix protein (SPON), olfactomedin 1 (OLFM1), thrombospondin repeat containing 1 (TSRC1), thrombospondin 2 (THBS2), adlican, cystatin SA (CST2), lysyl oxidase-like enzyme 2 (LOXL2), thyroglobulin (TG), transforming growth factor beta1 (TGFB1), transforming growth factor β induced protein (TGFB-I) serine or cysteine proteinase inhibitor clade B (SERPINB5) matrix metalloproteinase 2 (MMP2), proprotein convertase subtilisin/kexin type 5 (PCSK5), kallikrein 10 (KLK10), hyaluronin and proteoglycan link protein 4 (HAPLN4), serine protease 11 (PRSS11), and transmembrane 6 superfamily member 2 (TM6SF2).

3. The method of claim 2, wherein said step of detecting is carried out by detecting over-expression of GTM mRNA.

4. The method of claim 2, wherein said step of detecting is carried out by detecting cDNA.

5. The method of claim 1, further comprising detecting over-expression of SERPINB5 in said sample.

6. The method of claim 1, further comprising detecting over-expression of one or more of SFRP2, TSRC1, THBS2, LOXL2, SERPINB5, and human cell growth regulator with EF hand domain 1 (CGR11) in said sample.

7. The method of claim 1, further comprising detecting over-expression of one or more GTMs selected from the group consisting of adlican, ASPN, CSPG2, cystatin SA (CST2), cystatin S (CST4), EFEMP2, GGH, human insulin-like growth factor 7 (IGFBP7), kallikrein 10 (KLK10), LEPRE1, LUM, LOXL2, MMP12, TIMP1, ASAH1, SFRP2, SFRP4, human cell growth regulator with EF hand domain 1 (CGR11), THBS2, SPARC, PRSS11, TG, and human transforming growth factor, beta-induced, 68 kDa (TGFBI) in said sample.

* * * * *

SEQUENCE LISTING

```
<160> NUMBER OF SEQ ID NOS: 108

<210> SEQ ID NO 1
<211> LENGTH: 26
<212> TYPE: DNA
<213> ORGANISM: Homo sapiens

<400> SEQUENCE: 1
aaatacaaaa ggacacattc aaagga                                          26

<210> SEQ ID NO 2
<211> LENGTH: 20
<212> TYPE: DNA
<213> ORGANISM: Homo sapiens

<400> SEQUENCE: 2
gccagtggaa ggatgttccc                                                 20

<210> SEQ ID NO 3
<211> LENGTH: 19
<212> TYPE: DNA
<213> ORGANISM: Homo sapiens

<400> SEQUENCE: 3
agtcccagcc caacttgga                                                  19

<210> SEQ ID NO 4
<211> LENGTH: 17
```

<212> TYPE: DNA
<213> ORGANISM: Homo sapiens

<400> SEQUENCE: 4
gtggcaatgc cgctgaa                                                  17

<210> SEQ ID NO 5
<211> LENGTH: 18
<212> TYPE: DNA
<213> ORGANISM: Homo sapiens

<400> SEQUENCE: 5
caggtcagca agggcacc                                                 18

<210> SEQ ID NO 6
<211> LENGTH: 24
<212> TYPE: DNA
<213> ORGANISM: Homo sapiens

<400> SEQUENCE: 6
acaacatgat atgtgctgga ctgg                                          24

<210> SEQ ID NO 7
<211> LENGTH: 24
<212> TYPE: DNA
<213> ORGANISM: Homo sapiens

<400> SEQUENCE: 7
cttgagtaca acgctgacct cttc                                          24

<210> SEQ ID NO 8
<211> LENGTH: 24
<212> TYPE: DNA
<213> ORGANISM: Homo sapiens

<400> SEQUENCE: 8
gattcttgtc catagtgcat ctgc                                          24

<210> SEQ ID NO 9
<211> LENGTH: 19
<212> TYPE: DNA
<213> ORGANISM: Homo sapiens

<400> SEQUENCE: 9
aggccagctt ctgcttgga                                                19

<210> SEQ ID NO 10
<211> LENGTH: 23
<212> TYPE: DNA
<213> ORGANISM: Homo sapiens

<400> SEQUENCE: 10
gcctctctgc tgatgacata cgt                                           23

<210> SEQ ID NO 11
<211> LENGTH: 21
<212> TYPE: DNA
<213> ORGANISM: Homo sapiens

<400> SEQUENCE: 11
ccagaccacc ttataccagc g                                             21

<210> SEQ ID NO 12

```
<211> LENGTH: 17
<212> TYPE: DNA
<213> ORGANISM: Homo sapiens

<400> SEQUENCE: 12
cgcagaacgc ctgcaaa                                                   17

<210> SEQ ID NO 13
<211> LENGTH: 18
<212> TYPE: DNA
<213> ORGANISM: Homo sapiens

<400> SEQUENCE: 13
cgctagcagc gaccacct                                                  18

<210> SEQ ID NO 14
<211> LENGTH: 23
<212> TYPE: DNA
<213> ORGANISM: Homo sapiens

<400> SEQUENCE: 14
tcttccctgt acactggcag ttc                                            23

<210> SEQ ID NO 15
<211> LENGTH: 19
<212> TYPE: DNA
<213> ORGANISM: Homo sapiens

<400> SEQUENCE: 15
tcgggaggcc cgttagtaa                                                 19

<210> SEQ ID NO 16
<211> LENGTH: 23
<212> TYPE: DNA
<213> ORGANISM: Homo sapiens

<400> SEQUENCE: 16
tggaaggact acacggccta tag                                            23

<210> SEQ ID NO 17
<211> LENGTH: 20
<212> TYPE: DNA
<213> ORGANISM: Homo sapiens

<400> SEQUENCE: 17
gacggttcct cgcagttcaa                                                20

<210> SEQ ID NO 18
<211> LENGTH: 16
<212> TYPE: DNA
<213> ORGANISM: Homo sapiens

<400> SEQUENCE: 18
ctgcccaccc cttcca                                                    16

<210> SEQ ID NO 19
<211> LENGTH: 21
<212> TYPE: DNA
<213> ORGANISM: Homo sapiens

<400> SEQUENCE: 19
tccacgcatt ttccaggata a                                              21
```

```
<210> SEQ ID NO 20
<211> LENGTH: 22
<212> TYPE: DNA
<213> ORGANISM: Homo sapiens

<400> SEQUENCE: 20
ggtccatgtc atcaccaatg tt                                              22

<210> SEQ ID NO 21
<211> LENGTH: 21
<212> TYPE: DNA
<213> ORGANISM: Homo sapiens

<400> SEQUENCE: 21
aaaaatcttt gccggaaatg c                                               21

<210> SEQ ID NO 22
<211> LENGTH: 20
<212> TYPE: DNA
<213> ORGANISM: Homo sapiens

<400> SEQUENCE: 22
ttgatggcat cgctcagatc                                                 20

<210> SEQ ID NO 23
<211> LENGTH: 23
<212> TYPE: DNA
<213> ORGANISM: Homo sapiens

<400> SEQUENCE: 23
tgcttctgca attctgatat gga                                             23

<210> SEQ ID NO 24
<211> LENGTH: 23
<212> TYPE: DNA
<213> ORGANISM: Homo sapiens

<400> SEQUENCE: 24
tcttggcatt ttctacaaca ggg                                             23

<210> SEQ ID NO 25
<211> LENGTH: 24
<212> TYPE: DNA
<213> ORGANISM: Homo sapiens

<400> SEQUENCE: 25
gggaacttcg tagatctgga aaga                                            24

<210> SEQ ID NO 26
<211> LENGTH: 25
<212> TYPE: DNA
<213> ORGANISM: Homo sapiens

<400> SEQUENCE: 26
tgacagcaac aactcagtag gaaaa                                           25

<210> SEQ ID NO 27
<211> LENGTH: 22
<212> TYPE: DNA
<213> ORGANISM: Homo sapiens

<400> SEQUENCE: 27
tcacagctca agtacacctg gg                                              22
```

```
<210> SEQ ID NO 28
<211> LENGTH: 20
<212> TYPE: DNA
<213> ORGANISM: Homo sapiens

<400> SEQUENCE: 28
gagaggatgc cttggagggt                                              20

<210> SEQ ID NO 29
<211> LENGTH: 23
<212> TYPE: DNA
<213> ORGANISM: Homo sapiens

<400> SEQUENCE: 29
ccgtgacaca gttctgctta cag                                          23

<210> SEQ ID NO 30
<211> LENGTH: 21
<212> TYPE: DNA
<213> ORGANISM: Homo sapiens

<400> SEQUENCE: 30
ccaatcaatg ccaggaagag a                                            21

<210> SEQ ID NO 31
<211> LENGTH: 17
<212> TYPE: DNA
<213> ORGANISM: Homo sapiens

<400> SEQUENCE: 31
ccctgatcgc cgagttg                                                 17

<210> SEQ ID NO 32
<211> LENGTH: 25
<212> TYPE: DNA
<213> ORGANISM: Homo sapiens

<400> SEQUENCE: 32
agtgacagca tcaaaactca aattg                                        25

<210> SEQ ID NO 33
<211> LENGTH: 20
<212> TYPE: DNA
<213> ORGANISM: Homo sapiens

<400> SEQUENCE: 33
ggacctgtgg aagtatccgc                                              20

<210> SEQ ID NO 34
<211> LENGTH: 25
<212> TYPE: DNA
<213> ORGANISM: Homo sapiens

<400> SEQUENCE: 34
acaggacatc atacatggtt tcaaa                                        25

<210> SEQ ID NO 35
<211> LENGTH: 23
<212> TYPE: DNA
<213> ORGANISM: Homo sapiens

<400> SEQUENCE: 35
ttttgcaggc ttcacatacc ttt                                          23
```

<210> SEQ ID NO 36
<211> LENGTH: 18
<212> TYPE: DNA
<213> ORGANISM: Homo sapiens

<400> SEQUENCE: 36
gaaaaagcgg gtggtgca					18

<210> SEQ ID NO 37
<211> LENGTH: 23
<212> TYPE: DNA
<213> ORGANISM: Homo sapiens

<400> SEQUENCE: 37
aaggagattc cagctgtcac ttc				23

<210> SEQ ID NO 38
<211> LENGTH: 28
<212> TYPE: DNA
<213> ORGANISM: Homo sapiens

<400> SEQUENCE: 38
taggtttggt catagatagg tcctgagt				28

<210> SEQ ID NO 39
<211> LENGTH: 22
<212> TYPE: DNA
<213> ORGANISM: Homo sapiens

<400> SEQUENCE: 39
tgtaaaccgc tccacttcac at				22

<210> SEQ ID NO 40
<211> LENGTH: 25
<212> TYPE: DNA
<213> ORGANISM: Homo sapiens

<400> SEQUENCE: 40
ttctgtcctt cctagtccct ttagg				25

<210> SEQ ID NO 41
<211> LENGTH: 21
<212> TYPE: DNA
<213> ORGANISM: Homo sapiens

<400> SEQUENCE: 41
aagccgaatt tgctagttgc a					21

<210> SEQ ID NO 42
<211> LENGTH: 22
<212> TYPE: DNA
<213> ORGANISM: Homo sapiens

<400> SEQUENCE: 42
tctgcaagtt catcccctct tt				22

<210> SEQ ID NO 43
<211> LENGTH: 21
<212> TYPE: DNA
<213> ORGANISM: Homo sapiens

<400> SEQUENCE: 43

```
agtcctggcc gttgaaatac c                                              21

<210> SEQ ID NO 44
<211> LENGTH: 19
<212> TYPE: DNA
<213> ORGANISM: Homo sapiens

<400> SEQUENCE: 44
tgtcacgtgg cgtcacagt                                                 19

<210> SEQ ID NO 45
<211> LENGTH: 34
<212> TYPE: DNA
<213> ORGANISM: Homo sapiens

<400> SEQUENCE: 45
ttggaaatga gtgcaaaccc tcttgataat aatg                                34

<210> SEQ ID NO 46
<211> LENGTH: 23
<212> TYPE: DNA
<213> ORGANISM: Homo sapiens

<400> SEQUENCE: 46
aggaacagtt gcttgcggcc agc                                            23

<210> SEQ ID NO 47
<211> LENGTH: 29
<212> TYPE: DNA
<213> ORGANISM: Homo sapiens

<400> SEQUENCE: 47
agccagaact gcagaagaaa cagttgtgc                                      29

<210> SEQ ID NO 48
<211> LENGTH: 29
<212> TYPE: DNA
<213> ORGANISM: Homo sapiens

<400> SEQUENCE: 48
ttcactggag gtcaattgca cagcagaat                                      29

<210> SEQ ID NO 49
<211> LENGTH: 26
<212> TYPE: DNA
<213> ORGANISM: Homo sapiens

<400> SEQUENCE: 49
agcaaggtcc ttccatagtg acgccc                                         26

<210> SEQ ID NO 50
<211> LENGTH: 25
<212> TYPE: DNA
<213> ORGANISM: Homo sapiens

<400> SEQUENCE: 50
cttgccagag tgactctgga ggccc                                          25

<210> SEQ ID NO 51
<211> LENGTH: 30
<212> TYPE: DNA
<213> ORGANISM: Homo sapiens

<400> SEQUENCE: 51
```
ccatcacaga tcattacatc caggtcctca                                    30

<210> SEQ ID NO 52
<211> LENGTH: 36
<212> TYPE: DNA
<213> ORGANISM: Homo sapiens

<400> SEQUENCE: 52
taaggattca aaccatttgc caaaaatgag tctaag                             36

<210> SEQ ID NO 53
<211> LENGTH: 33
<212> TYPE: DNA
<213> ORGANISM: Homo sapiens

<400> SEQUENCE: 53
cgtaattctt ctggatgtct ccttcacatt ctg                                33

<210> SEQ ID NO 54
<211> LENGTH: 30
<212> TYPE: DNA
<213> ORGANISM: Homo sapiens

<400> SEQUENCE: 54
tcagtccctg tatggagacc caaaagagaa                                    30

<210> SEQ ID NO 55
<211> LENGTH: 33
<212> TYPE: DNA
<213> ORGANISM: Homo sapiens

<400> SEQUENCE: 55
caagatgacc aagatgtata aagggttcca agc                                33

<210> SEQ ID NO 56
<211> LENGTH: 28
<212> TYPE: DNA
<213> ORGANISM: Homo sapiens

<400> SEQUENCE: 56
tgtctgaacc gcaccagcca agagaata                                      28

<210> SEQ ID NO 57
<211> LENGTH: 22
<212> TYPE: DNA
<213> ORGANISM: Homo sapiens

<400> SEQUENCE: 57
ctgccagcca ccgaggaagc tc                                            22

<210> SEQ ID NO 58
<211> LENGTH: 22
<212> TYPE: DNA
<213> ORGANISM: Homo sapiens

<400> SEQUENCE: 58
tggaccagca ccccattgac gg                                            22

<210> SEQ ID NO 59
<211> LENGTH: 31
<212> TYPE: DNA
<213> ORGANISM: Homo sapiens

<400> SEQUENCE: 59
agtgttaatt ccaatcactt caccgtccag g  31

<210> SEQ ID NO 60
<211> LENGTH: 27
<212> TYPE: DNA
<213> ORGANISM: Homo sapiens

<400> SEQUENCE: 60
aggcccaaga ccggctacat cagagtc  27

<210> SEQ ID NO 61
<211> LENGTH: 25
<212> TYPE: DNA
<213> ORGANISM: Homo sapiens

<400> SEQUENCE: 61
tctggcagat tccgatgccc cacaa  25

<210> SEQ ID NO 62
<211> LENGTH: 20
<212> TYPE: DNA
<213> ORGANISM: Homo sapiens

<400> SEQUENCE: 62
ccaggccagg agcagctcgg  20

<210> SEQ ID NO 63
<211> LENGTH: 21
<212> TYPE: DNA
<213> ORGANISM: Homo sapiens

<400> SEQUENCE: 63
tgactccagg cccgcaatgg a  21

<210> SEQ ID NO 64
<211> LENGTH: 25
<212> TYPE: DNA
<213> ORGANISM: Homo sapiens

<400> SEQUENCE: 64
cagcctccag ccaacagacc tcagg  25

<210> SEQ ID NO 65
<211> LENGTH: 29
<212> TYPE: DNA
<213> ORGANISM: Homo sapiens

<400> SEQUENCE: 65
acagaatgta gggatgggtt aagcctgca  29

<210> SEQ ID NO 66
<211> LENGTH: 23
<212> TYPE: DNA
<213> ORGANISM: Homo sapiens

<400> SEQUENCE: 66
ttcaaggacc ggttcatttg gcg  23

<210> SEQ ID NO 67
<211> LENGTH: 1778
<212> TYPE: DNA
<213> ORGANISM: Homo sapiens

<400> SEQUENCE: 67

```
tagaagttta caatgaagtt tcttctaata ctgctcctgc aggccactgc ttctggagct      60
cttcccctga acagctctac aagcctggaa aaaataatg tgctatttgg tgagagatac     120
ttagaaaaat tttatggcct tgagataaac aaacttccag tgacaaaaat gaatatagt     180
ggaaacttaa tgaaggaaaa aatccaagaa atgcagcact tcttgggtct gaaagtgacc     240
gggcaactgg acacatctac cctggagatg atgcacgcac ctcgatgtgg agtccccgat     300
ctccatcatt tcagggaaat gccagggggg cccgtatgga ggaaacatta tatcacctac     360
agaatcaata attacacacc tgacatgaac cgtgaggatg ttgactacgc aatccggaaa     420
gctttccaag tatggagtaa tgttaccccc ttgaaattca gcaagattaa cacaggcatg     480
gctgacattt tggtggtttt tgcccgtgga gctcatggag acttccatgc ttttgatggc     540
aaaggtggaa tcctagccca tgcttttgga cctggatctg gcattggagg ggatgcacat     600
ttcgatgagg acgaattctg gactacacat tcaggaggca caaacttgtt cctcactgct     660
gttcacgaga ttggccattc cttaggtctt ggccattcta gtgatccaaa ggctgtaatg     720
ttccccacct acaaatatgt cgacataaac acatttcgcc tctctgctga tgacatacgt     780
ggcattcagt ccctgtatgg agacccaaaa gagaaccaac gcttgccaaa tcctgacaat     840
tcagaaccag ctctctgtga ccccaatttg agttttgatg ctgtcactac cgtgggaaat     900
aagatctttt tcttcaaaga caggttcttc tggctgaagg tttctgagag accaaagacc     960
agtgttaatt taatttcttc cttatggcca accttgccat ctggcattga agctgcttat    1020
gaaattgaag ccagaaatca agttttttct tttaaagatg acaaatactg gttaattagc    1080
aatttaagac cagagccaaa ttatcccaag agcatacatt cttttggttt tcctaacttt    1140
gtgaaaaaaa ttgatgcagc tgtttttaac ccacgttttt ataggaccta cttctttgta    1200
gataaccagt attggaggta tgatgaaagg agacagatga tggaccctgg ttatcccaaa    1260
ctgattacca agaacttcca aggaatcggg cctaaaattg atgcagtctt ctattctaaa    1320
aacaaatact actatttctt ccaaggatct aaccaatttg aatatgactt cctactccaa    1380
cgtatcacca aaacactgaa aagcaatagc tggtttggtt gttagaaatg gtgtaattaa    1440
tggttttgt tagttcactt cagcttaata agtatttatt gcatatttgc tatgtcctca    1500
gtgtaccact acttagagat atgtatcata aaaataaaat ctgtaaacca taggtaatga    1560
ttatataaaa tacataatat ttttcaattt tgaaaactct aattgtccat tcttgcttga    1620
ctctactatt aagtttgaaa atagttacct tcaaagcaag ataattctat ttgaagcatg    1680
ctctgtaagt tgcttcctaa catccttgga ctgagaaatt atacttactt ctggcataac    1740
taaaattaag tatatatatt ttggctcaaa taaaattg                            1778
```

<210> SEQ ID NO 68
<211> LENGTH: 1840
<212> TYPE: DNA
<213> ORGANISM: Homo sapiens

<400> SEQUENCE: 68

```
tccacacaca caaaaaacct gcgcgtgagg ggggaggaaa agcagggcct ttaaaaaggc      60
aatcacaaca acttttgctg ccaggatgcc cttgctttgg ctgagaggat ttctgttggc     120
aagttgctgg attatagtga ggagttcccc caccccagga tccgagggggc acagcgcggc     180
ccccgactgt ccgtcctgtg cgctggccgc cctcccaaag gatgtaccca actctcagcc     240
```

```
agagatggtg gaggccgtca agaagcacat tttaaacatg ctgcacttga agaagagacc      300
cgatgtcacc cagccggtac ccaaggcggc gcttctgaac gcgatcagaa agcttcatgt      360
gggcaaagtc ggggagaacg ggtatgtgga gatagaggat gacattggaa ggagggcaga      420
aatgaatgaa cttatggagc agacctcgga gatcatcacg tttgccgagt caggaacagc      480
caggaagacg ctgcacttcg agatttccaa ggaaggcagt gacctgtcag tggtggagcg      540
tgcagaagtc tggctcttcc taaaagtccc caaggccaac aggaccagga ccaaagtcac      600
catccgcctc ttccagcagc agaagcaccc gcagggcagc ttggacacag ggaagaggcc      660
cgaggaagtg ggcttaaagg gggagaggag tgaactgttg ctctctgaaa agtagtagaa      720
cgctcggaag agcacctggc atgtcttccc tgtctccagc agcatccagc ggttgctgga      780
ccagggcaag agctccctgg acgttcggat tgcctgtgag cagtgccagg agagtggcgc      840
cagcttggtt ctcctgggca agaagaagaa gaaagaagag gaggggggaag ggaaaaagaa      900
gggcggaggt gaaggtgggg caggagcaga tgaggaaaag gagcagtcgc acagaccttt      960
cctcatgctg caggcccggc agtctgaaga ccaccctcat cgccggcgtc ggcggggctt     1020
ggagtgtgat ggcaaggtca acatctgctg taagaaacag ttctttgtca gtttcaagga     1080
catcggctgg aatgactgga tcattgctcc ctctggctat catgccaact actgcgaggg     1140
tgagtgcccg agccatatag caggcacgtc cgggtcctca ctgtccttcc actcaacagt     1200
catcaaccac taccgcatgc ggggccctag ccccctttgcc aacctcaaat cgtgctgtgt     1260
gcccaccaag ctgagaccca tgtccatgtt gtactatgat gatggtcaaa acatcatcaa     1320
aaaggacatt cagaacatga tcgtggagga gtgtgggtgc tcatagagtt gcccagccca     1380
gggggaaagg gagcaagagt tgtccagaga agacagtggc aaaatgaaga aattttaag      1440
gtttctgagt taaccagaaa aatagaaatt aaaaacaaaa caaacaaaa aaaaaacaa      1500
aaaaaacaa aagtaaatta aaaacaaacc tgatgaaaca gatgaaacag atgaaggaag     1560
atgtggaaat cttagcctgc cttagccagg gctcagagat gaagcagtga agagacagat     1620
tgggagggaa agggagaatg gtgtaccctt tatttcttct gaaatcacac tgatgacatc     1680
agttgtttaa acgggtatt gtcctttccc cccttgaggt tccttgtga gcttgaatca     1740
accaatctga tctgcagtag tgtggactag aacaacccaa atagcatcta gaaagccatg     1800
agtttgaaag ggcccatcac aggcactttc ctagcctaat                          1840

<210> SEQ ID NO 69
<211> LENGTH: 1124
<212> TYPE: DNA
<213> ORGANISM: Homo sapiens

<400> SEQUENCE: 69
gccgctgcca ccgcaccccg ccatggagcg gccgtcgctg cgcgccctgc tcctcggcgc       60
cgctgggctg ctgctcctgc tcctgccccct ctcctcttcc tcctcttcgg acacctgcgg     120
cccctgcgag ccggcctcct gccgcccct gccccgctg gctgcctgc tgggcgagac        180
ccgcgacgcg tgcggctgct gccctatgtg cgcccgcggc gagggcgagc cgtgcggggg      240
tggcggcgcc ggcaggggt actgcgcgcc gggcatggag tgcgtgaaga gccgcaagag      300
gcggaagggt aaagccgggg cagcagccgg cggtccgggt gtaagcggcg tgtgcgtgtg      360
caagagccgc tacccggtgt gcggcagcga cggcaccacc tacccgagcg gctgccagct     420
gcgcgccgcc agccagaggg ccgagagccg cggggagaag gccatcaccc aggtcagcaa      480
gggcacctgc gagcaaggtc cttccatagt gacgcccccc aaggacatct ggaatgtcac     540
```

-continued

```
tggtgcccag gtgtacttga gctgtgaggt catcggaatc ccgacacctg tcctcatctg      600
gaacaaggta aaaggggtc actatggagt tcaaaggaca gaactcctgc ctggtgaccg       660
ggacaacctg gccattcaga cccggggtgg cccagaaaag catgaagtaa ctggctgggt      720
gctggtatct cctctaagta aggaagatgc tggagaatat gagtgccatg catccaattc     780
ccaaggacag gcttcagcat cagcaaaaat tacagtggtt gatgccttac atgaaatacc     840
agtgaaaaaa ggtgaaggtg ccgagctata aacctccaga atattattag tctgcatggt    900
taaaagtagt catggataac tacattacct gttcttgcct aataagtttc ttttaatcca     960
atccactaac actttagtta tattcactgg ttttacacag agaaatacaa aataaagatc    1020
acacatcaag actatctaca aaaatttatt atatatttac agaagaaaag catgcatatc   1080
attaaacaaa taaaatactt tttatcacaa aaaaaaaaaa aaaa                     1124
```

<210> SEQ ID NO 70
<211> LENGTH: 1280
<212> TYPE: DNA
<213> ORGANISM: Homo sapiens

<400> SEQUENCE: 70

```
tgccgcagcc cccgcccgcc cgcagagctt ttgaaaggcg gcgggaggcg gcgagcgcca      60
tggccagtcc gggctgcctg ctgtgcgtgc tgggcctgct actctgcggg gcggcgagcc     120
tcgagctgtc tagaccccac ggcgacaccg ccaagaagcc catcatcgga atattaatgc     180
aaaaatgccg taataaagtc atgaaaaact atggaagata ctatattgct gcgtcctatg    240
taaagtactt ggagtctgca ggtgcgagag ttgtaccagt aaggctggat cttacagaga    300
aagactatga atacttttc aaatctatta atggaatcct tttccctgga ggaagtgttg     360
acctcagacg ctcagattat gctaaagtgg ccaaaatatt ttataacttg tccatacaga    420
gttttgatga tggagactat tttcctgtgt ggggcacatg ccttggattt gaagagcttt    480
cactgctgat tagtggagag tgcttattaa ctgccacaga tactgttgac gtggcaatgc   540
cgctgaactt cactggaggt caattgcaca gcagaatgtt ccagaatttt cctactgagt   600
tgttgctgtc attagcagta gaacctctga ctgccaattt ccataagtgg agcctctccg   660
tgaagaattt tacaatgaat gaaaagttaa agaagttttt caatgtctta actacaaata    720
cagatggcaa gattgagttt atttcaacaa tggaaggata taagtatcca gtatatggtg   780
tccagtggca tccagagaaa gcaccttatg agtggaagaa tttggatggc atttcccatg   840
cacctaatgc tgtgaaaacc gcatttttatt tagcagagtt ttttgttaat gaagctcgga   900
aaaacaacca tcattttaaa tctgaatctg aagaggagaa agcattgatt tatcagttca    960
gtccaattta tactggaaat atttcttcat ttcagcaatg ttacatattt gattgaaagt    1020
cttcaatttg ttaacagagc aaatttgaat aattccatga ttaaactgtt agaataactt    1080
gctactcatg gcaagattag gaagtcacag attcttttct ataatgtgcc tggctctgat    1140
tcttcattat gtatgtgact atttatataa cattagataa ttaaatagtg agacataaat    1200
agagtgcttt ttcatggaaa agccttctta tatctgaaga ttgaaaaata aatttactga    1260
aatacaaaaa aaaaaaaaaa                                               1280
```

<210> SEQ ID NO 71
<211> LENGTH: 2993
<212> TYPE: DNA
<213> ORGANISM: Homo sapiens

<400> SEQUENCE: 71

```
ggtggcgggt ggctggcggt tccgttaggt ctgagggagc gatggcggta cgcgcgttga      60
agctgctgac cacactgctg gctgtcgtgg ccgctgcctc ccaagccgag gtcgagtccg     120
aggcaggatg gggcatggtg acgcctgatc tgctcttcgc cgaggggacc gcagcctacg     180
cgcgcgggga ctggcccggg gtggtcctga gcatggaacg ggcgctgcgc tcccgggcag     240
ccctccgcgc ccttcgcctg cgctgccgca cccagtgtgc cgccgacttc ccgtgggagc     300
tggaccccga ctggtccccc agcccggccc aggcctcggg cgccgccgcc ctgcgcgacc     360
tgagcttctt cggggggcctt ctgcgtcgcg ctgcctgcct cgccgctgc ctcgggccgc     420
cggccgccca ctcgctcagc gaagagatgg agctggagtt ccgcaagcgg agccccctaca   480
actacctgca ggtcgcctac ttcaagatca acaagttgga gaaagctgtt gctgcagcac     540
acaccttctt cgtgggcaat cctgagcaca tggaaatgca gcagaaccta gactattacc   600
aaaccatgtc tggagtgaag gaggccgact tcaaggatct tgagactcaa ccccatatgc     660
aagaatttcg actgggagtg cgactctact cagaggaaca gccacaggaa gctgtgcccc     720
acctagaggc ggcgctgcaa gaatactttg tggcctatga ggagtgccgt gccctctgcg     780
aagggcccta tgactacgat ggctacaact accttgagta caacgctgac ctcttccagg     840
ccatcacaga tcattacatc caggtcctca actgtaagca gaactgtgtc acggagcttg     900
cttcccaccc aagtcgagag aagcccttg aagacttcct cccatcgcat tataattatc    960
tgcagtttgc ctactataac attgggaatt atacacaggc tgttgaatgt gccaagacct   1020
atcttctctt cttccccaat gacgaggtga tgaaccaaaa tttggcctat tatgcagcta   1080
tgcttggaga agaacacacc agatccatcg gccccgtga gagtgccaag gagtaccgac     1140
agcgaagcct actggaaaaa gaactgcttt tcttcgctta tgatgttttt ggaattccct     1200
ttgtggatcc ggattcatgg actccaggag aagtgattcc caagagattg caagagaaac   1260
agaagtcaga acgggaaaca gccgtacgca tctcccagga gattgggaac cttatgaagg   1320
aaatcgagac ccttgtggaa gagaagacca aggagtcact ggatgtgagc agactgaccc   1380
gggaaggtgg ccccctgctg tatgaaggca tcagtctcac catgaactcc aaactcctga   1440
atggttccca gcgggtggtg atggacggcg taatctctga ccacgagtgt caggagctgc   1500
agagactgac caatgtggca gcaacctcag gagatggcta ccggggtcag acctccccac   1560
atactcccaa tgaaaagttc tatggtgtca ctgtcttcaa agccctcaag ctggggcaag   1620
aaggcaaagt tcctctgcag agtgccacc tgtactacaa cgtgacggag aaggtgcggc   1680
gcatcatgga gtcctacttc cgcctggata cgcccctcta cttttcctac tctcatctgg   1740
tgtgccgcac tgccatcgaa gaggtccagg cagagaggaa ggatgatagt catccagtcc   1800
acgtggacaa ctgcatcctg aatgccgaga ccctcgtgtg tgtcaaagag cccccagcct   1860
acaccttccg cgactacagc gccatccttt acctaaatgg ggacttcgat ggcggaaact   1920
tttatttcac tgaactggat gccaagaccg tgacggcaga ggtgcagcct cagtgtggaa   1980
gagccgtggg attctcttca ggcactgaaa acccacatgg agtgaaggct gtcaccaggg   2040
ggcagcgctg tgccatcgcc ctgtggttca ccctggaccc tcgacacagc gagcgggtga   2100
gagcagctcg agcgggtgag agcagctggt gctgtggtga cccgttccca gagcgccctt   2160
ggtttgcctt tctcttcccc aaatcccatt gccagtggct gagacacgaa aggagcactt   2220
gggacaccag ctccaacgcc ctgtcattat ggtcacattg ccttgtcctc cctgggcctg   2280
ctgtgaacgg gatccaggtg gggaaagagg tcaagacagg gagcgatgct gagttcttgg   2340
```

```
ttccctccctt gggccccact tcagctgtcc ttttccagag agtaggacct gctgggaagg    2400
agatgagcct ggggccatta aggaaccttc cttgtcccct gggaagtagc agctgagaga    2460
tagcgagtgt ctggagcgga ggcctctctg aatgggcagg ggtttgtcct tgcaggacag    2520
ggtgcaggca gatgacctgg tgaagatgct cttcagccca aagagatgg tcctctccca     2580 ggagcagccc ctggatgccc agcagggccc ccccgaacct gcacaagagt ctctctcagg    2640
cagtgaatcg aagcccaagg atgagctatg acagcgtcca ggtcagacgg atgggtgact    2700
agacccatgg agaggaactc ttctgcactc tgagctggcc agcccctcgg ggctgcagag    2760
cagtgagcct acatctgcca ctcagccgag gggaccctgc tcacagcctt ctacatggtg    2820
ctactgctct tggagtggac atgaccagac accgcacccc ctggatctgg ctgagggctc    2880
aggacacagg cccagccacc cccaggggcc tccacaggcc gctgcataac agcgatacag    2940
tacttaagtg tctgtgtaga caaccaaaga ataaatgatt catggttttt ttt           2993

<210> SEQ ID NO 72
<211> LENGTH: 736
<212> TYPE: DNA
<213> ORGANISM: Homo sapiens

<400> SEQUENCE: 72
ggctctcacc ctcctctcct gcagctccag ctttgtgctc tgcctctgag gagaccatgg      60
cccggcctct gtgtaccctg ctactcctga tggctaccct ggctggggct ctggcctcga    120
gctccaagga ggagaatagg ataatccag gtggcatcta tgatgcagac ctcaatgatg     180
agtgggtaca gcgtgccctt cacttcgcca tcagcgagta caacaaggcc accgaagatg    240
agtactacag acgcccgctg caggtgctgc gagccaggga gcagaccttt ggggggtga     300 attacttctt cgacgtagag gtgggccgca ccatatgtac caagtcccag cccaacttgg    360
acacctgtgc cttccatgaa cagccagaac tgcagaagaa acagttgtgc tcttttcgaga   420 tctacgaagt tccctgggag gacagaatgt ccctggtgaa ttccaggtgt caagaagcct    480 agggtctgt gccaggccag tcacaccgac caccacccac tcccacccac tgtagtgctc     540 ccaccctgg actggtggcc cccacctgc gggaggcctc cccatgtgcc tgtgccaaga     600
gacagacaga gaaggctgca ggagtccttt gttgctcagc agggcgctct gccctccctc    660
cttccttctt gcttctaata gacctggtac atggtacaca caccccccacc tcctgcaatt   720 aaacagtagc atcgcc                                                    736

<210> SEQ ID NO 73
<211> LENGTH: 2820
<212> TYPE: DNA
<213> ORGANISM: Homo sapiens

<400> SEQUENCE: 73
ggcgggttcg cgccccgaag gctgagagct ggcgctgctc gtgccctgtg tgccagacgg      60
cggagctccg cggccggacc ccgcggcccc gctttgctgc cgactggagt ttggggggaag   120 aaactctcct gcgccccaga agattctttc ctcggcgaag ggacagcgaa agatgagggt    180
ggcaggaaga gaaggcgctt tctgtctgcc ggggtcgcag cgcgagaggg cagtgccatg    240
ttcctctcca tcctagtggc gctgtgcctg tggctgcacc tggcgctggg cgtgcgcggc    300 gcgcctgcg aggcggtgcg catccctatg tgccggcaca tgcctggaa catcacgcgg      360 atgcccaacc acctgcacca cagcacgcag gagaacgcca tcctggccat cgagcagtac    420
```

```
gaggagctgg tggacgtgaa ctgcagcgcc gtgctgcgct tcttcttctg tgccatgtac    480
gcgcccattt gcaccctgga gttcctgcac gaccctatca agccgtgcaa gtcggtgtgc    540
caacgcgcgc gcgacgactg cgagcccctc atgaagatgt acaaccacag ctggcccgaa    600
agcctggcct gcgacgagct gcctgtctat gaccgtggcg tgtgcatttc gcctgaagcc    660
atcgtcacgg acctcccgga ggatgttaag tggatagaca tcacaccaga catgatggta    720
caggaaaggc ctcttgatgt tgactgtaaa cgcctaagcc ccgatcggtg caagtgtaaa    780
aaggtgaagc caactttggc aacgtatctc agcaaaaact acagctatgt tattcatgcc    840
aaaataaaag ctgtgcagag gagtggctgc aatgaggtca acggtggt ggatgtaaaa     900 gagatcttca agtcctcatc acccatccct cgaactcaag tcccgctcat tacaaattct    960
tcttgccagt gtccacacat cctgccccat caagatgttc tcatcatgtg ttacgagtgg   1020
cgttcaagga tgatgcttct tgaaaattgc ttagttgaaa aatggagaga tcagcttagt   1080
aaaagatcca tacagtggga agagaggctg caggaacagc ggagaacagt tcaggacaag   1140
aagaaaacag ccgggcgcac cagtcgtagt aatccccca aaccaaaggg aaagcctcct    1200
gctcccaaac cagccagtcc caagaagaac attaaaacta ggagtgccca gaagagaaca   1260
aacccgaaaa gagtgtgagc taactagttt ccaaagcgga gacttccgac ttccttacag   1320
gatgaggctg ggcattgcct gggacagcct atgtaaggcc atgtgcccct gccctaaca    1380 actcactgca gtgctcttca tagacacatc ttgcagcatt tttcttaagg ctatgcttca   1440
gttttctttt gtaagccatc acaagccata gtggtaggtt tgccctttgg tacagaaggt   1500
gagttaaagc tggtggaaaa ggcttattgc attgcattca gagtaacctg tgtgcatact   1560
ctagaagagt agggaaaata atgcttgtta caattcgacc taatatgtgc attgtaaaat   1620 aaaatgccata tttcaaacaa aacacgtaat ttttttacag tatgttttat taccttttga   1680
tatctgttgt tgcaatgtta gtgatgtttt aaaatgtgat gaaaatataa tgttttaag    1740 aaggaacagt agtggaatga atgttaaaag atctttatgt gtttatggtc tgcagaagga   1800 ttttgtgat gaaggggat ttttgaaaa attagagaag tagcatatgg aaaattataa     1860 tgtgttttt taccaatgac ttcagtttct gttttagct agaaacttaa aaacaaaat    1920 aataataaag aaaaataaat aaaaaggaga ggcagacaat gtctggattc ctgttttttg   1980
gttacctgat ttccatgatc atgatgcttc ttgtcaacac cctcttaagc agcaccagaa   2040
acagtgagtt tgtctgtacc attaggagtt aggtactaat tagttggcta atgctcaagt   2100
attttatacc cacaagagag gtatgtcact catcttactt cccaggacat ccaccctgag   2160
aataatttga caagcttaaa aatggccttc atgtgagtgc caaattttgt ttttcttcat   2220
ttaaatattt tctttgccta aatacatgtg agaggagtta aatataaatg tacagagagg   2280
aaagttgagt tccacctctg aaatgagaat tacttgacag ttgggatact ttaatcagaa   2340
aaaaagaact tatttgcagc atttttatcaa caaatttcat aattgtggac aattggaggc   2400 attatttta aaaacaatt ttattggcct tttgctaaca cagtaagcat gtattttata    2460
aggcattcaa taaatgcaca acgcccaaag gaaataaaat cctatctaat cctactctcc   2520
actacacaga ggtaatcact attagtattt tggcatatta ttctccaggt gtttgcttat   2580
gcacttataa aatgatttga acaaataaaa ctaggaacct gtatacatgt gtttcataac   2640
ctgcctcctt tgcttggccc tttattgaga taagttttcc tgtcaagaaa gcagaaacca   2700
tctcatttct aacagctgtg ttatattcca tagtatgcat tactcaacaa actgttgtgc   2760
tattggatac ttaggtggtt tcttcactga caatactgaa taaacatctc accggaattc   2820
```

<210> SEQ ID NO 74
<211> LENGTH: 2480
<212> TYPE: DNA
<213> ORGANISM: Homo sapiens

<400> SEQUENCE: 74

| | | | | | |
|---|---|---|---|---|---|
| agtactaaca | tggactaatc | tgtgggagca | gtttattcca | gtatcaccca | gggtgcagcc | 60 |
| acaccaggac | tgtgttgaag | ggtgttttt | ttcttttaaa | tgtaatacct | cctcatcttt | 120 |
| tcttcttaca | cagtgtctga | gaacatttac | attatagata | agtagtacat | ggtggataac | 180 |
| ttctactttt | aggaggacta | ctctcttctg | acagtcctag | actggtcttc | tacactaaga | 240 |
| caccatgaag | gagtatgtgc | tcctattatt | cctggctttg | tgctctgcca | aacccttctt | 300 |
| tagcccttca | cacatcgcac | tgaagaatat | gatgctgaag | gatatggaag | acacagatga | 360 |
| tgatgatgat | gatgatgatg | atgatgatga | tgatgatgag | gacaactctc | tttttccaac | 420 |
| aagagagcca | agaagccatt | ttttccatt | tgatctgttt | ccaatgtgtc | catttggatg | 480 |
| tcagtgctat | tcacgagttg | tacattgctc | agatttaggt | ttgacctcag | tcccaaccaa | 540 |
| cattccattt | gatactcgaa | tgcttgatct | tcaaaacaat | aaaattaagg | aaatcaaaga | 600 |
| aaatgatttt | aaaggactca | cttcacttta | tggtctgatc | ctgaacaaca | acaagctaac | 660 |
| gaagattcac | ccaaaagcct | ttctaaccac | aaagaagttg | cgaaggctgt | atctgtccca | 720 |
| caatcaacta | agtgaaatac | cacttaatct | tcccaaatca | ttagcagaac | tcagaattca | 780 |
| tgaaaataaa | gttaagaaaa | tacaaaagga | cacattcaaa | ggaatgaatg | ctttacacgt | 840 |
| tttggaaatg | agtgcaaacc | ctcttgataa | taatgggata | gagccagggg | catttgaagg | 900 |
| ggtgacggtg | ttccatatca | gaattgcaga | agcaaaactg | acctcagttc | ctaaaggctt | 960 |
| accaccaact | ttattggagc | ttcacttaga | ttataataaa | atttcaacag | tggaacttga | 1020 |
| ggatttaaa | cgatacaaag | aactacaaag | gctgggccta | ggaacaaca | aaatcacaga | 1080 |
| tatcgaaaat | gggagtcttg | ctaacatacc | acgtgtgaga | gaaatacatt | tggaaaacaa | 1140 |
| taaactaaaa | aaaatccctt | caggattacc | agagttgaaa | tacctccaga | taatcttcct | 1200 |
| tcattctaat | tcaattgcaa | gagtgggagt | aaatgacttc | tgtccaacag | tgccaaagat | 1260 |
| gaagaaatct | ttatacagtg | caataagttt | attcaacaac | ccggtgaaat | actgggaaat | 1320 |
| gcaacctgca | acatttcgtt | gtgttttgag | cagaatgagt | gttcagcttg | gaacttttgg | 1380 |
| aatgtaataa | ttagtaattg | gtaatgtcca | tttaatataa | gattcaaaaa | tccctacatt | 1440 |
| tggaatactt | gaactctatt | aataatggta | gtattatata | tacaagcaaa | tatctattct | 1500 |
| caagtggtaa | gtccactgac | ttattttatg | acaagaaatt | tcaacggaat | tttgccaaac | 1560 |
| tattgataca | taagggttga | gagaaacaag | catctattgc | agtttctttt | tgcgtacaaa | 1620 |
| tgatcttaca | taaatctcat | gcttgaccat | tcctttcttc | ataacaaaaa | agtaagatat | 1680 |
| tcggtattta | acactttgtt | atcaagcata | ttttaaaaag | aactgtactg | taaatggaat | 1740 |
| gcttgactta | gcaaaatttg | tgctctttca | tttgctgtta | gaaaaacaga | attaacaaag | 1800 |
| acagtaatgt | gaagagtgca | ttacactatt | cttattcttt | agtaacttgg | gtagtactgt | 1860 |
| aatatttta | atcatcttaa | agtatgattt | gatataatct | tattgaaatt | accttatcat | 1920 |
| gtccttagagc | ccgtctttat | gtttaaaact | aatttcttaa | aataaagcct | tcagtaaatg | 1980 |
| ttcattacca | acttgataaa | tgctactcat | aagagctggt | ttggggctat | agcatatgct | 2040 |
| tttttttttt | taattattac | ctgatttaaa | aatctctgta | aaaacgtgta | gtgtttcata | 2100 |

| | |
|---|---:|
| aaatctgtaa ctcgcatttt aatgatccgc tattataagc ttttaatagc atgaaaattg | 2160 |
| ttaggctata taacattgcc acttcaactc taaggaatat ttttgagata tccctttgga | 2220 |
| agaccttgct tggaagagcc tggacactaa caattctaca ccaaattgtc tcttcaaata | 2280 |
| cgtatggact ggataactct gagaaacaca tctagtataa ctgaataagc agagcatcaa | 2340 |
| attaaacaga cagaaaccga aagctctata taaatgctca gagttctttta tgtatttctt | 2400 |
| attggcattc aacatatgta aaatcagaaa acagggaaat tttcattaaa aatattggtt | 2460 |
| tgaaataaaa aaaaaaaaaa | 2480 |

```
<210> SEQ ID NO 75
<211> LENGTH: 1887
<212> TYPE: DNA
<213> ORGANISM: Homo sapiens

<400> SEQUENCE: 75
```

| | |
|---|---:|
| cgcgcagccc ctccggccgc gggcgcagcg ggggcgctgg tggagctgcg aagggccagg | 60 |
| tccggcgggc ggggcggcgg ctggcactgg ctccggactc tgcccggcca gggcggcggc | 120 |
| tccagccggg agggcgacgt ggagcggcca cgtggagcgg cccgggggag gctggcggcg | 180 |
| ggaggcgagg cgcgggcggc gcagcagcca ggagcgccca cggagctgga ccccccagagc | 240 |
| cgcgcggcgc cgcagcagtt ccaggaagga tgttaccttt gacgatgaca gtgttaatcc | 300 |
| tgctgctgct ccccacgggt caggctgccc caaaggatgg agtcacaagg ccagactctg | 360 |
| aagtgcagca tcagctcctg cccaaccccct tccagccagg ccaggagcag ctcggacttc | 420 |
| tgcagagcta cctaaaggga ctaggaagga cagaagtgca actggagcat ctgagccggg | 480 |
| agcaggttct cctctacctc tttgccctcc atgactatga ccagagtgga cagctggatg | 540 |
| gcctggagct gctgtccatg ttgacagctg ctctggcccc tggagctgcc aactctccta | 600 |
| ccaccaaccc ggtgatattg atagtggaca aagtgctcga gacgcaggac ctgaatgggg | 660 |
| atgggctcat gaccccctgct gagctcatca acttcccggg agtagccctc aggcacgtgg | 720 |
| agcccggaga gccccttgct ccatctcctc aggagccaca agctgttgga aggcagtccc | 780 |
| tattagctaa aagcccatta agacaagaaa cacaggaagc ccctggtccc agagaagaag | 840 |
| caaagggcca ggtagaggcc agaagggagt ctttggatcc tgtccaggag cctgggggcc | 900 |
| aggcagaggc tgatggagat gttccagggc ccagagggga agctgaggc caggcagagg | 960 |
| ctaaaggaga tgcccctggg cccagagggg aagctggggg ccaggcagag gctgaaggag | 1020 |
| atgcccccgg gccagagggg gaagctgggg gccaggcaga ggccagggag aatggagagg | 1080 |
| aggccaagga acttccaggg gaaacactgg agtctaagaa cacccaaaat gactttgagg | 1140 |
| tgcacattgt tcaagtggag aatgatgaga tctagatctt gaagatacag gtaccccacg | 1200 |
| aagtctcagt gccagaacat aagccctgaa gtgggcaggg gaaatgtacg ctgggacaag | 1260 |
| gaccatctct gtgcccctg tctggtccca gtaggtatca ggtctttctg tgcagctcag | 1320 |
| ggagaccta agttaagggg cagattacca ataaagaact gaatgaattc atcccccgg | 1380 |
| gccacctctc tacccgtcca gcctgcccag accctctcag aggaacgggg ttggggaccg | 1440 |
| aaaggacagg gatgccgcct gcccagtgtt tctgggcctc acggtgctcc ggcagcagag | 1500 |
| cgcatggtgc tagccatggc cggctgcaga ggacccagtg aggaaagctc agtctatccc | 1560 |
| tgggccccaa accctcaccg gttccccctc acctggtgtt cagacacccc atgctctcct | 1620 |
| gcagctcagg gcaggtgacc ccatcccag taatattaat catcactaga acttttttgag | 1680 |
| agccttgtac acatcaggca tcatgctggg cattttatat atgatttat cctcacaata | 1740 |

```
attctgtagc caagcagaat tggttccatt tgacagatga agaaattgag gcagattgcg    1800
ttaagtgctg taccctaagg tgatatgcag ctaattaaat ggcagatttg aaaaaaaaaa    1860
aaaaaaaaaa aaaaaaaaaa aaaaaaa                                        1887
```

<210> SEQ ID NO 76
<211> LENGTH: 1580
<212> TYPE: DNA
<213> ORGANISM: Homo sapiens

<400> SEQUENCE: 76

```
catcctgcca cccctagcct tgctggggac gtgaaccctc tccccgcgcc tgggaagcct      60
tcttggcacc gggacccgga gaatccccac ggaagccagt tccaaaaggg atgaaaaggg     120
ggcgtttcgg gcactgggag aagcctgtat tccaggggcc ctcccagagc aggaatctgg     180
gacccaggag tgccagcctc acccacgcag atcctggcca tgagagctcc gcacctccac     240
ctctccgccg cctctggcgc ccgggctctg gcgaagctgc tgccgctgct gatggcgcaa     300
ctctgggccg cagaggcggc gctgctcccc caaaacgaca cgcgcttgga ccccgaagcc     360
tatggctccc cgtgcgcgcg cggctcgcag ccctggcagg tctcgctctt caacggcctc     420
tcgttccact gcgcgggtgt cctggtggac cagagttggg tgctgacggc cgcgcactgc     480
ggaaacaagc cactgtgggc tcgagtaggg gatgaccacc tgctgcttct tcagggagag     540
cagctccgcc ggaccactcg ctctgttgtc catcccaagt accaccaggg ctcaggcccc     600
atcctgccaa ggcgaacgga tgagcacgat tcatgttgc tgaagctggc caggcccgta     660
gtgctggggc ccgcgtccg ggccctgcag cttccctacc gctgtgctca gcccggagac     720
cagtgccagg ttgctggctg gggcaccacg gccgcccgga gagtgaagta caacaagggc     780
ctgacctgct ccagcatcac tatcctgagc cctaaagagt gtgaggtctt ctaccctggc     840
gtggtcacca caacatgat atgtgctgga ctggaccggg gccaggaccc ttgccagagt     900
gactctggag gcccctggt ctgtgacgag accctccaag gcatcctctc gtggggtgtt     960
tacccctgtg gctctgccca gcatccagct gtctacaccc agatctgcaa atacatgtcc    1020
tggatcaata aagtcatacg ctccaactga tccagatgct acgctccagc tgatccagat    1080
gttatgctcc tgctgatcca gatgcccaga ggctccatcg tccatcctct tcctccccag    1140
tcggctgaac tctccccttg tctgcactgt tcaaacctct gccgcccctcc acacctctaa    1200 acatctcccc tctcacctca ttcccccacc tatccccatt ctctgcctgt actgaagctg    1260
aaatgcagga agtggtggca aaggtttatt ccagagaagc caggaagccg gtcatcaccc    1320
agcctctgag agcagttact ggggtcaccc aacctgactt cctctgccac tccctgctgt    1380
gtgactttgg gcaagccaag tgccctctct gaacctcagt ttcctcatct gcaaaatggg    1440
aacaatgacg tgcctaccte ttagacatgt tgtgaggaga ctatgatata acatgtgtat    1500
gtaaatcttc atggtgattg tcatgtaagg cttaacacag tgggtggtga gttctgacta    1560
aaggttacct gttgtcgtga                                                1580
```

<210> SEQ ID NO 77
<211> LENGTH: 1443
<212> TYPE: DNA
<213> ORGANISM: Homo sapiens

<400> SEQUENCE: 77

```
accagcggca gaccacaggc agggcagagg cacgtctggg tcccctcccct ccttcctatc     60
```

```
ggcgactccc aggatcctgg ccatgagagc tccgcacctc cacctctccg ccgcctctgg      120
cgcccgggct ctggcgaagc tgctgccgct gctgatggcg caactctggg ccgcagaggc      180
ggcgctgctc ccccaaaacg acacgcgctt ggaccccgaa gcctatggct ccccgtgcgc      240
gcgcggctcg cagccctggc aggtctcgct cttcaacggc ctctcgttcc actgcgcggg      300
tgtcctggtg gaccagagtt gggtgctgac ggccgcgcac tgcggaaaca agccactgtg      360
ggctcgagta ggggatgacc acctgctgct tcttcaggga gagcagctcc gccggaccac      420
tcgctctgtt gtccatccca agtaccacca gggctcaggc ccatcctgc caaggcgaac       480
ggatgagcac gatctcatgt tgctgaagct ggccaggccc gtagtgctgg ggccccgcgt      540
ccgggccctg cagcttccct accgctgtgc tcagcccgga gaccagtgcc aggttgctgg      600
ctggggcacc acggccgccc ggagagtgaa gtacaacaag ggcctgacct gctccagcat      660
cactatcctg agccctaaag agtgtgaggt cttctaccct ggcgtggtca ccaacaacat      720
gatatgtgct ggactggacc ggggccagga cccttgccag agtgactctg gaggccccct      780
ggtctgtgac gagaccctcc aaggcatcct ctcgtggggt gtttacccct gtggctctgc      840
ccagcatcca gctgtctaca cccagatctg caaatacatg tcctggatca ataaagtcat      900
acgctccaac tgatccagat gctacgctcc agctgatcca gatgttatgc tcctgctgat      960
ccagatgccc agaggctcca tcgtccatcc tcttcctccc cagtcggctg aactctcccc     1020
ttgtctgcac tgttcaaacc tctgccgccc tccacacctc taaacatctc ccctctcacc     1080
tcattccccc acctatcccc attctctgcc tgtactgaag ctgaaatgca ggaagtggtg     1140
gcaaaggttt attccagaga agccaggaag ccggtcatca cccagcctct gagagcagtt     1200
actggggtca cccaacctga cttcctctgc cactccctgc tgtgtgactt tgggcaagcc     1260
aagtgccctc tctgaacctc agtttcctca tctgcaaaat gggaacaatg acgtgcctac     1320
ctcttagaca tgttgtgagg agactatgat ataacatgtg tatgtaaatc ttcatggtga     1380
ttgtcatgta aggcttaaca cagtgggtgg tgagttctga ctaaaggtta cctgttgtcg     1440
tga                                                                   1443
```

<210> SEQ ID NO 78
<211> LENGTH: 782
<212> TYPE: DNA
<213> ORGANISM: Homo sapiens

<400> SEQUENCE: 78

```
aggggcctta gcgtgccgca tcgccgagat ccagcgccca gagagacacc agagaaccca       60
ccatggcccc ctttgagccc ctggcttctg gcatcctgtt gttgctgtgg ctgatagccc      120
ccagcagggc ctgcacctgt gtcccacccc acccacagac ggccttctgc aattccgacc      180
tcgtcatcag ggccaagttc gtggggacac cagaagtcaa ccagaccacc ttataccagc      240
gttatgagat caagatgacc aagatgtata aagggttcca agcttagggg atgccgctg      300
acatccggtt cgtctacacc cccgccatgg agagtgtctg cggatacttc acaggtccc       360
acaaccgcag cgaggagttt ctcattgctg gaaaactgca ggatggactc ttgcacatca      420
ctacctgcag tttcgtggct ccctggaaca ggctgagctt agctcagcgc cggggcttca      480
ccaagaccta cactgttggc tgtgaggaat gcacagtgtt tccctgtttta tccatccct      540
gcaaactgca gagtggcact cattgcttgt ggacggacca gctcctccaa ggctctgaaa      600
agggcttcca gtcccgtcac cttgcctgcc tgcctcggga gccagggctg tgcacctggc      660
agtccctgcg gtcccagata gcctgaatcc tgcccggagt ggaactgaag cctgcacagt      720
```

| | | |
|---|---|---|
| gtccaccctg ttcccactcc catctttctt ccggacaatg aaataaagag ttaccaccca | 780 | |
| gc | 782 | |

<210> SEQ ID NO 79
<211> LENGTH: 3178
<212> TYPE: DNA
<213> ORGANISM: Homo sapiens

<400> SEQUENCE: 79

| | |
|---|---|
| gttgcctgtc tctaaacccc tccacattcc cgcggtcctt cagactgccc ggagagcgcg | 60 |
| ctctgcctgc cgcctgcctg cctgccactg agggttccca gcaccatgag ggcctggatc | 120 |
| ttctttctcc tttgcctggc cgggagggcc ttggcagccc ctcagcaaga agccctgcct | 180 |
| gatgagacag aggtggtgga agaaactgtg gcagaggtga ctgaggtatc tgtgggagct | 240 |
| aatcctgtcc aggtggaagt aggagaattt gatgatggtg cagaggaaac cgaagaggag | 300 |
| gtggtggcgg aaaatccctg ccagaaccac cactgcaaac acggcaaggt gtgcgagctg | 360 |
| gatgagaaca caccccccat gtgcgtgtgc caggacccca ccagctgccc agccccccatt | 420 |
| ggcgagtttg agaaggtgtg cagcaatgac aacaagacct tcgactcttc ctgccacttc | 480 |
| tttgccacaa agtgcaccct ggagggcacc aagaagggcc acaagctcca cctggactac | 540 |
| atcgggcctt gcaaatacat ccccccttgc ctggactctg agctgaccga attcccctg | 600 |
| cgcatgcggg actggctcaa gaacgtcctg gtcaccctgt atgagaggga tgaggacaac | 660 |
| aaccttctga ctgagaagca gaagctgcgc gtgaagaaga tccatgagaa tgagaagcgc | 720 |
| ctggaggcag agaccacccc cgtggagctg ctggcccggg acttcgagaa gaactataac | 780 |
| atgtacatct tccctgtaca ctggcagttc ggccagctgg accagcaccc cattgacggg | 840 |
| tacctctccc acaccgagct ggctccactg cgtgctcccc tcatccccat ggagcattgc | 900 |
| accacccgct ttttcgagac ctgtgacctg gacaatgaca agtacatcgc cctggatgag | 960 |
| tgggccggct gcttcggcat caagcagaag gatatcgaca aggatcttgt gatctaaatc | 1020 |
| cactccttcc acagtaccgg attctctctt taaccctccc cttcgtgttt ccccaatgt | 1080 |
| ttaaaatgtt tggatggttt gttgttctgc ctggagacaa ggtgctaaca tagatttaag | 1140 |
| tgaatacatt aacggtgcta aaaatgaaaa ttctaaccca agacatgaca ttcttagctg | 1200 |
| taacttaact attaaggcct tttccacacg cattaatagt cccatttttc tcttgccatt | 1260 |
| tgtagctttg cccattgtct tattggcaca tgggtggaca cggatctgct gggctctgcc | 1320 |
| ttaaacacac attgcagctt caacttttct ctttagtgtt ctgtttgaaa ctaatactta | 1380 |
| ccgagtcaga ctttgtgttc atttcatttc agggtcttgg ctgcctgtgg gcttccccag | 1440 |
| gtggcctgga ggtgggcaaa gggaagtaac agacacacga tgttgtcaag gatggttttg | 1500 |
| ggactagagg ctcagtggtg ggagagatcc ctgcagaacc caccaaccag aacgtggttt | 1560 |
| gcctgaggct gtaactgaga gaaagattct ggggctgtgt tatgaaaata tagacattct | 1620 |
| cacataagcc cagttcatca ccatttcctc ctttaccttt cagtgcagtt tcttttcaca | 1680 |
| ttaggctgtt ggttcaaact tttgggagca cggactgtca gttctctggg aagtggtcag | 1740 |
| cgcatcctgc agggcttctc ctcctctgtc ttttggagaa ccaggctct ctcaggggc | 1800 |
| tctagggact gccaggctgt ttcagccagg aaggccaaaa tcaagagtga gatgtagaaa | 1860 |
| gttgtaaaat agaaaagtg gagttggtga atcggttgtt cttccctcac atttggatga | 1920 |
| ttgtcataag gtttttagca tgttcctcct tttcttcacc ctcccctttt ttcttctatt | 1980 |

| | |
|---|---|
| aatcaagaga aacttcaaag ttaatgggat ggtcggatct cacaggctga gaactcgttc | 2040 |
| acctccaagc atttcatgaa aaagctgctt cttattaatc atacaaactc tcaccatgat | 2100 |
| gtgaagagtt tcacaaatcc ttcaaaataa aaagtaatga cttagaaact gccttcctgg | 2160 |
| gtgatttgca tgtgtcttag tcttagtcac cttattatcc tgacacaaaa acacatgagc | 2220 |
| atacatgtct acacatgact acacaaatgc aaaccttttgc aaacacatta tgcttttgca | 2280 |
| cacacacacc tgtacacaca caccggcatg tttatacaca gggagtgtat ggttcctgta | 2340 |
| agcactaagt tagctgtttt catttaatga cctgtggttt aacccttttg atcactacca | 2400 |
| ccattatcag caccagactg agcagctata tccttttatt aatcatggtc attcattcat | 2460 |
| tcattcattc acaaaatatt tatgatgtat ttactctgca ccaggtccca tgccaagcac | 2520 |
| tggggacaca gttatggcaa agtagacaaa gcatttgttc atttggagct tagagtccag | 2580 |
| gaggaataca ttagataatg acacaatcaa atataaattg caagatgtca caggtgtgat | 2640 |
| gaagggagag taggagagac catgagtatg tgtaacagga ggacacagca ttattctagt | 2700 |
| gctgtactgt tccgtacggc agccactacc cacatgtaac tttttaagat ttaaatttaa | 2760 |
| attagttaac attcaaaacg cagctcccca atcacactag caacatttca agtgcttgag | 2820 |
| agccatgcat gattagtggt taccctattg aataggtcag aagtagaatc ttttcatcat | 2880 |
| cacagaaagt tctattggac agtgctcttc tagatcatca taagactaca gagcactttt | 2940 |
| caaagctcat gcatgttcat catgttagtg tcgtattttg agctgggtt ttgagactcc | 3000 |
| ccttagagat agagaaacag acccaagaaa tgtgctcaat tgcaatgggc cacatacca | 3060 |
| gatctccaga tgtcatttcc cctctcttat tttaagttat gttaagatta ctaaaacaat | 3120 |
| aaaagctcct aaaaaatcaa aaaaaaaaaa aaaaaaaaaa aaaaaaaaaa aaaaaaa | 3178 |

<210> SEQ ID NO 80
<211> LENGTH: 2691
<212> TYPE: DNA
<213> ORGANISM: Homo sapiens

<400> SEQUENCE: 80

| | |
|---|---|
| gcttgcccgt cggtcgctag ctcgctcggt gcgcgtcgtc ccgctccatg gcgctcttcg | 60 |
| tgcggctgct ggctctcgcc ctggctctgg ccctgggccc cgccgcgacc ctggcgggtc | 120 |
| ccgccaagtc gccctaccag ctggtgctgc agcacagcag gctccggggc cgccagcacg | 180 |
| gccccaacgt gtgtgctgtg cagaaggtta ttggcactaa taggaagtac ttcaccaact | 240 |
| gcaagcagtg gtaccaaagg aaaatctgtg gcaaatcaac agtcatcagc tacgagtgct | 300 |
| gtcctggata tgaaaaggtc cctggggaga agggctgtcc agcagcccta ccactctcaa | 360 |
| acctttacga gaccctggga gtcgttggat ccaccaccac tcagctgtac acggaccgca | 420 |
| cggagaagct gaggcctgag atggaggggc ccggcagctt caccatcttc gcccctagca | 480 |
| acgaggcctg ggcctccttg ccagctgaag tgctggactc cctggtcagc aatgtcaaca | 540 |
| ttgagctgct caatgccctc cgctaccata tggtgggcag gcgagtcctg actgatgagc | 600 |
| tgaaacacgg catgaccctc acctctatgt accagaattc caacatccag atccaccact | 660 |
| atcctaatgg gattgtaact gtgaactgtg cccggctcct gaaagccgac caccatgcaa | 720 |
| ccaacgggt ggtgcacctc atcgataagg tcatctccac catcaccaac aacatccagc | 780 |
| agatcattga gatcgaggac accttgaga cccttcgggc tgctgtggct gcatcagggc | 840 |
| tcaacacgat gcttgaaggt aacgccagt acacgctttt ggccccgacc aatgaggcct | 900 |
| tcgagaagat ccctagtgag actttgaacc gtatcctggg cgacccagaa gccctgagag | 960 |

```
acctgctgaa caaccacatc ttgaagtcag ctatgtgtgc tgaagccatc gttgcggggc    1020
tgtctgtaga gaccctggag ggcacgacac tggaggtggg ctgcagcggg gacatgctca    1080
ctatcaacgg gaaggcgatc atctccaata aagacatcct agccaccaac ggggtgatcc    1140
actacattga tgagctactc atcccagact cagccaagac actatttgaa ttggctgcag    1200
agtctgatgt gtccacagcc attgaccttt tcagacaagc cggcctcggc aatcatctct    1260
ctggaagtga gcggttgacc ctcctggctc ccctgaattc tgtattcaaa gatggaaccc    1320
ctccaattga tgcccataca aggaatttgc ttcggaacca cataattaaa gaccagctgg    1380
cctctaagta tctgtaccat ggacagaccc tggaaactct gggcggcaaa aaactgagag    1440
tttttgttta tcgtaatagc ctctgcattg agaacagctg catcgcggcc cacgacaaga    1500
gggggaggta cgggaccctg ttcacgatgg accgggtgct gacccccca atggggactg    1560 tcatggatgt cctgaaggga gacaatcgct ttagcatgct ggtagctgcc atccagtctg    1620
caggactgac ggagaccctc aaccgggaag gagtctacac agtctttgct cccacaaatg    1680
aagccttccg agccctgcca ccaagagaac ggagcagact cttgggagat gccaaggaac    1740
ttgccaacat cctgaaatac cacattggtg atgaaatcct ggttagcgga ggcatcgggg    1800
ccctggtgcg gctaaagtct ctccaaggtg acaagctgga agtcagcttg aaaaacaatg    1860
tggtgagtgt caacaaggag cctgttgccg agcctgacat catggccaca aatggcgtgg    1920
tccatgtcat caccaatgtt ctgcagcctc agccaacag acctcaggaa agaggggatg    1980
aacttgcaga ctctgcgctt gagatcttca acaagcatc agcgttttcc agggcttccc    2040
agaggtctgt gcgactagcc cctgtctatc aaaagttatt agagaggatg aagcattagc    2100
ttgaagcact acaggaggaa tgcaccacgg cagctctccg ccaatttctc tcagatttcc    2160
acagagactg tttgaatgtt tcaaaaacca agtatcacac tttaatgtac atgggccgca    2220
ccataatgag atgtgagcct tgtgcatgtg ggggaggagg gagagagatg tacttttttaa    2280 atcatgttcc ccctaaacat ggctgttaac ccactgcatg cagaaacttg gatgtcactg    2340
cctgacattc acttccagag aggacctatc ccaaatgtgg aattgactgc ctatgccaag    2400
tccctggaaa aggagcttca gtattgtggg gctcataaaa catgaatcaa gcaatccagc    2460
ctcatgggaa gtcctggcac agttttttgta aagcccttgc acagctggag aaatggcatc    2520
attataagct atgagttgaa atgttctgtc aaatgtgtct cacatctaca cgtggcttgg    2580
aggcttttat ggggccctgt ccaggtagaa agaaatggt atgtagagct tagatttccc    2640
tattgtgaca gagccatggt gtgtttgtaa taataaaacc aaagaaacat a    2691

<210> SEQ ID NO 81
<211> LENGTH: 1757
<212> TYPE: DNA
<213> ORGANISM: Homo sapiens

<400> SEQUENCE: 81
caagcttggc acgagggcag gcattgcccg agccagccga gccgccagag ccgcgggccg    60
cgcgggtgtc gcgggcccaa ccccaggatg ctcccctgcg cctcctgcct acccgggtct    120
ctactgctct gggcgctgct actgttgctc ttgggatcag cttctcctca ggattctgaa    180
gagcccgaca gctacacgga atgcacagat ggctatgagt gggacccaga cagccagcac    240
tgccgggatg tcaacgagtg tctgaccatc cctgaggcct gcaagggga atgaagtgc    300 atcaaccact acggggcta cttgtgcctg ccccgctccg ctgccgtcat caacgaccta    360
```

```
cacggcgagg gaccccgcc accagtgcct cccgctcaac accccaaccc ctgcccacca    420
ggctatgagc ccgacgatca ggacagctgt gtggatgtgg acgagtgtgc ccaggccctg    480
cacgactgtc gccccagcca ggactgccat aacttgcctg gctcctatca gtgcacctgc    540
cctgatggtt accgcaagat cgggcccgag tgtgtggaca tagacgagtg ccgctaccgc    600
tactgccagc accgctgcgt gaacctgcct ggctccttcc gctgccagtg cgagccgggc    660
ttccagctgg ggcctaacaa ccgctcctgt gttgatgtga acgagtgtga catgggggcc    720
ccatgcgagc agcgctgctt caactcctat gggaccttcc tgtgtcgctg ccaccagggc    780
tatgagctgc atcgggatgg cttctcctgc agtgatattg atgagtgtag ctactccagc    840
tacctctgtc agtaccgctg cgtcaacgag ccaggccgtt tctcctgcca ctgcccacag    900
ggttaccagc tgctgccacac acgcctctgc aagacattg atgagtgtga gtctggtgcg    960
caccagtgct ccgaggccca aacctgtgtc aacttccatg ggggctaccg ctgcgtggac   1020
accaaccgct gcgtggagcc ctacatccag gtctctgaga accgctgtct ctgcccggcc   1080
tccaaccctc tatgtcgaga gcagccttca tccattgtgc accgctacat gaccatcacc   1140
tcggagcgga gagtacccgc tgacgtgttc cagatccagg cgacctccgt ctaccccggt   1200
gcctacaatg cctttcagat ccgtgctgga aactcgcagg gggacttta cattaggcaa   1260 atcaacaacg tcagcgccat gctggtcctc gcccggccgg tgacgggccc ccgggagtac   1320
gtgctggacc tggagatggt caccatgaat ccctcatga gctaccgggc cagctctgta   1380
ctgaggctca ccgtctttgt aggggcctac accttctgag gagcaggagg gagccaccct   1440
ccctgcagct accctagctg aggagcctgt tgtgaggggc agaatgagaa aggcccaggg   1500 gccccccattg acaggagctg ggagctctgc accacgagct tcagtcaccc cgagaggaga   1560
ggaggtaacg aggagggcgg actccaggcc ccggcccaga gatttggact tggctggctt   1620 gcagggggtcc taagaaactc cactctggac agcgccagga ggccctgggt tccattccta   1680
actctgcctc aaactgtaca tttggataag ccctagtagt tccctgggcc tgttttttcta   1740 taaaacgagg caactgg                                                  1757
```

<210> SEQ ID NO 82
<211> LENGTH: 1804
<212> TYPE: DNA
<213> ORGANISM: Homo sapiens

<400> SEQUENCE: 82

```
gtatcactca gaatctggca gccagttccg tcctgacaga gttcacagca tatattggtg     60
gattcttgtc catagtgcat ctgctttaag aattaacgaa agcagtgtca agacagtaag    120
gattcaaacc atttgccaaa aatgagtcta agtgcattta ctctcttcct ggcattgatt    180
ggtggtacca gtggccagta ctatgattat gattttcccc tatcaattta tgggcaatca    240
tcaccaaact gtgcaccaga atgtaactgc cctgaaagct acccaagtgc catgtactgt    300
gatgagctga aattgaaaag tgtaccaatg gtgcctcctg gaatcaagta tctttacctt    360
aggaataacc agattgacca tattgatgaa aaggcctttg agaatgtaac tgatctgcag    420
tggctcattc tagatcacaa ccttctagaa aactccaaga taaagggag agttttctct    480 aaaattgaaac aactgaagaa gctgcatata aaccacaaca acctgacaga gtctgtgggc    540
ccacttccca atctctgga ggatctgcag cttactcata caagatcac aaagctgggc    600 tcttttgaag gattggtaaa cctgaccttc atccatctcc agcacaatcg gctgaaagag    660
gatgctgttt cagctgcttt taaaggtctt aaatcactcg aataccttga cttgagcttc    720
```

```
aatcagatag ccagactgcc ttctggtctc cctgtctctc ttctaactct ctacttagac      780
aacaataaga tcagcaacat ccctgatgag tatttcaagc gttttaatgc attgcagtat      840
ctgcgtttat ctcacaacga actggctgat agtggaatac ctggaaattc tttcaatgtg      900
tcatccctgg ttgagctgga tctgtcctat aacaagctta aaacatacc aactgtcaat       960 gaaaaccttg aaaactatta cctggaggtc aatcaacttg agaagtttga cataaagagc     1020
ttctgcaaga tcctggggcc attatcctac tccaagatca agcatttgcg tttggatggc     1080
aatcgcatct cagaaaccag tcttccaccg atatgtatg aatgtctacg tgttgctaac      1140
gaagtcactc ttaattaata tctgtatcct ggaacaatat tttatggtta tgttttctg     1200 tgtgtcagtt ttcatagtat ccatatttta ttactgttta ttacttccat gaattttaaa    1260
atctgaggga aatgttttgt aaacatttat tttttttaaa gaaagatgaa aaggcaggcc    1320
tatttcatca aagaacaca cacatataca cgaatagaca tcaaactcaa tgctttattt     1380
gtaaatttag tgtttttta tttctactgt caaatgatgt gcaaaacctt ttactggttg     1440
catggaaatc agccaagttt tataatcctt aaatcttaat gttcctcaaa gcttggatta    1500
aatacatatg gatgttactc tcttgcacca aattatcttg atacattcaa atttgtctgg    1560
ttaaaaaata ggtggtagat attgaggcca agaatattgc aaaatacatg aagcttcatg   1620
cacttaaaga agtattttta gaataagaat ttgcatactt acctagtgaa acttttctag   1680
aattattttt cactctaagt catgtatgtt tctctttgat tatttgcatg ttatgtttaa    1740
taagctacta gcaaaataaa acatagcaaa tgaaaaaaaa aaaaaaaaaa aaaaaaaaa     1800 aaaa                                                                 1804

<210> SEQ ID NO 83
<211> LENGTH: 3290
<212> TYPE: DNA
<213> ORGANISM: Homo sapiens

<400> SEQUENCE: 83
agcggggccg gaccgggcgg gcggagccgg gcccgcgggg ctgctgcggg gcgatcgggc      60
cgggccgctg ccgcgccatg gactcccgtg tccagcctga gttccagcct cactgagtgg     120 ccaccccaa agtgctgcca gccgaggaag cccccagcac tgaccatgtc tattatggac      180
cacagcccca ccacgggcgt ggtcacagtc atcgtcatcc tcattgccat cgcggccctg     240
ggggccttga tcctgggctg ctggtgctac ctgcggctgc agcgcatcag ccagtcagag     300
gacgaggaga gcatcgtggg ggatggggag accaaggaac ccttcctgct ggtgcagtat     360
tcggccaagg gaccgtgcgt ggagagaaag gccaagctga tgactcccaa cggcccggaa     420 gtccacgggct gagccaggat gcaaggctcc tggtcctgtt tgcagccggc caagaggcgc    480
tgggaggggc aaaaccatac ggatgcgctg ctgtctgaga ggaagggctg acacttgctg     540
gcatggcctc tgcgggcttc gtcatcgcat gcactgatgc ccggggacct ggctgtcctg     600
ggcttcccct cggcctccag gtgaggctgc ccattgcagg cactgggcag gcctgacctt     660 gctgggctc atggccctgt agcgcttttg ttacttgaat gtctagctga gcctgttttt      720
gatggagcta ctactgtaat gcgtgaacta acaaacctgt gaactgtaaa taggcccctg    780
gaagcacgtg cttaagccct tttgctgatt tttaaaaata tcatctagcg cacacgggac    840
tggtattctg gctgtactaa tgacaagctg agtcaagacc ctggagggtc ataggcttgt    900
aaaggcccac gccacactcg gcaggggtct ctcatgtgtg tccatctgcg tgtatgtcaa    960
```

```
ggaagtgaga tgccaatttg gggtcttgag gctgaccagt tggggtgctt gggtgatctc    1020
tgcttcatta gtcatgggtg gaagaaaaac cacaccccc gcaccctcc gttctttctg      1080
catagactca cttgttaaat agcagttctg ttgagagtgg agttactgca gggaagctac    1140
cggacctgcc tgggagccag tgaagggcga gtcaggcac cgtcctgga ggctgccagc      1200
gtccttgtag cagagcagtt tcttgccgct tgggtcttca gcacgccaag ccccccacca    1260
accctccacc ccgagtgaag gcttcgctga aattgctttg gtcctcatag agcctgtggt    1320
ggctactttt ggtctgaaac ccacttggcc caggaaagag aaaaggttgt atgttttgtg    1380
ttggtgtttc ctattttctg cactggaggg gaggggactg ttgaggttct gtctttttc     1440
ttcttttcct cttccctctt cacatcactt ggcttccttt cctctctgat gaccgtccgc    1500
ctatggggtt ctgacttcac tttcctcagc gggtctccag tccctgacc cagctctaaa    1560
ggcacttagg acccagggaa catttctcac gtgcacattc ccctaagagc caccagactg    1620
cttcctgcca gcctgtgctt gcggcaggga gccgggcag gcagaggtg aacttgaagt      1680
tcaggacttg actctcccac aggtggtgag ctggtggctc tctggtgagc tagtgtctcc    1740
acagcctgtc tccaaggcct cccctatgta catttcagtg agctcacttt gattttaat    1800
cccaccacaa gcacatacta attttattta tgattcaaat gtgactcgtg cctgcccatc    1860
cctgtaatag atggaaggtc agccccggct taaccacaga gcactggccc ttcatggctg    1920
agctcagagc tctggcctcc tgctcagact aaaggcacct cctctggcct cacccaagcc    1980
tcttctaaaa accatgttga atgaatccac gttctggaac cccgaggcgg gagaagtagg    2040
gagctgttcg tttaagcagc atacacctaa attgggggtt taaacattaa gtaggagctt    2100
ggggtggaag agggacagcc ggctgggcca cctgagcaga aggtggtaat gaaacacctc    2160
agctgggctc ttgggagacc ttaggaagca ggagaggcaa cacctctggc tactgatggt    2220
gtggcaagtt cagaagaggt ggtggtgggg taggcgtgat gtcagcagaa gccctgcagg    2280
ctgggtgggc aggacacgtg gtgggggcca ctgaaaccag gcctaggagg gagaacaagt    2340
tccaaaggtg ccgactggaa gaaggggggta aaagtttgct ttggtgagtg agaaaaggct   2400
ggggcgtgtg atccatcccc tcacgtttca gaacttccag gctttctacc tcgactctca   2460
ccacagccag cacatacacc taggctgttt ttccttcctc cacacctgag ggacgcagca    2520
acagctagga tctgcatttt caggttccga gcctgacccc tggaactgac cagcgctcga   2580
ttgtcagcct tggcctgggg ttttgacctt gccagtgaag tttcggtttt gaagtgatta   2640
aatgtcactt cctcatcagt ttcacttctg gaggttttct tatcctactc cctggtgcca   2700
gggacgtacc tgggagtttg aatcaggccc atttgagcgt ggcagccgtg ttgggtgaag   2760
gtccggggct cggtgaggca ctgggggggt tttcggagg aaaatgaaaa tgcttctaga    2820
atgagtgaac cacatcatag ctctcactgt tttttcaata gctactttt ttagcagaca    2880
ccagagccac actcaaatgg ctaagtaggt tatgacctct ctggattatt tttgaatgcc    2940
caactgttgc attcaagttt tctgactaat aagaaattaa gcattcatcc ttcgtatcac   3000
tgcagaagca acagtggggg cacagggagg gaactcttga cactgagcca ctaaaatatg    3060
gactaatttt ttggacaaat cttcaaacgg actgtgctac tgtatttgtc tcaaagctac    3120
caagtttgtg caataagtgg aagggatgtc atccttcttc aataaatgct gaatgacatt    3180
caagctgatt ttctagacca ctgagaaaat ctttatttac aataaatttc aataaaattt    3240
gcataaatat attcccaaaa aaaaaaaaaa aaaaaagaa aaaaaaaaa                 3290
```

<210> SEQ ID NO 84
<211> LENGTH: 1616
<212> TYPE: DNA
<213> ORGANISM: Homo sapiens

<400> SEQUENCE: 84

```
ctccctgtgt tggtggagga tgtctgcagc agcatttaaa ttctgggagg gcttggttgt      60
cagcagcagc aggaggaggc agagcacagc atcgtcggga ccagactcgt ctcaggccag     120
ttgcagcctt ctcagccaaa cgccgaccaa ggaaaactca ctaccatgag aattgcagtg     180
atttgctttt gcctcctagg catcacctgt gccataccag ttaaacaggc tgattctgga     240
agttctgagg aaaagcagct ttacaacaaa tacccagatg ctgtggccac atggctaaac     300
cctgacccat ctcagaagca gaatctccta gccccacaga cccttccaag taagtccaac     360
gaaagccatg accacatgga tgatatggat gatgaagatg atgatgacca tgtgacagc      420
caggactcca ttgactcgaa cgactctgat gatgtagatg acactgatga ttctcaccag     480
tctgatgagt ctcaccattc tgatgaatct gatgaactgg tcactgattt tcccacggac     540
ctgccagcaa ccgaagtttt cactccagtt gtccccacag tagacacata tgatggccga     600
ggtgatagtg tggtttatgg actgaggtca aaatctaaga gtttcgcag acctgacatc     660
cagtaccctg atgctacaga cgaggacatc acctcacaca tggaaagcga ggagttgaat     720
ggtgcataca aggccatccc cgttgcccag gacctgaacg cgccttctga ttgggacagc     780
cgtgggaagg acagttatga aacgagtcag ctggatgacc agagtgctga aacccacagc     840
cacaagcagt ccagattata taagcggaaa gccaatgatg agagcaatga gcattccgat     900
gtgattgata gtcaggaact tccaaagtc agccgtgaat tccacagcca tgaatttcac     960
agccatgaag atatgctggt tgtagacccc aaaagtaagg aagaagataa acacctgaaa    1020
tttcgtattt ctcatgaatt agatagtgca tcttctgagg tcaattaaaa ggagaaaaaa    1080
tacaatttct cactttgcat ttagtcaaaa gaaaaaatgc tttatagcaa atgaaagag    1140
aacatgaaat gcttctttct cagtttattg gttgaatgtg tatctatttg agtctggaaa    1200
taactaatgt gtttgataat tagtttagtt tgtggcttca tggaaactcc ctgtaaacta    1260
aaagcttcag ggttatgtct atgttcattc tatagaagaa atgcaaacta tcactgtatt    1320
ttaatatttg ttattctctc atgaatagaa atttatgtag aagcaaacaa aatacttta    1380
cccacttaaa aagagaatat aacatttat gtcactataa tcttttgttt tttaagttag    1440
tgtatatttt gttgtgatta tcttttgtg gtgtgaataa atcttttatc ttgaatgtaa    1500
taagaatttg gtggtgtcaa ttgcttattt gttttcccac ggttgtccag caattaataa    1560
aacataaccct tttactgc ctaaaaaaaa aaaaaaaaa aaaaaaaa aaaaaa          1616
```

<210> SEQ ID NO 85
<211> LENGTH: 11185
<212> TYPE: DNA
<213> ORGANISM: Homo sapiens

<400> SEQUENCE: 85

```
gctgccccga gcctttctgg ggaagaactc caggcgtgcg gacgcaacag ccgagaacat      60
taggtgttgt ggacaggagc tgggaccaag atcttcggcc agccccgcat cctcccgcat     120
cttccagcac cgtcccgcac cctccgcatc cttccccggg ccaccacgct tcctatgtga     180
cccgcctggg caacgccgaa cccagtcgcg cagcgctggt gtgaatttc cccccaaact     240
gcaataagcc gccttccaag gccaagatgt tcataaatat aaagagcatc ttatggatgt     300
```

```
gttcaacctt aatagtaacc catgcgctac ataaagtcaa agtgggaaaa agcccaccgg    360 tgagggctc cctctctgga aaagtcagcc taccttgtca tttttcaacg atgcctactt     420
tgccacccag ttacaacacc agtgaatttc tccgcatcaa atggtctaag attgaagtgg    480
acaaaaatgg aaaagatttg aaagagacta ctgtccttgt ggcccaaaat ggaaatatca    540
agattggtca ggactacaaa gggagagtgt ctgtgcccac acatcccgag ctgtgggcg     600 atgcctccct cactgtggtc aagctgctgg caagtgatgc gggtctttac cgctgtgacg    660
tcatgtacgg gattgaagac acacaagaca cggtgtcact gactgtggat ggggttgtgt    720
ttcactacag ggcggcaacc agcaggtaca cactgaattt tgaggctgct cagaaggctt    780
gtttggacgt tggggcagtc atagcaactc cagagcagct ctttgctgcc tatgaagatg    840
gatttgagca gtgtgacgca ggctggctgg ctgatcagac tgtcagatat cccatccggg    900
ctcccagagt aggctgttat ggagataaga tgggaaaggc aggagtcagg acttatggat    960
tccgttctcc ccaggaaact tacgatgtgt attgttatgt ggatcatctg gatggtgatg   1020
tgttccacct cactgtcccc agtaaattca ccttcgagga ggctgcaaaa gagtgtgaaa   1080
accaggatgc caggctggca acagtggggg aactccaggc ggcatggagg aacggctttg   1140
accagtgcga ttacgggtgg ctgtcggatg ccagcgtgcg ccaccctgtg actgtggcca   1200
gggcccagtg tggaggtggt ctacttgggg tgagaaccct gtatcgtttt gagaaccaga   1260
caggcttccc tcccctgat agcagatttg atgcctactg ctttaaacct aaagaggcta    1320
caaccatcga tttgagtatc ctcgcagaaa ctgcatcacc cagtttatcc aaagaaccac   1380
aaatggtttc tgatagaact acaccaatca tccctttagt tgatgaatta cctgtcattc   1440
caacagagtt ccctcccgtg ggaaatattg tcagttttga acagaaagcc acagtccaac   1500
ctcaggctat cacagatagt ttagccacca aattacccac acctactggc agtaccaaga   1560
agccctggga tatggatgac tactcacctt ctgcttcagg acctcttgga aagctagaca   1620
tatcagaaat taaggaagaa gtgctccaga gtacaactgg cgtctctcat tatgctacgg   1680
attcatggga tggtgtcgtg gaagataaac aaacacaaga atcggttaca cagattgaac   1740
aaatagaagt gggtccttg gtaacatcta tggaaatctt aaagcacatt ccttccaagg   1800
aattccctgt aactgaaaca ccattggtaa ctgcaagaat gatcctggaa tccaaaactg   1860 aaagaaaat ggtaagcact gtttctgaat tggtaaccac aggtcactat ggattcacct    1920
tgggagaaga ggatgatgaa gacagaacac ttacagttgg atctgatgag agcaccttga   1980
tctttgacca aattcctgaa gtcattacgg tgtcaaagac ttcagaagac accatccaca   2040
ctcatttaga agacttggag tcagtctcag catccacaac tgtttcccct taattatgc    2100 ctgataataa tggatcatcc atggatgact gggaagagag acaaactagt ggtaggataa   2160
cggaagagtt tcttggcaaa tatctgtcta ctacaccttt tccatcacag catcgtacag   2220
aaatagaatt gtttccttat tctggtgata aatattagt agagggaatt tccacagtta    2280
tttatccttc tctacaaaca gaaatgacac atagaagaga agaacagaa acactaatac     2340 cagagatgag aacagatact tatacagatg aaatacaaga agagatcact aaaagtccat   2400
ttatgggaaa aacagaagaa gaagtcttct ctgggatgaa actctctaca tctctctcag   2460
agccaattca tgttacagag tcttctgtgg aaatgaccaa gtcttttgat ttcccaacat   2520
tgataacaaa gttaagtgca gagccaacag aagtaagaga tatggaggaa gactttacag   2580
caactccagg tactacaaaa tatgatgaaa atattacaac agtgctttg gcccatggta    2640 cttaaagtgt tgaagcagcc actgtatcaa aatggtcatg ggatgaagat aatacaacat   2700
```

-continued

```
ccaagccttt agagtctaca gaaccttcag cctcttcaaa attgcccct gccttactca    2760
caactgtggg gatgaatgga aaggataaag acatcccaag tttcactgaa gatggagcag    2820
atgaatttac tcttattcca gatagtactc aaaagcagtt agaggaggtt actgatgaag    2880
acatagcagc ccatggaaaa ttcacaatta gatttcagcc aactacatca actggtattg    2940
cagaaaagtc aactttgaga gattctacaa ctgaagaaaa agttccacct atcacaagca    3000
ctgaaggcca agtttatgca accatggaag gaagtgcttt gggtgaagta aagatgtgg     3060
acctctctaa gccagtatct actgttcccc aatttgcaca cacttcagag gtggaaggat    3120
tagcatttgt tagttatagt agcacccaag agcctactac ttatgtagac tcttcccata    3180
ccattcctct ttctgtaatt cccaagacag actggggagt gttagtacct tctgttccat    3240
cagaagatga agttctaggt gaaccctctc aagacatact tgtcattgat cagactcgcc    3300
ttgaagcgac tatttctcca gaaactatga gaacaacaaa aatcacagag ggaacaactc    3360
aggaagaatt cccttggaaa gaacagactg cagagaaacc agttcctgct ctcagttcta    3420
cagcttggac tcccaaggag gcagtaacac cactggatga acaagagggc gatggatcag    3480
catatacagt ctctgaagat gaattgttga caggttctga gagggtccca gttttagaaa    3540
caactccagt tggaaaaatt gatcacagtg tgtcttatcc accaggtgct gtaactgagc    3600
acaaagtgaa aacagatgaa gtggtaacac taacaccacg cattgggcca aaagtatctt    3660
taagtccagg gcctgaacaa aaatatgaaa cagaaggtag tagtacaaca ggatttacat    3720
catctttgag tccttttagt acccacatta cccagcttat ggaagaaacc actactgaga    3780
aaacatccct agaggatatt gatttaggct caggattatt tgaaaagccc aaagccacag    3840
aactcatgaa attttcaaca atcaaagtca cagttccaag tgatattacc actgccttca    3900
gttcagtaga cagacttcac acaacttcag cattcaagcc atcttccgcg atcactaaga    3960
aaccacctct catcgacagg gaacctggtg aagaaacaac cagtgacatg gtaatcattg    4020
gagaatcaac atctcatgtt cctcccacta cccttgaaga tattgtagcc aaggaaacag    4080
aaaccgatat tgatagagag tatttcacga cttcaagtcc tcctgctaca cagccaacaa    4140
gaccacccac tgtggaagac aaagaggcct ttggacctca ggcgctttct acgccacagc    4200
ccccagcaag cacaaaattt caccctgaca ttaatgttta tattattgag gtcagagaaa    4260
ataagacagg tcgaatgagt gatttgagtg taattggtca tccaatagat tcagaatcta    4320
aagaagatga accttgtagt gaagaaacag atccagtgca tgatctaatg gctgaaattt    4380
tacctgaatt ccctgacata attgaaatag acctatacca cagtgaagaa atgaagaag     4440
aagaagaaga gtgtgcaaat gctactgatg tgacaaccac cccatctgtg cagtacataa    4500
atgggaagca tctcgttacc actgtgccca aggacccaga agctgcagaa gctaggcgtg    4560
gccagtttga aagtgttgca ccttctcaga atttctcgga cagctctgaa agtgatactc    4620
atccatttgt aatagccaaa acggaattgt ctactgctgt gcaacctaat gaatctacag    4680
aaacaactga gtctcttgaa gttacatgga agcctgagac ttaccctgaa acatcagaac    4740
attttcagg tggtgagcct gatgttttcc ccacagtccc attccatgag gaatttgaaa    4800
gtggaacagc caaaaaaggg gcagaatcag tcacagagag agatactgaa gttggtcatc    4860
aggcacatga acatactgaa cctgtatctc tgtttcctga agagtcttca ggagagattg    4920
ccattgacca agaatctcag aaaatagcct ttgcaagggc tacagaagta acatttggtg    4980
aagaggtaga aaaaagtact tctgtcacat acactcccac tatagttcca agttctgcat    5040
```

```
cagcatatgt tcagaggaa gaagcagtta ccctaatagg aaatccttgg ccagatgacc    5100
tgttgtctac caaagaaagc tgggtagaag caactcctag acaagttgta gagctctcag    5160
ggagttcttc gattccaatt acagaaggct ctggagaagc agaagaagat gaagatacaa    5220
tgttcaccat ggtaactgat ttatcacaga gaaatactac tgatacactc attactttag    5280
acactagcag gataatcaca gaaagctttt ttgaggttcc tgcaaccacc atttatccag    5340
tttctgaaca accttctgca aaagtggtgc taccaagtt tgtaagtgaa acagacactt    5400
ctgagtggat ttccagtacc actgttgagg aaaagaaaag gaaggaggag agggaacta    5460 caggtacggc ttctacattt gaggtatatt catctacaca gagatcggat caattaattt    5520 tacccttga attagaaagt ccaaatgtag ctacatctag tgattcaggt accaggaaaa    5580
gttttatgtc cttgacaaca ccaacacagt ctgaaaggga aatgacagat tctactcctg    5640
tctttacaga aacaaataca ttagaaaatt tgggggcaca gaccactgag cacagcagta    5700
tccatcaacc tggggttcag gaagggctga ccactctccc acgtagtcct gcctctgtct    5760
ttatggagca gggctctgga gaagctgctg ccgacccaga accaccact gtttcttcat    5820 tttcattaaa cgtagagtat gcaattcaag ccgaaaagga agtagctggc actttgtctc    5880
cgcatgtgga aactacattc tccactgagc caacaggact ggttttgagt acagtaatgg    5940
acagagtagt tgctgaaaat ataacccaaa catccaggga aatagtgatt tcagagcgat    6000
taggagaacc aaattatggg gcagaaataa ggggcttttc cacaggtttt cctttggagg    6060
aagatttcag tggtgacttt agagaatact caacagtgtc tcatcccata gcaaagaag    6120 aaacggtaat gatggaaggc tctggagatg cagcatttag ggacacccag acttcaccat    6180
ctacagtacc tacttcagtt cacatcagtc acatatctga ctcagaagga cccagtagca    6240
ccatggtcag cacttcagcc ttcccctggg aagagtttac atcctcagct gagggctcag    6300
gtgagcaact ggtcacagtc agcagctctg ttgttccagt gcttcccagt gctgtgcaaa    6360
agttttctgg tacagcttcc tccattatcg acgaaggatt gggagaagtg ggtactgtca    6420
atgaaattga tagaagatcc accatttac caacagcaga agtggaaggt acgaaagctc    6480
cagtagagaa ggaggaagta aaggtcagtg gcacagtttc aacaaacttt ccccaaaacta    6540 tagagccagc caaattatgg tctaggcaag aagtcaaccc tgtaagacaa gaaattgaaa    6600
gtgaaacaac atcagaggaa caaattcaag aagaaaagtc atttgaatcc cctcaaaact    6660
ctcctgcaac agaacaaaca atctttgatt cacagacatt tactgaaact gaactcaaaa    6720
ccacagatta ttctgtacta acaacaaaga aaacttacag tgatgataaa gaatgaagg    6780 aggaagacac ttctttagtt aacatgtcta ctccagatcc agatgcaaat ggcttggaat    6840 cttacaacaac tctccctgaa gctactgaaa agtcacattt tttcttagct actgcattag    6900
taactgaatc tataccagct gaacatgtag tcacagattc accaatcaaa aaggaagaaa    6960
gtacaaaaca ttttccgaaa ggcatgacc caacaattca agagtcagat actgagctct    7020
tattctctgg actgggatca ggagaagaag ttttacctac tctaccaaca gagtcagtga    7080 atttactga agtggaacaa atcaataaca cattatatcc ccacacttct caagtggaaa    7140
gtacctcaag tgcaaaaatt gaagactta acagaatgga aaatgtggca aaagaagttg    7200
gaccactcgt atctcaaaca gacatctttg aaggtagtgg gtcagtaacc agcacaacat    7260
taatagaaat ttaagtgac actggagcag aaggacccac ggtggcacct ctcccttct    7320 ccacggacat cggacatcct caaaatcaga ctgtcaggtg ggcagaagaa atccagacta    7380
gtagaccaca aaccataact gaacaagact ctaacaagaa ttcttcaaca gcagaaatta    7440
```

```
acgaaacaac aacctcatct actgattttc tggctagagc ttatggtttt gaaatggcca    7500
aagaatttgt tacatcagca ccaaaaccat ctgacttgta ttatgaacct tctggagaag    7560
gatctggaga agtggatatt gttgattcat ttcacacttc tgcaactact caggcaacca    7620
gacaagaaag cagcaccaca tttgtttctg atgggtccct ggaaaaacat cctgaggtgc    7680
caagcgctaa agctgttact gctgatggat tcccaacagt ttcagtgatg ctgcctcttc    7740
attcagagca gaacaaaagc tcccctgatc caactagcac actgtcaaat acagtgtcat    7800
atgagaggtc cacagacggt agtttccaag accgtttcag ggaattcgag gattccacct    7860
taaaacctaa cagaaaaaaa cccactgaaa atattatcat agacctggac aaagaggaca    7920
aggatttaat attgacaatt acagagagta ccatccttga aattctacct gagctgacat    7980
cggataaaaa tactatcata gatattgatc atactaaacc tgtgtatgaa gacattcttg    8040
gaatgcaaac agatatagat acagaggtac catcagaacc acatgacagt aatgatgaaa    8100
gtaatgatga cagcactcaa gttcaagaga tctatgaggc agctgtcaac ctttctttaa    8160
ctgaggaaac atttgagggc tctgctgatg ttctggctag ctacactcag gcaacacatg    8220
atgaatcaat gacttatgaa gatagaagcc aactagatca catgggcttt cacttcacaa    8280
ctgggatccc tgctcctagc acagaaacag aattagacgt tttacttccc acggcaacat    8340
ccctgccaat tcctcgtaag tctgccacag ttattccaga gattgaagga ataaaagctg    8400
aagcaaaagc cctggatgac atgtttgaat caagcacttt gtctgatggt caagctattg    8460
cagaccaaag tgaaataata ccaacattgg gccaatttga aaggactcag gaggagtatg    8520
aagacaaaaa acatgctggt ccttctttc agccagaatt ctcttcagga gctgaggagg    8580
cattagtaga ccatactccc tatctaagta ttgctactac ccaccttatg gatcagagtg    8640
taacagaggt gcctgatgtg atggaaggat ccaatccccc atattacact gatacaacat    8700
tagcagtttc aacatttgcg aagttgtctt ctcagacacc atcatctccc ctcactatct    8760
actcaggcag tgaagcctct ggacacacag agatccccca gcccagtgct ctgccaggaa    8820
tagacgtcgg ctcatctgta atgtccccac aggattcttt taaggaaatt catgtaaata    8880
ttgaagcaac tttcaaacca tcaagtgagg aatacttca cataactgag cctccctctt    8940
tatctcctga cacaaaatta gaaccttcag aagatgatgg taaacctgag ttattagaag    9000
aaatggaagc ttctcccaca gaacttattg ctgtggaagg aactgagatt ctccaagatt    9060
tccaaaacaa aaccgatggt caagtttctg gagaagcaat caagatgttt cccaccatta    9120
aaacacctga ggctggaact gttattacaa ctgccgatga aattgaatta gaaggtgcta    9180
cacagtggcc acactctact tctgcttctg ccacctatgg ggtcgaggca ggtgtggtgc    9240
cttggctaag tccacagact tctgagaggc ccacgctttc ttcttctcca gaaataaacc    9300
ctgaaactca agcagcttta atcagagggc aggattccac gatagcagca tcagaacagc    9360
aagtggcagc gagaattctt gattccaatg atcaggcaac agtaaaccct gtggaattta    9420
atactgaggt tgcaacacca ccatttttccc ttctggagac ttctaatgaa acagatttcc    9480
tgattggcat taatgaagag tcagtggaag gcacggcaat ctatttacca ggacctgatc    9540
gctgcaaaat gaacccgtgc cttaacggag gcacctgtta tcctactgaa acttcctacg    9600
tatgcacctg tgtgccagga tacagcggag accagtgtga acttgatttt gatgaatgtc    9660
actctaatcc ctgtcgtaat ggagccactt gtgttgatgg tttaacaca ttcaggtgcc    9720 tctgccttcc aagttatgtt ggtgcacttt gtgagcaaga taccgagaca tgtgactatg    9780
```

```
gctggcacaa attccaaggg cagtgctaca aatactttgc ccatcgacgc acatgggatg    9840
cagctgaacg ggaatgccgt ctgcagggtg cccatctcac aagcatcctg tctcacgaag    9900
aacaaatgtt tgttaatcgt gtgggccatg attatcagtg gataggcctc aatgacaaga    9960
tgtttgagca tgacttccgt tggactgatg cagcacact gcaatacgag aattggagac    10020
ccaaccagcc agacagcttc ttttctgctg gagaagactg tgttgtaatc atttggcatg    10080
agaatggcca gtggaatgat gttccctgca attaccatct cacctatacg tgcaagaaag    10140
gaacagttgc ttgcggccag cccctgttg tagaaaatgc caagaccttt ggaaagatga    10200
aacctcgtta tgaaatcaac tccctgatta gataccactg caaagatggt ttcattcaac    10260
gtcaccttcc aactatccgg tgcttaggaa atggaagatg ggctatacct aaaattacct    10320
gcatgaaccc atctgcatac caaaggactt attctatgaa atactttaaa aattcctcat    10380
cagcaaagga caattcaata aatacatcca acatgatca tcgttggagc cggaggtggc    10440
aggagtcgag gcgctgatcc ctaaaatggc gaacatgtgt tttcatcatt tcagccaaag    10500
tcctaacttc ctgtgccttt cctatcacct cgagaagtaa ttatcagttg gtttggattt    10560
ttggaccacc gttcagtcat tttgggttgc cgtgctccca aaacatttta aatgaaagta    10620
ttggcattca aaaagacagc agacaaaatg aaagaaaatg agagcagaaa gtaagcattt    10680
ccagcctatc taatttcttt agttttctat ttgcctccag tgcagtccat ttcctaatgt    10740
ataccagcct actgtactat ttaaaatgct caatttcagc accgatgcc atgtaaataa    10800 gatgatttaa tgttgatttt aatcctgtat ataaataaa aagtcacaat gagtttgggc    10860
atatttaatg atgattatgg agccttagag gtctttaatc attggttcgg ctgctttat    10920 gtagtttagg ctggaaatgg tttcacttgc tctttgactg tcagcaagac tgaagatggc    10980
ttttcctgga cagctagaaa acacaaaatc ttgtaggtca ttgcacctat ctcagccata    11040
ggtgcagttt gcttctacat gatgctaaag gctgcgaatg ggatcctgat ggaactaagg    11100
actccaatgt cgaactcttc tttgctgcat tcctttttct tcacttacaa gaaaggcctg    11160
aatggaggac ttttctgtaa ccagg    11185
```

<210> SEQ ID NO 86
<211> LENGTH: 2503
<212> TYPE: DNA
<213> ORGANISM: Homo sapiens

<400> SEQUENCE: 86

```
ggactttgaa atccaacccg gtcacctacc cgcgcgactg tgtccacgga tggcacgaaa      60
gccaagcgag tccccctgcc gagctactcg cgtccgcctc ctcccaagct gagctctgct     120
ccgcccacct gagtccttcg ccagttagga ggaaacacag ccgcttaatg aactgctgca     180
tcgggctggg agagaaagct cgcgggtccc accgggcctc ctacccaagt ctcagcgcgc     240
ttttcaccga ggcctcaatt ctgggatttg gcagctttgc tgtgaaagcc caatggacag     300
aggactgcag aaaatcaacc tatcctcctt caggaccaac gtacagaggt gcagttccat     360
ggtacaccat aaatcttgac ttaccaccct acaaagatg gcatgaattg atgcttgaca     420
aggcaccaat gctaaggtt atagtgaatt ctctgaagaa tatgataaat acattcgtgc     480
caagtggaaa agttatgcag gtggtggatg aaaaattgcc tggcctactt ggcaactttc     540
ctggcccttt tgaagaggaa atgaagggta ttgccgctgt tactgatata cctttaggag     600
agattatttc attcaatatt ttttatgaat tatttaccat ttgtacttca atagtagcag     660
aagacaaaaa aggtcatcta atacatggga gaaacatgga ttttggagta tttcttgggt     720
```

```
ggaacataaa taatgatacc tgggtcataa ctgagcaact aaaacccttta acagtgaatt      780 tggatttcca aagaaacaac aaaactgtct tcaaggcttc aagctttgct ggctatgtgg      840
gcatgttaac aggattcaaa ccaggactgt tcagtcttac actgaatgaa cgtttcagta      900
taaatggtgg ttatctgggt attctagaat ggattctggg aaagaaagat gccatgtgga      960
tagggttcct cactagaaca gttctggaaa atagcacaag ttatgaagaa gccaagaatt     1020
tattgaccaa gaccaagata ttggccccag cctactttat cctgggaggc aaccagtctg     1080
gggaaggttg tgtgattaca cgagacagaa aggaatcatt ggatgtatat gaactcgatg     1140
ctaagcaggg tagatggtat gtggtacaaa caaattatga ccgttggaaa catcccttct     1200
tccttgatga tcgcagaacg cctgcaaaga tgtgtctgaa ccgcaccagc caagagaata     1260
tctcatttga aaccatgtat gatgtcctgt caacaaaacc tgtcctcaac aagctgaccg     1320
tatacacaac cttgatagat gttaccaaag gtcaattcga aacttacctg cgggactgcc     1380 ctgaccettg tataggttgg tgagcacacg tctggcctac agaatgcggc ctctgagaca     1440
tgaagacacc atctccatgt gaccgaacac tgcagctgtc tgaccttcca aagactaaga     1500
ctcgcggcag gttctctttg agtcaaaagc ttgtcttcgt ccatctgttg acaaatgaca     1560 gaccttttt tttccccccat cagttgattt ttcttattta cagataactt ctttagggga     1620
agtaaaacag tcatctagaa ttcactgagt tttgtttcac tttgacattt ggggatctgg     1680
tgggcagtcg aaccatggtg aactccacct ccgtggaata aatggagatt cagcgtgggt     1740
gttgaatcca gcacgtctgt gtgagtaacg ggacagtaaa cactccacat tcttcagttt     1800
ttcacttcta cctacatatt tgtatgtttt tctgtataac agccttttcc ttctggttct     1860
aactgctgtt aaaattaata tatcattatc tttgctgtta ttgacagcga tataatttta     1920
ttacatatga ttagagggat gagacagaca ttcacctgta tatttctttt aatgggcaca     1980
aaatgggccc ttgcctctaa atagcacttt ttggggttca agaagtaatc agtatgcaaa     2040
gcaatctttt atacaataat tgaagtgttc ccttttttcat aattactgta cttcccagta     2100
accctaagga agttgctaac ttaaaaaaact gcatcccacg ttctgttaat ttagtaaata     2160
aacaagtcaa agacttgtgg aaaataggaa gtgaacccac attttaaatt ctcataagta     2220
gcattcatgt aataaacagg tttttagttt gttcttcaga ttgataggga gttttaaaga     2280
aattttagta gttactaaaa ttatgttact gtattttttca gaaatcaaac tgcttatgaa     2340
aagtactaat agaacttgtt aacctttcta accttcacga ttaactgtga aatgtacgtc     2400
atttgtgcaa gaccgtttgt ccacttcatt ttgtataatc acagttgtgt tcctgacact     2460
caataaacag tcattggaaa gagtgccagt cagcagtcat gca                        2503
```

<210> SEQ ID NO 87
<211> LENGTH: 2341
<212> TYPE: DNA
<213> ORGANISM: Homo sapiens

<400> SEQUENCE: 87

```
ggctcttctt tgcctctgct ggagtccggg gagtggcgtt ggctgctaga gcgatgccgg       60
gccggagttg cgtcgcctta gtcctcctgg ctgccgccgt cagctgtgcc gtcgcgcagc      120
acgcgccgcc gtggacagag gactgcagaa aatcaaccta tcctccttca ggaccaacgt      180
acagaggtgc agttccatgg taccaccataa atcttgactt accacccctac aaaagatggc      240 atgaattgat gcttgacaag gcaccaatgc taaaggttat agtgaattct ctgaagaata      300
```

```
tgataaaatac attcgtgcca agtggaaaag ttatgcaggt ggtggatgaa aaattgcctg      360
gcctacttgg caactttcct ggcccttttg aagaggaaat gaagggtatt gccgctgtta      420
ctgatatacc tttaggagag attatttcat tcaatatttt ttatgaatta tttaccattt      480
gtacttcaat agtagcagaa gacaaaaaag gtcatctaat acatgggaga acatggatt       540 ttggagtatt tcttgggtgg aacataaata atgatacctg ggtcataact gagcaactaa      600
aacctttaac agtgaatttg gatttccaaa gaaacaacaa aactgtcttc aaggcttcaa      660
gctttgctgg ctatgtgggc atgttaacag gattcaaacc aggactgttc agtcttacac      720
tgaatgaacg tttcagtata aatggtggtt atctgggtat tctagaatgg attctgggaa      780
agaaagatgc catgtggata gggttcctca ctagaacagt tctggaaaat agcacaagtt      840
atgaagaagc caagaattta ttgaccaaga ccaagatatt ggccccagcc tactttatcc      900
tgggaggcaa ccagtctggg aaggttgtg tgattacacg agacagaaag gaatcattgg       960
atgtatatga actcgatgct aagcagggta gatggtatgt ggtacaaaca aattatgacc     1020
gttggaaaca tccttcttc cttgatgatc gcagaacgcc tgcaaagatg tgtctgaacc      1080
gcaccagcca agagaatatc tcatttgaaa ccatgtatga tgtcctgtca acaaaacctg     1140
tcctcaacaa gctgaccgta tacacaacct tgatagatgt taccaaaggt caattcgaaa     1200
cttacctgcg ggactgccct gacccttgta taggttggtg agcacacgtc tggcctacag     1260
aatgcggcct ctgagacatg aagacaccat ctccatgtga ccgaacactg cagctgtctg     1320
accttccaaa gactaagact cgcggcaggt tctctttgag tcaaaagctt gtcttcgtcc     1380
atctgttgac aaatgacaga cctttttttt tcccccatca gttgattttt cttatttaca     1440
gataacttct ttaggggaag taaaacagtc atctagaatt cactgagttt tgtttcactt     1500
tgacatttgg ggatctggtg ggcagtcgaa ccatggtgaa ctccacctcc gtggaataaa     1560
tggagattca gcgtgggtgt tgaatccagc acgtctgtgt gagtaacggg acagtaaaca     1620
ctccacattc ttcagttttt cacttctacc tacatatttg tatgttttc tgtataacag      1680 ccttttcctt ctggttctaa ctgctgttaa aattaatata tcattatctt tgctgttatt     1740
gacagcgata taatttttatt acatatgatt agagggatga gacagacatt cacctgtata     1800
tttcttttaa tgggcacaaa atgggcccct gcctctaaat agcactttt ggggttcaag      1860 aagtaatcag tatgcaaagc aatcttttat acaataattg aagtgttccc ttttcataa      1920 ttactgtact tcccagtaac cctaaggaag ttgctaactt aaaaaactgc atcccacgtt     1980
ctgttaattt agtaaataaa caagtcaaag acttgtggaa aataggaagt gaacccatat     2040
tttaaattct cataagtagc attcatgtaa taaacaggtt tttagtttgt tcttcagatt     2100
gatagggagt tttaaagaaa ttttagtagt tactaaaatt atgttactgt attttttcaga    2160 aatcaaactg cttatgaaaa gtactaatag aacttgttaa cctttctaac cttcacgatt     2220
aactgtgaaa tgtacgtcat ttgtgcaaga ccgtttgtcc acttcatttt gtataatcac     2280
agttgtgttc ctgacactca ataaacagtc attggaaaga gtgccagtca gcagtcatgc     2340
a                                                                     2341

<210> SEQ ID NO 88
<211> LENGTH: 2039
<212> TYPE: DNA
<213> ORGANISM: Homo sapiens

<400> SEQUENCE: 88
ccggccctcg ccctgtccgc cgccaccgcc gccgccgcca gagtcgccat gcagatcccg       60
```

```
cgcgccgctc ttctcccgct gctgctgctg ctgctggcgg cgcccgcctc ggcgcagctg      120
tcccgggccg gccgctcggc gcctttggcc gccgggtgcc cagaccgctg cgagccggcg      180
cgctgcccgc cgcagccgga gcactgcgag ggcggccggg cccggacgc gtgcggctgc       240 tgcgaggtgt gcggcgcgcc cgagggcgcc gcgtgcggcc tgcaggaggg cccgtgcggc      300
gaggggctgc agtgcgtggt gcccttcggg gtgccagcct cggccacggt gcggcggcgc      360
gcgcaggccg gcctctgtgt gtgcgccagc agcgagccgg tgtgcggcag cgacgccaac      420
acctacgcca acctgtgcca gctgcgcgcc gccagccgcc gctccgagag gctgcaccgg      480
ccgccggtca tcgtcctgca gcgcggagcc tgcggccaag ggcaggaaga tcccaacagt      540
ttgcgccata aatataactt tatcgcggac gtggtggaga agatcgcccc tgccgtggtt      600
catatcgaat tgtttcgcaa gcttccgttt tctaaacgag aggtgccggt ggctagtggg      660
tctgggttta ttgtgtcgga agatggactg atcgtgacaa atgcccacgt ggtgaccaac      720
aagcaccggg tcaaagttga gctgaagaac ggtgccactt acgaagccaa atcaaggat      780 gtggatgaga aagcagacat cgcactcatc aaaattgacc accagggcaa gctgcctgtc      840
ctgctgcttg gccgctcctc agagctgcgg ccgggagagt tcgtggtcgc catcggaagc      900 ccgtttttccc ttcaaaacac agtcaccacc gggatcgtga gcaccaccca gcgaggcggc      960
aaagagctgg ggctccgcaa ctcagacatg gactacatcc agaccgacgc catcatcaac     1020
tatgaaaact cggaggccc gttagtaaac ctggacggtg aagtgattgg aattaacact     1080
ttgaaagtga cagctggaat ctcctttgca atcccatctg ataagattaa aaagttcctc     1140
acggagtccc atgaccgaca ggccaaagga aaagccatca ccaagaagaa gtatattggt     1200
atccgaatga tgtcactcac gtccagcaaa gccaaagagc tgaaggaccg gcaccgggac     1260
ttcccagacg tgatctcagg agcgtatata attgaagtaa ttcctgatac cccagcagaa     1320
gctggtggtc tcaaggaaaa cgacgtcata atcagcatca atggacagtc cgtggtctcc     1380
gccaatgatg tcagcgacgt cattaaaagg gaaagcaccc tgaacatggt ggtccgcagg     1440
ggtaatgaag atatcatgat cacagtgatt cccgaagaaa ttgacccata ggcagaggca     1500
tgagctggac ttcatgtttc cctcaaagac tctcccgtgg atgacggatg aggactctgg     1560
gctgctggaa taggacactc aagacttttg actgccattt tgtttgttca gtggagactc     1620
cctggccaac agaatccttc ttgatagttt gcaggcaaaa caaatgtaat gttgcagatc     1680
cgcaggcaga agctctgccc ttctgtatcc tatgtatgca gtgtgctttt tcttgccagc     1740
ttgggccatt cttgcttaga cagtcagcat ttgtctcctc ctttaactga gtcatcatct     1800
tagtccaact aatgcagtcg atacaatgcg tagatagaag aagccccacg ggagccagga     1860
tgggactggt cgtgtttgtg cttttctcca agtcagcacc caaaggtcaa tgcacagaga     1920
ccccgggtgg gtgagcgctg gcttctcaaa cggccgaagt tgcctctttt aggaatctct     1980
ttggaattgg gagcacgatg actctgagtt tgagctatta aagtacttct tacacattg     2039
```

<210> SEQ ID NO 89
<211> LENGTH: 1387
<212> TYPE: DNA
<213> ORGANISM: Homo sapiens

<400> SEQUENCE: 89

```
ccgggtcgga gcccccggga gctgcgcgcg ggcttgcagc gcctcgcccg cgctgtcctc       60
ccggtgtccc gcttctccgc gccccagccg ccggctgcca gcttttcggg gccccgagtc      120
```

```
gcacccagcg aagagagcgg gcccgggaca agctcgaact ccggccgcct cgcccttccc    180
cggctccgct ccctctgccc cctcggggtc gcgcgccacc gatgctgcag ggccctggct    240
cgctgctgct gctcttcctc gcctcgcact gctgcctggg ctcggcgcgc gggctcttcc    300
tctttggcca gcccgacttc tcctacaagc gcagcaattg caagcccatc cctgccaacc    360
tgcagctgtg ccacggcatc gaataccaga acatgcggct gcccaacctg ctgggccacg    420
agaccatgaa ggaggtgctg gagcaggccg gcgcttggat cccgctggtc atgaagcagt    480
gccacccgga caccaagaag ttcctgtgct cgctcttcgc ccccgtctgc ctcgatgacc    540
tagacgagac catccagcca tgccactcgc tctgcgtgca ggtgaaggac cgctgcgccc    600
cggtcatgtc cgccttcggc ttcccctggc ccgacatgct tgagtgcgac cgtttccccc    660
aggacaacga cctttgcatc cccctcgcta gcagcgacca cctcctgcca gccaccgagg    720
aagctccaaa ggtatgtgaa gcctgcaaaa ataaaaatga tgatgacaac gacataatgg    780
aaacgctttg taaaaatgat tttgcactga aaataaaagt gaaggagata acctacatca    840
accgagatac caaaatcatc ctggagacca agagcaagac catttacaag ctgaacggtg    900
tgtccgaaag ggacctgaag aaatcggtgc tgtggctcaa agacagcttg cagtgcacct    960
gtgaggagat gaacgacatc aacgcgccct atctggtcat gggacagaaa cagggtgggg   1020
agctggtgat cacctcggtg aagcggtggc agaaggggca gagagagttc aagcgcatct   1080
cccgcagcat ccgcaagctg cagtgctagt cccggcatcc tgatggctcc gacaggcctg   1140
ctccagagca cggctgacca tttctgctcc gggatctcag ctcccgttcc ccaagcacac   1200
tcctagctgc tccagtctca gcctgggcag cttccccctg ccttttgcac gtttgcatcc   1260
ccagcatttc ctgagttata aggccacagg agtggatagc tgttttcacc taaaggaaaa   1320 gcccaccccga atcttgtaga aatattcaaa ctaataaaat catgaatatt tttatgaagt   1380
ttaaaaa                                                             1387
```

<210> SEQ ID NO 90
<211> LENGTH: 1092
<212> TYPE: DNA
<213> ORGANISM: Homo sapiens

<400> SEQUENCE: 90

```
tgtccctgga attctgggac actggctggg gtttgaggag agaagccagt acctacctgg     60
ctgcaggatg aagctggcca gtggcttctt ggttttgtgg ctcagccttg ggggtggcct    120
ggctcagagc gacacgagcc ctgacacgga ggagtcctat tcagactggg gccttcggca    180
cctccgggga agctttgaat ccgtcaatag ctacttcgat tctttttctgg agctgctggg    240 agggaagaat ggagtctgtc agtacaggtg ccgatatgga aaggcaccaa tgcccagacc    300
tggctacaag ccccaagagc ccaatggctg cggctcctat ttcctgggtc tcaaggtacc    360
agaaagtatg gacttgggca ttccagcaat gacaaagtgc tgcaaccagc tggatgtctg    420
ttatgacact tgcggtgcca acaaatatcg ctgtgatgca aaattccgat ggtgtctcca    480
ctcgatctgc tctgacctta agcggagtct gggctttgtc tccaaagtgg aagcagcctg    540
tgattccctg gttgacactg tgttcaacac cgtgtggacc ttgggctgcc gcccctttat    600
gaatagtcag cgggcagctt gcatctgtgc agaggaggag aaggaagagt tatgaggaag    660
aagtgattcc ttcctggttt tgagtgacac cacagctgtc agccttcaag atgtcaagtc    720
ttcgagtcag cgtgactcat tcattcttcc aacagtttgg acaccacaaa gcaggagaaa    780
gggaacattt ttctacagct ggaaagtgag tcctatcctt tgaggaaatt tgaaaaaaga    840
```

```
catggagtgg tttgaaagct actcttcatt taagactgct ctccccaacc aagacacatt    900
tgcctggaaa ttcagttctt agcttaaaga ctaaaatgca agcaaaccct gcaattcctg    960
gacctgatag ttatattcat gagtgaaatt gtggggagtc cagccatttg ggaggcaatg   1020
actttctgct ggcccatgtt tcagttgcca gtaagcttct cacatttaat aaagtgtact   1080
ttttagaaca tt                                                      1092
```

<210> SEQ ID NO 91
<211> LENGTH: 1807
<212> TYPE: DNA
<213> ORGANISM: Homo sapiens

<400> SEQUENCE: 91

```
gcacgaggga agagggtgat ccgacccggg gaaggtcgct gggcagggcg agttgggaaa     60
gcggcagccc ccgccgcccc cgcagcccct tctcctcctt tctcccacgt cctatctgcc    120
tctcgctgga ggccaggccg tgcagcatcg aagacaggag gaactggagc tcattggcc     180
ggcccggggc gccggcctcg ggcttaaata ggagctccgg gctctggctg ggacccgacc    240
gctgccggcc gcgctcccgc tgctcctgcc gggtgatgga aaaccccagc ccggccgccg    300
ccctgggcaa ggccctctgc gctctcctcc tggccactct cggcgccgcc ggccagcctc    360
ttgggggaga gtccatctgt tccgccagag ccccggccaa atacagcatc accttcacgg    420
gcaagtggag ccagacggcc ttcccaagc agtacccct gttccgcccc cctgcgcagt     480
ggtcttcgct gctgggggcc gcgcatagct ccgactacag catgtggagg aagaaccagt    540
acgtcagtaa cgggctgcgc gactttgcgg agcgcggcga ggcctgggcg ctgatgaagg    600
agatcgaggc ggcgggggag gcgctgcaga gcgtgcacgc ggtgttttcg gcgcccgccg    660
tccccagcgg caccgggcag acgtcggcgg agctggaggt gcagcgcagg cactcgctgg    720
tctcgtttgt ggtgcgcatc gtgcccagcc ccgactggtt cgtgggcgtg acagcctgg    780
acctgtgcga cggggaccgt tggcgggaac aggcggcgct ggacctgtac ccctacgacg    840
ccgggacgga cagcggcttc accttctcct cccccaactt cgccaccatc ccgcaggaca    900
cggtgaccga gataacgtcc tcctctccca gccaccggc caactccttc tactacccgc     960
ggctgaaggc cctgcctccc atcgccaggg tgacactggt gcggctgcga cagagcccca   1020
gggccttcat ccctcccgcc ccagtcctgc ccagcaggga caatgagatt gtagacagcg   1080
cctcagttcc agaaacgccg ctggactgcg aggtctccct gtggtcgtcc tggggactgt   1140
gcggaggcca ctgtgggagg ctcgggacca agagcaggac tcgctacgtc cgggtccagc   1200
ccgccaacaa cgggagcccc tgccccgagc tcgaagaaga ggctgagtgc gtccctgata   1260
actgcgtcta agaccagagc cccgcagccc tggggcccc cggagccatg gggtgtcggg   1320
ggctcctgtg caggctcatg ctgcaggcgg ccgaggcaca gggggtttcg cgctgctcct   1380
gaccgcggtg aggccgcgcc gaccatctct gcactgaagg gccctctggt ggccggcacg   1440
ggcattggga aacagcctcc tcctttccca accttgcttc ttaggggccc ccgtgtcccg   1500
tctgctctca gcctcctcct cctgcaggat aaagtcatcc ccaaggctcc agctactcta   1560
aattatggtc tccttataag ttattgctgc tccaggagat tgtccttcat cgtccagggg   1620
cctggctccc acgtggttgc agatacctca gacctggtgc tctaggctgt gctgagccca   1680
ctctcccgag ggcgcatcca agcggggcc acttgagaag tgaataaatg gggcggtttc   1740
ggaagcgtca gtgtttccat gttatggatc tctctgcgtt tgaataaaga ctatctctgt   1800
```

-continued

| tgctcac | 1807 |

```
<210> SEQ ID NO 92
<211> LENGTH: 1077
<212> TYPE: DNA
<213> ORGANISM: Homo sapiens

<400> SEQUENCE: 92
```

| cccgccccg ccccttccga gcaaactttt ggcacccacc gcagcccagc gcgcgttcgt | 60 |
| gctccgcagg gcgcgcctct ctccgccaat gccaggcgcg cggggagcc attaggaggc | 120 |
| gaggagagag gagggcgcag ctcccgccca gcccagccct gcccagccct gcccggaggc | 180 |
| agacgcgccg gaaccgggac gcgataaata tgcagagcgg aggcttcgcg cagcagagcc | 240 |
| cgcgcgccgc ccgctccggg tgctgaatcc aggcgtgggg acacgagcca ggcgccgccg | 300 |
| ccggagccag cggagccggg gccagagccg gagcgcgtcc gcgtccacgc agccgccggc | 360 |
| cggccagcac ccagggccct gcatgccagg tcgttggagg tggcagcgag acatgcaccc | 420 |
| ggccccggaag ctcctcagcc tcctcttcct catcctgatg ggcactgaac tcactcaaaa | 480 |
| taaaagagaa aacaaagcag agaagatggg agggccagag agcgagagga agaccacagg | 540 |
| agagaagaca ctgaacgagc ttcccttgtt ttgcctggaa gcccacgctg gctccctggc | 600 |
| tctgcccagg atgtgcagtc caaatcccaa tccagcagtg gggttatgtc gtcccgctta | 660 |
| ccctcagagc ccttctcctg gtgctgccca gacgatcagc cagtccctcc tggagaggtt | 720 |
| ctgcatggcc tctaggagag aagttttctt ggccccagga aggcctggtg gagggtggtg | 780 |
| gttgtgcact gttgctggac agatgcattc attcatgtgc acacacacac acacacatgc | 840 |
| acacacaggg gagcagatac ctgcagagaa gagccaacca ggtcctgatt agtggcaagc | 900 |
| tgccccacaa agggctatgc ctgtgtctta ttgagacacc ttggcaaaga gatggctgat | 960 |
| tctgggtggt cctggacatg gccgcaccca agggccctcc aagccttaat ggcaccctga | 1020 |
| agcctccatg cccaggccaa aagatgcttt tcctccctaa aaaaaaaaaa aaaaaaa | 1077 |

```
<210> SEQ ID NO 93
<211> LENGTH: 4229
<212> TYPE: DNA
<213> ORGANISM: Homo sapiens

<400> SEQUENCE: 93
```

| ggggccccag tggccgccgc ggagcgaggt tgcctggaga gagcgcctgg gcgcagaagg | 60 |
| gttaacgggc caccggggc tcgcagagca ggagggtgct ctcggacggt gtgtccccca | 120 |
| ctgcactcct gaacttggag acagggtcg ccgcgaggga cgcagagagc accctccacg | 180 |
| cccagatgcc tgcgtagttt ttgtgaccag tccgctcctg cctcccctg ggcagtaga | 240 |
| gggggagcga tggagaactg gactggcagg ccctggctgt atctgctgct gcttctgtcc | 300 |
| ctccctcagc tctgcttgga tcaggaggtg ttgtccggac actctcttca gacacctaca | 360 |
| gaggagggcc agggccccga aggtgtctgg ggaccttggg tccagtgggc ctcttgctcc | 420 |
| cagccctgcg gggtggggt gcagcgcagg agccggacat gtcagctccc tacagtgcag | 480 |
| ctccacccga gtctgcccct ccctcccgg ccccaagac atccagaagc cctcctcccc | 540 |
| cggggccagg gtcccagacc ccagacttct ccagaaaccc tccccttgta caggacacag | 600 |
| tctcggggaa ggggtggccc acttcgaggt cccgcttccc acctagggag agaggagacc | 660 |
| caggagattc gagcggccag gaggtccgg cttcgagacc ccatcaagcc aggaatgttc | 720 |
| ggttatggga gagtgcccctt tgcattgcca ctgcaccgga accgcaggca ccctcggagc | 780 |

```
ccacccagat ctgagctgtc cctgatctct tctagagggg aagaggctat tccgtcccct    840
actccaagag cagagccatt ctccgcaaac ggcagccccc aaactgagct ccctcccaca    900
gaactgtctg tccacacccc atcccccaa gcagaacctc taagccctga aactgctcag     960
acagaggtgg cccccagaac caggcctgcc cccctacggc atcacccag agcccaggcc    1020 tctggcacag agccccctc acccacgcac tccttaggag aaggtggctt cttccgtgca    1080
tcccctcagc cacgaaggcc aagttcccag ggttgggcca gtccccaggt agcagggaga   1140
cgccctgatc cttttccttc ggtccctcgg ggccgaggcc agcagggcca agggccttgg    1200
ggaacggggg ggactcctca cgggccccgc ctggagcctg accctcagca cccgggcgcc    1260
tggctgcccc tgctgagcaa cggccccat gccagctccc tctggagcct ctttgctccc    1320
agtagcccta ttccaagatg ttctggggag agtgaacagc taagagcctg cagccaagcg   1380
ccctgccccc ctgagcagcc agaccccgg gccctgcagt gcgcagcctt taactcccag    1440
gaattcatgg gccagctgta tcagtgggag cccttcactg aagtccaggg ctcccagcgc    1500
tgtgaactga actgccggcc ccgtggcttc cgcttctatg tccgtcacac tgaaaaggtc    1560
caggatggga ccctgtgtca gcctggagcc cctgacatct gtgtggctgg acgtgtctg    1620 agccccggct gtgatgggat ccttggctct ggcaggcgtc ctgatggctg tggagtctgt   1680
gggggtgatg attctacctg tcgccttgtt tcggggaacc tcactgaccg agggggcccc    1740
ctgggctatc agaagatctt gtggattcca gcgggagcct tgcggctcca gattgcccag    1800
ctccggccta gctccaacta cctggcactt cgtggccctg ggggccggtc catcatcaat    1860
gggaactggg ctgtggatcc ccctgggtcc tacagggccg gcgggaccgt ctttcgatat    1920
aaccgtcctc ccagggagga gggcaaaggg gagagtctgt cggctgaagg ccccaccacc    1980
cagcctgtgg atgtctatat gatctttcag gaggaaaacc caggcgtttt ttatcagtat   2040
gtcatctctt cacctcctcc aatccttgag aaccccaccc cagagccccc tgtcccccag   2100
cttcagccgg agattctgag ggtggagccc ccacttgctc cggcaccccg cccagcccgg    2160
accccaggca ccctccagcg tcaggtgcgg atccccagga tgcccgcccc gcccatccc    2220 aggacacccc tggggtctcc agctgcgtac tggaaacgag tgggacactc tgcatgctca   2280
gcgtcctgcg ggaaaggtgt ctggcgcccc attttcctct gcatctcccg tgagtcggga   2340
gaggaactgg atgaacgcag ctgtgccgcg ggtgccaggc cccagcctc ccctgaaccc    2400 tgccacggca ccccatgccc cccatactgg gaggctggcg agtggacatc ctgcagccgc    2460
tcctgtggcc ccggcacccc agcaccgccag ctgcagtgcc ggcaggaatt tgggggggt   2520 ggctcctcgg tgcccccgga gcgctgtgga catctccccc ggcccaacat cacccagtct   2580
tgccagctgc gcctctgtgg ccattgggaa gttggctctc cttggagcca gtgctccgtg   2640
cggtgcggcc ggggccagag aagccggcag gttcgctgtg ttgggaacaa cggtgatgaa    2700
gtgagcgagc aggagtgtgc gtcaggcccc cgcagccccc cagcagaga ggcctgtgac    2760 atggggccct gtactactgc ctggttccac agcgactgga gctccaagtg ctcagccgag    2820
tgtgggacgg gaatccagcg gcgctctgtg gtctgccttg ggagtggggc agccctcggg    2880
ccaggccagg gggaagcagg agcaggaact gggcagagct gtccaacagg aagccggccc    2940
cctgacatgc gcgcctgcag cctggggccc tgtgagagaa cttggcgctg gtacacaggg    3000 ccctgggggtg agtgctcctc cgaatgtggc tctggcacac agcgtagaga catcatctgt   3060
gtatccaaac tggggacgga gttcaacgtg acttctccga gcaactgttc tcacctcccc   3120
```

|   |   |
|---|---|
| aggcccctg cctgcagcc ctgtcaaggg caggcctgcc aggaccgatg gttttccacg | 3180 |
| ccctggagcc catgttctcg ctcctgccaa gggggaacgc agacacggga ggtccagtgc | 3240 |
| ctgagcacca accagaccct cagcacccga tgccctcctc aactgcggcc ctccaggaag | 3300 |
| cgcccctgta acagccaacc ctgcagccag cgccctgatg atcaatgcaa ggacagctct | 3360 |
| ccacattgcc ccctggtggt acaggcccgg ctctgcgtct accctacta cacagccacc | 3420 |
| tgttgccgct cttgcgcaca tgtcctggag cggtctcccc aggatccctc ctgaaagggg | 3480 |
| tccggggcac cttcacggtt ttctgtgcca ccatcggtca cccattgatc ggcccactct | 3540 |
| gaaccccctg gctctccagc ctgtcccagt ctcagcaggg atgtcctcca ggtgacagag | 3600 |
| ggtggcaagg tgactgacac aaagtgactt tcagggctgt ggtcaggccc atgtggtggt | 3660 |
| gtgatgggtg tgtgcacata tgcctcaggt gtgcttttgg gactgcatgg atatgtgtgt | 3720 |
| gctcaaacgt gtatcacttt tcaaaaagag gttacacaga ctgagaagga caagacctgt | 3780 |
| ttccttgaga ctttcctagg tggaaaggaa agcaagtctg cagttccttg ctaatctgag | 3840 |
| ctacttagag tgtggtctcc ccaccaactc cagttttgtg ccctaagcct catttctcat | 3900 |
| gttcagacct cacatcttct aagccgccct gtgtctctga ccccttctca tttgcctagt | 3960 |
| atctctgccc ctgcctccct aattagctag ggctggggtc agccactgcc aatcctgcct | 4020 |
| tactcaggaa ggcaggagga aagagactgc ctctccagag caaggcccag ctgggcagag | 4080 |
| ggtgaaaaag agaaatgtga gcatccgctc ccccaccacc ccgcccagcc cctagcccca | 4140 |
| ctccctgcct cctgaaatgg ttcccaccca gaactaattt attttttatt aaagatggtc | 4200 |
| atgacaaatg aaaaaaaaaa aaaaaaaa | 4229 |

<210> SEQ ID NO 94
<211> LENGTH: 5826
<212> TYPE: DNA
<213> ORGANISM: Homo sapiens

<400> SEQUENCE: 94

|   |   |
|---|---|
| gaggaggaga cggcatccag tacagagggg ctggacttgg accctgcag cagccctgca | 60 |
| caggagaagc ggcatataaa gccgcgctgc ccgggagccg ctcggccacg tccaccggag | 120 |
| catcctgcac tgcagggccg gtctctcgct ccagcagagc ctgcgccttt ctgactcggt | 180 |
| ccggaacact gaaaccagtc atcactgcat cttttggca aaccaggagc tcagctgcag | 240 |
| gaggcaggat ggtctggagg ctggtcctgc tggctctgtg ggtgtggccc agcacgcaag | 300 |
| ctggtcacca ggacaaagac acgaccttcg acctttcag tatcagcaac atcaaccgca | 360 |
| agaccattgg cgccaagcag ttccgcgggc ccgaccccgg cgtgccggct taccgcttcg | 420 |
| tgcgctttga ctacatccca ccggtgaacg cagatgacct cagcaagatc accaagatca | 480 |
| tgcggcagaa ggagggcttc ttcctcacgg cccagctcaa gcaggacggc aagtccaggg | 540 |
| gcacgctgtt ggctctggag ggccccggtc tctcccagag gcagttcgag atcgtctcca | 600 |
| acggccccgc ggacacgctg gatctcacct actggattga cggcacccgg catgtggtct | 660 |
| ccctggagga cgtcggcctg gctgactcgc agtggaagaa cgtcaccgtg caggtggctg | 720 |
| gcgagaccta cagcttgcac gtgggctgcg acctcatgga cagcttcgct ctggacgagc | 780 |
| ccttctacga gcacctgcag gcggaaaaga gccggatgta cgtggccaaa ggctctgcca | 840 |
| gagagagtca cttcaggggt ttgcttcaga acgtccacct agtgtttgaa aactctgtgg | 900 |
| aagatattct aagcaagaag ggttgccagc aaggccaggg agctgagatc aacgccatca | 960 |
| gtgagaacac agagacgctg cgcctgggtc cgcatgtcac caccgagtac gtgggcccca | 1020 |

```
gctcggagag gaggcccgag gtgtgcgaac gctcgtgcga ggagctggga aacatggtcc    1080
aggagctctc ggggctccac gtcctcgtga accagctcag cgagaacctc aagagagtgt    1140
cgaatgataa ccagtttctc tgggagctca ttggtggccc tcctaagaca aggaacatgt    1200
cagcttgctg gcaggatggc cggttctttg cggaaaatga acgtgggtg gtggacagct     1260
gcaccacgtg tacctgcaag aaatttaaaa ccatttgcca ccaaatcacc tgcccgcctg    1320
caacctgcgc cagtccatcc tttgtggaag gcgaatgctg cccttcctgc ctccactcgg    1380
tggacggtga ggagggctgg tctccgtggg cagagtggac ccagtgctcc gtgacgtgtg    1440
gctctgggac ccagcagaga ggccggtcct gtgacgtcac cagcaacacc tgcttggggc    1500
cctccatcca gacacgggct tgcagtctga gcaagtgtga cacccgcatc cggcaggacg    1560
gcggctggag ccactggtca ccttggtctt catgctctgt gacctgtgga gttggcaata    1620
tcacacgcat ccgtctctgc aactccccag tgccccagat gggggggcaag aattgcaaag   1680
ggagtggccg ggagaccaaa gcctgccagg gcgcccatg cccaatcgat ggccgctgga     1740
gccctggtc ccgtggtcg gctgcactg tcacctgtgc cggtgggatc cgggagcgca       1800
cccgggtctg caacagccct gagcctcagt acggagggaa ggcctgcgtg ggggatgtgc    1860
aggagcgtca gatgtgcaac aagaggagct gccccgtgga tggctgttta ccaacccct    1920
gcttcccggg agcccagtgc agcagcttcc ccgatgggtc ctggtcatgc ggctcctgcc    1980
ctgtgggctt cttgggcaat ggcacccact gtgaggacct ggacgagtgt gccctggtcc    2040
ccgacatctg cttctccacc agcaaggtgc ctcgctgtgt caacactcag cctggcttcc    2100
actgcctgcc ctgcccgccc cgatacagag ggaaccagcc cgtcgggtc ggcctggaag     2160
cagccaagac ggaaaagcaa gtgtgtgagc ccgaaaaccc atgcaaggac aagcacacaca   2220
actgccacaa gcacgcggag tgcatctacc tgggccactt cagcgacccc atgtacaagt    2280
gcgagtgcca gacaggctac gcgggcgacg ggctcatctg cggggaggac tcggacctgg    2340
acggctggcc caacctcaat ctggtctgcg ccaccaacgc cacctaccac tgcatcaagg    2400
ataactgccc ccatctgcca aattctgggc aggaagactt tgacaaggac gggattggcg    2460
atgcctgtga tgatgacgat gacaatgacg gtgtgaccga tgagaaggac aactgccagc    2520
tcctcttcaa tccccgccag gctgactatg acaaggatga ggttggggac cgctgtgaca    2580
actgcccttg cgtgcacaac cctgcccaga tcgacacaga caacaatgga gagggtgacg    2640
cctgctccgt ggacattgat ggggacgatg tcttcaatga acgagacaat tgtccctacg    2700
tctacaacac tgaccagagg gacacggatg gtgacggtgt gggggatcac tgtgacaact    2760
gcccccctggt gcacaaccct gaccagaccg acgtggacaa tgaccttgtt ggggaccagt    2820
gtgacaacaa cggaggacata gatgacgacg ccaccagaa caaccaggac aactgccccct    2880
acatctccaa cgccaaccag gctgaccatg acagagacgg ccagggcgac gcctgtgacc    2940
ctgatgatga caacgatggc gtccccgatg acagggacaa ctgccggctt gtgttcaacc    3000
cagaccagga ggacttggac ggtgatggac ggggtgatat ttgtaaagat gattttgaca    3060
atgacaacat cccagatatt gatgatgtgt gtcctgaaaa caatgccatc agtgagacag    3120
acttcaggaa cttccagatg gtcccccttgg atcccaaagg gaccacccaa attgatccca   3180
actgggtcat tcgccatcaa ggcaaggagc tggttcagac agccaactcg gaccccggca    3240
tcgctgtagg ttttgacgag tttgggtctg tggacttcag tggcacattc tacgtaaaca    3300
ctgaccggga cgacgactat gccggcttcg tctttggtta ccagtcaagc agccgcttct    3360
```

```
atgtggtgat gtggaagcag gtgacgcaga cctactggga ggaccagccc acgcgggcct   3420
atggctactc cggcgtgtcc ctcaaggtgg tgaactccac cacggggacg ggcgagcacc   3480
tgaggaacgc gctgtggcac acggggaaca cgccggggca ggtgcgaacc ttatggcacg   3540
accccaggaa cattggctgg aaggactaca cggcctatag gtggcacctg actcacaggc   3600
ccaagactgg ctacatcaga gtcttagtgc atgaaggaaa acaggtcatg gcagactcag   3660
gacctatcta tgaccaaacc tacgctggcg ggcggctggg tctatttgtc ttctctcaag   3720
aaatggtcta tttctcagac ctcaagtacg aatgcagaga tatttaaaca agatttgctg   3780
catttccggc aatgccctgt gcatgccatg gtccctagac acctcagttc attgtggtcc   3840
ttgtggcttc tctctctagc agcacctcct gtcccttgac cttaactctg atggttcttc   3900
acctcctgcc agcaacccca aacccaagtg ccttcagagg ataaatatca atggaactca   3960
gagatgaaca tctaacccac tagaggaaac cagtttggtg atatatgaga ctttatgtgg   4020
agtgaaaatt gggcatgcca ttacattgct ttttcttgtt tgtttaaaaa gaatgacgtt   4080
tacatataaa atgtaattac ttattgtatt tatgtgtata tggagttgaa gggaatactg   4140
tgcataagcc attatgataa attaagcatg aaaaatattg ctgaactact tttggtgctt   4200
aaagttgtca ctattcttga attagagttg ctctacaatg acacacaaat cccattaaat   4260
aaattataaa caagggtcaa ttcaaatttg aagtaatgtt ttagtaagga gagattagaa   4320
gacaacaggc atagcaaatg acataagcta ccgattaact aatcggaaca tgtaaaacag   4380
ttacaaaaat aaacgaactc tcctcttgtc ctacaatgaa agccctcatg tgcagtagag   4440
atgcagtttc atcaaagaac aaacatcctt gcaaatgggt gtgacgcggt tccagatgtg   4500
gatttggcaa aacctcattt aagtaaaagg ttagcagagc aaagtgcggt gctttagctg   4560
ctgcttgtgc cgctgtggcg tcggggaggc tcctgcctga gcttccttcc ccagctttgc   4620
tgcctgagag gaaccagagc agacgcacag gccggaaaag gcgcatctaa cgcgtatcta   4680
ggctttggta actgcggaca agttgctttt acctgatttg atgatacatt tcattaaggt   4740
tccagttata aatattttgt taatatttat taagtgacta tagaatgcaa ctccatttac   4800
cagtaactta ttttaaatat gcctagtaac acatatgtag tataatttct agaaacaaac   4860
atctaataag tatataatcc tgtgaaaata tgaggcttga taatattagg ttgtcacgat   4920
gaagcatgct agaagctgta acagaataca tagagaataa tgaggagttt atgatggaac   4980
cttaaatata taatgttgcc agcgatttta gttcaatatt tgttactgtt atctatctgc   5040
tgtatatgga attcttttaa ttcaaacgct gaaaagaatc agcatttagt cttgccaggc   5100
acacccaata atcagtcatg tgtaatatgc acaagtttgt ttttgttttt gttttttttg   5160
ttggttggtt tgttttttg ctttaagttg catgatcttt ctgcaggaaa tagtcactca   5220
tcccactcca cataaggggt ttagtaagag aagtctgtct gtctgatgat ggataggggg   5280
caaatctttt tccccttcct gttaatagtc atcacatttc tatgccaaac aggaacaatc   5340
cataacttta gtcttaatgt acacattgca ttttgataaa attaattttg ttgtttcctt   5400
tgaggttgat cgttgtgttg ttgttttgct gcactttta cttttttgcg tgtggagctg   5460
tattcccgag accaacgaag cgttgggata cttcattaaa tgtagcgact gtcaacagcg   5520
tgcaggtttt ctgtttctgt gttgtggggt caaccgtaca atggtgtggg agtgacgatg   5580
atgtgaatat ttagaatgta ccatattttt tgtaaattat ttatgttttt ctaaacaaat   5640
ttatcgtata ggttgatgaa acgtcatgtg ttttgccaaa gactgtaaat atttatttat   5700
gtgttcacat ggtcaaaatt tcaccactga aaccctgcac ttagctagaa cctcattttt   5760
```

```
aaagattaac aacaggaaat aaattgtaaa aaaggttttc tatacatgaa aaaaaaaaaa    5820
aaaaaa                                                                5826

<210> SEQ ID NO 95
<211> LENGTH: 9645
<212> TYPE: DNA
<213> ORGANISM: Homo sapiens

<400> SEQUENCE: 95
atgcccaagc gcgcgcactg gggggccctc tccgtggtgc tgatcctgct ttggggccat      60
ccgcgagtgg cgctggcctg cccgcatcct tgtgcctgct acgtcccag cgaggtccac     120 tgcacgttcc gatccctggc ttccgtgccc gctggcattg ctagacacgt ggaaagaatc     180
aatttggggt taatagcat acaggccctg tcagaaacct catttgcagg actgaccaag     240
ttggagctac ttatgattca cggcaatgag atcccaagca tccccgatgg agctttaaga     300
gacctcagct ctcttcaggt tttcaagttc agctacaaca agctgagagt gatcacagga     360
cagaccctcc agggtctctc taacttaatg aggctgcaca ttgaccacaa caagatcgag     420
tttatccacc ctcaagcttt caacggctta acgtctctga ggctactcca tttggaagga     480
aatctcctcc accagctgca ccccagcacc ttctccacgt tcacattttt ggattatttc     540
agactctcca cctaaaggca cctctactta gcagagaaca tggttagaac tcttcctgcc     600
agcatgcttc ggaacatgcc gcttctggag aatctttact tgcagggaaa tccgtggacc     660
tgcgattgtg agatgagatg gtttttggaa tgggatgcaa aatccagagg aattctgaag     720
tgtaaaaagg acaaagctta tgaaggcggt cagttgtgtg caatgtgctt cagtccaaag     780
aagttgtaca acatgagat acacaagctg aaggacatga cttgtctgaa gccttcaata     840 gagtccccctc tgagacagaa caggagcagg agtattgagg aggagcaaga acaggaagag     900
gatggtggca gccagctcat cctggagaaa ttccaactgc ccagtggag catctctttg     960 aatatgaccg acgagcacgg gaacatggtg aacttggtct gtgacatcaa gaaaccaatg    1020
gatgtgtaca gattcactt gaaccaaacg gatcctccag atattgacat aaatgcaaca    1080
gttgccttgg actttgagtg tccaatgacc cgagaaaact atgaaaagct atggaaattg    1140
atagcatact acagtgaagt tcccgtgaag ctacacagag agctcatgct cagcaaagac    1200
cccagagtca gctaccagta caggcaggat gctgatgagg aagctctta ctacacaggt    1260 gtgagagccc agattcttgc agaaccagaa tgggtcatgc agccatccat agatatccag    1320
ctgaaccgac gtcagagtac ggccaagaag gtgctacttt cctactacac ccagtattct    1380
caaacaatat ccaccaaaga tacaaggcag gctcggggca aagctgggt aatgattgag    1440 cctagtggag ctgtgcaaag agatcagact gtcctggaag ggggtccatg ccagttgagc    1500
tgcaacgtga aagcttctga gagtccatct atcttctggg tgcttccaga tggctccatc    1560
ctgaaagcgc ccatggatga cccagacagc aagttctcca ttctcagcag tggctggctg    1620
aggatcaagt ccatggagcc atctgactca ggcttgtacc agtgcattgc tcaagtgagg    1680
gatgaaatgg accgcatggt atatagggta cttgtgcagt ctccctccac tcagccagcc    1740
gagaaagaca cagtgacaat tggcaagaac ccaggggagt cggtgacatt gccttgcaat    1800
gctttagcaa taccgaagc ccaccttagc tggattcttc caaacagaag gataattaat    1860
gatttggcta acacatcaca tgtatacatg ttgccaaatg gaactctttc catcccaaag    1920
gtccaagtca gtgatagtgg ttactacaga tgtgtggctg tcaaccagca aggggcagac    1980
```

```
cattttacgg tgggaatcac agtgaccaag aaagggtctg gcttgccatc caaaagaggc    2040
agacgcccag gtgcaaaggc tctttccaga gtcagagaag acatcgtgga ggatgaaggg    2100
ggctcgggca tgggagatga agagaacact tcaaggagac ttctgcatcc aaaggaccaa    2160
gaggtgttcc tcaaaacaaa ggatgatgcc atcaatggag acaagaaagc caagaaaggg    2220
agaagaaagc tgaaactctg gaagcattcg gaaaagaaac cagagaccaa tgttgcagaa    2280
ggtcgcagag tgtttgaatc tagacgaagg ataaacatgg caaacaaaca gattaatccg    2340
gagcgctggg ctgatatttt agccaaagtc cgtgggaaaa atctccctaa gggcacagaa    2400
gtaccccgt tgattaaaac cacaagtcct ccatccttga gcctagaagt cacaccacct     2460
tttcctgctg tttctccccc ctcagcatct cctgtgcaga cagtaaccag tgctgaagaa    2520
tcctcagcag atgtacctct acttggtgaa gaagagcacg ttttgggtac catttcctca    2580
gccagcatgg ggctagaaca caaccacaat ggagttattc ttgttgaacc tgaagtaaca    2640
agcacacctc tggaggaagt tgttgatgac ctttctgaga agactgagga gataacttcc    2700
actgaaggag acctgaaggg gacagcagcc cctacactta tatctgagcc ttatgaacca    2760
tctcctactc tgcacacatt agacacagtc tatgaaaagc ccacccatga agagacggca    2820
acagagggtt ggtctgcagc agatgttgga tcgtcaccag agcccacatc cagtgagtat    2880
gagcctccat tggatgctgt ctccttggct gagtctgagc ccatgcaata ctttgaccca    2940
gatttggaga ctaagtcaca accagatgag gataagatga agaagacac ctttgcacac     3000
cttactccaa cccccaccat ctgggttaat gactccagta catcacagtt atttgaggat    3060
tctactatag gggaaccagg tgtcccaggc caatcacatc tacaaggact gacagacaac    3120
atccaccttg tgaaaagtag tctaagcact caagacacct tactgattaa aaagggtatg    3180
aaagagatgt ctcagacact acaggaggga aatatgctag agggagaccc cacacactcc    3240
agaagttctg agagtgaggg ccaagagagc aaatccatca ctttgcctga ctccacactg    3300
ggtataatga gcagtatgtc tccagttaag aagcctgcgg aaaccacagt tggtaccctc    3360
ctagacaaag acaccacaac agtaacaaca acaccaaggc aaaaagttgc tccgtcatcc    3420
accatgagca ctcacccttc tcgaaggaga cccaacggga aaggagatt acgcccccaac     3480
aaattccgcc accggcacaa gcaaacccca cccacaactt tgccccatc agagacttt      3540
tctactcaac caactcaagc acctgacatt aagatttcaa gtcaagtgga gagttctctg    3600
gttcctacag cttgggtgga taacacagtt aataccccca acagttgga aatggagaag     3660
aatgcagaac ccacatccaa gggaacacca cggagaaaac acgggaagag gccaaacaaa    3720
catcgatata ccccttctac agtgagctca agagcgtccg gatccaagcc cagcccttct    3780
ccagaaaata aacatagaaa cattgttact cccagttcag aaactatact tttgcctaga    3840
actgtttctc tgaaaactga gggccttat gattccttag attacatgac aaccaccaga     3900
aaaatatatt catcttaccc taaagtccaa gagacacttc cagtcacata taaacccaca    3960
tcagatggaa aagaaattaa ggatgatgtt gccacaaatg ttgacaaaca taaaagtgac    4020
attttagtca ctggtgaatc aattactaat gccataccaa cttctcgctc cttggtctcc    4080
actatgggag aatttaagga agaatcctct cctgtaggct ttccaggaac tccaacctgg    4140
aatccctcaa ggacggccca gcctgggagg ctacagacag acatacctgt taccacttct    4200
ggggaaaatc ttacagaccc tccccttctt aaagagcttg aggatgtgga tttcacttcc    4260
gagttttgt cctctttgac agtctccaca ccatttcacc aggaagaagc tggttcttcc     4320
acaactctct caagcataaa agtggaggtg gcttcaagtc aggcagaaac caccacccttt   4380
```

```
gatcaagatc atcttgaaac cactgtggct attctccttt ctgaaactag accacagaat   4440 cacacccta ctgctgcccg gatgaaggag ccagcatcct cgtccccatc cacaattctc    4500
atgtctttgg gacaaaccac caccactaag ccagcacttc ccagtccaag aatatctcaa   4560
gcatctagag attccaagga aaatgttttc ttgaattatg tggggaatcc agaaacagaa   4620
gcaaccccag tcaacaatga aggaacacag catatgtcag ggccaaatga attatcaaca   4680
ccctcttccg accgggatgc atttaacttg tctacaaagc tggaattgga aaagcaagta   4740
tttggtagta ggagtctacc acgtggccca gatagccaac gccaggatgg aagagttcat   4800
gcttctcatc aactaaccag agtccctgcc aaacccatcc taccaacagc aacagtgagg   4860
ctacctgaaa tgtccacaca aagcgcttcc agatactttg taacttccca gtcacctcgt   4920
cactggacca acaaaccgga ataactaca tatccttctg gggctttgcc agagaacaaa    4980
cagtttacaa ctccaagatt atcaagtaca acaattcctc tcccattgca catgtccaaa   5040
cccagcattc ctagtaagtt tactgaccga agaactgacc aattcaatgg ttactccaaa   5100
gtgtttggaa ataacaacat ccctgaggca agaaacccag ttggaaagcc tcccagtcca   5160
agaattcctc attattccaa tggaagactc cctttctta ccaacaagac tctttctttt     5220
ccacagttgg gagtcacccg gagacccag atacccactt ctcctgcccc agtaatgaga    5280
gagagaaaag ttattccagg ttcctacaac aggatacatt cccatagcac cttccatctg   5340
gactttggcc ctccggcacc tccgttgttg cacactccgc agaccacggg atcaccctca   5400
actaacttac agaatatccc tatggtctct tccacccaga gttctatctc ctttataaca   5460
tcttctgtcc agtcctcagg aagcttccac cagagcagct caaagttctt tgcaggagga   5520
cctcctgcat ccaaattctg gtctcttggg gaaaagcccc aaatcctcac caagtcccca   5580
cagactgtgt ccgtcaccgc tgagacagac actgtgttcc cctgtgaggc aacaggaaaa   5640
ccaaagcctt tcgttacttg gacaaaggtt ccacaggag ctcttatgac tccgaatacc    5700
aggatacaac ggtttgaggt tctcaagaac ggtaccttag tgatacggaa ggttcaagta   5760
caagatcgag gccagtatat gtgcaccgcc agcaacctgc acggcctgga caggatggtg   5820
gtcttgcttt cggtcaccgt gcagcaacct caaatcctag cctcccacta ccaggacgtc   5880
actgtctacc tgggagacac cattgcaatg gagtgtctgg ccaaagggac cccagccccc   5940
caaatttcct ggatcttccc tgacaggagg gtgtggcaaa ctgtgtcccc cgtggagagc   6000
cgcatcaccc tgcacgaaaa ccggaccctt tccatcaagg aggcgtcctt ctcagacaga   6060
ggcgtctata agtgcgtggc cagcaatgca gccggggcgg acagcctggc catccgcctg   6120
cacgtggcgg cactgccccc cgttatccac caggagaagc tggagaacat ctcgctgccc   6180
ccggggctca gcattcacat tcactgcact gccaaggctg cgcccctgcc cagcgtgcgc   6240
tgggtgctcg gggacggtac ccagatccgc ccctcgcagt tcctccacgg gaacttgttt   6300
gttttcccca acgggacgct ctacatccgc aacctcgcgc caaggacag cgggcgctat    6360 gagtgcgtgg ccgccaacct ggtaggctcc gcgcgcagga cggtgcagct gaacgtgcag   6420
cgtgcagcag ccaacgcgcg catcacgggc acctccccgc ggaggacgga cgtcaggtac   6480
ggaggaaccc tcaagctgga ctgcagcgcc tcggggaccc cctggccgcg catcctctgg   6540
aggctgccgt ccaagaggat gatcgacgcg ctcttcagtt ttgatagcag aatcaaggtg   6600
tttgccaatg ggaccctggt ggtgaaatca gtgacggaca agatgccgg agattacctg    6660 tgcgtagctc gaaataaggt tggtgatgac tacgtggtgc tcaaagtgga tgtggtgatg   6720
```

```
aaaccggcca agattgaaca caaggaggag aacgaccaca aagtcttcta cggggtgac    6780
ctgaaagtgg actgtgtggc caccgggctt cccaatcccg agatctcctg gagcctccca  6840
gacgggagtc tggtgaactc cttcatgcag tcggatgaca gcggtggacg caccaagcgc  6900
tatgtcgtct tcaacaatgg gacactctac tttaacgaag tggggatgag ggaggaagga  6960
gactacacct gctttgctga aaatcaggtc gggaaggacg agatgagagt cagagtcaag  7020
gtggtgacag cgcccgccac catccggaac aagacttact ggcggttca ggtgccctat   7080
ggagacgtgg tcactgtagc ctgtgaggcc aaaggagaac ccatgcccaa ggtgacttgg  7140
ttgtccccaa ccaacaaggt gatccccacc tcctctgaga agtatcagat ataccaagat  7200
ggcactctcc ttattcagaa agcccagcgt tctgacagcg gcaactacac ctgcctggtc  7260
aggaacagcg cgggagagga taggaagacg gtgtggattc acgtcaacgt ccagccaccc  7320
aagatcaacg gtaaccccaa ccccatcacc accgtgcggg agatagcagc cggggggcagt 7380
cggaaactga ttgactgcaa agctgaaggc atccccaccc cgagggtgtt atgggctttt  7440
cccgagggtg tggttctgcc agctccatac tatggaaacc ggatcactgt ccatggcaac  7500
ggttccctgg acatcaggag tttgaggaag agcgactccg tccagctggt atgcatggca  7560
cgcaacgagg aggggaggc gaggttgatc gtgcagctca ctgtcctgga gcccatggag  7620
aaacccatct ccacgaccc gatcagcgag aagatcacgg ccatggcggg ccacaccatc  7680
agcctcaact gctctgccgc ggggacccccg acacccagcc tggtgtgggt ccttcccaat  7740
ggcaccgatc tgcagagtgg acagcagctg cagcgcttct accacaaggc tgacggcatg  7800
ctacacatta gcgtctctc ctcggtggac gctggggcct accgctgcgt ggcccgcaat   7860
gccgctggcc acacggagag gctggtctcc ctgaaggtgg gactgaagcc agaagcaaac  7920
aagcagtatc ataacctggt cagcatcatc aatggtgaga ccctgaagct cccctgcacc  7980
cctcccgggg ctgggcaggg acgtttctcc tggacgctcc ccaatggcat gcatctggag  8040
ggcccccaaa ccctgggacg cgtttctctt ctggacaatg gcaccctcac ggttcgtgag  8100
gcctcggtgt ttgacagggg tacctatgta tgcaggatgg agacggagta cggcccttcg  8160
gtcaccagca tccccgtgat tgtgatcgcc tatcctcccc ggatcaccag cgagcccacc  8220
ccggtcatct acaccccggcc cgggaacacc gtgaaactga actgcatggc tatggggatt  8280
cccaaagctg acatcacgtg ggagttaccg gataagtcgc atctgaaggc agggggttcag 8340
gctcgtctgt atggaaacag atttcttcac ccccagggat cactgaccat ccagcatgcc  8400
acacagagag atgccggctt ctacaagtgc atggcaaaaa acattctcgg cagtgactcc  8460
aaaacaactt acatccacgt cttctgaaat gtggattcca gaatgattgc ttaggaactg  8520
acaacaaagc ggggtttgta agggaagcca ggttggggaa taggagctct taaataatgt  8580
gtcacagtgc atggtggcct ctggtgggtt tcaagttgag gttgatcttg atctacaatt  8640
gttgggaaaa ggaagcaatg cagacacgag aaggagggct cagccttgct gagacacttt  8700
cttttgtgtt tacatcatgc caggggcttc attcagggtg tctgtgctct gactgcaatt  8760
tttcttcttt tgcaaatgcc actcgactgc cttcataagc gtccatagga tatctgagga  8820
acattcatca aaaataagcc atagacatga acaacacctc actacccat tgaagacgca   8880
tcacctagtt aacctgctgc agttttaca tgatagactt tgttccagat tgacaagtca   8940
tctttcagtt atttcctctg tcacttcaaa actccagctt gcccaataag gatttagaac  9000
cagagtgact gatatatata tatatatttt aattcagagt tacatacata cagctaccat  9060
tttatatgaa aaaagaaaaa catttcttcc tggaactcac tttttatata atgttttata  9120
```

```
tatatatttt ttcctttcaa atcagacgat gagactagaa ggagaaatac tttctgtctt    9180
attaaaatta ataaattatt ggtctttaca agacttggat acattacagc agacatggaa    9240
atataatttt aaaaaatttc tctccaacct ccttcaaatt cagtcaccac tgttatatta    9300
ccttctccag gaaccctcca gtggggaagg ctgcgatatt agatttcctt gtatgcaaag    9360
tttttgttga aagctgtgct cagaggaggt gagaggagag gaaggagaaa actgcatcat    9420
aactttacag aattgaatct agagtcttcc ccgaaaagcc cagaaacttc tctgcagtat    9480
ctggcttgtc catctggtct aaggtggctg cttcttcccc agccatgagt cagtttgtgc    9540
ccatgaataa tacacgacct gttatttcca tgactgcttt actgtatttt taaggtcaat    9600
atactgtaca tttgataata aaataatatt ctcccaaaaa aaaaa                    9645

<210> SEQ ID NO 96
<211> LENGTH: 694
<212> TYPE: DNA
<213> ORGANISM: Homo sapiens

<400> SEQUENCE: 96
gcctccgagg agaccatggc ctggcccctg tgcaccctgc tgctcctgct ggccacccag     60
gctgtggccc tggcctggag cccccaggag gaggacagga taatcgaggg tggcatctat    120
gatgcagacc tcaatgatga gcgggtacag cgtgcccttc actttgtcat cagcgagtat    180
aacaaggcca ctgaagatga gtactacaga cgcctgctgc gggtgctacg agccagggag    240
cagatcgtgg gcggggtgaa ttacttcttc gacatagagg tgggccgaac catatgtacc    300
aagtcccagc ccaacttgga cacctgtgcc ttccatgaac agccagaact gcagaagaaa    360
cagttgtgct ctttccagat ctacgaagtt ccctgggagg acagaatgtc cctggtgaat    420
tccaggtgtc aagaagccta gggatctgtg ccagggagtc acactgacca cctcctactc    480
ccaccccttg tagtgctccc acccctggac tggtggcccc cacccgtgg gaggtctccc    540 catgcacctg cagcaggaga agacagagaa ggctgcagga ggcctttgtt gctcagcagg    600
ggactctgcc ctccctcctt ccttttgctt ctcatagccc tggtacatgg tacacacacc    660
cccacctcct gcaattaaac agtagcatca cctc                                694

<210> SEQ ID NO 97
<211> LENGTH: 782
<212> TYPE: DNA
<213> ORGANISM: Homo sapiens

<400> SEQUENCE: 97
gggctccctg cctcgggctc tcaccctcct ctcctgcagc tccagctttg tgctctgcct     60
ctgaggagac catggcccag tatctgagta ccctgctgct cctgctggcc acccctagctg    120 tggccctggc ctggagcccc aaggaggagg ataggataat cccgggtggc atctataacg    180
cagacctcaa tgatgagtgg gtacagcgtg cccttcactt cgccatcagc gagtataaca    240
aggccaccaa agatgactac tacagacgtc cgctgcgggt actaagagcc aggcaacaga    300
ccgttggggg ggtgaattac ttcttcgacg tagaggtggg ccgcaccata tgtaccaagt    360
cccagcccaa cttggacacc tgtgccttcc atgaacagcc agaactgcag aagaaacagt    420
tgtgctcttt cgagatctac gaagttccct gggagaacag aaggtccctg gtgaaatcca    480
ggtgtcaaga atcctaggga tctgtgccag gccattcgca ccagccacca cccactccca    540 cccctgtag tgctcccacc cctggactgg tggccccac cctgcgggag gcctcccat    600
```

```
gtgcctgcgc caagagacag acagagaagg ctgcaggagt cctttgttgc tcagcagggc    660
gctctgccct ccctccttcc ttcttgcttc taatagccct ggtacatggt acacaccccc    720
ccacctcctg caattaaaca gtagcatcgc ctccctctga aaaaaaaaaa aaaaaaaaa     780 aa                                                                    782

<210> SEQ ID NO 98
<211> LENGTH: 3432
<212> TYPE: DNA
<213> ORGANISM: Homo sapiens

<400> SEQUENCE: 98
actccagcgc gcggctacct acgcttggtg cttgctttct ccagccatcg agaccagag     60 ccgccccctc tgctcgagaa agggctcag cggcggcgga agcggagggg gaccaccgtg    120
gagagcgcgg tcccagcccg gccactgcgg atccctgaaa ccaaaaagct cctgctgctt   180
ctgtaccccg cctgtccctc ccagctcgcg agggccccct cgtgggatca tcagcccgaa   240
gacagggatg gagaggcctc tgtgctccca cctctgcagc tgcctggcta tgctggccct   300
cctgtccccc ctgagcctgg cacagtatga cagctggccc cattaccccg agtacttcca   360
gcaaccggct cctgagtatc accagcccca ggccccgcc aacgtggcca agattcagct   420
gcgcctggct gggcagaaga ggaagcacag cgagggccgg gtggaggtgt actatgatgg   480
ccagtggggc accgtgtgcg atgacgactt ctccatccac gctgcccacg tcgtctgccg   540
ggagctgggc tatgtggagg ccaagtcctg gactgccagc cctcctacg gcaagggaga   600 agggcccatc tggttagaca atctccactg tactggcaac gaggcgaccc ttgcagcatg   660
cacctccaat ggctgggccg tcactgactg caagcacacg gaggatgtcg gtgtggtgtg   720
cagcgacaaa aggattcctg ggttcaaatt tgacaattcg ttgatcaacc agatagagaa   780
cctgaatatc caggtggagg acattcggat tcgagccatc ctctcaacct accgcaagcg   840 cacccccagtg atggagggct acgtggaggt gaaggagggc aagacctgga agcagatctg   900
tgacaagcac tggacggcca agaattcccg cgtggtctgc ggcatgtttg gcttccctgg   960
ggagaggaca tacaatacca aagtgtacaa aatgtttgcc tcacggagga agcagcgcta  1020
ctggccattc tccatggact gcaccggcac agaggcccac atctccagct gcaagctggg  1080 ccccaggtg tcactggacc ccatgaagaa tgtcacctgc gagaatgggc tgccggccgt  1140
ggtgagttgt gtgcctgggc aggtcttcag ccctgacgga ccctcgagat ccggaaaagc  1200
atacaagcca gagcaacccc tggtgcgact gagaggcggt gcctacatcg ggagggccg   1260 cgtggaggtg ctcaaaaatg gagaatgggg gaccgtctgc gacgacaagt gggacctggt  1320
gtcggccagt gtggtctgca gagagctggg cttggggagt gccaagagg cagtcactgg   1380 ctcccgactg gggcaaggga tcggacccat ccacctcaac gagatccagt gcacaggcaa  1440
tgagaagtcc attatagact gcaagttcaa tgccgagtct cagggctgca accacgagga  1500
ggatgctggt gtgagatgca acacccctgc catgggcttg cagaagaagc tgcgcctgaa  1560
cggcggccgc aatccctacg agggccgagt ggaggtgctg gtggagagaa cgggtcccgt  1620
tgtgtgggga atggtgtgtg gccaaaactg gggcatcgtg gaggccatgg tggtctgccg  1680
ccagctgggc ctgggattcg ccagcaacgc cttccaggag acctggtatt ggcacggaga  1740
tgtcaacagc aacaaagtgg tcatgagtgg agtgaagtgc tcgggaacgg agctgtccct  1800
ggcgcactgc cgccacgacg gggaggacgt ggcctgcccc cagggcggag tgcagtacgg  1860
ggccggagtt gcctgctcag aaaccgcccc tgacctggtc ctcaatgcgg agatggtgca  1920
```

```
gcagaccacc tacctggagg accggcccat gttcatgctg cagtgtgcca tggaggagaa    1980
ctgcctctcg gcctcagccg cgcagaccga ccccaccacg ggctaccgcc ggctcctgcg    2040
cttctcctcc cagatccaca acaatggcca gtccgacttc cggcccaaga acggccgcca    2100
cgcgtggatc tggcacgact gtcacaggca ctaccacagc atggaggtgt tcacccacta    2160
tgacctgctg aacctcaatg caccaaggt ggcagagggc cacaaggcca gcttctgctt    2220
ggaggacaca gaatgtgaag gagacatcca gaagaattac gagtgtgcca acttcggcga    2280
tcagggcatc accatgggct gctgggacat gtaccgccat gacatcgact gccagtgggt    2340
tgacatcact gacgtgcccc ctggagacta cctgttccag gttgttatta accccaactt    2400
cgaggttgca gaatccgatt actccaacaa catcatgaaa tgcaggagcc gctatgacgg    2460
ccaccgcatc tggatgtaca actgccacat aggtggttcc ttcagcgaag agacggaaaa    2520
aaagtttgag cacttcagcg ggctcttaaa caaccagctg tccccgcagt aaagaagcct    2580
gcgtggtcaa ctcctgtctt caggccacac acatcttcc atgggacttc ccccaacaa     2640 ctgagtctga acgaatgcca cgtgccctca cccagcccgg cccccaccct gtccagaccc    2700
ctacagctgt gtctaagctc aggaggaaag ggaccctccc atcattcatg ggggctgct    2760 acctgaccct tggggcctga gaaggccttg ggggggtggg gtttgtccac agagctgctg    2820
gagcagcacc aagagccagt cttgaccggg atgaggccca cagacaggtt gtcatcagct    2880
tgtcccattc aagccaccga gctcaccaca gacacagtgg agccgcgctc ttctccagtg    2940
acacgtggac aaatgcgggc tcatcagccc ccccagagag ggtcaggccg aaccccattt    3000
ctcctcctct taggtcattt tcagcaaact tgaatatcta gacctctctt ccaatgaaac    3060
cctccagtct attatagtca catagataat ggtgccacgt gttttctgat ttggtgagct    3120
cagacttggt gcttccctct ccacaacccc cacccttgt ttttcaagat actattatta     3180
tattttcaca gactttgaa gcacaaattt attggcattt aatattggac atctgggccc     3240
ttggaagtac aaatctaagg aaaaaccaac ccactgtgta agtgactcat cttcctgttg    3300
ttccaattct gtgggttttt gattcaacgg tgctataacc agggtcctgg gtgacagggc    3360
gctcactgag caccatgtgt catcacagac acttacacat acttgaaact tggaataaaa    3420
gaaagattta tg                                                       3432
```

<210> SEQ ID NO 99
<211> LENGTH: 8448
<212> TYPE: DNA
<213> ORGANISM: Homo sapiens

<400> SEQUENCE: 99

```
gcagtggttt ctcctccttc ctcccaggaa gggccaggaa aatggccctg gtcctggaga      60
tcttcaccct gctggcctcc atctgctggg tgtcggccaa tatcttcgag taccaggttg     120
atgcccagcc cctcgtccc tgtgagctgc agagggaaac ggcctttctg aagcaagcag      180
actacgtgcc ccagtgtgca gaggatggca gcttccagac tgtccagtgc cagaacgacg     240
gccgctcctg ctggtgtgtg ggtgccaacg gcagtgaagt gctgggcagc aggcagccag     300
gacggcctgt ggcttgtctg tcattttgtc agctacagaa acagcagatc ttactgagtg     360
gctacattaa cagcacagac acctcctacc tccctcagtg tcaggattca ggggactacg     420
cgcctgttca gtgtgatgtg cagcatgtcc agtgctggtg tgtggacgca gaggggatgg     480
aggtgtatgg gacccgccag ctggggaggc caaagcgatg tccaaggagc tgtgaaataa     540
```

```
gaaatcgtcg tcttctccac ggggtgggag ataagtcacc accccagtgt tctgcggagg    600
gagagtttat gcctgtccag tgcaaatttg tcaacaccac agacatgatg atttttgatc    660
tggtccacag ctacaacagg tttccagatg catttgtgac cttcagttcc ttccagagga    720
ggttccctga ggtatctggg tattgccact gtgctgacag ccaagggcgg gaactggctg    780
agacaggttt ggagttgtta ctggatgaaa tttatgacac catttttgct ggcctggacc    840
ttccttccac cttcactgaa accaccctgt accggatact gcagagacgg ttcctcgcag    900
ttcaatcagt catctctggc agattccgat gccccacaaa atgtgaagtg gagcggttta    960
cagcaaccag ctttggtcac ccctatgttc aagctgccg ccgaaatggc gactatcagg   1020
cggtgcagtg ccagacggaa gggccctgct ggtgtgtgga cgcccagggg aaggaaatgc   1080
atggaacccg gcagcaaggg gagccgccat cttgtgctga aggccaatct tgtgcctccg   1140
aaaggcagca ggccttgtcc agactctact ttgggacctc aggctacttc agccagcacg   1200
acctgttctc ttccccagag aaaagatggg cctctccaag agtagccaga tttgccacat   1260
cctgcccacc cacgatcaag gagctctttg tggactctgg gcttctccgc ccaatggtgg   1320
agggacagag ccaacagttt tctgtctcag aaaatcttct caaagaagcc atccgagcaa   1380
ttttccctc ccgagggctg gctcgtcttg cccttcagtt taccaccaac ccaaagagac   1440
tccagcaaaa ccttttttgga gggaaatttt tggtgaatgt tggccagttt aacttgtctg   1500
gagcccttgg cacaagaggc acatttaact tcagtcaatt ttttccagcaa cttggtcttg   1560
caagcttctt gaatggaggg agacaagaag atttggccaa gccactctct gtgggattag   1620
attcaaattc ttccacagga accctgaag ctgctaagaa ggatggtact atgaataagc   1680
caactgtggg cagctttggc tttgaaatta acctacaaga gaaccaaaat gccctcaaat   1740
tccttgcttc tctcctggag cttccagaat tccttctctt cttgcaacat gctatctctg   1800
tgccagaaga tgtggcaaga gatttaggtg atgtgatgga aacggtactc gactcccaga   1860
cctgtgagca gacacctgaa aggctatttg tcccatcatg cacgcacgaa ggaagctatg   1920
aggatgtcca atgcttttcc ggagagtgct ggtgtgtgaa ttcctggggc aaagagcttc   1980
caggctcaag agtcagagat ggacagccaa ggtgccccac agactgtgaa agcaaagggg   2040
ctcgcatgca aagcctcatg ggcagccagc ctgctggctc caccttgttt gtccctgctt   2100
gtactagtga gggacatttc ctgcctgtcc agtgcttcaa ctcagagtgc tactgtgttg   2160
atgctgaggg tcaggccatt cctggaactc gaagtgcaat agggaagccc aagaaatgcc   2220
ccacgccctg tcaattacag tctgagcaag ctttcctcag gacggtgcag gccctgctct   2280
ctaactccag catgctaccc acccttttccg acacctacat cccacagtgc agcaccgatg   2340
ggcagtggag acaagtgcaa tgcaatgggc ctcctgagca ggtcttcgag ttgtaccaac   2400
gatgggaggc tcagaacaag ggccaggatc tgacgcctgc caagctgcta gtgaagatca   2460
tgagctacag agaagcagct tccggaaact tcagtctctt tattcaaagt ctgtatgagg   2520
ctggccagca agatgtcttc ccggtgctgt cacaataccc ttctctgcaa gatgtcccac   2580
tagcagcact ggaagggaaa cggccccagc ccagggagaa tatcctcctg gagccctacc   2640
tcttctggca gatcttaaat ggccaactca gccaatacccc ggggtcctac tcagacttca   2700
gcactccttt ggcacatttt gatcttcgga actgctggtg tgtggatgag ctggccaag   2760
aactggaagg aatgcggtct gagccaagca agctcccaac gtgtcctggc tcctgtgagg   2820
aagcaaagct ccgtgtactg cagttcatta gggaaacgga agagattgtt tcagcttcca   2880
acagttctcg gttccctctg ggggagagtt tcctggtggc caagggaatc cggctgagga   2940
```

```
atgaggacct cggccttcct ccgctcttcc cgccccggga ggctttcgcg gagtttctgc    3000
gtgggagtga ttacgccatt cgcctggcgg ctcagtctac cttaagcttc tatcagagac    3060
gccgcttttc cccggacgac tcggctggag catccgccct tctgcggtcg ggcccctaca    3120
tgccacagtg tgatgcgttt ggaagttggg agcctgtgca gtgccacgct gggactgggc    3180
actgctggtg tgtagatgag aaaggagggt tcatccctgg ctcactgact gcccgctctc    3240
tgcagattcc acagtgcccg acaacctgcg agaaatctcg aaccagtggg ctgctttcca    3300
gttggaaaca ggctagatcc caagaaaacc catctccaaa agacctgttc gtcccagcct    3360
gcctagaaac aggagaatat gccaggctgc aggcatcggg ggctggcacc tggtgtgtgg    3420
accctgcatc aggagaagag ttgcggcctg gctcgagcag cagtgcccag tgcccaagcc    3480
tctgcaatgt gctcaagagt ggagtcctct ctaggagagt cagcccaggc tatgtcccag    3540
cctgcagggc agaggatggg ggcttttccc cagtgcaatg tgaccaggcc cagggcagct    3600
gctggtgtgt catggacagc ggagaagagg tgcctgggac gcgcgtgacc gggggccagc    3660
ccgcctgtga gagcccgcgg tgtccgctgc cattcaacgc gtcggaggtg gttggtggaa    3720
caatcctgtg tgagacaatc tcgggcccca caggctctgc catgcagcag tgccaattgc    3780
tgtgccgcca aggctcctgg agcgtgtttc caccagggcc attgatatgt agcctggaga    3840
gcggacgctg ggagtcacag ctgcctcagc cccgggcctg ccaacggccc cagctgtggc    3900
agaccatcca gacccaaggg cactttcagc tccagctccc gccgggcaag atgtgcagtg    3960
ctgactacgc gggtttgctg cagactttcc aggttttcat attggatgag ctgacagccc    4020
gcggcttctg ccagatccag gtgaagactt ttggcaccct ggtttccatt cctgtctgca    4080
acaactcctc tgtgcaggtg ggttgtctga ccagggagcg tttaggagtg aatgttacat    4140
ggaaatcacg gcttgaggac atcccagtgg cttctcttcc tgacttacat gacattgaga    4200
gagccttggt gggcaaggat ctccttgggc gcttcacaga tctgatccag agtggctcat    4260
tccagcttca tctggactcc aagacgttcc cagcggaaac catccgcttc ctccaagggg    4320
accactttgg cacctctcct aggacacggt ttgggtgctc ggaaggattc taccaagtct    4380
tgacaagtga ggccagtcag gacggactgg gatgcgttaa gtgccatgaa ggaagctatt    4440
cccaagatga ggaatgcatt ccttgtcctg ttggattcta ccaagaacag gcagggagct    4500
tggcctgtgt cccatgtcct gtgggcagaa cgaccatttc tgccgagct ttcagccaga    4560 ctcactgtgt cactgactgt cagaggaacg aagcaggcct gcaatgtgac cagaatggcc    4620
agtatcgagc cagccagaag gacaggggca gtgggaaggc cttctgtgtg gacggcgagg    4680
gcgggaggct gccatggtgg gaaacagagg cccctcttga ggactcacag tgtttgatga    4740
tgcagaagtt tgagaaggtt ccagaatcaa aggtgatctt cgacgccaat gctcctgtgg    4800
ctgtcagatc caaagttcct gattctgagt tccccgtgat gcagtgcttg acagattgca    4860
cagaggacga ggcctgcagc ttcttcaccg tgtccacgac ggagccagag atttcctgtg    4920
atttctatgc ttggacaagt gacaatgttg cctgcatgac ttctgaccag aaacgagatg    4980
cactggggaa ctcaaaggcc accagctttg gaagtcttcg ctgccaggtg aaagtgagga    5040
gccatggtca agattctcca gctgtgtatt tgaaaaaggg ccaaggatcc accacaacac    5100
ttcagaaacg cttgaaccc actggttttcc aaaacatgct ttctggattg tacaacccca    5160
ttgtgttctc agcctcagga gccaatccaa ccgatgctca cctcttctgt cttcttgcat    5220
gcgaccgtga tctgtgttgc gatggcttcg tcctcacaca ggttcaagga ggtgccatca    5280
```

```
tctgtgggtt gctgagctca cccagtgtcc tgctttgtaa tgtcaaagac tggatggatc    5340
cctctgaagc ctgggctaat gctacatgtc ctggtgtgac atatgaccag agagccacc    5400
aggtgatatt gcgtcttgga gaccaggagt tcatcaagag tctgacaccc ttagaaggaa    5460
ctcaagacac cttaccaat tttcagcagg tttatctctg aaagattct gacatggggt    5520
ctcggcctga gtctatggga tgtagaaaaa acacagtgcc aaggccagca tctccaacag    5580
aagcaggttt gacaacagaa cttttctccc ctgtggacct caaccaggtc attgtcaatg    5640
gaaatcaatc actatccagc cagaagcact ggcttttcaa gcacctgttt tcagcccagc    5700
aggcaaacct atggtgcctt tctcgttgtg tgcaggagca ctctttctgt cagctcgcag    5760
agataacaga gagtgcatcc ttgtacttca cctgcaccct tacccagag gcacaggtgt    5820
gtgatgacat catggagtcc aatacccagg gctgcagact gatcctgcct cagatgccaa    5880
aggccctgtt ccggaagaaa gttatactgg aagataaagt gaagaacttt tacactcgcc    5940
tgccgttcca aaaactgatg gggatatcca ttagaaataa agtgcccatg tctgaaaaat    6000
ctatttctaa tgggttcttt gaatgtgaac gacggtgcga tgcggaccca tgctgcactg    6060
gctttggatt tctaaatgtt tcccagttaa aggaggaga ggtgacatgt ctcactctga    6120
acagcttggg aattcagatg tgcagtgagg agaatggagg agcctggcgc attttggact    6180
gtggctctcc tgacattgaa gtccacacct atcccttcgg atggtaccag aagcccattg    6240
ctcaaaataa tgctcccagt ttttgccctt tggttgttct gccttccctc acagagaaag    6300
tgtctctgga atcgtggcag tccctggccc tctcttcagt ggttgttgat ccatccatta    6360
ggcactttga tgttgcccat gtcagcactg ctgccaccag caatttctct gctgtccgag    6420
acctctgttt gtcggaatgt tcccaacatg aggcctgtct catcaccact ctgcaaaccc    6480
aactcggggc tgtgagatgt atgttctatg ctgatactca aagctgcaca catagtctgc    6540
agggtcggaa ctgccgactt ctgcttcgtg aagaggccac ccacatctac cggaagccag    6600
gaatctctct gctcagctat gaggcatctg taccttctgt gcccatttcc acccatggcc    6660
ggctgctggg caggtcccag gccatccagg tgggtacctc atggaagcaa gtggaccagt    6720
tccttggagt tccatatgct gccccgcccc tggcagagag gcacttccag gcaccagagc    6780
ccttgaactg gacaggctcc tgggatgcca gcaagccaag ggccagctgc tggcagccag    6840
gcaccagaac atccacgtct cctggagtca gtgaagattg tttgtatctc aatgtgttca    6900
tccctcagaa tgtggcccct aacgcgtctg tgctggtgtt cttccacaac accatggaca    6960
gggaggagag tgaaggatgg ccggctatcg acggctcctt cttggctgct gttggcaacc    7020
tcatcgtggt cactgccagc taccgagtgg gtgtcttcgg cttcctgagt tctggatccg    7080
gagaggtgag tggcaactgg gggctgctgg accaggtggc ggctctgacc tgggtgcaga    7140
cccacatccg aggatttggc ggggaccctc ggcgcgtgtc cctggcagca gaccgtggcg    7200
gggctgatgt ggccagcatc caccttctca cggccagggc caccaactcc caacttttcc    7260
ggagagctgt gctgatggga ggctccgcac tctccccggc cgccgtcatc agccatgaga    7320
gggctcagca gcaggcaatt gctttggcaa aggaggtcag ttgccccatg tcatccagcc    7380
aagaagtggt gtcctgcctc cgccagaagc ctgccaatgt cctcaatgat gcccagacca    7440
agctcctggc cgtgagtggc cctttccact actgggtcc tgtgatcgat ggccacttcc    7500
tccgtgagcc tccagccaga gcactgaaga ggtctttatg ggtagaggtc gatctgctca    7560
ttgggagttc tcaggacgac gggctcatca acagagcaaa ggctgtgaag caatttgagg    7620
aaagtcgagg ccggaccagt agcaaaacag ccttttacca ggcactgcag aattctctgg    7680
```

```
gtggcgagga ctcagatgcc cgcgtcgagg ctgctgctac atggtattac tctctggagc    7740
actccacgga tgactatgcc tccttctccc gggctctgga gaatgccacc cgggactact    7800
ttatcatctg ccctataatc gacatggcca gtgcctgggc aaagagggcc cgaggaaacg    7860
tcttcatgta ccatgctcct gaaaactacg gccatggcag cctggagctg ctggcggatg    7920
ttcagtttgc cttggggctt cccttctacc cagcctacga ggggcagttt tctctggagg    7980
agaagagcct gtcgctgaaa atcatgcagt acttttccca cttcatcaga tcaggaaatc    8040
ccaactaccc ttatgagttc tcacggaaag tacccacatt tgcaaccccc tggcctgact    8100
ttgtaccccg tgctggtgga gagaactaca aggagttcag tgagctgctc cccaatcgac    8160
agggcctgaa gaaagccgac tgctccttct ggtccaagta catctcgtct ctgaagacat    8220
ctgcagatgg agccaagggc gggcagtcag cagagagtga agaggaggag ttgacggctg    8280
gatctgggct aagagaagat ctcctaagcc tccaggaacc aggctctaag acctacagca    8340
agtgaccagc ccttgagctc cccaaaaacc tcacccgagg ctgcccacta tggtcatctt    8400
tttctctaaa atagttactt accttcaata aagtatctac atgcggtg                8448

<210> SEQ ID NO 100
<211> LENGTH: 2745
<212> TYPE: DNA
<213> ORGANISM: Homo sapiens

<400> SEQUENCE: 100
acctccctcc gcggagcagc cagacagcga gggccccggc cggggcaggg gggacgccc      60 cgtccgggc acccccccg gctctgagcc gcccgcgggg ccggcctcgg cccggagcgg     120
aggaaggagt cgccgaggag cagcctgagg ccccagagtc tgagacgagc cgccgccgcc    180
cccgccactg cggggaggag ggggaggagg agcgggagga gggacgagct ggtcgggaga    240
agaggaaaaa aacttttgag acttttccgt tgccgctggg agccggaggc gcggggacct    300
cttggcgcga cgctgccccg cgaggaggca ggacttgggg accccagacc gcctcccttt    360
gccgccgggg acgcttgctc cctccctgcc ccctacacgg cgtccctcag gcgcccccat    420
tccggaccag ccctcgggag tcgccgaccc ggcctcccgc aaagactttt ccccagacct    480
cgggcgcacc ccctgcacgc cgccttcatc cccggcctgt ctcctgagcc ccgcgcatc     540 ctagacccctt tctcctccag gagacggatc tctctccgac ctgccacaga tcccctattc    600
aagaccaccc accttctggt accagatcgc gcccatctag gttatttccg tgggatactg    660 agacacccc ggtccaagcc tccctccac cactgcgccc ttctccctga ggagcctcag     720
ctttccctcg aggccctcct acctttgcc gggagacccc cagcccctgc aggggcgggg    780
cctccccacc acaccagccc tgttcgcgct ctcggcagtg ccgggggcg ccgcctcccc     840 catgccgccc tccgggctgc ggctgctgcc gctgctgcta ccgctgctgt ggctactggt    900
gctgacgcct ggcccgccgg ccgcgggact atccacctgc aagactatcg acatggagct    960
ggtgaagcgg aagcgcatcg aggccatccg cggccagatc ctgtccaagc tgcggctcgc    1020 cagcccccccg agccagggggg aggtgccgcc cggcccgctg cccgaggccg tgctcgccct    1080
gtacaacagc cccgcgacc gggtggccgg ggagagtgca gaaccggagc ccgagcctga    1140
ggccgactac tacgccaagg aggtcacccg cgtgctaatg gtggaaaccc acaacgaaat    1200
ctatgacaag ttcaagcaga gtacacacag catatatatg ttcttcaaca catcagagct    1260
ccgagaagcg gtacctgaac ccgtgttgct ctcccgggca gagctgcgtc tgctgaggag    1320
```

| | | | | | |
|---|---|---|---|---|---|
| gctcaagtta | aaagtggagc | agcacgtgga | gctgtaccag | aaatacagca | acaattcctg | 1380 |
| gcgatacctc | agcaaccggc | tgctggcacc | cagcgactcg | ccagagtggt | tatcttttga | 1440 |
| tgtcaccgga | gttgtgcggc | agtggttgag | ccgtggaggg | gaaattgagg | gctttcgcct | 1500 |
| tagcgcccac | tgctcctgtg | acagcaggga | taacacactg | caagtggaca | tcaacgggtt | 1560 |
| cactaccggc | cgccgaggtg | acctggccac | cattcatggc | atgaaccggc | ctttcctgct | 1620 |
| tctcatggcc | accccgctgg | agagggccca | gcatctgcaa | agctcccggc | accgccgagc | 1680 |
| cctggacacc | aactattgct | tcagctccac | ggagaagaac | tgctgcgtgc | ggcagctgta | 1740 |
| cattgacttc | cgcaaggacc | tcggctgaa | gtggatccac | gagcccaagg | gctaccatgc | 1800 |
| caacttctgc | ctcgggccct | gccctacat | ttggagcctg | gacacgcagt | acagcaaggt | 1860 |
| cctggccctg | tacaaccagc | ataacccggg | cgcctcggcg | gcgccgtgct | gcgtgccgca | 1920 |
| ggcgctggag | ccgctgccca | tcgtgtacta | cgtgggccgc | aagcccaagg | tggagcagct | 1980 |
| gtccaacatg | atcgtgcgct | cctgcaagtg | cagctgaggt | cccgcccgc | ccgccccgc | 2040 |
| cccggcaggc | ccggccccac | cccgccccgc | cccgctgcc | ttgcccatgg | gggctgtatt | 2100 |
| taaggacacc | gtgccccaag | cccacctggg | gccccattaa | agatggagag | aggactgcgg | 2160 |
| atctctgtgt | cattgggcgc | ctgcctgggg | tctccatccc | tgacgttccc | ccactcccac | 2220 |
| tccctctctc | tccctctctg | cctcctcctg | cctgtctgca | ctattccttt | gcccggcatc | 2280 |
| aaggcacagg | ggaccagtgg | ggaacactac | tgtagttaga | tctatttatt | gagcaccttg | 2340 |
| ggcactgttg | aagtgcctta | cattaatgaa | ctcattcagt | caccatagca | acactctgag | 2400 |
| atggcaggga | ctctgataac | acccatttta | aaggttgagg | aaacaagccc | agagaggtta | 2460 |
| agggaggagt | tcctgcccac | caggaacctg | ctttagtggg | ggatagtgaa | gaagacaata | 2520 |
| aaagatagta | gttcaggcca | ggcggggtgc | tcacgcctgt | aatcctagca | cttttgggag | 2580 |
| gcagagatgg | gaggatactt | gaatccaggc | atttgagacc | agcctgggta | acatagtgag | 2640 |
| accctatctc | tacaaaacac | ttttaaaaaa | tgtacacctg | tggtcccagc | tactctggag | 2700 |
| gctaaggtgg | gaggatcact | tgatcctggg | aggtcaaggc | tgcag | | 2745 |

```
<210> SEQ ID NO 101
<211> LENGTH: 2208
<212> TYPE: DNA
<213> ORGANISM: Homo sapiens

<400> SEQUENCE: 101
```

| | | | | | |
|---|---|---|---|---|---|
| tctttggctt | tttttggcgg | agctggggcg | ccctccggaa | gcgttccaa | ctttccagaa | 60 |
| gtttctcggg | acgggcagga | gggggtgggg | actgccatat | atagatcccg | ggagcagggg | 120 |
| agcgggctaa | gagtagaatc | gtgtcgcggc | tcgagagcga | gagtcacgtc | ccggcgctag | 180 |
| cccagcccga | cccaggccca | ccgtggtgca | cgcaaaccac | ttcctggcca | tgcgctccct | 240 |
| cctgcttctc | agcgccttct | gcctcctgga | ggcggccctg | gccgccgagg | tgaagaaacc | 300 |
| tgcagccgca | gcagctcctg | gcactgcgga | gaagttgagc | cccaaggcgg | ccacgcttgc | 360 |
| cgagcgcagc | gccggcctgg | ccttcagctt | gtaccaggcc | atggccaagg | accaggcagt | 420 |
| ggagaacatc | ctggtgtcac | ccgtggtggt | ggcctcgtcg | ctagggctcg | tgtcgctggg | 480 |
| cggcaaggcg | accacggcgt | cgcaggccaa | ggcagtgctg | agcgccgagc | agctgcgcga | 540 |
| cgaggaggtg | cacgccggcc | tgggcgagct | gctgcgctca | ctcagcaact | ccacggcgcg | 600 |
| caacgtgacc | tggaagctgg | gcagccgact | gtacggaccc | agctcagtga | gcttcgctga | 660 |
| tgacttcgtg | cgcagcagca | agcagcacta | caactgcgag | cactccaaga | tcaacttccg | 720 |

```
cgacaagcgc agcgcgctgc agtccatcaa cgagtgggcc gcgcagacca ccgacggcaa      780
gctgcccgag gtcaccaagg acgtggagcg cacggacggc gccctgctag tcaacgccat      840
gttcttcaag ccacactggg atgagaaatt ccaccacaag atggtggaca accgtggctt      900
catggtgact cggtcctata ccgtgggtgt catgatgatg caccggacag gcctctacaa      960
ctactacgac gacgagaagg aaaagctgca atcgtggag atgcccctgg cccacaagct     1020
ctccagcctc atcatcctca tgccccatca cgtggagcct ctcgagcgcc ttgaaaagct     1080
gctaaccaaa gagcagctga agatctggat ggggaagatg cagaagaagg ctgttgccat     1140
ctccttgccc aagggtgtgg tggaggtgac ccatgacctg cagaaacacc tggctgggct     1200
gggcctgact gaggccattg acaagaacaa ggccgacttg tcacgcatgt caggcaagaa     1260
ggacctgtac ctggccagcg tgttccacgc caccgccttt gagttggaca cagatggcaa     1320
ccccttttgac caggacatct acgggcgcga ggagctgcgc agccccaagc tgttctacgc     1380
cgaccacccc ttcatcttcc tagtgcggga cacccaaagc ggctccctgc tattcattgg     1440
gcgcctggtc cggcctaagg gtgacaagat gcgagacgag ttatagggcc tcagggtgca     1500
cacaggatgg caggaggcat ccaaaggctc ctgagcacac tgggtgctat tgggggttggg     1560
ggggaggtga ggtaccagcc ttggatactc catggggtgg gggtggaaaa acagaccggg     1620
gttcccgtgt gcctgagcgg accttcccag ctagaattca ctccacttgg acatgggccc     1680
cagataccat gatgctgagc ccggaaactc cacatcctgt gggacctggg ccatagtcat     1740
tctgcctgcc ctgaaagtcc cagatcaagc ctgcctcaat cagtattcat atttatagcc     1800
aggtaccttc tcacctgtga gaccaaattg agctagggggg gtcagccagc cctcttctga     1860
cactaaaaca cctcagctgc ctccccagct ctatcccaac ctctcccaac tataaaacta     1920
ggtgctgcag cccctgggac caggcacccc cagaatgacc tggccgcagt gaggcggatt     1980
gagaaggagc tcccaggagg ggcttctggg cagactctgg tcaagaagca tcgtgtctgg     2040
cgttgtgggg atgaactttt tgttttgttt cttcctttttt tagttcttca aagataggga     2100
gggaagggg aacatgagcc tttgttgcta tcaatccaag aacttatttg tacattttt      2160
ttttcaataa aacttttcca atgacatttt gttggagcgt ggaaaaaa                  2208
```

<210> SEQ ID NO 102
<211> LENGTH: 2566
<212> TYPE: DNA
<213> ORGANISM: Homo sapiens

<400> SEQUENCE: 102

```
ggcacgagtt gtgctcctcg cttgcctgtt ccttttccac gcattttcca ggataactgt       60
gactccaggc ccgcaatgga tgccctgcaa ctagcaaatt cggcttttgc cgttgatctg      120
ttcaaacaac tatgtgaaaa ggagccactg gcaatgtcc tcttctctcc aatctgtctc      180
tccacctctc tgtcacttgc tcaagtgggt gctaaaggtg acactgcaaa tgaaattgga      240
caggttcttc attttgaaaa tgtcaaagat atacccttg gatttcaaac agtaacatcg      300
gatgtaaaca aacttagttc cttttactca ctgaaactaa tcaagcggct ctacgtagac      360
aaatctctga atctttctac agagttcatc agctctacga agagaccctta tgcaaaggaa      420
ttggaaactg ttgacttcaa agataaattg gaagaaacga aggtcagat caacaactca      480
attaaggatc tcacagatgg ccactttgag aacatttttag ctgacaacag tgtgaacgac      540
cagaccaaaa tccttgtggt taatgctgcc tactttgttg gcaagtggat gaagaaattt      600
```

```
cctgaatcag aaacaaaaga atgtcctttc agactcaaca agacagacac caaaccagtg    660
cagatgatga acatggaggc cacgttctgt atgggaaaca ttgacagtat caattgtaag    720
atcatagagc ttccttttca aaataagcat ctcagcatgt tcatcctact acccaaggat    780
gtggaggatg agtccacagg cttggagaag attgaaaaac aactcaactc agagtcactg    840
tcacagtgga ctaatcccag caccatggcc aatgccaagg tcaaactctc cattccaaaa    900
tttaaggtgg aaaagatgat tgatcccaag gcttgtctgg aaaatctagg gctgaaacat    960
atcttcagtg aagacacatc tgatttctct ggaatgtcag agaccaaggg agtggcccta   1020
tcaaatgtta tccacaaagt gtgcttagaa ataactgaag atggtgggga ttccatagag   1080
gtgccaggag cacggatcct gcagcacaag gatgaattga atgctgacca tcccttttatt  1140 tacatcatca ggcacaacaa aactcgaaac atcattttct ttggcaaatt ctgttctcct   1200
taagtggcat agcccatgtt aagtcctccc tgacttttct gtggatgccg atttctgtaa   1260
actctgcatc cagagattca ttttctagat acaataaatt gctaatgttg ctggatcagg   1320
aagccgccag tacttgtcat atgtagcctt cacacagata gaccttttt ttttttccaat    1380 tctatctttt gtttccttt ttcccataag acaatgacat acgcttttaa tgaaaaggaa    1440
tcacgttaga ggaaaaatat ttattcatta tttgtcaaat tgtccggggt agttggcaga   1500
aatacagtct tccacaaaga aaattcctat aaggaagatt tggaagctct tcttcccagc   1560
actatgcttt ccttctttgg gatagagaat gttccagaca ttctcgcttc cctgaaagac   1620
tgaagaaagt gtagtgcatg ggacccacga aactgccctg gctccagtga aacttgggca   1680
catgctcagg ctactatagg tccagaagtc cttatgttaa gccctggcag gcaggtgttt   1740
attaaaattc tgaattttgg ggattttcaa aagataatat tttacataca ctgtatgtta   1800
tagaacttca tggatcagat ctggggcagc aacctataaa tcaacacctt aatatgctgc   1860
aacaaaatgt agaatattca gacaaaatgg atacataaag actaagtagc ccataagggg   1920
tcaaaatttg ctgccaaatg cgtatgccac caacttacaa aaacacttcg ttcgcagagc   1980
ttttcagatt gtggaatgtt ggataaggaa ttatagacct ctagtagctg aaatgcaaga   2040
ccccaagagg aagttcagat cttaatataa attcactttc attttgata gctgtcccat    2100 ctggtcatgt ggttggcact agactggtgg caggggcttc tagctgactc gcacagggat   2160
tctcacaata gccgatatca gaatttgtgt tgaaggaact tgtctcttca tctaatatga   2220
tagcgggaaa aggagaggaa actactgcct ttagaaaata taagtaaagt gattaaagtg   2280
ctcacgttac cttgacacat agttttttcag tctatgggtt tagttacttt agatggcaag   2340
catgtaactt atattaatag taatttgtaa agttgggtgg ataagctatc cctgttgccg   2400
gttcatggat tacttctcta taaaaaatat atatttacca aaaaattttg tgacattcct   2460
tctcccatct cttccttgac atgcattgta aataggttct tcttgttctg agattcaata   2520
ttgaatttct cctatgctat tgacaataaa atattattga actacc                  2566

<210> SEQ ID NO 103
<211> LENGTH: 2974
<212> TYPE: DNA
<213> ORGANISM: Homo sapiens

<400> SEQUENCE: 103
ctcagggcag agggaggaag gacagcagac cagacagtca cagcagcctt gacaaaacgt     60
tcctggaact caagctcttc tccacagagg aggacagagc agacagcaga gaccatggag    120 tctcccctcgg cccctcccca cagatggtgc atcccctggc agaggctcct gctcacagcc    180
```

```
tcacttctaa ccttctggaa cccgcccacc actgccaagc tcactattga atccacgccg    240
ttcaatgtcg cagaggggaa ggaggtgctt ctacttgtcc acaatctgcc ccagcatctt    300
tttggctaca gctggtacaa aggtgaaaga gtggatggca accgtcaaat tataggatat    360
gtaataggaa ctcaacaagc taccccaggg cccgcataca gtggtcgaga gataatatac    420
cccaatgcat ccctgctgat ccagaacatc atccagaatg acacaggatt ctacaccta    480 cacgtcataa agtcagatct tgtgaatgaa gaagcaactg ccagttccg ggtataccg    540 gagctgccca gccctccat ctccagcaac aactccaaac ccgtggagga caaggatgct    600
gtggccttca cctgtgaacc tgagactcag gacgcaacct acctgtggtg ggtaaacaat    660
cagagcctcc cggtcagtcc caggctgcag ctgtccaatg gcaacaggac cctcactcta    720
ttcaatgtca caagaaatga cacagcaagc tacaaatgtg aaacccagaa cccagtgagt    780
gccaggcgca gtgattcagt catcctgaat gtcctctatg gcccggatgc ccccaccatt    840
tcccctctaa acacatctta cagatcaggg aaaatctga acctctcctg ccacgcagcc    900
tctaacccac ctgcacagta ctcttggttt gtcaatggga ctttccagca atccacccaa    960
gagctcttta tccccaacat cactgtgaat aatagtggat cctatacgtg ccaagcccat   1020
aactcagaca ctggcctcaa taggaccaca gtcacgacga tcacagtcta tgcagagcca   1080
cccaaaccct tcatcaccag caacaactcc aaccccgtgg aggatgagga tgctgtagcc   1140
ttaacctgtg aacctgagat tcagaacaca acctacctgt ggtgggtaaa taatcagagc   1200
ctcccggtca gtcccaggct gcagctgtcc aatgacaaca ggaccctcac tctactcagt   1260
gtcacaagga atgatgtagg accctatgag tgtggaatcc agaacgaatt aagtgttgac   1320
cacagcgacc cagtcatcct gaatgtcctc tatggcccag acgacccac catttccccc   1380 tcatacacct attaccgtcc agggtgaac ctcagcctct cctgccatgc agcctctaac   1440
ccacctgcac agtattcttg gctgattgat gggaacatcc agcaacacac acaagagctc   1500
tttatctcca acatcactga gaagaacagc ggactctata cctgccaggc caataactca   1560
gccagtggcc acagcaggac tacagtcaag acaatcacag tctctgcgga gctgcccaag   1620
ccctccatct ccagcaacaa ctccaaaccc gtggaggaca aggatgctgt ggccttcacc   1680
tgtgaacctg aggctcagaa cacaacctac ctgtggtggg taaatggtca gagcctccca   1740
gtcagtccca ggctgcagct gtccaatggc aacaggaccc tcactctatt caatgtcaca   1800
agaaatgacg caagagccta tgtatgtgga atccagaact cagtgagtgc aaaccgcagt   1860
gacccagtca ccctggatgt cctctatggg ccggacaccc ccatcatttc cccccagac   1920 tcgtcttacc tttcgggagc gaacctcaac ctctcctgcc actcggcctc taacccatcc   1980
ccgcagtatt cttggcgtat caatgggata ccgcagcaac acacacaagt tctctttatc   2040
gccaaaatca cgccaaataa taacgggacc tatgcctgtt ttgtctctaa cttggctact   2100
ggccgcaata attccatagt caagagcatc acagtctctg catctggaac ttctcctggt   2160
ctctcagctg gggccactgt cggcatcatg attggagtgc tggttggggt tgctctgata   2220
tagcagccct ggtgtagttt cttcatttca ggaagactga cagttgtttt gcttcttcct   2280
taaagcattt gcaacagcta cagtctaaaa ttgcttcttt accaaggata tttacagaaa   2340
agactctgac cagagatcga gaccatccta gccaacatcg tgaaacccca tctctactaa   2400
aaatacaaaa atgagctggg cttggtggcg cgcacctgta gtcccagtta ctcgggaggc   2460
tgaggcagga gaatcgcttg aacccgggag gtggagattg cagtgagccc agatcgcacc   2520
```

```
actgcactcc agtctggcaa cagagcaaga ctccatctca aaagaaaag aaagaagac      2580 tctgacctgt actcttgaat acaagtttct gataccactg cactgtctga gaatttccaa      2640
aactttaatg aactaactga cagcttcatg aaactgtcca ccaagatcaa gcagagaaaa      2700
taattaattt catgggacta aatgaactaa tgaggattgc tgattcttta aatgtcttgt      2760
ttcccagatt tcaggaaact ttttttcttt taagctatcc actcttacag caatttgata      2820
aaatatactt ttgtgaacaa aaattgagac atttacattt tctccctatg tggtcgctcc      2880
agacttggga aactattcat gaatatttat attgtatggt aatatagtta ttgcacaagt      2940
tcaataaaaa tctgctcttt gtataacaga aaaa                                 2974
```

<210> SEQ ID NO 104
<211> LENGTH: 3069
<212> TYPE: DNA
<213> ORGANISM: Homo sapiens

<400> SEQUENCE: 104

```
tgtttccgct gcatccagac ttcctcaggc ggtggctgga ggctgcgcat ctggggcttt        60
aaacatacaa agggattgcc aggacctgcg gcggcggcgg cggcggcggg ggctggggcg       120 cggggccgg accatgagcc gctgagccgg gcaaacccca ggccaccgag ccagcggacc        180
ctcggagcgc agccctgcgc cgcggaccag gctccaacca ggcggcgagg cggccacacg       240
caccgagcca gcgaccccg ggcgacgcgc ggggccaggg agcgctacga tggaggcgct        300
aatggcccgg ggcgcgctca cgggtccct gagggcgctc tgtctcctgg gctgcctgct       360
gagccacgcc gccgccgcgc cgtcgccat catcaagttc cccggcgatg tcgccccaa        420 aacggacaaa gagttggcag tgcaatacct gaacaccttc tatggctgcc ccaaggagag       480
ctgcaacctg tttgtgctga aggacacact aaagaagatg cagaagttct ttggactgcc       540
ccagacaggt gatcttgacc agaataccat cgagaccatg cggaagccac gctgcggcaa       600
cccagatgtg gccaactaca acttcttccc tcgcaagccc aagtgggaca gaaccagat        660 cacatacagg atcattggct acacacctga tctggaccca gagacagtgg atgatgcctt       720
tgctcgtgcc ttccaagtct ggagcgatgt gacccactg cggttttctc gaatccatga       780
tggagaggca gacatcatga tcaactttgg ccgctgggag catggcgatg atacccctt        840 tgacggtaag gacggactcc tggctcatgc cttcgcccca ggcactggtg ttggggaga        900 ctcccatttt gatgacgatg agctatggac cttgggagaa ggccaagtgg tccgtgtgaa       960
gtatggcaac gccgatgggg agtactgcaa gttccccttc ttgttcaatg gcaaggagta      1020
caacagctgc actgatactg gccgcagcga tggcttcctc tggtgctcca ccacctacaa      1080
ctttgagaag gatggcaagt acggcttctg tccccatgaa gccctgttca ccatgggcgg      1140
caacgctgaa ggacagccct gcaagtttcc attccgcttc cagggcacat cctatgacag      1200
ctgcaccact gagggccgca cggatggcta ccgctggtgc ggcaccactg aggactacga      1260
ccgcgacaag aagtatggct tctgccctga gaccgccatg tccactgttg gtgggaactc      1320
agaaggtgcc ccctgtgtct tcccttcac tttcctgggc aacaaatatg agagctgcac      1380
cagcgccggc cgcagtgacg gaaagatgtg tgtgcgacc acagccaact acgatgacga      1440
ccgcaagtgg ggcttctgcc ctgaccaagg gtacagcctg ttcctcgtgg cagcccacga      1500
gtttggccac gccatgggc tggagcactc ccaagaccct gggggcctga tggcacccat      1560 ttacaccctac accaagaact tccgtctgtc ccaggatgac atcaagggca ttcaggagct      1620
ctatggggcc tctcctgaca ttgaccttgg caccggcccc accccccaca ctgggccttgt      1680
```

```
cactcctgag atctgcaaac aggacattgt atttgatggc atcgctcaga tccgtggtga    1740
gatcttcttc ttcaaggacc ggttcatttg gcggactgtg acgccacgtg acaagcccat    1800
ggggcccctg ctggtggcca cattctggcc tgagctcccg gaaaagattg atgcggtata    1860
cgaggcccca caggaggaga aggctgtgtt ctttgcaggg aatgaatact ggatctactc    1920
agccagcacc ctggagcgag ggtaccccaa gccactgacc agcctgggac tgcccctga     1980 tgtccagcga gtggatgccg cctttaactg gagcaaaaac aagaagacat acatctttgc    2040
tggagacaaa ttctggagat acaatgaggt gaagaagaaa atggatcctg ctttcccaa     2100 gctcatcgca gatgcctgga atgccatccc cgataacctg gatgccgtcg tggacctgca    2160
gggcggcggt cacagctact tcttcaaggg tgcctattac ctgaagctgg agaaccaaag    2220
tctgaagagc gtgaagtttg aagcatcaa  atccgactgg ctaggctgct gagctggccc    2280
tggctcccac aggcccttcc tctccactgc cttcgataca ccgggcctgg agaactagag    2340
aaggacccgg aggggcctgg cagccgtgcc ttcagctcta cagctaatca gcattctcac    2400
tcctacctgg taatttaaga ttccagagag tggctcctcc cggtgcccaa gaatagatgc    2460
tgactgtact cctcccaggc gccccttccc cctccaatcc caccaaccct cagagccacc    2520
cctaaagaga tcctttgata ttttcaacgc agccctgctt tgggctgccc tggtgctgcc    2580
acacttcagg ctcttctcct ttcacaacct tctgtggctc acagaaccct tggagccaat    2640
ggagactgtc tcaagagggc actggtggcc cgacagcctg gcacagggca gtgggacagg    2700
gcatggccag gtggccactc cagaccctg  gcttttcact gctggctgcc ttagaacctt    2760
tcttacatta gcagtttgct ttgtatgcac tttgtttttt tctttgggtc ttgtttttt     2820 tttccactta gaaattgcat ttcctgacag aaggactcag gttgtctgaa gtcactgcac    2880
agtgcatctc agcccacata gtgatggttc ccctgttcac tctacttagc atgtccctac    2940
cgagtctctt ctccactgga tggaggaaaa ccaagccgtg gcttcccgct cagccctccc    3000
tgcccctccc ttcaaccatt ccccatggga aatgtcaaca agtatgaata aagacaccta    3060
ctgagtggc                                                             3069
```

<210> SEQ ID NO 105
<211> LENGTH: 3299
<212> TYPE: DNA
<213> ORGANISM: Homo sapiens

<400> SEQUENCE: 105

```
cggagggagc gctgggagcg agcaagcgag cgtttggagc ccgggccagc agaggggcg      60 cccggtcgct gcctgtaccg ctcccgctgg tcatctccgc cgcgctcggg ggccccggga    120
ggagcgagac cgagtcggag agtccggag  ccaagccggg cgaaacccaa ctgcggagga    180
cgcccgcccc actcagcctc ctcctgcgtc cgagccgggg agcatcgccg agcgccccac    240
gggccggaga gctgggagca caggtcccgg cagcccagg  gatggtctag gagccggcgt    300
aaggctcgct gctctgctcc ctgccggggc tagccgcctc ctgccgatcg cccggggctg    360
cgagctgcgg cggccggggg ctgctcgccg ggcggcgcag gccggagaag ttagttgtgc    420
gcgcccttag tgcgcggaac cagccagcga gcgagggagc agcgaggcgc cgggaccatg    480
ggctggggga gccgctgctg ctgcccggga cgtttggacc tgctgtgcgt gctggcgctg    540 ctcggggct  gcctgctccc cgtgtgtcgg acgcgcgtct acaccaacca ctgggcagtc    600
aaaatcgccg ggggcttccc ggaggccaac cgtatcgcca gcaagtacgg attcatcaac    660
```

```
ataggacaga tagggccct gaaggactac taccacttct accatagcag gacgattaaa      720
aggtcagtta tctcgagcag agggacccac agtttcattt caatggaacc aaaggtggaa      780
tggatccaac agcaagtggt aaaaaagcgg acaaagaggg attatgactt cagtcgtgcc      840
cagtctacct atttcaatga tcccaagtgg cccagcatgt ggtatatgca ctgcagtgac      900
aatacacatc cctgccagtc tgacatgaat atcgaaggag cctggaagag aggctacacg      960
ggaaagaaca ttgtggtcac tatcctggat gacggaattg agagaaccca tccagatctg     1020
atgcaaaact acgatgctct ggcaagttgc gacgtgaatg ggaatgactt ggacccaatg     1080
cctcgttatg atgcaagcaa cgagaacaag catgggactc gctgtgctgg agaagtggca     1140
gccgctgcaa acaattcgca ctgcacagtc ggaattgctt tcaacgccaa gatcggagga     1200
gtgcgaatgc tggacggaga tgtcacggac atggttgaag caaaatcagt tagcttcaac     1260
ccccagcacg tgcacattta cagcgccagc tggggcccgg atgatgatgg caagactgtg     1320
gacggaccag ccccctcac ccggcaagcc tttgaaaacg gcgttagaat ggggcggaga     1380
ggcctcggct ctgtgtttgt ttgggcatct ggaaatggtg aaggagcaa agaccactgc     1440
tcctgtgatg gctacaccaa cagcatctac accatctcca tcagcagcac tgcagaaagc     1500
ggaaagaaac cttggtacct ggaagagtgt tcatccacgc tggccacaac ctacagcagc     1560
ggggagtcct acgataagaa aatcatcact acagatctga ggcagcgttg cacggacaac     1620
cacactggga cgtcagcctc agcccccatg gctgcaggca tcattgcgct ggccctggaa     1680
gccaatccgt ttctgacctg gagagacgta cagcatgtta ttgtcaggac ttcccgtgcg     1740
ggacatttga cgctaatga ctggaaaacc aatgctgctg gttttaaggt gagccatctt     1800
tatggatttg gactgatgga cgcagaagcc atggtgatgg aggcagagaa gtggaccacc     1860
gttcccggc agcacgtgtg tgtggagagc acagaccgac aaatcaagac aatccgccct     1920
aacagtgcag tgcgctccat ctacaaagct tcaggctgct cggataaccc caaccgccat     1980
gtcaactacc tggagcacgt cgttgtgcgc atcaccatca cccacccag gagaggagac     2040
ctggccatct acctgacctc gccctctgga actaggtctc agcttttggc caacaggcta     2100
tttgatcact ccatggaagg attcaaaaac tgggagttca tgaccattca ttgctgggga     2160
gaaagagctg ctggtgactg ggtccttgaa gtttatgata ctccctctca gctaaggaac     2220
tttaagactc caggtaaatt gaaagaatgg tctttggtcc tctacggcac ctccgtgcag     2280
ccatattcac caaccaatga atttccgaaa gtggaacggt tccgctatag ccgagttgaa     2340
gacccccacag acgactatgg cacagaggat tatgcgaggtc cctgcgaccc tgagtgcagt     2400
gaggttggct gtgacgggcc aggaccagac cactgcaatg actgtttgca ctactactac     2460
aagctgaaaa acaataccag gatctgtgtc tccagctgcc ccctggcca ctaccacgcc     2520
gacaagaagc gctgcaggaa gtgtgccccc aactgtgagt cctgctttgg gagccatggt     2580
gaccaatgca tgtcctgcaa atatggatac tttctgaatg aagaaccaa cagctgtgtt     2640
actcactgcc ctgatgggtc atatcaggat accaagaaaa tctttgccg gaaatgcagt     2700
gaaactgca agacatgtac tgaattccat aactgtacag aatgtaggga tgggttaagc     2760
ctgcagggat cccggtgctc tgtctcctgt gaagatggac ggtatttcaa cggccaggac     2820
tgccagccct gccaccgctt ctgcgccact tgtgctgggg caggagctga tgggtgcatt     2880
aactgcacag agggctactt catggaggat gggagatgcg tgcagagctg tagtatcagc     2940
tattactttg accactcttc agagaatgga tacaaatcct gcaaaaaatg tgatatcagt     3000
tgtttgacgt gcaatggccc aggattcaag aactgtacaa gctgccctag tgggtatctc     3060
```

| | |
|---|---|
| ttagacttag gaatgtgtca aatgggagcc atttgcaagg atgcaacgga agagtcctgg | 3120 |
| gcggaaggag gcttctgtat gcttgtgaaa aagaacaatc tgtgccaacg gaaggttctt | 3180 |
| caacaacttt gctgcaaaac atgtacattt caaggctgag cagccatctt agatttcttt | 3240 |
| gttcctgtag acttatagat tattccatat tattaaaaag aaaaaaaaaa gccaaaaag | 3299 |

<210> SEQ ID NO 106
<211> LENGTH: 1664
<212> TYPE: DNA
<213> ORGANISM: Homo sapiens

<400> SEQUENCE: 106

| | |
|---|---|
| atgggttgtg actgcttcgt ccaggaggtg ttctgctcag atgaggagct tgccaccgtc | 60 |
| ccgctggaca tcccgccata tacgaaaaac atcatctttg tggagacctc gttcaccaca | 120 |
| ttggaaaacca gagcttttgg cagtaacccc aacttgacca aggtggtctt cctcaacact | 180 |
| cagctctgcc agtttaggcc ggatgccttt gggggggctgc ccaggctgga ggacctggag | 240 |
| gtcacaggca gtagcttctt gaacctcagc accaacatct tctccaacct gacctcgctg | 300 |
| ggcaagctca ccctcaactt caacatgctg gaggctctgc ccgagggtct tttccagcac | 360 |
| ctggctgccc tggagtccct ccacctgcag gggaaccagc tccaggccct gcccaggagg | 420 |
| ctcttccagc tctgacccca tctgaagaca ctcaacctgg cccagaacct cctgcccag | 480 |
| ctcccggagg agctgttcca cccactcacc agcctgcaga ccctgaagct gagcaacaac | 540 |
| gcgctctctg gtctcccca gggtgtgttt ggcaaactgg gcagcctgca ggagctcttc | 600 |
| ctggacagca acaacatctc ggagctgccc cctcaggtgt tctcccagct cttctgccta | 660 |
| gagaggctgt ggctgcaacg caacgccatc acgcacctgc cgctctccat ctttgcctcc | 720 |
| ctgggtaatc tgacctttct gagcttgcag tggaacatgc ttcgggtcct gctgccggc | 780 |
| ctctttgccc acaccccatg cctggttggc ctgtctctga cccataacca gctggagact | 840 |
| gtcgctgagg gcacctttgc ccacctgtcc aacctgcgtt ccctcatgct ctcatacaat | 900 |
| gccattaccc acctcccagc tggcatcttc agagacctgg aggagttggt caaactctac | 960 |
| ctgggcagca acaaccttac ggcgctgcac ccagccctct tccagaacct gtccaagctg | 1020 |
| gagctgctca gcctctccaa gaaccagctg accacacttc cggagggcat cttcgacacc | 1080 |
| aactacaacc tgttcaacct ggccctgcac ggtaaccct ggcagtgcga ctgccacctg | 1140 |
| gcctacctct tcaactggct gcagcagtac accgatcggc tcctgaacat ccagacctac | 1200 |
| tgcgctggcc ctgcctacct caaaggccag gtggtgcccg ccttgaatga aagcagctg | 1260 |
| gtgtgtcccg tcacccggga ccacttgggc ttccaggtca cgtggccgga cgaaagcaag | 1320 |
| gcaggggggca gctgggatct ggctgtgcag gaaaggggcag cccggagcca gtgcacctac | 1380 |
| agcaaccccg agggcaccgt ggtgctcgcc tgtgaccagg cccagtgtcg ctggctgaac | 1440 |
| gtccagctct ctccttggca gggctccctg ggactgcagt acaatgctag tcaggagtgg | 1500 |
| gacctgaggt cgagctgcgg ttctctgcgg ctcaccgtgt ctatcgaggc tcgggcagca | 1560 |
| gggccctagt agcagcgcat acaggagctg gggaaggggg cttttggggcc tgcccacgcg | 1620 |
| acaggtaggg gcggagggga gctgagtctc cgaagcttgg cttt | 1664 |

<210> SEQ ID NO 107
<211> LENGTH: 3383
<212> TYPE: DNA
<213> ORGANISM: Homo sapiens

<400> SEQUENCE: 107

```
cgggggccgc gcgggcaaga tggtgtgcgc tcgggcggcc ctcggtcccg gcgcgctctg      60
ggccgcggcc tgggcgtcc tgctgctcac agccctgcg ggggcgcagc gtggccggaa      120
gaaggtcgtg cacgtgctgg agggtgagtc gggctcggta gtggtacaga cagcgcctgg      180
gcaggtggta agccaccgtg gtggcaccat cgtcttgccc tgccgctacc actatgaggc      240
agccgcccac ggtcacgacg gcgtccggct caagtggaca aaggtggtgg acccgctggc      300
cttcaccgac gtcttcgtgg cactaggccc ccagcaccgg gcattcggca gctaccgtgg      360
gcgggctgag ctgcagggcg acgggcctgg ggatgcctcc ctggtcctcc gcaacgtcac      420
gctgcaagac tacgggcgct atgagtgcga agtcaccaat gagctggaag atgacgctgg      480
catggtcaag ctggacctgg aaggcgtggt cttttccctac cacccccgtg gaggccgata      540
caagctgacc ttcgcggagg cgcagcgcgc gtgcgccgag caggacggca tcctggcatc      600
tgcagaacag ctgcacgcgg cctgcgcgca cggcctggac tggtgcaacg cgggctggtt      660
gcgcgacggc tcagtgcaat accccgtgaa ccggcccccgg gagccctgcg gcggcctggg      720
ggggaccggg agtgcagggg gcggcggtga tgccaacggg gcctgcgca actacgggta      780
tcgccataac gccgaggaac gctacgacgc cttctgcttc acgtccaacc tgccggggcg      840
cgtgttcttc ctgaagccgc tgcgacctgt acccttctcc ggagctgcgc gcgcgtgtgc      900
tgcgcgtggc gcggccgtgg ccaaggtggg gcagctgttc gccgcgtgga agctgcagct      960
gctagaccgc tgcaccgcgg gttggctggc cgatggcagt gcgcgctacc ccatcgtgaa     1020
cccgcgagcg cgctgcggag gccgcaggcc tggtgtgcgc agcctcggct tcccggacgc     1080
cacccgacgg ctcttcggcg tctactgcta ccgcgctcca ggagcaccgg acccggcacc     1140
tggcggctgg ggctggggct gggcgggcgg cggcggctgg gcaggggcg cgcgcgatcc     1200
tgctgcctgg accctctgc acgtctaggc tgggagtagg cggacagcca gggcgcttga     1260
ccactggtct agagccctgt ggtccctgg agcctggcca cgcccttgaa gccctggaca     1320
ctggccacat tccctgtggt cccttacaaa ctaactgtgc cctggggtc cctgaagact     1380
ggctagtcct ggcagaacag tactttggag ttccctggag cctggccagc cctcacctct     1440
tctggataga ggattccccc aactccccaa cttttctccat gagggtcacg cccctgagg     1500
acctcaggag gccagcagaa cccgcaggct cctgaagact ggccacgcct cctgagacca     1560
cttggaaaca gaccaactgc ccccgtggtc gcctggtggc tggaccccg ggattgacta     1620
gagaccggcc gtacaccttc tgcatctcac tggagactga acactagtcc cttgcggtca     1680
cgtgggacac tgggcgcctc ctcctccccc tcctcctcac ctggagagac tacaggaact     1740
tcagggtcac tccccgtggt cacatggagg ttgtgggccg aggcgcttat tttcccttat     1800
ggtgacctga gtcctggaga ctcccattct ccccctctcc ctgagagtcc cctgcagttt     1860
ctgggtaaca gggcacaccc ctctagtttc atgggcgagc accccatct gccacctcag     1920
actgacacac agccagctgg ctcacttact ggggggccacg tcccaccct cagatatttc     1980
tttgaaggga gagcaaaccc accctgtcct ctgacgtccc tttcccaact gtcaccaaac     2040
agaccatctt cccaggcctg gggaccggta agatccatgt cactagttat gcagagcagt     2100
tgccttgggt cccactgtca ccaaggcaac cagtcctgct gctacctgtc acctagagtc     2160
acacacccct tccctcatca ggcacaccca tgaagacagt gcctccctcc tccagctgta     2220
accatggata ccacacattt ctcatctcat tggcccccac cccagagacc tccacctcaa     2280
cttctggctg tccctaccct gactcaccgc catggagatc accctccccg aagctgtcgc     2340
```

```
cagggtgacc caacatccag ttctccggct ctcaccatgg aaacaaactg tccctgtccc    2400
caggcccact ccagttccag accaccctcc atgctccacc cccaggcggt ttggacccca    2460
ccactgttgc catggtgacc aaactctgga gtccgaggta acagaacacc tgtccccta    2520 ggcttttcct tgtggacaac ggggccctgt tcaccaagct gttgccatag agactgtcaa    2580
cgttgtcctc atgacaacca gacttccagt tctcaggaac ttctcattgt gggccagaag    2640
tcctgggtgc ctcctactag ggctacccta ctgcaccca tcaggggcct gatggctgcc     2700
ccttccccag acagggctgg acttctggag ctgctaagcc accctccgtt tgcacgttaa    2760
ctctatgccg gatagcagct gtgcacgaga caatcttgca acacccgggc atgtttgtcg    2820
tcgtcctaca aatgaggaaa ccgagcctat ggcgtgccct ggtctgttga gatatgcaag    2880
cactgagctc ctcttttgtc ctctgagacc ccatctccat tctcacccag ttcctctctc    2940
cttccctgac ccccacccac atttccctcc ttagagatcc aggagggatg gaatgttctt    3000
taaaattcaa cacccaccag gctctaagcg gcgatctgtg ctaagaggtc aggacccagc    3060
cgaagtcctc ggcgttgaca ggcagctggg gggacatgat ccatggacaa ggccatcccg    3120
gccgtgggag accccagtcc cgaagtcttg cctgcaggag tactgggtc ccctggggc      3180 cctctttact gtcacgtcat ctctaggaaa cctatctctg agttttggga ccaggtcggt    3240
ttgggtttga attctgcctc ttcttgctca ctgtgtgacc aagtgacaaa ctccttctga    3300
acctgtgttc tcccactgta ccagggctgt tctgtggtcc ccgtgagtgc caagcataca    3360 gtagggctc aataaatcct tgt                                              3383
```

<210> SEQ ID NO 108
<211> LENGTH: 17
<212> TYPE: PRT
<213> ORGANISM: Homo sapiens

<400> SEQUENCE: 108

```
Phe Ala Ile Ser Glu Tyr Asn Lys Ala Thr Lys Asp Asp Tyr Tyr Arg
  1               5                  10                  15

Arg
```